US012735406B2

(12) United States Patent
Sano et al.

(10) Patent No.: US 12,735,406 B2
(45) **Date of Patent: *Sep. 15, 2026**

(54) NITROGEN-CONTAINING CONDENSED HETEROCYCLIC COMPOUND HAVING AN OXIME GROUP, AGRICULTURAL OR HORTICULTURAL HERBICIDE COMPRISING THE COMPOUND, AND METHOD FOR USING THE COMPOUND OR THE HERBICIDE

(71) Applicant: NIHON NOHYAKU CO., LTD., Tokyo (JP)

(72) Inventors: Yusuke Sano, Osaka (JP); Tomoya Morita, Osaka (JP); Naoya Osato, Osaka (JP); Asuka Nishimoto, Osaka (JP)

(73) Assignee: NIHON NOHYAKU CO., LTD., Tokyo (JP)

( * ) Notice: Subject to any disclaimer, the term of this patent is extended or adjusted under 35 U.S.C. 154(b) by 414 days.

This patent is subject to a terminal disclaimer.

(21) Appl. No.: 18/032,900

(22) PCT Filed: Oct. 28, 2021

(86) PCT No.: PCT/JP2021/039753

§ 371 (c)(1),
(2) Date: Apr. 20, 2023

(87) PCT Pub. No.: WO2022/092180

PCT Pub. Date: May 5, 2022

(65) Prior Publication Data

US 2023/0357210 A1 Nov. 9, 2023

(30) Foreign Application Priority Data

Oct. 29, 2020 (JP) ................................ 2020-181875

(51) Int. Cl.

| | |
|---|---|
| ***C07D 405/14*** | (2006.01) |
| ***A01N 43/52*** | (2006.01) |
| ***A01N 43/76*** | (2006.01) |
| ***A01N 47/02*** | (2006.01) |
| ***A01P 13/00*** | (2006.01) |
| ***C07D 235/18*** | (2006.01) |
| ***C07D 401/04*** | (2006.01) |
| ***C07D 401/14*** | (2006.01) |
| ***C07D 403/04*** | (2006.01) |
| ***C07D 413/14*** | (2006.01) |
| ***C07D 417/14*** | (2006.01) |

(52) U.S. Cl.

CPC ........... *C07D 405/14* (2013.01); *A01N 43/52* (2013.01); *A01N 43/76* (2013.01); *A01N 47/02* (2013.01); *A01P 13/00* (2021.08); *C07D 235/18* (2013.01); *C07D 401/04* (2013.01); *C07D 401/14* (2013.01); *C07D 403/04* (2013.01); *C07D 413/14* (2013.01); *C07D 417/14* (2013.01)

(58) Field of Classification Search

None

See application file for complete search history.

(56) References Cited

U.S. PATENT DOCUMENTS

| | | | |
|---|---|---|---|
| 4,824,476 A | 4/1989 | Pissiotas et al. | |
| 5,670,455 A | 9/1997 | Selby et al. | |
| 5,977,028 A | 11/1999 | Selby et al. | |
| 6,358,885 B1 | 3/2002 | Selby et al. | |
| 6,387,849 B1 | 5/2002 | Menke et al. | |
| 10,856,548 B2 | 12/2020 | Yonemura et al. | |
| 2004/0110749 A1 | 6/2004 | Nakatani et al. | |
| 2016/0021886 A1 | 1/2016 | Yonemura et al. | |
| 2016/0255837 A1* | 9/2016 | Edmunds | A61P 33/00 |

(Continued)

FOREIGN PATENT DOCUMENTS

| | | |
|---|---|---|
| CN | 110114354 | 8/2019 |
| EP | 0 508 800 | 10/1992 |

(Continued)

OTHER PUBLICATIONS

International Preliminary Report on Patentability issued May 2, 2023 in International (PCT) Application No. PCT/JP2021/039753.

(Continued)

*Primary Examiner* — John Pak

(74) *Attorney, Agent, or Firm* — Wenderoth, Lind & Ponack, L.L.P.

(57) ABSTRACT

In order to resolve the food crisis that is anticipated to come in the near future due to global population growth, there is a demand for the creation of a novel herbicide having both high safety for crops and excellent herbicidal activity against weeds. This problem can be solved by an agricultural or horticultural herbicide comprising a compound represented by the following general formula (1):

(1)

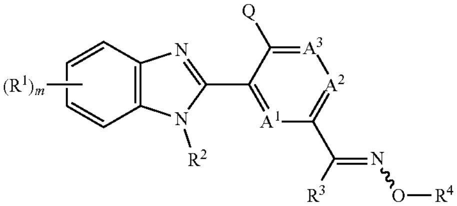

or a salt thereof as an active ingredient, and a method for using the herbicide.

17 Claims, No Drawings

(56) References Cited

U.S. PATENT DOCUMENTS

| | | | | |
|---|---|---|---|---|
| 2018/0271099 | A1* | 9/2018 | Fischer | C07D 409/10 |
| 2020/0085054 | A1 | 3/2020 | Yonemura et al. | |
| 2020/0214292 | A1 | 7/2020 | Yonemura et al. | |
| 2021/0002263 | A1* | 1/2021 | Sakanishi | A01N 47/02 |
| 2021/0204545 | A1 | 7/2021 | Fujihara et al. | |
| 2021/0371424 | A1 | 12/2021 | Sano et al. | |
| 2022/0340578 | A1 | 10/2022 | Yamauchi et al. | |
| 2023/0121730 | A1 | 4/2023 | Fujita et al. | |
| 2023/0338350 | A1 | 10/2023 | Fujihara et al. | |
| 2026/0014131 | A1 | 1/2026 | Fujihara et al. | |

FOREIGN PATENT DOCUMENTS

| | | | |
|---|---|---|---|
| JP | 62-463 | | 1/1987 |
| JP | 5-112557 | | 5/1993 |
| JP | 7-504403 | | 5/1995 |
| JP | 2001-517231 | | 10/2001 |
| JP | 2019-112369 | | 7/2019 |
| KR | 2003-0084922 | | 11/2003 |
| WO | 93/15074 | | 8/1993 |
| WO | 2017/065183 | | 4/2017 |
| WO | WO 2018/124129 | * | 7/2018 |
| WO | 2019/059244 | | 3/2019 |
| WO | WO 2019/176791 | * | 9/2019 |
| WO | 2019/225663 | | 11/2019 |
| WO | 2020/032071 | | 2/2020 |

OTHER PUBLICATIONS

International Search Report (ISR) issued Dec. 28, 2021 in International (PCT) Application No. PCT/JP2021/039753.

* cited by examiner

NITROGEN-CONTAINING CONDENSED HETEROCYCLIC COMPOUND HAVING AN OXIME GROUP, AGRICULTURAL OR HORTICULTURAL HERBICIDE COMPRISING THE COMPOUND, AND METHOD FOR USING THE COMPOUND OR THE HERBICIDE

TECHNICAL FIELD

The present invention relates to a nitrogen-containing condensed heterocyclic compound having an oxime group and a salt thereof, an agricultural or horticultural herbicide comprising the compound or the salt thereof as an active ingredient, and a method for using the compound or the salt thereof or the herbicide.

BACKGROUND ART

Patent literature 1 describes certain kinds of nitrogen-containing condensed heterocyclic compounds having an oxime group that have insecticidal activity. However, the literature does not describe the specific structure of the compound of the present invention, nor does it disclose or suggest any compounds useful as herbicides.

CITATION LIST

Patent Literature

Patent Literature 1: WO 2017/065183

SUMMARY OF INVENTION

Technical Problem

A stable and secure food supply is essential to resolve the food crisis that is anticipated to come in the near future due to global population growth. The stable and secure food supply requires economical and efficient elimination or control of weeds that interfere with crop cultivation and harvest. Therefore, it is becoming increasingly important to develop new herbicides and plant growth regulators that can provide solutions to this problem. In order to respond to such social demands, the present invention is intended to provide a novel herbicide having both high safety for crops and excellent herbicidal activity against weeds. In addition, in view of aging of farmers, there is a demand for various kinds of labor-saving application methods and for the creation of agricultural or horticultural herbicides suitable for such application methods.

Solution to Problem

The present inventors conducted extensive research to develop a novel agricultural or horticultural herbicide. As a result, the present inventors found that the nitrogen-containing condensed heterocyclic compound having an oxime group represented by the general formula (1) of the present invention or a salt thereof is useful as an agricultural or horticultural herbicide. Based on this finding, the present inventors completed the present invention.

That is, the present invention includes the following.

[1] A compound represented by the general formula (1):

[Chem. 1]

(1)

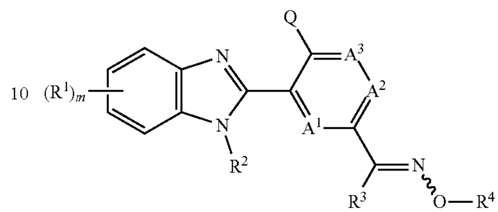

(wherein $R^1$ represents (a1) a halogen atom;
(a2) a cyano group;
(a3) a nitro group;
(a4) a formyl group;
(a5) a carboxyl group;
(a6) a $(C_1\text{-}C_6)$ alkyl group;
(a7) a $(C_2\text{-}C_6)$ alkenyl group;
(a8) a $(C_2\text{-}C_6)$ alkynyl group;
(a9) a $(C_3\text{-}C_6)$ cycloalkyl group;
(a10) a halo$(C_1\text{-}C_6)$ alkyl group;
(a11) a halo$(C_2\text{-}C_6)$ alkenyl group;
(a12) a halo$(C_2\text{-}C_6)$ alkynyl group;
(a13) a halo$(C_3\text{-}C_6)$ cycloalkyl group;
(a14) a hydroxy $(C_1\text{-}C_6)$ alkyl group;
(a15) a hydroxy halo$(C_1\text{-}C_6)$ alkyl group;
(a16) a $(C_1\text{-}C_6)$ alkoxy $(C_1\text{-}C_6)$ alkyl group;
(a17) a di-$(C_1\text{-}C_6)$ alkoxy $(C_1\text{-}C_6)$ alkyl group;
(a18) a halo$(C_1\text{-}C_6)$ alkoxy $(C_1\text{-}C_6)$ alkyl group;
(a19) a $(C_1\text{-}C_6)$ alkoxy halo$(C_1\text{-}C_6)$ alkyl group;
(a20) a halo$(C_1\text{-}C_6)$ alkoxy halo$(C_1\text{-}C_6)$ alkyl group;
(a21) a $(C_3\text{-}C_6)$ cycloalkyl $(C_1\text{-}C_6)$ alkyl group;
(a22) a $(C_1\text{-}C_6)$ alkoxy group;
(a23) a halo$(C_1\text{-}C_6)$ alkoxy group;
(a24) a $(C_1\text{-}C_6)$ alkylthio group;
(a25) a $(C_1\text{-}C_6)$ alkylsulfinyl group;
(a26) a $(C_1\text{-}C_6)$ alkylsulfonyl group;
(a27) a halo$(C_1\text{-}C_6)$ alkylthio group;
(a28) a halo$(C_1\text{-}C_6)$ alkylsulfinyl group;
(a29) a halo$(C_1\text{-}C_6)$ alkylsulfonyl group;
(a30) an $R^8(R^9)N$ group wherein $R^8$ and $R^9$ may be the same or different and each represent a hydrogen atom, a hydroxyl group, an amino group, a di-$(C_1\text{-}C_6)$ alkylamino group, a $(C_1\text{-}C_6)$ alkyl group, a $(C_3\text{-}C_6)$ cycloalkyl group, a $(C_2\text{-}C_6)$ alkenyl group, a $(C_2\text{-}C_6)$ alkynyl group, a $(C_1\text{-}C_6)$ alkoxy group, a $(C_2\text{-}C_6)$ alkenyloxy group, a halo$(C_1\text{-}C_6)$ alkyl group, a halo$(C_2\text{-}C_6)$ alkenyl group, a halo$(C_1\text{-}C_6)$ alkynyl group, a halo$(C_1\text{-}C_6)$ alkoxy group, a halo$(C_1\text{-}C_6)$ cycloalkyl group, a $(C_3\text{-}C_6)$ cycloalkyl $(C_1\text{-}C_6)$ alkyl group, a cyano $(C_1\text{-}C_6)$ alkyl group, a $(C_1\text{-}C_6)$ alkylcarbonyl group, a halo$(C_1\text{-}C_6)$ alkylcarbonyl group, a $(C_1\text{-}C_6)$ alkoxycarbonyl group, a halo$(C_1\text{-}C_6)$ alkoxycarbonyl group, a $(C_1\text{-}C_6)$ alkylsulfanylcarbonyl group, a $(C_1\text{-}C_6)$ alkylsulfonyl group, a halo$(C_1\text{-}C_6)$ alkylsulfonyl group, an N—$(C_1\text{-}C_6)$ alkylcarboxamide group, an N,N-di-$(C_1\text{-}C_6)$ alkylcarboxamide group, an N—$(C_1\text{-}C_6)$ alkylsulfamoyl group, an N,N-di-$(C_1\text{-}C_6)$ alkylsulfamoyl group, an N-halo$(C_1\text{-}C_6)$ alkylcarboxamide group, a $(C_1\text{-}C_6)$ alkoxycarbonyl $(C_1\text{-}C_6)$ alkyl group, a $(C_1\text{-}C_6)$ alkoxy $(C_1-C_6)$ alkyl group, a di-$(C_1-C_6)$ alkoxy $(C_1-C_6)$ alkyl group, a $(C_1-C_6)$ alkoxy $(C_1-C_6)$ alkylcarbonyl group, a thietanyl group, a 1,1-dioxothietanyl group, a tetrahydrofuranyl group, a thiazolyl group, a 2-oxotetrahydrofuranyl group, a phenyl group, a phenyl group having, on the ring, 1 to 5 substituting groups which may be the same or different and are selected from the group consisting of a halogen atom, a cyano group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group, or a phenyl$(C_1-C_6)$ alkyl group, or $R^8$ and $R^9$ may join together to form a 4- to 6-membered ring;

(a31) an $R^{10}(R^{11})N(C_1-C_6)$ alkyl group wherein $R^{10}$ and $R^{11}$ may be the same or different and each represent a hydrogen atom, a $(C_1-C_6)$ alkyl group, a halo$(C_1-C_6)$ alkyl group, a $(C_3-C_6)$ cycloalkyl group, a $(C_3-C_6)$ cycloalkyl $(C_1-C_6)$ alkyl group, a $(C_1-C_6)$ alkylcarbonyl group, a halo$(C_1-C_6)$ alkylcarbonyl group, a $(C_1-C_6)$ alkoxycarbonyl group, a halo$(C_1-C_6)$ alkoxycarbonyl group, a $(C_1-C_6)$ alkylsulfonyl group, or a halo$(C_1-C_6)$ alkylsulfonyl group, or $R^{10}$ and $R^{11}$ may join together to form a 4- to 6-membered ring;

(a32) a $(C_1-C_6)$ alkylthio $(C_1-C_6)$ alkyl group;

(a33) a $(C_1-C_6)$ alkylsulfinyl $(C_1-C_6)$ alkyl group;

(a34) a $(C_1-C_6)$ alkylsulfonyl $(C_1-C_6)$ alkyl group;

(a35) a halo$(C_1-C_6)$ alkylthio $(C_1-C_6)$ alkyl group;

(a36) a halo$(C_1-C_6)$ alkylsulfinyl $(C_1-C_6)$ alkyl group;

(a37) a halo$(C_1-C_6)$ alkylsulfonyl $(C_1-C_6)$ alkyl group;

(a38) a $(C_1-C_6)$ alkylthio halo$(C_1-C_6)$ alkyl group;

(a39) a $(C_1-C_6)$ alkylsulfinyl halo$(C_1-C_6)$ alkyl group;

(a40) a $(C_1-C_6)$ alkylsulfonyl halo$(C_1-C_6)$ alkyl group;

(a41) a halo$(C_1-C_6)$ alkylthio halo$(C_1-C_6)$ alkyl group;

(a42) a halo$(C_1-C_6)$ alkylsulfinyl halo$(C_1-C_6)$ alkyl group;

(a43) a halo$(C_1-C_6)$ alkylsulfonyl halo$(C_1-C_6)$ alkyl group;

(a44) a $(C_1-C_6)$ alkylcarbonyl group;

(a45) a $(C_1-C_6)$ alkoxycarbonyl group;

(a46) a halo$(C_1-C_6)$ alkylcarbonyl group;

(a47) a halo$(C_1-C_6)$ alkoxycarbonyl group;

(a48) a $(C_1-C_6)$ alkylcarbonyloxy group;

(a49) a halo$(C_1-C_6)$ alkylcarbonyloxy group;

(a50) an $R^{10}(R^{11})N$ carbonyl group wherein $R^{10}$ and $R^{11}$ are the same as above;

(a51) an $R^{10}(R^{11})N$ carbonyloxy group wherein $R^{10}$ and $R^{11}$ are the same as above;

(a52) an $R^{10}(R^{11})N$ sulfonyl group wherein $R^{10}$ and $R^{11}$ are the same as above;

(a53) a $(C_1-C_6)$ alkylsulfonyloxy group;

(a54) a halo$(C_1-C_6)$ alkylsulfonyloxy group;

(a55) a $(C_1-C_6)$ alkoxyimino $(C_1-C_3)$ alkyl group;

(a56) a halo$(C_1-C_6)$ alkoxyimino $(C_1-C_3)$ alkyl group;

(a57) a phenyl group;

(a58) a phenyl group having, on the ring, 1 to 5 substituting groups which may be the same or different and are selected from a halogen atom, a cyano group, a nitro group, a formyl group, a $(C_1-C_6)$ alkyl group, a halo $(C_1-C_6)$ alkyl group, a $(C_1-C_6)$ alkoxy group, a halo $(C_1-C_6)$ alkoxy group, a $(C_3-C_6)$ cycloalkyl $(C_1-C_6)$ alkyl group, an $R^{10}(R^{11})N(C_1-C_6)$ alkyl group wherein $R^{10}$ and $R^{11}$ are the same as above, an $R^{10}(R^{11})N$ group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(a59) a pyridyl group;

(a60) a pyridyl group having, on the ring, 1 to 4 substituting groups which may be the same or different and are selected from a halogen atom, a cyano group, a nitro group, a formyl group, a $(C_1-C_6)$ alkyl group, a halo $(C_1-C_6)$ alkyl group, a $(C_1-C_6)$ alkoxy group, a halo $(C_1-C_6)$ alkoxy group, a $(C_3-C_6)$ cycloalkyl $(C_1-C_6)$ alkyl group, an $R^{10}(R^{11})N(C_1-C_6)$ alkyl group wherein $R^{10}$ and $R^{11}$ are the same as above, an $R^{10}(R^{11})N$ group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(a61) a pyrazolyl group;

(a62) a pyrazolyl group having, on the ring, 1 to 3 substituting groups which may be the same or different and are selected from a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N(C_1-C_6)$ alkyl group wherein $R^{10}$ and $R^{11}$ are the same as above, an $R^{10}(R^{11})N$ group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(a63) a phenoxy group;

(a64) a phenoxy group having, on the ring, 1 to 5 substituting groups which may be the same or different and are selected from a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N(C_1-C_6)$ alkyl group wherein $R^{10}$ and $R^{11}$ are the same as above, an $R^{10}(R^{11})N$ group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(a65) a dioxolanyl group;

(a66) a dioxolanyl group having, on the ring, 1 to 4 substituting groups which may be the same or different and are selected from a halogen atom, a cyano group, a nitro group, a formyl group, a carbonyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ $(C_1-C_6)$ alkyl group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group, and a halo$(C_1-C_6)$ alkylsulfonyl group;

(a67) a dioxanyl group;

(a68) a dioxanyl group having, on the ring, 1 to 6 substituting groups which may be the same or different and are selected from a halogen atom, a cyano group, a nitro group, a formyl group, a carbonyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ $(C_1-C_6)$ alkyl group wherein $R^{10}$ and $R^{11}$ are the same as above, a ($C_1$-$C_6$) alkylthio group, a halo($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group, and a halo($C_1$-$C_6$) alkylsulfonyl group;

(a69) a ($C_1$-$C_6$) alkylene group formed together with one adjacent substituting group (another $R^1$), wherein the ($C_1$-$C_6$) alkylene group may be substituted with 1 to 4 substituting groups which may be the same or different and are selected from a halogen atom, a phenyl group, and a ($C_1$-$C_6$) alkyl group; or (a70) a methylenedioxy group formed together with one adjacent substituting group (another $R^1$), wherein the methylenedioxy group may be substituted by 1 or 2 substituting groups which may be the same or different and are selected from a halogen atom, a phenyl group, and a ($C_1$-$C_6$) alkyl group, wherein, when m represents an integer of 2 or more, $R^1$s may be the same or different, m represents 0, 1, 2, 3, or 4, $R^2$ represents (b1) a hydrogen atom;

(b2) a ($C_1$-$C_6$) alkyl group;

(b3) a ($C_3$-$C_6$) cycloalkyl group;

(b4) a ($C_2$-$C_6$) alkenyl group;

(b5) a ($C_2$-$C_6$) alkynyl group;

(b6) a halo($C_1$-$C_6$) alkyl group;

(b7) a halo($C_2$-$C_6$) alkenyl group;

(b8) a halo($C_2$-$C_6$) alkynyl group;

(b9) a ($C_1$-$C_6$) alkoxy ($C_1$-$C_6$) alkyl group;

(b10) a ($C_1$-$C_6$) alkylthio ($C_1$-$C_6$) alkyl group;

(b11) a ($C_1$-$C_6$) alkylsulfinyl ($C_1$-$C_6$) alkyl group;

(b12) a ($C_1$-$C_6$) alkylsulfonyl ($C_1$-$C_6$) alkyl group;

(b13) a ($C_3$-$C_6$) cycloalkyl ($C_1$-$C_6$) alkyl group;

(b14) a ($C_1$-$C_6$) alkoxy group;

(b15) a ($C_1$-$C_6$) alkylcarbonyl group;

(b16) a ($C_1$-$C_6$) alkoxycarbonyl group;

(b17) a halo($C_1$-$C_6$) alkoxy group;

(b18) a halo($C_1$-$C_6$) alkylcarbonyl group;

(b19) a halo($C_1$-$C_6$) alkoxycarbonyl group;

(b20) an $R^{10}(R^{11})N$ carbonyl group wherein $R^{10}$ and $R^{11}$ are the same as above; or (b21) an $R^{10}(R^{11})N$ sulfonyl group wherein $R^{10}$ and $R^{11}$ are the same as above, $R^3$ represents (c1) a hydrogen atom;

(c2) a halogen group;

(c3) a cyano group;

(c4) a carboxyl group;

(c5) a carboxamide group;

(c6) a ($C_1$-$C_6$) alkyl group;

(c7) a ($C_2$-$C_6$) alkenyl group;

(c8) a ($C_2$-$C_6$) alkynyl group;

(c9) a halo($C_1$-$C_6$) alkyl group;

(c10) a halo($C_2$-$C_6$) alkenyl group;

(c11) a halo($C_1$-$C_6$) alkynyl group;

(c12) an $R^8(R^9)N$ group wherein $R^8$ and $R^9$ are the same as above;

(c13) a ($C_1$-$C_6$) alkoxy group;

(c14) a halo($C_1$-$C_6$) alkoxy group;

(c15) a ($C_1$-$C_6$) alkoxy ($C_1$-$C_6$) alkyl group; or (c16) a ($C_1$-$C_6$) alkoxycarbonyl ($C_1$-$C_6$) alkyl group, $R^4$ represents (d1) a hydrogen atom;

(d2) a ($C_1$-$C_6$) alkyl group;

(d3) a ($C_2$-$C_6$) alkenyl group;

(d4) a ($C_1$-$C_6$) alkynyl group;

(d5) a ($C_3$-$C_6$) cycloalkyl group;

(d6) a halo($C_1$-$C_6$) alkyl group;

(d7) a halo($C_2$-$C_6$) alkenyl group;

(d8) a halo($C_2$-$C_6$) alkynyl group;

(d9) a ($C_1$-$C_6$) alkoxy ($C_1$-$C_6$) alkyl group;

(d10) a halo($C_1$-$C_6$) alkoxy ($C_1$-$C_6$) alkyl group;

(d11) a ($C_1$-$C_6$) alkoxy halo($C_1$-$C_6$) alkyl group;

(d12) a halo($C_1$-$C_6$) alkoxy halo($C_1$-$C_6$) alkyl group;

(d13) a ($C_1$-$C_6$) cycloalkyl ($C_1$-$C_6$) alkyl group;

(d14) a cyano ($C_1$-$C_6$) alkyl group;

(d15) a ($C_1$-$C_6$) alkylthio ($C_1$-$C_6$) alkyl group;

(d16) a ($C_1$-$C_6$) alkylsulfinyl ($C_1$-$C_6$) alkyl group;

(d17) a ($C_1$-$C_6$) alkylsulfonyl ($C_1$-$C_6$) alkyl group;

(d18) a carboxyl ($C_1$-$C_6$) alkyl group;

(d19) a phenyl($C_1$-$C_6$) alkyl group;

(d20) a phenyl($C_1$-$C_6$) alkyl group having, on the ring, 1 to 5 substituting groups which may be the same or different and are selected from a halogen atom, a cyano group, a nitro group, a formyl group, a ($C_1$-$C_6$) alkyl group, a halo($C_1$-$C_6$) alkyl group, a ($C_1$-$C_6$) alkoxy group, a halo($C_1$-$C_6$) alkoxy group, a ($C_3$-$C_6$) cycloalkyl ($C_1$-$C_6$) alkyl group, a ($C_1$-$C_6$) alkylthio group, a halo($C_1$-$C_6$) alkylthio group, a ($C_1$-$C_6$) alkylsulfinyl group, a halo($C_1$-$C_6$) alkylsulfinyl group, a ($C_1$-$C_6$) alkylsulfonyl group, and a halo($C_1$-$C_6$) alkylsulfonyl group;

(d21) an $R^{10}(R^{11})N$ alkyl group wherein $R^{10}$ and $R^{11}$ are the same as above;

(d22) a ($C_1$-$C_6$) alkylcarbonyl group;

(d23) a ($C_1$-$C_6$) alkoxycarbonyl group;

(d24) a ($C_1$-$C_6$) alkylsulfonyl group;

(d25) a halo($C_1$-$C_6$) alkylcarbonyl group;

(d26) a halo($C_1$-$C_6$) alkoxycarbonyl group;

(d27) a halo($C_1$-$C_6$) alkylsulfonyl group;

(d28) an $R^{10}(R^{11})N$ carbonyl group wherein $R^{10}$ and $R^{11}$ are the same as above;

(d29) an $R^{10}(R^{11})N$ sulfonyl group wherein $R^{10}$ and $R^{11}$ are the same as above;

(d30) a phenyl group;

(d31) a phenyl group having, on the ring, 1 to 5 substituting groups which may be the same or different and are selected from a halogen atom, a cyano group, a nitro group, a formyl group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_3$-$C_6$) cycloalkyl ($C_1$-$C_6$) alkyl group, an $R^{10}(R^{11})N$ group wherein $R^{10}$ and $R^{11}$ are the same as above, a ($C_1$-$C_6$) alkylthio group, a halo($C_1$-$C_6$) alkylthio group, a ($C_1$-$C_6$) alkylsulfinyl group, a halo($C_1$-$C_6$) alkylsulfinyl group, a ($C_1$-$C_6$) alkylsulfonyl group, and a halo($C_2$-$C_6$) alkylsulfonyl group; or (d32) a ($C_1$-$C_6$) alkoxycarbonyl ($C_1$-$C_6$) alkyl group, $A^1$, $A^2$, and $A^3$ may be the same or different and each represent $CR^5$ (wherein $R^5$ represents a hydrogen atom, a halogen atom, a cyano group, a ($C_1$-$C_6$) alkyl group, a halo($C_1$-$C_6$) alkyl group, a ($C_1$-$C_6$) alkoxy group, a halo($C_1$-$C_6$) alkoxy group, an $R^{10}(R^{11})N$ group wherein $R^{10}$ and $R^{11}$ are the same as above, a ($C_1$-$C_6$) alkylthio group, a ($C_1$-$C_6$) alkylsulfinyl group, or a ($C_1$-$C_6$) alkylsulfonyl group) or a nitrogen atom, and Q represents (e1) a halogen atom;

(e2) a cyano group;

(e3) a nitro group;

(e4) a formyl group;

(e5) a ($C_1$-$C_6$) alkyl group;

(e6) a ($C_1$-$C_6$) alkenyl group;

(e7) a $(C_2-C_6)$ alkynyl group;
(e8) a halo$(C_1-C_6)$ alkyl group;
(e9) a halo$(C_1-C_6)$ alkenyl group;
(e10) a halo$(C_2-C_6)$ alkynyl group;
(e11) a $(C_1-C_6)$ alkoxy group;
(e12) a halo$(C_1-C_6)$ alkoxy group;
(e13) a hydroxy $(C_1-C_6)$ alkyl group;
(e14) a dihydroxy $(C_1-C_6)$ alkyl group;
(e15) a $(C_1-C_6)$ alkoxy $(C_1-C_6)$ alkyl group;
(e16) a $(C_1-C_6)$ alkoxy $(C_1-C_6)$ alkenyl group;
(e17) an $R^8(R^9)N$ group wherein $R^8$ and $R^9$ are the same as above;
(e18) a dioxolanyl group;
(e19) a dioxolanyl group having, on the ring, 1 or 2 substituting groups which may be the same or different and are selected from a halogen atom, a cyano group, a nitro group, a formyl group, a carbonyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ $(C_1-C_6)$ alkyl group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group, and a halo$(C_1-C_6)$ alkylsulfonyl group;
(e20) a dioxanyl group;
(e21) a dioxanyl group having, on the ring, 1 to 3 substituting groups which may be the same or different and are selected from a halogen atom, a cyano group, a nitro group, a formyl group, a carbonyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ $(C_1-C_6)$ alkyl group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group, and a halo$(C_1-C_6)$ alkylsulfonyl group;
(e22) a phenyl group;
(e23) a phenyl group having, on the ring, 1 to 5 substituting groups which may be the same or different and are selected from a halogen atom, a cyano group, a nitro group, a formyl group, a $(C_1-C_6)$ alkyl group, a halo $(C_1-C_6)$ alkyl group, a $(C_1-C_6)$ alkoxy group, a halo $(C_1-C_6)$ alkoxy group, a $(C_3-C_6)$ cycloalkyl $(C_1-C_6)$ alkyl group, an $R^{10}(R^{11})N$ group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;
(e24) an imidazolyl group;
(e25) an imidazolyl group having, on the ring, 1 to 3 substituting groups which may be the same or different and are selected from a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;
(e26) an oxadiazolyl group;
(e27) an oxadiazolyl group having, on the ring, a substituting group selected from a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(e28) an $S(O)_pR^6$ group wherein $R^6$ represents a hydrogen atom, a $(C_1-C_6)$ alkyl group, a $(C_2-C_6)$ alkenyl group, a $(C_2-C_6)$ alkynyl group, a halo$(C_1-C_6)$ alkyl group, a halo$(C_2-C_6)$ alkenyl group, a halo$(C_2-C_6)$ alkynyl group, a $(C_1-C_6)$ alkoxy group, a $(C_3-C_6)$ cycloalkyl group, a halo$(C_3-C_6)$ cycloalkyl group, a phenyl $(C_1-C_6)$ alkyl group, a $(C_1-C_6)$ alkoxyphenyl$(C_1-C_6)$ alkyl group, a $(C_1-C_6)$ alkylphenyl$(C_1-C_6)$ alkyl group, a tri-$(C_1-C_6)$ alkylsilylphenyl$(C_1-C_6)$ alkyl group, or an $N(R^8)R^9$ group wherein $R^8$ and $R^9$ are the same as above, and p represents 0, 1, or 2;
(e29) a $C(O)R^7$ group wherein $R^7$ represents a hydroxyl group, a $(C_1-C_6)$ alkyl group, a $(C_2-C_6)$ alkenyl group, a $(C_2-C_6)$ alkynyl group, a halo$(C_1-C_6)$ alkyl group, a halo$(C_2-C_6)$ alkenyl group, a halo$(C_2-C_6)$ alkynyl group, a $(C_1-C_6)$ alkoxycarbonyl $(C_1-C_6)$ alkyl group, a phenyl$(C_1-C_6)$ alkyl group, a phenyl$(C_1-C_6)$ alkoxy group, a $(C_1-C_6)$ alkoxy group, a $(C_2-C_6)$ alkenyloxy group, a $(C_2-C_6)$ alkynyloxy group, a $(C_3-C_6)$ cycloalkoxy group, a halo$(C_1-C_6)$ alkoxy group, a halo$(C_2-C_6)$ alkynyloxy group, a phenyloxy group, a $(C_1-C_6)$ alkoxycarbonyl $(C_1-C_6)$ alkoxy group, a $(C_1-C_6)$ alkylthio group, a phenyl group, a thiazolidinyl group, or an $N(R^8)R^9$ group wherein $R^8$ and $R^9$ are the same as above;
(e30) a thiocarboxamide group;
(e31) an N—$(C_1-C_6)$ alkylaminothiocarbonyl group;
(e32) an N,N-di-$(C_1-C_6)$ alkylaminothiocarbonyl group;
(e33)

[Chem. 2]

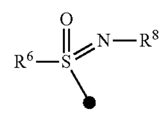

wherein $R^6$ and $R^8$ are the same as above;
(e34) a hydroxyimino $(C_1-C_3)$ alkyl group;
(e35) a $(C_1-C_6)$ alkoxyimino $(C_1-C_3)$ alkyl group;
(e36) a halo$(C_1-C_6)$ alkoxyimino $(C_1-C_3)$ alkyl group;
(e37) a hydrazono $(C_1-C_3)$ alkyl group;
(e38) a $(C_1-C_6)$ alkylhydrazono $(C_1-C_3)$ alkyl group;
(e39) a di-$(C_1-C_6)$ alkylhydrazono $(C_1-C_3)$ alkyl group;
(e40) a phenyl$(C_1-C_6)$ alkoxyimino $(C_1-C_3)$ alkyl group;
(e41) a $(C_2-C_6)$ alkenyloxyimino $(C_1-C_3)$ alkyl group;
(e42) a di-$(C_1-C_6)$ alkoxyphosphoryl group;
(e43) a di-$(C_1-C_6)$ alkoxyphosphorylamino group;
(e44) a hydroxyl group;
(e45) a $(C_1-C_6)$ alkoxy $(C_1-C_6)$ alkoxy group;
(e46) a $(C_1-C_6)$ alkoxyiminoamino $(C_1-C_3)$ alkyl group;
(e47) a cyano $(C_1-C_6)$ alkyl group;
(e48) a cyano $(C_2-C_6)$ alkenyl group;
(e49) a dicyano $(C_1-C_6)$ alkyl group; or
(e50) a dicyano $(C_2-C_6)$ alkenyl group), or a salt thereof.

[2] The compound or the salt thereof according to the above [1], wherein $A^1$, $A^2$, and $A^3$ are the same as in the above [1], $R^1$ represents (a1) a halogen atom;
(a2) a cyano group;
(a3) a nitro group;
(a4) a formyl group;
(a5) a carboxyl group;
(a6) a ($C_1$-$C_6$) alkyl group;
(a7) a ($C_2$-$C_6$) alkenyl group;
(a8) a ($C_2$-$C_6$) alkynyl group;
(a9) a ($C_3$-$C_6$) cycloalkyl group;
(a10) a halo($C_1$-$C_6$) alkyl group;
(a11) a halo($C_2$-$C_6$) alkenyl group;
(a12) a halo($C_1$-$C_6$) alkynyl group;
(a14) a hydroxy ($C_1$-$C_6$) alkyl group;
(a15) a hydroxy halo($C_1$-$C_6$) alkyl group;
(a16) a ($C_1$-$C_6$) alkoxy ($C_1$-$C_6$) alkyl group;
(a17) a di-($C_1$-$C_6$) alkoxy ($C_1$-$C_6$) alkyl group;
(a18) a halo($C_1$-$C_6$) alkoxy ($C_1$-$C_6$) alkyl group;
(a19) a ($C_1$-$C_6$) alkoxy halo($C_1$-$C_6$) alkyl group;
(a20) a halo($C_1$-$C_6$) alkoxy halo($C_1$-$C_6$) alkyl group;
(a21) a ($C_1$-$C_6$) cycloalkyl ($C_1$-$C_6$) alkyl group;
(a22) a ($C_1$-$C_6$) alkoxy group;
(a23) a halo($C_1$-$C_6$) alkoxy group;
(a24) a ($C_1$-$C_6$) alkylthio group;
(a25) a ($C_1$-$C_6$) alkylsulfinyl group;
(a26) a ($C_1$-$C_6$) alkylsulfonyl group;
(a27) a halo($C_1$-$C_6$) alkylthio group;
(a28) a halo($C_1$-$C_6$) alkylsulfinyl group;
(a29) a halo($C_1$-$C_6$) alkylsulfonyl group;
(a30) an $R^8(R^9)N$ group wherein $R^8$ and $R^9$ may be the same or different and each represent a hydrogen atom, a hydroxyl group, an amino group, a di-($C_1$-$C_6$) alkylamino group, a ($C_1$-$C_6$) alkyl group, a ($C_3$-$C_6$) cycloalkyl group, a ($C_2$-$C_6$) alkenyl group, a ($C_1$-$C_6$) alkynyl group, a ($C_1$-$C_6$) alkoxy group, a ($C_2$-$C_6$) alkenyloxy group, a halo($C_1$-$C_6$) alkyl group, a halo($C_2$-$C_6$) alkenyl group, a halo($C_2$-$C_6$) alkynyl group, a halo($C_3$-$C_6$) cycloalkyl group, a ($C_1$-$C_6$) cycloalkyl ($C_1$-$C_6$) alkyl group, a cyano ($C_1$-$C_6$) alkyl group, a ($C_1$-$C_6$) alkylcarbonyl group, a halo($C_1$-$C_6$) alkylcarbonyl group, a ($C_1$-$C_6$) alkoxycarbonyl group, a halo($C_1$-$C_6$) alkoxycarbonyl group, a ($C_1$-$C_6$) alkylsulfanylcarbonyl group, a ($C_1$-$C_6$) alkylsulfonyl group, a halo($C_1$-$C_6$) alkylsulfonyl group, an N—($C_1$-$C_6$) alkylcarboxamide group, an N, N-di-($C_1$-$C_6$) alkylcarboxamide group, an N—($C_1$-$C_6$) alkylsulfamoyl group, an N,N-di-($C_1$-$C_6$) alkylsulfamoyl group, an N-halo($C_1$-$C_6$) alkylcarboxamide group, a ($C_1$-$C_6$) alkoxycarbonyl ($C_1$-$C_6$) alkyl group, a ($C_1$-$C_6$) alkoxy ($C_1$-$C_6$) alkyl group, a di-($C_1$-$C_6$) alkoxy ($C_1$-$C_6$) alkyl group, a ($C_1$-$C_6$) alkoxy ($C_1$-$C_6$) alkylcarbonyl group, a thietanyl group, a 1,1-dioxothietanyl group, a tetrahydrofuranyl group, a thiazolyl group, a 2-oxotetrahydrofuranyl group, a phenyl group, a phenyl group having, on the ring, 1 to 5 substituting groups which may be the same or different and are selected from the group consisting of a halogen atom, a cyano group, a ($C_1$-$C_6$) alkyl group, a halo($C_1$-$C_6$) alkyl group, a ($C_1$-$C_6$) alkoxy group, and a halo ($C_1$-$C_6$) alkoxy group, or a phenyl($C_1$-$C_6$) alkyl group, or $R^8$ and $R^9$ may join together to form a 4- to 6-membered ring;
(a31) an $R^{10}(R^{11})N$($C_1$-$C_6$) alkyl group wherein $R^{10}$ and $R^{11}$ may be the same or different and each represent a hydrogen atom, a ($C_1$-$C_6$) alkyl group, a halo($C_1$-$C_6$) alkyl group, a ($C_3$-$C_6$) cycloalkyl group, a ($C_3$-$C_6$) cycloalkyl ($C_1$-$C_6$) alkyl group, a ($C_1$-$C_6$) alkylcarbonyl group, a halo($C_1$-$C_6$) alkylcarbonyl group, a ($C_1$-$C_6$) alkoxycarbonyl group, a halo($C_1$-$C_6$) alkoxycarbonyl group, a ($C_1$-$C_6$) alkylsulfonyl group, or a halo($C_1$-$C_6$) alkylsulfonyl group, or $R^{10}$ and $R^{11}$ may join together to form a 4- to 6-membered ring;
(a32) a ($C_1$-$C_6$) alkylthio ($C_1$-$C_6$) alkyl group;
(a33) a ($C_1$-$C_6$) alkylsulfinyl ($C_1$-$C_6$) alkyl group;
(a34) a ($C_1$-$C_6$) alkylsulfonyl ($C_1$-$C_6$) alkyl group;
(a35) a halo($C_1$-$C_6$) alkylthio ($C_1$-$C_6$) alkyl group;
(a36) a halo($C_1$-$C_6$) alkylsulfinyl ($C_1$-$C_6$) alkyl group;
(a37) a halo($C_1$-$C_6$) alkylsulfonyl ($C_1$-$C_6$) alkyl group;
(a44) a ($C_1$-$C_6$) alkylcarbonyl group;
(a45) a ($C_1$-$C_6$) alkoxycarbonyl group;
(a46) a halo($C_1$-$C_6$) alkylcarbonyl group;
(a47) a halo($C_1$-$C_6$) alkoxycarbonyl group;
(a50) an $R^{10}(R^{11})N$ carbonyl group wherein $R^{10}$ and $R^{11}$ are the same as above;
(a52) an $R^{10}(R^{11})N$ sulfonyl group wherein $R^{10}$ and $R^{11}$ are the same as above;
(a55) a ($C_1$-$C_6$) alkoxyimino ($C_1$-$C_3$) alkyl group;
(a56) a halo($C_1$-$C_6$) alkoxyimino ($C_1$-$C_3$) alkyl group;
(a57) a phenyl group;
(a58) a phenyl group having, on the ring, 1 to 5 substituting groups which may be the same or different and are selected from a halogen atom, a cyano group, a nitro group, a formyl group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_3$-$C_6$) cycloalkyl ($C_1$-$C_6$) alkyl group, an $R^{10}(R^{11})N$($C_1$-$C_6$) alkyl group wherein $R^{10}$ and $R^{11}$ are the same as above, an $R^{10}(R^{11})N$ group wherein $R^{10}$ and $R^{11}$ are the same as above, a ($C_1$-$C_6$) alkylthio group, a halo($C_1$-$C_6$) alkylthio group, a ($C_1$-$C_6$) alkylsulfinyl group, a halo($C_1$-$C_6$) alkylsulfinyl group, a ($C_1$-$C_6$) alkylsulfonyl group, and a halo($C_1$-$C_6$) alkylsulfonyl group;
(a59) a pyridyl group;
(a60) a pyridyl group having, on the ring, 1 to 4 substituting groups which may be the same or different and are selected from a halogen atom, a cyano group, a nitro group, a formyl group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_3$-$C_6$) cycloalkyl ($C_1$-$C_6$) alkyl group, an $R^{10}(R^{11})N$($C_1$-$C_6$) alkyl group wherein $R^{10}$ and $R^{11}$ are the same as above, an $R^{10}(R^{11})N$ group wherein $R^{10}$ and $R^{11}$ are the same as above, a ($C_1$-$C_6$) alkylthio group, a halo($C_1$-$C_6$) alkylthio group, a ($C_1$-$C_6$) alkylsulfinyl group, a halo($C_1$-$C_6$) alkylsulfinyl group, a ($C_1$-$C_6$) alkylsulfonyl group, and a halo($C_1$-$C_6$) alkylsulfonyl group;
(a61) a pyrazolyl group;
(a62) a pyrazolyl group having, on the ring, 1 to 3 substituting groups which may be the same or different and are selected from a halogen atom, a cyano group, a nitro group, a formyl group, a ($C_1$-$C_6$) alkyl group, a halo($C_1$-$C_6$) alkyl group, a ($C_1$-$C_6$) alkoxy group, a halo($C_1$-$C_6$) alkoxy group, a ($C_3$-$C_6$) cycloalkyl ($C_1$-$C_6$) alkyl group, an $R^{10}(R^{11})N$($C_1$-$C_6$) alkyl group wherein $R^{10}$ and $R^{11}$ are the same as above, an $R^{10}$ $(R^{11})N$ group wherein $R^{10}$ and $R^{11}$ are the same as above, a ($C_1$-$C_6$) alkylthio group, a halo($C_1$-$C_6$) alkylthio group, a ($C_1$-$C_6$) alkylsulfinyl group, a halo($C_1$-$C_6$) alkylsulfinyl group, a ($C_1$-$C_6$) alkylsulfonyl group, and a halo($C_1$-$C_6$) alkylsulfonyl group;

(a63) a phenoxy group;

(a64) a phenoxy group having, on the ring, 1 to 5 substituting groups which may be the same or different and are selected from a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N(C_1-C_6)$ alkyl group wherein $R^{10}$ and $R^{11}$ are the same as above, an $R^{10}(R^{11})N$ group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(a65) a dioxolanyl group;

(a66) a dioxolanyl group having, on the ring, 1 to 4 substituting groups which may be the same or different and are selected from a halogen atom, a cyano group, a nitro group, a formyl group, a carbonyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N(C_1-C_6)$ alkyl group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group, and a halo$(C_1-C_6)$ alkylsulfonyl group;

(a67) a dioxanyl group;

(a68) a dioxanyl group having, on the ring, 1 to 6 substituting groups which may be the same or different and are selected from a halogen atom, a cyano group, a nitro group, a formyl group, a carbonyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N(C_1-C_6)$ alkyl group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group, and a halo$(C_1-C_6)$ alkylsulfonyl group;

(a69) a $(C_1-C_6)$ alkylene group formed together with one adjacent substituting group (another $R^1$), wherein the $(C_1-C_6)$ alkylene group may be substituted with 1 or 2 substituting groups which may be the same or different and are selected from a halogen atom, a phenyl group, and a $(C_1-C_6)$ alkyl group; or (a70) a methylenedioxy group formed together with one adjacent substituting group (another $R^1$), wherein the methylenedioxy group may be substituted by 1 or 2 substituting groups which may be the same or different and are selected from a halogen atom, a phenyl group, and a $(C_1-C_6)$ alkyl group, wherein, when m represents an integer of 2 or more, $R^1$s may be the same or different, m represents 0, 1, 2, 3, or 4, $R^2$ represents (b1) a hydrogen atom;

(b2) a $(C_1-C_6)$ alkyl group;

(b3) a $(C_3-C_6)$ cycloalkyl group;

(b4) a $(C_1-C_6)$ alkenyl group;

(b5) a $(C_1-C_6)$ alkynyl group;

(b6) a halo$(C_1-C_6)$ alkyl group;

(b7) a halo$(C_1-C_6)$ alkenyl group;

(b8) a halo$(C_1-C_6)$ alkynyl group;

(b9) a $(C_1-C_6)$ alkoxy $(C_1-C_6)$ alkyl group;

(b10) a $(C_1-C_6)$ alkylthio $(C_1-C_6)$ alkyl group;

(b11) a $(C_1-C_6)$ alkylsulfinyl $(C_1-C_6)$ alkyl group;

(b12) a $(C_1-C_6)$ alkylsulfonyl $(C_1-C_6)$ alkyl group;

(b13) a $(C_3-C_6)$ cycloalkyl $(C_1-C_6)$ alkyl group;

(b15) a $(C_1-C_6)$ alkylcarbonyl group;

(b16) a $(C_1-C_6)$ alkoxycarbonyl group;

(b18) a halo$(C_1-C_6)$ alkylcarbonyl group; or (b21) an $R^{10}(R^{11})N$ sulfonyl group wherein $R^{10}$ and $R^{11}$ are the same as above, $R^3$ represents (c1) a hydrogen atom;

(c2) a halogen group;

(c3) a cyano group;

(c4) a carboxyl group;

(c5) a carboxamide group;

(c6) a $(C_1-C_6)$ alkyl group;

(c9) a halo$(C_1-C_6)$ alkyl group;

(c12) an $R^8(R^9)N$ group wherein $R^8$ and $R^9$ are the same as above;

(c13) a $(C_1-C_6)$ alkoxy group;

(c14) a halo$(C_1-C_6)$ alkoxy group;

(c15) a $(C_1-C_6)$ alkoxy $(C_1-C_6)$ alkyl group; or (c16) a $(C_1-C_6)$ alkoxycarbonyl $(C_1-C_6)$ alkyl group, $R^4$ represents (d1) a hydrogen atom;

(d2) a $(C_1-C_6)$ alkyl group;

(d3) a $(C_1-C_6)$ alkenyl group;

(d4) a $(C_2-C_6)$ alkynyl group;

(d5) a $(C_3-C_6)$ cycloalkyl group;

(d6) a halo$(C_1-C_6)$ alkyl group;

(d7) a halo$(C_2-C_6)$ alkenyl group;

(d8) a halo$(C_2-C_6)$ alkynyl group;

(d9) a $(C_1-C_6)$ alkoxy $(C_1-C_6)$ alkyl group;

(d10) a halo$(C_1-C_6)$ alkoxy $(C_1-C_6)$ alkyl group;

(d13) a $(C_3-C_6)$ cycloalkyl $(C_1-C_6)$ alkyl group;

(d14) a cyano $(C_1-C_6)$ alkyl group;

(d15) a $(C_1-C_6)$ alkylthio $(C_1-C_6)$ alkyl group;

(d16) a $(C_1-C_6)$ alkylsulfinyl $(C_1-C_6)$ alkyl group;

(d17) a $(C_1-C_6)$ alkylsulfonyl $(C_1-C_6)$ alkyl group;

(d18) a carboxyl $(C_1-C_6)$ alkyl group;

(d19) a phenyl$(C_1-C_6)$ alkyl group;

(d20) a phenyl$(C_1-C_6)$ alkyl group having, on the ring, 1 to 5 substituting groups which may be the same or different and are selected from a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(d22) a $(C_1-C_6)$ alkylcarbonyl group;

(d23) a $(C_1-C_6)$ alkoxycarbonyl group;

(d24) a $(C_1-C_6)$ alkylsulfonyl group;

(d25) a halo$(C_1-C_6)$ alkylcarbonyl group;

(d26) a halo$(C_1-C_6)$ alkoxycarbonyl group;

(d27) a halo$(C_1-C_6)$ alkylsulfonyl group;

(d30) a phenyl group;

(d31) a phenyl group having, on the ring, 1 to 5 substituting groups which may be the same or different and are selected from a halogen atom, a cyano group, a nitro group, a formyl group, a $(C_1-C_6)$ alkyl group, a halo $(C_1-C_6)$ alkyl group, a $(C_1-C_6)$ alkoxy group, a halo $(C_1-C_6)$ alkoxy group, a $(C_3-C_6)$ cycloalkyl $(C_1-C_6)$ alkyl group, an $R^{10}(R^{11})N$ group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo($C_1$-$C_6$) alkylsulfinyl group, a ($C_1$-$C_6$) alkylsulfonyl group, and a halo($C_1$-$C_6$) alkylsulfonyl group; or (d32) a ($C_1$-$C_6$) alkoxycarbonyl ($C_1$-$C_6$) alkyl group, and Q represents (e1) a halogen atom;

(e2) a cyano group;

(e4) a formyl group;

(e5) a ($C_1$-$C_6$) alkyl group;

(e6) a ($C_1$-$C_6$) alkenyl group;

(e7) a ($C_1$-$C_6$) alkynyl group;

(e8) a halo($C_1$-$C_6$) alkyl group;

(e11) a ($C_1$-$C_6$) alkoxy group;

(e12) a halo($C_1$-$C_6$) alkoxy group;

(e13) a hydroxy ($C_1$-$C_6$) alkyl group;

(e14) a dihydroxy ($C_1$-$C_6$) alkyl group;

(e15) a ($C_1$-$C_6$) alkoxy ($C_1$-$C_6$) alkyl group;

(e16) a ($C_1$-$C_6$) alkoxy ($C_2$-$C_6$) alkenyl group;

(e17) an $R^8(R^9)N$ group wherein $R^8$ and $R^9$ are the same as above;

(e18) a dioxolanyl group;

(e19) a dioxolanyl group having, on the ring, 1 or 2 substituting groups which may be the same or different and are selected from a carbonyl group and a ($C_1$-$C_6$) alkyl group;

(e20) a dioxanyl group;

(e21) a dioxanyl group having, on the ring, 1 to 3 substituting groups which may be the same or different and are selected from a halogen atom, a cyano group, a nitro group, a formyl group, a carbonyl group, a ($C_1$-$C_6$) alkyl group, a halo($C_1$-$C_6$) alkyl group, a ($C_1$-$C_6$) alkoxy group, a halo($C_1$-$C_6$) alkoxy group, a ($C_3$-$C_6$) cycloalkyl ($C_1$-$C_6$) alkyl group, an $R^{10}(R^{11})N$ ($C_1$-$C_6$) alkyl group wherein $R^{10}$ and $R^{11}$ are the same as above, a ($C_1$-$C_6$) alkylthio group, a halo($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group, and a halo($C_1$-$C_6$) alkylsulfonyl group;

(e22) a phenyl group;

(e23) a phenyl group having, on the ring, 1 to 5 substituting groups which may be the same or different and are selected from a halogen atom, a cyano group, a nitro group, a formyl group, a ($C_1$-$C_6$) alkyl group, a halo ($C_1$-$C_6$) alkyl group, a ($C_1$-$C_6$) alkoxy group, a halo ($C_1$-$C_6$) alkoxy group, a ($C_3$-$C_6$) cycloalkyl ($C_1$-$C_6$) alkyl group, an $R^{10}(R^{11})N$ group wherein $R^{10}$ and $R^{11}$ are the same as above, a ($C_1$-$C_6$) alkylthio group, a halo($C_1$-$C_6$) alkylthio group, a ($C_1$-$C_6$) alkylsulfinyl group, a halo($C_1$-$C_6$) alkylsulfinyl group, a ($C_1$-$C_6$) alkylsulfonyl group, and a halo($C_1$-$C_6$) alkylsulfonyl group;

(e24) an imidazolyl group;

(e25) an imidazolyl group having, on the ring, 1 to 3 substituting groups which may be the same or different and are selected from a halogen atom, a cyano group, a nitro group, a formyl group, a ($C_1$-$C_6$) alkyl group, a halo($C_1$-$C_6$) alkyl group, a ($C_1$-$C_6$) alkoxy group, a halo($C_1$-$C_6$) alkoxy group, a ($C_3$-$C_6$) cycloalkyl ($C_1$-$C_6$) alkyl group, an $R^{10}(R^{11})N$ group wherein $R^{10}$ and $R^{11}$ are the same as above, a ($C_1$-$C_6$) alkylthio group, a halo($C_1$-$C_6$) alkylthio group, a ($C_1$-$C_6$) alkylsulfinyl group, a halo($C_1$-$C_6$) alkylsulfinyl group, a ($C_1$-$C_6$) alkylsulfonyl group, and a halo($C_1$-$C_6$) alkylsulfonyl group;

(e26) an oxadiazolyl group;

(e27) an oxadiazolyl group having, on the ring, a substituting group selected from a halogen atom, a cyano group, a nitro group, a formyl group, a ($C_1$-$C_6$) alkyl group, a halo($C_1$-$C_6$) alkyl group, a ($C_1$-$C_6$) alkoxy group, a halo($C_1$-$C_6$) alkoxy group, a ($C_3$-$C_6$) cycloalkyl ($C_1$-$C_6$) alkyl group, an $R^{10}(R^{11})N$ group wherein $R^{10}$ and $R^{11}$ are the same as above, a ($C_1$-$C_6$) alkylthio group, a halo($C_1$-$C_6$) alkylthio group, a ($C_1$-$C_6$) alkylsulfinyl group, a halo ($C_1$-$C_6$) alkylsulfinyl group, a ($C_1$-$C_6$) alkylsulfonyl group, and a halo($C_1$-$C_6$) alkylsulfonyl group;

(e28) an $S(O)_pR^6$ group wherein $R^6$ represents a hydrogen atom, a ($C_1$-$C_6$) alkyl group, a ($C_2$-$C_6$) alkenyl group, a ($C_2$-$C_6$) alkynyl group, a halo($C_1$-$C_6$) alkyl group, a halo($C_5$-$C_6$) alkenyl group, a halo($C_2$-$C_6$) alkynyl group, a ($C_1$-$C_6$) alkoxy group, a ($C_3$-$C_6$) cycloalkyl group, a halo($C_3$-$C_6$) cycloalkyl group, a phenyl ($C_1$-$C_6$) alkyl group, a ($C_1$-$C_6$) alkoxyphenyl($C_1$-$C_6$) alkyl group, a ($C_1$-$C_6$) alkylphenyl($C_1$-$C_6$) alkyl group, a tri-($C_1$-$C_6$) alkylsilylphenyl($C_1$-$C_6$) alkyl group, or an $N(R^8)R^9$ group wherein $R^8$ and $R^9$ are the same as above, and p represents 0, 1, or 2;

(e29) a $C(O)R^7$ group wherein $R^7$ represents a hydroxyl group, a ($C_1$-$C_6$) alkyl group, a ($C_2$-$C_6$) alkenyl group, a ($C_2$-$C_6$) alkynyl group, a halo($C_1$-$C_6$) alkyl group, a halo($C_2$-$C_6$) alkenyl group, a halo($C_2$-$C_6$) alkynyl group, a ($C_1$-$C_6$) alkoxycarbonyl ($C_1$-$C_6$) alkyl group, a phenyl($C_1$-$C_6$) alkyl group, a phenyl($C_1$-$C_6$) alkoxy group, a ($C_1$-$C_6$) alkoxy group, a ($C_2$-$C_6$) alkenyloxy group, a ($C_2$-$C_6$) alkynyloxy group, a ($C_3$-$C_6$) cycloalkoxy group, a halo($C_1$-$C_6$) alkoxy group, a halo($C_1$-$C_6$) alkynyloxy group, a phenyloxy group, a ($C_1$-$C_6$) alkoxycarbonyl ($C_1$-$C_6$) alkoxy group, a ($C_1$-$C_6$) alkylthio group, a phenyl group, a thiazolidinyl group, or an$N(R^8)R^9$ group wherein $R^8$ and $R^9$ are the same as above;

(e30) a thiocarboxamide group;

(e31) an N—($C_1$-$C_6$) alkylaminothiocarbonyl group;

(e32) an N,N-di-($C_1$-$C_6$) alkylaminothiocarbonyl group;

(e33)

[Chem. 3]

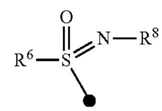

wherein $R^6$ and $R^8$ are the same as above;

(e34) a hydroxyimino ($C_1$-$C_3$) alkyl group;

(e35) a ($C_1$-$C_6$) alkoxyimino ($C_1$-$C_3$) alkyl group;

(e36) a halo($C_1$-$C_6$) alkoxyimino ($C_1$-$C_3$) alkyl group;

(e37) a hydrazono ($C_1$-$C_3$) alkyl group;

(e38) a ($C_1$-$C_6$) alkylhydrazono ($C_1$-$C_3$) alkyl group;

(e39) a di-($C_1$-$C_6$) alkylhydrazono ($C_1$-$C_3$) alkyl group;

(e40) a phenyl($C_1$-$C_6$) alkoxyimino ($C_1$-$C_3$) alkyl group;

(e41) a ($C_2$-$C_6$) alkenyloxyimino ($C_1$-$C_3$) alkyl group;

(e42) a di-($C_1$-$C_6$) alkoxyphosphoryl group;

(e43) a di-($C_1$-$C_6$) alkoxyphosphorylamino group;

(e44) a hydroxyl group;

(e45) a ($C_1$-$C_6$) alkoxy ($C_1$-$C_6$) alkoxy group; or (e46) a ($C_1$-$C_6$) alkoxyiminoamino ($C_1$-$C_3$) alkyl group.

[3] The compound or the salt thereof according to the above [1] or [2], wherein $R^1$ represents (a1) a halogen atom;

(a2) a cyano group;

(a3) a nitro group;

(a4) a formyl group;
(a5) a carboxyl group;
(a6) a $(C_1-C_6)$ alkyl group;
(a7) a $(C_2-C_6)$ alkenyl group;
(a9) a $(C_3-C_6)$ cycloalkyl group;
(a10) a halo$(C_1-C_6)$ alkyl group;
(a14) a hydroxy $(C_1-C_6)$ alkyl group;
(a16) a $(C_1-C_6)$ alkoxy $(C_1-C_6)$ alkyl group;
(a17) a di-$(C_3-C_6)$ alkoxy $(C_1-C_6)$ alkyl group;
(a22) a $(C_1-C_6)$ alkoxy group;
(a23) a halo$(C_1-C_6)$ alkoxy group;
(a24) a $(C_1-C_6)$ alkylthio group;
(a26) a $(C_1-C_6)$ alkylsulfonyl group;
(a27) a halo$(C_1-C_6)$ alkylthio group;
(a28) a halo$(C_1-C_6)$ alkylsulfinyl group;
(a29) a halo$(C_1-C_6)$ alkylsulfonyl group;
(a30) an $R^8(R^9)N$ group wherein $R^8$ and $R^9$ may be the same or different and each represent a hydrogen atom, a hydroxyl group, an amino group, a di-$(C_1-C_6)$ alkylamino group, a $(C_1-C_6)$ alkyl group, a $(C_3-C_6)$ cycloalkyl group, a $(C_2-C_6)$ alkenyl group, a $(C_2-C_6)$ alkynyl group, a $(C_1-C_6)$ alkoxy group, a $(C_2-C_6)$ alkenyloxy group, a halo$(C_1-C_6)$ alkyl group, a halo$(C_3-C_6)$ cycloalkyl group, a $(C_3-C_6)$ cycloalkyl $(C_1-C_6)$ alkyl group, a $(C_1-C_6)$ alkylcarbonyl group, a halo$(C_1-C_6)$ alkylcarbonyl group, a $(C_1-C_6)$ alkoxycarbonyl group, a $(C_1-C_6)$ alkylsulfonyl group, an N,N-di-$(C_1-C_6)$ alkylsulfamoyl group, a $(C_1-C_6)$ alkoxy $(C_1-C_6)$ alkyl group, a di-$(C_1-C_6)$ alkoxy $(C_1-C_6)$ alkyl group, a thietanyl group, a thiazolyl group, or a 2-oxotetrahydrofuranyl group, or $R^8$ and $R^9$ may join together to form a 4- to 6-membered ring;
(a31) an $R^{10}(R^{11})N(C_1-C_6)$ alkyl group wherein $R^{10}$ and $R^{11}$ may be the same or different and each represent a hydrogen atom or a $(C_1-C_6)$ alkyl group, or $R^{10}$ and $R^{11}$ may join together to form a 4- to 6-membered ring;
(a32) a $(C_1-C_6)$ alkylthio $(C_1-C_6)$ alkyl group;
(a33) a $(C_1-C_6)$ alkylsulfinyl $(C_1-C_6)$ alkyl group;
(a34) a $(C_1-C_6)$ alkylsulfonyl $(C_1-C_6)$ alkyl group;
(a45) a $(C_1-C_6)$ alkoxycarbonyl group;
(a52) an $R^{10}(R^{11})N$ sulfonyl group wherein $R^{10}$ and $R^{11}$ are the same as above;
(a55) a $(C_1-C_6)$ alkoxyimino $(C_1-C_6)$ alkyl group;
(a57) a phenyl group;
(a58) a phenyl group having, on the ring, 1 to 5 substituting groups which may be the same or different and are selected from a halogen atom and a $(C_1-C_6)$ alkoxy group;
(a59) a pyridyl group;
(a62) a pyrazolyl group having, on the ring, 1 to 3 $(C_1-C_6)$ alkyl groups which may be the same or different;
(a65) a dioxolanyl group;
(a67) a dioxanyl group;
(a69) a $(C_1-C_6)$ alkylene group formed together with one adjacent substituting group (another $R^1$); or
(a70) a methylenedioxy group formed together with one adjacent substituting group (another $R^1$), wherein the methylenedioxy group may be substituted with 1 or 2 halogen atoms, wherein, when m represents an integer of 2 or more, $R^1$s may be the same or different,
m represents 0, 1, 2, 3, or 4,
$R^2$ represents
(b1) a hydrogen atom;
(b2) a $(C_1-C_6)$ alkyl group;
(b3) a $(C_3-C_6)$ cycloalkyl group;
(b5) a $(C_2-C_6)$ alkynyl group;
(b6) a halo$(C_1-C_6)$ alkyl group; or
(b9) a $(C_1-C_6)$ alkoxy $C_1-C_6)$ alkyl group,
$R^3$ represents
(c1) a hydrogen atom;
(c3) a cyano group;
(c5) a carboxamide group;
(c6) a $(C_1-C_6)$ alkyl group;
(c12) an $R^8(R^9)N$ group wherein $R^8$ and $R^9$ are the same as above;
(c13) a $(C_1-C_6)$ alkoxy group; or
(c16) a $(C_1-C_6)$ alkoxycarbonyl $(C_1-C_6)$ alkyl group,
$R^4$ represents
(d1) a hydrogen atom;
(d2) a $(C_1-C_6)$ alkyl group;
(d3) a $(C_1-C_6)$ alkenyl group;
(d4) a $(C_1-C_6)$ alkynyl group;
(d6) a halo$(C_1-C_6)$ alkyl group;
(d9) a $(C_1-C_6)$ alkoxy $(C_1-C_6)$ alkyl group;
(d13) a $(C_3-C_6)$ cycloalkyl $(C_1-C_6)$ alkyl group;
(d14) a cyano $(C_1-C_6)$ alkyl group;
(d15) a $(C_1-C_6)$ alkylthio $(C_1-C_6)$ alkyl group;
(d16) a $(C_1-C_6)$ alkylsulfinyl $(C_1-C_6)$ alkyl group;
(d17) a $(C_1-C_6)$ alkylsulfonyl $(C_1-C_6)$ alkyl group;
(d18) a carboxyl $(C_1-C_6)$ alkyl group;
(d19) a phenyl$(C_1-C_6)$ alkyl group;
(d20) a phenyl$(C_1-C_6)$ alkyl group having, on the ring, 1 to 5 halogen atoms which may be the same or different;
(d22) a $(C_1-C_6)$ alkylcarbonyl group;
(d23) a $(C_1-C_6)$ alkoxycarbonyl group;
(d24) a $(C_1-C_6)$ alkylsulfonyl group;
(d30) a phenyl group; or
(d32) a $(C_1-C_6)$ alkoxycarbonyl $(C_1-C_6)$ alkyl group,
$A^1$, $A^2$, and $A^3$ may be the same or different and each represent $CR^5$ (wherein $R^5$ represents a hydrogen atom, a halogen atom, a $(C_1-C_6)$ alkyl group, or an $R^{10}(R^{11})N$ group wherein $R^{10}$ and $R^{11}$ are the same as above) or a nitrogen atom, and
Q represents
(e1) a halogen atom;
(e2) a cyano group;
(e4) a formyl group;
(e5) a $(C_1-C_6)$ alkyl group;
(e6) a $(C_2-C_6)$ alkenyl group;
(e5) a halo$(C_1-C_6)$ alkyl group;
(e11) a $(C_1-C_6)$ alkoxy group;
(e13) a hydroxy $(C_1-C_6)$ alkyl group;
(e14) a dihydroxy $(C_1-C_6)$ alkyl group;
(e16) a $(C_1-C_6)$ alkoxy $(C_2-C_6)$ alkenyl group;
(e17) an $R^8(R^9)N$ group wherein $R^8$ and $R^9$ are the same as above;
(e18) a dioxolanyl group;
(e19) a dioxolanyl group having, on the ring, 1 or 2 substituting groups which may be the same or different and are selected from a carbonyl group and a $(C_1-C_6)$ alkyl group;
(e20) a dioxanyl group;
(e22) a phenyl group;
(e24) an imidazolyl group;
(e27) an oxadiazolyl group having, on the ring, a $(C_1-C_6)$ alkyl group;
(e28) an $S(O)_pR^6$ group wherein $R^6$ represents a hydrogen atom, a $(C_1-C_6)$ alkyl group, a halo$(C_1-C_6)$ alkyl group, a phenyl$(C_1-C_6)$ alkyl group, a $(C_1-C_6)$ alkoxyphenyl $(C_1-C_6)$ alkyl group, a $(C_1-C_6)$ alkylphenyl$(C_1-C_6)$ alkyl group, a tri-$(C_1-C_6)$ alkylsilylphenyl $(C_1-C_6)$ alkyl group, or an $N(R^8)R^9$ group wherein $R^8$ and $R^9$ are the same as above, and p represents 0, 1, or 2;

(e29) a $C(O)R^7$ group wherein $R^7$ represents a hydroxyl group, a $(C_1-C_6)$ alkyl group, a $(C_1-C_6)$ alkoxycarbonyl $(C_1-C_6)$ alkyl group, a phenyl$(C_1-C_6)$ alkoxy group, a $(C_1-C_6)$ alkoxy group, a $(C_2-C_6)$ alkynyloxy group, a $(C_3-C_6)$ cycloalkoxy group, a phenyloxy group, a $(C_1-C_6)$ alkoxycarbonyl $(C_1-C_6)$ alkoxy group, a $(C_1-C_6)$ alkylthio group, a thiazolidinyl group, or an $N(R^8)R^9$ group wherein $R^8$ and $R^9$ are the same as above;

(e31) an N—$(C_1-C_6)$ alkylaminothiocarbonyl group;

(e33)

[Chem. 4]

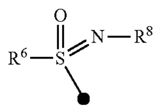

wherein $R^6$ and $R^8$ are the same as above;

(e35) a $(C_1-C_6)$ alkoxyimino $(C_1-C_3)$ alkyl group;

(e36) a halo$(C_1-C_6)$ alkoxyimino $(C_1-C_3)$ alkyl group;

(e37) a hydrazono $(C_1-C_3)$ alkyl group;

(e40) a phenyl$(C_1-C_6)$ alkoxyimino $(C_1-C_3)$ alkyl group;

(e41) a $(C_2-C_6)$ alkenyloxyimino $(C_1-C_3)$ alkyl group;

(e42) a di-$(C_1-C_6)$ alkoxyphosphoryl group;

(e43) a di-$(C_1-C_6)$ alkoxyphosphorylamino group;

(e44) a hydroxyl group; or (e45) a $(C_1-C_6)$ alkoxy $(C_1-C_6)$ alkoxy group.

[4] The compound or the salt thereof according to the above [1], wherein $A^1$ represents a nitrogen atom, and $A^2$ and $A^3$ may be the same or different and represent $CR^5$s.

[5] The compound or the salt thereof according to the above [2], wherein $A^1$ represents a nitrogen atom, and $A^2$ and $A^3$ may be the same or different and represent $CR^5$s.

[6] The compound or the salt thereof according to the above [3], wherein $A^1$ represents a nitrogen atom, and $A^2$ and $A^3$ may be the same or different and represent $CR^5$s.

[7] The compound or the salt thereof according to the above [2], wherein $A^1$, $A^2$, and $A^3$ may be the same or different and represent CRSs.

[8] The compound or the salt thereof according to the above [3], wherein $A^1$, $A^2$, and $A^3$ may be the same or different and represent $CR^5$s.

[9] The compound or the salt thereof according to the above [3], wherein $A^1$ and $A^3$ may be the same or different and represent $CR^5$s, and $A^2$ represents a nitrogen atom.

[10] The compound or the salt thereof according to the above [3], wherein $A^1$ and $A^2$ may be the same or different and represent $CR^5$s, and $A^3$ represents a nitrogen atom.

[11] The compound or the salt thereof according to the above [3], wherein $A^1$ and $A^2$ represent nitrogen atoms, and $A^2$ represents $CR^5$.

[12] The compound or the salt thereof according to the above [2], wherein $A^1$ and $A^2$ represent nitrogen atoms, and $A^3$ represents $CR^5$.

[13] The compound or the salt thereof according to the above [3], wherein $A^1$ and $A^2$ represent nitrogen atoms, and $A^3$ represents $CR^5$.

[14] The compound or the salt thereof according to the above [3], wherein $A^1$ represents $CR^5$, and $A^z$ and $A^3$ represent nitrogen atoms.

[15] An agricultural or horticultural herbicide comprising the compound or the salt thereof according to any one of the above [1] to [14] as an active ingredient.

[16] A method for using an agricultural or horticultural herbicide, comprising treating weeds, soil, paddy field, or growing media with an effective amount of the agricultural or horticultural herbicide according to the above [15].

[17] A method for controlling weeds, comprising treating weeds, soil, paddy field, or growing media with an effective amount of the agricultural or horticultural herbicide according to the above [15].

Advantageous Effects of Invention

The nitrogen-containing condensed heterocyclic compound having an oxime group of the present invention or a salt thereof is a highly effective agricultural or horticultural herbicide.

DESCRIPTION OF EMBODIMENTS

In the definitions of the general formula (1) representing the compound of the present invention, "halo" refers to a "halogen atom" and represents a chlorine atom, a bromine atom, an iodine atom, or a fluorine atom.

The "$(C_1-C_6)$ alkyl group" refers to a straight-chain or branched-chain alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2,3-dimethylpropyl group, an 1-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethyl propyl group, a 3,3-dimethylbutyl group or the like.

The "$(C_1-C_6)$ alkenyl group" refers to a straight-chain or branched-chain alkenyl group of 2 to 6 carbon atoms, for example, a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, a 3,3-dimethyl-1-butenyl group or the like. The "$(C_2-C_6)$ alkynyl group" refers to a straight-chain or branched-chain alkynyl group of 2 to 6 carbon atoms, for example, an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a 3-methyl-1-butynyl group, a 3,3-dimethyl-1-butynyl group or the like.

The "$(C_3-C_6)$ cycloalkyl group" refers to a cyclic alkyl group of 3 to 6 carbon atoms, for example, a cyclopropyl group, a cyclobutyl group, a cyclopentyl group, a cyclohexyl group or the like. The "$(C_1-C_6)$ alkoxy group" refers to a straight-chain or branched-chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a tert-pentyloxy group, a neopentyloxy group, a 2,3-dimethylpropyloxy group, an 1-ethylpropyloxy group, a 1-methylbutyloxy group, a n-hexyloxy group, an isohexyloxy group, a 1,1,2-trimethylpropyloxy group or the like. The "$(C_2-C_6)$ alkenyloxy group" refers to a straight-chain or branched-chain alkenyloxy group of 2 to 6 carbon atoms, for example, a propenyloxy group, a butenyloxy group, a pentenyloxy group, a hexenyloxy group or the like. The "$(C_1-C_6)$ alkynyloxy group" refers to a straight-chain or branched-chain alkynyloxy group of 2 to 6 carbon atoms, for example, a propynyloxy group, a butynyloxy group, a pentynyloxy group, a hexynyloxy group or the like.

The "($C_1$-$C_6$) alkylthio group" refers to a straight-chain or branched-chain alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a tert-pentylthio group, a neopentylthio group, a 2,3-dimethylpropylthio group, an 1-ethylpropylthio group, a 1-methylbutylthio group, a n-hexylthio group, an isohexylthio group, a 1,1,2-trimethylpropylthio group or the like.

The "($C_1$-$C_6$) alkylsulfinyl group" refers to a straight-chain or branched-chain alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a tert-pentylsulfinyl group, a neopentylsulfinyl group, a 2,3-dimethylpropylsulfinyl group, an 1-ethylpropylsulfinyl group, a 1-methylbutylsulfinyl group, a n-hexylsulfinyl group, an isohexylsulfinyl group, a 1,1,2-trimethylpropylsulfinyl group or the like.

The "($C_1$-$C_6$) alkylsulfonyl group" refers to a straight-chain or branched-chain alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a tert-pentylsulfonyl group, a neopentylsulfonyl group, a 2,3-dimethylpropylsulfonyl group, an 1-ethylpropylsulfonyl group, a 1-methylbutylsulfonyl group, a n-hexylsulfonyl group, an isohexylsulfonyl group, a 1,1,2-trimethylpropylsulfonyl group or the like.

The "($C_1$-$C_6$) alkylcarbonyl group" refers to an alkylcarbonyl group of 2 to 7 carbon atoms, for example, an alkylcarbonyl group in which the alkyl group is a ($C_1$-$C_6$) alkyl group as defined above, such as an acetyl group, a propanoyl group, a butanoyl group, a 2-methylpropanoyl group, a pentanoyl group, a 2-methylbutanoyl group, a 3-methylbutanoyl group, a pivaloyl group, a hexanoyl group, or the like.

The "($C_1$-$C_6$) alkylcarbonyloxy group" refers to an alkylcarbonyloxy group of 2 to 7 carbon atoms, for example, an alkylcarbonyloxy group in which the alkyl group is a ($C_1$-$C_6$) alkyl group as defined above, such as an acetyloxy group, a propanoyloxy group, a butanoyloxy group, a 2-methylpropionyloxy group, a pentanoyloxy group, a 2-methylbutanoyloxy group, a 3-methylbutanoyloxy group, a pivaloyloxy group, a hexanoyloxy group, or the like.

The "($C_1$-$C_6$) alkylsulfonyloxy group" refers to a straight-chain or branched-chain alkylsulfonyloxy group of 1 to 6 carbon atoms, for example, a methylsulfonyloxy group, an ethylsulfonyloxy group, a n-propylsulfonyloxy group, an isopropylsulfonyloxy group, a n-butylsulfonyloxy group, a sec-butylsulfonyloxy group, a tert-butylsulfonyloxy group, a n-pentylsulfonyloxy group, an isopentylsulfonyloxy group, a tert-pentylsulfonyloxy group, a neopentylsulfonyloxy group, a 2,3-dimethylpropylsulfonyloxy group, an 1-ethylpropylsulfonyloxy group, a 1-methylbutylsulfonyloxy group, a n-hexylsulfonyloxy group, an isohexylsulfonyloxy group, a 1,1,2-trimethylpropylsulfonyloxy group or the like.

The "N—($C_1$-$C_6$) alkylcarboxamide group" refers to an alkylcarboxamide group of 2 to 7 carbon atoms in which the alkyl group is a straight-chain or branched-chain alkyl group of 1 to 6 carbon atoms, for example, an N-methylcarboxamide group, an N-ethylcarboxamide group, an N-n-propylcarboxamide group, an N-isopropylcarboxamide group, an N-n-butylcarboxamide group, an N-isobutylcarboxamide group, an N-sec-butylcarboxamide group, an N-tert-butylcarboxamide group, an N-n-pentylcarboxamide group, an N-isopentylcarboxamide group, an N-tert-pentylcarboxamide group, an N-neopentylcarboxamide group, an N-n-hexylcarboxamide group, an N-isohexylcarboxamide group, or the like.

The "($C_1$-$C_6$) alkoxycarbonyl group" refers to an alkoxycarbonyl group of 2 to 7 carbon atoms, for example, an alkoxycarbonyl group in which the alkoxy group is a ($C_1$-$C_6$) alkoxy group as defined above, such as a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a pentyloxycarbonyl group, or the like.

The "N—($C_1$-$C_6$) alkylsulfamoyl group" refers to an N-alkylsulfamoyl group of 1 to 6 carbon atoms, for example, an N-methylsulfamoyl group, an N-ethylsulfamoyl group, an N-n-propylsulfamoyl group, an N-isopropylsulfamoyl group, an N-n-butylsulfamoyl group, an N-isobutylsulfamoyl group, an N-sec-butylsulfamoyl group, an N-tert-butylsulfamoyl group, an N-n-pentylsulfamoyl group, an N-isopentylsulfamoyl group, an N-tert-pentylsulfamoyl group, an N-neopentylsulfamoyl group, an N-(2,3-dimethylpropyl)sulfamoyl group, an N-(1-ethylpropyl)sulfamoyl group, an N-(1-methylbutyl)sulfamoyl group, an N-((2-methylbutyl)sulfamoyl group, an N-n-hexylsulphamoyl group, an N-isohexylsulfamoyl group, an N-(2-hexyl)sulfamoyl group, an N—(3-hexyl) sulfamoyl group, an N—(2-methylpentyl) sulfamoyl group, an N-(3-methylpentyl)sulfamoyl group, an N-(1,1,2-trimethylpropyl)sulfamoyl group, an N-(3,3-dimethylbutyl)sulfamoyl group, or the like.

The "($C_1$-$C_6$) alkylsulfanylcarbonyl group" refers to an alkylsulfanylcarbonyl group of 1 to 6 carbon atoms, for example, a methylsulfanylcarbonyl group, an ethylsulfanylcarbonyl group, a n-propylsulfanylcarbonyl group, an isopropylsulfanylcarbonyl group, a n-butylsulfanylcarbonyl group, an isobutylsulfanylcarbonyl group, a sec-butylsulfanylcarbonyl group, a tert-butylsulfanylcarbonyl group, a 2,3-dimethylpropylsulfanylcarbonyl group, or the like.

The above-mentioned "($C_1$-$C_6$) alkyl group", "($C_2$-$C_6$) alkenyl group", "($C_2$-$C_6$) alkynyl group", "($C_1$-$C_6$) alkoxy group", "($C_1$-$C_6$) alkylthio group", "($C_1$-$C_6$) alkylsulfinyl group", "($C_1$-$C_6$) alkylsulfonyl group", "($C_3$-$C_6$) cycloalkyl group", "($C_1$-$C_6$) alkylcarbonyl group", "($C_1$-$C_6$) alkoxycarbonyl group". "($C_1$-$C_6$) alkylcarbonyloxy group", "($C_1$-$C_6$) alkylsulfonyloxy group", etc. may be substituted with one or more halogen atoms at a substitutable position(s), and in the case where any of the above-listed groups is substituted with two or more halogen atoms, the halogen atoms may be the same or different.

The above-mentioned groups substituted with one or more halogen atoms are expressed as a "halo($C_1$-$C_6$) alkyl group", a "halo($C_1$-$C_6$) alkenyl group", a "halo($C_2$-$C_6$) alkynyl group", a "halo($C_1$-$C_6$) alkoxy group", a "halo($C_1$-$C_6$) alkylthio group", a "halo($C_1$-$C_6$) alkylsulfinyl group", a "halo($C_1$-$C_6$) alkylsulfonyl group", a "halo($C_3$-$C_6$) cycloalkyl group", a "halo($C_1$-$C_6$) alkylcarbonyl group", a "halo ($C_1$-$C_6$) alkoxycarbonyl group", a "halo($C_1$-$C_6$) alkylcarbonyloxy group", a "halo($C_1$-$C_6$) alkylsulfonyloxy group" etc.

The expressions "($C_1$-$C_6$)", "($C_2$-$C_6$)", "($C_3$-$C_6$)", etc. each represent the range of the number of carbon atoms in each group. The same definition holds true for groups in which two or more of the above-mentioned groups are coupled together, and for example, the "($C_1$-$C_6$) alkoxy ($C_1$-$C_6$) alkyl group" means that a straight-chain or branched-chain alkoxy group of 1 to 6 carbon atoms is bound to a straight-chain or branched-chain alkyl group of 1 to 6 carbon atoms.

Examples of the salt of the compound represented by the general formula (1) of the present invention include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

The nitrogen-containing condensed heterocyclic compound represented by the general formula (1) of the present invention and a salt thereof can have one or more chiral centers in the structural formula and can exist as two or more kinds of optical isomers or diastereomers. All the optical isomers and mixtures of the isomers at any ratio are also included in the present invention. Further, the nitrogen-containing condensed heterocyclic compound represented by the general formula (1) of the present invention and a salt thereof can exist as two kinds of geometric isomers due to a carbon-carbon double bond and a carbon-nitrogen double bond in the structural formula. All the geometric isomers and mixtures of the isomers at any ratio are also included in the present invention. In other words, the oxime group in the compound represented by the general formula (1) of the present invention may be in the form of an E (entgegen) isomer, a Z (zusammen) isomer, or a mixture of these isomers.

Preferable embodiments of the compound represented by the general formula (1) of the present invention are shown below.

$R^1$ is preferably a group of the above (a1), (a2), (a3), (a4), (a5), (a6), (a7), (a8), (a9), (a10), (a11), (a12), (a14), (a15), (a16), (a17), (a18), (a19), (a20), (a21), (a22), (a23), (a24), (a25), (a26), (a27), (a28), (a29), (a30), (a31), (a32), (a33), (a34), (a35), (a36), (a37), (a44), (a45), (a46), (a47), (a50), (a52), (a55), (a56), (a57), (a58), (a59), (a60), (a61), (a62), (a63), (a64), (a65), (a66), (a67), (a68), (a69), or (a70), and more preferably a group of the above (a1), (a2), (a3), (a4), (a5), (a6), (a7), (a9), (a10), (a14), (a16), (a17), (a22), (a23), (a24), (a26), (a27), (a28), (a29), (a30), (a31), (a32), (a33), (a34), (a45), (a52), (a55), (a57), (a58), (a59), (a62), (a65), (a67), (a69), or (a70).

m is preferably 0, 1, 2, 3, or 4.

$R^2$ is preferably a group of the above (b1), (b2), (b3), (b4), (b5), (b6), (b7), (b8), (b9), (b10), (b11), (b12), (b13), (b15), (b16), (b18), or (b21), and more preferably a group of the above (b1), (b2), (b3), (b5), (b6), or (b9).

$R^3$ is preferably a group of the above (c1), (c2), (c3), (c4), (c5), (c6), (c9), (c12), (c13), (c14), (c15), or (c16), and more preferably a group of the above (c1), (c3), (c5), (c6), (c12), (c13), or (c16).

$R^4$ is preferably a group of the above (d1), (d2), (d3), (d4), (d5), (d6), (d7), (d8), (d9), (d10), (d13), (d14), (d15), (d16), (d17), (d18), (d19), (d20), (d22), (d23), (d24), (d25), (d26), (d27), (d30), (d31), or (d32), and more preferably a group of the above (d1), (d2), (d3), (d4), (d6), (d9), (d13), (d14), (d15), (d16), (d17), (d18), (d19), (d20), (d22), (d23), (d24), (d30), or (d32).

$A^1$, $A^2$, and $A^3$ are each preferably $CR^5$ (wherein $R^5$ is a hydrogen atom, a halogen atom, a cyano group, a ($C_1$-$C_6$) alkyl group, a halo($C_1$-$C_6$) alkyl group, a ($C_1$-$C_6$) alkoxy group, a halo($C_1$-$C_6$) alkoxy group, an $R^{10}(R^{11})N$ group wherein $R^{10}$ and $R^{11}$ are the same as above, a ($C_1$-$C_6$) alkylthio group, a ($C_1$-$C_6$) alkylsulfinyl group, or a ($C_1$-$C_6$) alkylsulfonyl group) or a nitrogen atom. More preferably, $A^1$, $A^2$, and $A^3$ are each $CR^5$ (wherein $R^5$ is a hydrogen atom, a halogen atom, a ($C_1$-$C_6$) alkyl group, or an $R^{10}(R^{11})N$ group wherein $R^{10}$ and $R^{11}$ are the same as above) or a nitrogen atom.

$A^1$, $A^2$, and $A^3$ may be the same or different.

Q is preferably a group of the above (e1), (e2), (e4), (e5), (e6), (e7), (e8), (e11), (e12), (e13), (e14), (e15), (e16), (e17), (e18), (e19), (e20), (e21), (e22), (e23), (e24), (e25), (e26), (e27), (e28), (e29), (e30), (e31), (e32), (e33), (e34), (e35), (e36), (e37), (e38), (e39), (e40), (e41), (e42), (e43), (e44), (e45), or (e46), and more preferably a group of the above (e1), (e2), (e4), (e5), (e6), (e8), (e11), (e13), (e14), (e16), (e17), (e18), (e19), (e20), (e22), (e24), (e27), (e28), (e29), (e31), (e33), (e35), (e36), (e37), (e40), (e41), (e42), (e43), (e44), or (e45).

The compounds of the present invention can be produced according to, for example, the production methods described below, which are non-limiting examples.

Production Method 1

[Chem. 5]

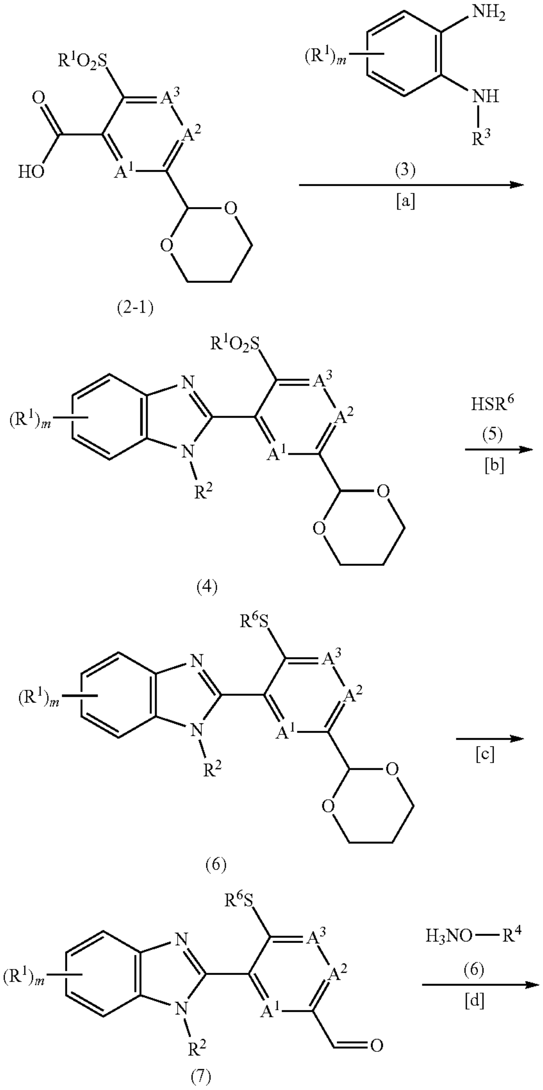

(2-1)

(4)

(6)

(7)

-continued

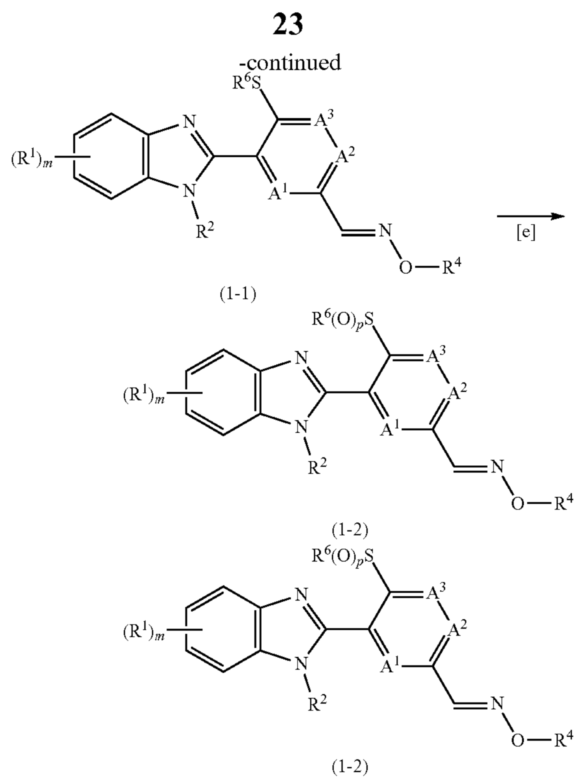

(1-1)

(1-2)

(1-2)

In the formula, $A^1$, $A^2$, $A^3$, $R^1$, $R^2$, $R^4$, $R^6$, and m are the same as above, p' represents 1 or 2, and R' represents a ($C_1$-$C_4$) alkyl group such as a methyl group or an ethyl group.

The compounds represented by the general formulae (1-1) and (1-2) of the present invention can be produced from the compound represented by the general formula (2-1) through the steps [a], [b], [c], [d], and [e] described below. The production method of the starting compound represented by the general formula (2-1) will be described later.

Production Method at Step [a]

The compound represented by the general formula (4) can be produced by condensing the compound represented by the general formula (2-1) with the compound represented by the general formula (3) in the presence of a base, a condensing agent, and an inert solvent and dehydrating the resulting amide compound in the presence of an acid and an inert solvent.

Examples of the condensing agent that can be used in this condensation reaction include acid-activating reagents such as phosgene, phosphorus trichloride, phosphorus oxychloride, oxalyl chloride, and thionyl chloride; carbodiimides such as N,N'-dicyclohexylcarbodiimide (DCC) and 1-(3-dimethylaminopropyl)-3-ethylcarbodiimide (EDCI); and other reagents such as phosphorus pentoxide, polyphosphoric acid, N,N'-carbonyldiimidazole, 2-chloropyridine-1-methiodide (Mukaiyama reagent), 2-ethoxy-N-ethoxycarbonyl-1,2-dihydroquinoline (EEDQ), triphenylphosphine/carbon tetrachloride, bromotripyrrolidinophosphonium hexafluorophosphate (BROP), O—(1H-benzotriazol-1-yloxy)tris(dimethylamino)phosphonium hexafluorophosphate (BOP), N,N,N',N'-bis(tetramethylene)chlorouronium tetrafluoroborate, O—(1H-benzotriazol-1-yl)-N,N,N',N'-tetramethyluronium hexafluorophosphate (HBTU), O—(1H-benzotriazol-1-yl)-N,N,N',N'-bis(tetramethylene)uronium hexafluorophosphate, O—(1H-benzotriazol-1-yl)-N,N,N',N'-tetramethyluronium tetrafluoroborate (TBTU), O—(1H-benzotriazol-1-yl)-N,N,N',N'-bis(tetramethylene)uronium tetrafluoroborate, O-(7-azabenzotriazol-1-yl)-N,N,N',N'-tetramethyluronium hexafluorophosphate (HATU), 1-hydroxybenzotriazole (HOBt), propylphosphonic anhydride ($T_3P$), and 4-(4,6-dimethoxy-1,3,5-triazin-2-yl)-4-methylmorpholinium salt (DMT-MM). One of these condensing agents may be used alone, and also two or more of them may be used as a mixture. The amount of the condensing agent used is appropriately selected from the range of a 0.5- to 5-fold molar amount relative to the compound represented by the general formula (2-1).

Examples of the base that can be used in this condensation reaction include carbonates such as lithium carbonate, lithium hydrogen carbonate, sodium carbonate, sodium hydrogen carbonate, potassium carbonate, potassium hydrogen carbonate, calcium carbonate and magnesium carbonate; acetates such as lithium acetate, sodium acetate and potassium acetate; and organic bases such as pyridine, picoline, lutidine, triethylamine, tributylamine and N,N-diisopropylethylamine. The amount of the base used is appropriately selected from the range of a 0.5- to 5-fold molar amount relative to the compound represented by the general formula (2-1). In some cases, the base can be used as the solvent as well.

The inert solvent used in this condensation reaction may be any solvent that does not markedly inhibit the reaction, and examples include chain or cyclic saturated hydrocarbons such as pentane, hexane, and cyclohexane; chain or cyclic ethers such as diethyl ether, tetrahydrofuran (THF), and dioxane; aromatic hydrocarbons such as benzene, toluene, and xylene; halogenated hydrocarbons such as methylene chloride, chloroform, and carbon tetrachloride; nitriles such as acetonitrile and isopropylnitrile; and polar solvents such as N,N-dimethylformamide, N,N-dimethylacetamide, dimethyl sulfoxide, and 1,3-dimethyl-2-imidazolidinone. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (2-1). In the case where the base is used also as the solvent, it is not necessary to use another solvent.

Since this condensation reaction is an equimolar reaction of the compounds, they are basically used in equimolar amounts, but either of them may be used in an excess amount. The reaction temperature is usually in the range of about 0° C. to the boiling point of the solvent used. The reaction time varies with the reaction scale, the reaction temperature and the like and is not the same in every case, but is basically selected as appropriate from the range of a few minutes to 48 hours.

After the reaction is completed, the compound of interest is isolated from the post-reaction mixture by the usual method. As needed, recrystallization, column chromatography, etc. can be employed for the purification of the compound of interest. The post-reaction mixture may be directly used in the next dehydration reaction without isolation of the compound of interest.

Examples of the acid used in this dehydration reaction include inorganic acids such as hydrochloric acid, sulfuric acid and nitric acid; organic acids such as formic acid, acetic acid, propionic acid, trifluoroacetic acid and benzoic acid; sulfonic acids such as methanesulfonic acid, trifluoromethanesulfonic acid and p-toluenesulfonic acid; and phosphoric acid. The amount of the acid used is appropriately selected from the range of a 0.01- to 10-fold molar amount relative to the amide compound. In some cases, the acid can be used as the solvent as well.

The inert solvent used in this dehydration reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; chain or cyclic ethers such as diethyl ether, methyl tert-butyl ether, dioxane and tetrahydrofuran; esters such as ethyl acetate; amides such as N,N-dimethylformamide and N,N-dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the amide compound obtained by the condensation reaction. In the case where the acid is used also as the solvent, it is not necessary to use another solvent.

The reaction temperature may be in the range of room temperature to the boiling point of the inert solvent used. The reaction time varies with the reaction scale and the reaction temperature, but is basically selected as appropriate from the range of a few minutes to 48 hours.

After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method at Step [b]

The compound represented by the general formula (6) can be produced by reacting the compound represented by the general formula (4) with the thiol compound represented by the general formula $HSR^6$ (5) in the presence of a base and an inert solvent.

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, N,N-diisopropylethylamine and 1,8-diazabicyclo[5.4.0]undec-7-ene; and nitrogen-containing aromatic compounds such as pyridine and N,N-dimethyl-4-aminopyridine. The amount of the base used is usually in the range of a 1- to 10-fold molar amount relative to the compound represented by the general formula (4). In the case where an alkali salt of the compound represented by the general formula (5) is used, it is not necessary to use a base.

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; chain or cyclic ethers such as diethyl ether, methyl tert-butyl ether, dioxane and tetrahydrofuran; esters such as ethyl acetate; amides such as N, N-dimethyl formamide and N,N-dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (4).

Since this reaction is an equimolar reaction of the reactants, the compound represented by the general formula (4) and the compound represented by the general formula (5) are used basically in equimolar amounts, but either of them may be used in an excess amount. The reaction temperature may be in the range of −20° C. to the boiling point of the inert solvent used. The reaction time varies with the reaction scale and the reaction temperature, but is basically in the range of a few minutes to 48 hours. After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method at Step [c]

The compound represented by the general formula (7) can be produced by deprotection of the compound represented by the general formula (6) in the presence of an acid and an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; sulfonic acids such as methanesulfonic acid, trifluoromethanesulfonic acid and p-toluenesulfonic acid; and phosphoric acid. The amount of the acid used is appropriately selected from the range of a 0.01- to 10-fold molar amount relative to the compound represented by the general formula (6). In some cases, the acid can be used as the solvent as well.

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; chain or cyclic ethers such as diethyl ether, methyl tert-butyl ether, dioxane and tetrahydrofuran; esters such as ethyl acetate; amides such as N,N-dimethylformamide and N,N-dimethylacetamide; ketones such as acetone and methyl ethyl ketone; and polar solvents such as dimethyl sulfoxide, 1,3-dimethyl-2-imidazolidinone, and water. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (6). In the case where the acid is used also as the solvent, it is not necessary to use another solvent.

The reaction temperature may be in the range of room temperature to the boiling point of the inert solvent used. The reaction time varies with the reaction scale and the reaction temperature, but is basically in the range of a few minutes to 48 hours.

After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method at Step [d]

The compound represented by the general formula (1-1) of the present invention can be produced by reacting the compound represented by the general formula (7) with the compound represented by the general formula (8) according to the method described in ORGANIC FUNCTIONAL GROUP PREPARATIONS III 2nd edition ACADEMIC PRESS, INC. After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method at Step [e]

The compound represented by the general formula (1-2) can be produced by reacting the compound represented by the general formula (1-1) with an oxidizing agent in an inert solvent.

Examples of the oxidizing agent used in this reaction include peroxides such as a hydrogen peroxide solution, peroxybenzoic acid and m-chloroperoxybenzoic acid. The amount of the oxidizing agent used is appropriately selected from the range of a 1- to 5-fold molar amount relative to the compound represented by the general formula (1-1).

The inert solvent used in this reaction may be any solvent that does not markedly inhibit the reaction, and examples include chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; organic acids such as formic acid and acetic acid; and polar solvents such as N,N-dimethylformamide, N,N-dimethylacetamide, 1,3-dimethyl-2-imidazolidinone and water. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (1-1).

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours.

After the reaction is completed, the compound of interest is isolated from the post-reaction mixture by the usual method. As needed, recrystallization, column chromatography, etc. can be employed for the purification of the compound of interest.

Production Method 2

[Chem. 6]

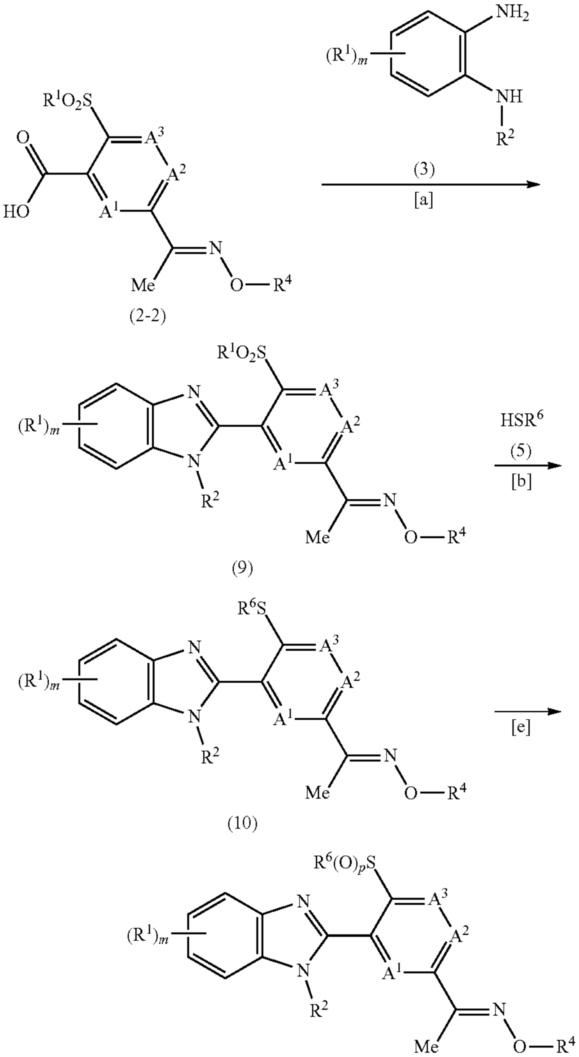

(2-2) (9) (10) (1-3)

In the formula, $A^1$, $A^2$, $A^3$, $R^1$, $R^2$, $R^4$, $R^6$, and m are the same as above, p' represents 1 or 2, and R' represents a ($C_1$-$C_4$) alkyl group such as a methyl group or an ethyl group.

The compound represented by the general formula (1-3) of the present invention can be produced from the compound represented by the general formula (2-2) through the steps [a], [b], and [e] of Production Method 1 above. The production method of the starting compound represented by the general formula (2-2) will be described later.

Production Method 3

[Chem. 7]

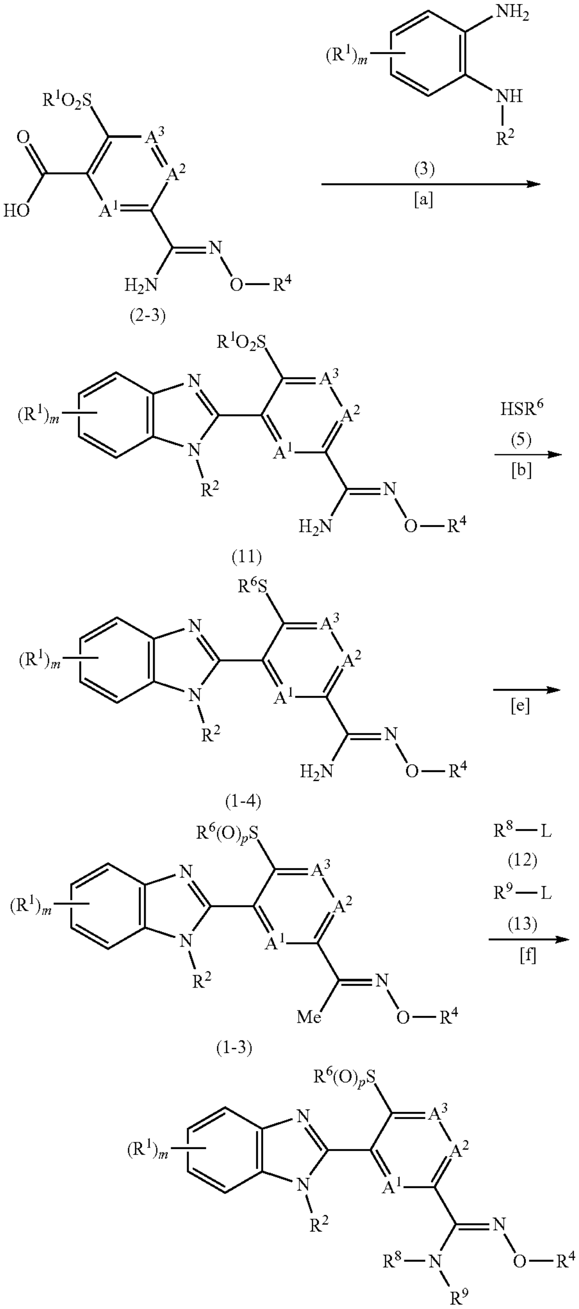

(2-3)

(11)

(1-4)

(1-3)

(1-6)

In the formula, $A^1$, $A^2$, $A^3$, $R^1$, $R^2$, $R^4$, $R^6$, $R^8$, $R^9$, and m are the same as above, p' represents 1 or 2, R' represents a $(C_1-C_4)$ alkyl group such as a methyl group or an ethyl group, and L represents a leaving group such as bromine or chlorine.

The compounds represented by the general formulae (1-4), (1-5), and (1-6) of the present invention can be produced from the compound represented by the general formula (2-3) through the step [f] described below and the steps [a], [b], and [e] of Production Method 1 above. The production method of the starting compound represented by the general formula (2-3) will be described later.

Production Method at Step [f]

The compound represented by the general formula (1-6) can be produced by reacting the compound represented by the general formula (1-5) with the compound represented by the general formula (12) or (13) in the presence of a base and an inert solvent.

Examples of the base that can be used in the present invention include alkyl lithium compounds such as methyl lithium, n-butyl lithium, sec-butyl lithium, and tert-butyl lithium; organometallic compounds such as lithium hexamethyldisilazane and sodium hexamethyldisilazane; hydroxides such as lithium hydroxide, sodium hydroxide, potassium hydroxide and calcium hydroxide; carbonates such as lithium carbonate, lithium hydrogen carbonate, sodium carbonate, sodium hydrogen carbonate, potassium carbonate, potassium hydrogen carbonate, calcium carbonate and magnesium carbonate; acetates such as lithium acetate, sodium acetate and potassium acetate; alkoxides such as sodium methoxide, sodium ethoxide, sodium tert-butoxide and potassium tert-butoxide; metal hydrides such as sodium hydride and potassium hydride; and organic bases such as pyridine, picoline, lutidine, triethylamine, tributylamine and N,N-diisopropylethylamine. The amount of the base used is usually in the range of a 1- to 10-fold molar amount relative to the compound represented by the general formula (1-5).

The inert solvent used in this reaction may be any solvent that does not markedly inhibit the reaction, and examples include chain or cyclic saturated hydrocarbons such as pentane, hexane, and cyclohexane; chain or cyclic ethers such as diethyl ether, tetrahydrofuran (THF), and dioxane; and aromatic hydrocarbons such as benzene, toluene, and xylene. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (1-5).

Since this reaction is an equimolar reaction of the compounds, they are basically used in equimolar amounts, but either of them may be used in an excess amount. The reaction temperature is usually in the range of about −78° C. to the boiling point of the solvent used. The reaction time varies with the reaction scale, the reaction temperature and the like and is not the same in every case, but is basically selected as appropriate from the range of a few minutes to 48 hours.

After the reaction is completed, the compound of interest is isolated from the post-reaction mixture by the usual method. As needed, recrystallization, column chromatography, etc. can be employed for the purification of the compound of interest.

Production Method 4

[Chem. 8]

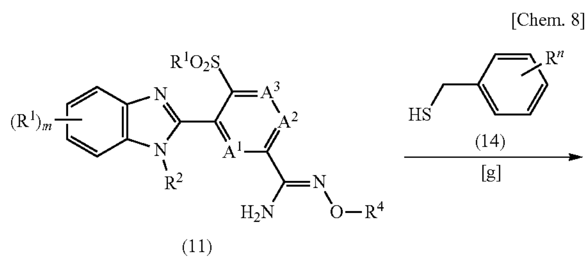

(11)

-continued

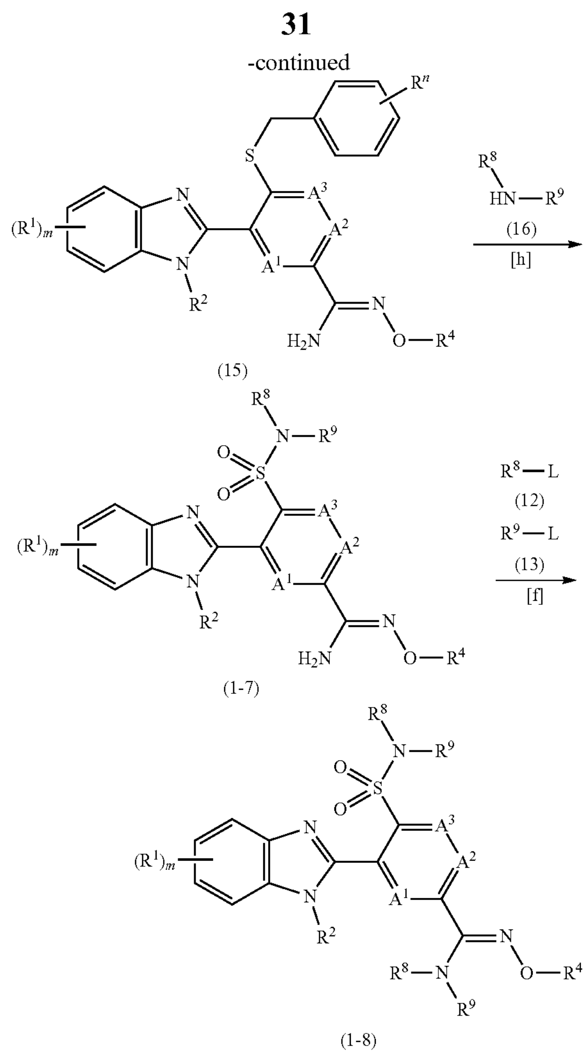

(15)

(1-7)

(1-8)

In the formula, $A^1$, $A^2$, $A^3$, $R^1$, $R^2$, $R^4$, $R^8$, $R^9$, and m are the same as above, and R' represents a ($C_1$-$C_4$) alkyl group such as a methyl group or an ethyl group, R" represents a tertiary ($C_4$-$C_6$) alkyl group such as a tert-butyl group or a tri-($C_1$-$C_6$) alkylsilyl group such as a trimethylsilyl group, and L represents a leaving group such as bromine or chlorine.

The compounds represented by the general formulae (1-7) and (1-8) of the present invention can be produced from the compound represented by the general formula (11) through the steps [g] and [h] described below, and the step [f] of Production Method 3 above.

Production Method at Step [g]

The compound represented by the general formula (15) can be produced by reacting the compound represented by the general formula (11) with the benzylthiol compound represented by the general formula (14) in the presence of a base and an inert solvent.

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, N,N-diisopropylethylamine and 1,8-diazabicyclo[5.4.0]undec-7-ene; and nitrogen-containing aromatic compounds such as pyridine and N,N-dimethyl-4-aminopyridine. The amount of the base used is usually in the range of a 1- to 10-fold molar amount relative to the compound represented by the general formula (11). In the case where an alkali salt of the compound represented by the general formula (14) is used, it is not necessary to use a base.

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; chain or cyclic ethers such as diethyl ether, methyl tert-butyl ether, dioxane and tetrahydrofuran; esters such as ethyl acetate; amides such as N,N-dimethylformamide and N, N-dimethylacetamide; ketones such as acetone and methyl ethyl ketone; and polar solvents such as dimethyl sulfoxide, 1,3-dimethyl-2-imidazolidinone, and water. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (11).

Since this reaction is an equimolar reaction of the compounds, the compound represented by the general formula (11) and the compound represented by the general formula (14) are used basically in equimolar amounts, but either of them may be used in an excess amount. The reaction temperature may be in the range of −20° C. to the boiling point of the inert solvent used. The reaction time varies with the reaction scale and the reaction temperature, but is basically in the range of a few minutes to 48 hours.

After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method at Step [h]

The compound represented by the general formula (15) is reacted with a halogenating agent in the presence of an inert solvent to yield a chlorosulfonylated compound. This chlorosulfonylated compound is then aminated with the compound represented by the general formula (16) in the presence or absence of an inert solvent and a base to yield the compound represented by the general formula (1-7).

Examples of the halogenating agent used in this chlorosulfonylation reaction include thionyl chloride, chlorine, sulfuryl chloride, 1,3-dichloro-5,5-dimethylhydantoin, and N-chlorosuccinimide. The amount of the halogenating agent used is appropriately selected from the range of a 0.5- to 5-fold molar amount relative to the compound represented by the general formula (15).

The inert solvent used in this chlorosulfonylation reaction may be any solvent that does not markedly inhibit the progress of the reaction, and examples include halogenated hydrocarbons such as methylene chloride, chloroform, and carbon tetrachloride; halogenated aromatic hydrocarbons such as chlorobenzene and dichlorobenzene; nitriles such as acetonitrile and propionitrile; organic acids such as acetic acid and propionic acid; and water. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (15).

Since this chlorosulfonyl reaction is an equimolar reaction of the reactants, they are basically used in equimolar amounts, but either of them may be used in an excess amount. The reaction temperature may be in the range of room temperature to the boiling point of the inert solvent used. The reaction time varies with the reaction scale and the reaction temperature, but is basically in the range of a few minutes to 48 hours.

After the reaction is completed, when the chlorosulfonylated product is stable, the product is isolated from the post-reaction mixture by the usual method. As needed, recrystallization, column chromatography, etc. can be employed for the purification of the product. When the chlorosulfonylated product is unstable, the post-reaction mixture is directly used in the next reaction without purification.

Examples of the base used in this amination reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, N,N-diisopropylethylamine and 1,8-diazabicyclo[5.4.0]undec-7-ene; and nitrogen-containing aromatic compounds such as pyridine and N,N-dimethyl-4-aminopyridine. The amount of the base used is usually in the range of a 1- to 10-fold molar amount relative to the compound represented by the general formula (15).

The inert solvent used in this amination reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; chain or cyclic ethers such as diethyl ether, methyl tert-butyl ether, dioxane and tetrahydrofuran; alcohols such as methanol, ethanol, propanol, and isopropyl alcohol; amides such as N,N-dimethylformamide and N,N-dimethylacetamide; and polar solvents such as dimethyl sulfoxide and 1,3-dimethyl-2-imidazolidinone. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (15).

Since this amination reaction is an equimolar reaction of the compounds, they are basically used in equimolar amounts, but either of them may be used in an excess amount. The reaction temperature may be in the range of room temperature to the boiling point of the inert solvent used. The reaction time varies with the reaction scale and the reaction temperature, but is basically in the range of a few minutes to 48 hours.

After the reaction is completed, the compound of interest is isolated from the post-reaction mixture by the usual method. As needed, recrystallization, column chromatography, etc. can be employed for the purification of the compound of interest.

Production Method 5

[Chem. 9]

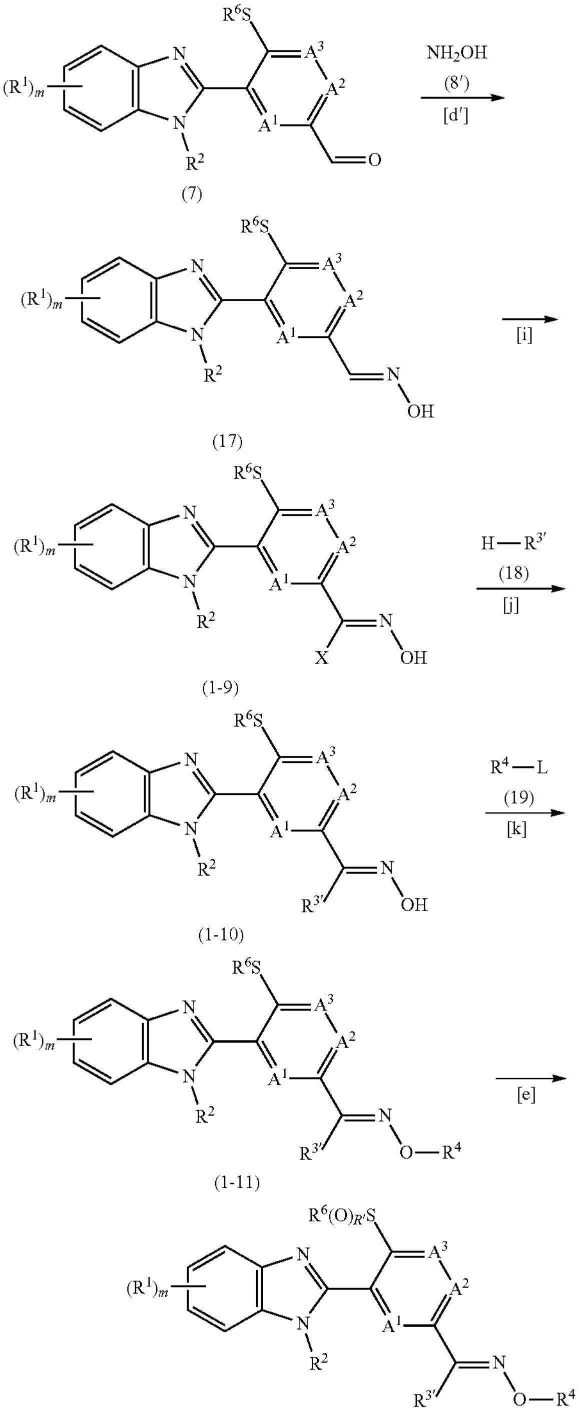

(7)

(17)

(1-9)

(1-10)

(1-11)

(1-12)

In the formula, $A^1$, $A^2$, $A^3$, $R^1$, $R^2$, $R^4$, $R^6$, and m are as above, p' represents 1 or 2, $R^{3'}$ represents a $(C_1\text{-}C_6)$ alkoxy group or an $R^8(R^9)N$ group wherein $R^8$ and $R^9$ are the same as above, X represents a halogen atom such as fluorine, chlorine, bromine, or iodine, and L represents a leaving group such as bromine or chlorine.

The compounds represented by the general formulae (1-9), (1-10), (1-11), and (1-12) of the present invention can be produced from the compound represented by the general formula (7) through the steps [d'], [i], [j], and [k] described below and the step [e] of Production Method 1 above.

Production Method at Step [d']

The compound represented by the general formula (17) of the present invention can be produced by reacting the compound represented by the general formula (7) with the compound represented by the general formula (8') according to the method described in ORGANIC FUNCTIONAL GROUP PREPARATIONS III 2nd edition ACADEMIC PRESS, INC. After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method at Step [i]

The compound represented by the general formula (1-9) can be produced by reacting the compound represented by the general formula (17) with a halogenating agent in the presence or absence of an inert solvent and a base.

The inert solvent used in this reaction may be any solvent that does not markedly inhibit the reaction, and examples include alcohols such as methanol and ethanol; aromatic hydrocarbons such as benzene, toluene, and xylene; ketones such as acetone, methyl ethyl ketone, and methyl isobutyl ketone; halogenated hydrocarbons such as chloroform and dichloromethane; esters such as ethyl acetate and methyl acetate; chain or cyclic ethers such as tetrahydrofuran, diethyl ether, methyl t-butyl ether, 1,2-dimethoxyethane, and dioxane; nitriles such as acetonitrile; and polar solvents such as N,N-dimethylformamide, N-methylpyrrolidone, dimethyl sulfoxide, and water. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (17).

Examples of the base that can be used in this reaction include alkali metal hydrides such as sodium hydride; alkali metal hydroxides such as sodium hydroxide and potassium hydroxide; alkali metal carbonates such as sodium carbonate and potassium carbonate; inorganic salts; and organic bases such as pyridine, DBU (1,8-diazabicyclo[5.4.0]undec-7-ene), and triethylamine. The amount of the base used is appropriately selected from the range of equimolar to excess molar amount relative to the compound represented by the general formula (17).

Examples of the halogenating agent that can be used in this reaction include N-halosuccinimides such as N-chlorosuccinimide and N-bromosuccinimide; hypohalogenous alkali metal salts such as sodium hypochlorite; hypohalogenous acid esters such as tert-butyl hypochlorite; simple halogens such as chlorine gas; and sulfuryl chloride. The amount of the halogenating agent used is appropriately selected from the range of equimolar to excess molar amount relative to the compound represented by the general formula (17).

The reaction temperature is appropriately selected from the range of −50° C. to the boiling point of the inert solvent used, and is preferably in the range of room temperature to 80° C. The reaction time varies with the reaction scale and the reaction temperature, but is basically in the range of a few minutes to 48 hours. After the reaction is completed, when the compound represented by the general formula (1-9) is stable, the compound is isolated from the post-reaction mixture by the usual method. As needed, recrystallization, column chromatography, etc. can be employed for the purification of the compound. The post-reaction mixture may be directly used in the next reaction without isolation of the compound. When the compound represented by the general formula (1-9) is unstable, the post-reaction mixture is directly used in the next reaction without purification.

Production Method at Step [j]

The compound represented by the general formula (1-10) can be produced by reacting the compound represented by the general formula (1-9) with the compound represented by the general formula (18) in the presence or absence of an inert solvent and a base.

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, N,N-diisopropylethylamine and 1,8-diazabicyclo[5.4.0]undec-7-ene; and nitrogen-containing aromatic compounds such as pyridine and N,N-dimethyl-4-aminopyridine. The amount of the base used is usually in the range of a 1- to 10-fold molar amount relative to the compound represented by the general formula (1-9). In the case where an alkali salt of the compound represented by the general formula (18) is used, it is not necessary to use a base.

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; chain or cyclic ethers such as diethyl ether, methyl tert-butyl ether, dioxane and tetrahydrofuran; esters such as ethyl acetate; amides such as N,N-dimethylformamide and N, N-dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (1-9).

Since this reaction is an equimolar reaction of the compounds, the compound represented by the general formula (1-9) and the compound represented by the general formula (18) are used basically in equimolar amounts, but either of them may be used in an excess amount. The reaction temperature may be in the range of −20° C. to the boiling point of the inert solvent used. The reaction time varies with the reaction scale and the reaction temperature, but is basically in the range of a few minutes to 48 hours.

After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method at Step [k]

The compound represented by the general formula (1-11) can be produced by reacting the compound represented by the general formula (1-10) with the general formula (19) in the presence of an inert solvent and a base.

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, N,N-diisopropylethylamine and 1,8-diazabicyclo[5.4.0]undec-7-ene; and nitrogen-containing aromatic compounds such as pyridine and N,N-dimethyl-4-aminopyridine. The amount of the base used is usually in the range of a 1- to 10-fold molar amount relative to the compound represented by the general formula (1-10).

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; chain or cyclic ethers such as diethyl ether, methyl tert-butyl ether, dioxane and tetrahydrofuran; esters such as ethyl acetate; amides such as N,N-dimethylformamide and N,N-dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (1-10).

Since this reaction is an equimolar reaction of the compounds, the compound represented by the general formula (1-10) and the compound represented by the general formula (19) are used basically in equimolar amounts, but either of them may be used in an excess amount. The reaction temperature may be in the range of −20° C. to the boiling point of the inert solvent used. The reaction time varies with the reaction scale and the reaction temperature, but is basically in the range of a few minutes to 48 hours.

After the reaction is completed, the compound of interest is isolated from the post-reaction mixture by the usual method. As needed, recrystallization, column chromatography, etc. can be employed for the purification of the compound of interest.

Production Method 6

[Chem. 10]

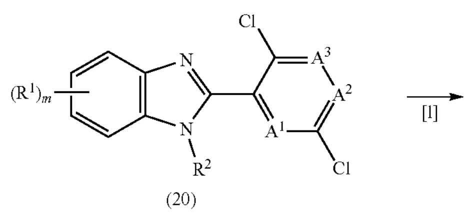

(20)

-continued

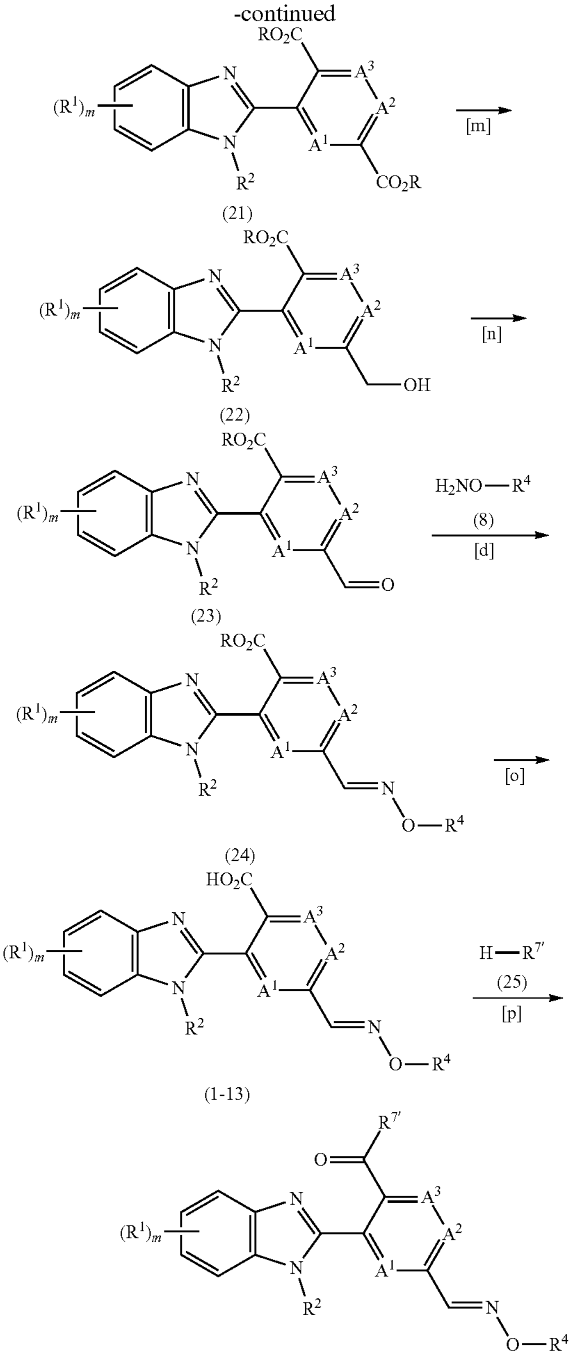

In the formula, $A^1$, $A^2$, $A^3$, $R^1$, $R^2$, $R^4$, and m are the same as above, $R^{7'}$ represents a $(C_1\text{-}C_6)$ alkoxy group, a $(C_2\text{-}C_6)$ alkynyloxy group, or an $R^8(R^9)N$ group wherein $R^8$ and $R^9$ are the same as above, and R represents a $(C_1\text{-}C_4)$ alkyl group such as a methyl group or an ethyl group.

The compounds represented by the general formulae (1-13) and (1-14) of the present invention can be produced from the compound represented by the general formula (20) through the steps [l], [m], [n], [o], and [p] described below and the step [d] of Production Method 1 above. The starting compound represented by the general formula (20) can be produced by the method described in WO 2013/018928.

Production Method at Step [l]

The compound represented by the general formula (21), which has ester groups introduced at C-3 and C-6 positions, can be synthesized from the compound represented by the general formula (20) according to the method described in JP 2005-272338 (Heck reaction). After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method at Step [m]

The compound represented by the general formula (22) can be produced by reducing the compound represented by the general formula (21) with a reducing agent in the presence of an inert solvent.

Examples of the reducing agent that can be used in this reaction include sodium borohydride, sodium cyanoborohydride, sodium bis(2-methoxyethoxy)aluminum hydride, hydrogen/palladium carbon, and hydrogen/Raney nickel. The amount of the reducing agent used is usually in the range of a 0.5- to 10-fold molar amount relative to the compound represented by the general formula (21).

The inert solvent used in this reaction may be any solvent that does not markedly inhibit the reaction, and examples include alcohols such as methanol, ethanol, propanol, butanol, and 2-propanol; chain or cyclic ethers such as diethyl ether, tetrahydrofuran (THF), and dioxane; and acids such as acetic acid and propionic acid. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (21).

The reaction temperature in this reaction is usually in the range of about 0° C. to the boiling point of the solvent used. The reaction time varies with the reaction scale, the reaction temperature and the like and is not the same in every case, but is usually selected as appropriate from the range of a few minutes to 48 hours.

After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method at Step [n]

The compound represented by the general formula (23) can be produced by oxidizing the compound represented by the general formula (22) with an oxidizing agent in the presence of an inert solvent.

Examples of the oxidizing agent that can be used in this reaction include manganese dioxide, chromic acid, cerium ammonium nitrate (CAN), silver carbonate, pyridine-anhydrous sulfuric acid, and activated DMSO (dimethyl sulfoxide). The oxidizing agent is used in accordance with commonly used methods for converting alcohols to aldehydes or ketones, which are described in known literature (see, for example, "New Lecture of Experimental Chemistry", vol. 15 (I), p. 71-84, 120-123, 804-843, 923, 1004-1006 (1977), edited by the Chemical Society of Japan, published by Maruzen Publishing Co., Ltd.; and Chem. Bull. 30(5), p. 1921-1924 (1982)).

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; chain or cyclic ethers such as diethyl ether, methyl tert-butyl ether, dioxane and tetrahydrofuran; esters such as ethyl acetate; amides such as N,N-dimethylformamide and N,N-dimethylacetamide; ketones such as acetone and methyl ethyl ketone; and polar solvents such as dimethyl sulfoxide, 1,3-dimethyl-2-imidazolidinone, and water. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (22).

Production Method at Step [o]

The compound represented by the general formula (1-13) can be produced by hydrolyzing the compound represented by the general formula (24) in the presence of a base, water and an inert solvent.

Examples of the base that can be used in this reaction include hydroxides such as lithium hydroxide, sodium hydroxide, potassium hydroxide, and calcium hydroxide, and organic bases.

The inert solvent used in this reaction may be any solvent that does not markedly inhibit the reaction, and examples include chain or cyclic saturated hydrocarbons such as pentane, hexane, and cyclohexane; chain or cyclic ethers such as diethyl ether, tetrahydrofuran (THF), and dioxane; aromatic hydrocarbons such as benzene, toluene, and xylene; and other nonpolar solvents. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (24).

The reaction temperature is usually in the range of about 0° C. to the boiling point of the solvent used. The reaction time varies with the reaction scale, the reaction temperature and the like and is not the same in every case, but is basically selected as appropriate from the range of a few minutes to 48 hours. After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method at Step [p]

The compound represented by the general formula (1-14) can be produced by reacting the compound represented by the general formula (1-13) and the compound represented by the general formula (25) with a condensing agent in the presence of a base and an inert solvent.

Examples of the condensing agent that can be used in this condensation reaction include acid-activating reagents such as phosgene, phosphorus trichloride, phosphorus oxychloride, oxalyl chloride, and thionyl chloride; carbodiimides such as N,N'-dicyclohexylcarbodiimide (DCC) and 1-(3-dimethylaminopropyl)-3-ethylcarbodiimide (EDCI); and other reagents such as phosphorus pentoxide, polyphosphoric acid, N,N'-carbonyldiimidazole, 2-chloropyridine-1- methiodide (Mukaiyama reagent), 2-ethoxy-N-ethoxycarbonyl-1,2-dihydroquinoline (EEDQ), triphenylphosphine/carbon tetrachloride, bromotripyrrolidinophosphonium hexafluorophosphate (BROP), O—(1H-benzotriazol-1-yloxy)tris(dimethylamino)phosphonium hexafluorophosphate (BOP), N,N,N',N'-bis(tetramethylene)chlorouronium tetrafluoroborate, O—(1H-benzotriazol-1-yl)-N,N,N',N'-tetramethyluronium hexafluorophosphate (HBTU), O—(1H-benzotriazol-1-yl)-N,N,N',N'-bis(tetramethylene)uronium hexafluorophosphate, O—(1H-benzotriazol-1-yl)-N,N,N',N'-tetramethyluronium tetrafluoroborate (TBTU), O—(1H-benzotriazol-1-yl)-N,N,N',N'-bis(tetramethylene)uronium tetrafluoroborate, O-(7-azabenzotriazol-1-yl)-N,N,N',N'-tetramethyluronium hexafluorophosphate (HATU), 1-hydroxybenzotriazole (HOBt), propylphosphonic anhydride ($T_3P$), and 4-(4,6-dimethoxy-1,3,5-triazin-2-yl)-4-methylmorpholinium salt (DMT-MM). One of these condensing agents may be used alone, and also two or more of them may be used as a mixture. The amount of the condensing agent used is appropriately selected from the range of a 0.5- to 5-fold molar amount relative to the compound represented by the general formula (1-13).

Examples of the base that can be used in this condensation reaction include carbonates such as lithium carbonate, lithium hydrogen carbonate, sodium carbonate, sodium hydrogen carbonate, potassium carbonate, potassium hydrogen carbonate, calcium carbonate and magnesium carbonate; acetates such as lithium acetate, sodium acetate and potassium acetate; and organic bases such as pyridine, picoline, lutidine, triethylamine, tributylamine and N,N-diisopropylethylamine. The amount of the base used is appropriately selected from the range of a 0.5- to 5-fold molar amount relative to the compound represented by the general formula (1-13). In some cases, the base can be used as the solvent as well.

The inert solvent used in this condensation reaction may be any solvent that does not markedly inhibit the reaction, and examples include chain or cyclic saturated hydrocarbons such as pentane, hexane, and cyclohexane; chain or cyclic ethers such as diethyl ether, tetrahydrofuran (THF), and dioxane; aromatic hydrocarbons such as benzene, toluene, and xylene; halogenated hydrocarbons such as methylene chloride, chloroform, and carbon tetrachloride; nitriles such as acetonitrile and isopropylnitrile; and polar solvents such as N,N-dimethylformamide, N,N-dimethylacetamide, dimethyl sulfoxide, and 1,3-dimethyl-2-imidazolidinone. One of these inert solvents may be used alone, and also two or more of them may be used as a mixture. In the case where the base is used also as the solvent, it is not necessary to use another solvent. The amount of the inert solvent used is not particularly limited as long as it is sufficient to dissolve the reaction reagents, and is appropriately selected from the range of 0.5 L to 100 L relative to 1 mole of the compound represented by the general formula (1-13).

Since this condensation reaction is an equimolar reaction of the compounds, they are basically used in equimolar amounts, but either of them may be used in an excess amount. The reaction temperature is usually in the range of about 0° C. to the boiling point of the solvent used. The reaction time varies with the reaction scale, the reaction temperature and the like and is not the same in every case, but is basically selected as appropriate from the range of a few minutes to 48 hours.

After the reaction is completed, the compound of interest is isolated from the post-reaction mixture by the usual method. As needed, recrystallization, column chromatography, etc. can be employed for the purification of the compound of interest.

Production Method 7

[Chem. 11]

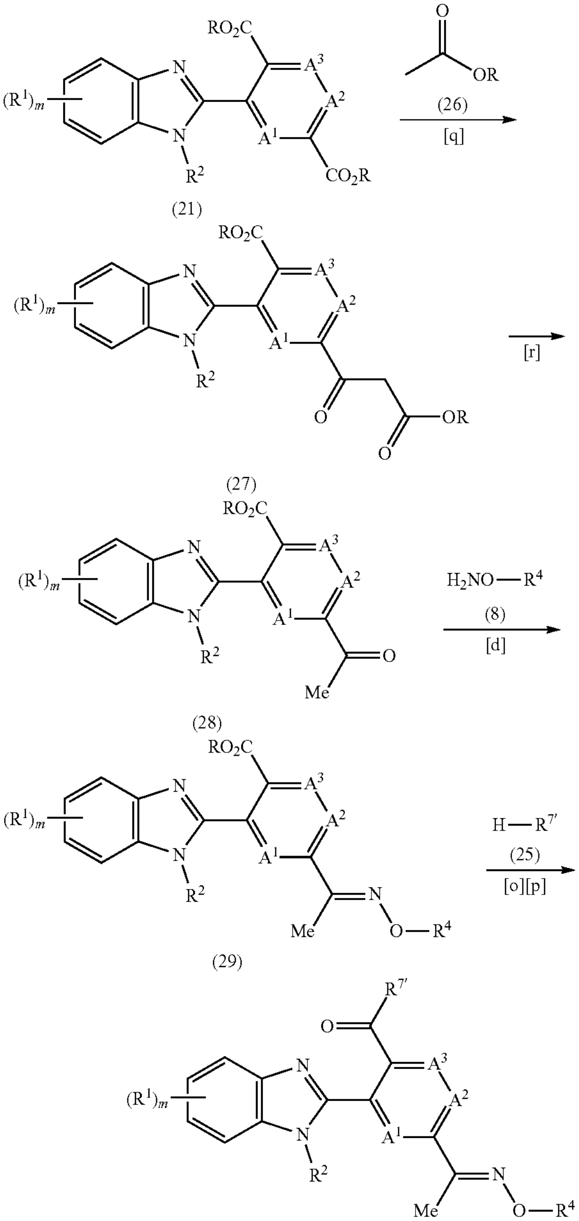

(21) (27) (28) (29) (1-15)

In the formula, $A^1$, $A^2$, $A^3$, $R^1$, $R^2$, $R^4$, and m are the same as above, $R^{7'}$ represents a ($C_1$-$C_6$) alkoxy group, a ($C_2$-$C_6$) alkynyloxy group, or an $R^8$ ($R^5$)N group wherein $R^8$ and $R^9$ are the same as above, and R represents a ($C_1$-$C_4$) alkyl group such as a methyl group or an ethyl group.

The compound represented by the general formula (1-15) of the present invention can be produced from the compound represented by the general formula (21) through the steps [q] and [r] described below, the step [d] of Production Method 1 above, and the steps [o] and [p] of Production Method 6 above.

Production Method at Step [q]

The compound represented by the general formula (27) can be produced by Claisen condensation (Org. React. 1942, 1, 266) of the aromatic carboxylic acid ester represented by the general formula (21) and the acetic acid ester represented by the general formula (26).

Production Method at Step [r]

The compound represented by the general formula (28) can be produced by decarboxylating the compound represented by the general formula (27) in the presence of an acid and an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; sulfonic acids such as methanesulfonic acid, trifluoromethanesulfonic acid and p-toluenesulfonic acid; and phosphoric acid. The amount of the acid used is appropriately selected from the range of a 0.01- to 10-fold molar amount relative to the compound represented by the general formula (27). In some cases, the acid can be used as the solvent as well.

The inert solvent used in this reaction may be any solvent that does not markedly inhibit the progress of the reaction, and examples include chain or cyclic saturated hydrocarbons such as pentane, hexane, and cyclohexane; aromatic hydrocarbons such as benzene, toluene, and xylene; halogenated aromatic hydrocarbons such as chlorobenzene and dichlorobenzene; chain or cyclic ethers such as diethyl ether, methyl tert-butyl ether, dioxane, and tetrahydrofuran; nitriles such as acetonitrile and propionitrile; aprotic polar solvents such as N,N-dimethylformamide, N,N-dimethylacetamide, dimethyl sulfoxide, and 1,3-dimethyl-2-imidazolidinone; alcohols such as methanol, ethanol, propanol, butanol, and 2-propanol; and water. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (27).

The reaction temperature in this reaction is usually in the range of about 0° C. to the boiling point of the solvent used. The reaction time varies with the reaction scale, the reaction temperature and the like and is not the same in every case, but is usually selected as appropriate from the range of a few minutes to 48 hours.

After the reaction is completed, the compound of interest is isolated from the post-reaction mixture by the usual method. As needed, recrystallization, column chromatography, etc. can be employed for the purification of the compound of interest.

Production Method 8

[Chem. 12]

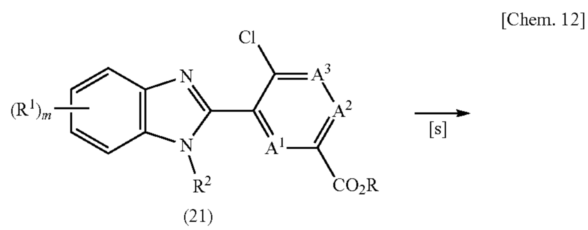

-continued

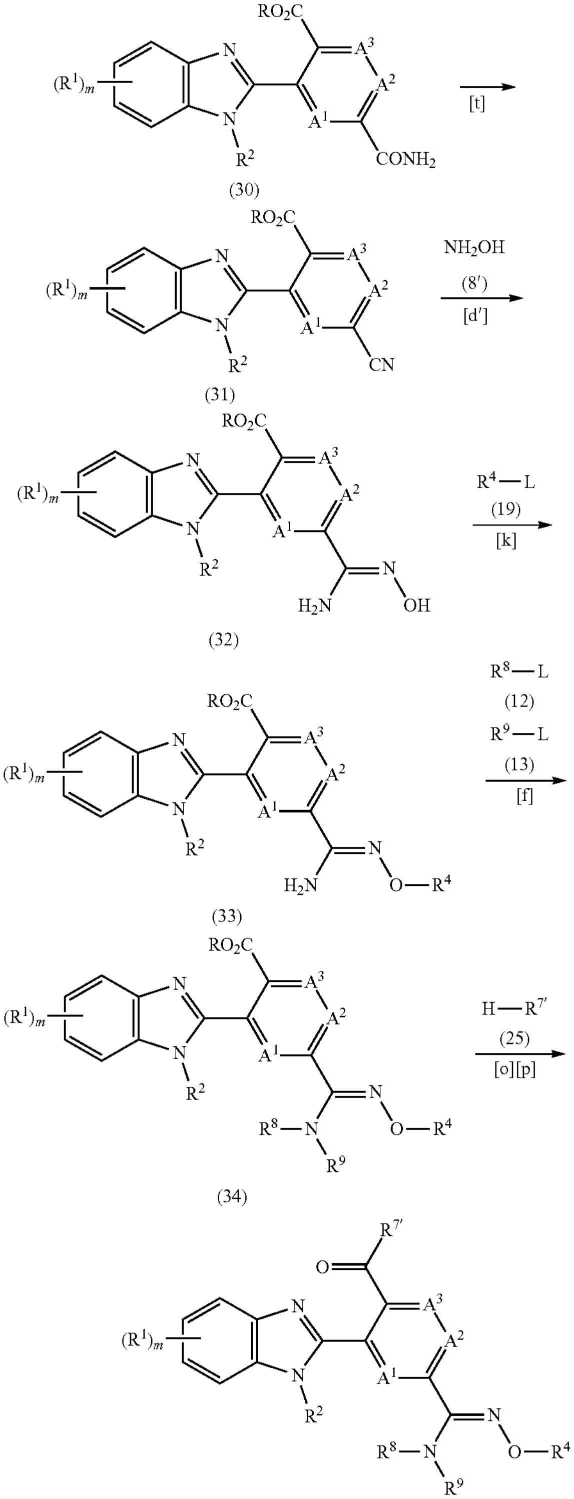

(1-16)

In the formula, $A^1$, $A^2$, $A^3$, $R^1$, $R^2$, $R^4$, $R^8$, $R^9$, and m are the same as above, R' represents a ($C_1$-$C_6$) alkoxy group, a ($C_2$-$C_6$) alkynyloxy group, or an $R^8(R^9)N$ group wherein $R^8$ and $R^9$ are the same as above, R represents a ($C_1$-$C_4$) alkyl group such as a methyl group or an ethyl group, and L represents a leaving group such as bromine or chlorine.

The compound represented by the general formula (1-16) of the present invention can be produced from the compound represented by the general formula (21) through the steps [s] and [t] described below, the step [f] of Production Method 3 above, the steps [d'] and [k] of Production Method 5 above, and the steps [o] and [p] of Production Method 6 above.

Production Method at Step [s]

The compound represented by the general formula (30) can be produced by reacting the compound represented by the general formula (21) with ammonia in the presence or absence of an inert solvent and a base.

The base used in this reaction may be an inorganic base or an organic base. Examples of the inorganic base include alkali metal hydroxides such as sodium hydroxide and potassium hydroxide; alkali metal hydrides such as sodium hydride and potassium hydride; alkali metal alkoxides such as sodium ethoxide and potassium t-butoxide; and carbonates such as sodium carbonate, potassium carbonate, and sodium hydrogen carbonate. Examples of the organic base include triethylamine, pyridine, and DBU. The amount of the base used is appropriately selected from the range of a 0.01- to 10-fold molar amount relative to the compound represented by the general formula (21).

The inert solvent used in this reaction may be any solvent that does not markedly inhibit the progress of the reaction, and examples include aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; chain or cyclic ethers such as diethyl ether, dioxane and tetrahydrofuran; esters such as ethyl acetate; amides such as N,N-dimethylformamide and N,N-dimethylacetamide; and others such as dimethyl sulfoxide, 1,3-dimethyl-2-imidazolidinone, acetone, methyl ethyl ketone, and water. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (21).

The reaction temperature in this reaction is usually in the range of about 0° C. to the boiling point of the solvent used. The reaction time varies with the reaction scale, the reaction temperature and the like and is not the same in every case, but is usually selected as appropriate from the range of a few minutes to 48 hours.

After the reaction is completed, the compound of interest is isolated from the post-reaction mixture by the usual method. As needed, recrystallization, column chromatography, etc. can be employed for the purification of the compound of interest. Alternatively, the crude product may be subjected to the next step without purification.

Production Method at Step [t]

The compound represented by the general formula (31) can be produced by reacting the compound represented by the general formula (30) with a dehydrating agent in the presence or absence of an inert solvent and a base.

Examples of the dehydrating agent used in this reaction include trifluoroacetic anhydride, phosphorus oxychloride, and phosphorus pentoxide. The amount of the dehydrating agent used is appropriately selected from the range of a 1- to 10-fold molar amount relative to the compound represented by the general formula (30).

The base used in this reaction may be an inorganic base or an organic base. Examples of the inorganic base include alkali metal hydroxides such as sodium hydroxide and potassium hydroxide; alkali metal hydrides such as sodium hydride and potassium hydride; alkali metal alkoxides such as sodium ethoxide and potassium t-butoxide; and carbonates such as sodium carbonate, potassium carbonate, and sodium hydrogen carbonate. Examples of the organic base include triethylamine, pyridine, and DBU. The amount of the base used is appropriately selected from the range of a 0.01- to 10-fold molar amount relative to the compound represented by the general formula (30).

The inert solvent used in this reaction may be any solvent that does not markedly inhibit the progress of the reaction, and examples include aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; chain or cyclic ethers such as diethyl ether, dioxane and tetrahydrofuran; esters such as ethyl acetate; amides such as N,N-dimethylformamide and N,N-dimethylacetamide; and others such as dimethyl sulfoxide, 1,3-dimethyl-2-imidazolidinone, acetone and methyl ethyl ketone. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (30).

The reaction temperature in this reaction is usually in the range of about 0° C. to the boiling point of the solvent used. The reaction time varies with the reaction scale, the reaction temperature and the like and is not the same in every case, but is usually selected as appropriate from the range of a few minutes to 48 hours.

After the reaction is completed, the compound of interest is isolated from the post-reaction mixture by the usual method. As needed, recrystallization, column chromatography, etc. can be employed for the purification of the compound of interest.

Production Method 9

[Chem. 13]

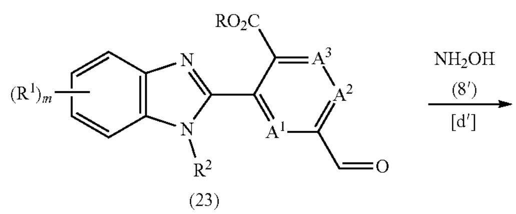

(23)

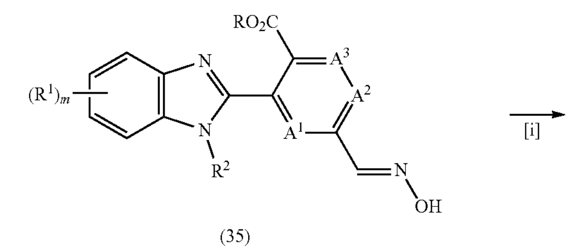

(35)

-continued

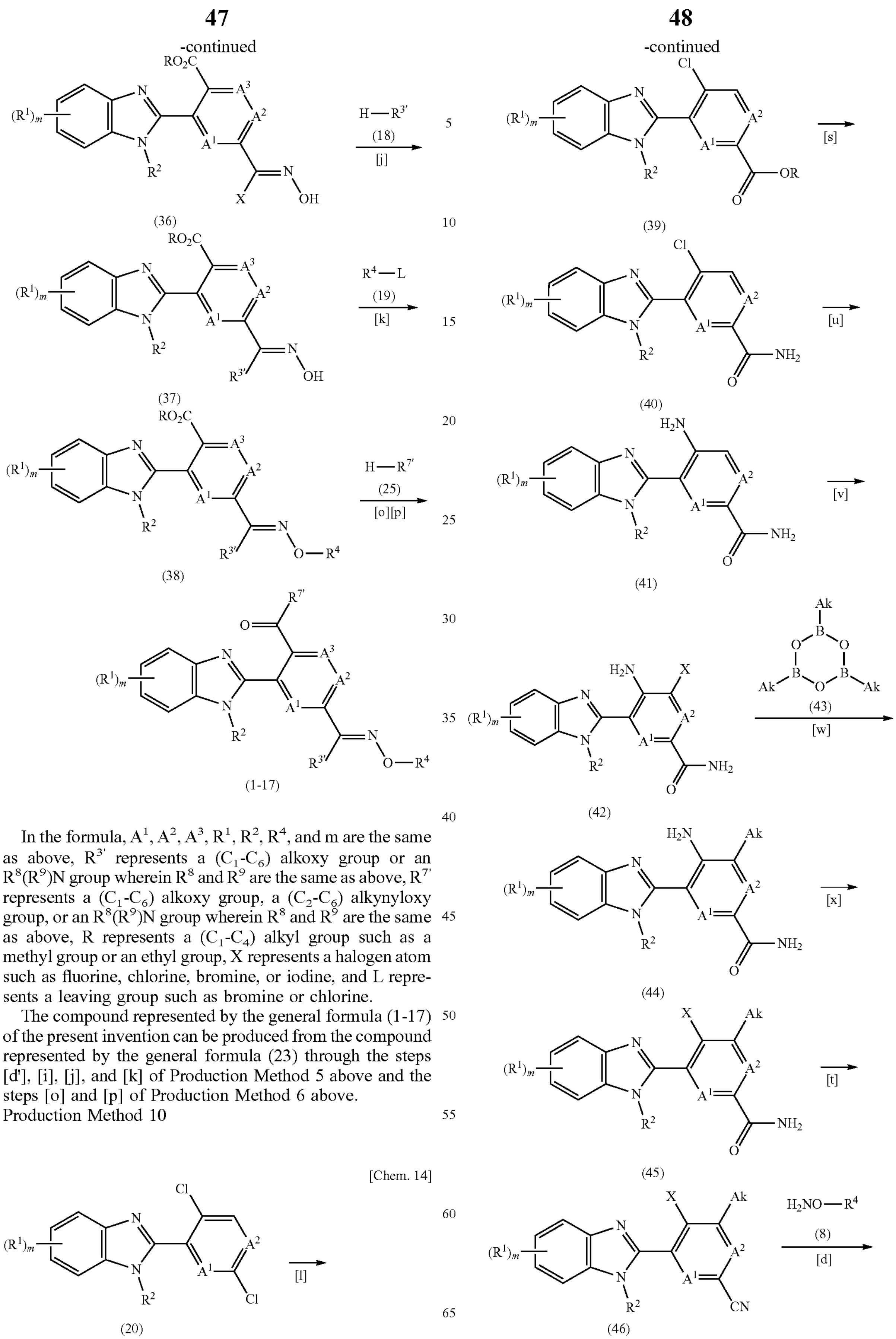

(36)

(37)

(38)

(1-17)

In the formula, $A^1$, $A^2$, $A^3$, $R^1$, $R^2$, $R^4$, and m are the same as above, $R^{3'}$ represents a ($C_1$-$C_6$) alkoxy group or an $R^8(R^9)N$ group wherein $R^8$ and $R^9$ are the same as above, $R^{7'}$ represents a ($C_1$-$C_6$) alkoxy group, a ($C_2$-$C_6$) alkynyloxy group, or an $R^8(R^9)N$ group wherein $R^8$ and $R^9$ are the same as above, R represents a ($C_1$-$C_4$) alkyl group such as a methyl group or an ethyl group, X represents a halogen atom such as fluorine, chlorine, bromine, or iodine, and L represents a leaving group such as bromine or chlorine.

The compound represented by the general formula (1-17) of the present invention can be produced from the compound represented by the general formula (23) through the steps [d'], [i], [j], and [k] of Production Method 5 above and the steps [o] and [p] of Production Method 6 above.

Production Method 10

[Chem. 14]

(20)

-continued (39)

(40)

(41)

(42)

(44)

(45)

(46)

-continued

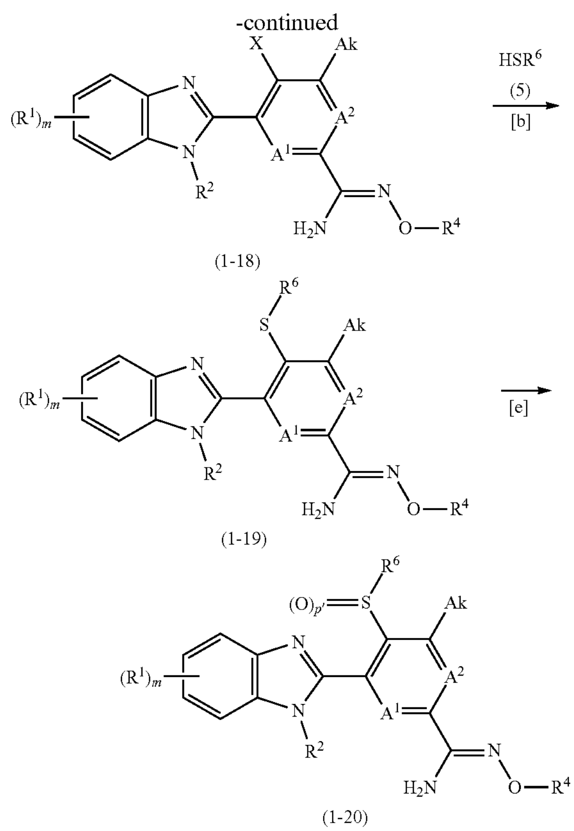

(1-18)

(1-19)

(1-20)

In the formula, $A^1$, $A^2$, $R^1$, $R^2$, $R^4$, $R^6$, and m are the same as above, p' represents 1 or 2, R represents a ($C_1$-$C_4$) alkyl group such as a methyl group or an ethyl group, Ak represents a ($C_1$-$C_6$) alkyl group, and X represents a halogen atom such as fluorine, chlorine, bromine, or iodine.

The compounds represented by the general formulae (1-18), (1-19), and (1-20) of the present invention can be produced from the compound represented by the general formula (20) through the steps [u], [v], [w], and [x] described below, the steps [b], [d], and [e] of Production Method 1 above, the step [1] of Production Method 6 above, and the steps [s] and [t] of Production Method 8 above.

Production Method at Step [u]

The compound represented by the general formula (41) can be produced by reacting the compound represented by the general formula (40) with sodium azide in an inert solvent and reducing the resulting compound with a reducing agent.

The inert solvent used in this reaction may be any solvent that does not markedly inhibit the progress of the reaction, and examples include aromatic hydrocarbons such as benzene, toluene, and xylene; halogenated aliphatic hydrocarbons such as methylene chloride, chloroform, and carbon tetrachloride; alcohols such as methanol and ethanol; halogenated aromatic hydrocarbons such as chlorobenzene and dichlorobenzene; chain or cyclic ethers such as diethyl ether, dioxane, and tetrahydrofuran; amides such as N,N-dimethylformamide and N,N-dimethylacetamide; and others such as dimethyl sulfoxide, 1,3-dimethyl-2-imidazolidinone, N-methyl-2-pyrrolidone, and water. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (40).

Examples of the reducing agent used in this reaction include triphenylphosphine, sodium borohydride, hydrogen/palladium carbon, and hydrogen/Raney nickel. The amount of the reducing agent used is usually in the range of a 0.5- to 10-fold molar amount relative to the compound represented by the general formula (40).

The reaction temperature in this reaction is usually in the range of about 0° C. to the boiling point of the solvent used. The reaction time varies with the reaction scale, the reaction temperature and the like and is not the same in every case, but is usually selected as appropriate from the range of a few minutes to 48 hours.

After the reaction is completed, the compound of interest is isolated from the post-reaction mixture by the usual method. As needed, recrystallization, column chromatography, etc. can be employed for the purification of the compound of interest.

Step [v]

The compound represented by the general formula (42) can be produced by halogenating the compound represented by the general formula (41) with a halogenating agent in the presence of an inert solvent.

The inert solvent used in this reaction may be any solvent that does not markedly inhibit the reaction, and examples include alcohols such as methanol, ethanol, propanol, butanol and 2-propanol; chain or cyclic ethers such as diethyl ether, tetrahydrofuran and dioxane; aromatic hydrocarbons such as benzene, toluene and xylene; esters such as ethyl acetate; and polar solvents such as N,N-dimethylformamide, N,N-dimethylacetamide, 1,3-dimethyl-2-imidazolidinone, water and acetic acid. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (41).

Examples of the halogenating agent include halogen molecules such as a chlorine, bromine, or iodine molecule; halogenated succinimides such as NCS and NBS; halogenated hydantoins such as DIH; and sulfuryl chloride. The amount of the halogenating agent used is appropriately selected from the range of a 0.5- to 10-fold molar amount relative to the compound represented by the general formula (41).

The reaction temperature in this reaction is appropriately selected from the range of −30° C. to the reflux temperature of the inert solvent used. The reaction time varies with the reaction scale, the reaction temperature and the like and is not the same in every case, but is basically selected as appropriate from the range of a few minutes to 48 hours. After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method at Step [w]

The compound represented by the general formula (44) can be produced by reacting the compound represented by the general formula (42) with the compound represented by the general formula (43) in the presence of a metal catalyst, a base, and an inert solvent.

Examples of the metal catalyst that can be used in this reaction include a palladium catalyst, a nickel catalyst, an iron catalyst, a ruthenium catalyst, a platinum catalyst, a rhodium catalyst and an iridium catalyst. Such a metal catalyst can be used in the form of "a metal", "a supported metal", "a metal salt such as a metal chloride, a metal bromide, a metal iodide, a metal nitrate, a metal sulfate, a metal carbonate, a metal oxalate, a metal acetate and a metal oxide", or "a complex compound such as an olefin complex, a phosphine complex, an amine complex, an ammine complex and an acetylacetonate complex". Preferred is a palladium catalyst.

Examples of the palladium catalyst include palladium metals such as palladium black and palladium sponge; and supported palladium metals such as palladium/alumina, palladium/carbon, palladium/silica and palladium/type Y zeolite. Also included are palladium metal salts such as palladium chloride, palladium bromide, palladium iodide and palladium acetate. Other examples of the palladium catalyst include palladium complex compounds such as n-allylpalladium chloride dimer, palladium acetylacetonate, dichlorobis(acetonitrile)palladium, dichlorobis (benzonitrile)palladium, bis(dibenzylideneacetone)palladium, tris (dibenzylideneacetone) dipalladium, tris (dibenzylideneacetone)dipalladium (chloroform adduct), dichlorodiamine palladium, dichlorobis(triphenylphosphine)palladium, dichlorobis(tricyclohexylphosphine) palladium, tetrakis(triphenylphosphine)palladium, dichloro[1, 2-bis(diphenylphosphino)ethane]palladium, dichloro[1,3-bis(diphenylphosphino)propane]palladium, dichloro[1,4-bis (diphenylphosphino) butane]palladium, dichloro[1,1'-bis (diphenylphosphino) ferrocene]palladium and a [(diphenylphosphino) ferrocene]dichloropalladium-dichloromethane complex. The amount of the metal catalyst used is appropriately selected from the range of a 0.001- to 0.5-fold molar amount relative to the compound represented by the general formula (42).

These palladium catalysts may be used alone or in combination with a tertiary phosphine. Examples of the tertiary phosphine that can be used in combination with the palladium catalyst include triphenylphosphine, trimethylphosphine, triethylphosphine, tributylphosphine, tri(tert-butyl) phosphine, tricyclohexylphosphine, tri-o-tolylphosphine, trioctylphosphine, 9,9-dimethyl-4,5-bis(diphenylphosphino) xanthene, 2-(di-tert-butylphosphino)biphenyl, 2-(dicyclohexylphosphino)biphenyl, 1,2-bis(diphenylphosphino)ethane, 1,3-bis(diphenylphosphino)propane, 1,4-bis (diphenylphosphino)butane, 1,1'-bis(diphenylphosphino) ferrocene, (R)-(+)-2,2'-bis(diphenylphosphino)-1,1'-binaphthyl, (S)-(−)-2,2'-bis(diphenylphosphino)-1,1'-binaphthyl and (±)-2,2'-bis(diphenylphosphino)-1,1'-binaphthyl. The amount of the tertiary phosphine used is appropriately selected from the range of a 0.5- to 10-fold molar amount relative to the metal catalyst.

Examples of the base that can be used in this reaction include inorganic bases such as sodium hydroxide, potassium hydroxide, sodium carbonate, potassium carbonate, cesium carbonate, sodium hydrogen carbonate and potassium hydrogen carbonate; alkali metal hydrides such as sodium hydride and potassium hydride; and alkoxides such as sodium methoxide, sodium ethoxide and potassium tert-butoxide. The amount of the base used is usually in the range of an about 1- to 5-fold molar amount relative to the compound represented by the general formula (42).

The inert solvent used in this reaction may be any solvent that does not markedly inhibit the reaction, and examples include alcohols such as methanol, ethanol, propanol, butanol and 2-propanol; chain or cyclic ethers such as diethyl ether, tetrahydrofuran, dioxane and 1,2-dimethoxyethane (DME); aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; polar solvents such as N,N-dimethylformamide, N,N-dimethylacetamide, dimethyl sulfoxide and 1,3-dimethyl-2-imidazolidinone; and water. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (42).

Since this reaction is an equimolar reaction of the compounds, they are basically used in equimolar amounts, but either of them may be used in an excess amount.

The reaction temperature in this reaction is usually in the range of about 0° C. to the boiling point of the solvent used. The reaction time varies with the reaction scale, the reaction temperature and the like, but is basically selected as appropriate from the range of a few minutes to 48 hours. This reaction may be conducted under the atmosphere of an inert gas such as nitrogen gas and argon gas.

After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method at Step [x]

The compound represented by the general formula (45) can be produced by conversion of the amino group of the compound represented by the general formula (44) to a halogen atom according to the method described in Chem. Rev. 1988, 88, 765, i.e., the Sandmeyer reaction.

After the reaction is completed, the compound of interest is isolated from the post-reaction mixture by the usual method. As needed, recrystallization, column chromatography, etc. can be employed for the purification of the compound of interest.

Production Method 11

[Chem. 15]

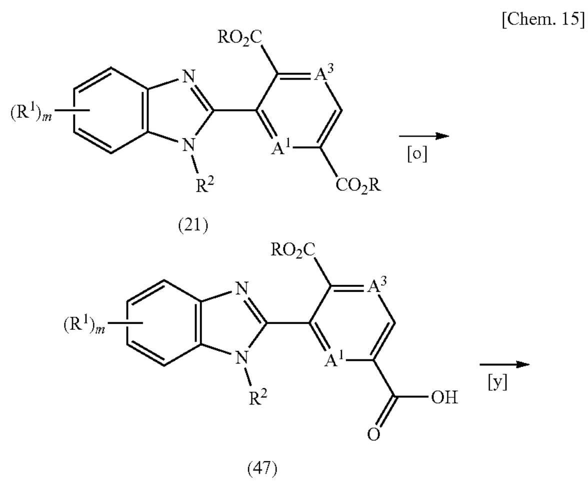

(21)

(47)

-continued

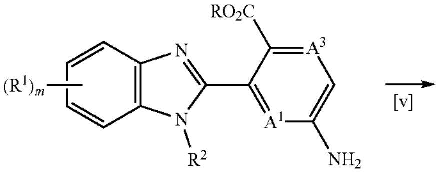

(48)

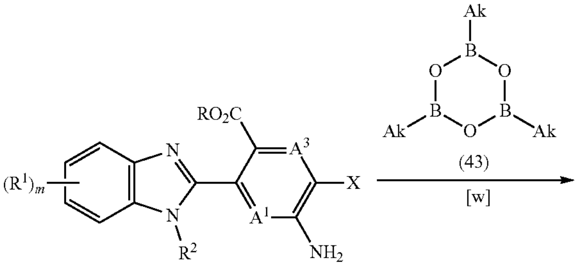

(49)

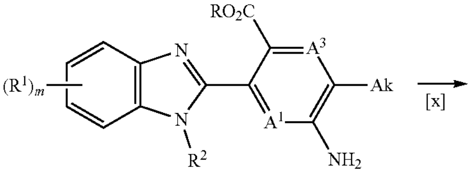

(50)

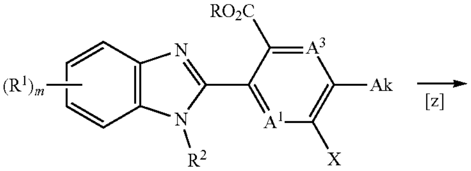

(51)

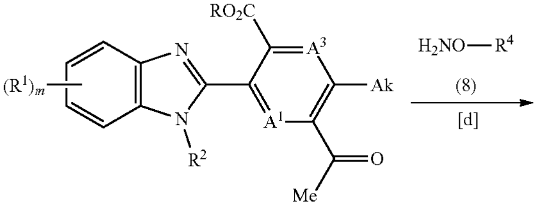

(52)

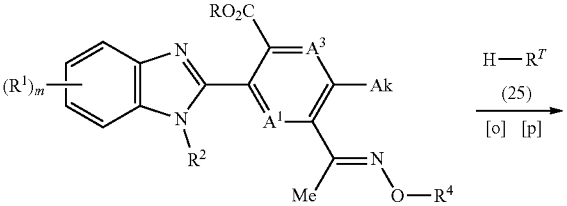

(1-21)

-continued

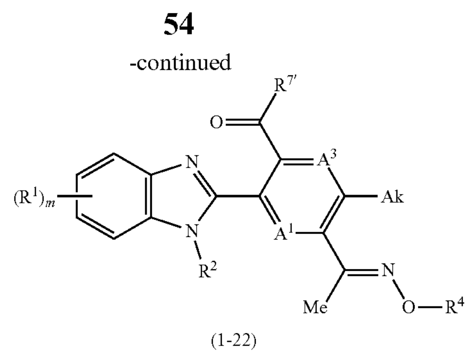

(1-22)

In the formula, $A^1$, $A^3$, $R^1$, $R^2$, $R^4$, and m are the same as above, $R^{7'}$ represents a ($C_1$-$C_6$) alkoxy group, a ($C_2$-$C_6$) alkynyloxy group, or an $R^8(R^9)N$ group wherein $R^8$ and $R^9$ are the same as above, R represents a ($C_1$-$C_4$) alkyl group such as a methyl group or an ethyl group, Ak represents a ($C_1$-$C_6$) alkyl group, and X represents a halogen atom such as fluorine, chlorine, bromine, or iodine.

The compounds represented by the general formulae (1-21) and (1-22) of the present invention can be produced from the compound represented by the general formula (21) through the steps [y] and [z] described below, the step [d] of Production Method 1 above, the steps [o] and [p] of Production Method 6 above, and the steps [v], [w], and [x] of Production Method 10 above.

Production Method at Step [y]

The compound represented by the general formula (48) can be produced by the Curtius rearrangement reaction, i.e., reaction of the compound represented by the general formula (47) with diphenylphosphoric acid amide in the presence of tertiary butyl alcohol according to the method described in J. A. Chem. Soc. 1972, 94, 6203-6205, followed by treatment of the resulting compound in the presence of an acid and an inert solvent.

Examples of the acid that can be used in this reaction include inorganic acids such as hydrochloric acid, sulfuric acid and nitric acid; organic acids such as formic acid, acetic acid, propionic acid, trifluoroacetic acid and benzoic acid; and sulfonic acids such as methanesulfonic acid and trifluoromethanesulfonic acid. The amount of the acid used is usually selected from the range of a 1- to 10-fold molar amount relative to the compound represented by the general formula (47). In some cases, the acid can be used as the solvent as well.

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; chain or cyclic ethers such as diethyl ether, methyl tert-butyl ether, dioxane and tetrahydrofuran; esters such as ethyl acetate; amides such as N,N-dimethylformamide and N,N-dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (47).

The reaction temperature is usually in the range of −10° C. to the boiling point of the inert solvent used. The reaction time varies with the reaction scale and the reaction temperature, but is usually in the range of a few minutes to 48 hours.

After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method at Step [z]

The compound represented by the general formula (52) can be produced by reaction of the compound represented by the general formula (51) with tributyl(1-ethoxyvinyl)tin in the presence of a palladium catalyst and an inert solvent, followed by acid treatment.

Examples of the palladium catalyst that can be used in this reaction include bis(triphenylphosphine)palladium(II) chloride, palladium(II) acetate, palladium(II) chloride, tetrakis (triphenylphosphine)palladium(0), and bis(tri-t-butylphosphine)palladium(0). The amount of the palladium catalyst used is appropriately selected from the range of a 0.001- to 0.5-fold molar amount relative to the compound represented by the general formula (51).

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; chain or cyclic ethers such as diethyl ether, methyl tert-butyl ether, dioxane and tetrahydrofuran; esters such as ethyl acetate; amides such as N, N-dimethylformamide and N,N-dimethylacetamide; ketones such as acetone and methyl ethyl ketone; alcohols such as methanol, ethanol, propanol, butanol, and 2-propanol; and polar solvents such as dimethyl sulfoxide and 1,3-dimethyl-2-imidazolidinone. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (51).

Examples of the acid that can be used in this reaction include inorganic acids such as hydrochloric acid, sulfuric acid and nitric acid; organic acids such as formic acid, acetic acid, propionic acid, trifluoroacetic acid and benzoic acid; and sulfonic acids such as methanesulfonic acid and trifluoromethanesulfonic acid. The amount of the acid used is usually selected as appropriate from the range of a 1- to 10-fold molar amount relative to the compound represented by the general formula (51).

The reaction temperature is usually in the range of 0° C. to the boiling point of the inert solvent used. The reaction time varies with the reaction scale and the reaction temperature, but is usually in the range of a few minutes to 48 hours.

After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method 12

[Chem. 16]

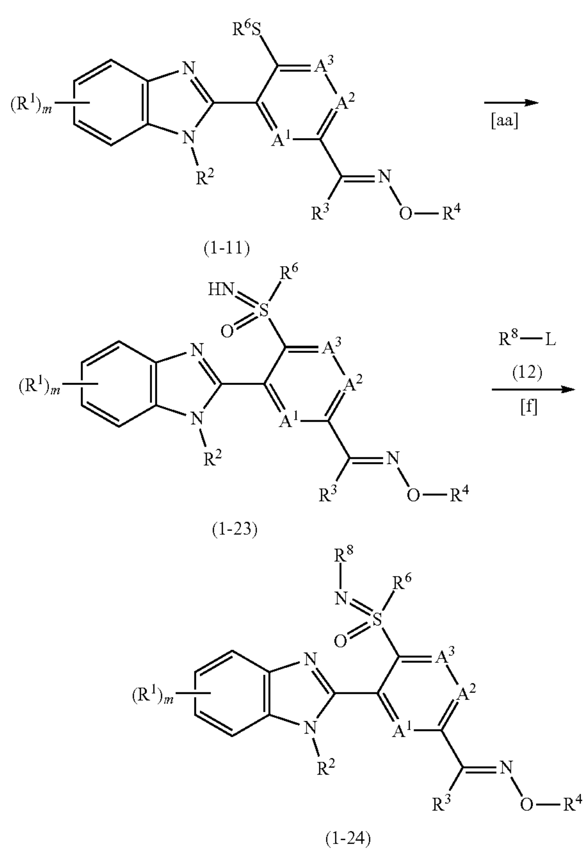

(1-11)

(1-23)

(1-24)

In the formula, $A^1$, $A^2$, $A^3$, $R^1$, $R^2$, $R^3$, $R^4$, $R^6$, $R^8$, and m are the same as above, and L represents a leaving group such as bromine or chlorine.

The compounds represented by the general formulae (1-23) and (1-24) of the present invention can be produced from the compound represented by the general formula (1-11) through the step [aa] described below and the step [f] of Production Method 3 above.

Production Method at Step [Aa]

The compound represented by the general formula (1-23) can be produced by reacting the compound represented by the general formula (1-11) with a nitrogen source in the presence of an inert solvent and a hypervalent iodine reagent.

Examples of the nitrogen source that can be used in this reaction include ammonia, ammonium carbamate, and ammonium carbonate. The amount of the nitrogen source used is usually selected as appropriate from the range of a 1- to 10-fold molar amount relative to the compound represented by the general formula (1-11).

Examples of the hypervalent iodine reagent that can be used in this reaction include diacetoxyiodobenzene. The amount of the hypervalent iodine reagent used is usually selected as appropriate from the range of a 1- to 10-fold molar amount relative to the compound represented by the general formula (1-11).

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; chain or cyclic ethers such as diethyl ether, methyl tert-butyl ether, dioxane and tetrahydrofuran; esters such as ethyl acetate; amides such as N, N-dimethylformamide and N,N-dimethylacetamide; ketones such as acetone and methyl ethyl ketone; alcohols such as methanol, ethanol, propanol, butanol, and 2-propanol; and polar solvents such as acetonitrile, dimethyl sulfoxide, and 1,3-dimethyl-2-imidazolidinone. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (1-11).

The reaction temperature is usually in the range of 0° C. to the boiling point of the inert solvent used. The reaction time varies with the reaction scale and the reaction temperature, but is usually in the range of a few minutes to 48 hours.

After the reaction is completed, the compound of interest is isolated from the post-reaction mixture by the usual method. As needed, recrystallization, column chromatography, etc. can be employed for the purification of the compound of interest.

Production Method 13

[Chem. 17]

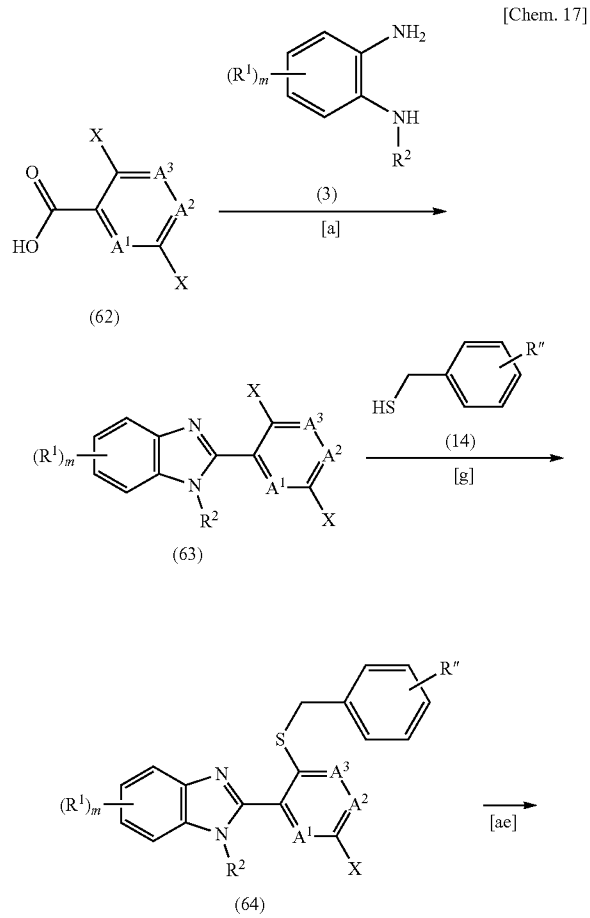

-continued

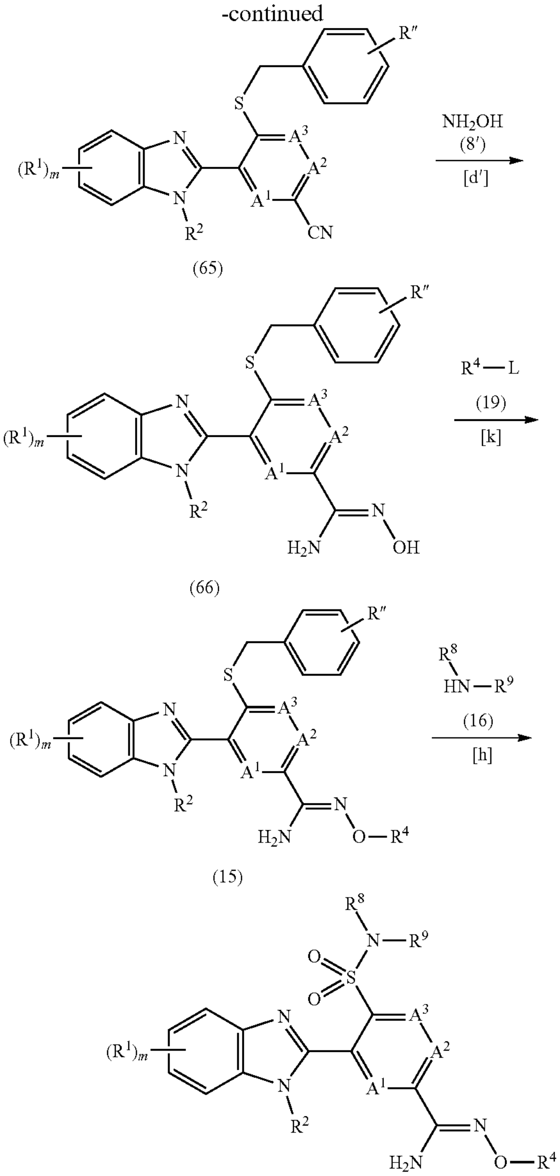

In the formula, $A^1$, $A^2$, $A^3$, $R^1$, $R^2$, $R^4$, $R^8$, $R^9$, and m are the same as above, R" represents a tertiary ($C_4$-$C_6$) alkyl group such as a tert-butyl group or a tri-($C_1$-$C_3$) alkylsilyl group such as a trimethylsilyl group, X represents a halogen atom such as fluorine, chlorine, bromine, or iodine, and L represents a leaving group such as bromine or chlorine.

The compound represented by the general formula (1-7) of the present invention can be produced from the compound represented by the general formula (62) through the step [ae] described below, the step [a] of Production Method 1 above, the steps [g] and [h] of Production Method 4 above, and the steps [d'] and [k] of Production Method 5 above.

Production Method at Step [Ae]

This step is to react the compound represented by the general formula (64) with a cyanizing agent in the presence or absence of a metal catalyst and in the presence of a base and an inert solvent to produce the compound represented by the general formula (65).

Examples of the cyanizing agent that can be used in this reaction include sodium cyanide, potassium cyanide, trimethylsilyl cyanide, and zinc cyanide. The amount of the cyanizing agent used is usually in the range of an about 1- to 10-fold molar amount relative to the compound represented by the general formula (64).

Examples of the base that can be used in this reaction include carbonates such as lithium carbonate, lithium hydrogen carbonate, sodium carbonate, sodium hydrogen carbonate, potassium carbonate, potassium hydrogen carbonate, calcium carbonate and magnesium carbonate; acetates such as lithium acetate, sodium acetate and potassium acetate; and organic bases such as pyridine, picoline, lutidine, triethylamine, tributylamine, N,N-diisopropylethylamine, and 1,4-diazabicyclo[2.2.2]octane. The amount of the base used is usually in the range of an about 1- to 5-fold molar amount relative to the compound represented by the general formula (64).

Examples of the metal catalyst that can be used in this reaction include a palladium catalyst, a nickel catalyst, an iron catalyst, a ruthenium catalyst, a platinum catalyst, a rhodium catalyst and an iridium catalyst. Such a metal catalyst can be used in the form of "a metal", "a supported metal", "a metal salt such as a metal chloride, a metal bromide, a metal iodide, a metal nitrate, a metal sulfate, a metal carbonate, a metal oxalate, a metal acetate and a metal oxide", or "a complex compound such as an olefin complex, a phosphine complex, an amine complex, an ammine complex and an acetylacetonate complex". Preferred is a palladium catalyst.

Examples of the palladium catalyst include palladium metals such as palladium black and palladium sponge; and supported palladium metals such as palladium/alumina, palladium/carbon, palladium/silica and palladium/type Y zeolite. Also included are palladium metal salts such as palladium chloride, palladium bromide, palladium iodide and palladium acetate. Other examples of the palladium catalyst include palladium complex compounds such as π-allylpalladium chloride dimer, palladium acetylacetonate, dichlorobis(acetonitrile)palladium, dichlorobis (benzonitrile)palladium, bis(dibenzylideneacetone) palladium, tris (dibenzylideneacetone) dipalladium, tris (dibenzylideneacetone) dipalladium (chloroform adduct), dichlorodiamine palladium, dichlorobis(triphenylphosphine)palladium, dichlorobis(tricyclohexylphosphine)palladium, tetrakis(triphenylphosphine)palladium, dichloro[1,2-bis(diphenylphosphino)ethane]palladium, dichloro[1,3-bis (diphenylphosphino)propane]palladium, dichloro[1,4-bis (diphenylphosphino)butane]palladium, dichloro[1,1'-bis (diphenylphosphino)ferrocene]palladium and a [(diphenylphosphino)ferrocene]dichloropalladium-dichloromethane complex. The amount of the metal catalyst used is appropriately selected from the range of a 0.001- to 0.5-fold molar amount relative to the compound represented by the general formula (64).

These palladium catalysts may be used alone or in combination with a tertiary phosphine. Examples of the tertiary phosphine that can be used in combination with the palladium catalyst include triphenylphosphine, trimethylphosphine, triethylphosphine, tributylphosphine, tri(tert-butyl) phosphine, tricyclohexylphosphine, tri-o-tolylphosphine, trioctylphosphine, 9,9-dimethyl-4,5-bis(diphenylphosphino) xanthene, 2-(di-tert-butylphosphino)biphenyl, 2-(dicyclohexylphosphino)biphenyl, 1,2-bis(diphenylphosphino)ethane, 1,3-bis(diphenylphosphino)propane, 1,4-bis (diphenylphosphino)butane, 1,1'-bis(diphenylphosphino) ferrocene, (R)-(+)-2,2'-bis(diphenylphosphino)-1,1'-binaphthyl, (S)-(−)-2,2'-bis(diphenylphosphino)-1,1'-binaphthyl and (±)-2,2'-bis(diphenylphosphino)-1,1'-binaphthyl. The amount of the tertiary phosphine used is appropriately selected from the range of a 0.5- to 10-fold molar amount relative to the metal catalyst.

The inert solvent used in this reaction may be any solvent that does not markedly inhibit the reaction, and examples include alcohols such as methanol, ethanol, propanol, butanol, and 2-propanol; chain or cyclic saturated hydrocarbons such as pentane, hexane, and cyclohexane; aromatic hydrocarbons such as benzene, toluene, and xylene; halogenated hydrocarbons such as methylene chloride, chloroform, and carbon tetrachloride; halogenated aromatic hydrocarbons such as chlorobenzene and dichlorobenzene; chain or cyclic ethers such as diethyl ether, methyl tert-butyl ether, dioxane, tetrahydrofuran, and cyclopentyl methyl ether; esters such as ethyl acetate; nitriles such as acetonitrile and propionitrile; amides such as N,N-dimethylformamide and N,N-dimethylacetamide; ketones such as acetone and methyl ethyl ketone; polar solvents such as dimethyl sulfoxide and 1,3-dimethyl-2-imidazolidinone; and water. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (64).

The reaction temperature in this reaction is usually in the range of about 0° C. to the boiling point of the solvent used. The reaction time varies with the reaction scale, the reaction temperature and the like and is not the same in every case, but is basically selected as appropriate from the range of a few minutes to 48 hours.

After the reaction is completed, the compound of interest is isolated from the post-reaction mixture by the usual method. As needed, recrystallization, column chromatography, etc. can be employed for the purification of the compound of interest. The post-reaction mixture may be directly used in the next reaction without isolation of the compound of interest.

Production Method 14

[Chem. 18]

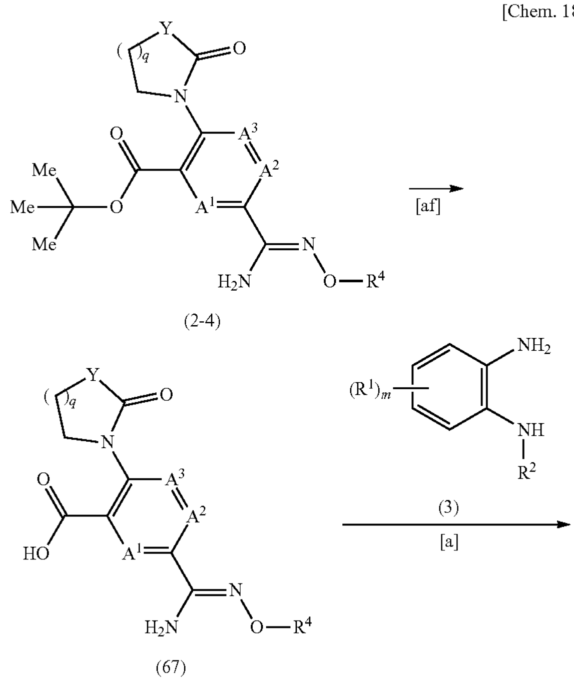

(2-4)

(67)

(3)

-continued

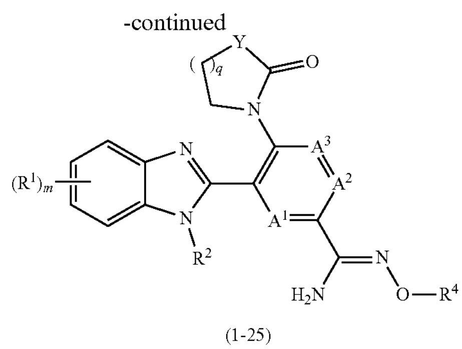

(1-25)

In the formula, $A^1$, $A^2$, $A^3$, $R^1$, $R^2$, $R^4$, and m are the same as above, Y represents a carbon atom, an oxygen atom, a sulfur atom, or a nitrogen atom optionally substituted with a ($C_1$-$C_4$) alkyl group such as a methyl group or an ethyl group, and q represents 1 or 2.

The compound represented by the general formula (1-25) of the present invention can be produced from the compound represented by the general formula (2-4) through the step [af] described below and the step [a] of Production Method 1 above. The production method of the starting compound represented by the general formula (2-4) will be described later.

Production Method at Step [Af]

The compound represented by the general formula (67) can be produced by hydrolyzing the compound represented by the general formula (2-4) in the presence of an acid and an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; sulfonic acids such as methanesulfonic acid, trifluoromethanesulfonic acid and p-toluenesulfonic acid; and phosphoric acid. The amount of the acid used is appropriately selected from the range of a 0.01- to 10-fold molar amount relative to the compound represented by the general formula (2-4). In some cases, the acid can be used as the solvent as well.

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; chain or cyclic ethers such as diethyl ether, methyl tert-butyl ether, dioxane and tetrahydrofuran; esters such as ethyl acetate; amides such as N,N-dimethylformamide and N,N-dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (2-4). In the case where the acid is used also as the solvent, it is not necessary to use another solvent.

The reaction temperature may be in the range of room temperature to the boiling point of the inert solvent used. The reaction time varies with the reaction scale and the reaction temperature, but is basically selected as appropriate from the range of a few minutes to 48 hours.

After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method 15

[Chem. 19]

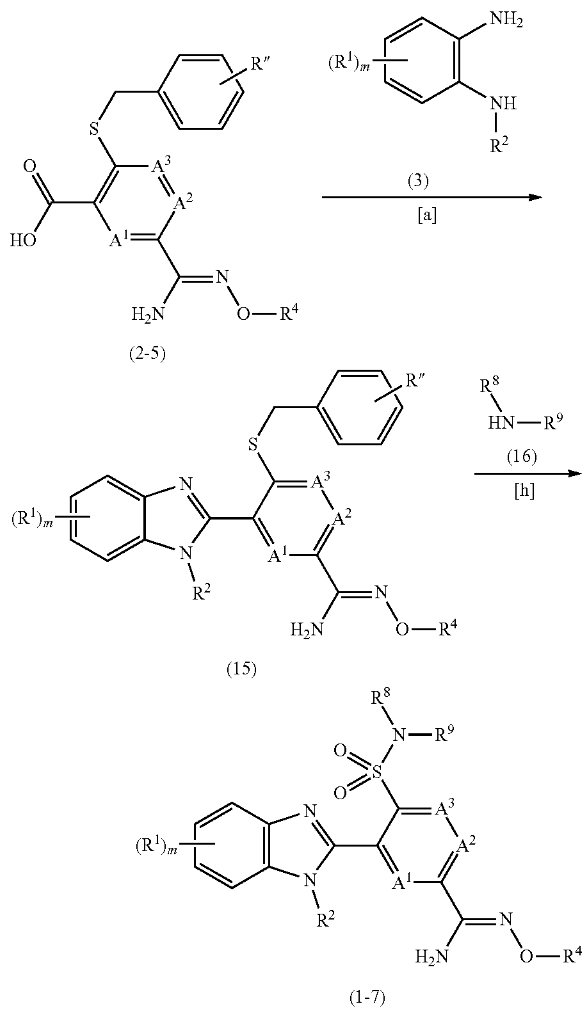

(2-5)

(15)

(1-7)

In the formula, $A^1$, $A^2$, $A^3$, $R^1$, $R^7$, $R^4$, $R^8$, $R^9$, and m are the same as above, and R" represents a tertiary ($C_4$-$C_6$) alkyl group such as a tert-butyl group or a tri-($C_1$-$C_3$) alkylsilyl group such as a trimethylsilyl group.

The compound represented by the general formula (1-7) of the present invention can be produced from the compound represented by the general formula (2-5) through the step [a] of Production Method 1 above and the step [h] of Production Method 4 above. The production method of the starting compound represented by the general formula (2-5) will be described later.

Production Method 16

[Chem. 20]

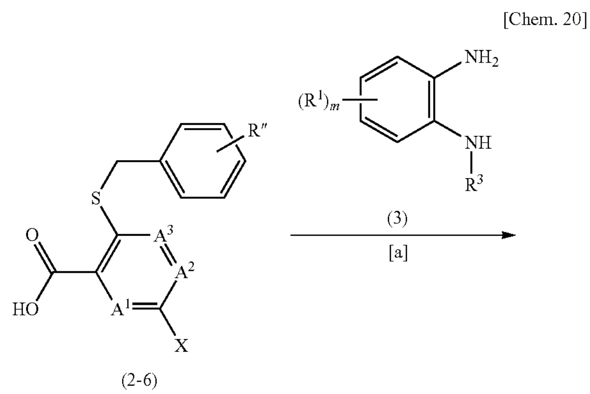

(2-6)

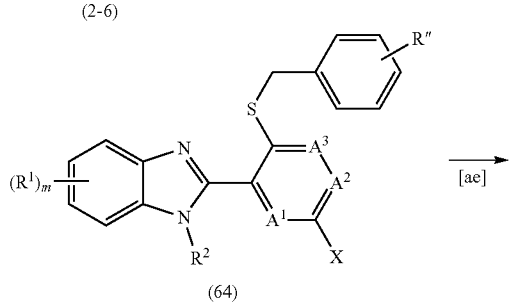

(64)

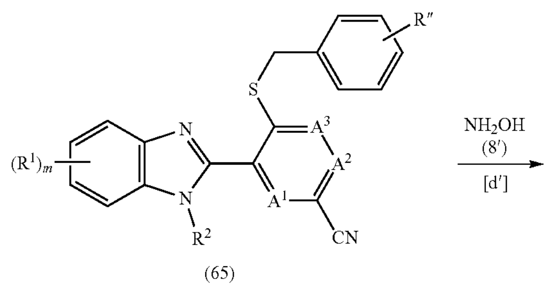

(65)

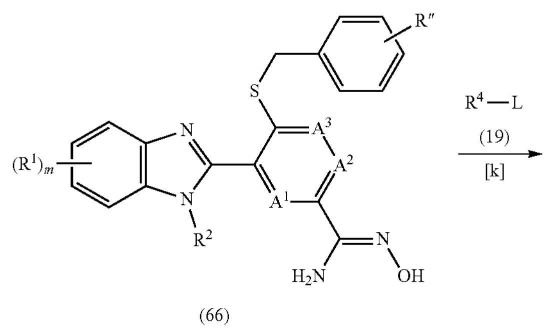

(66)

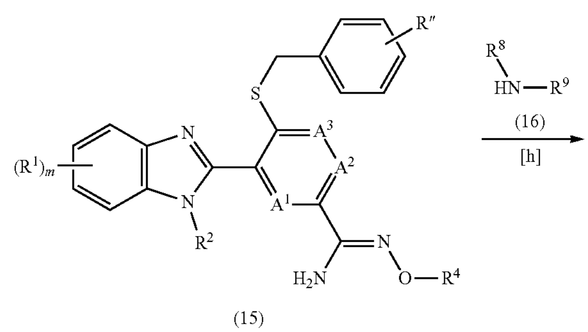

(15)

-continued

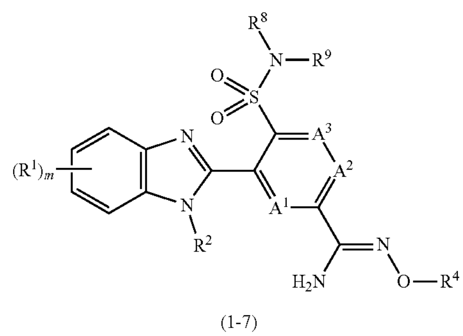

(1-7)

In the formula, $A^1$, $A^2$, $A^3$, $R^1$, $R^2$, $R^4$, $R^8$, $R^9$, and m are the same as above, R" represents a tertiary ($C_4$-$C_6$) alkyl group such as a tert-butyl group or a tri-($C_1$-$C_3$) alkylsilyl group such as a trimethylsilyl group, X represents a halogen atom such as fluorine, chlorine, bromine, or iodine, and L represents a leaving group such as bromine or chlorine.

The compound represented by the general formula (1-7) of the present invention can be produced from the compound represented by the general formula (2-6) through the step [a] of Production Method 1 above, the step [h] of Production Method 4 above, the steps [d'] and [k] of Production Method 5 above, and the step [ae] of Production Method 4 above. The production method of the starting compound represented by the general formula (2-6) will be described later.

Production Method of Compound Represented by General Formula (2-1)

[Chem. 21]

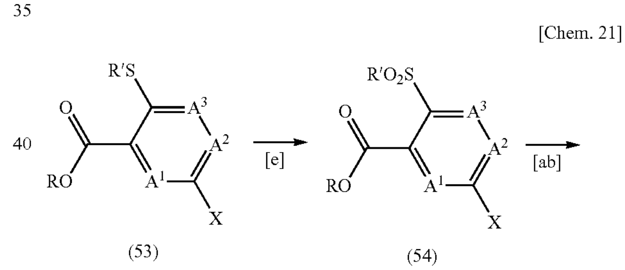

(53) (54)

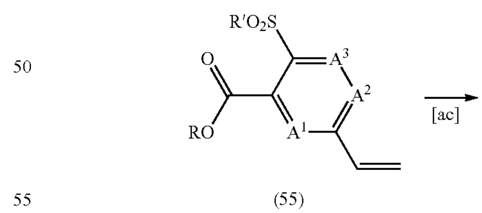

(55)

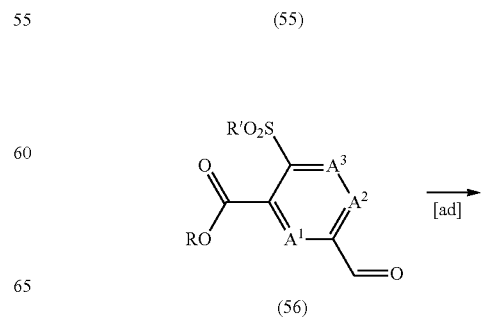

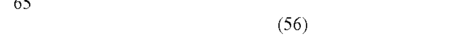

(56)

-continued

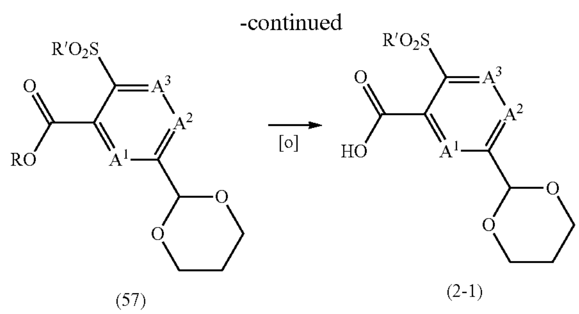

(57) (2-1)

In the formula, $A^1$, $A^2$, and $A^3$ are the same as above, R and R' each represent a ($C_1$-$C_4$) alkyl group such as a methyl group or an ethyl group, and X represents a halogen atom such as fluorine, chlorine, bromine, or iodine.

The starting compound of Production Method 1, represented by the general formula (2-1), can be produced from the compound represented by the general formula (53) through the steps [ab], [ac], and [ad] described below, the step [e] of Production Method 1 above, and the step [o] of Production Method 6 above.

Production Method at Step [Ab]

The compound represented by the general formula (55) can be produced by reacting the compound represented by the general formula (54) with a vinyl metal compound in the presence of an inert solvent, a metal catalyst, and a base.

Examples of the metal catalyst that can be used in this reaction include a palladium catalyst, a nickel catalyst, an iron catalyst, a ruthenium catalyst, a platinum catalyst, a rhodium catalyst and an iridium catalyst. Such a metal catalyst can be used in the form of "a metal", "a supported metal", "a metal salt such as a metal chloride, a metal bromide, a metal iodide, a metal nitrate, a metal sulfate, a metal carbonate, a metal oxalate, a metal acetate and a metal oxide", or "a complex compound such as an olefin complex, a phosphine complex, an amine complex, an ammine complex and an acetylacetonate complex". Preferred is a palladium catalyst.

Examples of the palladium catalyst include palladium metals such as palladium black and palladium sponge; and supported palladium metals such as palladium/alumina, palladium/carbon, palladium/silica and palladium/type Y zeolite. Also included are palladium metal salts such as palladium chloride, palladium bromide, palladium iodide and palladium acetate. Other examples of the palladium catalyst include palladium complex compounds such as n-allylpalladium chloride dimer, palladium acetylacetonate, dichlorobis(acetonitrile)palladium, dichlorobis (benzonitrile)palladium, bis(dibenzylideneacetone) palladium, tris (dibenzylideneacetone) dipalladium, tris (dibenzylideneacetone)dipalladium (chloroform adduct), dichlorodiamine palladium, dichlorobis(triphenylphosphine) palladium, dichlorobis(tricyclohexylphosphine) palladium, tetrakis(triphenylphosphine)palladium, dichloro[1, 2-bis(diphenylphosphino)ethane]palladium, dichloro[1,3-bis(diphenylphosphino)propane]palladium, dichloro[1,4-bis (diphenylphosphino)butane]palladium, dichloro[1,1'-bis (diphenylphosphino)ferrocene]palladium and a [(diphenylphosphino)ferrocene]dichloropalladium-dichloromethane complex. The amount of the palladium catalyst used is appropriately selected from the range of a 0.001- to 0.5-fold molar amount relative to the compound represented by the general formula (54).

These palladium catalysts may be used alone or in combination with a tertiary phosphine. Examples of the tertiary phosphine that can be used in combination with the palladium catalyst include triphenylphosphine, trimethylphosphine, triethylphosphine, tributylphosphine, tri(tert-butyl) phosphine, tricyclohexylphosphine, tri-o-tolylphosphine, trioctylphosphine, 9,9-dimethyl-4,5-bis(diphenylphosphino) xanthene, 2-(di-tert-butylphosphino)biphenyl, 2-(dicyclohexylphosphino)biphenyl, 1,2-bis(diphenylphosphino)ethane, 1,3-bis(diphenylphosphino)propane, 1,4-bis (diphenylphosphino)butane, 1,1'-bis(diphenylphosphino) ferrocene, (R)-(+)-2,2'-bis(diphenylphosphino)-1,1'-binaphthyl, (S)-(−)-2,2'-bis(diphenylphosphino)-1,1'-binaphthyl and (±)-2,2'-bis(diphenyphosphino)-1,1'-binaphthyl. The amount of the tertiary phosphine used is appropriately selected from the range of a 0.5- to 10-fold molar amount relative to the palladium catalyst.

Examples of the vinyl metal compound that can be used in this reaction include vinylmagnesium bromide, vinylmagnesium chloride, vinylzinc chloride, tributylvinyltin, potassium vinyltrifluoroborate, vinylboronic acid, vinylboronic anhydride, vinylboronic acid 2-methyl-2,4-pentanediol ester, vinylboronic acid pinacol ester and triethoxyvinylsilane. Preferred is vinylboronic acid. The amount of the vinyl metal compound used is appropriately selected from the range of a 0.8- to 3-fold molar amount relative to the compound represented by the general formula (54).

Examples of the base that can be used in this reaction include inorganic bases such as sodium hydroxide, potassium hydroxide, sodium carbonate, potassium carbonate, cesium carbonate, sodium hydrogen carbonate and potassium hydrogen carbonate; alkali metal hydrides such as sodium hydride and potassium hydride; and alkoxides such as sodium methoxide, sodium ethoxide and potassium tert-butoxide. The amount of the base used is usually in the range of an about 1- to 5-fold molar amount relative to the compound represented by the general formula (54).

The inert solvent used in this reaction may be any solvent that does not markedly inhibit the reaction, and examples include alcohols such as methanol, ethanol, propanol, butanol and 2-propanol; chain or cyclic ethers such as diethyl ether, tetrahydrofuran, dioxane and 1,2-dimethoxyethane (DME); aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; polar solvents such as N,N-dimethylformamide, N,N-dimethylacetamide, dimethyl sulfoxide and 1,3-dimethyl-2-imidazolidinone; and water. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (54).

The reaction temperature in this reaction is usually in the range of about 0° C. to the boiling point of the solvent used. The reaction time varies with the reaction scale, the reaction temperature and the like, but is basically selected as appropriate from the range of a few minutes to 48 hours. This reaction may be conducted under the atmosphere of an inert gas such as nitrogen gas and argon gas. After the reaction is completed, the compound of interest is isolated from the post-reaction mixture by the usual method. As needed, recrystallization, column chromatography, etc. can be employed for the purification of the compound of interest.

The post-reaction mixture may be directly used in the next step without isolation of the compound of interest.

Production Method at Step [Ac]

The compound represented by the general formula (55) is made into a diol in the presence of osmium tetroxide and an oxidizing agent according to the method described in "Lecture of Experimental Chemistry", 4th edition, vol. 23, Organic Chemistry V: Oxidation Reaction (published by Maruzen Publishing Co., Ltd.). The diol is then reacted with aperiodic acid compound in the presence of an inert solvent according to the method described in "New Lecture of Experimental Chemistry", vol. 15, Oxidation and Reduction I-1 (published by Maruzen Publishing Co., Ltd.) to yield the compound represented by the general formula (56) of the present invention. After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method at Step [Ad]

The formyl group of the compound represented by the general formula (56) is converted to a cyclic acetal group according to the method described in Greene's Productive Groups in Organic Synthesis (4th Edition) to yield the compound represented by the general formula (57) of the present invention. After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method of Compound Represented by General Formula (2-2)

[Chem. 22]

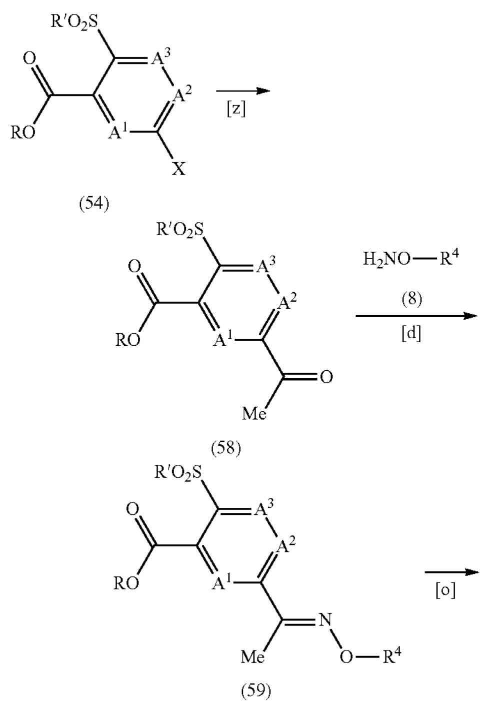

(54)

(58)

(59)

-continued

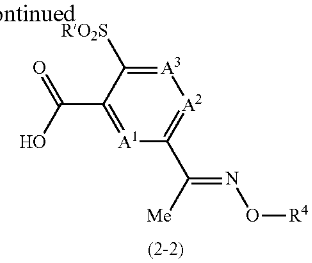

(2-2)

In the formula, $A^1$, $A^2$, $A^3$, and $R^4$ are the same as above, R and R' each represent a ($C_1$-$C_4$) alkyl group such as a methyl group or an ethyl group, and X represents a halogen atom such as fluorine, chlorine, bromine, or iodine.

The starting compound of Production Method 2, represented by the general formula (2-2), can be produced from the compound represented by the general formula (54) through the step [d] of Production Method 1 above, the step [o] of Production Method 6 above, and the step [z] of Production Method 11 above.

Production Method of Compound Represented by General Formula (2-3)

[Chem. 23]

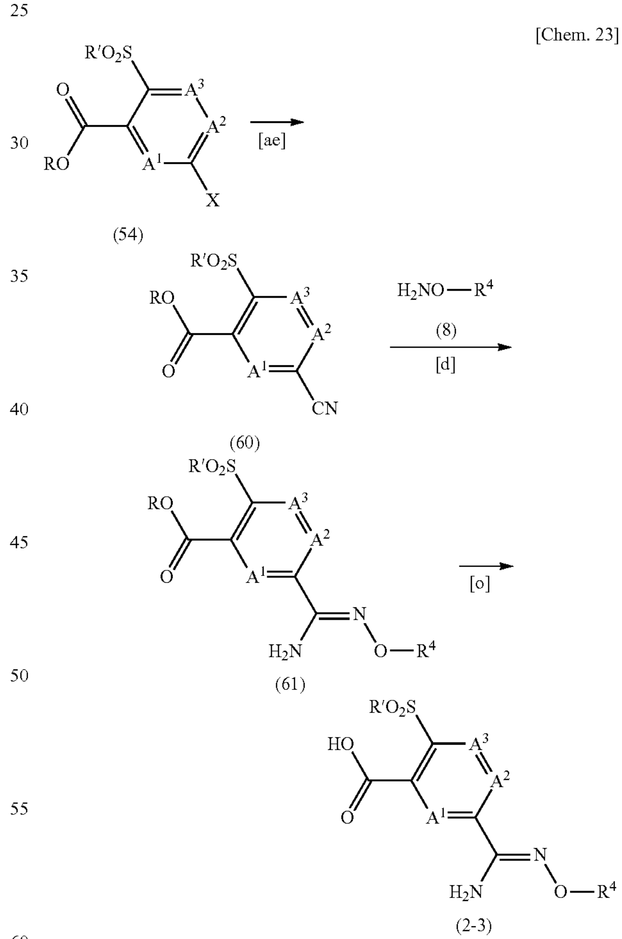

(54)

(60)

(61)

(2-3)

In the formula, $A^1$, $A^2$, $A^3$, and $R^4$ are the same as above, R and R' each represent a ($C_1$-$C_4$) alkyl group such as a methyl group or an ethyl group, and X represents a halogen atom such as fluorine, chlorine, bromine, or iodine.

The starting compound of Production Method 3, represented by the general formula (2-3), can be produced from the compound represented by the general formula (54) through the step [d] of Production Method 1 above, the step [o] of Production Method 6 above, and the step [ae] of Production Method 13 above.

Production Method of Compound Represented by General Formula (2-4)

[Chem. 24]

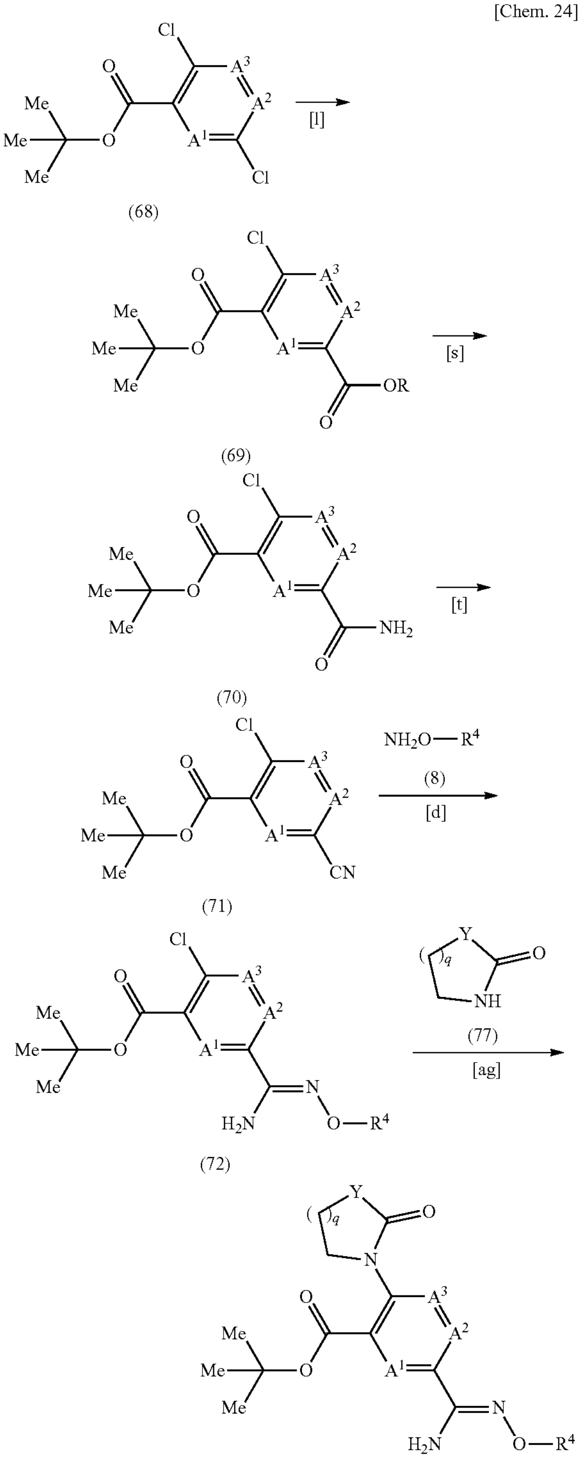

(68)

(69)

(70)

(71)

(72)

(2-4)

In the formula, $A^1$, $A^2$, $A^3$, and $R^4$ are the same as above, ID R represents a $(C_1-C_4)$ alkyl group such as a methyl group or an ethyl group, Y represents a carbon atom, an oxygen atom, a sulfur atom, or a nitrogen atom optionally substituted with a $(C_1-C_4)$ alkyl group such as a methyl group or an ethyl group, and q represents 1 or 2.

The starting compound of Production Method 14, represented by the general formula (2-4), can be produced from the compound represented by the general formula (68) through the step [ag] described below, the step [d] of Production Method 1 above, the step [1] of Production Method 6 above, and the steps [s] and [t] of Production Method 8 above.

Production Method at Step [Ag]

The compound represented by the general formula (2-4) can be produced by reacting the compound represented by the general formula (72) with the compound represented by the general formula (77) in the presence of a metal catalyst, a base and an inert solvent.

Examples of the metal catalyst that can be used in this reaction include a palladium catalyst, a nickel catalyst, an iron catalyst, a ruthenium catalyst, a platinum catalyst, a rhodium catalyst and an iridium catalyst. Such a metal catalyst can be used in the form of “a metal”, “a supported metal”, “a metal salt such as a metal chloride, a metal bromide, a metal iodide, a metal nitrate, a metal sulfate, a metal carbonate, a metal oxalate, a metal acetate and a metal oxide”, or “a complex compound such as an olefin complex, a phosphine complex, an amine complex, an ammine complex and an acetylacetonate complex”. Preferred is a palladium catalyst.

Examples of the palladium catalyst include palladium metals such as palladium black and palladium sponge; and supported palladium metals such as palladium/alumina, palladium/carbon, palladium/silica and palladium/type Y zeolite. Also included are palladium metal salts such as palladium chloride, palladium bromide, palladium iodide and palladium acetate. Other examples of the palladium catalyst include palladium complex compounds such as x-allylpalladium chloride dimer, palladium acetylacetonate, dichlorobis(acetonitrile)palladium, dichlorobis (benzonitrile)palladium, bis(dibenzylideneacetone) palladium, tris (dibenzylideneacetone) dipalladium, tris (dibenzylideneacetone) dipalladium (chloroform adduct), dichlorodiamine palladium, dichlorobis(triphenylphosphine)palladium, dichlorobis(tricyclohexylphosphine)palladium, tetrakis(triphenylphosphine)palladium, dichloro[1,2-bis(diphenylphosphino)ethane]palladium, dichloro[1,3-bis (diphenylphosphino)propane]palladium, dichloro[1,4-bis (diphenylphosphino)butane]palladium, dichloro[1,1'-bis (diphenylphosphino)ferrocene]palladium and a [(diphenylphosphino)ferrocene]dichloropalladium-dichloromethane complex. The amount of the metal catalyst used is appropriately selected from the range of a 0.001- to 0.5-fold molar amount relative to the compound represented by the general formula (72).

These palladium catalysts may be used alone or in combination with a tertiary phosphine. Examples of the tertiary phosphine that can be used in combination with the palladium catalyst include triphenylphosphine, trimethylphosphine, triethylphosphine, tributylphosphine, tri(tert-butyl) phosphine, tricyclohexylphosphine, tri-o-tolylphosphine, trioctylphosphine, 9,9-dimethyl-4,5-bis(diphenylphosphino) xanthene, 2-(di-tert-butylphosphino)biphenyl, 2-(dicyclohexylphosphino)biphenyl, 1,2-bis(diphenylphosphino)ethane, 1,3-bis(diphenylphosphino)propane, 1,4-bis (diphenylphosphino)butane, 1,1'-bis(diphenylphosphino)

ferrocene, (R)-(+)-2,2'-bis(diphenylphosphino)-1,1'-binaphthyl, (S)-(−)-2,2'-bis(diphenylphosphino)-1,1'-binaphthyl and (±)-2,2'-bis(diphenylphosphino)-1,1'-binaphthyl. The amount of the tertiary phosphine used is appropriately selected from the range of a 0.5- to 10-fold molar amount relative to the metal catalyst.

Examples of the base that can be used in this reaction include inorganic bases such as sodium hydroxide, potassium hydroxide, sodium carbonate, potassium carbonate, cesium carbonate, sodium hydrogen carbonate and potassium hydrogen carbonate; alkali metal hydrides such as sodium hydride and potassium hydride; and alkoxides such as sodium methoxide, sodium ethoxide and potassium tert-butoxide. The amount of the base used is usually in the range of an about 1- to 5-fold molar amount relative to the compound represented by the general formula (72).

The inert solvent used in this reaction may be any solvent that does not markedly inhibit the reaction, and examples include alcohols such as methanol, ethanol, propanol, butanol and 2-propanol; chain or cyclic ethers such as diethyl ether, tetrahydrofuran, dioxane and 1,2-dimethoxyethane (DME); aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; polar solvents such as N,N-dimethylformamide, N,N-dimethylacetamide, dimethyl sulfoxide and 1,3-dimethyl-2-imidazolidinone; and water. One of these inert solvents may be used alone, and also two or more of them may be used as a mixture. The amount of the inert solvent used is not particularly limited as long as it is sufficient to dissolve the reaction reagents, and is appropriately selected from the range of 0.5 L to 100 L relative to 1 mole of the compound represented by the general formula (72).

Since this reaction is an equimolar reaction of the compounds, they are basically used in equimolar amounts, but either of them may be used in an excess amount.

The reaction temperature in this reaction is usually in the range of about 0° C. to the boiling point of the solvent used. The reaction time varies with the reaction scale, the reaction temperature and the like, but is basically selected as appropriate from the range of a few minutes to 48 hours. This reaction may be conducted under the atmosphere of an inert gas such as nitrogen gas and argon gas.

After the reaction is completed, the compound of interest is isolated from the post-reaction mixture by the usual method. As needed, recrystallization, column chromatography, etc. can be employed for the purification of the compound of interest. The post-reaction mixture may be directly used in the next step without isolation of the compound of interest.

Production Method of Compound Represented by General Formula (2-5)

[Chem. 25]

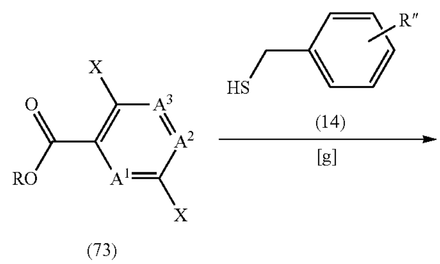

(73)

-continued

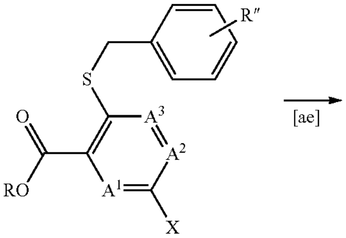

(74)

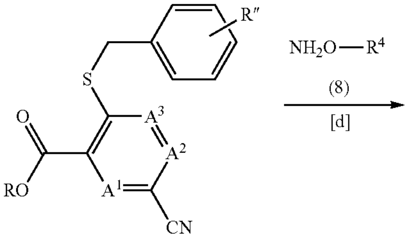

(75)

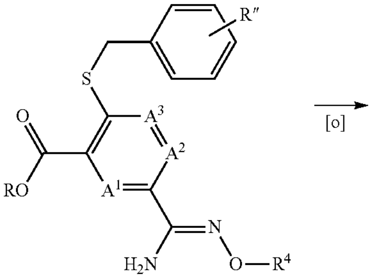

(76)

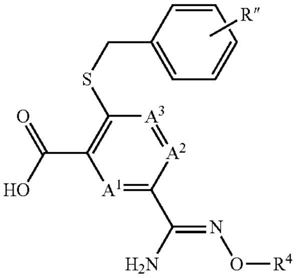

(2-5)

In the formula, $A^1$, $A^2$, $A^3$, and $R^4$ are the same as above, R represents a ($C_1$-$C_4$) alkyl group such as a methyl group or an ethyl group, R" represents a tertiary ($C_4$-$C_6$) alkyl group such as a tert-butyl group or a tri-($C_1$-$C_3$) alkylsilyl group such as a trimethylsilyl group, and X represents a halogen atom such as fluorine, chlorine, bromine, or iodine. The starting compound of Production Method 15, represented by the general formula (2-5), can be produced from the compound represented by the general formula (73) through the step [g] of Production Method 4 above, the step

[d] of Production Method 5 above, the step [o] of Production Method 6 above, and the step [ae] of Production Method 13 above.

Production Method of Compound Represented by General Formula (2-6)

[Chem. 26]

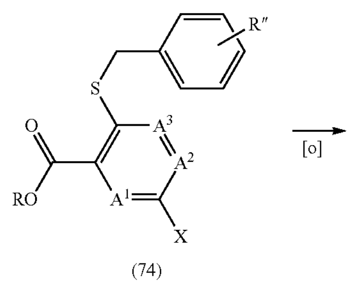

(74)

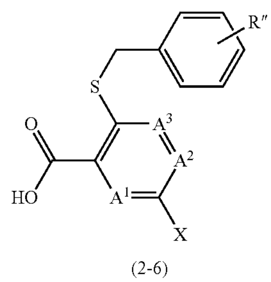

(2-6)

In the formula, $A^1$, $A^2$, and $A^3$ are the same as above, R represents a ($C_1$-$C_4$) alkyl group such as a methyl group or an ethyl group, R' represents a tertiary ($C_4$-$C_6$) alkyl group such as a tert-butyl group or a tri-($C_1$-$C_3$) alkylsilyl group such as a trimethylsilyl group, and X represents a halogen atom such as fluorine, chlorine, bromine, or iodine.

The starting compound of Production Method 16, represented by the general formula (2-6), can be produced from the compound represented by the general formula (74) through the step [o] of Production Method 6 above.

Representative examples of the compound represented by the general formula (1) of the present invention are shown in Tables 1 to 8, but the present invention is not limited thereto. Specific examples of the compound of the present invention are shown below. In the tables below, Me stands for a methyl group, Et stands for an ethyl group, i-Pr stands for an isopropyl group, n-Pr stands for a n-propyl group, c-Pr stands for a cyclopropyl group, n-Bu stands for a n-butyl group, i-Bu stands for an isobutyl group, c-Bu stands for a cyclobutyl group, t-Bu stands for a tert-butyl group, Ac stands for an acetyl group, Ph stands for a phenyl group, Bn stands for a benzyl group, and TMS stands for a trimethylsilyl group. Shown in the column of "Physical property value" is a melting point (° C.), a refractive index ($n_D$), or "$^1$H-NMR". The number in the parentheses for the refractive index represents measurement temperature (° C.). $^1$H-NMR data are shown in Table 10.

[Chem. 27]

(1a)

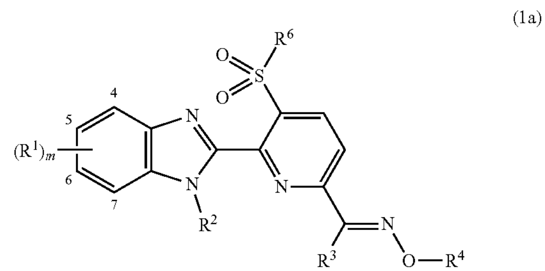

The position numbers in the table are the numbers designated in the general formula (1a).

TABLE 1-1

| Compound No. | $R^1$ | $R^2$ | $R^3$ | $R^4$ | $R^6$ | Physical property value |
|---|---|---|---|---|---|---|
| 1-1 | H | H | H | Et | Et | |
| 1-2 | H | H | H | i-Pr | Et | |
| 1-3 | H | H | H | $CH_2CF_3$ | Et | 167-168 |
| 1-4 | H | Me | H | Et | Et | |
| 1-5 | H | Me | H | i-Pr | Et | |
| 1-6 | H | Me | H | $CH_2CF_3$ | Et | NMR |
| 1-7 | H | Me | Me | Et | Me | NMR |
| 1-8 | H | Me | Me | i-Pr | Me | |
| 1-9 | H | Me | Me | $CH_2CF_3$ | Me | |
| 1-10 | H | Me | $NH_2$ | H | Me | NMR |
| 1-11 | H | Me | $NH_2$ | Et | Me | 78-80 |
| 1-12 | H | Me | $NH_2$ | n-Pr | Me | 131-132 |
| 1-13 | H | Me | $NH_2$ | i-Pr | Me | 178-180 |
| 1-14 | H | Me | $NH_2$ | $CH_2CF_3$ | Me | |
| 1-15 | H | Me | $NH_2$ | Et | NHMe | 97-98 |
| 1-16 | H | Me | $NH_2$ | n-Pr | NHMe | NMR |
| 1-17 | H | Me | $NH_2$ | i-Pr | NHMe | 98-99 |
| 1-18 | H | Me | $NH_2$ | $CH_2CF_3$ | NHMe | 170-171 |
| 1-19 | H | Me | $NHCOCF_3$ | Et | Me | 78-80 |
| 1-20 | H | Me | $NHCOCF_3$ | i-Pr | Me | |
| 1-21 | H | Me | $NHCOCF_3$ | $CH_2CF_3$ | Me | |
| 1-22 | H | Me | NHMe | Et | Me | NMR |
| 1-23 | H | Me | NHMe | i-Pr | Me | |
| 1-24 | H | Me | NHMe | $CH_2CF_3$ | Me | |
| 1-25 | H | Et | H | i-Pr | Et | |
| 1-26 | H | Et | H | $CH_2CF_3$ | Et | NMR |
| 1-27 | H | i-Pr | H | Et | Et | |
| 1-28 | H | i-Pr | H | i-Pr | Et | |
| 1-29 | H | i-Pr | H | $CH_2CF_3$ | Et | NMR |
| 1-30 | H | $CH_2C{\equiv}CH$ | H | Et | Et | |

TABLE 1-2

| Compound No. | $R^1$ | $R^2$ | $R^3$ | $R^4$ | $R^6$ | Physical property value |
|---|---|---|---|---|---|---|
| 1-31 | H | $CH_2C{\equiv}CH$ | H | i-Pr | Et | |
| 1-32 | H | $CH_2C{\equiv}CH$ | H | $CH_2CF_3$ | Et | NMR |
| 1-33 | H | $CH_2CF_3$ | H | Et | Et | |
| 1-34 | H | $CH_2CF_3$ | H | i-Pr | Et | |
| 1-35 | H | $CH_2CF_3$ | H | $CH_2CF_3$ | Et | NMR |
| 1-36 | H | $CH_2OCH_3$ | H | Et | Et | |
| 1-37 | H | $CH_2OCH_3$ | H | i-Pr | Et | |
| 1-38 | H | $CH_2OCH_3$ | H | $CH_2CF_3$ | Et | NMR |
| 1-39 | 4-Br | Me | H | Et | Et | NMR |
| 1-40 | 4-Br | Me | H | i-Pr | Et | |
| 1-41 | 4-Br | Me | H | $CH_2CF_3$ | Et | NMR |
| 1-42 | 4-Br | Me | Me | Et | Et | |
| 1-43 | 4-Br | Me | Me | i-Pr | Et | |
| 1-44 | 4-Br | Me | Me | $CH_2CF_3$ | Et | |
| 1-45 | 4-Br | Me | $NH_2$ | Et | Et | |

TABLE 1-2-continued

| Compound No. | $R^1$ | $R^2$ | $R^3$ | $R^4$ | $R^6$ | Physical property value |
|---|---|---|---|---|---|---|
| 1-46 | 4-Br | Me | $NH_2$ | i-Pr | Et | |
| 1-47 | 4-Br | Me | $NH_2$ | $CH_2CF_3$ | Et | |
| 1-48 | 4-Me | Me | H | Et | Et | |
| 1-49 | 4-Me | Me | H | i-Pr | Et | |
| 1-50 | 4-Me | Me | H | $CH_2CF_3$ | Et | |
| 1-51 | 4-Me | Me | Me | Et | Me | NMR |
| 1-52 | 4-Me | Me | Me | i-Pr | Me | |
| 1-53 | 4-Me | Me | Me | $CH_2CF_3$ | Me | |
| 1-54 | 4-Me | Me | $NH_2$ | Et | Me | 170-171 |
| 1-55 | 4-Me | Me | $NH_2$ | i-Pr | Me | |
| 1-56 | 4-Me | Me | $NH_2$ | $CH_2CF_3$ | Me | |
| 1-57 | 4-Me | Me | $NH_2$ | Et | NHMe | 187-188 |
| 1-58 | 4-Et | Me | $NH_2$ | Et | Me | 214-215 |
| 1-59 | 4-Et | Me | $NH_2$ | i-Pr | Me | |
| 1-60 | 4-Et | Me | $NH_2$ | $CH_2CF_3$ | Me | |

TABLE 1-3

| Compound No. | $R^1$ | $R^2$ | $R^3$ | $R^4$ | $R^6$ | Physical property value |
|---|---|---|---|---|---|---|
| 1-61 | 4-Et | Me | $NH_2$ | Et | NHMe | NMR |
| 1-62 | 5-F | Me | H | Et | Me | |
| 1-63 | 5-F | Me | Me | Et | Me | NMR |
| 1-64 | 5-F | Me | $NH_2$ | Et | Me | 155-156 |
| 1-65 | 5-F | Me | $NH_2$ | n-Pr | Me | 110-111 |
| 1-66 | 5-F | Me | $NH_2$ | Et | NHMe | NMR |
| 1-67 | 5-F | Me | $NH_2$ | n-Pr | NHMe | NMR |
| 1-68 | 5-Cl | Me | H | Et | Me | |
| 1-69 | 5-Cl | Me | Me | Et | Me | 143-144 |
| 1-70 | 5-Cl | Me | $NH_2$ | Me | Me | 218-221 |
| 1-71 | 5-Cl | Me | $NH_2$ | Et | Me | 176-177 |
| 1-72 | 5-Cl | Me | H | i-Pr | Me | |
| 1-73 | 5-Cl | Me | Me | i-Pr | Me | |
| 1-74 | 5-Cl | Me | $NH_2$ | i-Pr | Me | 172-173 |
| 1-75 | 5-Cl | Me | $NH_2$ | Me | NHMe | 190-191 |
| 1-76 | 5-Cl | Me | $NH_2$ | Et | NHMe | 203-204 |
| 1-77 | 5-Cl | Me | $NH_2$ | i-Pr | NHMe | 190-191 |
| 1-78 | 5-Cl | Me | $NH_2$ | $CH_2CF_3$ | NHMe | |
| 1-79 | 5-Cl | Me | $NH_2$ | Et | $NMe_2$ | |
| 1-80 | 5-Cl | Me | $NH_2$ | i-Pr | $NMe_2$ | 154-156 |
| 1-81 | 5-Br | H | H | Et | Et | |
| 1-82 | 5-Br | H | H | i-Pr | Et | |
| 1-83 | 5-Br | H | H | $CH_2CF_3$ | Et | 187-188 |
| 1-84 | 5-Br | Me | H | Et | Et | 152-153 |
| 1-85 | 5-Br | Me | H | i-Pr | Et | |
| 1-86 | 5-Br | Me | H | $CH_2CF_3$ | Et | NMR |
| 1-87 | 5-Br | Me | Me | Et | Me | 171-172 |
| 1-88 | 5-Br | Me | Me | i-Pr | Me | |
| 1-89 | 5-Br | Me | Me | $CH_2CF_3$ | Me | |
| 1-90 | 5-Br | Me | $NH_2$ | Et | Me | 151-152 |

TABLE 1-4

| Compound No. | $R^1$ | $R^2$ | $R^3$ | $R^4$ | $R^6$ | Physical property value |
|---|---|---|---|---|---|---|
| 1-91 | 5-Br | Me | $NH_2$ | i-Pr | Me | |
| 1-92 | 5-Br | Me | $NH_2$ | $CH_2CF_3$ | Me | |
| 1-93 | 5-Br | Me | $NH_2$ | Et | NHMe | |
| 1-94 | 5-Br | Me | $NH_2$ | i-Pr | NHMe | |
| 1-95 | 5-Br | Me | $NH_2$ | $CH_2CF_3$ | NHMe | |
| 1-96 | 5-Me | H | H | Et | Me | |
| 1-97 | 5-Me | H | Me | Et | Me | |
| 1-98 | 5-Me | H | $NH_2$ | Et | Me | 226-227 |
| 1-99 | 5-Me | Me | H | Me | Me | |
| 1-100 | 5-Me | Me | Me | Me | Me | |
| 1-101 | 5-Me | Me | $NH_2$ | H | Me | NMR |
| 1-102 | 5-Me | Me | $NH_2$ | Me | Me | 170-171 |

TABLE 1-4-continued

| Compound No. | $R^1$ | $R^2$ | $R^3$ | $R^4$ | $R^6$ | Physical property value |
|---|---|---|---|---|---|---|
| 1-103 | 5-Me | Me | $NH_2$ | i-Pr | Me | 171-172 |
| 1-104 | 5-Me | Me | $NH_2$ | n-Pr | Me | 188-189 |
| 1-105 | 5-Me | Me | $NH_2$ | $CH_2CF_3$ | Me | |
| 1-106 | 5-Me | Me | H | Et | Me | |
| 1-107 | 5-Me | Me | Me | Et | Me | 144-145 |
| 1-108 | 5-Me | Me | $NH_2$ | Et | Me | 80-83 |
| 1-109 | 5-Me | Me | $NHCOCF_3$ | Et | Me | 95-97 |
| 1-110 | 5-Me | Me | $NH_2$ | $CH_2CH_2OCH_3$ | Me | 143-144 |
| 1-111 | 5-Me | Me | $NH_2$ | Et | Et | NMR |
| 1-112 | 5-Me | Me | $NH_2$ | i-Pr | Et | |
| 1-113 | 5-Me | Me | $NH_2$ | $CH_2CF_3$ | Et | |
| 1-114 | 5-Me | Me | $NH_2$ | Me | NHMe | 165-167 |
| 1-115 | 5-Me | Me | $NH_2$ | Et | NHMe | 196-197 |
| 1-116 | 5-Me | Me | $NH_2$ | Et | $NMe_2$ | NMR |
| 1-117 | 5-Me | Me | $NH_2$ | n-Pr | NHMe | 161-162 |
| 1-118 | 5-Me | Me | $NH_2$ | i-Pr | NHMe | 172-173 |
| 1-119 | 5-Me | Me | $NH_2$ | $CH_2CF_3$ | NHMe | |
| 1-120 | 5-Me | Me | CN | H | Me | 267-268 |

TABLE 1-5

| Compound No. | $R^1$ | $R^2$ | $R^3$ | $R^4$ | $R^6$ | Physical property value |
|---|---|---|---|---|---|---|
| 1-121 | 5-Me | Me | CN | Et | Me | 202-203 |
| 1-122 | 5-Me | Me | CN | i-Pr | Me | |
| 1-123 | 5-Me | Me | CN | $CH_2CF_3$ | Me | |
| 1-124 | 5-Me | Et | $NH_2$ | Et | Me | 79-80 |
| 1-125 | 5-Me | Et | $NH_2$ | Et | NHMe | 153-154 |
| 1-126 | 5-Me | n-Pr | $NH_2$ | Et | Me | 157-158 |
| 1-127 | 5-Me | i-Pr | $NH_2$ | Et | Me | 216-217 |
| 1-128 | 5-Me | c-Pr | $NH_2$ | Et | Me | NMR |
| 1-129 | 5-Et | Me | H | Me | Me | |
| 1-130 | 5-Et | Me | Me | Me | Me | |
| 1-131 | 5-Et | Me | $NH_2$ | Me | Me | 76 |
| 1-132 | 5-Et | Me | $NH_2$ | Me | NHMe | 98 |
| 1-133 | 5-Et | Me | H | Et | Me | |
| 1-134 | 5-Et | Me | Me | Et | Me | NMR |
| 1-135 | 5-Et | Me | $NH_2$ | Et | Me | 137-138 |
| 1-136 | 5-Et | Me | $NH_2$ | Et | NHMe | 166-167 |
| 1-137 | 5-Et | Me | H | Et | Me | |
| 1-138 | 5-Et | Me | Me | Et | Me | |
| 1-139 | 5-Et | Me | $NH_2$ | i-Pr | Me | 80-81 |
| 1-140 | 5-Et | Me | $NH_2$ | i-Pr | NHMe | 73-74 |
| 1-141 | 5-CH=CH$_2$ | Me | H | Et | Et | NMR |
| 1-142 | 5-CH=CH$_2$ | Me | Me | Et | Me | |
| 1-143 | 5-CH=CH$_2$ | Me | $NH_2$ | Et | Me | NMR |
| 1-144 | 5-C≡CH | Me | H | Et | Me | |
| 1-145 | 5-C≡CH | Me | Me | Et | Me | |
| 1-146 | 5-C≡CH | Me | $NH_2$ | Et | Me | |
| 1-147 | 5-c-Pr | Me | H | Et | Me | |
| 1-148 | 5-c-Pr | Me | Me | Et | Me | NMR |
| 1-149 | 5-c-Pr | Me | $NH_2$ | Et | Me | |
| 1-150 | 5-n-Pr | Me | H | Et | Me | |

TABLE 1-6

| Compound No. | $R^1$ | $R^2$ | $R^3$ | $R^4$ | $R^6$ | Physical property value |
|---|---|---|---|---|---|---|
| 1-151 | 5-n-Pr | Me | Me | Et | Me | NMR |
| 1-152 | 5-n-Pr | Me | $NH_2$ | Et | Me | |
| 1-153 | 5-i-Pr | Me | H | Et | Me | |
| 1-154 | 5-i-Pr | Me | Me | Et | Me | NMR |
| 1-155 | 5-i-Pr | Me | $NH_2$ | Et | Me | 65-66 |
| 1-156 | 5-i-Pr | Me | $NH_2$ | Et | NHMe | 65-66 |
| 1-157 | 5-n-pentyl | Me | Me | Et | Me | NMR |
| 1-158 | 5-t-Bu | Me | Me | Et | Me | NMR |
| 1-159 | 5-$CH_2OH$ | Me | H | Et | Me | |

TABLE 1-6-continued

| Compound No. | $R^1$ | $R^2$ | $R^3$ | $R^4$ | $R^6$ | Physical property value |
|---|---|---|---|---|---|---|
| 1-160 | 5-$CH_2OH$ | Me | Me | Et | Me | 112-113 |
| 1-161 | 5-$CH_2OH$ | Me | $NH_2$ | Et | Me | 178-179 |
| 1-162 | 5-$CH_2OCH_3$ | Me | H | Et | Me | |
| 1-163 | 5-$CH_2OCH_3$ | Me | Me | Et | Me | 123-124 |
| 1-164 | 5-$CH_2OCH_3$ | Me | $NH_2$ | Et | Me | NMR |
| 1-165 | 5-$CH_2SCH_3$ | Me | Me | Et | Me | NMR |
| 1-166 | 5-$CH_2SOCH_3$ | Me | Me | Et | Me | NMR |
| 1-167 | 5-$CH_2SO_2CH_3$ | Me | Me | Et | Me | NMR |
| 1-168 | 5-$CH_2SCH_3$ | Me | $NH_2$ | Et | Me | |
| 1-169 | 5-$CH_2SOCH_3$ | Me | $NH_2$ | Et | Me | |
| 1-170 | 5-$CH_2SO_2CH_3$ | Me | $NH_2$ | Et | Me | |
| 1-171 | 5-$CH_2NHCH_3$ | Me | Me | Et | Me | NMR |
| 1-172 | 5-$CH_2N(CH_3)_2$ | Me | Me | Et | Me | NMR |
| 1-173 | 5-$CH_2N(CH_2CH_3)_2$ | Me | Me | Et | Me | NMR |
| 1-174 | 5-$CH_2F$ | Me | Me | Et | Me | 109-110 |
| 1-175 | 5-$CH_2Cl$ | Me | Me | Et | Me | NMR |
| 1-176 | 5-$CHF_2$ | Me | H | Et | Me | |
| 1-177 | 5-$CHF_2$ | Me | Me | Et | Me | 178-179 |
| 1-178 | 5-$CHF_2$ | Me | $NH_2$ | H | Me | 259-260 |
| 1-179 | 5-$CHF_2$ | Me | $NH_2$ | Me | Me | 81-82 |
| 1-180 | 5-$CHF_2$ | Me | $NH_2$ | Et | Me | 172-173 |

TABLE 1-7

| Compound No. | $R^1$ | $R^2$ | $R^3$ | $R^4$ | $R^6$ | Physical property value |
|---|---|---|---|---|---|---|
| 1-181 | 5-$CHF_2$ | Me | $NH_2$ | i-Pr | Me | 205-206 |
| 1-182 | 5-$CHF_2$ | Me | $NH_2$ | $CH_2CF_3$ | Me | |
| 1-183 | 5-$CHF_2$ | Me | $NH_2$ | Et | Et | 87-88 |
| 1-184 | 5-$CHF_2$ | Me | $NH_2$ | Et | n-Pr | NMR |
| 1-185 | 5-$CHF_2$ | Me | $NH_2$ | Et | i-Pr | 185-186 |
| 1-186 | 5-$CHF_2$ | Me | $NH_2$ | Et | NHMe | 175-176 |
| 1-187 | 5-$CHF_2$ | Me | $NH_2$ | Ac | Me | 195-196 |
| 1-188 | 5-$CHF_2$ | Me | $NH_2$ | $CH_2C{\equiv}CH$ | Me | 142-143 |
| 1-189 | 5-$CHF_2$ | Me | $NH_2$ | $CH_2CF_3$ | Me | 184-185 |
| 1-190 | 5-$CHF_2$ | Me | $NH_2$ | $CH_2CH{=}CH_2$ | Me | 164-165 |
| 1-191 | 5-$CHF_2$ | Me | $NH_2$ | $CH_2CHF_2$ | Me | 161-162 |
| 1-192 | 5-$CHF_2$ | Me | $NH_2$ | $CH_2CN$ | Me | 227-228 |
| 1-193 | 5-$CHF_2$ | Me | $NH_2$ | $CH_2$—c-Pr | Me | 206-207 |
| 1-194 | 5-$CHF_2$ | Me | $NH_2$ | $CH_2SCH_3$ | Me | 161-162 |
| 1-195 | 5-$CHF_2$ | Me | $NH_2$ | $CH_2SOCH_3$ | Me | 47-48 |
| 1-196 | 5-$CHF_2$ | Me | $NH_2$ | $CH_2SO_2CH_3$ | Me | 79-80 |
| 1-197 | 5-$CHF_2$ | Me | $NH_2$ | $CO_2Me$ | Me | 224-225 |
| 1-198 | 5-$CHF_2$ | Me | $NH_2$ | Ph | Me | 187-188 |
| 1-199 | 5-$CHF_2$ | Me | $NH_2$ | $SO_2Me$ | Me | 225-226 |
| 1-200 | 5-$CF_3$ | Me | Me | Et | Me | 132-133 |
| 1-201 | 5-$CF_3$ | Me | Me | i-Pr | Me | |
| 1-202 | 5-$CF_3$ | Me | Me | $CH_2CF_3$ | Me | |
| 1-203 | 5-$CF_3$ | Me | Me | Et | NHMe | 217-218 |
| 1-204 | 5-$CF_3$ | Me | $NH_2$ | Me | Me | 108 |
| 1-205 | 5-$CF_3$ | Me | $NH_2$ | Et | Me | 149-150 |
| 1-206 | 5-$CF_3$ | Me | $NH_2$ | i-Pr | Me | NMR |
| 1-207 | 5-$CF_3$ | Me | $NH_2$ | $CH_2CF_3$ | Me | |
| 1-208 | 5-$CF_3$ | Me | $NH_2$ | $CH_2C(CH_3){=}CH_2$ | Me | 168-169 |
| 1-209 | 5-$CF_3$ | Me | $NH_2$ | Me | NHMe | 212-213 |
| 1-210 | 5-$CF_3$ | Me | $NH_2$ | Et | NHMe | 173-174 |

TABLE 1-8

| Compound No. | $R^1$ | $R^2$ | $R^3$ | $R^4$ | $R^6$ | Physical property value |
|---|---|---|---|---|---|---|
| 1-211 | 5-$CF_3$ | Me | $NH_2$ | i-Pr | NHMe | 103-104 |
| 1-212 | 5-$CF_3$ | Me | $NH_2$ | $CH_2CF_3$ | NHMe | |
| 1-213 | 5-$CF_3$ | Me | $NH_2$ | Et | $NMe_2$ | |
| 1-214 | 5-$CF_3$ | Me | $NH_2$ | i-Pr | $NMe_2$ | 171-173 |
| 1-215 | 5-$CF_3$ | Me | $NH_2$ | i-Pr | NHOMe | 103-105 |
| 1-216 | 5-$CF_3$ | Me | NHMe | Et | Me | 154-155 |

TABLE 1-8-continued

| Compound No. | $R^1$ | $R^2$ | $R^3$ | $R^4$ | $R^6$ | Physical property value |
|---|---|---|---|---|---|---|
| 1-217 | 5-$CF_3$ | Me | NHMe | Et | NHMe | 204-205 |
| 1-218 | 5-$CF_3$ | Me | NHMe | i-Pr | Me | |
| 1-219 | 5-$CF_3$ | Me | NHMe | i-Pr | NHMe | |
| 1-220 | 5-$CF_3$ | Me | $NMe_2$ | Et | Me | 150-151 |
| 1-221 | 5-$CF_3$ | Me | $NMe_2$ | Et | NHMe | 183-184 |
| 1-222 | 5-$CF_3$ | Me | $NMe_2$ | i-Pr | Me | |
| 1-223 | 5-$CF_3$ | Me | $NMe_2$ | i-Pr | NHMe | |
| 1-224 | 5-OMe | Me | H | Et | Me | |
| 1-225 | 5-OMe | Me | Me | Et | Me | NMR |
| 1-226 | 5-OMe | Me | $NH_2$ | Et | Me | 115-118 |
| 1-227 | 5-OMe | Me | $NH_2$ | Et | NHMe | 186-188 |
| 1-228 | 5-OMe | Me | $NH_2$ | i-Pr | Me | 168-170 |
| 1-229 | 5-OMe | Me | $NH_2$ | i-Pr | NHMe | 159 |
| 1-230 | 5-OEt | Me | H | Et | Me | |
| 1-231 | 5-OEt | Me | Me | Et | Me | |
| 1-232 | 5-OEt | Me | $NH_2$ | Et | Me | |
| 1-233 | 5-OEt | Me | $NH_2$ | Et | NHMe | 232 |
| 1-234 | 5-O—i-Pr | Me | $NH_2$ | Et | Me | 104-106 |
| 1-235 | 5-$OCHF_2$ | Me | H | Et | Me | |
| 1-236 | 5-$OCHF_2$ | Me | Me | Et | Me | |
| 1-237 | 5-$OCHF_2$ | Me | $NH_2$ | Et | Me | 140 |
| 1-238 | 5-$OCHF_2$ | Me | $NH_2$ | i-Pr | Me | 121-122 |
| 1-239 | 5-$OCHF_2$ | Me | $NH_2$ | Et | NHMe | 151-153 |
| 1-240 | 5-$OCHF_2$ | Me | $NH_2$ | i-Pr | NHMe | 96 |

TABLE 1-9

| Compound No. | $R^1$ | $R^2$ | $R^3$ | $R^4$ | $R^6$ | Physical property value |
|---|---|---|---|---|---|---|
| 1-241 | 5-$OCF_3$ | Me | H | Et | Et | 51-52 |
| 1-242 | 5-$OCF_3$ | Me | H | $CH_2CF_3$ | Et | 39-40 |
| 1-243 | 5-$OCF_3$ | Me | H | $CH_2CHF_2$ | Et | 50-51 |
| 1-244 | 5-$OCF_3$ | Me | Me | Et | Et | |
| 1-245 | 5-$OCF_3$ | Me | $NH_2$ | Et | Me | 87-88 |
| 1-246 | 5-$NO_2$ | Me | Me | Et | Me | 174-175 |
| 1-247 | 5-$NH_2$ | Me | Me | Et | Me | NMR |
| 1-248 | 5-NHAc | Me | Me | Et | Me | NMR |
| 1-249 | 5-SMe | Me | $NH_2$ | Et | Me | NMR |
| 1-250 | 5-SOMe | Me | $NH_2$ | Et | Me | |
| 1-251 | 5-$SO_2Me$ | Me | $NH_2$ | Et | Me | |
| 1-252 | 5-SEt | Me | Me | Et | Me | NMR |
| 1-253 | 5-SOEt | Me | Me | Et | Me | |
| 1-254 | 5-$SO_2Et$ | Me | Me | Et | Me | |
| 1-255 | 5-$SCF_3$ | Me | H | Me | Et | NMR |
| 1-256 | 5-$SCF_3$ | Me | H | Et | Me | 73-74 |
| 1-257 | 5-$SCF_3$ | Me | H | Et | Et | NMR |
| 1-258 | 5-$SCF_3$ | Me | H | Et | i-Pr | 157-158 |
| 1-259 | 5-$SCF_3$ | Me | H | Et | n-Pr | 102-103 |
| 1-260 | 5-$SCF_3$ | Me | H | $CH_2CF_2CF_3$ | Et | 45-46 |
| 1-261 | 5-$SCF_3$ | Me | H | $CH_2CF_2CHF_2$ | Et | NMR |
| 1-262 | 5-$SCF_3$ | Me | H | $CH_2CF_3$ | Et | NMR |
| 1-263 | 5-$SCF_3$ | Me | H | $CH_2CHF_2$ | Et | NMR |
| 1-264 | 5-$SCF_3$ | Me | H | i-Pr | Et | 139-140 |
| 1-265 | 5-$SCF_3$ | Me | Me | Et | Me | 101-102 |
| 1-266 | 5-$SCF_3$ | Me | Me | i-Pr | Me | |
| 1-267 | 5-$SCF_3$ | Me | $NH_2$ | Et | Me | |
| 1-268 | 5-$SCF_3$ | Me | $NH_2$ | i-Pr | Me | |
| 1-269 | 5-$SOCF_3$ | Me | H | Et | Me | 80-81 |
| 1-270 | 5-$SOCF_3$ | Me | H | Et | Et | NMR |

TABLE 1-10

| Compound No. | $R^1$ | $R^2$ | $R^3$ | $R^4$ | $R^6$ | Physical property value |
|---|---|---|---|---|---|---|
| 1-271 | 5-$SOCF_3$ | Me | H | $CH_2CF_2CF_3$ | Et | 52-53 |
| 1-272 | 5-$SOCF_3$ | Me | H | $CH_2CF_3$ | Et | NMR |
| 1-273 | 5-$SOCF_3$ | Me | H | $CH_2CHF_2$ | Et | NMR |

TABLE 1-10-continued

| Compound No. | $R^1$ | $R^2$ | $R^3$ | $R^4$ | $R^6$ | Physical property value |
|---|---|---|---|---|---|---|
| 1-274 | 5-$SOCF_3$ | Me | H | i-Pr | Et | 52-53 |
| 1-275 | 5-$SOCF_3$ | Me | Me | Et | Me | NMR |
| 1-276 | 5-$SOCF_3$ | Me | Me | i-Pr | Me | |
| 1-277 | 5-$SOCF_3$ | Me | $NH_2$ | Et | Me | |
| 1-278 | 5-$SOCF_3$ | Me | $NH_2$ | i-Pr | Me | |
| 1-279 | 5-$SO_2CF_3$ | Me | H | Et | Me | 84-85 |
| 1-280 | 5-$SO_2CF_3$ | Me | H | Et | Et | NMR |
| 1-281 | 5-$SO_2CF_3$ | Me | H | $CH_2CF_2CF_3$ | Et | 59-60 |
| 1-282 | 5-$SO_2CF_3$ | Me | H | $CH_2CF_2CHF_2$ | Et | NMR |
| 1-283 | 5-$SO_2CF_3$ | Me | H | $CH_2CF_3$ | Et | NMR |
| 1-284 | 5-$SO_2CF_3$ | Me | H | $CH_2CHF_2$ | Et | NMR |
| 1-285 | 5-$SO_2CF_3$ | Me | H | i-Bu | Et | NMR |
| 1-286 | 5-$SO_2CF_3$ | Me | H | i-Pr | Et | 50-51 |
| 1-287 | 5-$SO_2CF_3$ | Me | H | n-Bu | Et | NMR |
| 1-288 | 5-$SO_2CF_3$ | Me | H | n-Pr | Et | NMR |
| 1-289 | 5-$SO_2CF_3$ | Me | Me | Et | Me | NMR |
| 1-290* | 5-$SO_2CF_3$ | Me | Me | Et | Me | 1.5424 (22.1° C.) |
| 1-291 | 5-$SO_2CF_3$ | Me | Me | Et | Et | NMR |
| 1-292 | 5-$SO_2CF_3$ | Me | Me | Et | $NH_2$ | 247-249 |
| 1-293 | 5-$SO_2CF_3$ | Me | Me | Et | NHAc | 208-210 |
| 1-294 | 5-$SO_2CF_3$ | Me | Me | Et | NHMe | 200-203 |
| 1-295 | 5-$SO_2CF_3$ | Me | Me | Et | $NMe_2$ | 1.3568 (20.0° C.) |
| 1-296 | 5-$SO_2CF_3$ | Me | Me | Et | $NHCH_2CHF_2$ | 1.4270 (21.4° C.) |
| 1-297 | 5-$SO_2CF_3$ | Me | Me | i-Pr | Et | |
| 1-298 | 5-$SO_2CF_3$ | Me | Me | $CH_2CF_3$ | Et | NMR |
| 1-299 | 5-$SO_2CF_3$ | Me | Me | $CH_2CHF_2$ | Et | 157-158 |
| 1-300 | 5-$SO_2CF_3$ | Me | $NH_2$ | H | Me | 252-255 |

The symbol "*" next to the compound number indicates the Z-isomer.

TABLE 1-11

| Compound No. | $R^1$ | $R^2$ | $R^3$ | $R^4$ | $R^6$ | Physical property value |
|---|---|---|---|---|---|---|
| 1-301 | 5-$SO_2CF_3$ | Me | $NH_2$ | Et | Me | 1.4292 (21.6° C.) |
| 1-302 | 5-$SO_2CF_3$ | Me | $NH_2$ | i-Pr | Me | |
| 1-303 | 5-$SO_2NMe_2$ | Me | Me | Et | Me | |
| 1-304 | 5-CHO | Me | Me | Et | Me | 190-191 |
| 1-305 | 5-CHO | Me | $NH_2$ | Et | Me | 242-243 |
| 1-306 | 5-CN | Me | Me | Et | Me | 119-120 |
| 1-307 | 5-COMe | Me | Me | Et | Me | |
| 1-308 | 5-$CO_2H$ | Me | Me | Et | Me | 265-266 |
| 1-309 | 5-$CO_2Me$ | Me | Me | Et | Me | 162-163 |
| 1-310 | 5-$CO_2Me$ | Me | $NH_2$ | Et | Me | 198-199 |
| 1-311 | 5-$CO_2Et$ | Me | $NH_2$ | Et | Me | 190-191 |
| 1-312 | 5-CONHMe | Me | Me | Et | Me | |
| 1-313 | 5-CH═N—OMe | Me | Me | Et | Me | 176-177 |
| 1-314 | 5-$CH(OCH_3)_2$ | Me | Me | Et | Me | NMR |
| 1-315 | 5-dioxan-2-yl | Me | Me | Et | Me | 92-93 |
| 1-316 | 5-dioxolan-2-yl | Me | Me | Et | Me | NMR |
| 1-317 | 5-Ph | Me | Me | Et | Me | NMR |
| 1-318 | 5-(4-F—Ph) | Me | Me | Et | Me | 168-169 |
| 1-319 | 5-(4-OMe—Ph) | Me | Me | Et | Me | 88-89 |
| 1-320 | 5-(pyridin-3-yl) | Me | Me | Et | Me | NMR |
| 1-321 | 5-(1-Me—1H-pyrazol-5-yl) | Me | Me | Et | Me | NMR |
| 1-322 | 6-F | Me | H | Et | Et | 1.4237 (24.4° C.) |
| 1-323 | 6-F | Me | H | i-Pr | Et | 1.4289 (24.2° C.) |
| 1-324 | 6-F | Me | H | $CH_2CF_3$ | Et | 1.4664 (24.0° C.) |
| 1-325 | 6-Cl | Me | H | Et | Et | 1.4198 (24.8° C.) |
| 1-326 | 6-Cl | Me | H | i-Pr | Et | 1.4025 (24.8° C.) |
| 1-327 | 6-Cl | Me | H | $CH_2CF_3$ | Et | 1.4707 (24.7° C.) |
| 1-328 | 6-Br | Me | H | Et | Et | 90-91 |
| 1-329 | 6-Me | Me | H | Et | Et | 1.4235 (24.5° C.) |
| 1-330 | 6-CH═$CH_2$ | Me | H | Et | Et | 1.3319 (24.5° C.) |

TABLE 1-12

| Table 1 (Continued) | | | | | | |
|---|---|---|---|---|---|---|
| Compound No. | $R^1$ | $R^2$ | $R^3$ | $R^4$ | $R^6$ | Physical property value |
| 1-331 | 6-SEt | Me | H | Et | Et | 1.4222 (23.1° C.) |
| 1-332 | 6-SOEt | Me | H | Et | Et | |
| 1-333 | 6-$SO_2Et$ | Me | H | Et | Et | 1.3353 (24.7° C.) |
| 1-334 | 7-Br | Me | H | Et | Et | 139-140 |
| 1-335 | 7-Br | Me | H | $CH_2CF_3$ | Et | 148-150 |
| 1-336 | 7-Me | Me | H | Et | Et | 139-140 |
| 1-337 | 7-Me | Me | H | $CH_2CF_3$ | Et | 117-118 |
| 1-338 | 7-Me | Me | H | i-Pr | Et | NMR |
| 1-339 | 4-Et-5-Cl | Me | $NH_2$ | Et | NHMe | |
| 1-340 | 4.6-di-F | Me. | H | Et | Et | 59-60 |
| 1-341 | 4,6-di-F | Me | H | $CH_2CF_3$ | Et | 64-65 |
| 1-342 | 5.6-di-Me | Me | $NH_2$ | Et | Me | 216-218 |
| 1-343 | 4,6-di-Cl-5-OMe | Me | $NH_2$ | Et | NHMe | 159-161 |
| 1-344 | 4,6-di-Cl-5-OMe | Me | $NH_2$ | i-Pr | NHMe | 177 |
| 1-345 | 4,6,7-tri-Cl-5-OMe | Me | $NH_2$ | i-Pr | NHMe | 228-229 |
| 1-346 | 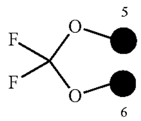 | Me | H | Et | Et | 49-50 |

TABLE 1-12-continued

| Table 1 (Continued) | | | | | | |
|---|---|---|---|---|---|---|
| Compound No. | $R^1$ | $R^2$ | $R^3$ | $R^4$ | $R^6$ | Physical property value |
| 1-347 | 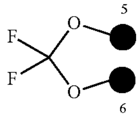 | Me | H | $CH_2CF_3$ | Et | 61-62 |
| 1-348 | 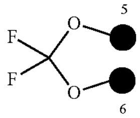 | Me | H | $CH_2CHF_2$ | Et | 55-56 |
| 1-349 | 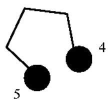 | H | Me | Et | Me | 252-253 |
| 1-350 | 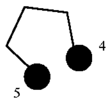 | Me | Me | Et | Me | 161-162 |
| 1-351 | H | Me | $NH_2$ | n-Bu | Me | |
| 1-352 | H | Me | $NH_2$ | i-Bu | Me | |

The black solid circle represents binding to the benzimidazole ring, and the number represents the position of the binding.

TABLE 1-13

| Compound No. | $R^1$ | $R^2$ | $R^3$ | $R^4$ | $R^6$ | Physical property value |
|---|---|---|---|---|---|---|
| 1-353 | H | Me | $NH_2$ | n-Bu | NHMe | |
| 1-354 | H | Me | $NH_2$ | i-Bu | NHMe | |
| 1-355 | 4-Cl | Me | $NH_2$ | Et | Me | 198-199 |
| 1-356 | 4-Cl | Me | $NH_2$ | Et | NHMe | 186-187 |
| 1-357 | $4-CF_3$ | Me | $NH_2$ | Et | Me | |
| 1-358 | $4-CF_3$ | Me | $NH_2$ | Et | NHMe | |
| 1-359 | 4-OMe | Me | $NH_2$ | Me | Me | 168-169 |
| 1-360 | 4-OMe | Me | $NH_2$ | Et | Me | 160-161 |
| 1-361 | 4-OMe | Me | $NH_2$ | i-Pr | Me | 188-190 |
| 1-362 | 4-OMe | Me | $NH_2$ | Me | NHMe | 173-174 |
| 1-363 | 4-OMe | Me | $NH_2$ | Et | NHMe | 176-177 |
| 1-364 | 4-OMe | Me | $NH_2$ | i-Pr | NHMe | 185-186 |
| 1-365 | 5-Cl | Me | $NH_2$ | Me | $NMe_2$ | 106-108 |
| 1-366 | 5-I | Me | $NH_2$ | Et | Me | |
| 1-367 | 5-I | Me | $NH_2$ | Et | NHMe | |
| 1-368 | 5-Me | Me | $NH_2$ | $CH_2CH_2OCH_3$ | NHMe | 154-155 |
| 1-369 | 5-Me | Me | $NH_2$ | n-Bu | Me | 167-168 |
| 1-370 | 5-Me | Me | $NH_2$ | i-Bu | Me | 170-171 |
| 1-371 | 5-Me | Me | $NH_2$ | n-Bu | NHMe | |
| 1-372 | 5-Me | Me | $NH_2$ | i-Bu | NHMe | |
| 1-373 | 5-Me | Me | $NH_2$ | $CH_2CF_3$ | Me | 66-67 |
| 1-374 | 5-Me | Me | $NH_2$ | $CH_2CF_3$ | NHMe | |
| 1-375 | 5-Me | Me | $NH_2$ | c-Pr | Me | |
| 1-376 | 5-Me | Me | $NH_2$ | c-Pr | NHMe | |
| 1-377 | 5-c-Pr | Me | $NH_2$ | Et | Me | |
| 1-378 | 5-c-Pr | Me | $NH_2$ | Et | NHMe | |
| 1-379 | 5-OMe | Me | $NH_2$ | Me | NHMe | 182-185 |
| 1-380 | 5-OMe | Me | $NH_2$ | Me | Me | 181-182 |
| 1-381 | $5-OCHF_2$ | Me | $NH_2$ | Me | Me | |
| 1-382 | $5-OCHF_2$ | Me | $NH_2$ | Me | NHMe | 181-182 |

TABLE 1-14

| Compound No. | $R^1$ | $R^2$ | $R^3$ | $R^4$ | $R^6$ | Physical property value |
|---|---|---|---|---|---|---|
| 1-383 | $5-CF_3$ | Me | $NH_2$ | c-Pr | Me | |
| 1-384 | $5-CF_3$ | Me | $NH_2$ | c-Pr | NHMe | |
| 1-385 | 4,5-di-Me | Me | $NH_2$ | Et | Me | |
| 1-386 | 4,5-di-Me | Me | $NH_2$ | Et | NHMe | |
| 1-387 | $5-NO_2$ | Me | $NH_2$ | Et | Me | 238-239 |
| 1-388 | H | Me | $NH_2$ | Et | Me | |
| 1-389 | H | Me | $NH_2$ | Et | NHMe | |
| 1-390 | 4,5-diMe | Me | $NH_2$ | Et | Me | NMR |
| 1-391 | H | Me | $NH_2$ | Me | Me | 84-85 |
| 1-392 | H | Me | $NH_2$ | Me | NHMe | 94-96 |
| 1-393 | $4-CF_3$ | Me | $NH_2$ | Me | Me | 245-246 |
| 1-394 | $4-CF_3$ | Me | $NH_2$ | Et | Me | 224-225 |
| 1-395 | $4-CF_3$ | Me | $NH_2$ | Me | NHMe | NMR |
| 1-396 | $4-CF_3$ | Me | $NH_2$ | Et | NHMe | NMR |
| 1-397 | 5-Me | Me | $NH_2$ | $CH_2CH{=}CH_2$ | NHMe | 170-171 |
| 1-398 | 5-F | Me | $NH_2$ | Me | NHMe | NMR |
| 1-399 | 5-F | Me | $NH_2$ | Me | Me | NMR |
| 1-400 | H | Me | $NH_2$ | Et | N(Me)Ac | 219-220 |
| 1-401 | H | Me | $NH_2$ | Et | $NMe_2$ | NMR |
| 1-402 | 5-OMe | Me | $NH_2$ | Me | $NMe_2$ | 154-156 |
| 1-403 | $5-CF_3$ | Me | $NH_2$ | $CH_2CO_2Me$ | Me | NMR |
| 1-404 | $5-CHF_2$ | Me | $NH_2$ | n-Pr | Me | |
| 1-405 | H | Me | $NH_2$ | n-Bu | Me | |
| 1-406 | 5-OMe | Me | $NH_2$ | n-Pr | Me | |
| 1-407 | $5-CF_3$ | Me | $NH_2$ | n-Pr | Me | |
| 1-408 | 5-F | Me | $NH_2$ | i-Pr | Me | |
| 1-409 | 5-Cl | Me | $NH_2$ | n-Pr | Me | |
| 1-410 | 5-Et | Me | $NH_2$ | n-Pr | Me | |
| 1-411 | 5-Br | Me | $NH_2$ | Me | Me | |
| 1-412 | 5-F | Me | $NH_2$ | i-Pr | NHMe | |
| 1-413 | 5-OMe | Me | $NH_2$ | n-Pr | NHMe | |

TABLE 1-15

| Compound No. | $R^1$ | $R^2$ | $R^3$ | $R^4$ | $R^6$ | Physical property value |
|---|---|---|---|---|---|---|
| 1-414 | 5-Et | Me | $NH_2$ | n-Pr | NHMe | |
| 1-415 | 5-$CF_3$ | Me | $NH_2$ | n-Pr | NHMe | |
| 1-416 | 5-Cl | Me | $NH_2$ | n-Pr | NHMe | |
| 1-417 | 5-i-Pr | Me | $NH_2$ | n-Pr | NHMe | |
| 1-418 | 5-$CHF_2$ | Me | $NH_2$ | n-Pr | NHMe | |
| 1-419 | 5-i-Pr | Me | $NH_2$ | i-Pr | NHMe | |
| 1-420 | 5-$CHF_2$ | Me | $NH_2$ | i-Pr | NHMe | |
| 1-421 | 5-$CHF_2$ | Me | $NH_2$ | Me | NHMe | |
| 1-422 | 5-i-Pr | Me | $NH_2$ | Me | NHMe | |
| 1-423 | 5-Br | Me | $NH_2$ | i-Pr | Me | |
| 1-424 | 5-Br | Me | $NH_2$ | n-Pr | Me | |

[Chem. 28]

(1b)

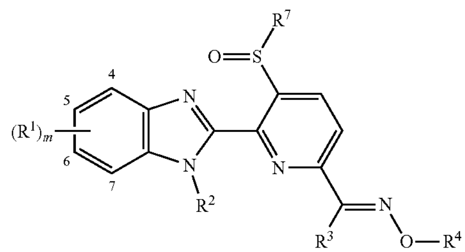

The position numbers in the table are the numbers designated in the general formula (Mb).

TABLE 2-1

| Compound No. | $R^1$ | $R^2$ | $R^3$ | $R^4$ | $R^7$ | Physical property value |
|---|---|---|---|---|---|---|
| 2-1 | H | Me | H | Et | OMe | 109-110 |
| 2-2 | H | Me | Me | Et | OH | 239-241 |
| 2-3 | H | Me | Me | Et | OMe | 111-113 |
| 2-4 | H | Me | Me | Et | OEt | 80-83 |
| 2-5 | H | Me | Me | Et | $NMe_2$ | 136-138 |
| 2-6 | H | Me | $NH_2$ | H | OMe | 232-233 |
| 2-7 | H | Me | $NH_2$ | Me | OMe | 172-173 |
| 2-8 | H | Me | $NH_2$ | Et | OMe | |
| 2-9 | 4-$CO_2$Me | Me | Me | Et | OMe | |
| 2-10 | 4-$CO_2$Me | Me | $NH_2$ | Et | OMe | 177-178 |
| 2-11 | 4-$CO_2$Me | Me | $NH_2$ | $CH_2CF_3$ | OMe | 77-78 |
| 2-12 | 5-Cl | Me | $NH_2$ | H | OMe | 256-258 |
| 2-13 | 5-Cl | Me | $NH_2$ | Et | OH | 277 |
| 2-14 | 5-Cl | Me | H | Et | OMe | |
| 2-15 | 5-Cl | Me | Me | Et | OMe | |
| 2-16 | 5-Cl | Me | $NH_2$ | Et | OMe | 175-176 |
| 2-17 | 5-Cl | Me | $NH_2$ | Et | OEt | |
| 2-18 | 5-Cl | Me | $NH_2$ | Et | NH—t-Bu | 81 |
| 2-19 | 5-Cl | Me | $NH_2$ | Et | $NMe_2$ | |
| 2-20 | 5-Cl | Me | $NH_2$ | i-Pr | OH | 223-225 |
| 2-21 | 5-Cl | Me | $NH_2$ | i-Pr | OMe | 156 |
| 2-22 | 5-Cl | Me | $NH_2$ | i-Pr | OEt | |
| 2-23 | 5-Cl | Me | $NH_2$ | i-Pr | NH—t-Bu | 85-87 |
| 2-24 | 5-Cl | Me | $NH_2$ | i-Pr | $NMe_2$ | |
| 2-25 | 5-Br | Me | H | Et | OMe | 119-120 |
| 2-26 | 5-Br | Me | Me | Et | OMe | |
| 2-27 | 5-Br | Me | $NH_2$ | Et | OMe | |
| 2-28 | 5-Me | Me | Me | Et | Me | 135-138 |
| 2-29 | 5-Me | Me | Me | Et | $CH_2CO_2$Me | 169-171 |
| 2-30 | 5-Me | Me | Me | Et | OH | 252-253 |

TABLE 2-2

| Compound No. | $R^1$ | $R^2$ | $R^3$ | $R^4$ | $R^7$ | Physical property value |
|---|---|---|---|---|---|---|
| 2-31 | 5-Me | Me | Me | Et | OMe | 142-144 |
| 2-32 | 5-Me | Me | Me | Et | OEt | 121-122 |
| 2-33 | 5-Me | Me | Me | Et | $NMe_2$ | 199-201 |
| 2-34 | 5-Me | Me | $NH_2$ | Et | H | 206-207 |
| 2-35 | 5-Me | Me | $NH_2$ | Et | Me | NMR |
| 2-36 | 5-Me | Me | $NH_2$ | Et | OMe | 137-138 |
| 2-37 | 5-Me | Me | $NH_2$ | Et | OEt | 108-109 |
| 2-38 | 5-Me | Me | $NH_2$ | Et | O—i-Pr | |
| 2-39 | 5-$CF_3$ | Me | H | Et | OEt | |
| 2-40 | 5-$CF_3$ | Me | Me | Et | OEt | |
| 2-41 | 5-$CF_3$ | Me | $NH_2$ | H | OMe | 241-242 |
| 2-42 | 5-$CF_3$ | Me | $NH_2$ | Me | OMe | 170-171 |
| 2-43 | 5-$CF_3$ | Me | $NH_2$ | Et | OH | 121-122 |
| 2-44 | 5-$CF_3$ | Me | $NH_2$ | Et | OMe | 153-154 |
| 2-45 | 5-$CF_3$ | Me | $NH_2$ | Et | OEt | 119-120 |
| 2-46 | 5-$CF_3$ | Me | $NH_2$ | Et | O—i-Pr | NMR |
| 2-47 | 5-$CF_3$ | Me | $NH_2$ | Et | $OCH_2CO_2$Me | 99-100 |
| 2-48 | 5-$CF_3$ | Me | $NH_2$ | Et | NHMe | 153-154 |
| 2-49 | 5-$CF_3$ | Me | $NH_2$ | Et | NHEt | 178-179 |
| 2-50 | 5-$CF_3$ | Me | $NH_2$ | Et | NH—i-Pr | 182-183 |
| 2-51 | 5-$CF_3$ | Me | $NH_2$ | Et | NH—t-Bu | 107-108 |
| 2-52 | 5-$CF_3$ | Me | $NH_2$ | Et | $NMe_2$ | NMR |
| 2-53 | 5-$CF_3$ | Me | $NH_2$ | n-Pr | OH | 202-203 |
| 2-54 | 5-$CF_3$ | Me | $NH_2$ | n-Pr | OMe | 145-146 |
| 2-55 | 5-$CF_3$ | Me | $NH_2$ | n-Pr | NHMe | 178-179 |
| 2-56 | 5-$CF_3$ | Me | $NH_2$ | n-Pr | NHEt | 136-137 |
| 2-57 | 5-$CF_3$ | Me | $NH_2$ | n-Pr | NH—i-Pr | 180-181 |
| 2-58 | 5-$CF_3$ | Me | $NH_2$ | n-Pr | NH—t-Bu | NMR |
| 2-59 | 5-$CF_3$ | Me | $NH_2$ | n-Pr | OEt | 110-111 |
| 2-60 | 5-$CF_3$ | Me | $NH_2$ | i-Pr | OH | 256-257 |

TABLE 2-3

| Compound No. | $R^1$ | $R^2$ | $R^3$ | $R^4$ | $R^7$ | Physical property value |
|---|---|---|---|---|---|---|
| 2-61 | 5-$CF_3$ | Me | $NH_2$ | i-Pr | OMe | 108-109 |
| 2-62 | 5-$CF_3$ | Me | $NH_2$ | i-Pr | OEt | NMR |
| 2-63 | 5-$CF_3$ | Me | $NH_2$ | i-Pr | O—i-Pr | NMR |
| 2-64 | 5-$CF_3$ | Me | $NH_2$ | i-Pr | $OCH_2CO_2$Me | 108-109 |
| 2-65 | 5-$CF_3$ | Me | $NH_2$ | i-Pr | NHMe | NMR |
| 2-66 | 5-$CF_3$ | Me | $NH_2$ | i-Pr | NHEt | 91-92 |
| 2-67 | 5-$CF_3$ | Me | $NH_2$ | i-Pr | NH—i-Pr | 87-88 |
| 2-68 | 5-$CF_3$ | Me | $NH_2$ | i-Pr | NH—t-Bu | 72-73 |
| 2-69 | 5-$CF_3$ | Me | $NH_2$ | i-Pr | $NMe_2$ | NMR |
| 2-70 | 5-$CF_3$ | Me | $NH_2$ | i-Pr | N(Me)OMe | 138-139 |
| 2-71 | 5-$CF_3$ | Me | $NH_2$ | i-Pr | SEt | NMR |
| 2-72 | 5-$CF_3$ | Me | $NH_2$ | $CH_2CF_3$ | OMe | 150-151 |
| 2-73 | 5-$CF_3$ | Me | $NH_2$ | $CH_2CF_3$ | OEt | NMR |
| 2-74 | 5-$CF_3$ | Me | NHAc | Et | OEt | 131-132 |
| 2-75 | 5-SMe | Me | $NH_2$ | Et | OMe | |
| 2-76 | 5-SOMe | Me | $NH_2$ | Et | OMe | |
| 2-77 | 5-$SO_2$Me | Me | $NH_2$ | Et | OMe | 180-181 |
| 2-78 | 5-SMe | Me | $NH_2$ | $CH_2CF_3$ | OMe | |
| 2-79 | 5-SOMe | Me | $NH_2$ | $CH_2CF_3$ | OMe | |
| 2-80 | 5-$SO_2$Me | Me | $NH_2$ | $CH_2CF_3$ | OMe | 230-231 |
| 2-81 | 5-$SCF_3$ | Me | H | Et | OH | 195-196 |
| 2-82 | 5-$SCF_3$ | Me | H | Et | OMe | NMR |
| 2-83 | 5-$SCF_3$ | Me | H | Et | OEt | NMR |
| 2-84 | 5-$SCF_3$ | Me | H | Et | O—n-Pr | NMR |
| 2-85 | 5-$SCF_3$ | Me | H | Et | O—i-Pr | NMR |
| 2-86 | 5-$SCF_3$ | Me | H | Et | O—t-Bu | 85-86 |
| 2-87 | 5-$SCF_3$ | Me | H | Et | $OCH_2C{\equiv}CH$ | 151-152 |
| 2-88 | 5-$SCF_3$ | Me | H | Et | $NH_2$ | 233-234 |
| 2-89 | 5-$SCF_3$ | Me | H | Et | NHMe | 169-170 |
| 2-90 | 5-$SCF_3$ | Me | H | Et | NHEt | 140-141 |

TABLE 2-4

| Table 2 (Continued) | | | | | | |
|---|---|---|---|---|---|---|
| Compound No. | $R^1$ | $R^2$ | $R^3$ | $R^4$ | $R^7$ | Physical property value |
| 2-91 | 5-$SCF_3$ | Me | H | Et | NH-i-Pr | 142-143 |
| 2-92 | 5-$SCF_3$ | Me | H | Et | NH-c-Pr | 175-176 |
| 2-93 | 5-$SCF_3$ | Me | H | Et | $NHCH_2CF_3$ | 160-161 |
| 2-94 | 5-$SCF_3$ | Me | H | Et | $NHCH_2CHF_2$ | 162-163 |
| 2-95 | 5-$SCF_3$ | Me | H | Et | $NMe_2$ | 118-119 |
| 2-96 | 5-$SCF_3$ | Me | H | Et | $NEt_2$ | 109-110 |
| 2-97 | 5-$SCF_3$ | Me | H | Et | N(Me)Et | 114-115 |
| 2-98 | 5-$SCF_3$ | Me | H | Et | N(Me)-i-Pr | 153-154 |
| 2-99 | 5-$SCF_3$ | Me | H | Et | $NHSO_2NMe_2$ | 173-175 |
| 2-100 | 5-$SCF_3$ | Me | H | Et | pyrrolidin-1-yl | 72-73 |
| 2-101 | 5-$SCF_3$ | Me | H | $CH_2CF_3$ | OMe | 92-93 |
| 2-102 | 5-$SCF_3$ | Me | Me | H | OMe | NMR |
| 2-103 | 5-$SCF_3$ | Me | Me | Me | OMe | NMR |
| 2-104 | 5-$SCF_3$ | Me | Me | Et | OH | 164-165 |
| 2-105 | 5-$SCF_3$ | Me | Me | Et | OMe | 121-122 |
| 2-106* | 5-$SCF_3$ | Me | Me | Et | OMe | NMR |
| 2-107 | 5-$SCF_3$ | Me | Me | Et | OEt | 106-107 |
| 2-108 | 5-$SCF_3$ | Me | Me | Et | NHMe | 161-162 |
| 2-109 | 5-$SCF_3$ | Me | Me | Et | $NMe_2$ | 159-160 |
| 2-110 | 5-$SCF_3$ | Me | Me | i-Pr | OMe | NMR |
| 2-111 | 5-$SCF_3$ | Me | Me | t-Bu | OMe | NMR |
| 2-112 | 5-$SCF_3$ | Me | Me | $CH_2CF_3$ | OMe | 159-160 |
| 2-113 | 5-$SCF_3$ | Me | Me | $CH_2CH{=}CH_2$ | OMe | NMR |
| 2-114 | 5-$SCF_3$ | Me | Me | $CH_2CHF_2$ | OMe | NMR |
| 2-115 | 5-$SCF_3$ | Me | Me | $CH_2CO_2H$ | OMe | |
| 2-116 | 5-$SCF_3$ | Me | Me | Bn | OMe | NMR |
| 2-117 | 5-$SCF_3$ | Me | Me | $CH_2$(4-Cl—Ph) | OMe | NMR |
| 2-118 | 5-$SCF_3$ | Me | Me | $CH(CH_3)Ph$ | OMe | |
| 2-119 | 5-$SCF_3$ | Me | Me | $CH_2CH_2$(4-Cl—Ph) | OMe | NMR |
| 2-120 | 5-$SCF_3$ | Me | $CH_2CO_2CH_3$ | Et | OMe | 1.4963 (20.1° C.) |

The symbol "*" next to the compound number indicates the Z-isomer.

TABLE 2-5

| Table 2 (Continued) | | | | | | |
|---|---|---|---|---|---|---|
| Compound No. | $R^1$ | $R^2$ | $R^3$ | $R^4$ | $R^7$ | Physical property value |
| 2-121 | 5-$SCF_3$ | Me | $NH_2$ | H | OMe | 199-200 |
| 2-122 | 5-$SCF_3$ | Me | $NH_2$ | Me | OMe | 59-60 |
| 2-123 | 5-$SCF_3$ | Me | $NH_2$ | Et | OMe | 46-47 |
| 2-124 | 5-$SCF_3$ | Me | $NH_2$ | Et | OEt | |
| 2-125 | 5-$SCF_3$ | Me | $NH_2$ | i-Pt | OMe | |
| 2-126 | 5-$SCF_3$ | Me | $NH_2$ | n-Pr | OMe | NMR |
| 2-127 | 5-$SCF_3$ | Me | $NH_2$ | n-Bu | OMe | NMR |
| 2-128 | 5-$SCF_3$ | Me | $NH_2$ | n-Bu | O-n-Bu | 92-93 |
| 2-129 | 5-$SCF_3$ | Me | $NH_2$ | $CH_2CF_3$ | OMe | 145-146 |
| 2-130 | 5-$SCF_3$ | Me | $NH_2$ | $CH_2CF_3$ | OEt | |
| 2-131 | 5-$SCF_3$ | Me | $NH_2$ | $CH_2CF_3$ | $NMe_2$ | |
| 2-132 | 5-$SCF_3$ | Me | $NH_2$ | Bn | OBn | NMR |
| 2-133 | 5-$SCF_3$ | Me | $NH_2$ | Bn | OMe | NMR |
| 2-134 | 5-$SCF_3$ | Me | NHMe | H | OMe | NMR |
| 2-135 | 5-$SCF_3$ | Me | NHMe | Et | OMe | NMR |
| 2-136 | 5-$SCF_3$ | Me | $NMe_2$ | Et | OMe | NMR |

TABLE 2-5-continued

| Table 2 (Continued) | | | | | | |
|---|---|---|---|---|---|---|
| Compound No. | $R^1$ | $R^2$ | $R^3$ | $R^4$ | $R^7$ | Physical property value |
| 2-137 | 5-$SCF_3$ | Me | OMe | H | OMe | 224-226 |
| 2-138 | 5-$SCF_3$ | Me | OMe | Et | OMe | 108-109 |
| 2-139 | 5-$SOCF_3$ | Me | H | Et | OH | |
| 2-140 | 5-$SOCF_3$ | Me | H | Et | OMe | |
| 2-141 | 5-$SOCF_3$ | Me | H | Et | OEt | |
| 2-142 | 5-$SOCF_3$ | Me | H | Et | O-n-Pr | |
| 2-143 | 5-$SOCF_3$ | Me | H | Et | O-i-Pr | |
| 2-144 | 5-$SOCF_3$ | Me | H | Et | O-t-Bu | |
| 2-145 | 5-$SOCF_3$ | Me | H | Et | $OCH_2C{\equiv}CH$ | |
| 2-146 | 5-$SOCF_3$ | Me | H | Et | $NH_2$ | |
| 2-147 | 5-$SOCF_3$ | Me | H | Et | NHMe | NMR |
| 2-148 | 5-$SOCF_3$ | Me | H | Et | NHEt | |
| 2-149 | 5-$SOCF_3$ | Me | H | Et | NH-i-Pr | |
| 2-150 | 5-$SOCF_3$ | Me | H | Et | NH-c-Pr | |

TABLE 2-6

| Table 2 (Continued) | | | | | | |
|---|---|---|---|---|---|---|
| Compound No. | $R^1$ | $R^2$ | $R^3$ | $R^4$ | $R^7$ | Physical property value |
| 2-151 | 5-$SOCF_3$ | Me | H | Et | $NHCH_2CF_3$ | |
| 2-152 | 5-$SOCF_3$ | Me | H | Et | $NHCH_2CHF_2$ | |
| 2-153 | 5-$SOCF_3$ | Me | H | Et | $NMe_2$ | |
| 2-154 | 5-$SOCF_3$ | Me | H | Et | $NEt_2$ | |

TABLE 2-6-continued

| Table 2 (Continued) | | | | | | |
|---|---|---|---|---|---|---|
| Compound No. | $R^1$ | $R^2$ | $R^3$ | $R^4$ | $R^7$ | Physical property value |
| 2-155 | 5-$SOCF_3$ | Me | H | Et | N(Me)Et | |
| 2-156 | 5-$SOCF_3$ | Me | H | Et | N(Me)-i-Pr | |
| 2-157 | 5-$SOCF_3$ | Me | H | Et | $NHSO_2NMe_2$ | |
| 2-158 | 5-$SOCF_3$ | Me | H | Et | pyrrolidin-1-yl | |
| 2-159 | 5-$SOCF_3$ | Me | H | $CH_2CF_3$ | OMe | NMR |
| 2-160 | 5-$SOCF_3$ | Me | Me | H | OMe | |
| 2-161 | 5-$SOCF_3$ | Me | Me | Me | OMe | |
| 2-162 | 5-$SOCF_3$ | Me | Me | Et | OH | |
| 2-163 | 5-$SOCF_3$ | Me | Me | Et | OMe | 166-167 |
| 2-164 | 5-$SOCF_3$ | Me | Me | Et | OEt | |
| 2-165 | 5-$SOCF_3$ | Me | Me | Et | NHMe | NMR |
| 2-166 | 5-$SOCF_3$ | Me | Me | Et | $NMe_2$ | |
| 2-167 | 5-$SOCF_3$ | Me | Me | i-Pr | OMe | |
| 2-168 | 5-$SOCF_3$ | Me | Me | t-Bu | OMe | |
| 2-169 | 5-$SOCF_3$ | Me | Me | $CH_2CF_3$ | OMe | |
| 2-170 | 5-$SOCF_3$ | Me | Me | $CH_2CH{=}CH_2$ | OMe | |
| 2-171 | 5-$SOCF_3$ | Me | Me | $CH_2CHF_2$ | OMe | |
| 2-172 | 5-$SOCF_3$ | Me | Me | $CH_2CO_2H$ | OMe | |
| 2-173 | 5-$SOCF_3$ | Me | Me | Bn | OMe | |
| 2-174 | 5-$SOCF_3$ | Me | Me | $CH_2$(4-Cl—Ph) | OMe | |
| 2-175 | 5-$SOCF_3$ | Me | Me | CH(CH3)Ph | OMe | |
| 2-176 | 5-$SOCF_3$ | Me | Me | $CH_2CH_2$(4-Cl—Ph) | OMe | |
| 2-177 | 5-$SOCF_3$ | Me | $CH_2CO_2CH_3$ | Et | OMe | |
| 2-178 | 5-$SOCF_3$ | Me | $NH_2$ | H | OMe | |
| 2-179 | 5-$SOCF_3$ | Me | $NH_2$ | Me | OMe | |
| 2-180 | 5-$SOCF_3$ | Me | $NH_2$ | Et | OMe | |

TABLE 2-7

| Table 2 (Continued) | | | | | | |
|---|---|---|---|---|---|---|
| Compound No. | $R^1$ | $R^2$ | $R^3$ | $R^4$ | $R^7$ | Physical property value |
| 2-181 | 5-$SOCF_3$ | Me | $NH_2$ | Et | OEt | NMR |
| 2-182 | 5-$SOCF_3$ | Me | $NH_2$ | i-Pr | OMe | |
| 2-183 | 5-$SOCF_3$ | Me | $NH_2$ | n-Pr | OMe | |
| 2-184 | 5-$SOCF_3$ | Me | $NH_2$ | n-Bu | OMe | |
| 2-185 | 5-$SOCF_3$ | Me | $NH_2$ | n-Bu | O-n-Bu | |
| 2-186 | 5-$SOCF_3$ | Me | $NH_2$ | $CH_2CF_3$ | OMe | |
| 2-187 | 5-$SOCF_3$ | Me | $NH_2$ | $CH_2CF_3$ | OEt | |
| 2-188 | 5-$SOCF_3$ | Me | $NH_2$ | $CH_2CF_3$ | $NMe_2$ | |
| 2-189 | 5-$SOCF_3$ | Me | $NH_2$ | Bn | OBn | |
| 2-190 | 5-$SOCF_3$ | Me | $NH_2$ | Bn | OMe | |
| 2-191 | 5-$SOCF_3$ | Me | NHMe | H | OMe | |
| 2-192 | 5-$SOCF_3$ | Me | NHMe | Et | OMe | |
| 2-193 | 5-$SOCF_3$ | Me | $NMe_2$ | Et | OMe | |
| 2-194 | 5-$SOCF_3$ | Me | OMe | H | OMe | |
| 2-195 | 5-$SOCF_3$ | Me | OMe | Et | OMe | |
| 2-196 | 5-$SO_2CF_3$ | Me | H | Et | OH | |

TABLE 2-7-continued

| Table 2 (Continued) | | | | | | |
|---|---|---|---|---|---|---|
| Compound No. | $R^1$ | $R^2$ | $R^3$ | $R^4$ | $R^7$ | Physical property value |
| 2-197 | 5-$SO_2CF_3$ | Me | H | Et | OMe | |
| 2-198 | 5-$SO_2CF_3$ | Me | H | Et | OEt | |
| 2-199 | 5-$SO_2CF_3$ | Me | H | Et | O-n-Pr | |
| 2-200 | 5-$SO_2CF_3$ | Me | H | Et | O-i-Pr | |
| 2-201 | 5-$SO_2CF_3$ | Me | H | Et | O-t-Bu | |
| 2-202 | 5-$SO_2CF_3$ | Me | H | Et | $OCH_2C{\equiv}CH$ | |
| 2-203 | 5-$SO_2CF_3$ | Me | H | Et | $NH_2$ | |
| 2-204 | 5-$SO_2CF_3$ | Me | H | Et | NHMe | 203-204 |
| 2-205 | 5-$SO_2CF_3$ | Me | H | Et | NHEt | |
| 2-206 | 5-$SO_2CF_3$ | Me | H | Et | NH-i-Pr | |
| 2-207 | 5-$SO_2CF_3$ | Me | H | Et | NH-c-Pr | |
| 2-208 | 5-$SO_2CF_3$ | Me | H | Et | $NHCH_2CF_3$ | |
| 2-209 | 5-$SO_2CF_3$ | Me | H | Et | $NHCH_2CHF_2$ | |
| 2-210 | 5-$SO_2CF_3$ | Me | H | Et | $NMe_2$ | |

TABLE 2-8

| Table 2 (Continued) | | | | | | |
|---|---|---|---|---|---|---|
| Compound No. | $R^1$ | $R^2$ | $R^3$ | $R^4$ | $R^7$ | Physical property value |
| 2-211 | 5-$SO_2CF_3$ | Me | H | Et | $NEt_2$ | |
| 2-212 | 5-$SO_2CF_3$ | Me | H | Et | N(Me)Et | |
| 2-213 | 5-$SO_2CF_3$ | Me | H | Et | N(Me)-i-Pr | |
| 2-214 | 5-$SO_2CF_3$ | Me | H | Et | $NHSO_2NMe_2$ | |
| 2-215 | 5-$SO_2CF_3$ | Me | H | Et | pyrrolidin-1-yl | |
| 2-216 | 5-$SO_2CF_3$ | Me | H | $CH_2CF_3$ | OMe | NMR |
| 2-217 | 5-$SO_2CF_3$ | Me | Me | H | OMe | |
| 2-218 | 5-$SO_2CF_3$ | Me | Me | Me | OMe | |
| 2-219 | 5-$SO_2CF_3$ | Me | Me | Et | OH | 249-250 |
| 2-220 | 5-$SO_2CF_3$ | Me | Me | Et | OMe | 88-89 |

TABLE 2-8-continued

Table 2 (Continued)

| Compound No. | $R^1$ | $R^2$ | $R^3$ | $R^4$ | $R^7$ | Physical property value |
|---|---|---|---|---|---|---|
| 2-221 | 5-$SO_2CF_3$ | Me | Me | Et | OEt | NMR |
| 2-222 | 5-$SO_2CF_3$ | Me | Me | Et | Me | 179-180 |
| 2-223 | 5-$SO_2CF_3$ | Me | Me | Et | $NH_2$ | 239-240 |
| 2-224 | 5-$SO_2CF_3$ | Me | Me | Et | NHAc | 181-184 |
| 2-225 | 5-$SO_2CF_3$ | Me | Me | Et | NHMe | 199-200 |
| 2-226 | 5-$SO_2CF_3$ | Me | Me | Et | $NMe_2$ | 191-193 |
| 2-227 | 5-$SO_2CF_3$ | Me | Me | Et | N(Me)OMe | 141-143 |
| 2-228 | 5-$SO_2CF_3$ | Me | Me | i-Pr | OMe | |
| 2-229 | 5-$SO_2CF_3$ | Me | Me | i-Pr | OEt | |
| 2-230 | 5-$SO_2CF_3$ | Me | Me | t-Bu | OMe | |
| 2-231 | 5-$SO_2CF_3$ | Me | Me | $CH_2CF_3$ | OMe | 186-187 |
| 2-232 | 5-$SO_2CF_3$ | Me | Me | $CH_2CH{=}CH_2$ | OMe | |
| 2-233 | 5-$SO_2CF_3$ | Me | Me | $CH_2CHF_2$ | OMe | |
| 2-234 | 5-$SO_2CF_3$ | Me | Me | $CH_2CO_2H$ | OMe | |
| 2-235 | 5-$SO_2CF_3$ | Me | Me | Bn | OMe | |
| 2-236 | 5-$SO_2CF_3$ | Me | Me | $CH_2$(4-Cl—Ph) | OMe | |
| 2-237 | 5-$SO_2CF_3$ | Me | Me | $CH(CH_3)Ph$ | OMe | |
| 2-238 | 5-$SO_2CF_3$ | Me | Me | $CH_2CH_2$(4-Cl—Ph) | OMe | |
| 2-239 | 5-$SO_2CF_3$ | Me | $CH_2CO_2CH_3$ | Et | OMe | |
| 2-240 | 5-$SO_2CF_3$ | Me | NHa | H | OMe | |

TABLE 2-9

Table 2 (Continued)

| Compound No. | $R^1$ | $R^2$ | $R^3$ | $R^4$ | $R^7$ | Physical property value |
|---|---|---|---|---|---|---|
| 2-241 | 5-$SO_2CF_3$ | Me | $NH_2$ | Me | OMe | |
| 2-242 | 5-$SO_2CF_3$ | Me | $NH_2$ | Et | OMe | |
| 2-243 | 5-$SO_2CF_3$ | Me | $NH_2$ | Et | OEt | NMR |
| 2-244 | 5-$SO_2CF_3$ | Me | $NH_2$ | i-Pr | OMe | |
| 2-245 | 5-$SO_2CF_3$ | Me | $NH_2$ | n-Pr | OMe | |
| 2-246 | 5-$SO_2CF_3$ | Me | $NH_2$ | n-Bu | OMe | |
| 2-247 | 5-$SO_2CF_3$ | Me | $NH_2$ | n-Bu | O-n-Bu | |
| 2-248 | 5-$SO_2CF_3$ | Me | $NH_2$ | $CH_2CF_3$ | OMe | |
| 2-249 | 5-$SO_2CF_3$ | Me | $NH_2$ | $CH_2CF_3$ | OEt | 137-138 |
| 2-250 | 5-$SO_2CF_3$ | Me | $NH_2$ | $CH_2CF_3$ | $NMe_2$ | 207-208 |
| 2-251 | 5-$SO_2CF_3$ | Me | $NH_2$ | Bn | OBn | |
| 2-252 | 5-$SO_2CF_3$ | Me | $NH_2$ | Bn | OMe | |
| 2-253 | 5-$SO_2CF_3$ | Me | NHMe | H | OMe | |
| 2-254 | 5-$SO_2CF_3$ | Me | NHMe | Et | OMe | |
| 2-255 | 5-$SO_2CF_3$ | Me | $NMe_2$ | Et | OMe | |
| 2-256 | 5-$SO_2CF_3$ | Me | OMe | H | OMe | |
| 2-257 | 5-$SO_2CF_3$ | Me | OMe | Et | OMe | |
| 2-258 | 5-Me-6-Br | Me | Me | Et | Me | 192-193 |
| 2-259 | 5,7-di-Br | Me | H | Et | OMe | 127-128 |
| 2-260 | 5,7-di-Cl | Me | H | Et | OMe | NMR |
| 2-261 | 5-Me-6,7-di-Br | Me | Me | Et | Me | 221-224 |
| 2-262 | H | Me | $NH_2$ | i-Pr | OMe | NMR |
| 2-263 | H | Me | $NH_2$ | i-Pr | OH | 183-184 |
| 2-264 | H | Me | $NH_2$ | i-Pr | NHEt | |
| 2-265 | H | Me | $NH_2$ | i-Pr | $NEt_2$ | |
| 2-266 | H | Me | $NH_2$ | i-Pr | $NHCH_2CF_3$ | 188-189 |
| 2-267 | H | Me | $NH_2$ | i-Pr | pyrrolidin-1-yl | |
| 2-268 | H | Me | $NH_2$ | 1-Pr | N(Me)OMe | |
| 2-269 | H | Me | $NH_2$ | $CH_2CF_3$ | OH | NMR |
| 2-270 | H | Me | $NH_2$ | $CH_2CF_3$ | OMe | NMR |

TABLE 2-10

Table 2 (Continued)

| Compound No. | $R^1$ | $R^2$ | $R^3$ | $R^4$ | $R^7$ | Physical property value |
|---|---|---|---|---|---|---|
| 2-271 | H | Me | $NH_2$ | $CH_2CF_3$ | NHEt | |
| 2-272 | H | Me | $NH_2$ | $CH_2CF_3$ | $NEt_2$ | |
| 2-273 | H | Me | $NH_2$ | $CH_2CF_3$ | $NHCH_2CF_3$ | |
| 2-274 | H | Me | $NH_2$ | $CH_2CF_3$ | pyrrolidin-1-yl | |
| 2-275 | H | Me | $NH_2$ | $CH_2CF_3$ | N(Me)OMe | NMR |
| 2-276 | 5-Me | Me | $NH_2$ | Et | $NMe_2$ | 175-176 |
| 2-277 | 5-Me | Me | $NH_2$ | Et | $NEt_2$ | 161-162 |
| 2-278 | 5-Me | Me | $NH_2$ | Et | NH(thiethan-3-yl) | 199-200 |
| 2-279 | 5-Me | Me | $NH_2$ | Et | NHEt | |
| 2-280 | 5-Me | Me | $NH_2$ | Et | NH(1,1-dioxothietan-3-yl) | |
| 2-281 | 5-Me | Me | $NH_2$ | Et | $NHCH_2CF_3$ | 194-195 |
| 2-282 | 5-Me | Me | $NH_2$ | $CH_2CF_3$ | OH | NMR |
| 2-283 | 5-Me | Me | $NH_2$ | $CH_2CF_3$ | OMe | NMR |
| 2-284 | 5-Me | Me | $NH_2$ | $CH_2CF_3$ | $NHCH_2CF_3$ | |
| 2-285 | 5-Me | Me | $NH_2$ | $CH_2CF_3$ | $NEt_2$ | NMR |
| 2-286 | 5-Me | Me | $NH_2$ | $CH_2CF_3$ | NHEt | NMR |
| 2-287 | 5-Me | Me | $NH_2$ | $CH_2CF_3$ | pyrrolidin-1-yl | |
| 2-288 | 5-Me | Me | $NH_2$ | $CH_2CF_3$ | N(Me)OMe | NMR |
| 2-289 | 5-$CF_3$ | Me | $NH_2$ | i-Pr | $NHNH_2$ | NMR |
| 2-290 | 5-$CF_3$ | Me | $NH_2$ | Me | NHEt | 193-194 |
| 2-291 | 5-$CF_3$ | Me | $NH_2$ | Me | $NH_2$ | 233-234 |
| 2-292 | 5-$CF_3$ | Me | $NH_2$ | Me | OH | 161-162 |
| 2-293 | 5-$CF_3$ | Me | $NH_2$ | Me | OPh | 69-70 |
| 2-294 | 5-$CF_3$ | Me | $NH_2$ | Me | O-c-Bu | NMR |
| 2-295 | 5-$CF_3$ | Me | $NH_2$ | Et | NH-c-Pr | |
| 2-296 | 5-$CF_3$ | Me | $NH_2$ | Et | NHPh | |
| 2-297 | 5-$CF_3$ | Me | $NH_2$ | Et | NH(4-OMePh) | |
| 2-298 | 5-$CF_3$ | Me | $NH_2$ | Et | NH(4-$CF_3$Ph) | |
| 2-299 | 5-$CF_3$ | Me | $NH_2$ | Et | $NHCH_2CH_2Cl$ | |
| 2-300 | 5-$CF_3$ | Me | $NH_2$ | Et | NHOMe | |

TABLE 2-11

Table 2 (Continued)

| Compound No. | $R^1$ | $R^2$ | $R^3$ | $R^4$ | $R^7$ | Physical property value |
|---|---|---|---|---|---|---|
| 2-301 | 5-$CF_3$ | Me | $NH_2$ | Et | NH(thiethan-3-yl) | |
| 2-302 | 5-$CF_3$ | Me | $NH_2$ | Et | $NHCH_2CF_3$ | NMR |

TABLE 2-11-continued

Table 2 (Continued)

| Compound No. | $R^1$ | $R^2$ | $R^3$ | $R^4$ | $R^7$ | Physical property value |
|---|---|---|---|---|---|---|
| 2-303 | 5-$CF_3$ | Me | $NH_2$ | Et | $NHCH_2CN$ | |
| 2-304 | 5-$CF_3$ | Me | $NH_2$ | Et | NHOEt | NMR |
| 2-305 | 5-$CF_3$ | Me | $NH_2$ | Et | NHO-i-Pr | NMR |
| 2-306 | 5-$CF_3$ | Me | $NH_2$ | Et | NHO-n-Pr | NMR |
| 2-307 | 5-$CF_3$ | Me | $NH_2$ | Et | $NHCH_2CHF_2$ | |
| 2-308 | 5-$CF_3$ | Me | $NH_2$ | Et | NH(3,3-difluorocyclobutane) | NMR |
| 2-309 | 5-$CF_3$ | Me | $NH_2$ | Et | $NMe_2$ | |
| 2-310 | 5-$CF_3$ | Me | $NH_2$ | Et | $NEt_2$ | NMR |
| 2-311 | 5-$CF_3$ | Me | $NH_2$ | Et | $N(Me)CH_2C\equiv CH$ | NMR |
| 2-312 | 5-$CF_3$ | Me | $NH_2$ | Et | $NH(CH_2C\equiv CH)$ | NMR |
| 2-313 | 5-$CF_3$ | Me | $NH_2$ | Et | $NHOCH_2CH{=}CH_2$ | NMR |
| 2-314 | 5-$CF_3$ | Me | $NH_2$ | Et | N(Me)Et | NMR |
| 2-315 | 5-$CF_3$ | Me | $NH_2$ | Et | N(Me)-i-Pr | NMR |
| 2-316 | 5-$CF_3$ | Me | $NH_2$ | Et | N(Et)-i-Pr | NMR |
| 2-317 | 5-$CF_3$ | Me | $NH_2$ | Et | N(Me)OMe | NMR |
| 2-318 | 5-$CF_3$ | Me | $NH_2$ | Et | NH(tetrahydrofuran-3-yl) | |
| 2-319 | 5-$CF_3$ | Me | $NH_2$ | Et | pyrrolidin-1-yl | NMR |
| 2-320 | 5-$CF_3$ | Me | $NH_2$ | Et | 3-pyrrolin-1-yl | |
| 2-321 | 5-$CF_3$ | Me | $NH_2$ | Et | morphorin-4-yl | NMR |
| 2-322 | 5-$CF_3$ | Me | $NH_2$ | Et | 3,3,4,4-tetrafluoropyrrolidin-1-yl | NMR |
| 2-323 | 5-$CF_3$ | Me | $NH_2$ | Et | thiazolidin-3-yl | NMR |
| 2-324 | 5-$CF_3$ | Me | $NH_2$ | Et | NH(thiazol-2-yl) | NMR |
| 2-325 | 5-$CF_3$ | Me | $NH_2$ | Et | $NHCH_2CHF_2$ | NMR |
| 2-326 | 5-$CF_3$ | Me | $NH_2$ | Et | $NHNMe_2$ | NMR |
| 2-327 | 5-Me | Me | $NH_2$ | $CH_2CF_3$ | $NHCH_2CH_2F$ | NMR |
| 2-328 | 5-Me | Me | $NH_2$ | $CH_2CF_3$ | $NHCH_2CHF_2$ | NMR |
| 2-329 | 5-Me | Me | $NH_2$ | $CH_2CF_3$ | NH-c-Pr | NMR |
| 2-330 | 5-Me | Me | $NH_2$ | $CH_2CF_3$ | NHCH(Me)-c-Pr | NMR |

TABLE 2-12

Table 2 (Continued)

| Compound No. | $R^1$ | $R^2$ | $R^3$ | $R^4$ | $R^7$ | Physical property value |
|---|---|---|---|---|---|---|
| 2-331 | 5-Me | Me | $NH_2$ | $CH_2CF_3$ | $NHCH_2CH{=}CH_2$ | NMR |
| 2-332 | 5-Me | Me | $NH_2$ | $CH_2CF_3$ | $NHCH_2CH_2OMe$ | NMR |
| 2-333 | 5-Me | Me | $NH_2$ | $CH_2CF_3$ | NH-oxolane-2-one-3-yl | NMR |
| 2-334 | 5-Me | Me | $NH_2$ | $CH_2CF_3$ | NH[(1R)-2-methoxy-1-methylethyl] | NMR |
| 2-335 | 5-Me | Me | $NH_2$ | $CH_2CF_3$ | $NHCH_2CH(OMe)_2$ | NMR |
| 2-336 | 5-Me | Me | $NH_2$ | $CH_2CF_3$ | NHOMe | NMR |
| 2-337 | 5-Me | Me | $NH_2$ | $CH_2CF_3$ | NHOEt | NMR |
| 2-338 | 5-Me | Me | $NH_2$ | $CH_2CF_3$ | $NHOCH_2CH{=}CH_2$ | NMR |
| 2-339 | 5-Me | Me | $NH_2$ | $CH_2CF_3$ | N(Me)Et | NMR |
| 2-340 | 5-Me | Me | $NH_2$ | $CH_2CF_3$ | N(Me)-i-Pr | NMR |
| 2-341 | 5-Me | Me | $NH_2$ | $CH_2CF_3$ | N(Et)-i-Pr | NMR |
| 2-342 | 5-Me | Me | $NH_2$ | $CH_2CF_3$ | 3,3,4,4-tetrafluoropyrrolidin-1-yl | NMR |
| 2-343 | 5-Me | Me | $NH_2$ | $CH_2CF_3$ | $N(Me)CH_2C\equiv CH$ | NMR |
| 2-344 | 5-Me | Me | $NH_2$ | $CH_2CF_3$ | N(Me)OH | NMR |
| 2-345 | 5-$CF_3$ | Me | $NH_2$ | Me | N(Me)OMe | NMR |
| 2-346 | 5-Me | Me | $NH_2$ | Et | N(Me)OMe | NMR |

[Chem. 29]

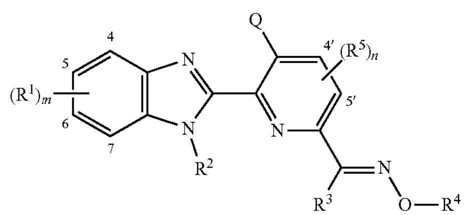

(1c)

The position numbers in the table are the numbers designated in the general formula (1c).

TABLE 3-1

Table 3

| Compound No. | $R^1$ | $R^2$ | $R^3$ | $R^4$ | $R^5$ | Q | Physical property value |
|---|---|---|---|---|---|---|---|
| 3-1 | H | Me | Me | Et | H | H | |
| 3-2 | H | Me | Me | Et | H | Cl | 116-118 |
| 3-3 | H | Me | Me | Et | H | C(Me)=N—OEt | 142-143 |
| 3-4 | H | Me | Me | $CH_2CF_3$ | H | H | 145-146 |

TABLE 3-1-continued

Table 3

| Compound No. | $R^1$ | $R^2$ | $R^3$ | $R^4$ | $R^5$ | Q | Physical property value |
|---|---|---|---|---|---|---|---|
| 3-5 | H | Me | Me | $CH_2CF_3$ | H | Cl | |
| 3-6 | 5-Me | Me | Me | H | H | Cl | 212-213 |
| 3-7 | 5-Me | Me | Me | Et | H | F | |
| 3-8 | 5-Me | Me | Me | Et | H | Cl | 133-135 |
| 3-9 | 5-Me | Me | Me | Et | H | OMe | 130-131 |
| 3-10 | 5-Me | Me | Me | Et | H | OEt | 153-155 |
| 3-11 | 5-Me | Me | Me | Et | H | SMe | 87-89 |
| 3-12 | 5-Me | Me | Me | Et | H | SOMe | 202-203 |
| 3-13 | 5-Me | Me | Me | Et | H | C(OEt)=$CH_2$ | 90-93 |
| 3-14 | 5-Me | Me | $CONH_2$ | Et | H | OEt | 224-225 |
| 3-15 | 5-Me | Me | $NH_2$ | Me | H | $SCH_2$(4-t-BuPh) | NMR |
| 3-16 | 5-Me | Me | $NH_2$ | Et | H | F | 87-88 |
| 3-17 | 5-Me | Me | $NH_2$ | Et | H | Cl | 131-132 |
| 3-18 | 5-Me | Me | $NH_2$ | Et | H | CN | 235-237 |
| 3-19 | 5-Me | Me | $NH_2$ | Et | H | $CF_3$ | NMR |
| 3-20 | 5-Me | Me | $NH_2$ | Et | H | $CH_2OH$ | 134-136 |
| 3-21 | 5-Me | Me | $NH_2$ | Et | H | $CH(OH)CH_3$ | NMR |
| 3-22 | 5-Me | Me | $NH_2$ | Et | H | $CH(OH)CH_2OH$ | NMR |
| 3-23 | 5-Me | Me | $NH_2$ | Et | H | CH=$CH_2$ | NMR |
| 3-24 | 5-Me | Me | $NH_2$ | Et | H | C(Me)=$CH_2$ | NMR |
| 3-25 | 5-Me | Me | $NH_2$ | Et | H | CH=N—NHMe | 84-85 |
| 3-26 | 5-Me | Me | $NH_2$ | Et | H | CH=N—OMe | 212-213 |
| 3-27 | 5-Me | Me | $NH_2$ | Et | H | $SCF_3$ | 116-117 |
| 3-28 | 5-Me | Me | $NH_2$ | Et | H | $SCH_2$(4-t-BuPh) | 116-117 |
| 3-29 | 5-Me | Me | $NH_2$ | Et | H | SMe | 165-166 |
| 3-30 | 5-Me | Me | $NH_2$ | Et | H | SOMe | |

TABLE 3-2

Table 3 (Continued)

| Compound No. | $R^1$ | $R^2$ | $R^3$ | $R^4$ | $R^5$ | Q | Physical property value |
|---|---|---|---|---|---|---|---|
| 3-31 | 5-Me | Me | $NH_2$ | Et | H | SEt | 119-120 |
| 3-32 | 5-Me | Me | $NH_2$ | Et | H | SOEt | |
| 3-33 | 5-Me | Me | $NH_2$ | Et | H | SO(=NH)Me | NMR |
| 3-34 | 5-Me | Me | $NH_2$ | Et | H | 2,2-di-Me-1,3-dioxolan-4-yl | NMR |
| 3-35 | 5-Me | Me | $NH_2$ | Et | H | 2-oxo-1,3-dioxolan-4-yl | NMR |
| 3-36 | 5-Me | Me | $NH_2$ | Et | H | 1,3-dioxan-2-yl | NMR |
| 3-37 | 5-Me | Me | $NH_2$ | Et | H | 1,3-dioxolan-2-yl | NMR |
| 3-38 | 5-Me | Me | $NH_2$ | Et | H | Me | |
| 3-39 | 5-Me | Me | $NH_2$ | Et | H | 5-Me-1,2,4-oxadiazol-3-yl | 147-148 |
| 3-40 | 5-Me | Me | $NH_2$ | Et | H | 1H-imidazol-2-yl | 243-244 |
| 3-41 | 5-Me | Me | $NH_2$ | Et | 4'-Me | Cl | 200-201 |
| 3-42 | 5-Me | Me | $NH_2$ | Et | 4'-Me | $CO_2Me$ | |
| 3-43 | 5-Me | Me | $NH_2$ | Et | 4'-Me | $SO_2Me$ | 251-252 |
| 3-44 | 5-Me | Me | $NH_2$ | Et | 4'-Me | $SO_2NHMe$ | NMR |
| 3-45 | 5-Et | Me | $NH_2$ | Me | H | $SCH_2$(4-t-BuPh) | NMR |
| 3-46 | 5-Et | Me | $NH_2$ | Et | 4'-Me | $SO_2Me$ | |
| 3-47 | 5-Et | Me | $NH_2$ | Et | 4'-Me | $SO_2NHMe$ | NMR |
| 3-48 | 5-$CHF_2$ | Me | Me | Et | H | SMe | 201-202 |
| 3-49 | 5-$CHF_2$ | Me | Me | Et | H | SOMe | |
| 3-50 | 5-$CHF_2$ | Me | Me | Et | H | SO(=NH)Me | 100-101 |
| 3-51 | 5-$CHF_2$ | Me | Me | Et | H | SO(=NMe)Me | NMR |
| 3-52 | 5-$CHF_2$ | Me | $NH_2$ | Et | H | SEt | 141-142 |
| 3-53 | 5-$CHF_2$ | Me | $NH_2$ | Et | H | SOEt | |
| 3-54 | 5-$CHF_2$ | Me | $NH_2$ | Et | H | S—n-Pr | NMR |
| 3-55 | 5-$CHF_2$ | Me | $NH_2$ | Et | H | SO—n-Pr | |
| 3-56 | 5-$CHF_2$ | Me | $NH_2$ | Et | H | S—i-Pr | NMR |
| 3-57 | 5-$CHF_2$ | Me | $NH_2$ | Et | H | SO—i-Pr | |
| 3-58 | 5-$CF_3$ | Me | $NH_2$ | Me | H | $SCH_2$(4-t-BuPh) | NMR |
| 3-59 | 5-$CF_3$ | Me | $NH_2$ | Et | H | $SCH_2$(4-t-BuPh) | NMR |
| 3-60 | 5-$CF_3$ | Me | $NH_2$ | Et | 4'-Br | $SO_2NHMe$ | 205-206 |

TABLE 3-3

Table 3 (Continued)

| Compound No. | $R^1$ | $R^2$ | $R^3$ | $R^4$ | $R^5$ | Q | Physical property value |
|---|---|---|---|---|---|---|---|
| 3-61 | 5-$CF_3$ | Me | $NH_2$ | Et | 4'-Et | Cl | NMR |
| 3-62 | 5-$CF_3$ | Me | $NH_2$ | Et | 4'-Et | SMe | NMR |
| 3-63 | 5-$CF_3$ | Me | $NH_2$ | Et | 4'-Et | SOMe | 208-209 |
| 3-64 | 5-$CF_3$ | Me | $NH_2$ | Et | 4'-Et | $SO_2Me$ | 201-202 |
| 3-65 | 5-$CF_3$ | Me | $NH_2$ | Et | 4'-Me | Cl | 144-145 |
| 3-66 | 5-$CF_3$ | Me | $NH_2$ | Et | 4'-Me | Br | 128-129 |
| 3-67 | 5-$CF_3$ | Me | $NH_2$ | Et | 4'-Me | $CO_2Et$ | 139-140 |
| 3-68 | 5-$CF_3$ | Me | $NH_2$ | Et | 4'-Me | SMe | NMR |
| 3-69 | 5-$CF_3$ | Me | $NH_2$ | Et | 4'-Me | SOMe | NMR |
| 3-70 | 5-$CF_3$ | Me | $NH_2$ | Et | 4'-Me | $SO_2Me$ | 246-247 |
| 3-71 | 5-$CF_3$ | Me | $NH_2$ | Et | 4'-Me | $SO_2NHMe$ | 102-103 |
| 3-72 | 5-$CF_3$ | Me | $NH_2$ | Et | 4'-$NH_2$ | $SO_2NHMe$ | NMR |
| 3-73 | 5-$CF_3$ | Me | $NH_2$ | Et | 4'-NHMe | $SO_2NHMe$ | 134-135 |
| 3-74 | 5-$CF_3$ | Me | $NH_2$ | i-Pr | H | $SCH_2$(4-t-BuPh) | NMR |
| 3-75 | 5-$CF_3$ | Me | NHMe | Et | H | $SCH_2$(4-t-BuPh) | NMR |
| 3-76 | 5-$CF_3$ | Me | $NMe_2$ | Et | H | $SCH_2$(4-t-BuPh) | NMR |
| 3-77 | 5-$OCHF_2$ | Me | $NH_2$ | Et | H | $SO_2NHMe$ | |
| 3-78 | 5-$OCHF_2$ | Me | $NH_2$ | i-Pr | H | $SO_2NHMe$ | |
| 3-79 | 5-$OCHF_2$ | Me | $NH_2$ | Et | H | $SCH_2$(4-t-BuPh) | 142 |
| 3-80 | 5-$OCHF_2$ | Me | $NH_2$ | i-Pr | H | $SCH_2$(4-t-BuPh) | 154-157 |
| 3-81 | 5-$SCF_3$ | Me | H | Et | H | CN | 135-136 |
| 3-82 | 5-$SCF_3$ | Me | H | Et | H | SMe | 116-117 |
| 3-83 | 5-$SCF_3$ | Me | H | Et | H | SOMe | 202-203 |
| 3-84 | 5-$SCF_3$ | Me | H | $CH_2CF_3$ | H | $CH_2OH$ | NMR |

TABLE 3-3-continued

Table 3 (Continued)

| Compound No. | $R^1$ | $R^2$ | $R^3$ | $R^4$ | $R^5$ | Q | Physical property value |
|---|---|---|---|---|---|---|---|
| 3-85 | 5-$SCF_3$ | Me | H | $CH_2CF_3$ | H | SEt | 134-135 |
| 3-86* | 5-$SCF_3$ | Me | H | $CH_2CF_3$ | H | SEt | 106-107 |
| 3-87 | 5-$SCF_3$ | Me | H | $CH_2CF_3$ | H | SOEt | |
| 3-88 | 5-$SCF_3$ | Me | Me | Me | H | C(Me)═N—OMe | |
| 3-89 | 5-$SCF_3$ | Me | Me | Et | H | H | 130-131 |
| 3-90 | 5-$SCF_3$ | Me | Me | Et | H | C(Me)═N—OEt | NMR |

The symbol "*" next to the compound number indicates the Z-isomer.

TABLE 3-4

Table 3 (Continued)

| Compound No. | $R^1$ | $R^2$ | $R^3$ | $R^4$ | $R^5$ | Q | Physical property value |
|---|---|---|---|---|---|---|---|
| 3-91 | 5-$SCF_3$ | Me | Me | Et | 5'-Me | $CO_2Et$ | 1.3386 (22.2° C.) |
| 3-92* | 5-$SCF_3$ | Me | Me | Et | 5'-Me | $CO_2Et$ | 139-141 |
| 3-93 | 5-$SCF_3$ | Me | Me | i-Pr | H | C(Me)═N—O—i-Pr | NMR |
| 3-94 | 5-$SCF_3$ | Me | Me | t-Bu | H | C(Me)═N—O—t-Bu | NMR |
| 3-95 | 5-$SCF_3$ | Me | Me | Bn | H | C(Me)═N—OBn | NMR |
| 3-96 | 5-$SCF_3$ | Me | Me | $CH_2CF3$ | H | C(Me)═N—$OCH_2CF3$ | NMR |
| 3-97 | 5-$SCF_3$ | Me | Me | $CH_2CHF_2$ | H | C(Me)═N—$OCH_2CHF_2$ | NMR |
| 3-98 | 5-$SCF_3$ | Me | Me | $CH_2CH$═$CH_2$ | H | C(Me)═N—$OCH_2CH$═$CH_2$ | NMR |
| 3-99 | 5-$SOCF_3$ | Me | Me | Et | H | H | 104-106 |
| 3-100 | 5-$SO_2CF_3$ | Me | Me | Et | H | H | 138-140 |
| 3-101 | 5-$SO_2CF_3$ | Me | Me | Et | H | OMe | 1.3913 (19.8° C.) |
| 3-102 | 5-$SO_2CF_3$ | Me | Me | Et | H | SH | 139-141 |
| 3-103 | 5-$SO_2CF_3$ | Me | Me | Et | H | SMe | 107-110 |
| 3-104 | 5-$SO_2CF_3$ | Me | Me | Et | H | SOMe | |
| 3-105 | 5-$SO_2CF_3$ | Me | Me | Et | H | $SCH_2CFa$ | 70-75 |
| 3-106 | 5-$SO_2CF_3$ | Me | Me | Et | H | $SOCH_2CF3$ | |
| 3-107 | 5-$SO_2CF_3$ | Me | Me | Et | H | SBn | 170-173 |
| 3-108 | 5-$SO_2CF_3$ | Me | Me | Et | H | $SCH_2$(4-OMePh) | 223-224 |
| 3-109 | 5-$SO_2CF_3$ | Me | Me | Et | H | $SCH_2$(4-t-BuPh) | 186-187 |
| 3-110 | 5-$SO_2CF_3$ | Me | Me | Et | H | $SCH_2$(4-TMSPh) | 172-175 |
| 3-111 | 5-$SO_2CF_3$ | Me | Me | Et | H | $NH_2$ | 258-259 |
| 3-112 | 5-$SO_2CF_3$ | Me | Me | Et | H | NHAc | 189-190 |
| 3-113 | 5-$SO_2CF_3$ | Me | Me | Et | H | $NAc_2$ | NMR |
| 3-114 | 5-Ph | Me | H | Et | H | Ph | NMR |
| 3-115 | 5,6-di-Me | Me | $NH_2$ | Et | H | H | 187-189 |
| 3-116 | 5-$CF_3$ | Me | $NH_2$ | Me | H | C(═S)NHEt | 123-124 |

The symbol "*" next to the compound number indicates the Z-isomer.

TABLE 3-5

Table 3 (Continued)

| Compound No. | $R^1$ | $R^2$ | $R^3$ | $R^4$ | $R^5$ | Q | Physical property value |
|---|---|---|---|---|---|---|---|
| 3-117 | H | Me | $NH_2$ | Me | H | $SCH_2$(4-t-BuPh) | NMR |
| 3-118 | H | Me | $NH_2$ | Et | H | $SCH_2$(4-t-BuPh) | 98-99 |
| 3-119 | 5-$OCHF_2$ | Me | $NH_2$ | Me | H | $SCH_2$(4-t-BuPh) | 181-182 |
| 3-120 | 5-$CF_3$ | Me | $NH_2$ | Et | H | Cl | NMR |
| 3-121 | 5-$CF_3$ | Me | $NH_2$ | Et | H | P(═O)$(OMe)_2$ | NMR |
| 3-122 | 5-$CF_3$ | Me | $NH_2$ | Et | H | NHP(═O)$(OEt)_2$ | NMR |
| 3-123 | 5-Me | Me | $NH_2$ | Et | H | NHAc | NMR |
| 3-124 | 5-$CF_3$ | Me | $NH_2$ | Et | H | $NHSO_2Me$ | 182-183 |

TABLE 3-5-continued

Table 3 (Continued)

| Compound No. | $R^1$ | $R^2$ | $R^3$ | $R^4$ | $R^5$ | Q | Physical property value |
|---|---|---|---|---|---|---|---|
| 3-125 | 5-$CF_3$ | Me | $NH_2$ | Me | H | 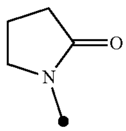 | |
| 3-126 | 5-$CF_3$ | Me | $NH_2$ | Et | H | 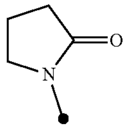 | NMR |

TABLE 3-5-continued

| Table 3 (Continued) | | | | | | | |
|---|---|---|---|---|---|---|---|
| Compound No. | $R^1$ | $R^2$ | $R^3$ | $R^4$ | $R^5$ | Q | Physical property value |
| 3-127 | 5-$CF_3$ | Me | $NH_2$ | iPr | H | 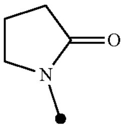 | |
| 3-128 | 5-Me | Me | $NH_2$ | Et | H | 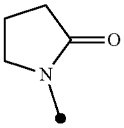 | NMR |
| 3-129 | H | Me | $NH_2$ | Et | H | 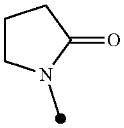 | NMR |
| 3-130 | 5-$CF_3$ | Me | $NH_2$ | Et | H | 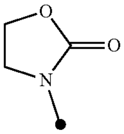 | NMR |
| 3-131 | 5-$CF_3$ | Me | $NH_2$ | iPr | H | 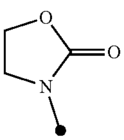 | |
| 3-132 | 5-Me | Me | $NH_2$ | Et | H | 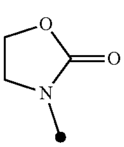 | |
| 3-133 | H | Me | $NH_2$ | Et | H | 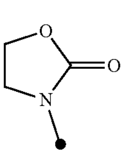 | |
| 3-134 | 5-$CF_3$ | Me | $NH_2$ | Et | H | 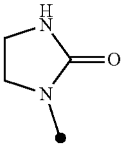 | 130-131 |

The black solid circle in the structural formula represents a binding position.

TABLE 3-6

| Table 3 (Continued) | | | | | | | |
|---|---|---|---|---|---|---|---|
| Compound No. | $R^1$ | $R^2$ | $R^3$ | $R^4$ | $R^5$ | Q | Physical property value |
| 3-135 | 5-$CF_3$ | Me | $NH_2$ | iPr | H | 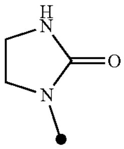 | |
| 3-136 | 5-Me | Me | $NH_2$ | Et | H | 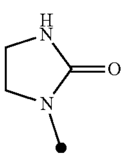 | |
| 3-137 | H | Me | $NH_2$ | Et | H | 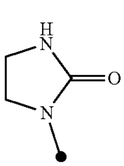 | |
| 3-138 | 5-$CF_3$ | Me | $NH_2$ | Et | H | 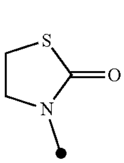 | NMR |
| 3-139 | 5-$CF_3$ | Me | $NH_2$ | iPr | H | 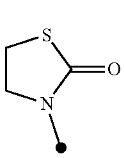 | |
| 3-140 | 5-Me | Me | $NH_2$ | Et | H | 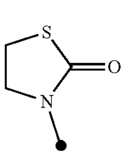 | |
| 3-141 | H | Me | $NH_2$ | Et | H | 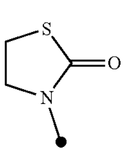 | |
| 3-142 | 5-$CF_3$ | Me | $NH_2$ | Et | H | 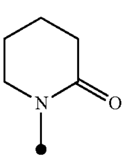 | |
| 3-143 | 5-$CF_3$ | Me | $NH_2$ | iPr | H | 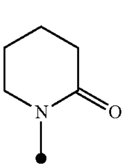 | |

TABLE 3-6-continued

Table 3 (Continued)

| Compound No. | $R^1$ | $R^2$ | $R^3$ | $R^4$ | $R^5$ | Q | Physical property value |
|---|---|---|---|---|---|---|---|
| 3-144 | 5-Me | Me | $NH_2$ | Et | H | 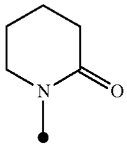 | |
| 3-145 | H | Me | $NH_2$ | Et | H | 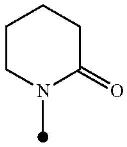 | |
| 3-146 | 5-$CF_3$ | Me | $NH_2$ | Et | H | 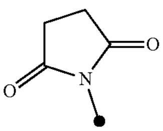 | |
| 3-147 | 5-$CF_3$ | Me | $NH_2$ | iPr | H | 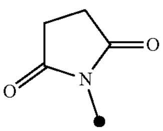 | |

The black solid circle in the structural formula represents a binding position.

TABLE 3-7

Table 3 (Continued)

| Compound No. | $R^1$ | $R^2$ | $R^3$ | $R^4$ | $R^5$ | Q | Physical property value |
|---|---|---|---|---|---|---|---|
| 3-148 | 5-Me | Me | $NH_2$ | Et | H | 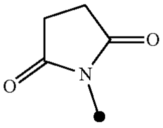 | |
| 3-149 | H | Me | $NH_2$ | Et | H | 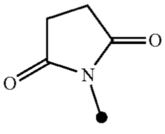 | |
| 3-150 | 5-$CF_3$ | Me | $NH_2$ | Et | H | 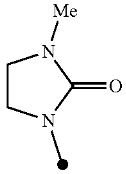 | |
| 3-151 | 5-$CF_3$ | Me | $NH_2$ | iPr | H | 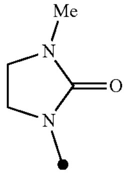 | |

TABLE 3-7-continued

Table 3 (Continued)

| Compound No. | $R^1$ | $R^2$ | $R^3$ | $R^4$ | $R^5$ | Q | Physical property value |
|---|---|---|---|---|---|---|---|
| 3-152 | 5-Me | Me | $NH_2$ | Et | H | 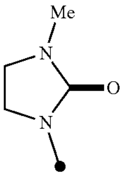 | |
| 3-153 | H | Me | $NH_2$ | Et | H | 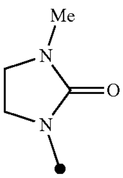 | |
| 3-154 | 5-$CF_3$ | Me | $NH_2$ | Et | H | $N(Me)SO_2Me$ | |
| 3-155 | 5-$CF_3$ | Me | $NH_2$ | iPr | H | $N(Me)SO_2Me$ | |
| 3-156 | 5-Me | Me | $NH_2$ | Et | H | $N(Me)SO_2Me$ | |
| 3-157 | H | Me | $NH_2$ | Et | H | $N(Me)SO_2Me$ | |
| 3-158 | 5-$CF_3$ | Me | $NH_2$ | Et | H | $N(Et)SO_2Me$ | |
| 3-159 | 5-$CF_3$ | Me | $NH_2$ | iPr | H | $N(Et)SO_2Me$ | |
| 3-160 | 5-Me | Me | $NH_2$ | Et | H | $N(Et)SO_2Me$ | |
| 3-161 | H | Me | $NH_2$ | Et | H | $N(Et)SO_2Me$ | |
| 3-162 | 5-$CF_3$ | Me | $NH_2$ | Et | H | $N(Me)CO_2Me$ | |
| 3-163 | 5-$CF_3$ | Me | $NH_2$ | iPr | H | $N(Me)CO_2Me$ | |
| 3-164 | 5-Me | Me | $NH_2$ | Et | H | $N(Me)CO_2Me$ | |

The black solid circle in the structural formula represents a binding position.

TABLE 3-8

Table 3 (Continued)

| Compound No. | $R^1$ | $R^2$ | $R^3$ | $R^4$ | $R^5$ | Q | Physical property value |
|---|---|---|---|---|---|---|---|
| 3-165 | H | Me | $NH_2$ | Et | H | $N(Me)CO_2Me$ | |
| 3-166 | 5-$CF_3$ | Me | $NH_2$ | Et | H | $N(Et)CO_2Me$ | |
| 3-167 | 5-$CF_3$ | Me | $NH_2$ | iPr | H | $N(Et)CO_2Me$ | |
| 3-168 | 5-Me | Me | $NH_2$ | Et | H | $N(Et)CO_2Me$ | |
| 3-169 | H | Me | $NH_2$ | Et | H | $N(Et)CO_2Me$ | |
| 3-170 | 5-$CF_3$ | Me | $NH_2$ | Et | H | $NHCO_2Me$ | |
| 3-171 | 5-$CF_3$ | Me | $NH_2$ | iPr | H | $NHCO_2Me$ | |
| 3-172 | 5-Me | Me | $NH_2$ | Et | H | $NHCO_2Me$ | |
| 3-173 | H | Me | $NH_2$ | Et | H | $NHCO_2Me$ | |
| 3-174 | 5-$CF_3$ | Me | $NH_2$ | Et | H | $NHCO_2Et$ | |
| 3-175 | 5-$CF_3$ | Me | $NH_2$ | iPr | H | $NHCO_2Et$ | |
| 3-176 | 5-Me | Me | $NH_2$ | Et | H | $NHCO_2Et$ | |
| 3-177 | H | Me | $NH_2$ | Et | H | $NHCO_2Et$ | |
| 3-178 | 5-$CF_3$ | Me | $NH_2$ | Et | H | N(Me)Ac | |
| 3-179 | 5-$CF_3$ | Me | $NH_2$ | iPr | H | N(Me)Ac | |
| 3-180 | 5-Me | Me | $NH_2$ | Et | H | N(Me)Ac | |
| 3-181 | H | Me | $NH_2$ | Et | H | N(Me)Ac | |
| 3-182 | 5-$CF_3$ | Me | $NH_2$ | Et | H | N(Et)Ac | |
| 3-183 | 5-$CF_3$ | Me | $NH_2$ | iPr | H | N(Et)Ac | |
| 3-184 | 5-Me | Me | $NH_2$ | Et | H | N(Et)Ac | |
| 3-185 | H | Me | $NH_2$ | Et | H | N(Et)Ac | |
| 3-186 | 5-$CF_3$ | Me | $NH_2$ | Et | H | $N(NH_2)CO_2Me$ | |
| 3-187 | 5-$CF_3$ | Me | $NH_2$ | iPr | H | $N(NH_2)CO_2Me$ | |
| 3-188 | 5-Me | Me | $NH_2$ | Et | H | $N(NH_2)CO_2Me$ | |
| 3-189 | H | Me | $NH_2$ | Et | H | $N(NH_2)CO_2Me$ | |

TABLE 3-9

Table 3 (Continued)

| Compound No. | $R^1$ | $R^2$ | $R^3$ | $R^4$ | $R^5$ | Q | Physical property value |
|---|---|---|---|---|---|---|---|
| 3-190 | 5-$CF_3$ | Me | $NH_2$ | Et | H | 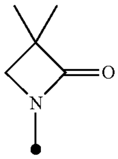 | |
| 3-191 | 5-$CF_3$ | Me | $NH_2$ | iPr | H | 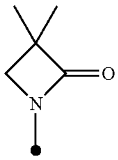 | |
| 3-192 | 5-Me | Me | $NH_2$ | Et | H | 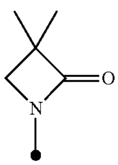 | |
| 3-193 | H | Me | $NH_2$ | Et | H | 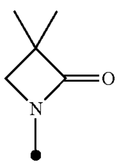 | |
| 3-194 | 5-$CF_3$ | Me | $NH_2$ | Et | H | 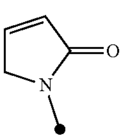 | |
| 3-195 | 5-$CF_3$ | Me | $NH_2$ | iPr | H | 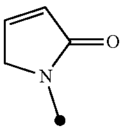 | |
| 3-196 | 5-Me | Me | $NH_2$ | Et | H | 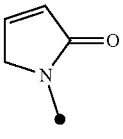 | |
| 3-197 | H | Me | $NH_2$ | Et | H | 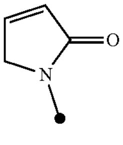 | |
| 3-198 | 5-$CF_3$ | Me | $NH_2$ | Et | H | NHC(=O)NHMe | |
| 3-199 | 5-$CF_3$ | Me | $NH_2$ | iPr | H | NHC(=O)NHMe | |
| 3-200 | 5-Me | Me | $NH_2$ | Et | H | NHC(=O)NHMe | |
| 3-201 | H | Me | $NH_2$ | Et | H | NHC(=O)NHMe | |
| 3-202 | 5-$CF_3$ | Me | $NH_2$ | Et | H | NHC(=O)$NMe_2$ | |
| 3-203 | 5-$CF_3$ | Me | $NH_2$ | iPr | H | NHC(=O)$NMe_2$ | |
| 3-204 | 5-Me | Me | $NH_2$ | Et | H | NHC(=O)$NMe_2$ | |
| 3-205 | H | Me | $NH_2$ | Et | H | NHC(=O)$NMe_2$ | |
| 3-206 | 5-$CF_3$ | Me | $NH_2$ | Et | H | N(Me)C(=O)NHMe | |

TABLE 3-9-continued

Table 3 (Continued)

| Compound No. | $R^1$ | $R^2$ | $R^3$ | $R^4$ | $R^5$ | Q | Physical property value |
|---|---|---|---|---|---|---|---|
| 3-207 | 5-$CF_3$ | Me | $NH_2$ | iPr | | N(Me)C(=O)NHMe | |
| 3-208 | 5-Me | Me | $NH_2$ | Et | H | N(Me)C(=O)NHMe | |
| 3-209 | H | Me | $NH_2$ | Et | H | N(Me)C(=O)NHMe | |

The black solid circle in the structural formula represents a binding position.

TABLE 3-10

Table 3 (Continued)

| Compound No. | $R^1$ | $R^2$ | $R^3$ | $R^4$ | $R^5$ | Q | Physical property value |
|---|---|---|---|---|---|---|---|
| 3-210 | 5-$CF_3$ | Me | $NH_2$ | Et | H | N(Me)C(=O)$NMe_2$ | |
| 3-211 | 5-$CF_3$ | Me | $NH_2$ | iPr | H | N(Me)C(=O)$NMe_2$ | |
| 3-212 | 5-Me | Me | $NH_2$ | Et | H | N(Me)C(=O)$NMe_2$ | |
| 3-213 | H | Me | $NH_2$ | Et | H | N(Me)C(=O)$NMe_2$ | |
| 3-214 | 5-$CF_3$ | Me | $NH_2$ | Et | H | NHC(=O)$CH_2$OMe | |
| 3-215 | 5-$CF_3$ | Me | $NH_2$ | iPr | H | NHC(=O)$CH_2$OMe | |
| 3-216 | 5-Me | Me | $NH_2$ | Et | H | NHC(=O)$CH_2$OMe | |
| 3-217 | H | Me | $NH_2$ | Et | H | NHC(=O)$CH_2$OMe | |
| 3-218 | H | Me | $NH_2$ | Me | 4'-Me | $CO_2$Me | |
| 3-219 | H | Me | $NH_2$ | Me | 4'-Me | $SO_2$Me | |
| 3-220 | H | Me | $NH_2$ | Me | 4'-Me | $SO_2$NHMe | |
| 3-221 | H | Me | $NH_2$ | Et | 4'-Me | $CO_2$Me | |
| 3-222 | H | Me | $NH_2$ | Et | 4'-Me | $SO_2$Me | |
| 3-223 | H | Me | $NH_2$ | Et | 4'-Me | $SO_2$NHMe | |
| 3-224 | H | Me | $NH_2$ | i-Pr | 4'-Me | $CO_2$Me | |
| 3-225 | H | Me | $NH_2$ | i-Pr | 4'-Me | $SO_2$Me | |
| 3-226 | H | Me | $NH_2$ | i-Pr | 4'-Me | $SO_2$NHMe | |
| 3-227 | 5-Me | Me | $NH_2$ | Me | 4'-Me | $CO_2$Me | |
| 3-228 | 5-Me | Me | $NH_2$ | Me | 4'-Me | $SO_2$Me | |
| 3-229 | 5-Me | Me | $NH_2$ | Me | 4'-Me | $SO_2$NHMe | |
| 3-230 | 5-Me | Me | $NH_2$ | i-Pr | 4'-Me | $CO_2$Me | |
| 3-231 | 5-Me | Me | $NH_2$ | i-Pr | 4'-Me | $SO_2$Me | |
| 3-232 | 5-Me | Me | $NH_2$ | i-Pr | 4'-Me | $SO_2$NHMe | |
| 3-233 | 5-OMe | Me | $NH_2$ | Me | 4'-Me | $CO_2$Me | |
| 3-234 | 5-OMe | Me | $NH_2$ | Me | 4'-Me | $SO_2$Me | |
| 3-235 | 5-OMe | Me | $NH_2$ | Me | 4'-Me | $SO_2$NHMe | |
| 3-236 | 5-OMe | Me | $NH_2$ | Et | 4'-Me | $CO_2$Me | |
| 3-237 | 5-OMe | Me | $NH_2$ | Et | 4'-Me | $SO_2$Me | |
| 3-238 | 5-OMe | Me | $NH_2$ | Et | 4'-Me | $SO_2$NHMe | |
| 3-239 | 5-OMe | Me | $NH_2$ | i-Pr | 4'-Me | $CO_2$Me | |
| 3-240 | 5-OMe | Me | $NH_2$ | i-Pr | 4'-Me | $SO_2$Me | |
| 3-241 | 5-OMe | Me | $NH_2$ | i-Pr | 4'-Me | $SO_2$NHMe | |

TABLE 3-11

Table 3 (Continued)

| Compound No. | $R^1$ | $R^2$ | $R^3$ | $R^4$ | $R^5$ | Q | Physical property value |
|---|---|---|---|---|---|---|---|
| 3-242 | 5-$CHF_2$ | Me | $NH_2$ | Me | 4'-Me | $CO_2$Me | |
| 3-243 | 5-$CHF_2$ | Me | $NH_2$ | Me | 4'-Me | $SO_2$Me | |
| 3-244 | 5-$CHF_2$ | Me | $NH_2$ | Me | 4'-Me | $SO_2$NHMe | |
| 3-245 | 5-$CHF_2$ | Me | $NH_2$ | Et | 4'-Me | $CO_2$Me | |
| 3-246 | 5-$CHF_2$ | Me | $NH_2$ | Et | 4'-Me | $SO_2$Me | |
| 3-247 | 5-$CHF_2$ | Me | $NH_2$ | Et | 4'-Me | $SO_2$NHMe | |
| 3-248 | 5-$CHF_2$ | Me | $NH_2$ | i-Pr | 4'-Me | $CO_2$Me | |
| 3-249 | 5-$CHF_2$ | Me | $NH_2$ | i-Pr | 4'-Me | $SO_2$Me | |
| 3-250 | 5-$CHF_2$ | Me | $NH_2$ | i-Pr | 4'-Me | $SO_2$NHMe | |
| 3-251 | 5-$CF_3$ | Me | $NH_2$ | Me | 4'-Me | $CO_2$Me | |
| 3-252 | 5-$CF_3$ | Me | $NH_2$ | Me | 4'-Me | $SO_2$Me | |
| 3-253 | 5-$CF_3$ | Me | $NH_2$ | Me | 4'-Me | $SO_2$NHMe | |
| 3-254 | 5-$CF_3$ | Me | $NH_2$ | Et | 4'-Me | $CO_2$Me | |
| 3-255 | 5-$CF_3$ | Me | $NH_2$ | i-Pr | 4'-Me | $CO_2$Me | |
| 3-256 | 5-$CF_3$ | Me | $NH_2$ | i-Pr | 4'-Me | $SO_2$Me | |

TABLE 3-11-continued

Table 3 (Continued)

| Compound No. | $R^1$ | $R^2$ | $R^3$ | $R^4$ | $R^5$ | Q | Physical property value |
|---|---|---|---|---|---|---|---|
| 3-257 | 5-$CF_3$ | Me | $NH_2$ | i-Pr | 4'-Me | $SO_2NHMe$ | |
| 3-258 | H | Me | Me | Me | 4'-Me | $CO_2Me$ | |
| 3-259 | H | Me | Me | Me | 4'-Me | $SO_2Me$ | |
| 3-260 | H | Me | Me | Me | 4'-Me | $SO_2NHMe$ | |
| 3-261 | H | Me | Me | Et | 4'-Me | $CO_2Me$ | |
| 3-262 | H | Me | Me | Et | 4'-Me | $SO_2Me$ | |
| 3-263 | H | Me | Me | Et | 4'-Me | $SO_2NHMe$ | |
| 3-264 | H | Me | Me | i-Pr | 4'-Me | $CO_2Me$ | |
| 3-265 | H | Me | Me | i-Pr | 4'-Me | $SO_2Me$ | |
| 3-266 | H | Me | Me | i-Pr | 4'-Me | $SO_2NHMe$ | |
| 3-267 | 5-Me | Me | Me | Me | 4'-Me | $CO_2Me$ | |
| 3-268 | 5-Me | Me | Me | Me | 4'-Me | $SO_2Me$ | |
| 3-269 | 5-Me | Me | Me | Me | 4'-Me | $SO_2NHMe$ | |
| 3-270 | 5-Me | Me | Me | Et | 4'-Me | $CO_2Me$ | |
| 3-271 | 5-Me | Me | Me | Et | 4'-Me | $SO_2Me$ | |
| 3-272 | 5-Me | Me | Me | Et | 4'-Me | $SO_2NHMe$ | |

TABLE 3-12

Table 3 (Continued)

| Compound No. | $R^1$ | $R^2$ | $R^3$ | $R^4$ | $R^5$ | Q | Physical property value |
|---|---|---|---|---|---|---|---|
| 3-273 | 5-Me | Me | Me | i-Pr | 4'-Me | $CO_2Me$ | |
| 3-274 | 5-Me | Me | Me | i-Pr | 4'-Me | $SO_2Me$ | |
| 3-275 | 5-Me | Me | Me | i-Pr | 4'-Me | $SO_2NHMe$ | |
| 3-276 | 5-OMe | Me | Me | Me | 4'-Me | $CO_2Me$ | |
| 3-277 | 5-OMe | Me | Me | Me | 4'-Me | $SO_2Me$ | |
| 3-278 | 5-OMe | Me | Me | Me | 4'-Me | $SO_2NHMe$ | |
| 3-279 | 5-OMe | Me | Me | Et | 4'-Me | $CO_2Me$ | |
| 3-280 | 5-OMe | Me | Me | Et | 4'-Me | $SO_2Me$ | |
| 3-281 | 5-OMe | Me | Me | Et | 4'-Me | $SO_2NHMe$ | |
| 3-282 | 5-OMe | Me | Me | i-Pr | 4'-Me | $CO_2Me$ | |
| 3-283 | 5-OMe | Me | Me | i-Pr | 4'-Me | $SO_2Me$ | |
| 3-284 | 5-OMe | Me | Me | i-Pr | 4'-Me | $SO_2NHMe$ | |
| 3-285 | 5-$CHF_2$ | Me | Me | Me | 4'-Me | $CO_2Me$ | |
| 3-286 | 5-$CHF_2$ | Me | Me | Me | 4'-Me | $SO_2Me$ | |
| 3-287 | 5-$CHF_2$ | Me | Me | Me | 4'-Me | $SO_2NHMe$ | |
| 3-288 | 5-$CHF_2$ | Me | Me | Et | 4'-Me | $CO_2Me$ | |
| 3-289 | 5-CHFz | Me | Me | Et | 4'-Me | $SO_2Me$ | |
| 3-290 | 5-$CHF_2$ | Me | Me | Et | 4'-Me | $SO_2NHMe$ | |
| 3-291 | 5-$CHF_2$ | Me | Me | i-Pr | 4'-Me | $CO_2Me$ | |
| 3-292 | 5-$CHF_2$ | Me | Me | i-Pr | 4'-Me | $SO_2Me$ | |
| 3-293 | 5-$CHF_2$ | Me | Me | i-Pr | 4'-Me | $SO_2NHMe$ | |
| 3-294 | 5-$CF_3$ | Me | Me | Me | 4'-Me | $CO_2Me$ | |
| 3-295 | 5-$CF_3$ | Me | Me | Me | 4'-Me | $SO_2Me$ | |
| 3-296 | 5-$CF_3$ | Me | Me | Me | 4'-Me | $SO_2NHMe$ | |
| 3-297 | 5-$CF_3$ | Me | Me | Et | 4'-Me | $CO_2Me$ | |
| 3-298 | 5-$CF_3$ | Me | Me | Et | 4'-Me | $SO_2Me$ | |
| 3-299 | 5-$CF_3$ | Me | Me | Et | 4'-Me | $SO_2NHMe$ | |
| 3-300 | 5-$CF_3$ | Me | Me | i-Pr | 4'-Me | $CO_2Me$ | |
| 3-301 | 5-$CF_3$ | Me | Me | i-Pr | 4'-Me | $SO_2Me$ | |
| 3-302 | 5-$CF_3$ | Me | Me | i-Pr | 4'-Me | $SO_2NHMe$ | |

[Chem. 30]

(1d)

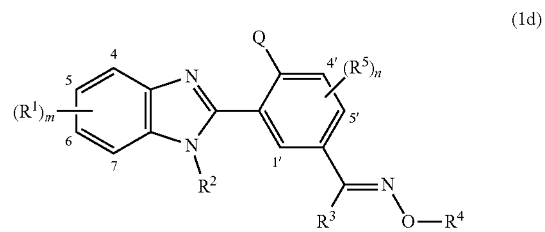

The position numbers in the table are the numbers designated in the general formula (1d).

TABLE 4-1

| Compound No. | $R^1$ | $R^2$ | $R^3$ | $R^4$ | $R^5$ | Q | Physical property value |
|---|---|---|---|---|---|---|---|
| 4-1 | H | Me | $NH_2$ | Me | H | $CO_2Me$ | |
| 4-2 | H | Me | $NH_2$ | Me | H | $SO_2Me$ | |
| 4-3 | H | Me | $NH_2$ | Me | H | $SO_2NHMe$ | |
| 4-4 | H | Me | $NH_2$ | Et | H | $CO_2Me$ | |
| 4-5 | H | Me | $NH_2$ | Et | H | $SO_2Me$ | |
| 4-6 | H | Me | $NH_2$ | Et | H | $SO_2NHMe$ | |
| 4-7 | H | Me | $NH_2$ | i-Pr | H | $CO_2Me$ | |
| 4-8 | H | Me | $NH_2$ | i-Pr | H | $SO_2Me$ | |
| 4-9 | H | Me | $NH_2$ | i-Pr | H | $SO_2NHMe$ | |
| 4-10 | 5-Me | Me | $NH_2$ | Me | H | $CO_2Me$ | |
| 4-11 | 5-Me | Me | $NH_2$ | Me | H | $SO_2Me$ | |
| 4-12 | 5-Me | Me | $NH_2$ | Me | H | $SO_2NHMe$ | |
| 4-13 | 5-Me | Me | $NH_2$ | Et | H | $CO_2Me$ | |
| 4-14 | 5-Me | Me | $NH_2$ | Et | H | CONMez | 212-213 |
| 4-15 | 5-Me | Me | $NH_2$ | Et | H | $SO_2Me$ | 72-73 |
| 4-16 | 5-Me | Me | $NH_2$ | Et | H | $SO_2NHMe$ | NMR |
| 4-17 | 5-Me | Me | $NH_2$ | i-Pr | H | $CO_2Me$ | |
| 4-18 | 5-Me | Me | $NH_2$ | i-Pr | H | SOMe | |
| 4-19 | 5-Me | Me | $NH_2$ | i-Pr | H | $SO_2NHMe$ | |
| 4-20 | 5-Me | Me | $NH_2$ | Et | 4'-Me | Br | 224-226 |
| 4-21 | 5-Me | Me | $NH_2$ | Et | 4'-Me | CO2H | |
| 4-22 | 5-Me | Me | $NH_2$ | Et | 4'-Me | $CO_2Me$ | 1.3869(21.0° C.) |
| 4-23 | 5-OMe | Me | $NH_2$ | Me | H | $CO_2Me$ | |
| 4-24 | 5-OMe | Me | $NH_2$ | Me | H | $SO_2Me$ | |
| 4-25 | 5-OMe | Me | $NH_2$ | Me | H | $SO_2NHMe$ | |
| 4-26 | 5-OMe | Me | $NH_2$ | Et | H | $CO_2Me$ | |
| 4-27 | 5-OMe | Me | $NH_2$ | Et | H | $SO_2Me$ | |
| 4-28 | 5-OMe | Me | $NH_2$ | Et | H | $SO_2NHMe$ | |
| 4-29 | 5-OMe | Me | $NH_2$ | i-Pr | H | $CO_2Me$ | |
| 4-30 | 5-OMe | Me | $NH_2$ | i-Pr | H | $SO_2Me$ | |

TABLE 4-2

Table 4 (Continued)

| Compound No. | $R^1$ | $R^2$ | $R^3$ | $R^4$ | $R^5$ | Q | Physical property value |
|---|---|---|---|---|---|---|---|
| 4-31 | 5-OMe | Me | $NH_2$ | i-Pr | H | $SO_2NHMe$ | |
| 4-32 | 5-$CHF_2$ | Me | $NH_2$ | Me | H | $CO_2Me$ | |
| 4-33 | 5-$CHF_2$ | Me | $NH_2$ | Me | H | $SO_2Me$ | |
| 4-34 | 5-$CHF_2$ | Me | $NH_2$ | Me | H | $SO_2NHMe$ | |
| 4-35 | 5-$CHF_2$ | Me | $NH_2$ | Et | H | $CO_2Me$ | |
| 4-36 | 5-$CHF_2$ | Me | $NH_2$ | Et | H | $SO_2Me$ | |
| 4-37 | 5-$CHF_2$ | Me | $NH_2$ | Et | H | $SO_2NHMe$ | |

TABLE 4-2-continued

Table 4 (Continued)

| Compound No. | $R^1$ | $R^2$ | $R^3$ | $R^4$ | $R^5$ | Q | Physical property value |
|---|---|---|---|---|---|---|---|
| 4-38 | 5-$CHF_2$ | Me | $NH_2$ | i-Pr | H | $CO_2Me$ | |
| 4-39 | 5-$CHF_2$ | Me | $NH_2$ | i-Pr | H | $SO_2Me$ | |
| 4-40 | 5-$CHF_2$ | Me | $NH_2$ | i-Pr | H | $SO_2NHMe$ | |
| 4-41 | 5-$CF_3$ | Me | $NH_2$ | Me | H | $CO_2Me$ | |
| 4-42 | 5-$CF_3$ | Me | $NH_2$ | Me | H | $SO_2Me$ | |
| 4-43 | 5-$CF_3$ | Me | $NH_2$ | Me | H | $SO_2NHMe$ | |
| 4-44 | 5-$CF_3$ | Me | $NH_2$ | Et | H | $CO_2Me$ | |
| 4-45 | 5-$CF_3$ | Me | $NH_2$ | Et | H | $SO_2Me$ | |
| 4-46 | 5-$CF_3$ | Me | $NH_2$ | Et | H | $SO_2NHMe$ | NMR |
| 4-47 | 5-$CF_3$ | Me | $NH_2$ | i-Pr | H | $CO_2Me$ | |
| 4-48 | 5-$CF_3$ | Me | $NH_2$ | i-Pr | H | $SO_2Me$ | |
| 4-49 | 5-$CF_3$ | Me | $NH_2$ | i-Pr | H | $SO_2NHMe$ | 118-119 |
| 4-50 | 5-$CF_3$ | Me | $NH_2$ | i-Pr | H | $SO_2NMe_2$ | NMR |
| 4-51 | H | Me | Me | Me | H | $CO_2Me$ | |
| 4-52 | H | Me | Me | Me | H | $SO_2Me$ | |
| 4-53 | H | Me | Me | Me | H | $SO_2NHMe$ | |
| 4-54 | H | Me | Me | Et | H | $CO_2Me$ | 120-121 |
| 4-55 | H | Me | Me | Et | H | $SO_2Me$ | |
| 4-56 | H | Me | Me | Et | H | $SO_2NHMe$ | |
| 4-57 | H | Me | Me | i-Pr | H | $CO_2Me$ | |
| 4-58 | H | Me | Me | i-Pr | H | $SO_2Me$ | |
| 4-59 | H | Me | Me | i-Pr | H | $SO_2NHMe$ | |
| 4-60 | H | Me | Me | $CH_2CF_3$ | H | C(Me)═N—$OCH_2CF_3$ | NMR |

TABLE 4-3

Table 4 (Continued)

| Compound No. | $R^1$ | $R^2$ | $R^3$ | $R^4$ | $R^5$ | Q | Physical property value |
|---|---|---|---|---|---|---|---|
| 4-61 | H | Me | Me | $CH_2CF_3$ | H | $CO_2Me$ | 133-134 |
| 4-62* | H | Me | Me | $CH_2CF_3$ | H | $CO_2Me$ | NMR |
| 4-63 | 5-Me | Me | Me | Me | H | $CO_2Me$ | |
| 4-64 | 5-Me | Me | Me | Me | H | $SO_2Me$ | |
| 4-65 | 5-Me | Me | Me | Me | H | $SO_2NHMe$ | |
| 4-66 | 5-Me | Me | Me | Et | H | $CO_2Me$ | |
| 4-67 | 5-Me | Me | Me | Et | H | SMe | NMR |
| 4-68 | 5-Me | Me | Me | Et | H | $SO_2Me$ | NMR |
| 4-69 | 5-Me | Me | Me | Et | H | $SO_2NHMe$ | |
| 4-70 | 5-Me | Me | Me | i-Pr | H | $CO_2Me$ | |
| 4-71 | 5-Me | Me | Me | i-Pr | H | $SO_2Me$ | |
| 4-72 | 5-Me | Me | Me | i-Pr | H | $SO_2NHMe$ | |
| 4-73 | 5-OMe | Me | Me | Me | H | $CO_2Me$ | |
| 4-74 | 5-OMe | Me | Me | Me | H | $SO_2Me$ | |
| 4-75 | 5-OMe | Me | Me | Me | H | $SO_2NHMe$ | |
| 4-76 | 5-OMe | Me | Me | Et | H | $CO_2Me$ | |

TABLE 4-3-continued

Table 4 (Continued)

| Compound No. | $R^1$ | $R^2$ | $R^3$ | $R^4$ | $R^5$ | Q | Physical property value |
|---|---|---|---|---|---|---|---|
| 4-77 | 5-OMe | Me | Me | Et | H | $SO_2Me$ | |
| 4-78 | 5-OMe | Me | Me | Et | H | $SO_2NHMe$ | |
| 4-79 | 5-OMe | Me | Me | i-Pr | H | $CO_2Me$ | |
| 4-80 | 5-OMe | Me | Me | i-Pr | H | $SO_2Me$ | |
| 4-81 | 5-OMe | Me | Me | i-Pr | H | $SO_2NHMe$ | |
| 4-82 | 5-$CHF_2$ | Me | Me | Me | H | $CO_2Me$ | |
| 4-83 | 5-$CHF_2$ | Me | Me | Me | H | $SO_2Me$ | |
| 4-84 | 5-$CHF_2$ | Me | Me | Me | H | $SO_2NHMe$ | |
| 4-85 | 5-$CHF_2$ | Me | Me | Et | H | $CO_2Me$ | |
| 4-86 | 5-$CHF_2$ | Me | Me | Et | H | $SO_2Me$ | |
| 4-87 | 5-$CHF_2$ | Me | Me | Et | H | $SO_2NHMe$ | |
| 4-88 | 5-$CHF_2$ | Me | Me | i-Pr | H | $CO_2Me$ | |
| 4-89 | 5-$CHF_2$ | Me | Me | i-Pr | H | $SO_2Me$ | |
| 4-90 | 5-$CHF_2$ | Me | Me | i-Pr | H | $SO_2NHMe$ | |

The symbol "*" next to the compound number indicates the Z-isomer.

TABLE 4-4

Table 4 (Continued)

| Compound No. | $R^1$ | $R^2$ | $R^3$ | $R^4$ | $R^5$ | Q | Physical property value |
|---|---|---|---|---|---|---|---|
| 4-91 | 5-$CF_3$ | Me | Me | Me | H | $CO_2Me$ | |
| 4-92 | 5-$CF_3$ | Me | Me | Me | H | $SO_2Me$ | |
| 4-93 | 5-$CF_3$ | Me | Me | Me | H | $SO_2NHMe$ | |
| 4-94 | 5-$CF_3$ | Me | Me | Et | H | $CO_2Me$ | |
| 4-95 | 5-$CF_3$ | Me | Me | Et | H | $SO_2Me$ | |
| 4-96 | 5-$CF_3$ | Me | Me | Et | H | $SO_2NHMe$ | |
| 4-97 | 5-$CF_3$ | Me | Me | i-Pr | H | $CO_2Me$ | |
| 4-98 | 5-$CF_3$ | Me | Me | i-Pr | H | $SO_2Me$ | |
| 4-99 | 5-$CF_3$ | Me | Me | i-Pr | H | $SO_2NHMe$ | |
| 4-100 | 5-$SCF_3$ | Me | Me | Et | H | Me | NMR |
| 4-101* | 5-$SCF_3$ | Me | Me | Et | H | Me | NMR |
| 4-102 | 5-$SCF_3$ | Me | Me | Et | H | OH | 134-135 |
| 4-103 | 5-$SCF_3$ | Me | Me | Et | H | $OCH_2OMe$ | 72-73 |
| 4-104* | 5-$SCF_3$ | Me | Me | Et | H | $OCH_2OMe$ | NMR |
| 4-105 | 5-$SCF_3$ | Me | Me | Et | 4'-Me | Br | 166 |
| 4-106* | 5-$SCF_3$ | Me | Me | Et | 4'-Me | Br | 1.6285(24.2° C.) |
| 4-107 | 5-$SCF_3$ | Me | Me | Et | 4'-Me | $CO_2Me$ | 112-115 |

TABLE 4-4-continued

Table 4 (Continued)

| Compound No. | $R^1$ | $R^2$ | $R^3$ | $R^4$ | $R^5$ | Q | Physical property value |
|---|---|---|---|---|---|---|---|
| 4-108 | 5-$SCF_3$ | Me | Me | Et | 4'-Me | $CO_2Me$ | 1.3494(26.7° C.) |
| 4-109* | 5-$SCF_3$ | Me | Me | Et | 4'-Me | $CO_2Me$ | NMR |
| 4-110 | 5-Br | Me | Me | $CH_2CF_3$ | H | $CO_2Me$ | 129-130 |
| 4-111 | 5-I | Me | Me | Et | H | $CO_2Me$ | NMR |
| 4-112 | 5-$SO_2NH_2$ | Me | Me | Et | H | $CO_2Me$ | 177-178 |
| 4-113 | 5-$SO_2NMe_2$ | Me | Me | Et | H | $CO_2Me$ | NMR |
| 4-114 | 6-Br | Me | Me | $CH_2CF_3$ | H | $CO_2Me$ | 147-148 |
| 4-115 | 5-$SO_2NH_2$ | Me | Me | Et | H | $CO_2Me$ | 89-90 |
| 4-116 | 5.6-di-Br | Me | Me | $CH_2CF_3$ | H | $CO_2Me$ | 173-174 |
| 4-117 | 5-$SCF_3$ | Me | H | Et | H | $SO_2Et$ | 1.4796(20.0° C.) |
| 4-118 | 5-$SCF_3$ | Me | H | CH2CHF2 | H | $SO_2Et$ | 1.4029(20.1° C.) |
| 4-119 | 5-$SCF_3$ | Me | H | $CH_2CF_3$ | H | $SO_2Et$ | 1.4292(20.1° C.) |
| 4-120 | 5-$SO_2CF_3$ | Me | H | $CH_2CHF_2$ | H | $SO_2Et$ | 47-48 |

The symbol "*" next to the compound number indicates the Z-isomer.

TABLE 4-5

Table 4 (Continued)

| Compound No. | $R^1$ | $R^2$ | $R^3$ | $R^4$ | $R^5$ | Q | Physical property value |
|---|---|---|---|---|---|---|---|
| 4-121 | 5-$SO_2CF_3$ | Me | H | $CH_2CF_3$ | H | $SO_2Et$ | 58-59 |
| 4-122 | H | Me | $NH_2$ | Me | 4'-Me | $CO_2Me$ | |
| 4-123 | H | Me | $NH_2$ | Me | 4'-Me | $SO_2Me$ | |
| 4-124 | H | Me | $NH_2$ | Me | 4'-Me | $SO_2NHMe$ | |
| 4-125 | H | Me | $NH_2$ | Et | 4'-Me | $CO_2Me$ | |
| 4-126 | H | Me | $NH_2$ | Et | 4'-Me | $SO_2Me$ | |
| 4-127 | H | Me | $NH_2$ | Et | 4'-Me | $SO_2NHMe$ | |
| 4-128 | H | Me | $NH_2$ | i-Pr | 4'-Me | $CO_2Me$ | |
| 4-129 | H | Me | $NH_2$ | i-Pr | 4'-Me | $SO_2Me$ | |
| 4-130 | H | Me | $NH_2$ | i-Pr | 4'-Me | $SO_2NHMe$ | |
| 4-131 | 5-Me | Me | $NH_2$ | Me | 4'-Me | $CO_2Me$ | |
| 4-132 | 5-Me | Me | $NH_2$ | Me | 4'-Me | $SO_2Me$ | |
| 4-133 | 5-Me | Me | $NH_2$ | Me | 4'-Me | $SO_2NHMe$ | |
| 4-134 | 5-Me | Me | $NH_2$ | Et | 4'-Me | $SO_2Me$ | |
| 4-135 | 5-Me | Me | $NH_2$ | Et | 4'-Me | $SO_2NHMe$ | |
| 4-136 | 5-Me | Me | $NH_2$ | i-Pr | 4'-Me | $CO_2Me$ | |
| 4-137 | 5-Me | Me | $NH_2$ | i-Pr | 4'-Me | $SO_2Me$ | |
| 4-138 | 5-Me | Me | $NH_2$ | i-Pr | 4'-Me | $SO_2NHMe$ | |
| 4-139 | 5-OMe | Me | $NH_2$ | Me | 4'-Me | $CO_2Me$ | |
| 4-140 | 5-OMe | Me | $NH_2$ | Me | 4'-Me | $SO_2Me$ | |
| 4-141 | 5-OMe | Me | $NH_2$ | Me | 4'-Me | $SO_2NHMe$ | |
| 4-142 | 5-OMe | Me | $NH_2$ | Et | 4'-Me | $CO_2Me$ | |
| 4-143 | 5-OMe | Me | $NH_2$ | Et | 4'-Me | $SO_2Me$ | |
| 4-144 | 5-OMe | Me | $NH_2$ | Et | 4'-Me | $SO_2NHMe$ | |
| 4-145 | 5-OMe | Me | $NH_2$ | i-Pr | 4'-Me | $CO_2Me$ | |
| 4-146 | 5-OMe | Me | $NH_2$ | i-Pr | 4'-Me | $SO_2Me$ | |
| 4-147 | 5-OMe | Me | $NH_2$ | i-Pr | 4'-Me | $SO_2NHMe$ | |
| 4-148 | 5-$CHF_2$ | Me | $NH_2$ | Me | 4'-Me | $CO_2Me$ | |
| 4-149 | 5-$CHF_2$ | Me | $NH_2$ | Me | 4'-Me | $SO_2Me$ | |
| 4-150 | 5-$CHF_2$ | Me | $NH_2$ | Me | 4'-Me | $SO_2NHMe$ | |

TABLE 4-6

Table 4 (Continued)

| Compound No. | $R^1$ | $R^2$ | $R^3$ | $R^4$ | $R^5$ | Q | Physical property value |
|---|---|---|---|---|---|---|---|
| 4-151 | 5-$CHF_2$ | Me | $NH_2$ | Et | 4'-Me | $CO_2Me$ | |
| 4-152 | 5-$CHF_2$ | Me | $NH_2$ | Et | 4'-Me | $SO_2Me$ | |
| 4-153 | 5-$CHF_2$ | Me | $NH_2$ | Et | 4'-Me | $SO_2NHMe$ | |
| 4-154 | 5-$CHF_2$ | Me | $NH_2$ | i-Pr | 4'-Me | $CO_2Me$ | |
| 4-155 | 5-$CHF_2$ | Me | $NH_2$ | i-Pr | 4'-Me | $SO_2Me$ | |
| 4-156 | 5-$CHF_2$ | Me | $NH_2$ | i-Pr | 4'-Me | $SO_2NHMe$ | |
| 4-157 | 5-$CF_3$ | Me | $NH_2$ | Me | 4'-Me | $CO_2Me$ | |
| 4-158 | 5-$CF_3$ | Me | $NH_2$ | Me | 4'-Me | $SO_2Me$ | |
| 4-159 | 5-$CF_3$ | Me | $NH_2$ | Me | 4'-Me | $SO_2NHMe$ | |

TABLE 4-6-continued

Table 4 (Continued)

| Compound No. | $R^1$ | $R^2$ | $R^3$ | $R^4$ | $R^5$ | Q | Physical property value |
|---|---|---|---|---|---|---|---|
| 4-160 | 5-$CF_3$ | Me | $NH_2$ | Et | 4'-Me | $CO_2Me$ | |
| 4-161 | 5-$CF_3$ | Me | $NH_2$ | Et | 4'-Me | $SO_2Me$ | |
| 4-162 | 5-$CF_3$ | Me | $NH_2$ | Et | 4'-Me | $SO_2NHMe$ | |
| 4-163 | 5-$CF_3$ | Me | $NH_2$ | i-Pr | 4'-Me | $CO_2Me$ | |
| 4-164 | 5-$CF_3$ | Me | $NH_2$ | i-Pr | 4'-Me | $SO_2Me$ | |
| 4-165 | 5-$CF_3$ | Me | $NH_2$ | i-Pr | 4'-Me | $SO_2NHMe$ | |
| 4-166 | H | Me | Me | Me | 4'-Me | $CO_2Me$ | |
| 4-167 | H | Me | Me | Me | 4'-Me | $SO_2Me$ | |
| 4-168 | H | Me | Me | Me | 4'-Me | $SO_2NHMe$ | |
| 4-169 | H | Me | Me | Et | 4'-Me | $CO_2Me$ | |
| 4-170 | H | Me | Me | Et | 4'-Me | $SO_2Me$ | |
| 4-171 | H | Me | Me | Et | 4'-Me | $SO_2NHMe$ | |
| 4-172 | H | Me | Me | i-Pr | 4'-Me | $CO_2Me$ | |
| 4-173 | H | Me | Me | i-Pr | 4'-Me | SO-Me | |
| 4-174 | H | Me | Me | i-Pr | 4'-Me | $SO_2NHMe$ | |
| 4-175 | 5-Me | Me | Me | Me | 4'-Me | $CO_2Me$ | |
| 4-176 | 5-Me | Me | Me | Me | 4'-Me | $SO_2Me$ | |
| 4-177 | 5-Me | Me | Me | Me | 4'-Me | $SO_2NHMe$ | |
| 4-178 | 5-Me | Me | Me | Et | 4'-Me | $CO_2Me$ | |
| 4-179 | 5-Me | Me | Me | Et | 4'-Me | $SO_2Me$ | |
| 4-180 | 5-Me | Me | Me | Et | 4'-Me | $SO_2NHMe$ | |

TABLE 4-7

Table 4 (Continued)

| Compound No. | $R^1$ | $R^2$ | $R^3$ | $R^4$ | $R^5$ | Q | Physical property value |
|---|---|---|---|---|---|---|---|
| 4-181 | 5-Me | Me | Me | i-Pr | 4'-Me | $CO_2Me$ | |
| 4-182 | 5-Me | Me | Me | i-Pr | 4'-Me | $SO_2Me$ | |
| 4-183 | 5-Me | Me | Me | i-Pr | 4'-Me | $SO_2NHMe$ | |
| 4-184 | 5-OMe | Me | Me | Me | 4'-Me | $CO_2Me$ | |
| 4-185 | 5-OMe | Me | Me | Me | 4'-Me | $SO_2Me$ | |
| 4-186 | 5-OMe | Me | Me | Me | 4'-Me | $SO_2NHMe$ | |
| 4-187 | 5-OMe | Me | Me | Et | 4'-Me | $CO_2Me$ | |
| 4-188 | 5-OMe | Me | Me | Et | 4'-Me | $SO_2Me$ | |
| 4-189 | 5-OMe | Me | Me | Et | 4'-Me | $SO_2NHMe$ | |
| 4-190 | 5-OMe | Me | Me | i-Pr | 4'-Me | $CO_2Me$ | |
| 4-191 | 5-OMe | Me | Me | i-Pr | 4'-Me | $SO_2Me$ | |
| 4-192 | 5-OMe | Me | Me | i-Pr | 4'-Me | $SO_2NHMe$ | |
| 4-193 | 5-$CHF_2$ | Me | Me | Me | 4'-Me | $CO_2Me$ | |
| 4-194 | 5-$CHF_2$ | Me | Me | Me | 4'-Me | $SO_2Me$ | |
| 4-195 | 5-$CHF_2$ | Me | Me | Me | 4'-Me | $SO_2NHMe$ | |
| 4-196 | 5-$CHF_2$ | Me | Me | Et | 4'-Me | $CO_2Me$ | |
| 4-197 | 5-$CHF_2$ | Me | Me | Et | 4'-Me | $SO_2Me$ | |
| 4-198 | 5-$CHF_2$ | Me | Me | Et | 4'-Me | $SO_2NHMe$ | |

TABLE 4-7-continued

Table 4 (Continued)

| Compound No. | $R^1$ | $R^2$ | $R^3$ | $R^4$ | $R^5$ | Q | Physical property value |
|---|---|---|---|---|---|---|---|
| 4-199 | 5-$CHF_2$ | Me | Me | i-Pr | 4'-Me | $CO_2Me$ | |
| 4-200 | 5-$CHF_2$ | Me | Me | i-Pr | 4'-Me | $SO_2Me$ | |
| 4-201 | 5-$CHF_2$ | Me | Me | i-Pr | 4'-Me | $SO_2NHMe$ | |
| 4-202 | 5-$CF_3$ | Me | Me | Me | 4'-Me | $CO_2Me$ | |
| 4-203 | 5-$CF_3$ | Me | Me | Me | 4'-Me | $SO_2Me$ | |
| 4-204 | 5-$CF_3$ | Me | Me | Me | 4'-Me | $SO_2NHMe$ | |
| 4-205 | 5-$CF_3$ | Me | Me | Et | 4'-Me | $CO_2Me$ | |
| 4-206 | 5-$CF_3$ | Me | Me | Et | 4'-Me | $SO_2Me$ | |
| 4-207 | 5-$CF_3$ | Me | Me | Et | 4'-Me | $SO_2NHMe$ | |
| 4-208 | 5-$CF_3$ | Me | Me | i-Pr | 4'-Me | $CO_2Me$ | |
| 4-209 | 5-$CF_3$ | Me | Me | i-Pr | 4'-Me | $SO_2Me$ | |
| 4-210 | 5-$CF_3$ | Me | Me | i-Pr | 4'-Me | $SO_2NHMe$ | |

TABLE 4-8

Table 4 (Continued)

| Compound No. | $R^1$ | $R^2$ | $R^3$ | $R^4$ | $R^5$ | Q | Physical property value |
|---|---|---|---|---|---|---|---|
| 4-211 | H | Me | $NH_2$ | Me | H | 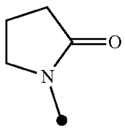 | |
| 4-212 | H | Me | $NH_2$ | Et | H | 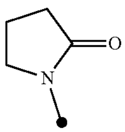 | |
| 4-213 | H | Me | $NH_2$ | i-Pr | H | 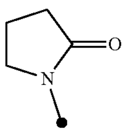 | |
| 4-214 | 5-Me | Me | $NH_2$ | Me | H | 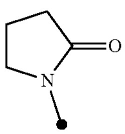 | |
| 4-215 | 5-Me | Me | $NH_2$ | Et | H | 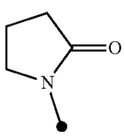 | |
| 4-216 | 5-Me | Me | $NH_2$ | i-Pr | H | 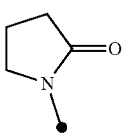 | |
| 4-217 | 5-OMe | Me | $NH_2$ | Me | H | 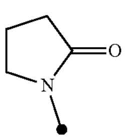 | |

TABLE 4-8-continued

Table 4 (Continued)

| Compound No. | $R^1$ | $R^2$ | $R^3$ | $R^4$ | $R^5$ | Q | Physical property value |
|---|---|---|---|---|---|---|---|
| 4-218 | 5-OMe | Me | $NH_2$ | Et | H | 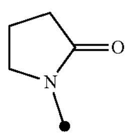 | |
| 4-219 | 5-OMe | Me | $NH_2$ | i-Pr | H | 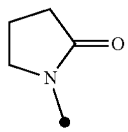 | |
| 4-220 | 5-$CHF_2$ | Me | $NH_2$ | Me | H | 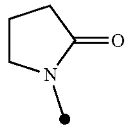 | |
| 4-221 | 5-$CHF_2$ | Me | $NH_2$ | Et | H | 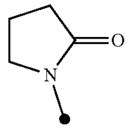 | |
| 4-222 | 5-$CHF_2$ | Me | $NH_2$ | i-Pr | H | 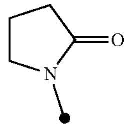 | |
| 4-223 | 5-$CF_3$ | Me | $NH_2$ | Me | H | 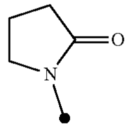 | |
| 4-224 | 5-$CF_3$ | Me | $NH_2$ | Et | H | 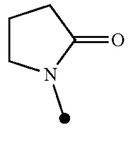 | |
| 4-225 | 5-$CF_3$ | Me | $NH_2$ | i-Pr | H | 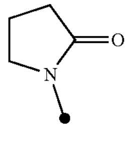 | |
| 4-226 | H | Me | $NH_2$ | Me | H | 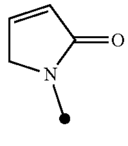 | |

The black solid circle in the structural formula represents a binding position.

TABLE 4-9

| Table 4 (Continued) | | | | | | | |
|---|---|---|---|---|---|---|---|
| Compound No. | $R^1$ | $R^2$ | $R^3$ | $R^4$ | $R^5$ | Q | Physical property value |
| 4-227 | H | Me | $NH_2$ | Et | H | 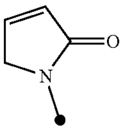 | |
| 4-228 | H | Me | $NH_2$ | i-Pr | H | 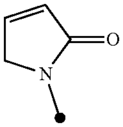 | |
| 4-229 | 5-Me | Me | $NH_2$ | Me | H | 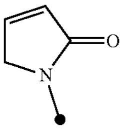 | |
| 4-230 | 5-Me | Me | $NH_2$ | Et | H | 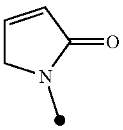 | |
| 4-231 | 5-Me | Me | $NH_2$ | i-Pr | H | 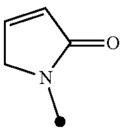 | |
| 4-232 | 5-OMe | Me | $NH_2$ | Me | H | 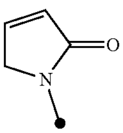 | |
| 4-233 | 5-OMe | Me | $NH_2$ | Et | H | 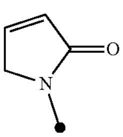 | |
| 4-234 | 5-OMe | Me | $NH_2$ | i-Pr | H | 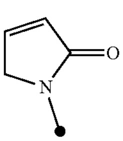 | |
| 4-235 | 5-$CHF_2$ | Me | $NH_2$ | Me | H | 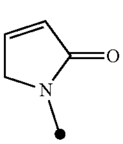 | |
| 4-236 | 5-$CHF_2$ | Me | $NH_2$ | Et | H | 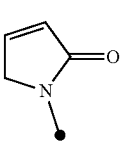 | |

TABLE 4-9-continued

| Table 4 (Continued) | | | | | | | |
|---|---|---|---|---|---|---|---|
| Compound No. | $R^1$ | $R^2$ | $R^3$ | $R^4$ | $R^5$ | Q | Physical property value |
| 4-237 | 5-$CHF_2$ | Me | $NH_2$ | i-Pr | H | 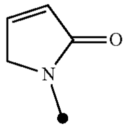 | |
| 4-238 | 5-$CF_3$ | Me | $NH_2$ | Me | H | 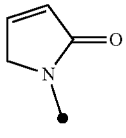 | |
| 4-239 | 5-$CF_3$ | Me | $NH_2$ | Et | H | 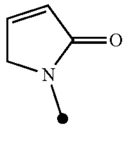 | |
| 4-240 | 5-$CF_3$ | Me | $NH_2$ | i-Pr | H | 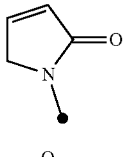 | |
| 4-241 | H | Me | $NH_2$ | Me | H | 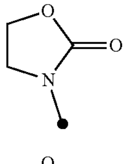 | |
| 4-242 | H | Me | $NH_2$ | Et | H | 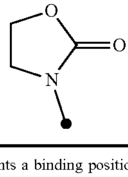 | |

The black solid circle in the structural formula represents a binding position.

TABLE 4-10

| Table 4 (Continued) | | | | | | | |
|---|---|---|---|---|---|---|---|
| Compound No. | $R^1$ | $R^2$ | $R^3$ | $R^4$ | $R^5$ | Q | Physical property value |
| 4-243 | H | Me | $NH_2$ | i-Pr | H | 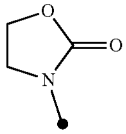 | |
| 4-244 | 5-Me | Me | $NH_2$ | Me | H | 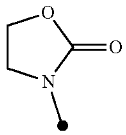 | |
| 4-245 | 5-Me | Me | $NH_2$ | Et | H | 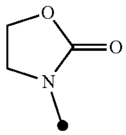 | |

TABLE 4-10-continued

Table 4 (Continued)

| Compound No. | $R^1$ | $R^2$ | $R^3$ | $R^4$ | $R^5$ | Q | Physical property value |
|---|---|---|---|---|---|---|---|
| 4-246 | 5-Me | Me | $NH_2$ | i-Pr | H | 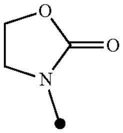 | |
| 4-247 | 5-OMe | Me | $NH_2$ | Me | H | 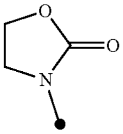 | |
| 4-248 | 5-OMe | Me | $NH_2$ | Et | H | 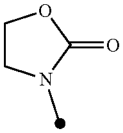 | |
| 4-249 | 5-OMe | Me | $NH_2$ | i-Pr | H | 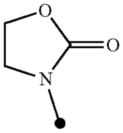 | |
| 4-250 | 5-$CHF_2$ | Me | $NH_2$ | Me | H | 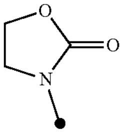 | |
| 4-251 | 5-$CHF_2$ | Me | $NH_2$ | Et | H | 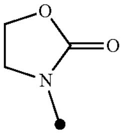 | |
| 4-252 | 5-$CHF_2$ | Me | $NH_2$ | i-Pr | H | 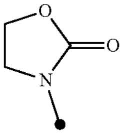 | |
| 4-253 | 5-$CF_3$ | Me | $NH_2$ | Me | H | 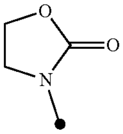 | |
| 4-254 | 5-$CF_3$ | Me | $NH_2$ | Et | H | 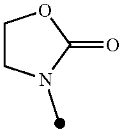 | |
| 4-255 | 5-$CF_3$ | Me | $NH_2$ | i-Pr | H | 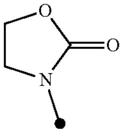 | |
| 4-256 | H | Me | $NH_2$ | Me | H | 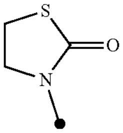 | |
| 4-257 | H | Me | $NH_2$ | Et | H | 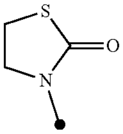 | |
| 4-258 | H | Me | $NH_2$ | i-Pr | H | 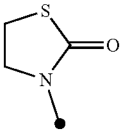 | |

The black solid circle in the structural formula represents a binding position.

TABLE 4-11

Table 4 (Continued)

| Compound No. | $R^1$ | $R^2$ | $R^3$ | $R^4$ | $R^5$ | Q | Physical property value |
|---|---|---|---|---|---|---|---|
| 4-259 | 5-Me | Me | $NH_2$ | Me | H | 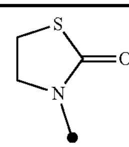 | |
| 4-260 | 5-Me | Me | $NH_2$ | Et | H | 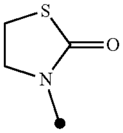 | |
| 4-261 | 5-Me | Me | $NH_2$ | i-Pr | H | 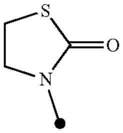 | |
| 4-262 | 5-OMe | Me | $NH_2$ | Me | H | 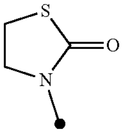 | |
| 4-263 | 5-OMe | Me | $NH_2$ | Et | H | 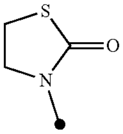 | |

TABLE 4-11-continued

| Table 4 (Continued) | | | | | | | |
|---|---|---|---|---|---|---|---|
| Compound No. | $R^1$ | $R^2$ | $R^3$ | $R^4$ | $R^5$ | Q | Physical property value |
| 4-264 | 5-OMe | Me | $NH_2$ | i-Pr | H | 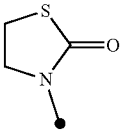 | |
| 4-265 | 5-$CHF_2$ | Me | $NH_2$ | Me | H | 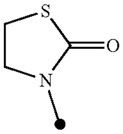 | |
| 4-266 | 5-$CHF_2$ | Me | $NH_2$ | Et | H | 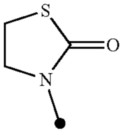 | |
| 4-267 | 5-$CHF_2$ | Me | $NH_2$ | i-Pr | H | 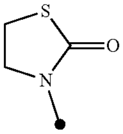 | |
| 4-268 | 5-$CF_3$ | Me | $NH_2$ | Me | H | 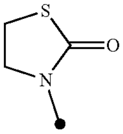 | |
| 4-269 | 5-$CF_3$ | Me | $NH_2$ | Et | H | 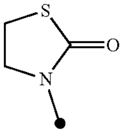 | |
| 4-270 | 5-$CF_3$ | Me | $NH_2$ | i-Pr | H | 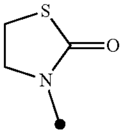 | |
| 4-271 | H | Me | $NH_2$ | Me | H | 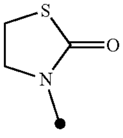 | |
| 4-272 | H | Me | $NH_2$ | Et | H | 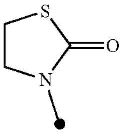 | |
| 4-273 | H | Me | $NH_2$ | i-Pr | H | 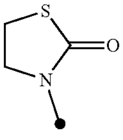 | |
| 4-274 | 5-Me | Me | $NH_2$ | Me | H | 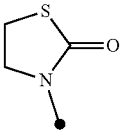 | |

The black solid circle in the structural formula represents a binding position.

TABLE 4-12

| Table 4 (Continued) | | | | | | | |
|---|---|---|---|---|---|---|---|
| Compound No. | $R^1$ | $R^2$ | $R^3$ | $R^4$ | $R^5$ | Q | Physical property value |
| 4-275 | 5-Me | Me | $NH_2$ | Et | H | 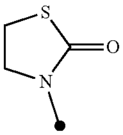 | |
| 4-276 | 5-Me | Me | $NH_2$ | i-Pr | H | 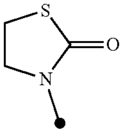 | |
| 4-277 | 5-OMe | Me | $NH_2$ | Me | H | 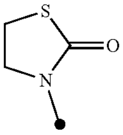 | |
| 4-278 | 5-OMe | Me | $NH_2$ | Et | H | 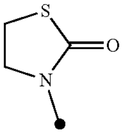 | |
| 4-279 | 5-OMe | Me | $NH_2$ | i-Pr | H | 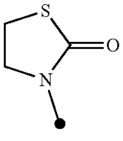 | |
| 4-280 | 5-$CHF_2$ | Me | $NH_2$ | Me | H | 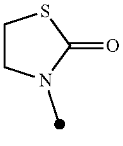 | |
| 4-281 | 5-$CHF_2$ | Me | $NH_2$ | Et | H | 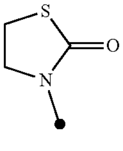 | |

TABLE 4-12-continued

| Table 4 (Continued) | | | | | | | |
|---|---|---|---|---|---|---|---|
| Compound No. | $R^1$ | $R^2$ | $R^3$ | $R^4$ | $R^5$ | Q | Physical property value |
| 4-282 | 5-$CHF_2$ | Me | $NH_2$ | i-Pr | H | 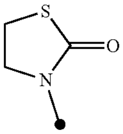 | |
| 4-283 | 5-$CF_3$ | Me | $NH_2$ | Me | H | 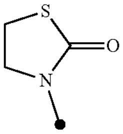 | |
| 4-284 | 5-$CF_3$ | Me | $NH_2$ | Et | H | 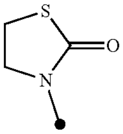 | |
| 4-285 | 5-$CF_3$ | Me | $NH_2$ | i-Pr | H | 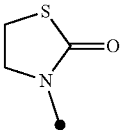 | |
| 4-286 | H | Me | $NH_2$ | Me | H | 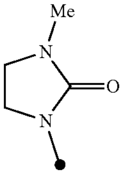 | |
| 4-287 | H | Me | $NH_2$ | Et | H | 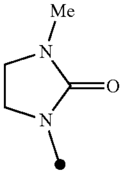 | |
| 4-288 | H | Me | $NH_2$ | i-Pr | H | 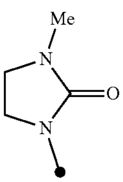 | |

The black solid circle in the structural formula represents a binding position.

TABLE 4-13

| Table 4 (Continued) | | | | | | | |
|---|---|---|---|---|---|---|---|
| Compound No. | $R^1$ | $R^2$ | $R^3$ | $R^4$ | $R^5$ | Q | Physical property value |
| 4-289 | 5-Me | Me | $NH_2$ | Me | H | 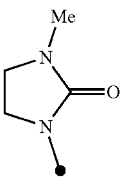 | |
| 4-290 | 5-Me | Me | $NH_2$ | Et | H | 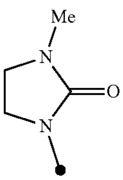 | |
| 4-291 | 5-Me | Me | $NH_2$ | i-Pr | H | 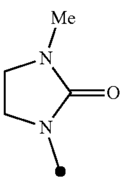 | |
| 4-292 | 5-OMe | Me | $NH_2$ | Me | H | 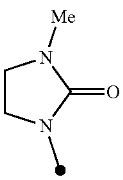 | |
| 4-293 | 5-OMe | Me | $NH_2$ | Et | H | 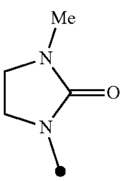 | |
| 4-294 | 5-OMe | Me | $NH_2$ | i-Pr | H | 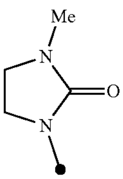 | |
| 4-295 | 5-$CHF_2$ | Me | $NH_2$ | Me | H | 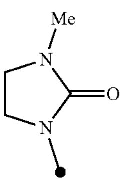 | |
| 4-296 | 5-$CHF_2$ | Me | $NH_2$ | Et | H | 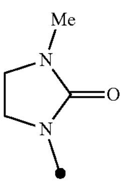 | |

TABLE 4-13-continued

Table 4 (Continued)

| Compound No. | $R^1$ | $R^2$ | $R^3$ | $R^4$ | $R^5$ | Q | Physical property value |
|---|---|---|---|---|---|---|---|
| 4-297 | 5-$CHF_2$ | Me | $NH_2$ | i-Pr | H | 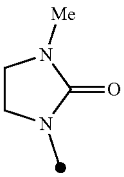 | |
| 4-298 | 5-$CF_3$ | Me | $NH_2$ | Me | H | 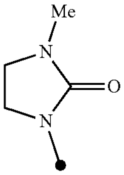 | |

The black solid circle in the structural formula represents a binding position.

TABLE 4-14

Table 4 (Continued)

| Compound No. | $R^1$ | $R^2$ | $R^3$ | $R^4$ | $R^5$ | Q | Physical property value |
|---|---|---|---|---|---|---|---|
| 4-299 | 5-$CF_3$ | Me | $NH_2$ | Et | H | 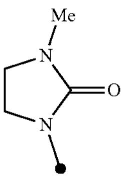 | |
| 4-300 | 5-$CF_3$ | Me | $NH_2$ | i-Pr | H | 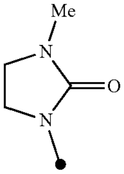 | |
| 4-301 | H | Me | $NH_2$ | Me | H | 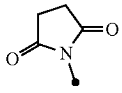 | |
| 4-302 | H | Me | $NH_2$ | Et | H | 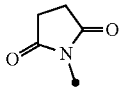 | |
| 4-303 | H | Me | $NH_2$ | i-Pr | H | 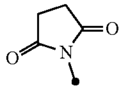 | |
| 4-304 | 5-Me | Me | $NH_2$ | Me | H | 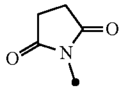 | |
| 4-305 | 5-Me | Me | $NH_2$ | Et | H | 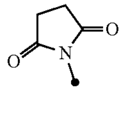 | |

TABLE 4-14-continued

Table 4 (Continued)

| Compound No. | $R^1$ | $R^2$ | $R^3$ | $R^4$ | $R^5$ | Q | Physical property value |
|---|---|---|---|---|---|---|---|
| 4-306 | 5-Me | Me | $NH_2$ | i-Pr | H | 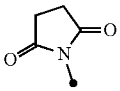 | |
| 4-307 | 5-OMe | Me | $NH_2$ | Me | H | 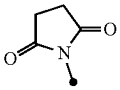 | |
| 4-308 | 5-OMe | Me | $NH_2$ | Et | H | 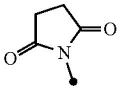 | |
| 4-309 | 5-OMe | Me | $NH_2$ | i-Pr | H | 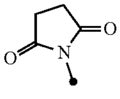 | |
| 4-310 | 5-$CHF_2$ | Me | $NH_2$ | Me | H | 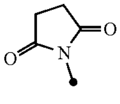 | |
| 4-311 | 5-$CHF_2$ | Me | $NH_2$ | Et | H | 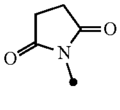 | |
| 4-312 | 5-$CHF_2$ | Me | $NH_2$ | i-Pr | H | 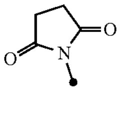 | |
| 4-313 | 5-$CF_3$ | Me | $NH_2$ | Me | H | 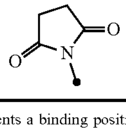 | |

The black solid circle in the structural formula represents a binding position.

TABLE 4-15

Table 4 (Continued)

| Compound No. | $R^1$ | $R^2$ | $R^3$ | $R^4$ | $R^5$ | Q | Physical property value |
|---|---|---|---|---|---|---|---|
| 4-314 | 5-$CF_3$ | Me | $NH_2$ | Et | H | 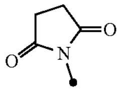 | |
| 4-315 | 5-$CF_3$ | Me | $NH_2$ | i-Pr | H | 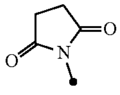 | |
| 4-316 | H | Me | $NH_2$ | Me | H | 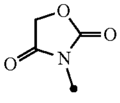 | |
| 4-317 | H | Me | $NH_2$ | Et | H | 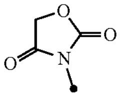 | |

TABLE 4-15-continued

Table 4 (Continued)

| Compound No. | $R^1$ | $R^2$ | $R^3$ | $R^4$ | $R^5$ | Q | Physical property value |
|---|---|---|---|---|---|---|---|
| 4-318 | H | Me | $NH_2$ | i-Pr | H | 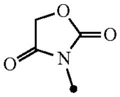 | |
| 4-319 | 5-Me | Me | $NH_2$ | Me | H | 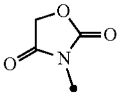 | |
| 4-320 | 5-Me | Me | $NH_2$ | Et | H | 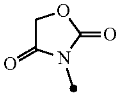 | |
| 4-321 | 5-Me | Me | $NH_2$ | i-Pr | H | 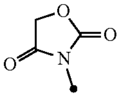 | |
| 4-322 | 5-OMe | Me | $NH_2$ | Me | H | 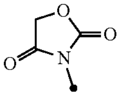 | |
| 4-323 | 5-OMe | Me | $NH_2$ | Et | H | 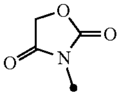 | |
| 4-324 | 5-OMe | Me | $NH_2$ | i-Pr | H | 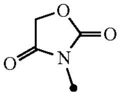 | |
| 4-325 | 5-$CHF_2$ | Me | $NH_2$ | Me | H | 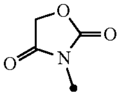 | |
| 4-326 | 5-$CHF_2$ | Me | $NH_2$ | Et | H | 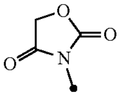 | |
| 4-327 | 5-$CHF_2$ | Me | $NH_2$ | i-Pr | H | 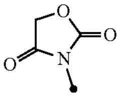 | |
| 4-328 | 5-$CF_3$ | Me | $NH_2$ | Me | H | 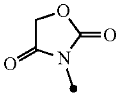 | |
| 4-329 | 5-$CF_3$ | Me | $NH_2$ | Et | H | 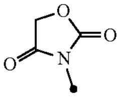 | |
| 4-330 | 5-$CF_3$ | Me | $NH_2$ | i-Pr | H | 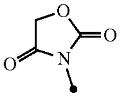 | |

The black solid circle in the structural formula represents a binding position.

[Chem. 31]

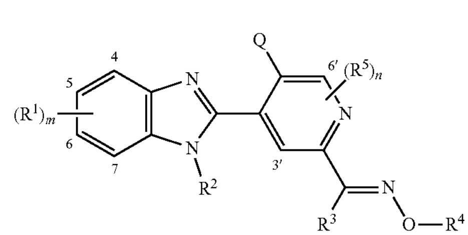

(1e)

The position numbers in the table are the numbers designated in the general formula (1e).

TABLE 5-1

| Compound No. | $R^1$ | $R^2$ | $R^3$ | $R^4$ | $R^5$ | Q | Physical property value |
|---|---|---|---|---|---|---|---|
| 5-1 | H | Me | $NH_2$ | Me | H | $CO_2Me$ | |
| 5-2 | H | Me | $NH_2$ | Me | H | $SO_2Me$ | |
| 5-3 | H | Me | $NH_2$ | Me | H | $SO_2NHMe$ | |
| 5-4 | H | Me | $NH_2$ | Et | H | $CO_2Me$ | |
| 5-5 | H | Me | $NH_2$ | Et | H | $SO_2Me$ | |
| 5-6 | H | Me | $NH_2$ | Et | H | $SO_2NHMe$ | |
| 5-7 | H | Me | $NH_2$ | i-Pr | H | $CO_2Me$ | |
| 5-8 | H | Me | $NH_2$ | i-Pr | H | $SO_2Me$ | |
| 5-9 | H | Me | $NH_2$ | i-Pr | H | $SO_2NHMe$ | |
| 5-10 | 5-Me | Me | $NH_2$ | Me | H | $CO_2Me$ | |
| 5-11 | 5-Me | Me | $NH_2$ | Me | H | $SO_2Me$ | |
| 5-12 | 5-Me | Me | $NH_2$ | Me | H | $SO_2NHMe$ | |
| 5-13 | 5-Me | Me | $NH_2$ | Et | H | Cl | 130-131 |
| 5-14 | 5-Me | Me | $NH_2$ | Et | H | $CO_2Me$ | |
| 5-15 | 5-Me | Me | $NH_2$ | Et | H | SMe | 133-134 |
| 5-16 | 5-Me | Me | $NH_2$ | Et | H | $SO_2Me$ | 181-182 |
| 5-17 | 5-Me | Me | $NH_2$ | Et | H | $SO_2NHMe$ | |
| 5-18 | 5-Me | Me | $NH_2$ | i-Pr | H | $CO_2Me$ | |
| 5-19 | 5-Me | Me | $NH_2$ | i-Pr | H | $SO_2Me$ | |
| 5-20 | 5-Me | Me | $NH_2$ | i-Pr | H | $SO_2NHMe$ | |
| 5-21 | 5-OMe | Me | $NH_2$ | Me | H | $CO_2Me$ | |
| 5-22 | 5-OMe | Me | $NH_2$ | Me | H | $SO_2Me$ | |
| 5-23 | 5-OMe | Me | $NH_2$ | Me | H | $SO_2NHMe$ | |
| 5-24 | 5-OMe | Me | $NH_2$ | Et | H | $CO_2Me$ | |
| 5-25 | 5-OMe | Me | $NH_2$ | Et | H | $SO_2Me$ | |
| 5-26 | 5-OMe | Me | $NH_2$ | Et | H | $SO_2NHMe$ | |
| 5-27 | 5-OMe | Me | $NH_2$ | i-Pr | H | $CO_2Me$ | |
| 5-28 | 5-OMe | Me | $NH_2$ | i-Pr | H | $SO_2Me$ | |
| 5-29 | 5-OMe | Me | $NH_2$ | i-Pr | H | $SO_2NHMe$ | |
| 5-30 | 5-$CHF_2$ | Me | $NH_2$ | Me | H | $CO_2Me$ | |

TABLE 5-2

Table 5 (Continued)

| Compound No. | $R^1$ | $R^2$ | $R^3$ | $R^4$ | $R^5$ | Q | Physical property value |
|---|---|---|---|---|---|---|---|
| 5-31 | 5-$CHF_2$ | Me | $NH_2$ | Me | H | $SO_2Me$ | |
| 5-32 | 5-$CHF_2$ | Me | $NH_2$ | Me | H | $SO_2NHMe$ | |
| 5-33 | 5-$CHF_2$ | Me | $NH_2$ | Et | H | $CO_2Me$ | |
| 5-34 | 5-$CHF_2$ | Me | $NH_2$ | Et | H | $SO_2Me$ | |
| 5-35 | 5-$CHF_2$ | Me | $NH_2$ | Et | H | $SO_2NHMe$ | |
| 5-36 | 5-$CHF_2$ | Me | $NH_2$ | i-Pr | H | $CO_2Me$ | |
| 5-37 | 5-$CHF_2$ | Me | $NH_2$ | i-Pr | H | $SO_2Me$ | |
| 5-38 | 5-$CHF_2$ | Me | $NH_2$ | i-Pr | H | $SO_2NHMe$ | |
| 5-39 | 5-$CF_3$ | Me | $NH_2$ | Me | H | $CO_2Me$ | |
| 5-40 | 5-$CF_3$ | Me | NH3 | Me | H | $SO_2Me$ | |
| 5-41 | 5-$CF_3$ | Me | $NH_2$ | Me | H | $SO_2NHMe$ | |
| 5-42 | 5-$CF_3$ | Me | $NH_2$ | Et | H | $CO_2Me$ | |
| 5-43 | 5-$CF_3$ | Me | $NH_2$ | Et | H | $SO_2Me$ | |
| 5-44 | 5-$CF_3$ | Me | $NH_2$ | Et | H | $SO_2NHMe$ | |
| 5-45 | 5-$CF_3$ | Me | $NH_2$ | i-Pr | H | $CO_2Me$ | |

TABLE 5-2-continued

| Table 5 (Continued) | | | | | | | |
|---|---|---|---|---|---|---|---|
| Compound No. | $R^1$ | $R^2$ | $R^3$ | $R^4$ | $R^5$ | Q | Physical property value |
| 5-46 | 5-$CF_3$ | Me | $NH_2$ | i-Pr | H | $SO_2Me$ | |
| 5-47 | 5-$CF_3$ | Me | $NH_2$ | i-Pr | H | $SO_2NHMe$ | |
| 5-48 | H | Me | Me | Me | H | $CO_2Me$ | |
| 5-49 | H | Me | Me | Me | H | $SO_2Me$ | |
| 5-50 | H | Me | Me | Me | H | $SO_2NHMe$ | |
| 5-51 | H | Me | Me | Et | H | $CO_2Me$ | |
| 5-52 | H | Me | Me | Et | H | $SO_2Me$ | |
| 5-53 | H | Me | Me | Et | H | $SO_2NHMe$ | |
| 5-54 | H | Me | Me | i-Pr | H | $CO_2Me$ | |
| 5-55 | H | Me | Me | i-Pr | H | $SO_2Me$ | |
| 5-56 | H | Me | Me | i-Pr | H | $SO_2NHMe$ | |
| 5-57 | 5-Me | Me | Me | Me | H | $CO_2Me$ | |
| 5-58 | 5-Me | Me | Me | Me | H | $SO_2Me$ | |
| 5-59 | 5-Me | Me | Me | Me | H | $SO_2NHMe$ | |
| 5-60 | 5-Me | Me | Me | Et | H | $CO_2Me$ | |

TABLE 5-3

| Table 5 (Continued) | | | | | | | |
|---|---|---|---|---|---|---|---|
| Compound No. | $R^1$ | $R^2$ | $R^3$ | $R^4$ | $R^5$ | Q | Physical property value |
| 5-61 | 5-Me | Me | Me | Et | H | $SO_2Me$ | 183-184 |
| 5-62 | 5-Me | Me | Me | Et | H | $SO_2NHMe$ | |
| 5-63 | 5-Me | Me | Me | i-Pr | H | $CO_2Me$ | |

TABLE 5-3-continued

| Table 5 (Continued) | | | | | | | |
|---|---|---|---|---|---|---|---|
| Compound No. | $R^1$ | $R^2$ | $R^3$ | $R^4$ | $R^5$ | Q | Physical property value |
| 5-64 | 5-Me | Me | Me | i-Pr | H | $SO_2Me$ | |
| 5-65 | 5-Me | Me | Me | i-Pr | H | $SO_2NHMe$ | |
| 5-66 | 5-OMe | Me | Me | Me | H | $CO_2Me$ | |
| 5-67 | 5-OMe | Me | Me | Me | H | $SO_2Me$ | |
| 5-68 | 5-OMe | Me | Me | Me | H | $SO_2NHMe$ | |
| 5-69 | 5-OMe | Me | Me | Et | H | $CO_2Me$ | |
| 5-70 | 5-OMe | Me | Me | Et | H | $SO_2Me$ | |
| 5-71 | 5-OMe | Me | Me | Et | H | $SO_2NHMe$ | |
| 5-72 | 5-OMe | Me | Me | i-Pr | H | $CO_2Me$ | |
| 5-73 | 5-OMe | Me | Me | i-Pr | H | $SO_2Me$ | |
| 5-74 | 5-OMe | Me | Me | i-Pr | H | $SO_2NHMe$ | |
| 5-75 | 5-$CHF_2$ | Me | Me | Me | H | $CO_2Me$ | |
| 5-76 | 5-$CHF_2$ | Me | Me | Me | H | $SO_2Me$ | |
| 5-77 | 5-$CHF_2$ | Me | Me | Me | H | $SO_2NHMe$ | |
| 5-78 | 5-$CHF_2$ | Me | Me | Et | H | $CO_2Me$ | |
| 5-79 | 5-$CHF_2$ | Me | Me | Et | H | $SO_2Me$ | |
| 5-80 | 5-$CHF_2$ | Me | Me | Et | H | $SO_2NHMe$ | |
| 5-81 | 5-$CHF_2$ | Me | Me | i-Pr | H | $CO_2Me$ | |
| 5-82 | 5-$CHF_2$ | Me | Me | i-Pr | H | $SO_2Me$ | |
| 5-83 | 5-$CHF_2$ | Me | Me | i-Pr | H | $SO_2NHMe$ | |
| 5-84 | 5-$CF_3$ | Me | Me | Me | H | $CO_2Me$ | |
| 5-85 | 5-$CF_3$ | Me | Me | Me | H | $SO_2Me$ | |
| 5-86 | 5-CFa | Me | Me | Me | H | $SO_2NHMe$ | |
| 5-87 | 5-$CF_3$ | Me | Me | Et | H | $CO_2Me$ | |
| 5-88 | 5-$CF_3$ | Me | Me | Et | H | $SO_2Me$ | |
| 5-89 | 5-$CF_3$ | Me | Me | Et | H | $SO_2NHMe$ | |
| 5-90 | 5-$CF_3$ | Me | Me | i-Pr | H | $CO_2Me$ | |

TABLE 5-4

| Table 5 (Continued) | | | | | | | |
|---|---|---|---|---|---|---|---|
| Compound No. | $R^1$ | $R^2$ | $R^3$ | $R^4$ | $R^5$ | Q | Physical property value |
| 5-91 | 5-$CF_3$ | Me | Me | i-Pr | H | $SO_2Me$ | |
| 5-92 | 5-$CF_3$ | Me | Me | i-Pr | H | $SO_2NHMe$ | |
| 5-93 | 5-$SCF_3$ | Me | Me | Me | H | C(Me)=N—OMe | 141-143 |
| 5-94 | 5-$SCF_3$ | Me | Me | Et | H | SEt | 113-115 |
| 5-95 | 5-$SCF_3$ | Me | H | Et | H | $CO_2H$ | 240-246 |
| 5-96 | 5-$SCF_3$ | Me | H | Et | H | $CO_2Me$ | 178-180 |
| 5-97 | 5-$SCF_3$ | Me | H | Et | H | CONHMe | 187-190 |
| 5-98 | 5-$SCF_3$ | Me | H | Et | H | $CONMe_2$ | 172-175 |
| 5-99 | 5-$SCF_3$ | Me | H | $CH_2CF_3$ | H | $CO_2Me$ | 149-152 |
| 5-100 | 5-$SO_2CF_3$ | Me | H | $CH_2CF_3$ | H | $CO_2Me$ | 155-160 |
| 5-101 | H | Me | $NH_2$ | Me | 6'-Me | $CO_2Me$ | |
| 5-102 | H | Me | $NH_2$ | Me | 6'-Me | $SO_2Me$ | |
| 5-103 | H | Me | $NH_2$ | Me | 6'-Me | $SO_2NHMe$ | |
| 5-104 | H | Me | $NH_2$ | Et | 6'-Me | $CO_2Me$ | |
| 5-105 | H | Me | $NH_2$ | Et | 6'-Me | $SO_2Me$ | |
| 5-106 | H | Me | $NH_2$ | Et | 6'-Me | $SO_2NHMe$ | |
| 5-107 | H | Me | $NH_2$ | i-Pr | 6'-Me | $CO_2Me$ | |
| 5-108 | H | Me | $NH_2$ | i-Pr | 6'-Me | $SO_2Me$ | |
| 5-109 | H | Me | $NH_2$ | i-Pr | 6'-Me | $SO_2NHMe$ | |
| 5-110 | 5-Me | Me | $NH_2$ | Me | 6'-Me | $CO_2Me$ | |
| 5-111 | 5-Me | Me | $NH_2$ | Me | 6'-Me | $SO_2Me$ | |
| 5-112 | 5-Me | Me | $NH_2$ | Me | 6'-Me | $SO_2NHMe$ | |
| 5-113 | 5-Me | Me | $NH_2$ | Et | 6'-Me | $CO_2Me$ | |
| 5-114 | 5-Me | Me | $NH_2$ | Et | 6'-Me | $SO_2Me$ | |
| 5-115 | 5-Me | Me | $NH_2$ | Et | 6'-Me | $SO_2NHMe$ | |
| 5-116 | 5-Me | Me | $NH_2$ | i-Pr | 6'-Me | $CO_2Me$ | |
| 5-117 | 5-Me | Me | $NH_2$ | i-Pr | 6'-Me | $SO_2Me$ | |
| 5-118 | 5-Me | Me | $NH_2$ | i-Pr | 6'-Me | $SO_2NHMe$ | |
| 5-119 | 5-OMe | Me | $NH_2$ | Me | 6'-Me | $CO_2Me$ | |
| 5-120 | 5-OMe | Me | $NH_2$ | Me | 6'-Me | $SO_2Me$ | |

TABLE 5-5

Table 5 (Continued)

| Compound No. | $R^1$ | $R^2$ | $R^3$ | $R^4$ | $R^5$ | Q | Physical property value |
|---|---|---|---|---|---|---|---|
| 5-121 | 5-OMe | Me | $NH_2$ | Me | 6'-Me | $SO_2NHMe$ | |
| 5-122 | 5-OMe | Me | $NH_2$ | Et | 6'-Me | $CO_2Me$ | |
| 5-123 | 5-OMe | Me | $NH_2$ | Et | 6'-Me | $SO_2Me$ | |
| 5-124 | 5-OMe | Me | $NH_2$ | Et | 6'-Me | SONHMe | |
| 5-125 | 5-OMe | Me | $NH_2$ | i-Pr | 6'-Me | $CO_2Me$ | |
| 5-126 | 5-OMe | Me | $NH_2$ | i-Pr | 6'-Me | $SO_2Me$ | |
| 5-127 | 5-OMe | Me | $NH_2$ | i-Pr | 6'-Me | $SO_2NHMe$ | |
| 5-128 | 5-$CHF_2$ | Me | $NH_2$ | Me | 6'-Me | $CO_2Me$ | |
| 5-129 | 5-$CHF_2$ | Me | $NH_2$ | Me | 6'-Me | $SO_2Me$ | |
| 5-130 | 5-$CHF_2$ | Me | $NH_2$ | Me | 6'-Me | $SO_2NHMe$ | |
| 5-131 | 5-$CHF_2$ | Me | $NH_2$ | Et | 6'-Me | $CO_2Me$ | |
| 5-132 | 5-$CHF_2$ | Me | $NH_2$ | Et | 6'-Me | $SO_2Me$ | |
| 5-133 | 5-$CHF_2$ | Me | $NH_2$ | Et | 6'-Me | $SO_2NHMe$ | |
| 5-134 | 5-$CHF_2$ | Me | $NH_2$ | i-Pr | 6'-Me | $CO_2Me$ | |
| 5-135 | 5-$CHF_2$ | Me | $NH_2$ | i-Pr | 6'-Me | $SO_2Me$ | |
| 5-136 | 5-$CHF_2$ | Me | $NH_2$ | i-Pr | 6'-Me | $SO_2NHMe$ | |
| 5-137 | 5-$CF_3$ | Me | $NH_2$ | Me | 6'-Me | $CO_2Me$ | |
| 5-138 | 5-$CF_3$ | Me | $NH_2$ | Me | 6'-Me | $SO_2Me$ | |
| 5-139 | 5-$CF_3$ | Me | $NH_2$ | Me | 6'-Me | $SO_2NHMe$ | |
| 5-140 | 5-$CF_3$ | Me | $NH_2$ | Et | 6'-Me | $CO_2Me$ | |
| 5-141 | 5-$CF_3$ | Me | $NH_2$ | Et | 6'-Me | $SO_2Me$ | |
| 5-142 | 5-$CF_3$ | Me | $NH_2$ | Et | 6'-Me | $SO_2NHMe$ | |
| 5-143 | 5-$CF_3$ | Me | $NH_2$ | i-Pr | 6'-Me | $CO_2Me$ | |
| 5-144 | 5-$CF_3$ | Me | $NH_2$ | i-Pr | 6'-Me | $SO_2Me$ | |
| 5-145 | 5-$CF_3$ | Me | $NH_2$ | i-Pr | 6'-Me | $SO_2NHMe$ | |
| 5-146 | H | Me | Me | Me | 6'-Me | $CO_2Me$ | |
| 5-147 | H | Me | Me | Me | 6'-Me | $SO_2Me$ | |
| 5-148 | H | Me | Me | Me | 6'-Me | $SO_2NHMe$ | |
| 5-149 | H | Me | Me | Et | 6'-Me | $CO_2Me$ | |
| 5-150 | H | Me | Me | Et | 6'-Me | $SO_2Me$ | |

TABLE 5-6

Table 5 (Continued)

| Compound No. | $R^1$ | $R^2$ | $R^3$ | $R^4$ | $R^5$ | Q | Physical property value |
|---|---|---|---|---|---|---|---|
| 5-151 | H | Me | Me | Et | 6'-Me | $SO_2NHMe$ | |
| 5-152 | H | Me | Me | i-Pr | 6'-Me | $CO_2Me$ | |
| 5-153 | H | Me | Me | i-Pr | 6'-Me | $SO_2Me$ | |
| 5-154 | H | Me | Me | i-Pr | 6'-Me | $SO_2NHMe$ | |
| 5-155 | 5-Me | Me | Me | Me | 6'-Me | $CO_2Me$ | |
| 5-156 | 5-Me | Me | Me | Me | 6'-Me | $SO_2Me$ | |
| 5-157 | 5-Me | Me | Me | Me | 6'-Me | $SO_2NHMe$ | |
| 5-158 | 5-Me | Me | Me | Et | 6'-Me | $CO_2Me$ | |
| 5-159 | 5-Me | Me | Me | Et | 6'-Me | $SO_2Me$ | |
| 5-160 | 5-Me | Me | Me | Et | 6'-Me | $SO_2NHMe$ | |
| 5-161 | 5-Me | Me | Me | i-Pr | 6'-Me | $CO_2Me$ | |
| 5-162 | 5-Me | Me | Me | i-Pr | 6'-Me | $SO_2Me$ | |
| 5-163 | 5-Me | Me | Me | i-Pr | 6'-Me | $SO_2NHMe$ | |
| 5-164 | 5-OMe | Me | Me | Me | 6'-Me | $CO_2Me$ | |
| 5-165 | 5-OMe | Me | Me | Me | 6'-Me | $SO_2Me$ | |
| 5-166 | 5-OMe | Me | Me | Me | 6'-Me | $SO_2NHMe$ | |
| 5-167 | 5-OMe | Me | Me | Et | 6'-Me | $CO_2Me$ | |
| 5-168 | 5-OMe | Me | Me | Et | 6'-Me | $SO_2Me$ | |
| 5-169 | 5-OMe | Me | Me | Et | 6'-Me | $SO_2NHMe$ | |
| 5-170 | 5-OMe | Me | Me | i-P | 6'-Me | $CO_2Me$ | |
| 5-171 | 5-OMe | Me | Me | i-Pr | 6'-Me | $SO_2Me$ | |
| 5-172 | 5-OMe | Me | Me | i-Pr | 6'-Me | $SO_2NHMe$ | |
| 5-173 | 5-$CHF_2$ | Me | Me | Me | 6'-Me | $CO_2Me$ | |
| 5-174 | 5-$CHF_2$ | Me | Me | Me | 6'-Me | $SO_2Me$ | |
| 5-175 | 5-$CHF_2$ | Me | Me | Me | 6'-Me | $SO_2NHMe$ | |
| 5-176 | 5-$CHF_2$ | Me | Me | Et | 6'-Me | $CO_2Me$ | |
| 5-177 | 5-$CHF_2$ | Me | Me | Et | 6'-Me | $SO_2Me$ | |
| 5-178 | 5-$CHF_2$ | Me | Me | Et | 6'-Me | $SO_2NHMe$ | |
| 5-179 | 5-$CHF_2$ | Me | Me | i-Pr | 6'-Me | $CO_2Me$ | |
| 5-180 | 5-$CHF_2$ | Me | Me | i-Pr | 6'-Me | $SO_2Me$ | |

TABLE 5-7

Table 5 (Continued)

| Compound No. | $R^1$ | $R^2$ | $R^3$ | $R^4$ | $R^5$ | Q | Physical property value |
|---|---|---|---|---|---|---|---|
| 5-181 | 5-$CHF_2$ | Me | Me | i-Pr | 6'-Me | $SO_2NHMe$ | |
| 5-182 | 5-$CF_3$ | Me | Me | Me | 6'-Me | $CO_2Me$ | |
| 5-183 | 5-$CF_3$ | Me | Me | Me | 6'-Me | $SO_2Me$ | |
| 5-184 | 5-$CF_3$ | Me | Me | Me | 6'-Me | $SO_2NHMe$ | |
| 5-185 | 5-$CF_3$ | Me | Me | Et | 6'-Me | $CO_2Me$ | |
| 5-186 | 5-$CF_3$ | Me | Me | Et | 6'-Me | $SO_2Me$ | |
| 5-187 | 5-$CF_3$ | Me | Me | Et | 6'-Me | $SO_2NHMe$ | |
| 5-188 | 5-$CF_3$ | Me | Me | i-Pr | 6'-Me | $CO_2Me$ | |
| 5-189 | 5-$CF_3$ | Me | Me | i-Pr | 6'-Me | $SO_2Me$ | |
| 5-190 | 5-$CF_3$ | Me | Me | i-Pr | 6'-Me | $SO_2NHMe$ | |
| 5-191 | H | Me | $NH_2$ | Me | H | 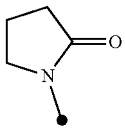 | |
| 5-192 | H | Me | $NH_2$ | Et | H | 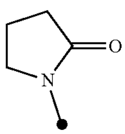 | |
| 5-193 | H | Me | $NH_2$ | i-Pr | H | 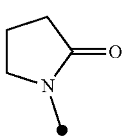 | |
| 5-194 | 5-Me | Me | $NH_2$ | Me | H | 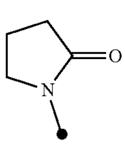 | |
| 5-195 | 5-Me | Me | $NH_2$ | Et | H | 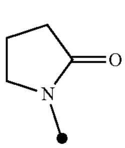 | |
| 5-196 | 5-Me | Me | $NH_2$ | i-Pr | H | 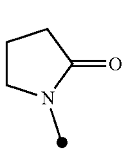 | |
| 5-197 | 5-OMe | Me | $NH_2$ | Me | H | 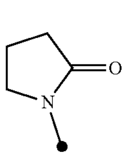 | |

TABLE 5-7-continued

Table 5 (Continued)

| Compound No. | $R^1$ | $R^2$ | $R^3$ | $R^4$ | $R^5$ | Q | Physical property value |
|---|---|---|---|---|---|---|---|
| 5-198 | 5-OMe | Me | $NH_2$ | Et | H | 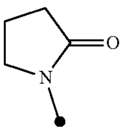 | |
| 5-199 | 5-OMe | Me | $NH_2$ | i-Pr | H | 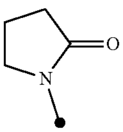 | |
| 5-200 | 5-$CHF_2$ | Me | $NH_2$ | Me | H | 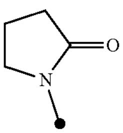 | |

The black solid circle in the structural formula represents a binding position.

TABLE 5-8

Table 5 (Continued)

| Compound No. | $R^1$ | $R^2$ | $R^3$ | $R^4$ | $R^5$ | Q | Physical property value |
|---|---|---|---|---|---|---|---|
| 5-201 | 5-$CHF_2$ | Me | $NH_2$ | Et | H | 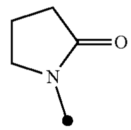 | |
| 5-202 | 5-$CHF_2$ | Me | $NH_2$ | i-Pr | H | 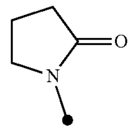 | |
| 5-203 | 5-$CF_3$ | Me | $NH_2$ | Me | H | 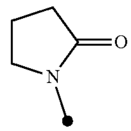 | |
| 5-204 | 5-$CF_3$ | Me | $NH_2$ | Et | H | 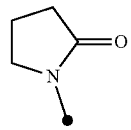 | |
| 5-205 | 5-$CF_3$ | Me | $NH_2$ | i-Pr | H | 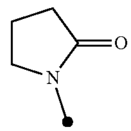 | |
| 5-206 | H | Me | $NH_2$ | Me | H | 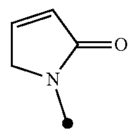 | |

TABLE 5-8-continued

Table 5 (Continued)

| Compound No. | $R^1$ | $R^2$ | $R^3$ | $R^4$ | $R^5$ | Q | Physical property value |
|---|---|---|---|---|---|---|---|
| 5-207 | H | Me | $NH_2$ | Et | H | 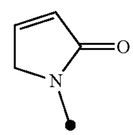 | |
| 5-208 | H | Me | $NH_2$ | i-Pr | H | 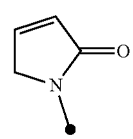 | |
| 5-209 | 5-Me | Me | $NH_2$ | Me | H | 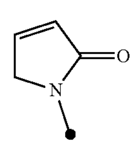 | |
| 5-210 | 5-Me | Me | $NH_2$ | Et | H | 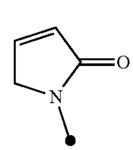 | |
| 5-211 | 5-Me | Me | $NH_2$ | i-Pr | H | 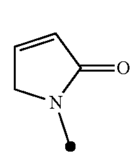 | |
| 5-212 | 5-OMe | Me | $NH_2$ | Me | H | 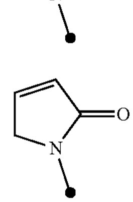 | |
| 5-213 | 5-OMe | Me | $NH_2$ | Et | H | 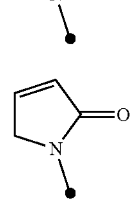 | |
| 5-214 | 5-OMe | Me | $NH_2$ | i-Pr | H | 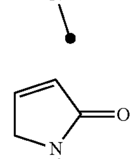 | |
| 5-215 | 5-$CHF_2$ | Me | $NH_2$ | Me | H | 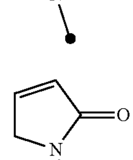 | |
| 5-216 | 5-$CHF_2$ | Me | $NH_2$ | Et | H | 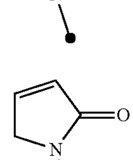 | |

The black solid circle in the structural formula represents a binding position.

TABLE 5-9

| Table 5 (Continued) | | | | | | | |
|---|---|---|---|---|---|---|---|
| Compound No. | $R^1$ | $R^2$ | $R^3$ | $R^4$ | $R^5$ | Q | Physical property value |
| 5-217 | 5-$CHF_2$ | Me | $NH_2$ | i-Pr | H | 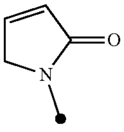 | |
| 5-218 | 5-$CF_3$ | Me | $NH_2$ | Me | H | 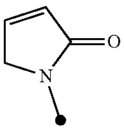 | |
| 5-219 | 5-$CF_3$ | Me | $NH_2$ | Et | H | 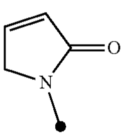 | |
| 5-220 | 5-$CF_3$ | Me | $NH_2$ | i-Pr | H | 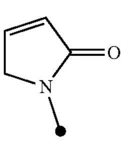 | |
| 5-221 | H | Me | $NH_2$ | Me | H | 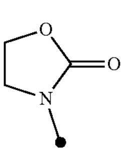 | |
| 5-222 | H | Me | $NH_2$ | Et | H | 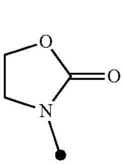 | |
| 5-223 | H | Me | $NH_2$ | i-Pr | H | 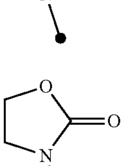 | |
| 5-224 | 5-Me | Me | $NH_2$ | Me | H | 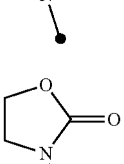 | |
| 5-225 | 5-Me | Me | $NH_2$ | Et | H | 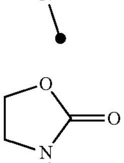 | |
| 5-226 | 5-Me | Me | $NH_2$ | i-Pr | H | 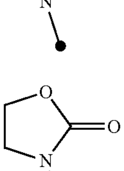 | |

TABLE 5-9-continued

| Table 5 (Continued) | | | | | | | |
|---|---|---|---|---|---|---|---|
| Compound No. | $R^1$ | $R^2$ | $R^3$ | $R^4$ | $R^5$ | Q | Physical property value |
| 5-227 | 5-OMe | Me | $NH_2$ | Me | H | 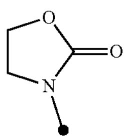 | |
| 5-228 | 5-OMe | Me | $NH_2$ | Et | H | 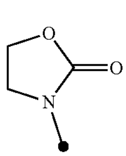 | |
| 5-229 | 5-OMe | Me | $NH_2$ | i-Pr | H | 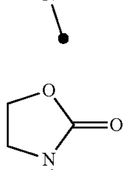 | |
| 5-230 | 5-$CHF_2$ | Me | $NH_2$ | Me | H | 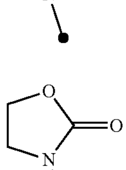 | |
| 5-231 | 5-$CHF_2$ | Me | $NH_2$ | Et | H | 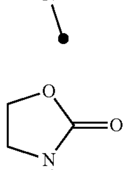 | |
| 5-232 | 5-$CHF_2$ | Me | $NH_2$ | i-Pr | H | 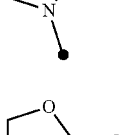 | |

The black solid circle in the structural formula represents a binding position.

TABLE 5-10

| Table 5 (Continued) | | | | | | | |
|---|---|---|---|---|---|---|---|
| Compound No. | $R^1$ | $R^2$ | $R^3$ | $R^4$ | $R^5$ | Q | Physical property value |
| 5-233 | 5-$CF_3$ | Me | $NH_2$ | Me | H | 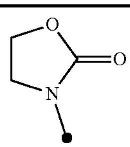 | |
| 5-234 | 5-$CF_3$ | Me | $NH_2$ | Et | H | 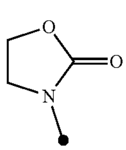 | |

TABLE 5-10-continued

Table 5 (Continued)

| Compound No. | $R^1$ | $R^2$ | $R^3$ | $R^4$ | $R^5$ | Q | Physical property value |
|---|---|---|---|---|---|---|---|
| 5-235 | 5-$CF_3$ | Me | $NH_2$ | i-Pr | H | 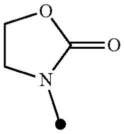 | |
| 5-236 | H | Me | $NH_2$ | Me | H | 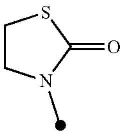 | |
| 5-237 | H | Me | $NH_2$ | Et | H | 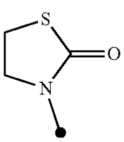 | |
| 5-238 | H | Me | $NH_2$ | i-Pr | H | 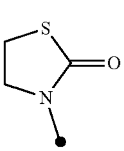 | |
| 5-239 | 5-Me | Me | $NH_2$ | Me | H | 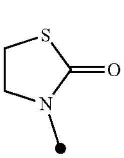 | |
| 5-240 | 5-Me | Me | $NH_2$ | Et | H | 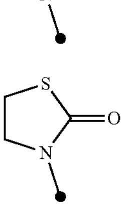 | |
| 5-241 | 5-Me | Me | $NH_2$ | i-Pr | H | 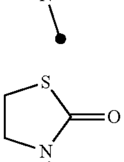 | |
| 5-242 | 5-OMe | Me | $NH_2$ | Me | H | 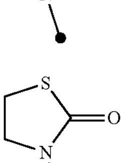 | |
| 5-243 | 5-OMe | Me | $NH_2$ | Et | H | 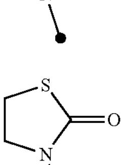 | |
| 5-244 | 5-OMe | Me | $NH_2$ | i-Pr | H | 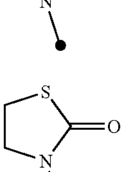 | |

TABLE 5-10-continued

Table 5 (Continued)

| Compound No. | $R^1$ | $R^2$ | $R^3$ | $R^4$ | $R^5$ | Q | Physical property value |
|---|---|---|---|---|---|---|---|
| 5-245 | 5-$CHF_2$ | Me | $NH_2$ | Me | H | 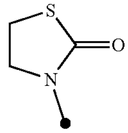 | |
| 5-246 | 5-$CHF_2$ | Me | $NH_2$ | Et | H | 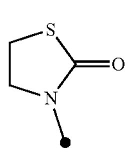 | |
| 5-247 | 5-$CHF_2$ | Me | $NH_2$ | i-Pr | H | 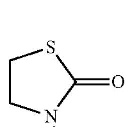 | |
| 5-248 | 5-$CF_3$ | Me | $NH_2$ | Me | H | 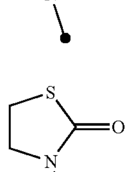 | |

The black solid circle in the structural formula represents a binding position.

TABLE 5-11

Table 5 (Continued)

| Compound No. | $R^1$ | $R^2$ | $R^3$ | $R^4$ | $R^5$ | Q | Physical property value |
|---|---|---|---|---|---|---|---|
| 5-249 | 5-$CF_3$ | Me | $NH_2$ | Et | H | 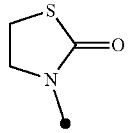 | |
| 5-250 | 5-$CF_3$ | Me | $NH_2$ | i-Pr | H | 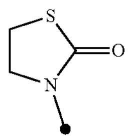 | |
| 5-251 | H | Me | $NH_2$ | Me | H | 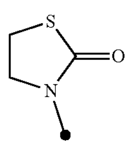 | |
| 5-252 | H | Me | $NH_2$ | Et | H | 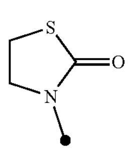 | |

TABLE 5-11-continued

Table 5 (Continued)

| Compound No. | $R^1$ | $R^2$ | $R^3$ | $R^4$ | $R^5$ | Q | Physical property value |
|---|---|---|---|---|---|---|---|
| 5-253 | H | Me | $NH_2$ | i-Pr | H | 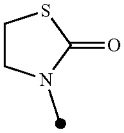 | |
| 5-254 | 5-Me | Me | $NH_2$ | Me | H | 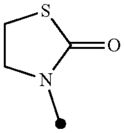 | |
| 5-255 | 5-Me | Me | $NH_2$ | Et | H | 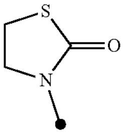 | |
| 5-256 | 5-Me | Me | $NH_2$ | i-Pr | H | 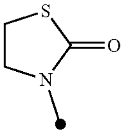 | |
| 5-257 | 5-OMe | Me | $NH_2$ | Me | H | 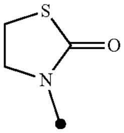 | |
| 5-258 | 5-OMe | Me | $NH_2$ | Et | H | 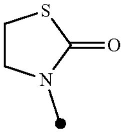 | |
| 5-259 | 5-OMe | Me | $NH_2$ | i-Pr | H | 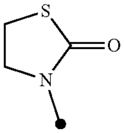 | |
| 5-260 | 5-$CHF_2$ | Me | $NH_2$ | Me | H | 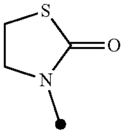 | |
| 5-261 | 5-$CHF_2$ | Me | $NH_2$ | Et | H | 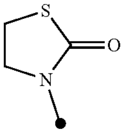 | |
| 5-262 | 5-$CHF_2$ | Me | $NH_2$ | i-Pr | H | 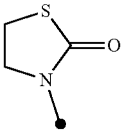 | |

TABLE 5-11-continued

Table 5 (Continued)

| Compound No. | $R^1$ | $R^2$ | $R^3$ | $R^4$ | $R^5$ | Q | Physical property value |
|---|---|---|---|---|---|---|---|
| 5-263 | 5-$CF_3$ | Me | $NH_2$ | Me | H | 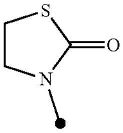 | |
| 5-264 | 5-$CF_3$ | Me | $NH_2$ | Et | H | 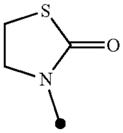 | |

The black solid circle in the structural formula represents a binding position.

TABLE 5-12

Table 5 (Continued)

| Compound No. | $R^1$ | $R^2$ | $R^3$ | $R^4$ | $R^5$ | Q | Physical property value |
|---|---|---|---|---|---|---|---|
| 5-265 | 5-$CF_3$ | Me | $NH_2$ | i-Pr | H | 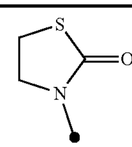 | |
| 5-266 | H | Me | $NH_2$ | Me | H | 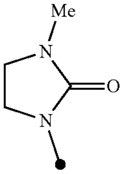 | |
| 5-267 | H | Me | $NH_2$ | Et | H | 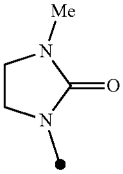 | |
| 5-268 | H | Me | $NH_2$ | i-Pr | H | 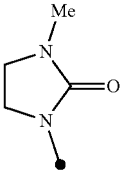 | |
| 5-269 | 5-Me | Me | $NH_2$ | Me | H | 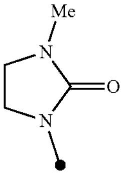 | |

TABLE 5-12-continued

| Table 5 (Continued) | | | | | | | |
|---|---|---|---|---|---|---|---|
| Compound No. | $R^1$ | $R^2$ | $R^3$ | $R^4$ | $R^5$ | Q | Physical property value |
| 5-270 | 5-Me | Me | $NH_2$ | Et | H | 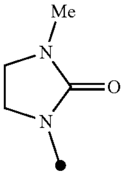 | |
| 5-271 | 5-Me | Me | $NH_2$ | i-Pr | H | 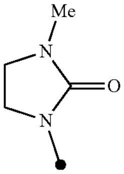 | |
| 5-272 | 5-OMe | Me | $NH_2$ | Me | H | 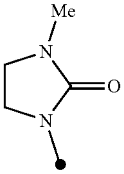 | |
| 5-273 | 5-OMe | Me | $NH_2$ | Et | H | 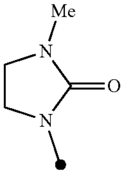 | |
| 5-274 | 5-OMe | Me | $NH_2$ | i-Pr | H | 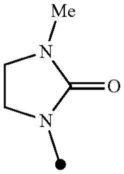 | |
| 5-275 | 5-$CHF_2$ | Me | $NH_2$ | Me | H | 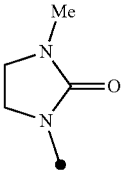 | |

The black solid circle in the structural formula represents a binding position.

TABLE 5-13

| Table 5 (Continued) | | | | | | | |
|---|---|---|---|---|---|---|---|
| Compound No. | $R^1$ | $R^2$ | $R^3$ | $R^4$ | $R^5$ | Q | Physical property value |
| 5-276 | 5-$CHF_2$ | Me | $NH_2$ | Et | H | 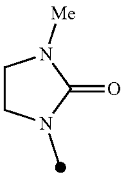 | |

TABLE 5-13-continued

| Table 5 (Continued) | | | | | | | |
|---|---|---|---|---|---|---|---|
| Compound No. | $R^1$ | $R^2$ | $R^3$ | $R^4$ | $R^5$ | Q | Physical property value |
| 5-277 | 5-$CHF_2$ | Me | $NH_2$ | i-Pr | H | 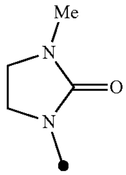 | |
| 5-278 | 5-$CF_3$ | Me | $NH_2$ | Me | H | 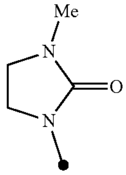 | |
| 5-279 | 5-$CF_3$ | Me | $NH_2$ | Et | H | 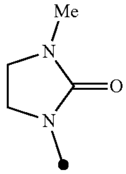 | |
| 5-280 | 5-$CF_3$ | Me | $NH_2$ | i-Pr | H | 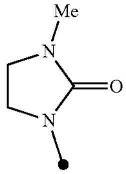 | |
| 5-281 | H | Me | $NH_2$ | Me | H | 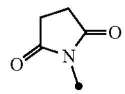 | |
| 5-282 | H | Me | $NH_2$ | Et | H | 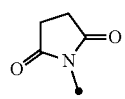 | |
| 5-283 | H | Me | $NH_2$ | i-Pr | H | 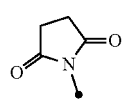 | |
| 5-284 | 5-Me | Me | $NH_2$ | Me | H | 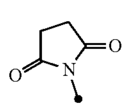 | |
| 5-285 | 5-Me | Me | $NH_2$ | Et | H | 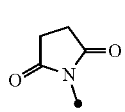 | |
| 5-286 | 5-Me | Me | $NH_2$ | i-Pr | H | 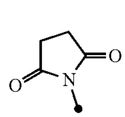 | |
| 5-287 | 5-OMe | Me | $NH_2$ | Me | H | 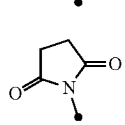 | |

TABLE 5-13-continued

| Table 5 (Continued) | | | | | | | |
|---|---|---|---|---|---|---|---|
| Compound No. | $R^1$ | $R^2$ | $R^3$ | $R^4$ | $R^5$ | Q | Physical property value |
| 5-288 | 5-OMe | Me | $NH_2$ | Et | H | 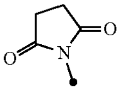 | |

The black solid circle in the structural formula represents a binding position.

TABLE 5-14

| Table 5 (Continued) | | | | | | | |
|---|---|---|---|---|---|---|---|
| Compound No. | $R^1$ | $R^2$ | $R^3$ | $R^4$ | $R^5$ | Q | Physical property value |
| 5-289 | 5-OMe | Me | $NH_2$ | i-Pr | H | 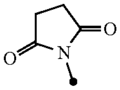 | |
| 5-290 | 5-$CHF_2$ | Me | $NH_2$ | Me | H | 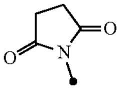 | |
| 5-291 | 5-$CHF_2$ | Me | $NH_2$ | Et | H | 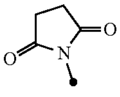 | |
| 5-292 | 5-$CHF_2$ | Me | $NH_2$ | i-Pr | H | 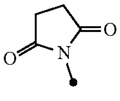 | |
| 5-293 | 5-$CF_3$ | Me | $NH_2$ | Me | H | 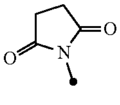 | |
| 5-294 | 5-$CF_3$ | Me | $NH_2$ | Et | H | 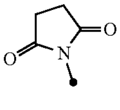 | |
| 5-295 | 5-$CF_3$ | Me | $NH_2$ | i-Pr | H | 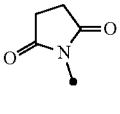 | |
| 5-296 | H | Me | $NH_2$ | Me | H | 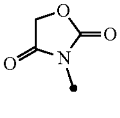 | |
| 5-297 | H | Me | $NH_2$ | Et | H | 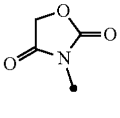 | |
| 5-298 | H | Me | $NH_2$ | i-Pr | H | 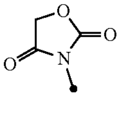 | |

TABLE 5-14-continued

| Table 5 (Continued) | | | | | | | |
|---|---|---|---|---|---|---|---|
| Compound No. | $R^1$ | $R^2$ | $R^3$ | $R^4$ | $R^5$ | Q | Physical property value |
| 5-299 | 5-Me | Me | $NH_2$ | Me | H | 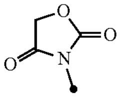 | |
| 5-300 | 5-Me | Me | $NH_2$ | Et | H | 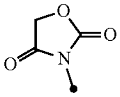 | |
| 5-301 | 5-Me | Me | $NH_2$ | i-Pr | H | 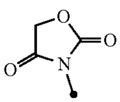 | |
| 5-302 | 5-OMe | Me | $NH_2$ | Me | H | 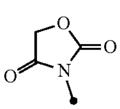 | |
| 5-303 | 5-OMe | Me | $NH_2$ | Et | H | 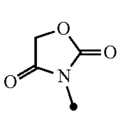 | |
| 5-304 | 5-OMe | Me | $NH_2$ | i-Pr | H | 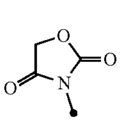 | |

The black solid circle in the structural formula represents a binding position.

TABLE 5-15

| Table 5 (Continued) | | | | | | | |
|---|---|---|---|---|---|---|---|
| Compound No. | $R^1$ | $R^2$ | $R^3$ | $R^4$ | $R^5$ | Q | Physical property value |
| 5-305 | 5-$CHF_2$ | Me | $NH_2$ | Me | H | 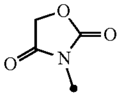 | |
| 5-306 | 5-$CHF_2$ | Me | $NH_2$ | Et | H | 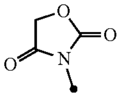 | |
| 5-307 | 5-$CHF_2$ | Me | $NH_2$ | i-Pr | H | 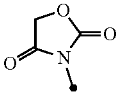 | |
| 5-308 | 5-$CF_3$ | Me | $NH_2$ | Me | H | 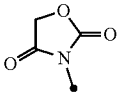 | |
| 5-309 | 5-$CF_3$ | Me | $NH_2$ | Et | H | 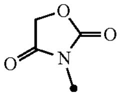 | |

TABLE 5-15-continued

Table 5 (Continued)

| Compound No. | $R^1$ | $R^2$ | $R^3$ | $R^4$ | $R^5$ | Q | Physical property value |
|---|---|---|---|---|---|---|---|
| 5-310 | 5-$CF_3$ | Me | $NH_2$ | i-Pr | H | 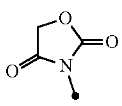 | |

The black solid circle in the structural formula represents a binding position.

[Chem. 32]

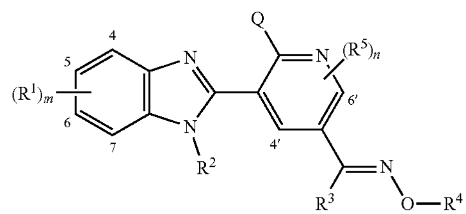

(1f)

The position numbers in the table are the numbers designated in the general formula (1f).

TABLE 6-1

| Compound No. | $R^1$ | $R^2$ | $R^3$ | $R^4$ | $R^5$ | Q | Physical property value |
|---|---|---|---|---|---|---|---|
| 6-1 | H | Me | $NH_2$ | Me | H | $CO_2Me$ | |
| 6-2 | H | Me | $NH_2$ | Me | H | $SO_2Me$ | |
| 6-3 | H | Me | $NH_2$ | Me | H | $SO_2NHMe$ | |
| 6-4 | H | Me | $NH_2$ | Et | H | $CO_2Me$ | |
| 6-5 | H | Me | $NH_2$ | Et | H | $SO_2Me$ | |
| 6-6 | H | Me | $NH_2$ | Et | H | $SO_2NHMe$ | |
| 6-7 | H | Me | $NH_2$ | i-Pr | H | $CO_2Me$ | |
| 6-8 | H | Me | $NH_2$ | i-Pr | H | $SO_2Me$ | |
| 6-9 | H | Me | $NH_2$ | i-Pr | H | $SO_2NHMe$ | |
| 6-10 | 5-Me | Me | $NH_2$ | Me | H | $CO_2Me$ | |
| 6-11 | 5-Me | Me | $NH_2$ | Me | H | $SO_2Me$ | |
| 6-12 | 5-Me | Me | $NH_2$ | Me | H | $SO_2NHMe$ | |
| 6-13 | 5-Me | Me | $NH_2$ | Et | H | $CO_2Me$ | |
| 6-14 | 5-Me | Me | $NH_2$ | Et | H | $CO_2Et$ | 197-198 |
| 6-15 | 5-Me | Me | $NH_2$ | Et | H | $SO_2Me$ | 238-239 |
| 6-16 | 5-Me | Me | $NH_2$ | Et | H | $SO_2NHMe$ | |
| 6-17 | 5-Me | Me | $NH_2$ | Et | H | $C(NH_2){=}N{-}OEt$ | 94-95 |
| 6-18 | 5-Me | Me | $NH_2$ | i-Pr | H | $CO_2Me$ | |
| 6-19 | 5-Me | Me | $NH_2$ | i-Pr | H | $SO_2Me$ | |
| 6-20 | 5-Me | Me | $NH_2$ | i-Pr | H | $SO_2NHMe$ | |
| 6-21 | 5-OMe | Me | $NH_2$ | Me | H | $CO_2Me$ | |
| 6-22 | 5-OMe | Me | $NH_2$ | Me | H | $SO_2Me$ | |
| 6-23 | 5-OMe | Me | $NH_2$ | Me | H | $SO_2NHMe$ | |
| 6-24 | 5-OMe | Me | $NH_2$ | Et | H | $CO_2Me$ | |
| 6-25 | 5-OMe | Me | $NH_2$ | Et | H | $SO_2Me$ | |
| 6-26 | 5-OMe | Me | $NH_2$ | Et | H | $SO_2NHMe$ | |
| 6-27 | 5-OMe | Me | $NH_2$ | i-Pr | H | $CO_2Me$ | |
| 6-28 | 5-OMe | Me | $NH_2$ | i-Pr | H | $SO_2Me$ | |
| 6-29 | 5-OMe | Me | $NH_2$ | i-Pr | H | $SO_2NHMe$ | |
| 6-30 | 5-$CHF_2$ | Me | $NH_2$ | Me | H | $CO_2Me$ | |

TABLE 6-2

| Compound No. | $R^1$ | $R^2$ | $R^3$ | $R^4$ | $R^5$ | Q | Physical property value |
|---|---|---|---|---|---|---|---|
| 6-31 | 5-$CHF_2$ | Me | $NH_2$ | Me | H | $SO_2Me$ | |
| 6-32 | 5-$CHF_2$ | Me | $NH_2$ | Me | H | $SO_2NHMe$ | |
| 6-33 | 5-$CHF_2$ | Me | $NH_2$ | Et | H | $CO_2Me$ | |
| 6-34 | 5-$CHF_2$ | Me | $NH_2$ | Et | H | $SO_2Me$ | |
| 6-35 | 5-$CHF_2$ | Me | $NH_2$ | Et | H | $SO_2NHMe$ | |
| 6-36 | 5-$CHF_2$ | Me | $NH_2$ | i-Pr | H | $CO_2Me$ | |
| 6-37 | 5-$CHF_2$ | Me | $NH_2$ | i-Pr | H | $SO_2Me$ | |
| 6-38 | 5-$CHF_2$ | Me | $NH_2$ | i-Pr | H | $SO_2NHMe$ | |
| 6-39 | 5-$CF_3$ | Me | $NH_2$ | Me | H | $CO_2Me$ | |
| 6-40 | 5-$CF_3$ | Me | $NH_2$ | Me | H | $SO_2Me$ | |
| 6-41 | 5-$CF_3$ | Me | $NH_2$ | Me | H | $SO_2NHMe$ | |
| 6-42 | 5-$CF_3$ | Me | $NH_2$ | Et | H | $CO_2Me$ | |
| 6-43 | 5-$CF_3$ | Me | $NH_2$ | Et | H | $SO_2Me$ | |
| 6-44 | 5-$CF_3$ | Me | $NH_2$ | Et | H | $SO_2NHMe$ | |
| 6-45 | 5-$CF_3$ | Me | $NH_2$ | i-Pr | H | $CO_2Me$ | |
| 6-46 | 5-$CF_3$ | Me | $NH_2$ | i-Pr | H | $SO_2Me$ | |
| 6-47 | 5-$CF_3$ | Me | $NH_2$ | i-Pr | H | $SO_2NHMe$ | |
| 6-48 | H | Me | Me | Me | H | $CO_2Me$ | |
| 6-49 | H | Me | Me | Me | H | $SO_2Me$ | |
| 6-50 | H | Me | Me | Me | H | $SO_2NHMe$ | |
| 6-51 | H | Me | Me | Et | H | $CO_2Me$ | |
| 6-52 | H | Me | Me | Et | H | $SO_2Me$ | |
| 6-53 | H | Me | Me | Et | H | $SO_2NHMe$ | |
| 6-54 | H | Me | Me | i-Pr | H | $CO_2Me$ | |
| 6-55 | H | Me | Me | i-Pr | H | $SO_2Me$ | |
| 6-56 | H | Me | Me | i-Pr | H | $SO_2NHMe$ | |
| 6-57 | 5-Me | Me | Me | Me | H | $CO_2Me$ | |
| 6-58 | 5-Me | Me | Me | Me | H | $SO_2Me$ | |
| 6-59 | 5-Me | Me | Me | Me | H | $SO_2NHMe$ | |
| 6-60 | 5-Me | Me | Me | Et | H | $CO_2Me$ | |

TABLE 6-3

| Compound No. | $R^1$ | $R^2$ | $R^3$ | $R^4$ | $R^5$ | Q | Physical property value |
|---|---|---|---|---|---|---|---|
| 6-61 | 5-Me | Me | Me | Et | H | $SO_2Me$ | |
| 6-62 | 5-Me | Me | Me | Et | H | $SO_2NHMe$ | |
| 6-63 | 5-Me | Me | Me | i-Pr | H | $CO_2Me$ | |
| 6-64 | 5-Me | Me | Me | i-Pr | H | $SO_2Me$ | |
| 6-65 | 5-Me | Me | Me | i-Pr | H | $SO_2NHMe$ | |
| 6-66 | 5-OMe | Me | Me | Me | H | $CO_2Me$ | |
| 6-67 | 5-OMe | Me | Me | Me | H | $SO_2Me$ | |
| 6-68 | 5-OMe | Me | Me | Me | H | $SO_2NHMe$ | |
| 6-69 | 5-OMe | Me | Me | Et | H | $CO_2Me$ | |
| 6-70 | 5-OMe | Me | Me | Et | H | $SO_2Me$ | |
| 6-71 | 5-OMe | Me | Me | Et | H | $SO_2NHMe$ | |
| 6-72 | 5-OMe | Me | Me | i-Pr | H | $CO_2Me$ | |
| 6-73 | 5-OMe | Me | Me | i-Pr | H | $SO_2Me$ | |
| 6-74 | 5-OMe | Me | Me | i-Pr | H | $SO_2NHMe$ | |
| 6-75 | 5-$CHF_2$ | Me | Me | Me | H | $CO_2Me$ | |
| 6-76 | 5-$CHF_2$ | Me | Me | Me | H | $SO_2Me$ | |
| 6-77 | 5-$CHF_2$ | Me | Me | Me | H | $SO_2NHMe$ | |
| 6-78 | 5-$CHF_2$ | Me | Me | Et | H | $CO_2Me$ | |
| 6-79 | 5-$CHF_2$ | Me | Me | Et | H | $SO_2Me$ | |
| 6-80 | 5-$CHF_2$ | Me | Me | Et | H | $SO_2NHMe$ | |
| 6-81 | 5-$CHF_2$ | Me | Me | i-Pr | H | $CO_2Me$ | |
| 6-82 | 5-$CHF_2$ | Me | Me | i-Pr | H | $SO_2Me$ | |
| 6-83 | 5-$CHF_2$ | Me | Me | i-Pr | H | $SO_2NHMe$ | |
| 6-84 | 5-$CF_3$ | Me | Me | Me | H | $CO_2Me$ | |
| 6-85 | 5-$CF_3$ | Me | Me | Me | H | $SO_2Me$ | |
| 6-86 | 5-$CF_3$ | Me | Me | Me | H | $SO_2NHMe$ | |
| 6-87 | 5-$CF_3$ | Me | Me | Et | H | $CO_2Me$ | |
| 6-88 | 5-$CF_3$ | Me | Me | Et | H | $SO_2Me$ | |
| 6-89 | 5-$CF_3$ | Me | Me | Et | H | $SO_2NHMe$ | 189-190 |
| 6-90 | 5-$CF_3$ | Me | Me | i-Pr | H | $CO_2Me$ | |
| 6-91 | 5-$CF_3$ | Me | Me | i-Pr | H | $SO_2Me$ | |
| 6-92 | 5-$CF_3$ | Me | Me | i-Pr | H | $SO_2NHMe$ | |

TABLE 6-4

| [Table 6 (Continued)] | | | | | | | |
|---|---|---|---|---|---|---|---|
| Compound No. | $R^1$ | $R^2$ | $R^3$ | $R^4$ | $R^5$ | Q | Physical property value |
| 6-93 | H | Me | $NH_2$ | Me | H | 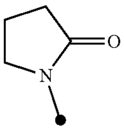 | |
| 6-94 | H | Me | $NH_2$ | Et | H | 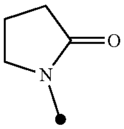 | |
| 6-95 | H | Me | $NH_2$ | i-Pr | H | 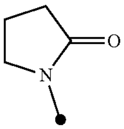 | |
| 6-96 | 5-Me | Me | $NH_2$ | Me | H | 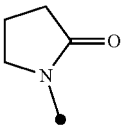 | |
| 6-97 | 5-Me | Me | $NH_2$ | Et | H | 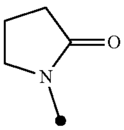 | |
| 6-98 | 5-Me | Me | $NH_2$ | i-Pr | H | 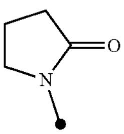 | |
| 6-99 | 5-OMe | Me | $NH_2$ | Me | H | 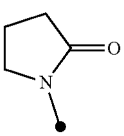 | |
| 6-100 | 5-OMe | Me | $NH_2$ | Et | H | 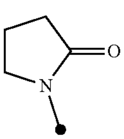 | |
| 6-101 | 5-OMe | Me | $NH_2$ | i-Pr | H | 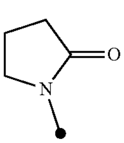 | |
| 6-102 | 5-$CHF_2$ | Me | $NH_2$ | Me | H | 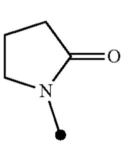 | |

TABLE 6-4-continued

| [Table 6 (Continued)] | | | | | | | |
|---|---|---|---|---|---|---|---|
| Compound No. | $R^1$ | $R^2$ | $R^3$ | $R^4$ | $R^5$ | Q | Physical property value |
| 6-103 | 5-$CHF_2$ | Me | $NH_2$ | Et | H | 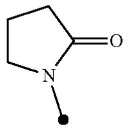 | |
| 6-104 | 5-$CHF_2$ | Me | $NH_2$ | i-Pr | H | 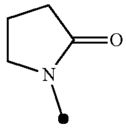 | |
| 6-105 | 5-$CF_3$ | Me | $NH_2$ | Me | H | 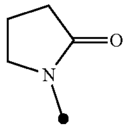 | |
| 6-106 | 5-$CF_3$ | Me | $NH_2$ | Et | H | 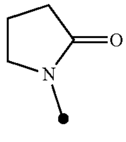 | |
| 6-107 | 5-$CF_3$ | Me | $NH_2$ | i-Pr | H | 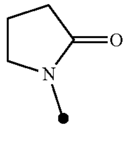 | |
| 6-108 | H | Me | $NH_2$ | Me | H | 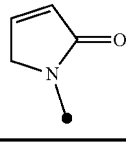 | |

The black solid circle in the structural formula represents a binding position.

TABLE 6-5

| Table 6 (Continued) | | | | | | | |
|---|---|---|---|---|---|---|---|
| Compound No. | $R^1$ | $R^2$ | $R^3$ | $R^4$ | $R^5$ | Q | Physical property value |
| 6-109 | H | Me | $NH_2$ | Et | H | 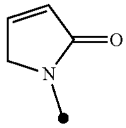 | |
| 6-110 | H | Me | $NH_2$ | i-Pr | H | 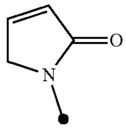 | |
| 6-111 | 5-Me | Me | $NH_2$ | Me | H | 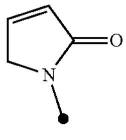 | |

TABLE 6-5-continued

Table 6 (Continued)

| Compound No. | $R^1$ | $R^2$ | $R^3$ | $R^4$ | $R^5$ | Q | Physical property value |
|---|---|---|---|---|---|---|---|
| 6-112 | 5-Me | Me | $NH_2$ | Et | H | 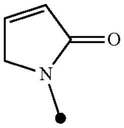 | |
| 6-113 | 5-Me | Me | $NH_2$ | i-Pr | H | 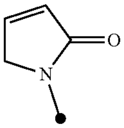 | |
| 6-114 | 5-OMe | Me | $NH_2$ | Me | H | 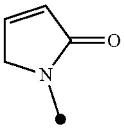 | |
| 6-115 | 5-OMe | Me | $NH_2$ | Et | H | 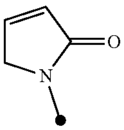 | |
| 6-116 | 5-OMe | Me | $NH_2$ | i-Pr | H | 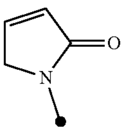 | |
| 6-117 | 5-$CHF_2$ | Me | $NH_2$ | Me | H | 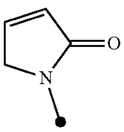 | |
| 6-118 | 5-$CHF_2$ | Me | $NH_2$ | Et | H | 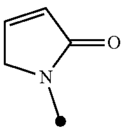 | |
| 6-119 | 5-$CHF_2$ | Me | $NH_2$ | i-Pr | H | 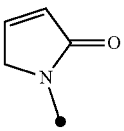 | |
| 6-120 | 5-$CF_3$ | Me | $NH_2$ | Me | H | 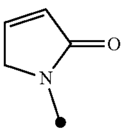 | |
| 6-121 | 5-$CF_3$ | Me | $NH_2$ | Et | H | 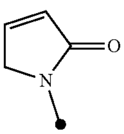 | |
| 6-122 | 5-$CF_3$ | Me | $NH_2$ | i-Pr | H | 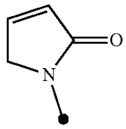 | |
| 6-123 | H | Me | $NH_2$ | Me | H | 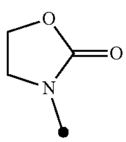 | |
| 6-124 | H | Me | $NH_2$ | Et | H | 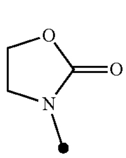 | |

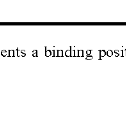

The black solid circle in the structural formula represents a binding position.

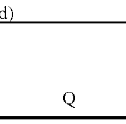

TABLE 6-6

Table 6 (Continued)

| Compound No. | $R^1$ | $R^2$ | $R^3$ | $R^4$ | $R^5$ | Q | Physical property value |
|---|---|---|---|---|---|---|---|
| 6-125 | H | Me | $NH_2$ | i-Pr | H | 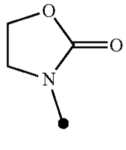 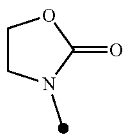 | |
| 6-126 | 5-Me | Me | $NH_2$ | Me | H | 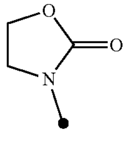 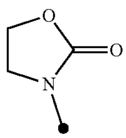 | |
| 6-127 | 5-Me | Me | $NH_2$ | Et | H | 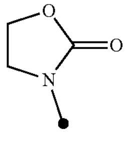 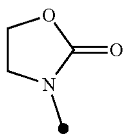 | |
| 6-128 | 5-Me | Me | $NH_2$ | i-Pr | H | 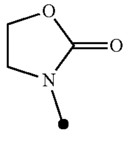 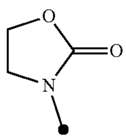 | |
| 6-129 | 5-OMe | Me | $NH_2$ | Me | H | 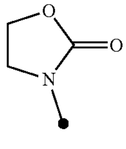 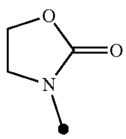 | |

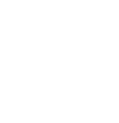

TABLE 6-6-continued

Table 6 (Continued)

| Compound No. | $R^1$ | $R^2$ | $R^3$ | $R^4$ | $R^5$ | Q | Physical property value |
|---|---|---|---|---|---|---|---|
| 6-130 | 5-OMe | Me | $NH_2$ | Et | H | 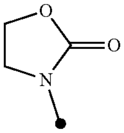 | |
| 6-131 | 5-OMe | Me | $NH_2$ | i-Pr | H | 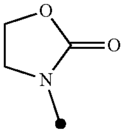 | |
| 6-132 | 5-$CHF_2$ | Me | $NH_2$ | Me | H | 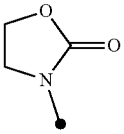 | |
| 6-133 | 5-$CHF_2$ | Me | $NH_2$ | Et | H | 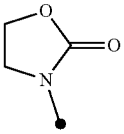 | |
| 6-134 | 5-$CHF_2$ | Me | $NH_2$ | i-Pr | H | 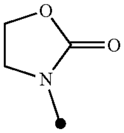 | |
| 6-135 | 5-$CF_3$ | Me | $NH_2$ | Me | H | 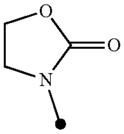 | |
| 6-136 | 5-$CF_3$ | Me | $NH_2$ | Et | H | 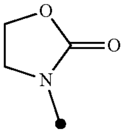 | |
| 6-137 | 5-$CF_3$ | Me | $NH_2$ | i-Pr | H | 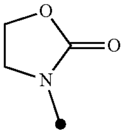 | |
| 6-138 | H | Me | $NH_2$ | Me | H | 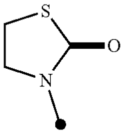 | |
| 6-139 | H | Me | $NH_2$ | Et | H | 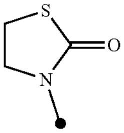 | |

TABLE 6-6-continued

Table 6 (Continued)

| Compound No. | $R^1$ | $R^2$ | $R^3$ | $R^4$ | $R^5$ | Q | Physical property value |
|---|---|---|---|---|---|---|---|
| 6-140 | H | Me | $NH_2$ | i-Pr | H | 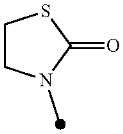 | |

The black solid circle in the structural formula represents a binding position.

TABLE 6-7

Table 6 (Continued)

| Compound No. | $R^1$ | $R^2$ | $R^3$ | $R^4$ | $R^5$ | Q | Physical property value |
|---|---|---|---|---|---|---|---|
| 6-141 | 5-Me | Me | $NH_2$ | Me | H | 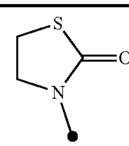 | |
| 6-142 | 5-Me | Me | $NH_2$ | Et | H | 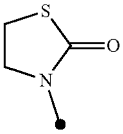 | |
| 6-143 | 5-Me | Me | $NH_2$ | i-Pr | H | 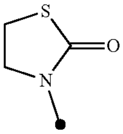 | |
| 6-144 | 5-OMe | Me | $NH_2$ | Me | H | 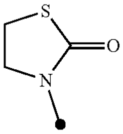 | |
| 6-145 | 5-OMe | Me | $NH_2$ | Et | H | 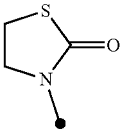 | |
| 6-146 | 5-OMe | Me | $NH_2$ | i-Pr | H | 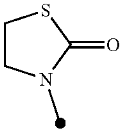 | |
| 6-147 | 5-$CHF_2$ | Me | $NH_2$ | Me | H | 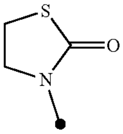 | |

TABLE 6-7-continued

| Table 6 (Continued) | | | | | | | |
|---|---|---|---|---|---|---|---|
| Compound No. | $R^1$ | $R^2$ | $R^3$ | $R^4$ | $R^5$ | Q | Physical property value |
| 6-148 | 5-$CHF_2$ | Me | $NH_2$ | Et | H | 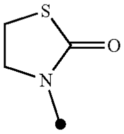 | |
| 6-149 | 5-$CHF_2$ | Me | $NH_2$ | i-Pr | H | 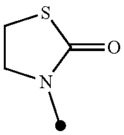 | |
| 6-150 | 5-$CF_3$ | Me | $NH_2$ | Me | H | 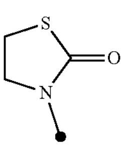 | |
| 6-151 | 5-$CF_3$ | Me | $NH_2$ | Et | H | 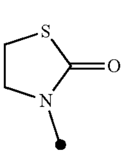 | |
| 6-152 | 5-$CF_3$ | Me | $NH_2$ | i-Pr | H | 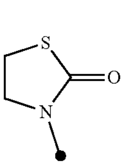 | |
| 6-153 | H | Me | $NH_2$ | Me | H | 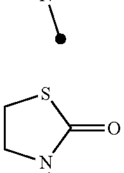 | |
| 6-154 | H | Me | $NH_2$ | Et | H | 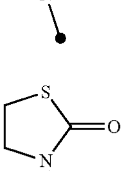 | |
| 6-155 | H | Me | $NH_2$ | i-Pr | H | 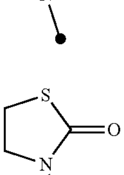 | |
| 6-156 | 5-Me | Me | $NH_2$ | Me | H | 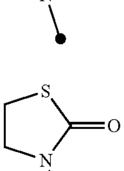 | |

The black solid circle in the structural formula represents a binding position.

TABLE 6-8

| Table 6 (Continued) | | | | | | | |
|---|---|---|---|---|---|---|---|
| Compound No. | $R^1$ | $R^2$ | $R^3$ | $R^4$ | $R^5$ | Q | Physical property value |
| 6-157 | 5-Me | Me | $NH_2$ | E | H | 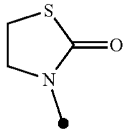 | |
| 6-158 | 5-Me | Me | $NH_2$ | i-Pr | H | 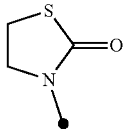 | |
| 6-159 | 5-OMe | Me | $NH_2$ | Me | H | 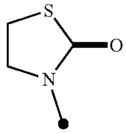 | |
| 6-160 | 5-OMe | Me | $NH_2$ | Et | H | 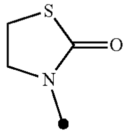 | |
| 6-161 | 5-OMe | Me | $NH_2$ | i-Pr | H | 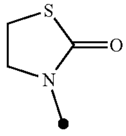 | |
| 6-162 | 5-$CHF_2$ | Me | $NH_2$ | Me | H | 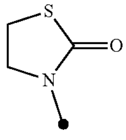 | |
| 6-163 | 5-$CHF_2$ | Me | $NH_2$ | Et | H | 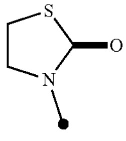 | |
| 6-164 | 5-$CHF_2$ | Me | $NH_2$ | i-Pr | H | 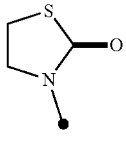 | |
| 6-165 | 5-$CF_3$ | Me | $NH_2$ | Me | H | 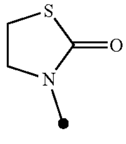 | |
| 6-166 | 5-$CF_3$ | Me | $NH_2$ | Et | H | 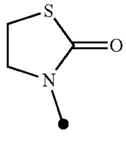 | |

TABLE 6-8-continued

| Table 6 (Continued) | | | | | | | |
|---|---|---|---|---|---|---|---|
| Compound No. | $R^1$ | $R^2$ | $R^3$ | $R^4$ | $R^5$ | Q | Physical property value |
| 6-167 | 5-$CF_3$ | Me | $NH_2$ | i-Pr | H | 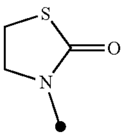 | |
| 6-168 | H | Me | $NH_2$ | Me | H | 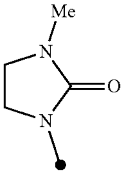 | |
| 6-169 | H | Me | $NH_2$ | Et | H | 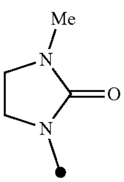 | |
| 6-170 | H | Me | $NH_2$ | i-Pr | H | 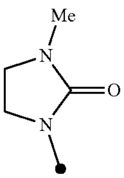 | |

The black solid circle in the structural formula represents a binding position.

TABLE 6-9

| Table 6 (Continued) | | | | | | | |
|---|---|---|---|---|---|---|---|
| Compound No. | $R^1$ | $R^2$ | $R^3$ | $R^4$ | $R^5$ | Q | Physical property value |
| 6-171 | 5-Me | Me | $NH_2$ | Me | H | 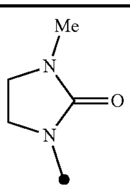 | |
| 6-172 | 5-Me | Me | $NH_2$ | Et | H | 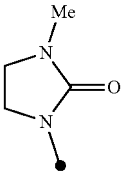 | |
| 6-173 | 5-Me | Me | $NH_2$ | i-Pr | H | 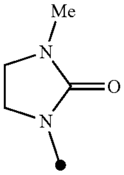 | |

TABLE 6-9-continued

| Table 6 (Continued) | | | | | | | |
|---|---|---|---|---|---|---|---|
| Compound No. | $R^1$ | $R^2$ | $R^3$ | $R^4$ | $R^5$ | Q | Physical property value |
| 6-174 | 5-OMe | Me | $NH_2$ | Me | H | 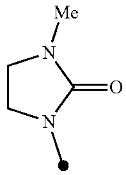 | |
| 6-175 | 5-OMe | Me | $NH_2$ | Et | H | 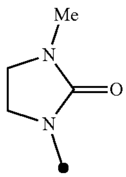 | |
| 6-176 | 5-OMe | Me | $NH_2$ | i-Pr | H | 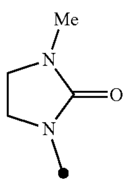 | |
| 6-177 | 5-$CHF_2$ | Me | $NH_2$ | Me | H | 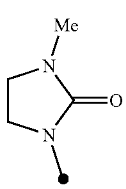 | |
| 6-178 | 5-$CHF_2$ | Me | $NH_2$ | Et | H | 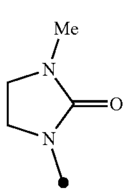 | |
| 6-179 | 5-$CHF_2$ | Me | $NH_2$ | i-Pr | H | 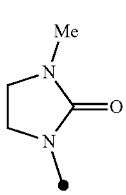 | |
| 6-180 | 5-$CF_3$ | Me | $NH_2$ | Me | H | 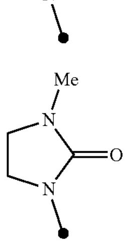 | |
| 6-181 | 5-$CF_3$ | Me | $NH_2$ | Et | H | 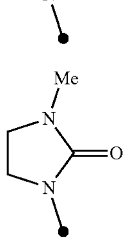 | |

The black solid circle in the structural formula represents a binding position.

TABLE 6-10

Table 6 (Continued)

| Compound No. | $R^1$ | $R^2$ | $R^3$ | $R^4$ | $R^5$ | Q | Physical property value |
|---|---|---|---|---|---|---|---|
| 6-182 | 5-$CF_3$ | Me | $NH_2$ | i-Pr | H | 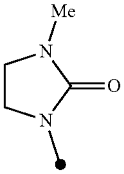 | |
| 6-183 | H | Me | $NH_2$ | Me | H | 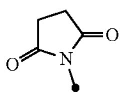 | |
| 6-184 | H | Me | $NH_2$ | Et | H | 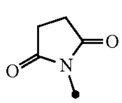 | |
| 6-185 | H | Me | $NH_2$ | i-Pr | H | 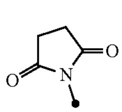 | |
| 6-186 | 5-Me | Me | $NH_2$ | Me | H | 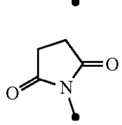 | |
| 6-187 | 5-Me | Me | $NH_2$ | Et | H | 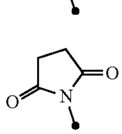 | |
| 6-188 | 5-Me | Me | $NH_2$ | i-Pr | H | 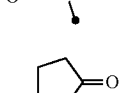 | |
| 6-189 | 5-OMe | Me | $NH_2$ | Me | H | 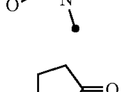 | |
| 6-190 | 5-OMe | Me | $NH_2$ | Et | H | 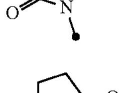 | |
| 6-191 | 5-OMe | Me | $NH_2$ | i-Pr | H | 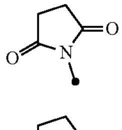 | |
| 6-192 | 5-$CHF_2$ | Me | $NH_2$ | Me | H | 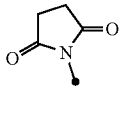 | |
| 6-193 | 5-$CHF_2$ | Me | $NH_2$ | Et | H | 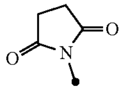 | |
| 6-194 | 5-$CHF_2$ | Me | $NH_2$ | i-Pr | H | 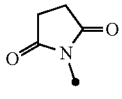 | |

TABLE 6-10-continued

Table 6 (Continued)

| Compound No. | $R^1$ | $R^2$ | $R^3$ | $R^4$ | $R^5$ | Q | Physical property value |
|---|---|---|---|---|---|---|---|
| 6-195 | 5-$CF_3$ | Me | $NH_2$ | Me | H | 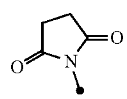 | |
| 6-196 | 5-$CF_3$ | Me | $NH_2$ | Et | H | 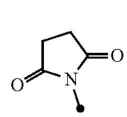 | |

The black solid circle in the structural formula represents a binding position.

TABLE 6-11

Table 6 (Continued)

| Compound No. | $R^1$ | $R^2$ | $R^3$ | $R^4$ | $R^5$ | Q | Physical property value |
|---|---|---|---|---|---|---|---|
| 6-197 | 5-$CF_3$ | Me | $NH_2$ | i-Pr | H | 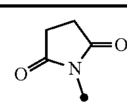 | |
| 6-198 | H | Me | $NH_2$ | Me | H | 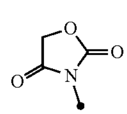 | |
| 6-199 | H | Me | $NH_2$ | Et | H | 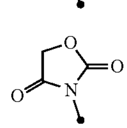 | |
| 6-200 | H | Me | $NH_2$ | i-Pr | H | 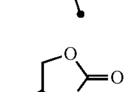 | |
| 6-201 | 5-Me | Me | $NH_2$ | Me | H | 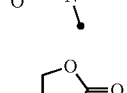 | |
| 6-202 | 5-Me | Me | $NH_2$ | Et | H | 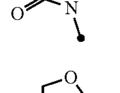 | |
| 6-203 | 5-Me | Me | $NH_2$ | i-Pr | H | 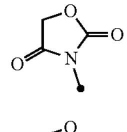 | |
| 6-204 | 5-OMe | Me | $NH_2$ | Me | H | 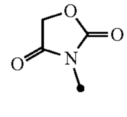 | |
| 6-205 | 5-OMe | Me | $NH_2$ | Et | H | 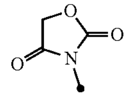 | |

TABLE 6-11-continued

| Table 6 (Continued) | | | | | | | |
|---|---|---|---|---|---|---|---|
| Compound No. | $R^1$ | $R^2$ | $R^3$ | $R^4$ | $R^5$ | Q | Physical property value |
| 6-206 | 5-OMe | Me | $NH_2$ | i-Pr | H | 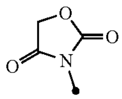 | |
| 6-207 | 5-$CHF_2$ | Me | $NH_2$ | Me | H | 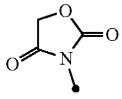 | |
| 6-208 | 5-$CHF_2$ | Me | $NH_2$ | Et | H | 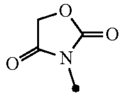 | |
| 6-209 | 5-$CHF_2$ | Me | $NH_2$ | i-Pr | H | 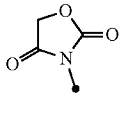 | |
| 6-210 | 5-$CF_3$ | Me | $NH_2$ | Me | H | 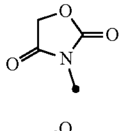 | |
| 6-211 | 5-$CF_3$ | Me | $NH_2$ | Et | H | 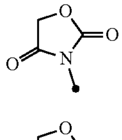 | |
| 6-212 | 5-$CF_3$ | Me | $NH_2$ | I-Pr | H | 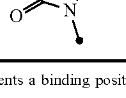 | |

The black solid circle in the structural formula represents a binding position.

[Chem. 33]

(1g)

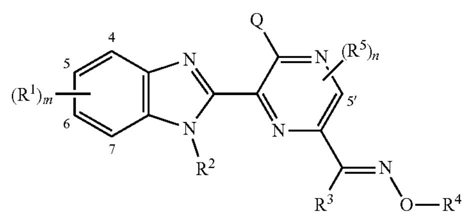

The position numbers in the table are the numbers designated in the general formula (Ig).

TABLE 7-1

| Compound No. | $R^1$ | $R^2$ | $R^3$ | $R^4$ | $R^5$ | Q | Physical property value |
|---|---|---|---|---|---|---|---|
| 7-1 | H | Me | $NH_2$ | Me | H | $CO_2Me$ | |
| 7-2 | H | Me | $NH_2$ | Me | H | $SO_2Me$ | |
| 7-3 | H | Me | $NH_2$ | Me | H | $SO_2NHMe$ | |
| 7-4 | H | Me | $NH_2$ | Et | H | $CO_2Me$ | |
| 7-5 | H | Me | $NH_2$ | Et | H | $SO_2Me$ | |
| 7-6 | H | Me | $NH_2$ | Et | H | $SO_2NHMe$ | 242-244 |
| 7-7 | H | Me | $NH_2$ | Et | H | NHMe | 139-140 |

TABLE 7-1-continued

| Compound No. | $R^1$ | $R^2$ | $R^3$ | $R^4$ | $R^5$ | Q | Physical property value |
|---|---|---|---|---|---|---|---|
| 7-8 | H | Me | $NH_2$ | i-Pr | H | $CO_2Me$ | |
| 7-9 | H | Me | $NH_2$ | i-Pr | H | $SO_2Me$ | |
| 7-10 | H | Me | $NH_2$ | i-Pr | H | $SO_2NHMe$ | |
| 7-11 | 5-Me | Me | $NH_2$ | Me | H | $CO_2Me$ | |
| 7-12 | 5-Me | Me | $NH_2$ | Me | H | $SO_2Me$ | |
| 7-13 | 5-Me | Me | $NH_2$ | Me | H | $SO_2NHMe$ | |
| 7-14 | 5-Me | Me | $NH_2$ | Et | H | $CO_2Me$ | |
| 7-15 | 5-Me | Me | $NH_2$ | Et | H | $SCH_2$(4-t-BuPh) | 194-195 |
| 7-16 | 5-Me | Me | $NH_2$ | Et | H | $SO_2Me$ | |
| 7-17 | 5-Me | Me | $NH_2$ | Et | H | $SO_2NHMe$ | 202-203 |
| 7-18 | 5-Me | Me | $NH_2$ | i-Pr | H | $CO_2Me$ | |
| 7-19 | 5-Me | Me | $NH_2$ | i-Pr | H | $SO_2Me$ | |
| 7-20 | 5-Me | Me | $NH_2$ | i-Pr | H | $SO_2NHMe$ | |
| 7-21 | 5-OMe | Me | $NH_2$ | Me | H | $CO_2Me$ | |
| 7-22 | 5-OMe | Me | $NH_2$ | Me | H | $SO_2Me$ | |
| 7-23 | 5-OMe | Me | $NH_2$ | Me | H | $SO_2NHMe$ | |
| 7-24 | 5-OMe | Me | $NH_2$ | Et | H | $CO_2Me$ | |
| 7-25 | 5-OMe | Me | $NH_2$ | Et | H | $SO_2Me$ | |
| 7-26 | 5-OMe | Me | $NH_2$ | Et | H | $SO_2NHMe$ | |
| 7-27 | 5-OMe | Me | $NH_2$ | i-Pr | H | $CO_2Me$ | |
| 7-28 | 5-OMe | Me | $NH_2$ | i-Pr | H | $SO_2Me$ | |
| 7-29 | 5-OMe | Me | $NH_2$ | i-Pr | H | $SO_2NHMe$ | |
| 7-30 | 5-$CHF_2$ | Me | $NH_2$ | Me | H | $CO_2Me$ | |

TABLE 7-2

| Compound No. | $R^1$ | $R^2$ | $R^3$ | $R^4$ | $R^5$ | Q | Physical property value |
|---|---|---|---|---|---|---|---|
| 7-31 | 5-$CHF_2$ | Me | $NH_2$ | Me | H | $SO_2Me$ | |
| 7-32 | 5-$CHF_2$ | Me | $NH_2$ | Me | H | $SO_2NHMe$ | |
| 7-33 | 5-$CHF_2$ | Me | $NH_2$ | Et | H | $CO_2Me$ | |
| 7-34 | 5-$CHF_2$ | Me | $NH_2$ | Et | H | $SO_2Me$ | |
| 7-35 | 5-$CHF_2$ | Me | $NH_2$ | Et | H | $SO_2NHMe$ | |
| 7-36 | 5-$CHF_2$ | Me | $NH_2$ | i-Pr | H | $CO_2Me$ | |
| 7-37 | 5-$CHF_2$ | Me | $NH_2$ | i-Pr | H | $SO_2Me$ | |
| 7-38 | 5-$CHF_2$ | Me | $NH_2$ | i-Pr | H | $SO_2NHMe$ | |
| 7-39 | 5-$CF_3$ | Me | $NH_2$ | Me | H | $CO_2Me$ | |
| 7-40 | 5-$CF_3$ | Me | $NH_2$ | Me | H | $SO_2Me$ | |
| 7-41 | 5-$CF_3$ | Me | $NH_2$ | Me | H | $SO_2NHMe$ | |
| 7-42 | 5-$CF_3$ | Me | $NH_2$ | Et | H | Cl | 166-167 |
| 7-43 | 5-$CF_3$ | Me | $NH_2$ | Et | H | $CO_2Me$ | |
| 7-44 | 5-$CF_3$ | Me | $NH_2$ | Et | H | $SCH_2$(4-t-BuPh) | 180-181 |
| 7-45 | 5-$CF_3$ | Me | $NH_2$ | Et | H | $SO_2Me$ | |
| 7-46 | 5-$CF_3$ | Me | $NH_2$ | Et | H | $SO_2NHMe$ | 244-246 |
| 7-47 | 5-$CF_3$ | Me | $NH_2$ | Et | H | NHMe | 145-148 |
| 7-48 | 5-$CF_3$ | Me | $NH_2$ | Et | H | $NMe_2$ | NMR |
| 7-49 | 5-$CF_3$ | Me | $NH_2$ | i-Pr | H | $CO_2Me$ | |
| 7-50 | 5-$CF_3$ | Me | $NH_2$ | i-Pr | H | $SO_2Me$ | |
| 7-51 | 5-$CF_3$ | Me | $NH_2$ | i-Pr | H | $SO_2NHMe$ | |
| 7-52 | H | Me | Me | Me | H | $CO_2Me$ | |
| 7-53 | H | Me | Me | Me | H | $SO_2Me$ | |
| 7-54 | H | Me | Me | Me | H | $SO_2NHMe$ | |
| 7-55 | H | Me | Me | Et | H | $CO_2Me$ | |
| 7-56 | H | Me | Me | Et | H | $SO_2Me$ | |
| 7-57 | H | Me | Me | Et | H | $SO_2NHMe$ | |
| 7-58 | H | Me | Me | Et | H | NHMe | |
| 7-59 | H | Me | Me | i-Pr | H | $CO_2Me$ | |
| 7-60 | H | Me | Me | i-Pr | H | $SO_2Me$ | |

TABLE 7-3

| Compound No. | $R^1$ | $R^2$ | $R^3$ | $R^4$ | $R^5$ | Q | Physical property value |
|---|---|---|---|---|---|---|---|
| 7-61 | H | Me | Me | i-Pr | H | $SO_2NHMe$ | |
| 7-62 | 5-Me | Me | Me | Me | H | $CO_2Me$ | |
| 7-63 | 5-Me | Me | Me | Me | H | $SO_2Me$ | |
| 7-64 | 5-Me | Me | Me | Me | H | $SO_2NHMe$ | |

TABLE 7-3-continued

| Compound No. | $R^1$ | $R^2$ | $R^3$ | $R^4$ | $R^5$ | Q | Physical property value |
|---|---|---|---|---|---|---|---|
| 7-65 | 5-Me | Me | Me | Et | H | $CO_2Me$ | |
| 7-66 | 5-Me | Me | Me | Et | H | $SO_2Me$ | |
| 7-67 | 5-Me | Me | Me | Et | H | $SO_2NHMe$ | |
| 7-68 | 5-Me | Me | Me | i-Pr | H | $CO_2Me$ | |
| 7-69 | 5-Me | Me | Me | i-Pr | H | $SO_2Me$ | |
| 7-70 | 5-Me | Me | Me | i-Pr | H | $SO_2NHMe$ | |
| 7-71 | 5-OMe | Me | Me | Me | H | $CO_2Me$ | |
| 7-72 | 5-OMe | Me | Me | Me | H | $SO_2Me$ | |
| 7-73 | 5-OMe | Me | Me | Me | H | $SO_2NHMe$ | |
| 7-74 | 5-OMe | Me | Me | Et | H | $CO_2Me$ | |
| 7-75 | 5-OMe | Me | Me | Et | H | $SO_2Me$ | |
| 7-76 | 5-OMe | Me | Me | Et | H | $SO_2NHMe$ | |
| 7-77 | 5-OMe | Me | Me | i-Pr | H | $CO_2Me$ | |
| 7-78 | 5-OMe | Me | Me | i-Pr | H | $SO_2Me$ | |
| 7-79 | 5-OMe | Me | Me | i-Pr | H | $SO_2NHMe$ | |
| 7-80 | 5-$CHF_2$ | Me | Me | Me | H | $CO_2Me$ | |
| 7-81 | 5-$CHF_2$ | Me | Me | Me | H | $SO_2Me$ | |
| 7-82 | 5-$CHF_2$ | Me | Me | Me | H | $SO_2NHMe$ | |
| 7-83 | 5-$CHF_2$ | Me | Me | Et | H | $CO_2Me$ | |
| 7-84 | 5-$CHF_2$ | Me | Me | Et | H | $SO_2Me$ | |
| 7-85 | 5-$CHF_2$ | Me | Me | Et | H | $SO_2NHMe$ | |
| 7-86 | 5-$CHF_2$ | Me | Me | i-Pr | H | $CO_2Me$ | |
| 7-87 | 5-$CHF_2$ | Me | Me | i-Pr | H | $SO_2Me$ | |
| 7-88 | 5-$CHF_2$ | Me | Me | i-Pr | H | $SO_2NHMe$ | |
| 7-89 | 5-$CF_3$ | Me | Me | Me | H | $CO_2Me$ | |
| 7-90 | 5-$CF_3$ | Me | Me | Me | H | $SO_2Me$ | |

TABLE 7-4

Table 7 (Continued)

| Compound No. | $R^1$ | $R^2$ | $R^3$ | $R^4$ | $R^5$ | Q | Physical property value |
|---|---|---|---|---|---|---|---|
| 7-91 | 5-$CF_3$ | Me | Me | Me | H | $SO_2NHMe$ | |
| 7-92 | 5-$CF_3$ | Me | Me | Et | H | $CO_2Me$ | |
| 7-93 | 5-$CF_3$ | Me | Me | Et | H | $SO_2Me$ | |
| 7-94 | 5-$CF_3$ | Me | Me | Et | | $SO_2NHMe$ | |
| 7-95 | 5-$CF_3$ | Me | Me | Et | H | NHMe | |
| 7-96 | 5-$CF_3$ | Me | Me | i-Pr | H | $CO_2Me$ | |
| 7-97 | 5-$CF_3$ | Me | Me | i-Pr | H | $SO_2Me$ | |
| 7-98 | 5-$CF_3$ | Me | Me | i-Pr | H | $SO_2NHMe$ | |
| 7-99 | 5-$SCF_3$ | Me | H | Et | H | $CO_2Me$ | 134-135 |
| 7-100 | H | Me | $NH_2$ | Me | H | 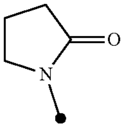 | |
| 7-101 | H | Me | $NH_2$ | Et | H | 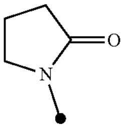 | |
| 7-102 | H | Me | $NH_2$ | i-Pr | H | 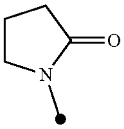 | |

TABLE 7-4-continued

Table 7 (Continued)

| Compound No. | $R^1$ | $R^2$ | $R^3$ | $R^4$ | $R^5$ | Q | Physical property value |
|---|---|---|---|---|---|---|---|
| 7-103 | 5-Me | Me | $NH_2$ | Me | H | 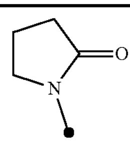 | |
| 7-104 | 5-Me | Me | $NH_2$ | Et | H | 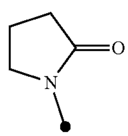 | |
| 7-105 | 5-Me | Me | $NH_2$ | i-Pr | H | 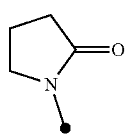 | |
| 7-106 | 5-OMe | Me | $NH_2$ | Me | H | 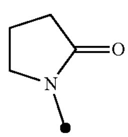 | |
| 7-107 | 5-OMe | Me | $NH_2$ | Et | H | 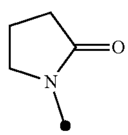 | |
| 7-108 | 5-OMe | Me | $NH_2$ | i-Pr | H | 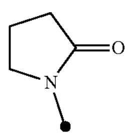 | |
| 7-109 | 5-$CHF_2$ | Me | $NH_2$ | Me | H | 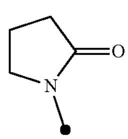 | |
| 7-110 | 5-$CHF_2$ | Me | $NH_2$ | Et | H | 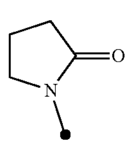 | |

The black solid circle in the structural formula represents a binding position.

TABLE 7-5

Table 7 (Continued)

| Compound No. | $R^1$ | $R^2$ | $R^3$ | $R^4$ | $R^5$ | Q | Physical property value |
|---|---|---|---|---|---|---|---|
| 7-111 | 5-$CHF_2$ | Me | $NH_2$ | i-Pr | H | 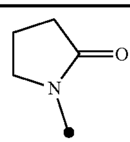 | |

TABLE 7-5-continued

| Table 7 (Continued) | | | | | | | |
|---|---|---|---|---|---|---|---|
| Compound No. | $R^1$ | $R^2$ | $R^3$ | $R^4$ | $R^5$ | Q | Physical property value |
| 7-112 | 5-$CF_3$ | Me | $NH_2$ | Me | H | 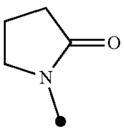 | |
| 7-113 | 5-$CF_3$ | Me | $NH_2$ | Et | H | 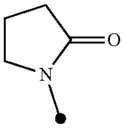 | |
| 7-114 | 5-$CF_3$ | Me | $NH_2$ | i-Pr | H | 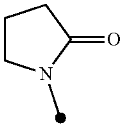 | |
| 7-115 | H | Me | $NH_2$ | Me | H | 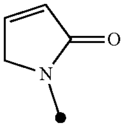 | |
| 7-116 | H | Me | $NH_2$ | Et | H | 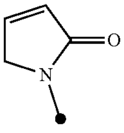 | |
| 7-117 | H | Me | $NH_2$ | i-Pr | H | 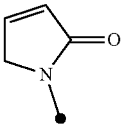 | |
| 7-118 | 5-Me | Me | $NH_2$ | Me | H | 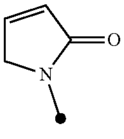 | |
| 7-119 | 5-Me | Me | $NH_2$ | Et | H | 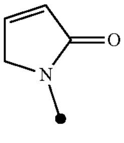 | |
| 7-120 | 5-Me | Me | $NH_2$ | i-Pr | H | 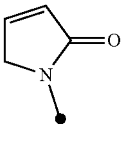 | |
| 7-121 | 5-OMe | Me | $NH_2$ | Me | H | 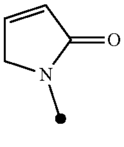 | |
| 7-122 | 5-OMe | Me | $NH_2$ | Et | H | 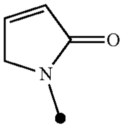 | |
| 7-123 | 5-OMe | Me | $NH_2$ | i-Pr | H | 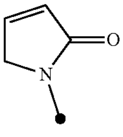 | |
| 7-124 | 5-$CHF_2$ | Me | $NH_2$ | Me | H | 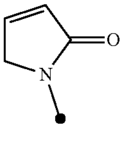 | |
| 7-125 | 5-$CHF_2$ | Me | $NH_2$ | Et | H | 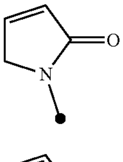 | |
| 7-126 | 5-$CHF_2$ | Me | $NH_2$ | i-Pr | H | 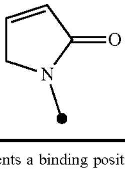 | |

The black solid circle in the structural formula represents a binding position.

TABLE 7-6

| Table 7 (Continued) | | | | | | | |
|---|---|---|---|---|---|---|---|
| Compound No. | $R^1$ | $R^2$ | $R^3$ | $R^4$ | $R^5$ | Q | Physical property value |
| 7-127 | 5-$CF_3$ | Me | $NH_2$ | Me | H | 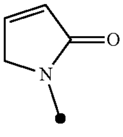 | |
| 7-128 | 5-$CF_3$ | Me | $NH_2$ | Et | H | 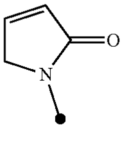 | |
| 7-129 | 5-$CF_3$ | Me | $NH_2$ | i-Pr | H | 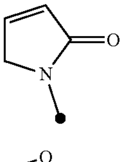 | |
| 7-130 | H | Me | $NH_2$ | Me | H | 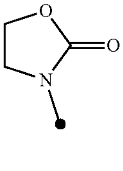 | |

TABLE 7-6-continued

Table 7 (Continued)

| Compound No. | $R^1$ | $R^2$ | $R^3$ | $R^4$ | $R^5$ | Q | Physical property value |
|---|---|---|---|---|---|---|---|
| 7-131 | H | Me | $NH_2$ | Et | H | 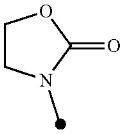 | |
| 7-132 | H | Me | $NH_2$ | i-Pr | H | 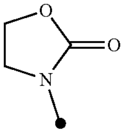 | |
| 7-133 | 5-Me | Me | $NH_2$ | Me | H | 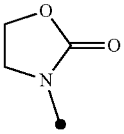 | |
| 7-134 | 5-Me | Me | $NH_2$ | Et | H | 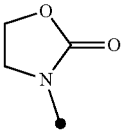 | |
| 7-135 | 5-Me | Me | $NH_2$ | i-Pr | H | 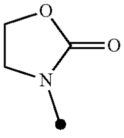 | |
| 7-136 | 5-OMe | Me | $NH_2$ | Me | H | 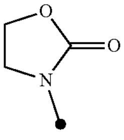 | |
| 7-137 | 5-OMe | Me | $NH_2$ | Et | H | 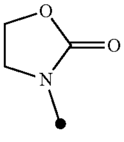 | |
| 7-138 | 5-OMe | Me | $NH_2$ | i-Pr | H | 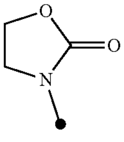 | |
| 7-139 | 5-$CHF_2$ | Me | $NH_2$ | Me | H | 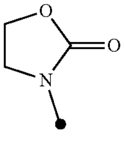 | |
| 7-140 | 5-$CHF_2$ | Me | $NH_2$ | Et | H | 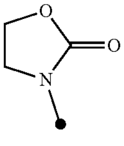 | |
| 7-141 | 5-$CHF_2$ | Me | $NH_2$ | i-Pr | H | 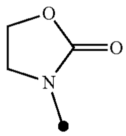 | |
| 7-142 | 5-$CF_3$ | Me | $NH_2$ | Me | H | 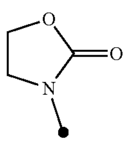 | |

The black solid circle in the structural formula represents a binding position.

TABLE 7-7

Table 7 (Continued)

| Compound No. | $R^1$ | $R^2$ | $R^3$ | $R^4$ | $R^5$ | Q | Physical property value |
|---|---|---|---|---|---|---|---|
| 7-143 | 5-$CF_3$ | Me | $NH_2$ | Et | H | 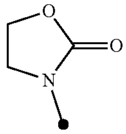 | |
| 7-144 | 5-$CF_3$ | Me | $NH_2$ | i-Pr | H | 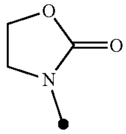 | |
| 7-145 | H | Me | $NH_2$ | Me | H | 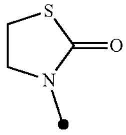 | |
| 7-146 | H | Me | $NH_2$ | Et | H | 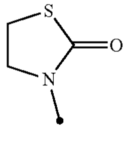 | |
| 7-147 | H | Me | $NH_2$ | i-Pr | H | 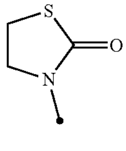 | |
| 7-148 | 5-Me | Me | $NH_2$ | Me | H | 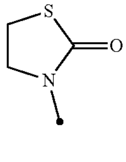 | |

TABLE 7-7-continued

| Table 7 (Continued) | | | | | | | |
|---|---|---|---|---|---|---|---|
| Compound No. | $R^1$ | $R^2$ | $R^3$ | $R^4$ | $R^5$ | Q | Physical property value |
| 7-149 | 5-Me | Me | $NH_2$ | Et | H | 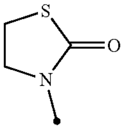 | |
| 7-150 | 5-Me | Me | $NH_2$ | i-Pr | H | 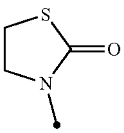 | |
| 7-151 | 5-OMe | Me | $NH_2$ | Me | H | 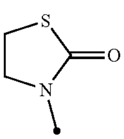 | |
| 7-152 | 5-OMe | Me | $NH_2$ | Et | H | 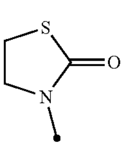 | |
| 7-153 | 5-OMe | Me | $NH_2$ | i-Pr | H | 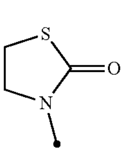 | |
| 7-154 | 5-$CHF_2$ | Me | $NH_2$ | Me | H | 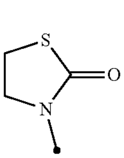 | |
| 7-155 | 5-$CHF_2$ | Me | $NH_2$ | Et | H | 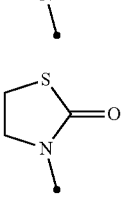 | |
| 7-156 | 5-$CHF_2$ | Me | $NH_2$ | i-Pr | H | 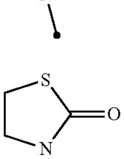 | |
| 7-157 | 5-$CF_3$ | Me | $NH_2$ | Me | H | 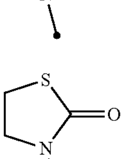 | |
| 7-158 | 5-$CF_3$ | Me | $NH_2$ | Et | H | 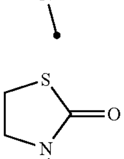 | |

The black solid circle in the structural formula represents a binding position.

TABLE 7-8

| Table 7 (Continued) | | | | | | | |
|---|---|---|---|---|---|---|---|
| Compound No. | $R^1$ | $R^2$ | $R^3$ | $R^4$ | $R^5$ | Q | Physical property value |
| 7-159 | 5-$CF_3$ | Me | $NH_2$ | i-Pr | H | 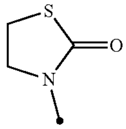 | |
| 7-160 | H | Me | $NH_2$ | Me | H | 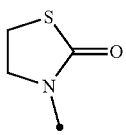 | |
| 7-161 | H | Me | $NH_2$ | Et | H | 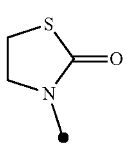 | |
| 7-162 | H | Me | $NH_2$ | i-Pr | H | 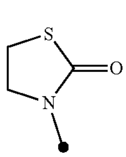 | |
| 7-163 | 5-Me | Me | $NH_2$ | Me | H | 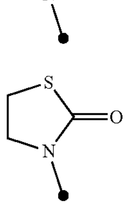 | |
| 7-164 | 5-Me | Me | $NH_2$ | Et | H | 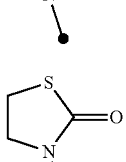 | |
| 7-165 | 5-Me | Me | $NH_2$ | i-Pr | H | 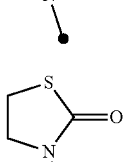 | |
| 7-166 | 5-OMe | Me | $NH_2$ | Me | H | 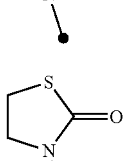 | |
| 7-167 | 5-OMe | Me | $NH_2$ | Et | H | 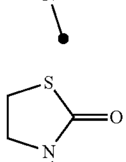 | |
| 7-168 | 5-OMe | Me | $NH_2$ | i-Pr | H | 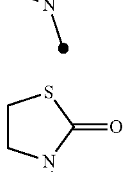 | |

TABLE 7-8-continued

Table 7 (Continued)

| Compound No. | $R^1$ | $R^2$ | $R^3$ | $R^4$ | $R^5$ | Q | Physical property value |
|---|---|---|---|---|---|---|---|
| 7-169 | 5-$CHF_2$ | Me | $NH_2$ | Me | H | 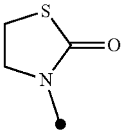 | |
| 7-170 | 5-$CHF_2$ | Me | $NH_2$ | Et | H | 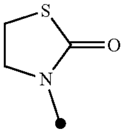 | |
| 7-171 | 5-$CHF_2$ | Me | $NH_2$ | i-Pr | H | 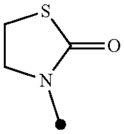 | |
| 7-172 | 5-$CF_3$ | Me | $NH_2$ | Me | H | 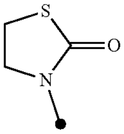 | |
| 7-173 | 5-$CF_3$ | Me | $NH_2$ | Et | H | 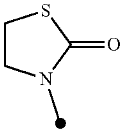 | |
| 7-174 | 5-$CF_3$ | Me | $NH_2$ | i-Pr | H | 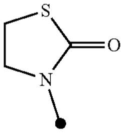 | |

The black solid circle in the structural formula represents a binding position.

TABLE 7-9

Table 7 (Continued)

| Compound No. | $R^1$ | $R^2$ | $R^3$ | $R^4$ | $R^5$ | Q | Physical property value |
|---|---|---|---|---|---|---|---|
| 7-175 | H | Me | $NH_2$ | Me | H | 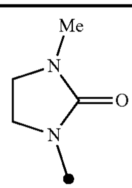 | |
| 7-176 | H | Me | $NH_2$ | Et | H | 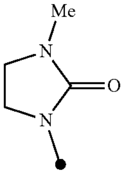 | |

TABLE 7-9-continued

Table 7 (Continued)

| Compound No. | $R^1$ | $R^2$ | $R^3$ | $R^4$ | $R^5$ | Q | Physical property value |
|---|---|---|---|---|---|---|---|
| 7-177 | H | Me | $NH_2$ | i-Pr | H | 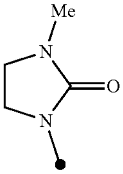 | |
| 7-178 | 5-Me | Me | $NH_2$ | Me | H | 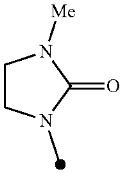 | |
| 7-179 | 5-Me | Me | $NH_2$ | E | H | 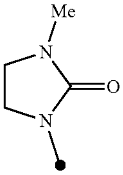 | |
| 7-180 | 5-Me | Me | $NH_2$ | i-Pr | H | 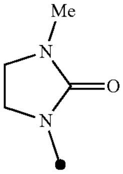 | |
| 7-181 | 5-OMe | Me | $NH_2$ | Me | H | 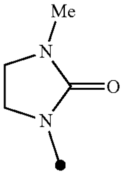 | |
| 7-182 | 5-OMe | Me | $NH_2$ | Et | H | 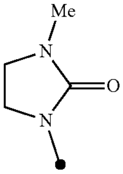 | |
| 7-183 | 5-OMe | Me | $NH_2$ | i-Pr | H | 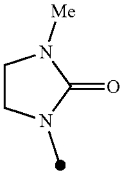 | |
| 7-184 | 5-$CHF_2$ | Me | $NH_2$ | Me | H | 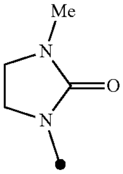 | |

The black solid circle in the structural formula represents a binding position.

TABLE 7-10

Table 7 (Continued)

| Compound No. | $R^1$ | $R^2$ | $R^3$ | $R^4$ | $R^5$ | Q | Physical property value |
|---|---|---|---|---|---|---|---|
| 7-185 | 5-$CHF_2$ | Me | $NH_2$ | Et | H | 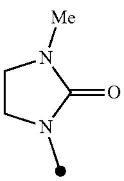 | |
| 7-186 | 5-$CHF_2$ | Me | $NH_2$ | i-Pr | H | 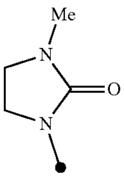 | |
| 7-187 | 5-$CF_3$ | Me | $NH_2$ | Me | H | 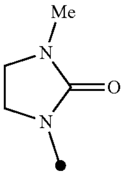 | |
| 7-188 | 5-$CF_3$ | Me | $NH_2$ | Et | H | 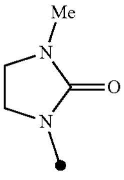 | |
| 7-189 | 5-$CF_3$ | Me | $NH_2$ | i-Pr | H | 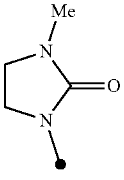 | |
| 7-190 | H | Me | $NH_2$ | Me | H | 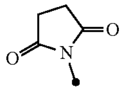 | |
| 7-191 | H | Me | $NH_2$ | Et | H | 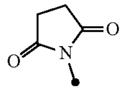 | |
| 7-192 | H | Me | $NH_2$ | i-Pr | H | 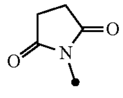 | |
| 7-193 | 5-Me | Me | $NH_2$ | Me | H | 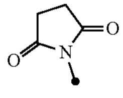 | |
| 7-194 | 5-Me | Me | $NH_2$ | Et | H | 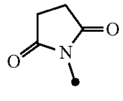 | |

TABLE 7-10-continued

Table 7 (Continued)

| Compound No. | $R^1$ | $R^2$ | $R^3$ | $R^4$ | $R^5$ | Q | Physical property value |
|---|---|---|---|---|---|---|---|
| 7-195 | 5-Me | Me | $NH_2$ | i-Pr | H | 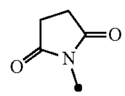 | |
| 7-196 | 5-OMe | Me | $NH_2$ | Me | H | 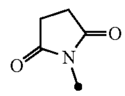 | |
| 7-197 | 5-OMe | Me | $NH_2$ | Et | H | 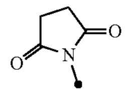 | |

The black solid circle in the structural formula represents a binding position.

TABLE 7-11

Table 7 (Continued)

| Compound No. | $R^1$ | $R^2$ | $R^3$ | $R^4$ | $R^5$ | Q | Physical property value |
|---|---|---|---|---|---|---|---|
| 7-198 | 5-OMe | Me | $NH_2$ | i-Pr | H | 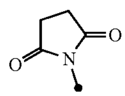 | |
| 7-199 | 5-$CHF_2$ | Me | $NH_2$ | Me | H | 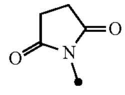 | |
| 7-200 | 5-$CHF_2$ | Me | $NH_2$ | Et | H | 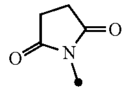 | |
| 7-201 | 5-$CHF_2$ | Me | $NH_2$ | i-Pr | H | 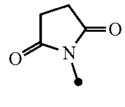 | |
| 7-202 | 5-$CF_3$ | Me | $NH_2$ | Me | H | 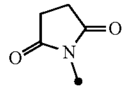 | |
| 7-203 | 5-$CF_3$ | Me | $NH_2$ | Et | H | 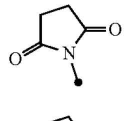 | |
| 7-204 | 5-$CF_3$ | Me | $NH_2$ | i-Pr | H | 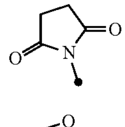 | |
| 7-205 | H | Me | $NH_2$ | Me | H | 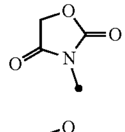 | |
| 7-206 | H | Me | $NH_2$ | Et | H | 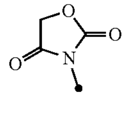 | |

TABLE 7-11-continued

| Table 7 (Continued) | | | | | | | |
|---|---|---|---|---|---|---|---|
| Compound No. | $R^1$ | $R^2$ | $R^3$ | $R^4$ | $R^5$ | Q | Physical property value |
| 7-207 | H | Me | $NH_2$ | i-Pr | H | 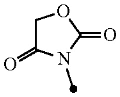 | |
| 7-208 | 5-Me | Me | $NH_2$ | Me | H | 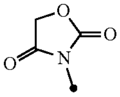 | |
| 7-209 | 5-Me | Me | $NH_2$ | Et | H | 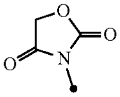 | |
| 7-210 | 5-Me | Me | $NH_2$ | i-Pr | H | 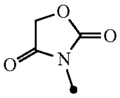 | |
| 7-211 | 5-OMe | Me | $NH_2$ | Me | H | 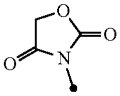 | |
| 7-212 | 5-OMe | Me | $NH_2$ | Et | H | 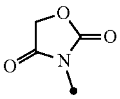 | |
| 7-213 | 5-OMe | Me | $NH_2$ | i-Pr | H | 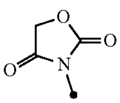 | |

The black solid circle in the structural formula represents a binding position.

TABLE 7-12

| Table 7 (Continued) | | | | | | | |
|---|---|---|---|---|---|---|---|
| Compound No. | $R^1$ | $R^2$ | $R^3$ | $R^4$ | $R^5$ | Q | Physical property value |
| 7-214 | 5-$CHF_2$ | Me | $NH_2$ | Me | H | 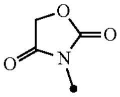 | |
| 7-215 | 5-$CHF_2$ | Me | $NH_2$ | Et | H | 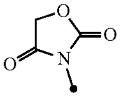 | |
| 7-216 | 5-$CHF_2$ | Me | $NH_2$ | i-Pr | H | 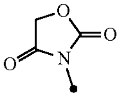 | |
| 7-217 | 5-$CF_3$ | Me | $NH_2$ | Me | H | 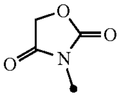 | |

TABLE 7-12-continued

| Table 7 (Continued) | | | | | | | |
|---|---|---|---|---|---|---|---|
| Compound No. | $R^1$ | $R^2$ | $R^3$ | $R^4$ | $R^5$ | Q | Physical property value |
| 7-218 | 5-$CF_3$ | Me | $NH_2$ | Et | H | 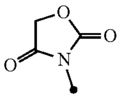 | |
| 7-219 | 5-$CF_3$ | Me | $NH_2$ | i-Pr | H | 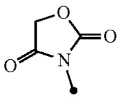 | |

The black solid circle in the structural formula represents a binding position.

[Chem. 34]

(1h)

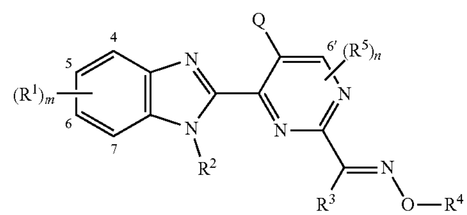

The position numbers in the table are the numbers designated in the general formula (1h).

TABLE 8-1

| Compound No. | $R^1$ | $R^2$ | $R^3$ | $R^4$ | $R^5$ | Q | Physical property value |
|---|---|---|---|---|---|---|---|
| 8-1 | H | Me | $NH_2$ | Me | H | $CO_2Me$ | |
| 8-2 | H | Me | $NH_2$ | Me | H | $SO_2Me$ | |
| 8-3 | H | Me | $NH_2$ | Me | H | $SO_2NHMe$ | |
| 8-4 | H | Me | $NH_2$ | Et | H | $CO_2Me$ | |
| 8-5 | H | Me | $NH_2$ | Et | H | $SO_2Me$ | |
| 8-6 | H | Me | $NH_2$ | Et | H | $SO_2NHMe$ | 222-223 |
| 8-7 | H | Me | $NH_2$ | i-Pr | H | $CO_2Me$ | |
| 8-8 | H | Me | $NH_2$ | i-Pr | H | $SO_2Me$ | |
| 8-9 | H | Me | $NH_2$ | i-Pr | H | $SO_2NHMe$ | 204-205 |
| 8-10 | 5-Me | Me | $NH_2$ | Me | H | $CO_2Me$ | |
| 8-11 | 5-Me | Me | $NH_2$ | Me | H | $SO_2Me$ | |
| 8-12 | 5-Me | Me | $NH_2$ | Me | H | $SO_2NHMe$ | |
| 8-13 | 5-Me | Me | $NH_2$ | Et | H | $CO_2Me$ | |
| 8-14 | 5-Me | Me | $NH_2$ | Et | H | $SO_2Me$ | |
| 8-15 | 5-Me | Me | $NH_2$ | Et | H | $SO_2NHMe$ | |
| 8-16 | 5-Me | Me | $NH_2$ | i-Pr | H | $CO_2Me$ | |
| 8-17 | 5-Me | Me | $NH_2$ | i-Pr | H | $SO_2Me$ | |
| 8-18 | 5-Me | Me | $NH_2$ | i-Pr | H | $SO_2NHMe$ | |
| 8-19 | 5-OMe | Me | $NH_2$ | Me | H | $CO_2Me$ | |
| 8-20 | 5-OMe | Me | $NH_2$ | Me | H | $SO_2Me$ | |
| 8-21 | 5-OMe | Me | $NH_2$ | Me | H | $SO_2NHMe$ | |
| 8-22 | 5-OMe | Me | $NH_2$ | Et | H | $CO_2Me$ | |
| 8-23 | 5-OMe | Me | $NH_2$ | Et | H | $SO_2Me$ | |
| 8-24 | 5-OMe | Me | $NH_2$ | Et | H | $SO_2NHMe$ | |
| 8-25 | 5-OMe | Me | $NH_2$ | i-Pr | H | $CO_2Me$ | |
| 8-26 | 5-OMe | Me | $NH_2$ | i-Pr | H | $SO_2Me$ | |
| 8-27 | 5-OMe | Me | $NH_2$ | i-Pr | H | $SO_2NHMe$ | |
| 8-28 | 5-$CHF_2$ | Me | $NH_2$ | Me | H | $CO_2Me$ | |
| 8-29 | 5-$CHF_2$ | Me | $NH_2$ | Me | H | $SO_2Me$ | |
| 8-30 | 5-$CHF_2$ | Me | $NH_2$ | Me | H | $SO_2NHMe$ | |

TABLE 8-2

| Compound No. | $R^1$ | $R^2$ | $R^3$ | $R^4$ | $R^5$ | Q | Physical property value |
|---|---|---|---|---|---|---|---|
| 8-31 | 5-$CHF_2$ | Me | $NH_2$ | Et | H | $CO_2Me$ | |
| 8-32 | 5-$CHF_2$ | Me | $NH_2$ | Et | H | $SO_2Me$ | |
| 8-33 | 5-$CHF_2$ | Me | $NH_2$ | Et | H | $SO_2NHMe$ | |
| 8-34 | 5-$CHF_2$ | Me | $NH_2$ | i-Pr | H | $CO_2Me$ | |
| 8-35 | 5-$CHF_2$ | Me | $NH_2$ | i-Pr | H | $SO_2Me$ | |
| 8-36 | 5-$CHF_2$ | Me | $NH_2$ | i-Pr | H | $SO_2NHMe$ | |
| 8-37 | 5-$CF_3$ | Me | $NH_2$ | Me | H | $CO_2Me$ | |
| 8-38 | 5-$CF_3$ | Me | $NH_2$ | Me | H | $SO_2Me$ | |
| 8-39 | 5-$CF_3$ | Me | $NH_2$ | Me | H | $SO_2NHMe$ | |
| 8-40 | 5-$CF_3$ | Me | $NH_2$ | Et | H | $CO_2Me$ | |
| 8-41 | 5-$CF_3$ | Me | $NH_2$ | Et | H | $SO_2Me$ | |
| 8-42 | 5-$CF_3$ | Me | $NH_2$ | Et | H | $SO_2NHMe$ | 198-199 |
| 8-43 | 5-$CF_3$ | Me | $NH_2$ | i-Pr | H | $CO_2Me$ | |
| 8-44 | 5-$CF_3$ | Me | $NH_2$ | i-Pr | H | $CO_2Et$ | 134-135 |
| 8-45 | 5-$CF_3$ | Me | $NH_2$ | i-Pr | H | $SO_2Me$ | |
| 8-46 | 5-$CF_3$ | Me | $NH_2$ | i-Pr | H | $SO_2NHMe$ | |
| 8-47 | H | Me | Me | Me | H | $CO_2Me$ | |
| 8-48 | H | Me | Me | Me | H | $SO_2Me$ | |
| 8-49 | H | Me | Me | Me | H | $SO_2NHMe$ | |
| 8-50 | H | Me | Me | Et | H | $CO_2Me$ | |
| 8-51 | H | Me | Me | Et | H | $SO_2Me$ | |
| 8-52 | H | Me | Me | Et | H | $SO_2NHMe$ | |
| 8-53 | H | Me | Me | i-Pr | H | $CO_2Me$ | |
| 8-54 | H | Me | Me | i-Pr | H | $SO_2Me$ | |
| 8-55 | H | Me | Me | i-Pr | H | $SO_2NHMe$ | |
| 8-56 | 5-Me | Me | Me | Me | H | $CO_2Me$ | |
| 8-57 | 5-Me | Me | Me | Me | H | $SO_2Me$ | |
| 8-58 | 5-Me | Me | Me | Me | H | $SO_2NHMe$ | |
| 8-59 | 5-Me | Me | Me | Et | H | $CO_2Me$ | |
| 8-60 | 5-Me | Me | Me | Et | H | $SO_2Me$ | |

TABLE 8-3

| Compound No. | $R^1$ | $R^2$ | $R^3$ | $R^4$ | $R^5$ | Q | Physical property value |
|---|---|---|---|---|---|---|---|
| 8-61 | 5-Me | Me | Me | Et | H | $SO_2NHMe$ | |
| 8-62 | 5-Me | Me | Me | i-Pr | H | $CO_2Me$ | |
| 8-63 | 5-Me | Me | Me | i-Pr | H | $SO_2Me$ | |
| 8-64 | 5-Me | Me | Me | i-Pr | H | $SO_2NHMe$ | |
| 8-65 | 5-OMe | Me | Me | Me | H | $CO_2Me$ | |
| 8-66 | 5-OMe | Me | Me | Me | H | $SO_2Me$ | |
| 8-67 | 5-OMe | Me | Me | Me | H | $SO_2NHMe$ | |
| 8-68 | 5-OMe | Me | Me | Et | H | $CO_2Me$ | |
| 8-69 | 5-OMe | Me | Me | Et | H | $SO_2Me$ | |
| 8-70 | 5-OMe | Me | Me | Et | H | $SO_2NHMe$ | |
| 8-71 | 5-OMe | Me | Me | i-Pr | H | $CO_2Me$ | |
| 8-72 | 5-OMe | Me | Me | i-Pr | H | $SO_2Me$ | |
| 8-73 | 5-OMe | Me | Me | i-Pr | H | $SO_2NHMe$ | |
| 8-74 | 5-$CHF_2$ | Me | Me | Me | H | $CO_2Me$ | |
| 8-75 | 5-$CHF_2$ | Me | Me | Me | H | $SO_2Me$ | |
| 8-76 | 5-$CHF_2$ | Me | Me | Me | H | $SO_2NHMe$ | |
| 8-77 | 5-$CHF_2$ | Me | Me | Et | H | $CO_2Me$ | |
| 8-78 | 5-$CHF_2$ | Me | Me | Et | H | $SO_2Me$ | |
| 8-79 | 5-$CHF_2$ | Me | Me | Et | H | $SO_2NHMe$ | |
| 8-80 | 5-CHFz | Me | Me | i-Pr | H | $CO_2Me$ | |
| 8-81 | 5-$CHF_2$ | Me | Me | i-Pr | H | $SO_2Me$ | |
| 8-82 | 5-$CHF_2$ | Me | Me | i-Pr | H | $SO_2NHMe$ | |
| 8-83 | 5-$CF_3$ | Me | Me | Me | H | $CO_2Me$ | |
| 8-84 | 5-$CF_3$ | Me | Me | Me | H | $SO_2Me$ | |
| 8-85 | 5-$CF_3$ | Me | Me | Me | H | $SO_2NHMe$ | |
| 8-86 | 5-$CF_3$ | Me | Me | Et | H | $CO_2Me$ | |
| 8-87 | 5-$CF_3$ | Me | Me | Et | H | $SO_2Me$ | |
| 8-88 | 5-$CF_3$ | Me | Me | Et | H | $SO_2NHMe$ | |
| 8-89 | 5-$CF_3$ | Me | Me | i-Pr | H | $CO_2Me$ | |
| 8-90 | 5-$CF_3$ | Me | Me | i-Pr | H | $SO_2Me$ | |

TABLE 8-4

| Compound No. | $R^1$ | $R^2$ | $R^3$ | $R^4$ | $R^5$ | Q | Physical property value |
|---|---|---|---|---|---|---|---|
| 8-91 | 5-$CF_3$ | Me | Me | i-Pr | H | $SO_2NHMe$ | |
| 8-92 | H | Me | $NH_2$ | Me | 6'-Me | $CO_2Me$ | |
| 8-93 | H | Me | $NH_2$ | Me | 6'-Me | $SO_2Me$ | |
| 8-94 | H | Me | $NH_2$ | Me | 6'-Me | $SO_2NHMe$ | |
| 8-95 | H | Me | $NH_2$ | Et | 6'-Me | $CO_2Me$ | |
| 8-96 | H | Me | $NH_2$ | Et | 6'-Me | $SO_2Me$ | |
| 8-97 | H | Me | $NH_2$ | Et | 6'-Me | $SO_2NHMe$ | |
| 8-98 | H | Me | $NH_2$ | i-Pr | 6'-Me | $CO_2Me$ | |
| 8-99 | H | Me | $NH_2$ | i-Pr | 6'-Me | $SO_2Me$ | |
| 8-100 | H | Me | $NH_2$ | i-Pr | 6'-Me | $SO_2NHMe$ | |
| 8-101 | 5-Me | Me | $NH_2$ | Me | 6'-Me | $CO_2Me$ | |
| 8-102 | 5-Me | Me | $NH_2$ | Me | 6'-Me | $SO_2Me$ | |
| 8-103 | 5-Me | Me | $NH_2$ | Me | 6'-Me | $SO_2NHMe$ | |
| 8-104 | 5-Me | Me | $NH_2$ | Et | 6'-Me | $CO_2Me$ | |
| 8-105 | 5-Me | Me | $NH_2$ | Et | 6'-Me | $SO_2Me$ | |
| 8-106 | 5-Me | Me | $NH_2$ | Et | 6'-Me | $SO_2NHMe$ | |
| 8-107 | 5-Me | Me | $NH_2$ | i-Pr | 6'-Me | $CO_2Me$ | |
| 8-108 | 5-Me | Me | $NH_2$ | i-Pr | 6'-Me | $SO_2Me$ | |
| 8-109 | 5-Me | Me | $NH_2$ | i-Pr | 6'-Me | $SO_2NHMe$ | |
| 8-110 | 5-OMe | Me | $NH_2$ | Me | 6'-Me | $CO_2Me$ | |
| 8-111 | 5-OMe | Me | $NH_2$ | Me | 6'-Me | $SO_2Me$ | |
| 8-112 | 5-OMe | Me | $NH_2$ | Me | 6'-Me | $SO_2NHMe$ | |
| 8-113 | 5-OMe | Me | $NH_2$ | Et | 6'-Me | $CO_2Me$ | |
| 8-114 | 5-OMe | Me | $NH_2$ | Et | 6'-Me | $SO_2Me$ | |
| 8-115 | 5-OMe | Me | $NH_2$ | Et | 6'-Me | $SO_2NHMe$ | |
| 8-116 | 5-OMe | Me | $NH_2$ | i-Pr | 6'-Me | $CO_2Me$ | |
| 8-117 | 5-OMe | Me | $NH_2$ | i-Pr | 6'-Me | $SO_2Me$ | |
| 8-118 | 5-OMe | Me | $NH_2$ | i-Pr | 6'-Me | $SO_2NHMe$ | |
| 8-119 | 5-$CHF_2$ | Me | $NH_2$ | Me | 6'-Me | $CO_2Me$ | |
| 8-120 | 5-$CHF_2$ | Me | $NH_2$ | Me | 6'-Me | $SO_2Me$ | |

TABLE 8-5

| Compound No. | $R^1$ | $R^2$ | $R^3$ | $R^4$ | $R^5$ | Q | Physical property value |
|---|---|---|---|---|---|---|---|
| 8-121 | 5-$CHF_2$ | Me | $NH_2$ | Me | 6'-Me | $SO_2NHMe$ | |
| 8-122 | 5-$CHF_2$ | Me | $NH_2$ | Et | 6'-Me | $CO_2Me$ | |
| 8-123 | 5-$CHF_2$ | Me | $NH_2$ | Et | 6'-Me | $SO_2Me$ | |
| 8-124 | 5-$CHF_2$ | Me | $NH_2$ | Et | 6'-Me | $SO_2NHMe$ | |
| 8-125 | 5-$CHF_2$ | Me | $NH_2$ | i-Pr | 6'-Me | $CO_2Me$ | |
| 8-126 | 5-$CHF_2$ | Me | $NH_2$ | i-Pr | 6'-Me | $SO_2Me$ | |
| 8-127 | 5-$CHF_2$ | Me | $NH_2$ | i-Pr | 6'-Me | $SO_2NHMe$ | |
| 8-128 | 5-$CF_3$ | Me | $NH_2$ | Me | 6'-Me | $CO_2Me$ | |
| 8-129 | 5-$CF_3$ | Me | $NH_2$ | Me | 6'-Me | $SO_2Me$ | |
| 8-130 | 5-$CF_3$ | Me | $NH_2$ | Me | 6'-Me | $SO_2NHMe$ | |
| 8-131 | 5-$CF_3$ | Me | $NH_2$ | Et | 6'-Me | $CO_2Me$ | |
| 8-132 | 5-$CF_3$ | Me | $NH_2$ | Et | 6'-Me | $SO_2Me$ | |
| 8-133 | 5-$CF_3$ | Me | $NH_2$ | Et | 6'-Me | $SO_2NHMe$ | |
| 8-134 | 5-$CF_3$ | Me | $NH_2$ | i-Pr | 6'-Me | $CO_2Me$ | |
| 8-135 | 5-$CF_3$ | Me | $NH_2$ | i-Pr | 6'-Me | $SO_2Me$ | |
| 8-136 | 5-$CF_3$ | Me | $NH_2$ | i-Pr | 6'-Me | $SO_2NHMe$ | |
| 8-137 | H | Me | Me | Me | 6'-Me | $CO_2Me$ | |
| 8-138 | H | Me | Me | Me | 6'-Me | $SO_2Me$ | |
| 8-139 | H | Me | Me | Me | 6'-Me | $SO_2NHMe$ | |
| 8-140 | H | Me | Me | Et | 6'-Me | $CO_2Me$ | |
| 8-141 | H | Me | Me | Et | 6'-Me | $SO_2Me$ | |
| 8-142 | H | Me | Me | Et | 6'-Me | $SO_2NHMe$ | |
| 8-143 | H | Me | Me | i-Pr | 6'-Me | $CO_2Me$ | |
| 8-144 | H | Me | Me | i-Pr | 6'-Me | $SO_2Me$ | |
| 8-145 | H | Me | Me | i-Pr | 6'-Me | $SO_2NHMe$ | |
| 8-146 | 5-Me | Me | Me | Me | 6'-Me | $CO_2Me$ | |
| 8-147 | 5-Me | Me | Me | Me | 6'-Me | $SO_2Me$ | |
| 8-148 | 5-Me | Me | Me | Me | 6'-Me | $SO_2NHMe$ | |
| 8-149 | 5-Me | Me | Me | Et | 6'-Me | $CO_2Me$ | |
| 8-150 | 5-Me | Me | Me | Et | 6'-Me | $SO_2Me$ | |

TABLE 8-6

| Compound No. | $R^1$ | $R^2$ | $R^3$ | $R^4$ | $R^5$ | Q | Physical property value |
|---|---|---|---|---|---|---|---|
| 8-151 | 5-Me | Me | Me | Et | 6'-Me | $SO_2NHMe$ | |
| 8-152 | 5-Me | Me | Me | i-Pr | 6'-Me | $CO_2Me$ | |
| 8-153 | 5-Me | Me | Me | i-Pr | 6'-Me | $SO_2Me$ | |
| 8-154 | 5-Me | Me | Me | i-Pr | 6'-Me | $SO_2NHMe$ | |
| 8-155 | 5-OMe | Me | Me | Me | 6'-Me | $CO_2Me$ | |
| 8-156 | 5-OMe | Me | Me | Me | 6'-Me | $SO_2Me$ | |
| 8-157 | 5-OMe | Me | Me | Me | 6'-Me | $SO_2NHMe$ | |
| 8-158 | 5-OMe | Me | Me | Et | 6'-Me | $CO_2Me$ | |
| 8-159 | 5-OMe | Me | Me | Et | 6'-Me | $SO_2Me$ | |
| 8-160 | 5-OMe | Me | Me | Et | 6'-Me | $SO_2NHMe$ | |
| 8-161 | 5-OMe | Me | Me | i-Pr | 6'-Me | $CO_2Me$ | |
| 8-162 | 5-OMe | Me | Me | i-Pr | 6'-Me | $SO_2Me$ | |
| 8-163 | 5-OMe | Me | Me | i-Pr | 6'-Me | $SO_2NHMe$ | |
| 8-164 | 5-$CHF_2$ | Me | Me | Me | 6'-Me | $CO_2Me$ | |
| 8-165 | 5-$CHF_2$ | Me | Me | Me | 6'-Me | $SO_2Me$ | |
| 8-166 | 5-$CHF_2$ | Me | Me | Me | 6'-Me | $SO_2NHMe$ | |
| 8-167 | 5-$CHF_2$ | Me | Me | Et | 6'-Me | $CO_2Me$ | |
| 8-168 | 5-$CHF_2$ | Me | Me | Et | 6'-Me | $SO_2Me$ | |
| 8-169 | 5-$CHF_2$ | Me | Me | Et | 6'-Me | $SO_2NHMe$ | |
| 8-170 | 5-$CHF_2$ | Me | Me | i-Pr | 6'-Me | $CO_2Me$ | |
| 8-171 | 5-$CHF_2$ | Me | Me | i-Pr | 6'-Me | $SO_2Me$ | |
| 8-172 | 5-$CHF_2$ | Me | Me | i-Pr | 6'-Me | $SO_2NHMe$ | |
| 8-173 | 5-$CF_3$ | Me | Me | Me | 6'-Me | $CO_2Me$ | |
| 8-174 | 5-$CF_3$ | Me | Me | Me | 6'-Me | $SO_2Me$ | |
| 8-175 | 5-$CF_3$ | Me | Me | Me | 6'-Me | $SO_2NHMe$ | |
| 8-176 | 5-$CF_3$ | Me | Me | Et | 6'-Me | $CO_2Me$ | |
| 8-177 | 5-$CF_3$ | Me | Me | Et | 6'-Me | $SO_2Me$ | |
| 8-178 | 5-$CF_3$ | Me | Me | Et | 6'-Me | $SO_2NHMe$ | |
| 8-179 | 5-$CF_3$ | Me | Me | i-Pr | 6'-Me | $CO_2Me$ | |
| 8-180 | 5-$CF_3$ | Me | Me | i-Pr | 6'-Me | $SO_2Me$ | |
| 8-181 | 5-$CF_3$ | Me | Me | i-Pr | 6'-Me | $SO_2NHMe$ | |

TABLE 8-7

Table 8 (Continued)

| Compound No. | $R^1$ | $R^2$ | $R^3$ | $R^4$ | $R^5$ | Q | Physical property value |
|---|---|---|---|---|---|---|---|
| 8-182 | H | Me | $NH_2$ | Me | H | 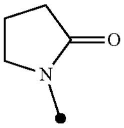 | |
| 8-183 | H | Me | $NH_2$ | Et | H | 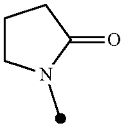 | |
| 8-184 | H | Me | $NH_2$ | i-Pr | H | 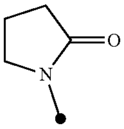 | |
| 8-185 | 5-Me | Me | $NH_2$ | Me | H | 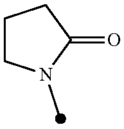 | |
| 8-186 | 5-Me | Me | $NH_2$ | Et | H | 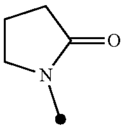 | |

TABLE 8-7-continued

Table 8 (Continued)

| Compound No. | $R^1$ | $R^2$ | $R^3$ | $R^4$ | $R^5$ | Q | Physical property value |
|---|---|---|---|---|---|---|---|
| 8-187 | 5-Me | Me | $NH_2$ | i-Pr | H | 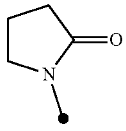 | |
| 8-188 | 5-OMe | Me | $NH_2$ | Me | H | 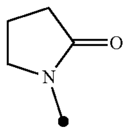 | |
| 8-189 | 5-OMe | Me | $NH_2$ | Et | H | 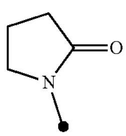 | |
| 8-190 | 5-OMe | Me | $NH_2$ | i-Pr | H | 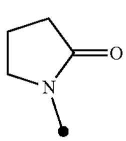 | |
| 8-191 | 5-$CHF_2$ | Me | $NH_2$ | Me | H | 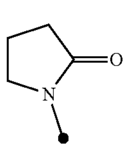 | |
| 8-192 | 5-$CHF_2$ | Me | $NH_2$ | Et | H | 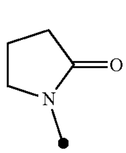 | |
| 8-193 | 5-$CHF_2$ | Me | $NH_2$ | i-Pr | H | 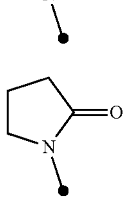 | |
| 8-194 | 5-$CF_3$ | Me | $NH_2$ | Me | H | 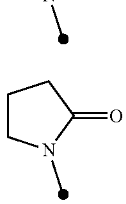 | |
| 8-195 | 5-$CF_3$ | Me | $NH_2$ | Et | H | 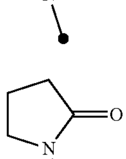 | |
| 8-196 | 5-$CF_3$ | Me | $NH_2$ | i-Pt | H | 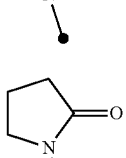 | |

TABLE 8-7-continued

| Table 8 (Continued) | | | | | | | |
|---|---|---|---|---|---|---|---|
| Compound No. | $R^1$ | $R^2$ | $R^3$ | $R^4$ | $R^5$ | Q | Physical property value |
| 8-197 | H | Me | $NH_2$ | Me | H | 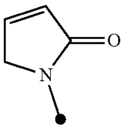 | |

The black solid circle in the structural formula represents a binding position.

TABLE 8-8

| Table 8 (Continued) | | | | | | | |
|---|---|---|---|---|---|---|---|
| Compound No. | $R^1$ | $R^2$ | $R^3$ | $R^4$ | $R^5$ | Q | Physical property value |
| 8-198 | H | Me | $NH_2$ | Et | H | 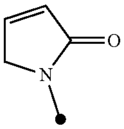 | |
| 8-199 | H | Me | $NH_2$ | i-Pr | H | 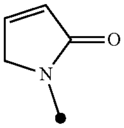 | |
| 8-200 | 5-Me | Me | $NH_2$ | Me | H | 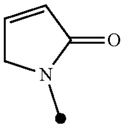 | |
| 8-201 | 5-Me | Me | $NH_2$ | Et | H | 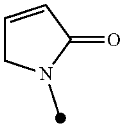 | |
| 8-202 | 5-Me | Me | $NH_2$ | i-Pr | H | 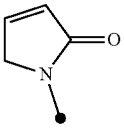 | |
| 8-203 | 5-OMe | Me | $NH_2$ | Me | H | 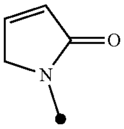 | |
| 8-204 | 5-OMe | Me | $NH_2$ | Et | H | 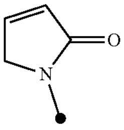 | |
| 8-205 | 5-OMe | Me | $NH_2$ | i-Pr | H | 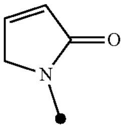 | |

TABLE 8-8-continued

| Table 8 (Continued) | | | | | | | |
|---|---|---|---|---|---|---|---|
| Compound No. | $R^1$ | $R^2$ | $R^3$ | $R^4$ | $R^5$ | Q | Physical property value |
| 8-206 | 5-$CHF_2$ | Me | $NH_2$ | Me | H | 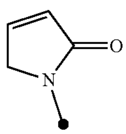 | |
| 8-207 | 5-$CHF_2$ | Me | $NH_2$ | Et | H | 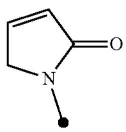 | |
| 8-208 | 5-$CHF_2$ | Me | $NH_2$ | i-Pr | H | 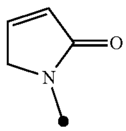 | |
| 8-209 | 5-$CF_3$ | Me | $NH_2$ | Me | H | 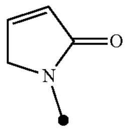 | |
| 8-210 | 5-$CF_3$ | Me | $NH_2$ | Et | H | 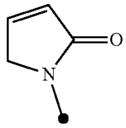 | |
| 8-211 | 5-$CF_3$ | Me | $NH_2$ | i-Pr | H | 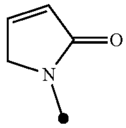 | |
| 8-212 | H | Me | $NH_2$ | Me | H | 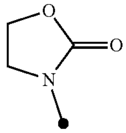 | |
| 8-213 | H | Me | $NH_2$ | Et | H | 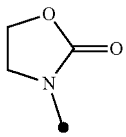 | |

The black solid circle in the structural formula represents a binding position.

TABLE 8-9

| Table 8 (Continued) | | | | | | | |
|---|---|---|---|---|---|---|---|
| Compound No. | $R^1$ | $R^2$ | $R^3$ | $R^4$ | $R^5$ | Q | Physical property value |
| 8-214 | H | Me | $NH_2$ | i-Pr | H | 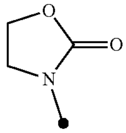 | |

TABLE 8-9-continued

| Table 8 (Continued) | | | | | | | |
|---|---|---|---|---|---|---|---|
| Compound No. | $R^1$ | $R^2$ | $R^3$ | $R^4$ | $R^5$ | Q | Physical property value |
| 8-215 | 5-Me | Me | $NH_2$ | Me | H | 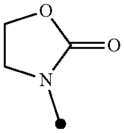 | |
| 8-216 | 5-Me | Me | $NH_2$ | Et | H | 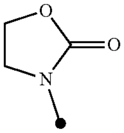 | |
| 8-217 | 5-Me | Me | $NH_2$ | i-P | H | 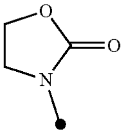 | |
| 8-218 | 5-OMe | Me | $NH_2$ | Me | H | 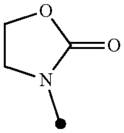 | |
| 8-219 | 5-OMe | Me | $NH_2$ | Et | H | 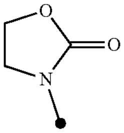 | |
| 8-220 | 5-OMe | Me | $NH_2$ | i-Pr | H | 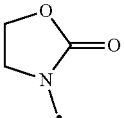 | |
| 8-221 | 5-$CHF_2$ | Me | $NH_2$ | Me | H | 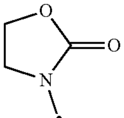 | |
| 8-222 | 5-$CHF_2$ | Me | $NH_2$ | Et | H | 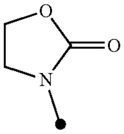 | |
| 8-223 | 5-$CHF_2$ | Me | $NH_2$ | i-Pr | H | 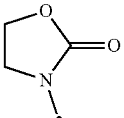 | |
| 8-224 | 5-$CF_3$ | Me | $NH_2$ | Me | H | 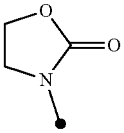 | |

TABLE 8-9-continued

| Table 8 (Continued) | | | | | | | |
|---|---|---|---|---|---|---|---|
| Compound No. | $R^1$ | $R^2$ | $R^3$ | $R^4$ | $R^5$ | Q | Physical property value |
| 8-225 | 5-$CF_3$ | Me | $NH_2$ | Et | H | 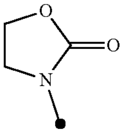 | |
| 8-226 | 5-$CF_3$ | Me | $NH_2$ | i-Pr | H | 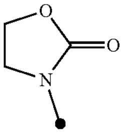 | |
| 8-227 | H | Me | $NH_2$ | Me | H | 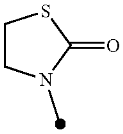 | |
| 8-228 | H | Me | $NH_2$ | Et | H | 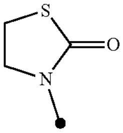 | |
| 8-229 | H | Me | $NH_2$ | i-Pr | H | 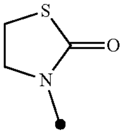 | |

The black solid circle in the structural formula represents a binding position.

TABLE 8-10

| Table 8 (Continued) | | | | | | | |
|---|---|---|---|---|---|---|---|
| Compound No. | $R^1$ | $R^2$ | $R^3$ | $R^4$ | $R^5$ | Q | Physical property value |
| 8-230 | 5-Me | Me | $NH_2$ | Me | H | 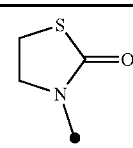 | |
| 8-231 | 5-Me | Me | $NH_2$ | Et | H | 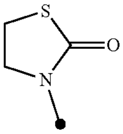 | |
| 8-232 | 5-Me | Me | $NH_2$ | i-Pr | H | 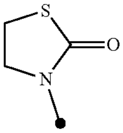 | |

TABLE 8-10-continued

| Table 8 (Continued) | | | | | | | |
|---|---|---|---|---|---|---|---|
| Compound No. | $R^1$ | $R^2$ | $R^3$ | $R^4$ | $R^5$ | Q | Physical property value |
| 8-233 | 5-OMe | Me | $NH_2$ | Me | H | 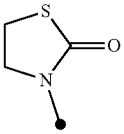 | |
| 8-234 | 5-OMe | Me | $NH_2$ | Et | H | 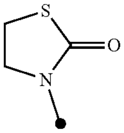 | |
| 8-235 | 5-OMe | Me | $NH_2$ | i-Pr | H | 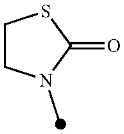 | |
| 8-236 | 5-$CHF_2$ | Me | $NH_2$ | Me | H | 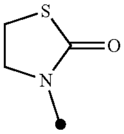 | |
| 8-237 | 5-$CHF_2$ | Me | $NH_2$ | Et | H | 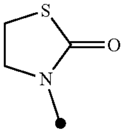 | |
| 8-238 | 5-$CHF_2$ | Me | $NH_2$ | i-Pr | H | 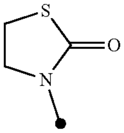 | |
| 8-239 | 5-$CF_3$ | Me | $NH_2$ | Me | H | 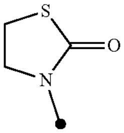 | |
| 8-240 | 5-$CF_3$ | Me | $NH_2$ | Et | H | 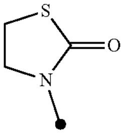 | |
| 8-241 | 5-$CF_3$ | Me | $NH_2$ | i-Pr | H | 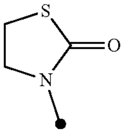 | |
| 8-242 | H | Me | $NH_2$ | Me | H | 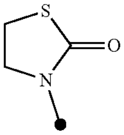 | |
| 8-243 | H | Me | $NH_2$ | Et | H | 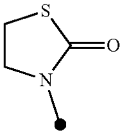 | |
| 8-244 | H | Me | $NH_2$ | i-Pr | H | 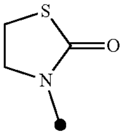 | |
| 8-245 | 5-Me | Me | $NH_2$ | Me | H | 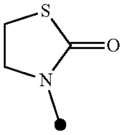 | |

The black solid circle in the structural formula represents a binding position.

TABLE 8-11

| Table 8 (Continued) | | | | | | | |
|---|---|---|---|---|---|---|---|
| Compound No. | $R^1$ | $R^2$ | $R^3$ | $R^4$ | $R^5$ | Q | Physical property value |
| 8-246 | 5-Me | Me | $NH_2$ | Et | H | 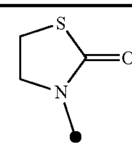 | |
| 8-247 | 5-Me | Me | $NH_2$ | i-Pr | H | 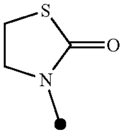 | |
| 8-248 | 5-OMe | Me | $NH_2$ | Me | H | 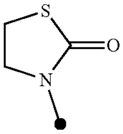 | |
| 8-249 | 5-OMe | Me | $NH_2$ | Et | H | 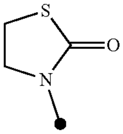 | |
| 8-250 | 5-OMe | Me | $NH_2$ | i-Pr | H | 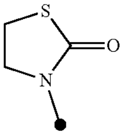 | |

TABLE 8-11-continued

Table 8 (Continued)

| Compound No. | $R^1$ | $R^2$ | $R^3$ | $R^4$ | $R^5$ | Q | Physical property value |
| --- | --- | --- | --- | --- | --- | --- | --- |
| 8-251 | 5-$CHF_2$ | Me | $NH_2$ | Me | H | 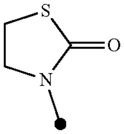 | |
| 8-252 | 5-$CHF_2$ | Me | $NH_2$ | Et | H | 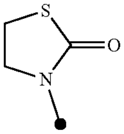 | |
| 8-253 | 5-$CHF_2$ | Me | $NH_2$ | i-Pr | H | 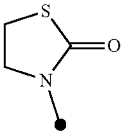 | |
| 8-254 | 5-$CF_3$ | Me | $NH_2$ | Me | H | 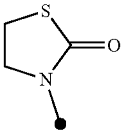 | |
| 8-255 | 5-$CF_3$ | Me | $NH_2$ | Et | H | 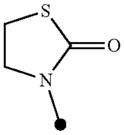 | |
| 8-256 | 5-$CF_3$ | Me | $NH_2$ | i-Pr | H | 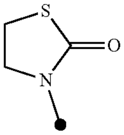 | |
| 8-257 | H | Me | $NH_2$ | Me | H | 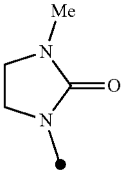 | |
| 8-258 | H | Me | $NH_2$ | Et | H | 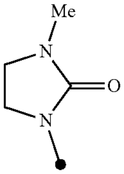 | |
| 8-259 | H | Me | $NH_2$ | i-Pr | H | 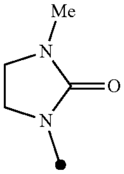 | |
| 8-260 | 5-Me | Me | $NH_2$ | Me | H | 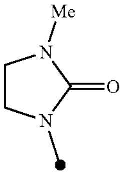 | |
| 8-261 | 5-Me | Me | $NH_2$ | Et | H | 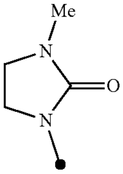 | |

The black solid circle in the structural formula represents a binding position.

TABLE 8-12

Table 8 (Continued)

| Compound No. | $R^1$ | $R^2$ | $R^3$ | $R^4$ | $R^5$ | Q | Physical property value |
| --- | --- | --- | --- | --- | --- | --- | --- |
| 8-262 | 5-Me | Me | $NH_2$ | i-Pr | H | 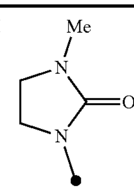 | |
| 8-263 | 5-OMe | Me | $NH_2$ | Me | H | 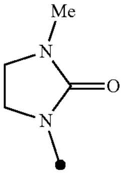 | |
| 8-264 | 5-OMe | Me | $NH_2$ | Et | H | 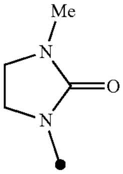 | |
| 8-265 | 5-OMe | Me | $NH_2$ | i-Pr | H | 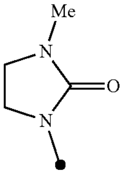 | |
| 8-266 | 5-$CHF_2$ | Me | $NH_2$ | Me | H | 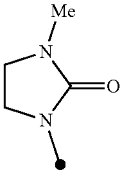 | |

TABLE 8-12-continued

Table 8 (Continued)

| Compound No. | $R^1$ | $R^2$ | $R^3$ | $R^4$ | $R^5$ | Q | Physical property value |
|---|---|---|---|---|---|---|---|
| 8-267 | 5-$CHF_2$ | Me | $NH_2$ | Et | H | 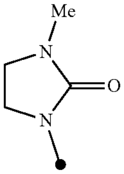 | |
| 8-268 | 5-$CHF_2$ | Me | $NH_2$ | i-Pr | H | 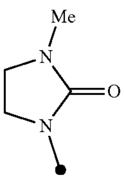 | |
| 8-269 | 5-$CF_3$ | Me | $NH_2$ | Me | H | 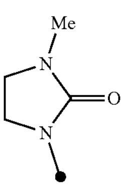 | |
| 8-270 | 5-$CF_3$ | Me | $NH_2$ | Et | H | 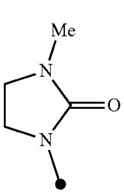 | |
| 8-271 | 5-$CF_3$ | Me | $NH_2$ | i-Pr | H | 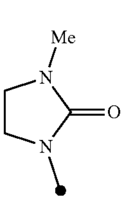 | |
| 8-272 | H | Me | $NH_2$ | Me | H | 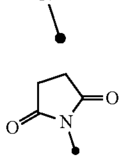 | |
| 8-273 | H | Me | $NH_2$ | Et | H | 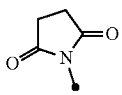 | |
| 8-274 | H | Me | $NH_2$ | i-Pr | H | 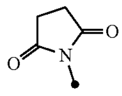 | |
| 8-275 | 5-Me | Me | $NH_2$ | Me | H | 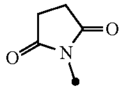 | |
| 8-276 | 5-Me | Me | $NH_2$ | Et | H | 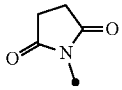 | |
| 8-277 | 5-Me | Me | $NH_2$ | i-Pr | H | 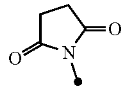 | |

The black solid circle in the structural formula represents a binding position.

TABLE 8-13

Table 8 (Continued)

| Compound No. | $R^1$ | $R^2$ | $R^3$ | $R^4$ | $R^5$ | Q | Physical property value |
|---|---|---|---|---|---|---|---|
| 8-278 | 5-OMe | Me | $NH_2$ | Me | H | 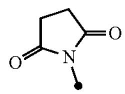 | |
| 8-279 | 5-OMe | Me | $NH_2$ | Et | H | 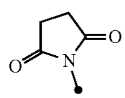 | |
| 8-280 | 5-OMe | Me | $NH_2$ | i-Pr | H | 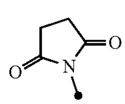 | |
| 8-281 | 5-$CHF_2$ | Me | $NH_2$ | Me | H | 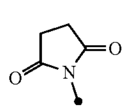 | |
| 8-282 | 5-$CHF_2$ | Me | $NH_2$ | Et | H | 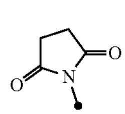 | |
| 8-283 | 5-$CHF_2$ | Me | $NH_2$ | i-Pr | H | 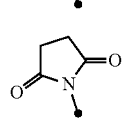 | |
| 8-284 | 5-$CF_3$ | Me | $NH_2$ | Me | H | 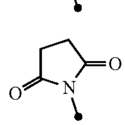 | |
| 8-285 | 5-$CF_3$ | Me | $NH_2$ | Et | H | 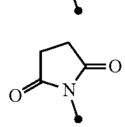 | |
| 8-286 | 5-$CF_3$ | Me | $NH_2$ | i-Pr | H | 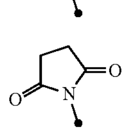 | |
| 8-287 | H | Me | $NH_2$ | Me | H | 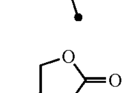 | |
| 8-288 | H | Me | $NH_2$ | Et | H | 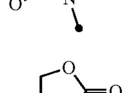 | |

TABLE 8-13-continued

| Table 8 (Continued) | | | | | | | |
|---|---|---|---|---|---|---|---|
| Compound No. | $R^1$ | $R^2$ | $R^3$ | $R^4$ | $R^5$ | Q | Physical property value |
| 8-289 | H | Me | $NH_2$ | i-Pr | H | 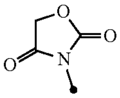 | |
| 8-290 | 5-Me | Me | $NH_2$ | Me | H | 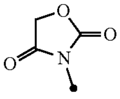 | |
| 8-291 | 5-Me | Me | $NH_2$ | Et | H | 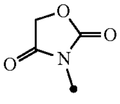 | |
| 8-292 | 5-Me | Me | $NH_2$ | i-Pr | H | 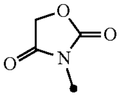 | |
| 8-293 | 5-OMe | Me | $NH_2$ | Me | H | 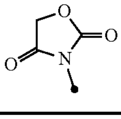 | |

The black solid circle in the structural formula represents a binding position.

TABLE 8-14

| Table 8 (Continued) | | | | | | | |
|---|---|---|---|---|---|---|---|
| Compound No. | $R^1$ | $R^2$ | $R^3$ | $R^4$ | $R^5$ | Q | Physical property value |
| 8-294 | 5-OMe | Me | $NH_2$ | Et | H | 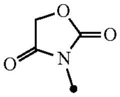 | |
| 8-295 | 5-OMe | Me | $NH_2$ | i-Pr | H | 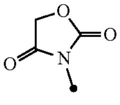 | |
| 8-296 | 5-$CHF_2$ | Me | $NH_2$ | Me | H | 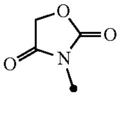 | |
| 8-297 | 5-$CHF_2$ | Me | $NH_2$ | Et | H | 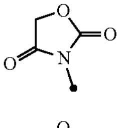 | |
| 8-298 | 5-$CHF_2$ | Me | $NH_2$ | i-Pr | H | 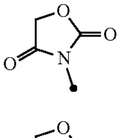 | |
| 8-299 | 5-$CF_3$ | Me | $NH_2$ | Me | H | 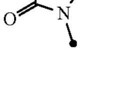 | |

TABLE 8-14-continued

| Table 8 (Continued) | | | | | | | |
|---|---|---|---|---|---|---|---|
| Compound No. | $R^1$ | $R^2$ | $R^3$ | $R^4$ | $R^5$ | Q | Physical property value |
| 8-300 | 5-$CF_3$ | Me | $NH_2$ | Et | H | 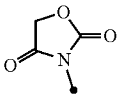 | |
| 8-301 | 5-$CF_3$ | Me | $NH_2$ | i-Pr | H | 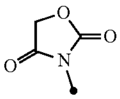 | |

The black solid circle in the structural formula represents a binding position.

[Chem. 35]

(1i)

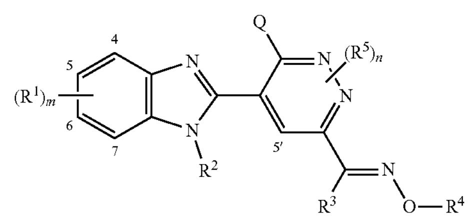

The position numbers in the table are the numbers designated in the general formula (1i).

TABLE 9-1

| Compound No. | $R^1$ | $R^2$ | $R^3$ | $R^4$ | $R^5$ | Q | Physical property value |
|---|---|---|---|---|---|---|---|
| 9-1 | H | Me | $NH_2$ | Me | H | $CO_2Me$ | |
| 9-2 | H | Me | $NH_2$ | Me | H | $SO_2Me$ | |
| 9-3 | H | Me | $NH_2$ | Me | H | $SO_2NHMe$ | |
| 9-4 | H | Me | $NH_2$ | Et | H | $CO_2Me$ | |
| 9-5 | H | Me | $NH_2$ | Et | H | $SCH_2$(4-t-BuPh) | NMR |
| 9-6 | H | Me | $NH_2$ | Et | H | $SO_2Me$ | |
| 9-7 | H | Me | $NH_2$ | Et | H | $SO_2NHMe$ | |
| 9-8 | H | Me | $NH_2$ | i-Pr | H | Cl | NMR |
| 9-9 | H | Me | $NH_2$ | i-Pr | H | $CO_2Me$ | |
| 9-10 | H | Me | $NH_2$ | i-Pr | H | $SO_2Me$ | |
| 9-11 | H | Me | $NH_2$ | i-Pr | H | $SO_2NHMe$ | NMR |
| 9-12 | 5-Me | Me | $NH_2$ | Me | H | $CO_2Me$ | |
| 9-13 | 5-Me | Me | $NH_2$ | Me | H | $SO_2Me$ | |
| 9-14 | 5-Me | Me | $NH_2$ | Me | H | $SO_2NHMe$ | |
| 9-15 | 5-Me | Me | $NH_2$ | Et | H | $CO_2Me$ | |
| 9-16 | 5-Me | Me | $NH_2$ | Et | H | $SO_2Me$ | |
| 9-17 | 5-Me | Me | $NH_2$ | Et | H | $SO_2NHMe$ | |
| 9-18 | 5-Me | Me | $NH_2$ | i-Pr | H | $CO_2Me$ | |
| 9-19 | 5-Me | Me | $NH_2$ | i-Pr | H | $SO_2Me$ | |
| 9-20 | 5-Me | Me | $NH_2$ | i-Pr | H | $SO_2NHMe$ | |
| 9-21 | 5-OMe | Me | $NH_2$ | Me | H | $CO_2Me$ | |
| 9-22 | 5-OMe | Me | $NH_2$ | Me | H | $SO_2Me$ | |
| 9-23 | 5-OMe | Me | $NH_2$ | Me | H | $SO_2NHMe$ | |
| 9-24 | 5-OMe | Me | $NH_2$ | Et | H | $CO_2Me$ | |
| 9-25 | 5-OMe | Me | $NH_2$ | Et | H | $SO_2Me$ | |
| 9-26 | 5-OMe | Me | $NH_2$ | Et | H | $SO_2NHMe$ | |
| 9-27 | 5-OMe | Me | $NH_2$ | i-Pr | H | $CO_2Me$ | |
| 9-28 | 5-OMe | Me | $NH_2$ | i-Pr | H | $SO_2Me$ | |
| 9-29 | 5-OMe | Me | $NH_2$ | i-Pr | H | $SO_2NHMe$ | |
| 9-30 | 5-$CHF_2$ | Me | $NH_2$ | Me | H | $CO_2Me$ | |

TABLE 9-2

Table 9 (Continued)

| Compound No. | $R^1$ | $R^2$ | $R^3$ | $R^4$ | $R^5$ | Q | Physical property value |
|---|---|---|---|---|---|---|---|
| 9-31 | 5-$CHF_2$ | Me | $NH_2$ | Me | H | $SO_2Me$ | |
| 9-32 | 5-$CHF_2$ | Me | $NH_2$ | Me | H | $SO_2NHMe$ | |
| 9-33 | 5-$CHF_2$ | Me | $NH_2$ | Et | H | $CO_2Me$ | |
| 9-34 | 5-$CHF_2$ | Me | $NH_2$ | Et | H | $SO_2Me$ | |
| 9-35 | 5-$CHF_2$ | Me | $NH_2$ | Et | H | $SO_2NHMe$ | |
| 9-36 | 5-$CHF_2$ | Me | $NH_2$ | i-Pr | H | $CO_2Me$ | |
| 9-37 | 5-$CHF_2$ | Me | $NH_2$ | i-Pr | H | $SO_2Me$ | |
| 9-38 | 5-$CHF_2$ | Me | $NH_2$ | i-Pr | H | $SO_2NHMe$ | |
| 9-39 | 5-$CF_3$ | Me | $NH_2$ | Me | H | $CO_2Me$ | |
| 9-40 | 5-$CF_3$ | Me | $NH_2$ | Me | H | $SO_2Me$ | |
| 9-41 | 5-$CF_3$ | Me | $NH_2$ | Me | H | $SO_2NHMe$ | |
| 9-42 | 5-$CF_3$ | Me | $NH_2$ | Et | H | $CO_2Me$ | |
| 9-43 | 5-$CF_3$ | Me | $NH_2$ | Et | H | $SO_2Me$ | |
| 9-44 | 5-$CF_3$ | Me | $NH_2$ | Et | H | $SO_2NHMe$ | |
| 9-45 | 5-$CF_3$ | Me | $NH_2$ | i-Pr | H | $CO_2Me$ | |
| 9-46 | 5-$CF_3$ | Me | $NH_2$ | i-Pr | H | $SO_2Me$ | |
| 9-47 | 5-$CF_3$ | Me | $NH_2$ | i-Pr | H | $SO_2NHMe$ | |
| 9-48 | H | Me | $NH_2$ | Me | H | 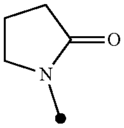 | |
| 9-49 | H | Me | $NH_2$ | Et | H | 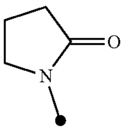 | |
| 9-50 | H | Me | $NH_2$ | i-Pr | H | 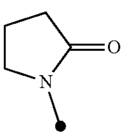 | |
| 9-51 | 5-Me | Me | $NH_2$ | Me | H | 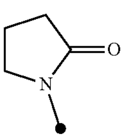 | |
| 9-52 | 5-Me | Me | $NH_2$ | Et | H | 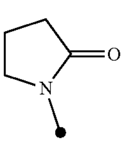 | |

TABLE 9-2-continued

Table 9 (Continued)

| Compound No. | $R^1$ | $R^2$ | $R^3$ | $R^4$ | $R^5$ | Q | Physical property value |
|---|---|---|---|---|---|---|---|
| 9-53 | 5-Me | Me | $NH_2$ | i-Pr | H | 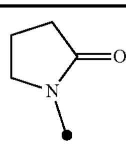 | |
| 9-54 | 5-OMe | Me | $NH_2$ | Me | H | 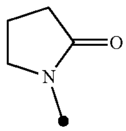 | |

The black solid circle in the structural formula represents a binding position.

TABLE 9-3

Table 9 (Continued)

| Compound No. | $R^1$ | $R^2$ | $R^3$ | $R^4$ | $R^5$ | Q | Physical property value |
|---|---|---|---|---|---|---|---|
| 9-55 | 5-OMe | Me | $NH_2$ | Et | H | 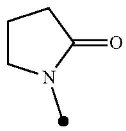 | |
| 9-56 | 5-OMe | Me | $NH_2$ | i-Pr | H | 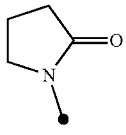 | |
| 9-57 | 5-$CHF_2$ | Me | $NH_2$ | Me | H | 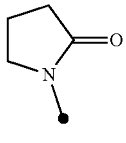 | |
| 9-58 | 5-$CHF_2$ | Me | $NH_2$ | Et | H | 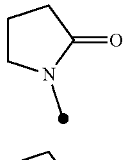 | |
| 9-59 | 5-$CHF_2$ | Me | $NH_2$ | i-Pr | H | 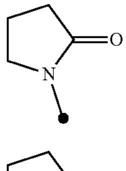 | |
| 9-60 | 5-$CF_3$ | Me | $NH_2$ | Me | H | 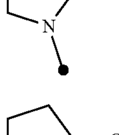 | |
| 9-61 | 5-$CF_3$ | Me | $NH_2$ | Et | H | 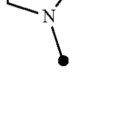 | |

TABLE 9-3-continued

Table 9 (Continued)

| Compound No. | $R^1$ | $R^2$ | $R^3$ | $R^4$ | $R^5$ | Q | Physical property value |
|---|---|---|---|---|---|---|---|
| 9-62 | 5-$CF_3$ | Me | $NH_2$ | i-Pr | H | 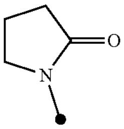 | |
| 9-63 | H | Me | $NH_2$ | Me | H | 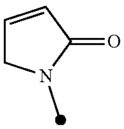 | |
| 9-64 | H | Me | $NH_2$ | Et | H | 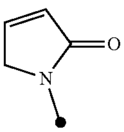 | |
| 9-65 | H | Me | $NH_2$ | i-Pr | H | 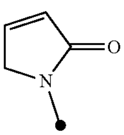 | |
| 9-66 | 5-Me | Me | $NH_2$ | Me | H | 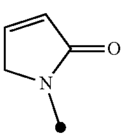 | |
| 9-67 | 5-Me | Me | $NH_2$ | Et | H | 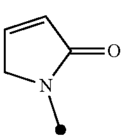 | |
| 9-68 | 5-Me | Me | $NH_2$ | i-Pr | H | 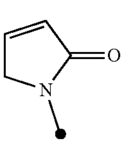 | |
| 9-69 | 5-OMe | Me | $NH_2$ | Me | H | 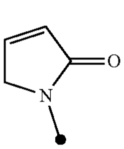 | |
| 9-70 | 5-OMe | Me | $NH_2$ | Et | H | 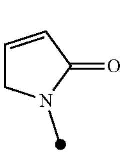 | |

The black solid circle in the structural formula represents a binding position.

[Table 9-4]

| Compound No. | $R^1$ | $R^2$ | $R^3$ | $R^4$ | $R^5$ | Q | Physical property value |
|---|---|---|---|---|---|---|---|
| 9-71 | 5-OMe | Me | $NH_2$ | i-Pr | H | 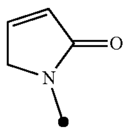 | |
| 9-72 | 5-$CHF_2$ | Me | $NH_2$ | Me | H | 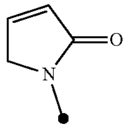 | |
| 9-73 | 5-$CHF_2$ | Me | $NH_2$ | Et | H | 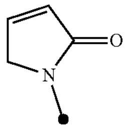 | |
| 9-74 | 5-$CHF_2$ | Me | $NH_2$ | i-Pr | H | 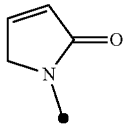 | |
| 9-75 | 5-$CF_3$ | Me | $NH_2$ | Me | H | 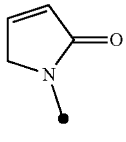 | |
| 9-76 | 5-$CF_3$ | Me | $NH_2$ | Et | H | 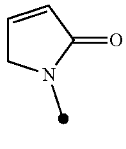 | |
| 9-77 | 5-$CF_3$ | Me | $NH_2$ | i-Pr | H | 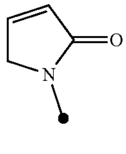 | |
| 9-78 | H | Me | $NH_2$ | Me | H | 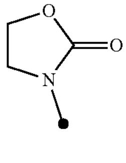 | |
| 9-79 | H | Me | $NH_2$ | Et | H | 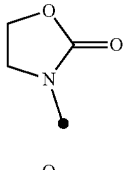 | |
| 9-80 | H | Me | $NH_2$ | i-Pr | H | 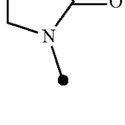 | |

-continued

[Table 9-4]

| Compound No. | $R^1$ | $R^2$ | $R^3$ | $R^4$ | $R^5$ | Q | Physical property value |
|---|---|---|---|---|---|---|---|
| 9-81 | 5-Me | Me | $NH_2$ | Me | H | 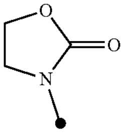 | |
| 9-82 | 5-Me | Me | $NH_2$ | Et | H | 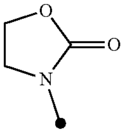 | |
| 9-83 | 5-Me | Me | $NH_2$ | i-Pr | H | 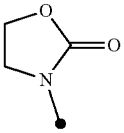 | |
| 9-84 | 5-OMe | Me | $NH_2$ | Me | H | 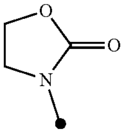 | |
| 9-85 | 5-OMe | Me | $NH_2$ | Et | H | 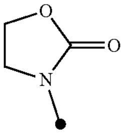 | |
| 9-86 | 5-OMe | Me | $NH_2$ | i-Pr | H | 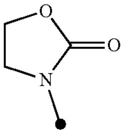 | |

The black solid circle in the structural formula represents a binding position.

TABLE 9-5

Table 9 (Continued)

| Compound No. | $R^1$ | $R^2$ | $R^3$ | $R^4$ | $R^5$ | Q | Physical property value |
|---|---|---|---|---|---|---|---|
| 9-87 | 5-$CHF_2$ | Me | $NH_2$ | Me | H | 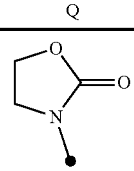 | |
| 9-88 | 5-$CHF_2$ | Me | $NH_2$ | Et | H | 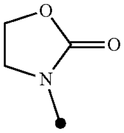 | |
| 9-89 | 5-$CHF_2$ | Me | $NH_2$ | i-Pr | H | 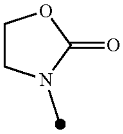 | |
| 9-90 | 5-$CF_3$ | Me | $NH_2$ | Me | H | 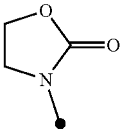 | |
| 9-91 | 5-$CF_3$ | Me | $NH_2$ | Et | H | 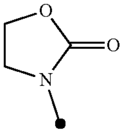 | |
| 9-92 | 5-$CF_3$ | Me | $NH_2$ | i-Pr | H | 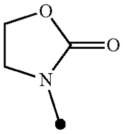 | |
| 9-93 | H | Me | $NH_2$ | Me | H | 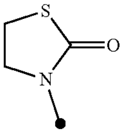 | |
| 9-94 | H | Me | $NH_2$ | Et | H | 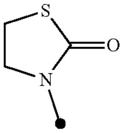 | |
| 9-95 | H | Me | $NH_2$ | i-Pr | H | 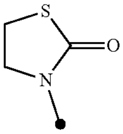 | |
| 9-96 | 5-Me | Me | $NH_2$ | Me | H | 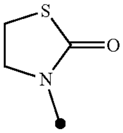 | |
| 9-97 | 5-Me | Me | $NH_2$ | Et | H | 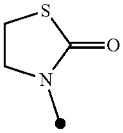 | |
| 9-98 | 5-Me | Me | $NH_2$ | i-Pr | H | 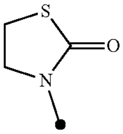 | |

TABLE 9-5-continued

| Table 9 (Continued) | | | | | | | |
|---|---|---|---|---|---|---|---|
| Compound No. | $R^1$ | $R^2$ | $R^3$ | $R^4$ | $R^5$ | Q | Physical property value |
| 9-99 | 5-OMe | Me | $NH_2$ | Me | H | 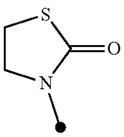 | |
| 9-100 | 5-OMe | Me | $NH_2$ | Et | H | 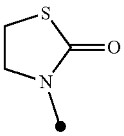 | |
| 9-101 | 5-OMe | Me | $NH_2$ | i-Pr | H | 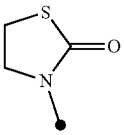 | |
| 9-102 | 5-$CHF_2$ | Me | $NH_2$ | Me | H | 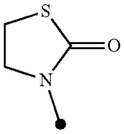 | |

The black solid circle in the structural formula represents a binding position.

TABLE 9-6

| Table 9 (Continued) | | | | | | | |
|---|---|---|---|---|---|---|---|
| Compound No. | $R^1$ | $R^2$ | $R^3$ | $R^4$ | $R^5$ | Q | Physical property value |
| 9-103 | 5-$CHF_2$ | Me | $NH_2$ | Et | H | 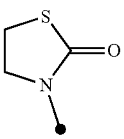 | |
| 9-104 | 5-$CHF_2$ | Me | $NH_2$ | i-Pr | H | 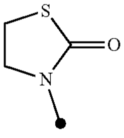 | |
| 9-105 | 5-$CF_3$ | Me | $NH_2$ | Me | | 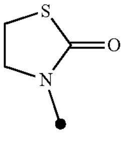 | |
| 9-106 | 5-$CF_3$ | Me | $NH_2$ | Et | H | 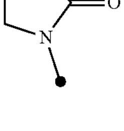 | |

TABLE 9-6-continued

| Table 9 (Continued) | | | | | | | |
|---|---|---|---|---|---|---|---|
| Compound No. | $R^1$ | $R^2$ | $R^3$ | $R^4$ | $R^5$ | Q | Physical property value |
| 9-107 | 5-$CF_3$ | Me | $NH_2$ | i-Pr | H | 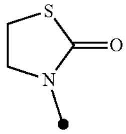 | |
| 9-108 | H | Me | $NH_2$ | Me | H | 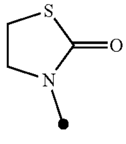 | |
| 9-109 | H | Me | $NH_2$ | Et | H | 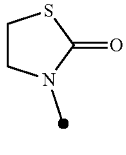 | |
| 9-110 | H | Me | $NH_2$ | i-Pr | H | 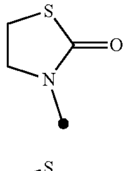 | |
| 9-111 | 5-Me | Me | $NH_2$ | Me | H | 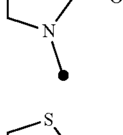 | |
| 9-112 | 5-Me | Me | $NH_2$ | Et | H | 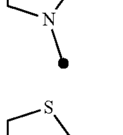 | |
| 9-113 | 5-Me | Me | $NH_2$ | i-Pr | H | 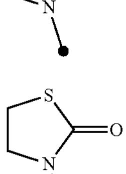 | |
| 9-114 | 5-OMe | Me | $NH_2$ | Me | H | 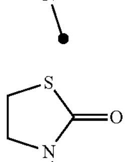 | |
| 9-115 | 5-OMe | Me | $NH_2$ | Et | H | 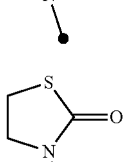 | |
| 9-116 | 5-OMe | Me | $NH_2$ | i-Pr | H | 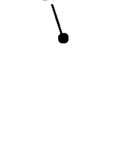 | |

TABLE 9-6-continued

| Table 9 (Continued) | | | | | | | |
|---|---|---|---|---|---|---|---|
| Compound No. | $R^1$ | $R^2$ | $R^3$ | $R^4$ | $R^5$ | Q | Physical property value |
| 9-117 | 5-$CHF_2$ | Me | $NH_2$ | Me | H | 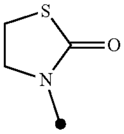 | |
| 9-118 | 5-$CHF_2$ | Me | $NH_2$ | Et | H | 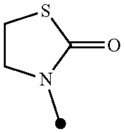 | |

The black solid circle in the structural formula represents a binding position.

TABLE 9-7

| Table 9 (Continued) | | | | | | | |
|---|---|---|---|---|---|---|---|
| Compound No. | $R^1$ | $R^2$ | $R^3$ | $R^4$ | $R^5$ | Q | Physical property value |
| 9-119 | 5-$CHF_2$ | Me | $NH_2$ | i-Pr | H | 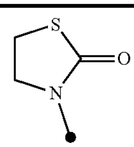 | |
| 9-120 | 5-$CF_3$ | Me | $NH_2$ | Me | H | 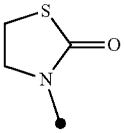 | |
| 9-121 | 5-$CF_3$ | Me | $NH_2$ | Et | H | 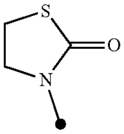 | |
| 9-122 | 5-$CF_3$ | Me | $NH_2$ | i-Pr | H | 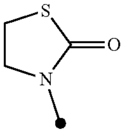 | |
| 9-123 | H | Me | $NH_2$ | Me | H | 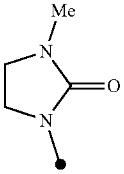 | |
| 9-124 | H | Me | $NH_2$ | Et | H | 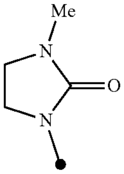 | |

TABLE 9-7-continued

| Table 9 (Continued) | | | | | | | |
|---|---|---|---|---|---|---|---|
| Compound No. | $R^1$ | $R^2$ | $R^3$ | $R^4$ | $R^5$ | Q | Physical property value |
| 9-125 | H | Me | $NH_2$ | i-Pr | H | 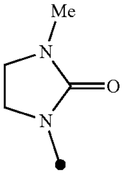 | |
| 9-126 | 5-Me | Me | $NH_2$ | Me | H | 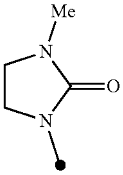 | |
| 9-127 | 5-Me | Me | $NH_2$ | Et | H | 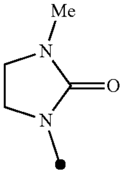 | |
| 9-128 | 5-Me | Me | $NH_2$ | i-Pr | H | 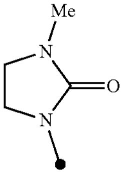 | |
| 9-129 | 5-OMe | Me | $NH_2$ | Me | H | 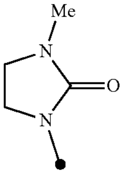 | |
| 9-130 | 5-OMe | Me | $NH_2$ | Et | H | 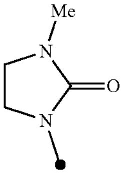 | |
| 9-131 | 5-OMe | Me | $NH_2$ | i-Pr | H | 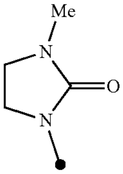 | |
| 9-132 | 5-$CHF_2$ | Me | $NH_2$ | Me | H | 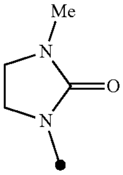 | |

TABLE 9-7-continued

| Table 9 (Continued) | | | | | | | |
|---|---|---|---|---|---|---|---|
| Compound No. | $R^1$ | $R^2$ | $R^3$ | $R^4$ | $R^5$ | Q | Physical property value |
| 9-133 | 5-$CHF_2$ | Me | $NH_2$ | Et | H | 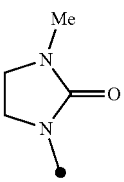 | |
| 9-134 | 5-$CHF_2$ | Me | $NH_2$ | i-Pr | H | 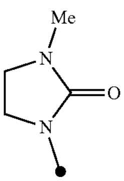 | |

The black solid circle in the structural formula represents a binding position.

TABLE 9-8

| Table 9 (Continued) | | | | | | | |
|---|---|---|---|---|---|---|---|
| Compound No. | $R^1$ | $R^2$ | $R^3$ | $R^4$ | $R^5$ | Q | Physical property value |
| 9-135 | 5-$CF_3$ | Me | $NH_2$ | Me | H | 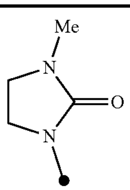 | |
| 9-136 | 5-$CF_3$ | Me | $NH_2$ | Et | H | 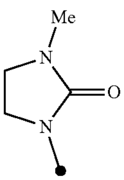 | |
| 9-137 | 5-$CF_3$ | Me | $NH_2$ | i-Pr | H | 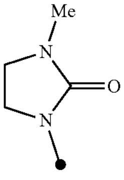 | |
| 9-138 | H | Me | $NH_2$ | Me | H | 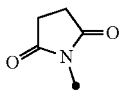 | |
| 9-139 | H | Me | $NH_2$ | Et | H | 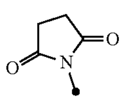 | |
| 9-140 | H | Me | $NH_2$ | i-Pr | H | 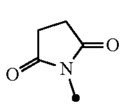 | |

TABLE 9-8-continued

| Table 9 (Continued) | | | | | | | |
|---|---|---|---|---|---|---|---|
| Compound No. | $R^1$ | $R^2$ | $R^3$ | $R^4$ | $R^5$ | Q | Physical property value |
| 9-141 | 5-Me | Me | $NH_2$ | Me | H | 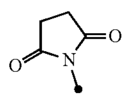 | |
| 9-142 | 5-Me | Me | $NH_2$ | Et | H | 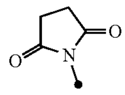 | |
| 9-143 | 5-Me | Me | $NH_2$ | i-Pr | H | 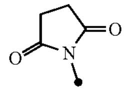 | |
| 9-144 | 5-OMe | Me | $NH_2$ | Me | H | 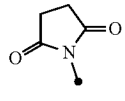 | |
| 9-145 | 5-OMe | Me | $NH_2$ | Et | H | 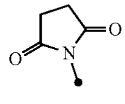 | |
| 9-146 | 5-OMe | Me | $NH_2$ | i-Pr | H | 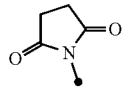 | |
| 9-147 | 5-$CHF_2$ | Me | $NH_2$ | Me | H | 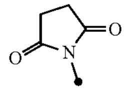 | |
| 9-148 | 5-$CHF_2$ | Me | $NH_2$ | Et | H | 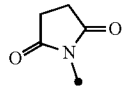 | |
| 9-149 | 5-$CHF_2$ | Me | $NH_2$ | i-Pr | H | 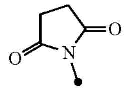 | |
| 9-150 | 5-$CF_3$ | Me | $NH_2$ | Me | H | 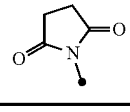 | |

The black solid circle in the structural formula represents a binding position.

TABLE 9-9

| Table 9 (Continued) | | | | | | | |
|---|---|---|---|---|---|---|---|
| Compound No. | $R^1$ | $R^2$ | $R^3$ | $R^4$ | $R^5$ | Q | Physical property value |
| 9-151 | 5-$CF_3$ | Me | $NH_2$ | Et | H | 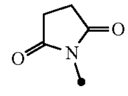 | |
| 9-152 | 5-$CF_3$ | Me | $NH_2$ | i-Pr | H | 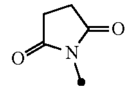 | |

TABLE 9-9-continued

Table 9 (Continued)

| Compound No. | $R^1$ | $R^2$ | $R^3$ | $R^4$ | $R^5$ | Q | Physical property value |
|---|---|---|---|---|---|---|---|
| 9-153 | H | Me | $NH_2$ | Me | H | 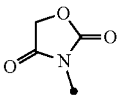 | |
| 9-154 | H | Me | $NH_2$ | Et | H | 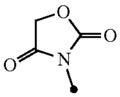 | |
| 9-155 | H | Me | $NH_2$ | i-Pr | H | 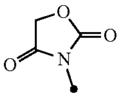 | |
| 9-156 | 5-Me | Me | NHz | Me | H | 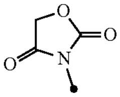 | |
| 9-157 | 5-Me | Me | $NH_2$ | Et | H | 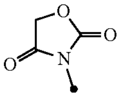 | |
| 9-158 | 5-Me | Me | $NH_2$ | i-Pr | H | 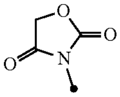 | |
| 9-159 | 5-OMe | Me | $NH_2$ | Me | H | 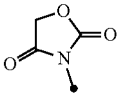 | |
| 9-160 | 5-OMe | Me | $NH_2$ | Et | | 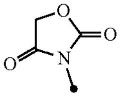 | |
| 9-161 | 5-OMe | Me | $NH_2$ | i-Pr | H | 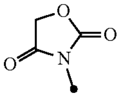 | |
| 9-162 | 5-$CHF_2$ | Me | $NH_2$ | Me | H | 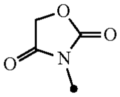 | |
| 9-163 | 5-$CHF_2$ | Me | $NH_2$ | Et | H | 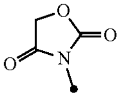 | |
| 9-164 | 5-$CHF_2$ | Me | $NH_2$ | i-Pr | H | 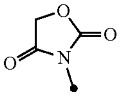 | |
| 9-165 | 5-$CF_3$ | Me | $NH_2$ | Me | H | 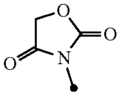 | |
| 9-166 | 5-$CF_3$ | Me | $NH_2$ | Et | H | 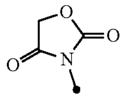 | |
| 9-167 | 5-$CF_3$ | Me | $NH_2$ | i-Pr | H | 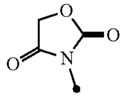 | |

The black solid circle in the structural formula represents a binding position.

TABLE 9-10

| Compound No. | $R^1$ | $R^2$ | $R^3$ | $R^4$ | $R^5$ | Q | Physical property value |
|---|---|---|---|---|---|---|---|
| 9-168 | H | Me | Me | Me | H | $CO_2Me$ | |
| 9-169 | H | Me | Me | Me | H | $SO_2Me$ | |
| 9-170 | H | Me | Me | Me | H | $SO_2NHMe$ | |
| 9-171 | H | Me | Me | Et | H | $CO_2Me$ | |
| 9-172 | H | Me | Me | Et | H | $SO_2Me$ | |
| 9-173 | H | Me | Me | Et | H | $SO_2NHMe$ | |
| 9-174 | H | Me | Me | i-Pr | H | $CO_2Me$ | |
| 9-175 | H | Me | Me | i-Pr | H | $SO_2Me$ | |
| 9-176 | H | Me | Me | i-Pr | H | $SO_2NHMe$ | |
| 9-177 | 5-Me | Me | Me | Me | H | $CO_2Me$ | |
| 9-178 | 5-Me | Me | Me | Me | H | $SO_2Me$ | |
| 9-179 | 5-Me | Me | Me | Me | H | $SO_2NHMe$ | |
| 9-180 | 5-Me | Me | Me | Et | H | $CO_2Me$ | |
| 9-181 | 5-Me | Me | Me | Et | H | $SO_2Me$ | |
| 9-182 | 5-Me | Me | Me | Et | H | $SO_2NHMe$ | |
| 9-183 | 5-Me | Me | Me | i-Pr | H | $CO_2Me$ | |
| 9-184 | 5-Me | Me | Me | i-Pr | H | $SO_2Me$ | |
| 9-185 | 5-Me | Me | Me | i-Pr | H | $SO_2NHMe$ | |
| 9-186 | 5-OMe | Me | Me | Me | H | $CO_2Me$ | |
| 9-187 | 5-OMe | Me | Me | Me | H | $SO_2Me$ | |
| 9-188 | 5-OMe | Me | Me | Me | H | $SO_2NHMe$ | |
| 9-189 | 5-OMe | Me | Me | Et | H | $CO_2Me$ | |
| 9-190 | 5-OMe | Me | Me | Et | H | $SO_2Me$ | |
| 9-191 | 5-OMe | Me | Me | Et | H | $SO_2NHMe$ | |
| 9-192 | 5-OMe | Me | Me | i-Pr | H | $CO_2Me$ | |
| 9-193 | 5-OMe | Me | Me | i-Pr | H | $SO_2Me$ | |
| 9-194 | 5-OMe | Me | Me | i-Pr | H | $SO_2NHMe$ | |
| 9-195 | 5-$CHF_2$ | Me | Me | Me | H | $CO_2Me$ | |
| 9-196 | 5-$CHF_2$ | Me | Me | Me | H | $SO_2Me$ | |
| 9-197 | 5-$CHF_2$ | Me | Me | Me | H | $SO_2NHMe$ | |
| 9-198 | 5-$CHF_2$ | Me | Me | Et | H | $CO_2Me$ | |
| 9-199 | 5-$CHF_2$ | Me | Me | Et | H | $SO_2Me$ | |

TABLE 9-11

| Compound No. | $R^1$ | $R^2$ | $R^3$ | $R^4$ | $R^5$ | Q | Physical property value |
|---|---|---|---|---|---|---|---|
| 9-200 | 5-$CHF_2$ | Me | Me | Et | H | $SO_2NHMe$ | |
| 9-201 | 5-$CHF_2$ | Me | Me | i-Pr | H | $CO_2Me$ | |
| 9-202 | 5-$CHF_2$ | Me | Me | i-Pr | H | $SO_2Me$ | |
| 9-203 | 5-$CHF_2$ | Me | Me | i-Pr | H | $SO_2NHMe$ | |
| 9-204 | 5-$CF_3$ | Me | Me | Me | H | $CO_2Me$ | |
| 9-205 | 5-$CF_3$ | Me | Me | Me | H | $SO_2Me$ | |

TABLE 9-11-continued

| Compound No. | $R^1$ | $R^2$ | $R^3$ | $R^4$ | $R^5$ | Q | Physical property value |
|---|---|---|---|---|---|---|---|
| 9-206 | 5-$CF_3$ | Me | Me | Me | H | $SO_2NHMe$ | |
| 9-207 | 5-$CF_3$ | Me | Me | Et | H | $CO_2Me$ | |
| 9-208 | 5-$CF_3$ | Me | Me | Et | H | $SO_2Me$ | |
| 9-209 | 5-$CF_3$ | Me | Me | Et | H | $SO_2NHMe$ | |
| 9-210 | 5-$CF_3$ | Me | Me | i-Pr | H | $CO_2Me$ | |
| 9-211 | 5-$CF_3$ | Me | Me | i-Pr | H | $SO_2Me$ | |
| 9-212 | 5-$CF_3$ | Me | Me | i-Pr | H | $SO_2NHMe$ | |

TABLE 10-1

| Compound No. | $^1$H-NMR Data ($CDCl_3$/TMS, ppm) |
|---|---|
| 1-6 | δ 8.51(d, 1H), 8.33(s, 1H), 8.16(s, 1H), 7.78(dd, 1H), 7.46(dd, 1H), 7.39(ddd, 1H), 7.33(ddd, 1H), 4.63(q, 2H), 3.84(q, 2H), 3.76(s, 3H), 1.34(t, 3H) |
| 1-7 | δ 8.47(d, 1H), 8.26(d, 1H), 7.79(d, 1H), 7.47(d, 1H), 7.39(dt, 1H), 7.33(dt, 1H), 4.34(q, 2H), 3.79(s, 3H), 3.63(s, 3H), 2.29(s, 3H), 1.38(t, 3H) |
| 1-10 | δ 8.53(d, 1H), 8.22(d, 1H), 7.81(dd, 1H), 7.49(d, 1H), 7.42(dt, 1H), 7.36(dt, 1H), 5.53(s, 2H), 3.76(s, 3H), 3.57(s, 3H) |
| 1-16 | δ 8.45(d, 1H), 8.24(d, 1H), 8.03(q, 1H), 7.78(d, 1H), 7.48(d, 1H), 7.41(t, 1H), 7.35(t, 1H), 5.45 (s, 2H), 4.15(t, 2H), 3.91(s, 3H), 2.80(d, 3H), 1.78(sext, 2H), 1.00(t, 3H) |
| 1-22 | δ 8.50(d, 1H), 8.21 (d, 1H), 7.79(d, 1H), 7.47(dd, 1H), 7.40(dt, 1H), 7.34(dt, 1H),5.59 (s, 1H), 4.15(q, 2H), 3.74(s, 3H), 3.56(s, 3H), 3.08(d, 3H), 1.34(t, 3H) |
| 1-26 | δ 8.52(d, 1H), 8.32(s, 1H), 8.16(d, 1H), 7.78(d, 1H), 7.49(dd, 1H), 7.38(dd, 1H), 7.32(dd, 1H), 4.64(q, 2H), 4.22(q, 2H), 3.93(q, 2H), 1.44(t, 3H), 1.36(t, 3H) |
| 1-29 | δ 8.49(d, 1H), 8.29(s, 1H), 8.16(d, 1H), 7.77(d, 1H), 7.66(d, 1H), 7.32(dd, 1H), 7.30(dd, 1H), 4.64(q, 2H), 4.45(sep, 2H), 3.84(q, 2H), 1.65(d, 6H), 1.34(t, 3H) |
| 1-32 | δ 8.53(d, 1H), 8.34(s, 1H), 8.17(d, 1H), 7.80(d, 1H), 7.64(dd, 1H), 7.42(dd, 1H), 7.36(dd, 1H), 4.95(d, 2H), 4.64(q, 2H), 3.94(q, 2H), 2.35(t, 1H), 1.37(t, 3H) |
| 1-35 | δ 8.55(d, 1H), 8.32(s, 1H), 8.17(d, 1H), 7.82(d, 1H), 7.53(d, 1H), 7.45(dd, 1H), 7.39(dd, 1H), 4.92(q, 2H), 4.64(q, 2H), 3.91 (q, 2H), 1.37(t, 3H) |
| 1-38 | δ 8.52(d, 1H), 8.30(s, 1H), 8.15(d, 1H), 7.79(d, 1H), 7.64(d, 1H), 7.41(dd, 1H), 7.36(dd, 1H), 5.58(s, 2H), 4.63(q, 2H), 3.93(q, 2H), 3.24(s, 3H), 1.37(t, 3H) |
| 1-39 | δ 8.47(d, 1H), 8.19(s, 1H), 8.17(d, 1H), 7.51 (d, 1H), 7.40(d, 1H), 7.24(dd, 1H), 4.35(q, 2H), 3.97(q, 2H), 3.79(s, 3H), 1.39(t, 3H), 1.38(t, 3H) |
| 1-41 | δ 8.52(d, 1H), 8.32(s, 1H), 8.15(d, 1H), 7.52(d, 1H), 7.41(d, 1H), 7.26(dd, 1H), 4.64(q, 2H), 4.00(q, 2H), 3.80(s, 3H), 1.40(t, 3H) |
| 1-51 | δ 8.47(d, 1H), 8.24(d, 1H), 7.32-7.25(m, 2H), 7.13(dd, 1H), 4.35(q, 2H), 3.79(s, 3H), 3.69(s, 3H), 2.66(s, 3H), 2.29(s, 3H), 1.38(s, 3H) |
| 1-61 | δ 8.47(d, 1H), 8.45(q, 1H), 8.23(d, 1H), 7.33(d, 1H), 7.32(t, 1H), 7.18(d, 1H), 5.45 (s, 2H), 4.24(q, 2H), 3.92(s, 3H), 3.05(q, 2H), 2.81(d, 3H), 1.39(t, 3H), 1.37(t, 3H) |
| 1-63 | δ 8.47(d, 1H), 8.27(d, 1H), 7.45(dd, 1H), 7.39(dd, 1H), 7.16(ddd, 1H), 4.35(q, 2H), 3.78(s, 3H), 3.61(s, 3H), 2.30(s, 3H), 1.37(t, 3H) |
| 1-66 | δ 8.45(d, 1H), 8.25(d, 1H), 7.79(d, 1H), 7.45(dd, 1H), 7.40(dd, 1H), 7.18(q, 1H), 5.44(s, 2H), 4.24(t, 2H), 3.89(s, 3H), 2.80(d, 3H), 1.37(1, 3H) |
| 1-67 | δ 8.45(d, 1H), 8.25(d, 1H), 7.79(d, 1H), 7.45(dd, 1H), 7.40(dd, 1H), 7.18(q, 1H), 5.45(s, 2H), 4.15(t, 2H), 3.89(s, 3H), 2.80(d, 3H), 1.78(sq, 2H), 1.01(t, 4H) |

TABLE 10-2

| Compound No | $^1$H-NMR Data ($CDCl_3$/TMS, ppm) |
|---|---|
| 1-86 | δ 8.51(d, 1H), 8.32(s, 1H), 8.18(d, 1H), 7.93(d, 1H), 7.49(dd, 1H), 7.34(d, 1H), 4.64 (q, 2H), 3.81(q, 2H), 3.74(s, 3H), 1.34(1, 3H) |
| 1-101 | δ 8.53(d, 1H), 8.24(d, 1H), 7.58(d, 1H), 7.36(d, 1H), 7.23(d, 1H), 6.57(s, 1H), 5.54(s, 2H), 3.73(s, 3H), 3.59(s, 3H), 2.53(s, 3H) |
| 1-111 | δ 8.43(d, 1H), 8.30(d, 1H), 7.57(d, 1H), 7.33(d, 1H), 7.21(dd, 1H), 5.46(s, 2H), 4.23(q, 2H), 3.78(q, 2H), 3.70(s, 3H), 2.51(s, 3H), 1.36(t, 3H), 1.32(t, 3H) |
| 1-116 | δ 8.35(d, 1H), 8.27(d, 1H), 7.56(d, 1H), 7.32(d, 1H), 7.20(dd, 1H), 5.45(s, 2H), 4.22(q, 2H), 3.62(s, 3H), 2.70(s, 6H), 2.51(s, 3H), 1.35(t, 3H) |
| 1-128 | δ 8.48(d, 1H), 8.29(d, 1H), 7.63(d, 1H), 7.54(s, 1H), 7.20(dd, 1H), 5.48(s, 2H), 4.23(q, 2H), 3.59(s, 3H), 3.39(m, 1H), 1.36(t, 3H), 0.92(m, 2H), 0.82(m, 2H) |
| 1-134 | δ 8.46(d, 1H), 8.24(d, 1H), 7.60(s, 1H), 7.37(d, 1H), 7.24(dd, 1H), 4.35(q, 2H), 3.77(s, 3H), 3.66(s, 3H), 2.81(q, 2H), 2.29(s, 3H), 1.38(t, 3H), 1.32(t, 3H) |

TABLE 10-2-continued

| Compound No | $^{1}$H-NMR Data ($CDCl_3$/TMS, ppm) |
|---|---|
| 1-141 | δ 8.44(d, 1H), 8.19(s, 1H), 8.18(d, 1H), 7.84(bs, 1H), 7.52(dd, 1H), 7.39(d, 1H), 6.88(dd, 1H), 5.78(d, 1H), 5.26(d, 1H), 4.35(q, 2H), 3.76(q, 2H), 3.71(s, 3H), 1.37(t, 3H), 1.33(t, 3H) |
| 1-143 | δ 8.49(d, 1H), 8.31(d, 1H), 7.79(d, 1H), 7.51(dd, 1H), 7.40(d, 1H), 6.88(dd, 1H), 5.79(dd, 1H), 5.47(bs, 2H), 5.25(dd, 1H), 4.24(q, 2H), 3.72(s, 3H), 3.57(s, 3H), 1.36(t, 3H) |
| 1-148 | δ 10.13(s, 1H), 8.48(d, 1H), 8.32(s, 1H), 8.30(d, 1H), 7.99(dd, 1H), 7.58(d, 1H), 4.36(q, 1H), 3.83(s, 3H), 3.74(s, 4H), 3.62(s, 3H), 2.30(s, 3H), 1.38(t, 3H) |
| 1-151 | δ 8.46(d, 1H), 8.23(d, 1H), 7.57(s, 1H), 7.36(d, 1H), 7.22(dd, 1H), 4.35(q, 2H), 3.77(s, 3H), 3.65(s, 3H), 2.75(t, 3H), 2.29(s, 3H), 1.72(sext, 2H), 1.39(t, 3H), 0.98(t, 3H) |
| 1-154 | δ 8.46(d, 1H), 8.24(d, 1H), 7.62(s, 1H), 7.38(d, 1H), 7.28(dd, 1H), 4.35(q, 2H), 3.76(s, 3H), 3.65(s, 3H), 3.08(sep, 1H), 2.28(s, 3H), 1.33(d, 6H) |
| 1-157 | δ 8.46(d, 1H), 8.24(d, 1H), 7.57(s, 1H), 7.36(d, 1H), 7.23(dd, 1H), 4.35(q, 2H), 3.77(s, 3H), 3.66(s, 3H), 2.75(t, 2H), 2.29(s, 3H), 1.70(quin, 2H), 1.43-1.33(m, 4H), 0.91(t, 3H) |
| 1-158 | δ 8.47(d, 1H), 8.25(d, 1H), 7.78(d, 1H), 7.48(dd, 1H), 7.39(d, 1H), 4.34(q, 2H), 3.77(s, 3H), 3.67(s, 3H), 2.28(s, 3H), 1.42(s, 9H) |
| 1-164 | δ 8.49(d, 1H), 8.31(d, 1H), 7.75(s, 1H), 7.75(d, 1H), 7.40(dd, 1H), 5.47(s, 2H), 4.62(s, 2H), 4.24(q, 2H), 3.74(s, 3H), 3.57(s, 3H), 3.43(s, 3H), 1.36(t, 3H) |
| 1-165 | δ 8.47(d, 1H), 8.26(d, 1H), 7.68(s, 1H), 7.42(d, 1H), 7.38(dd, 1H), 4.35(q, 2H), 3.85(s, 2H), 3.78(s, 3H), 3.65(s, 3H), 2.30(s, 3H), 2.05(s, 3H), 1.38(t, 3H) |
| 1-166 | δ 8.47(d, 1H), 8.28(d, 1H), 7.72(d, 1H), 7.48(d, 1H), 7.33(dd, 1H), 4.36(q, 2H), 4.28(d, 1H), 4.09(d, 1H), 3.80(s, 3H), 3.63(s, 3H), 2.51(s, 3H), 2.29(s, 3H), 1.38(s, 3H) |
| 1-167 | δ 8.48(d, 1H), 8.28(d, 1H), 7.83(d, 1H), 7.51(dd, 1H), 7.46(d, 1H), 4.42(s, 2H), 4.36(q, 2H), 3.81(s, 3H), 3.64(s, 3H), 2.79(s, 3H), 2.29(s, 3H), 1.39(t, 3H) |

TABLE 10-3

| Compound No. | $^{1}$H-NMR Data ($CDCl_3$/TMS, ppm) |
|---|---|
| 1-171 | δ 8.46(d, 1H), 8.25(d, 1H), 7.74(d, 1H), 7.43(d, 1H), 7.39(dd, 1H), 4.35(q, 2H), 3.94(s, 1H), 3.78(s, 3H), 3.64(s, 3H), 3.49(s, 2H), 2.51(s, 3H), 2.30(s, 3H), 1.39(t, 3H) |
| 1-172 | δ 8.47(d, 1H), 8.25(d, 1H), 7.69(d, 1H), 7.41(d, 1H), 7.38(dd, 1H), 4.35(q, 2H), 3.79(s, 3H), 3.65(s, 3H), 3.58(s, 3H), 2.30(s, 6H), 2.30(s, 2H), 1.37(t, 3H) |
| 1-173 | δ 8.48(d, 1H), 8.24(d, 1H), 7.72(d, 1H), 7.42(d, 1H), 7.40(d, 1H), 4.35(q, 2H), 3.78(s, 3H), 3.75(s, 2H), 3.66(s, 3H), 2.60(q, 4H), 2.30(s, 3H), 1.38(t, 3H), 1.09(s, 6H) |
| 1-175 | δ 8.47(d, 1H), 8.27(d, 1H), 7.81(s, 1H), 7.46(bs, 2H), 4.78(s, 2H), 4.34(q, 2H), 3.79(s, 3H), 3.62(s, 3H), 2.29(s, 3H), 1.38(t, 3H) |
| 1-184 | δ 8.46(d, 1H), 8.33(d, 1H), 7.94(d, 1H), 7.57(dd, 1H), 7.54(dd, 1H), 6.82(t, 1H), 5.46(s, 2H), 4.24(q, 2H), 3.75(s, 3H), 1.78(td, 2H), 1.37(t, 3H), 1.07(t, 3H |
| 1-206 | δ 8.50(d, 1H), 8.36(d, 1H), 8.09(s, 1H), 7.66(d, 1H), 7.56(dd, 1H), 5.43(s, 2H), 4.44(m, 1H), 3.77(s, 3H), 3.56(s, 3H), 1.34(d, 6H) |
| 1-225 | δ 8.47(d, 1H), 8.24(d, 1H), 7.35(d, 1H), 7.24(d, 1H), 7.04(dd, 1H), 4.35(q, 2H), 3.90(s, 3H), 3.77(s, 3H), 3.66(s, 3H), 2.30(s, 3H), 1.38(t, 3H) |
| 1-247 | δ 8.44(d, 1H), 8.22(d, 1H), 7.24(d, 1H), 7.06(d, 1H), 6.82(dd, 1H), 4.34(q, 2H), 3.73(s, 3H), 3.63(s, 3H), 2.29(s, 3H), 1.38(t, 3H) |
| 1-248 | δ 8.45(d, 1H), 8.24(d, 1H), 8.02(d, 1H), 7.67(bs, 1H), 7.40(dd, 1H), 7.33(d, 1H), 4.35(q, 2H), 3.75(s, 3H), 3.63(s, 3H), 2.30(s, 3H), 2.18(s, 3H), 1.38(t, 3H) |
| 1-249 | δ 8.50(d, 1H), 8.32(d, 1H), 7.73(d, 1H), 7.39(dd, 2H), 5.47(bs, 2H), 4.24(q, 2H), 3.72(s, 3H), 3.57(s, 3H), 2.57(s, 3H), 1.36(t, 3H) |
| 1-252 | δ 8.46(d, 1H), 8.26(d, 1H), 7.83(d, 1H), 7.45(dd, 1H), 7.39(d, 1H), 4.35(q, 2H), 3.78(s, 3H), 3.63(s, 3H), 2.97(q, 2H), 2.30(s, 3H), 1.38(t, 3H), 1.32(t, 3H) |
| 1-255 | δ 8.48(d, 1H), 8.19(d, 1H), 8.18(s, 1H), 8.12(d, 1H), 7.66(dd, 1H), 7.49(d, 1H), 4.10(s, 3H), 3.80(g, 2H), 3.77(s, 3H), 1.35(t, 3H) |
| 1-257 | δ 8.47(d, 1H), 8.20(d, 1H), 8.19(s, 1H), 8.12(d, 1H), 7.66(dd, 1H), 7.49(d, 1H), 4.35(q, 2H), 3.80(q, 2H), 3.77(s, 3H), 1.38(t, 3H), 1.35(t, 3H) |
| 1-261 | δ 8.52(d, 1H), 8.29(s, 1H), 8.19(d, 1H), 8.12(s, 1H), 7.67(dd, 1H), 7.50(d, 1H), 5.92(tt, 1H), 4.69(t, 2H), 3.82(q, 2H), 3.77(s, 3H), 1.35(t, 3H) |
| 1-262 | δ 8.52(d, 1H), 8.32(s, 1H), 8.19(d, 1H), 8.12(s, 1H), 7.67(dd, 1H), 7.50(d, 1H), 4.64(q, 2H), 3.82(q, 2H), 3.78(s, 3H), 1.35(t, 3H) |
| 1-263 | δ 8.51(d, 1H), 8.29(s, 1H), 8.17(d, 1H), 8.11(s, 1H), 7.66(dd, 1H), 7.49(d, 1H), 6.07(tt, 1H), 4.46(td, 2H), 3.81 (q, 2H), 3.77(s, 3H), 1.35(t, 3H) |
| 1-270 | δ 8.48(d, 1H), 8.27(s, 1H), 8.23(d, 1H), 8.19(s, 1H), 7.80(dd, 1H), 7.68(d, 1H), 4.35(q, 2H), 3.81(s, 3H), 3.79(q, 2H), 1.38(t, 3H), 1.36(t, 3H) |

TABLE 10-4

| Table 10 (Continued) | |
|---|---|
| Compound No. | $^1$H-NMR Data ($CDCl_3$/TMS, ppm) |
| 1-272 | δ 8.53(d, 1H), 8.32(s, 1H), 8.27(s, 1H), 8.21(d, 1H), 7.80(dd, 1H), 7.68(d, 1H), 4.64(q, 2H), 3.82(s, 3H), 3.81(q, 2H), 1.36(t, 3H) |
| 1-273 | δ 8.52(d, 1H), 8.29(s, 1H), 8.27(s, 1H), 8.20(d, 1H), 7.80(dd, 1H), 7.68(d, 1H), 6.07(tt, 1H), 4.47(td, 2H), 3.81(s, 3H), 3.80(q, 2H), 1.36(t, 3H) |
| 1-275 | δ 8.49(d, 1H), 8.31(d, 1H), 8.28(s, 1H), 7.81(d, 1H), 7.69(d, 1H), 4.36 (q, 2H), 3.85(s, 3H), 3.61(s, 3H), 2.30(s, 3H), 1.38(t, 3H) |
| 1-280 | δ 8.52(d, 1H), 8.49(dd, 1H), 8.25(d, 1H), 8.19(s, 1H), 8.03(dd, 1H), 7.70(d, 1H), 4.36(q, 2H), 3.83(s, 3H), 3.78(q, 2H), 1.38(t, 3H), 1.37(t, 3H) |
| 1-282 | δ 8.54(d, 1H), 8.53(s, 1H), 8.30(s, 1H), 8.22(d, 1H), 8.04(dd, 1H), 7.70(d, 1H), 5.91(tt, 1H), 4.70(t, 2H), 3.84(s, 3H), 3.79(q, 2H), 1.37(t, 3H) |
| 1-283 | δ 8.54(d, 1H), 8.53(s, 1H), 8.32(s, 1H), 8.23(d, 1H), 8.03(dd, 1H), 7.70(d, 1H), 4.64(q, 3H), 3.84(s, 3H), 3.79(q, 2H), 1.37(t, 3H) |
| 1-284 | δ 8.53(d, 1H), 8.52(s, 1H), 8.29(s, 1H), 8.22(d, 1H), 8.03(dd, 1H), 7.70(d, 1H), 6.07(tt, 1H), 4.48(td, 2H), 3.83(s, 3H), 3.79(q, 2H), 1.37(t, 3H) |
| 1-285 | δ 8.52(s, 1H), 8.48(d, 1H), 8.22(d, 1H), 8.20(s, 1H), 8.03(dd, 1H), 7.69(d, 1H), 4.07(d, 2H), 3.83(s, 3H), 3.77(q, 2H), 2.09(m, 1H), 1.36(t, 3H), 0.99(d, 6H) |
| 1-287 | δ 8.52(s, 1H), 8.48(d, 1H), 8.23(d, 1H), 8.19(s, 1H), 8.03(dd, 1H), 7.69(d, 1H), 4.30(t, 2H), 3.83(s, 3H), 3.77(q, 2H), 1.75(quin, 2H), 1.45(td, 2H), 1.36(t, 3H), 0.98(t, 3H) |
| 1-288 | δ 8.52(s, 1H), 8.48(d, 1H), 8.23(d, 1H), 8.20(s, 1H), 8.03(dd, 1H), 7.69(d, 1H), 4.26(t, 2H), 3.83(s, 3H), 3.77(q, 2H), 1.78(td, 2H), 1.36(t, 3H), 1.00(t, 3H) |
| 1-289 | δ 8.53(d, 1H), 8.49(d, 1H), 8.33(d, 1H), 8.03(dd, 1H), 7.70(d, 1H), 4.36(q, 2H), 3.86(5, 3H), 3.61(s, 3H), 2.30(s, 3H), 1.38(t, 3H) |
| 1-291 | δ 8.53(s, 1H), 8.44(d, 1H), 8.33(d, 1H), 8.04(dd, 1H), 7.70(d, 1H), 4.36(q, 2H), 3.85(s, 3H), 3.81(q, 2H), 2.29(s, 3H), 1.38(t, 3H), 1.36(t, 3H) |
| 1-298 | δ 8.43(s, 1H), 8.49(d, 1H), 8.30(d, 1H), 8.04(dd, 1H), 7.71(d, 1H), 4.66(q, 2H), 3.85(s, 3H), 3.81(q, 2H), 2.37(s, 3H), 1.37(t, 3H) |
| 1-314 | δ 8.47(d, 1H), 8.25(d, 1H), 7.89(d, 1H), 7.50(dd, 1H), 7.46(d, 1H), 5.55(s, 1H), 4.35(q, 2H), 3.79(s, 3H), 3.64(s, 3H), 3.38(s, 6H), 2.29(s, 3H), 1.38(t, 3H) |
| 1-316 | δ 10.1(s, 1H), 8.49(d, 1H), 8.30(s, 1H), 8.30(d, 1H), 7.99(d, 1H), 7.59(d, 1H), 4.36(q, 2H), 3.83(s, 3H), 3.74(s, 4H), 3.62(s, 3H), 2.31(s, 3H), 1.39(t, 3H) |
| 1-317 | δ 8.47(d, 1H), 8.26(d, 1H), 7.99(s, 1H), 7.70-7.63(m, 3H), 7.53(d, 1H), 7.47(t, 2H), 7.35(dt, 1H), 4.36(q, 2H), 3.81(s, 3H), 3.66(s, 3H), 2.30(s, 3H), 1.38(t, 3H) |

TABLE 10-5

| Table 10 (Continued) | |
|---|---|
| Compound No. | $^1$H-NMR Data ($CDCl_3$/TMS, ppm) |
| 1-320 | δ 8.94(d, 1H), 8.60(dd, 1H), 8.48(d, 1H), 8.29(d, 1H), 7.99(d, 1H), 7.96(dt, 1H), 7.47(ddt, 2H), 7.39(dd, 1H), 4.36(q, 2H), 3.83(s, 3H), 3.66(s, 3H), 2.31(s, 3H), 1.39(t, 3H) |
| 1-321 | δ 8.48(d, 1H), 8.28(d, 1H), 7.82(s, 1H), 7.54(d, 1H), 7.54(s, 1H), 7.44(dd, 1H), 6.36(d, 1H), 4.36(q, 2H), 3.94(s, 3H), 3.83(s, 3H), 3.64(s, 3H), 2.30(s, 3H), 1.39(t, 3H) |
| 1-338 | δ 8.44(d, 1H), 8.18(d, 1H), 8.18(s, 1H), 7.58(d, 1H), 7.17(t, 1H), 7.06(d, 1H), 4.57(seq, 1H), 3.92(s, 3H), 3.74(q, 2H), 2.78(s, 3H), 1.35(d, 6H), 1.32(t, 3H) |
| 1-390 | δ 8.51-8.47 (m, 1H), 8.31-8.27 (m , 1H), 7.20-7.18 (m, 2H), 5.47 (s, 2H), 4.27-4.20 (m, 2H), 3.72-3.57 (m, 3H), 2.58 (d,3H), 2.43 (s, 3H), 1.38-1.33 (m, 3H) |
| 1-395 | δ 8.48(d, 1H), 8.26(d, 1H), 7.67(m, 3H), 7.48(d, 1H), 5.44(s, 2H), 4.01(s, 3H), 3.97(s, 3H), 2.82(d, 3H) |
| 1-396 | δ 8.47(d, 1H), 8.26(d, 1H), 7.67(m, 3H), 7.48(d, 1H), 5.43(s, 2H), 4.24(q, 2H), 3.97(s, 3H), 2.82(d, 3H), 1.37(t, 2H) |
| 1-398 | δ 8.45(d, 1H), 8.24(d, 1H), 7.80(q, 1H), 7.45(dd, 1H), 7.39(m, 1H), 7.17(m, 1H), 5.45(s, 2H), 4.00(s, 3H), 3.89(s, 3H), 2.79(d, 3H) |
| 1-399 | δ 8.21(d, 1H), 8.32(d, 1H), 7.46(dd, 1H), 7.39(dd, 1H), 7.17(ddd, 1H), 5.47(s, 2H), 4.00(s, 3H), 3.73(s, 3H), 3.56(s, 3H) |
| 1-401 | δ 8.37-8.27 (m, 1H), 7.80-7.77 (m, 1H), 5.48-5.43 (m, 1H), 3.64-3.64 (m, 1H), 2.71-2.71 (m, 3H), 1.35 (t, 3H) |
| 1-403 | δ 8.47 (d, 1H), 8.25(d, 1H), 8.08(s, 1H), 7.65(d, 1H), 7.54(d, 1H), 5.66(s, 2H), 4.65(s, 2H), 3.76(s, 3H), 3.69(s, 3H), 3.52(s, 3H) |

TABLE 10-6

Table 10 (Continued)

| Compound No. | $^1$H-NMR Data ($CDCl_3$/TMS, ppm) |
|---|---|
| 2-35 | δ 8.13(d 1H), 7.95(d, 1H), 7.59(d, 1H), 7.34(dd, 1H), 7.21(d, 1H), 5.48(s, 2H), 4.22(q, 2H), 4.03(s, 3H), 2.50(s, 3H), 2.30(s, 3H), 1.37(t, 3H) |
| 2-46 | δ 8.30(d, 1H), 8.22(d, 1H), 8.07(t, 1H), 7.62(dd, 1H), 7.53(d, 1H), 5.48(brs, 2H), 5.05(quin, 1H), 4.23(q, 2H), 3.82(s, 3H), 1.36(t, 3H), 1.01(d, 6H) |
| 2-52 | δ 8.62(d, 1H), 8.15(d, 1H), 7.77(d, 1H), 7.59(dd, 1H), 7.50(d, 1H), 5.47(brs, 2H), 4.23(q, 2H), 4.08(s, 3H), 3.10(s, 3H), 2.99(s, 3H), 2.80(s, 3H), 1.37(t, 3H |
| 2-58 | δ 8.28(d, 1H), 8.20(d, 1H), 8.06(s, 1H), 8.01(s, 1H), 7.66(dd, 1H), 7.56(d, 1H), 5.45(s, 2H), 3.83(s, 3H), 1.24(s, 9H), 1.77-1.79(m, 2H), 1.30-1.25(m, 2H), 1.24(s, 9H), 1.00(t, 3H) |
| 2-62 | δ 8.30(d, 1H), 8.23(d, 1H), 8.08(s, 1H), 7.62(dd, 1H), 7.53(d, 1H), 5.44(brs, 2H), 4.42(quin, 1H), 4.18(q, 2H), 3.84(s, 3H), 1.34(d, 6H), 1.02(t, 3H) |
| 2-63 | δ 8.29(d, 1H), 8.23(d, 1H), 8.07(s, 1H), 7.62(dd, 1H), 7.52(d, 1H), 5.45(brs, 2H), 5.05(quin, 1H), 4.42(quin, 1H), 3.82(s, 3H), 1.34(d, 6H), 1.01(d, 6H) |
| 2-65 | δ 8.93(d, 1H), 8.23(d, 1H), 8.15(d, 1H), 8.09(s, 1H), 7.66(d, 1H), 7.56(d, 1H), 5.38(s, 2H), 4.41 (quin, 1H), 3.85(s, 3H), 2.90(s, 3H), 1.34(d, 6H) |
| 2-69 | δ 8.17(d, 1H), 8.07(s, 1H), 7.92(d, 1H), 7.58(d, 1H), 7.50(d, 1H), 5.45(s, 2H), 4.42(quin, 1H), 4.09(s, 3H), 3.45(s, 3H), 3.28(s, 3H), 1.35(d, 6H) |
| 2-71 | δ 8.22(d, 1H), 8.14(d, 1H), 8.07(s, 1H), 7.61(dd, 1H), 7.53(d, 1H), 5.44(s, 2H), 4.41 (quin, 1H), 3.91(s, 3H), 2.97(t, 2H), 1.34(d, 6H), 1.25(t, 3H) |
| 2-73 | δ 8.30(d, 1H), 8.22(d, 1H), 8.08(s, 1H), 7.62(dd, 1H), 7.53(d, 1H), 5.47(s, 2H), 4.22(q, 2H), 4.19(q, 2H), 3.84(s, 3H), 1.36 (t, 3H) |
| 2-82 | δ 8.24(d 1H), 8.20(s, 1H), 8.12(d, 1H), 8.07(d, 1H), 7.63(dd, 1H), 7.47(d, 1H), 4.32(q, 2H), 3.91(s, 3H), 3.79(s, 3H), 1.37(t, 3H) |
| 2-83 | δ 8.28(d 1H), 8.21(s, 1H), 8.12(d, 1H), 8.08(d, 1H), 7.63(dd, 1H), 7.47(d, 1H), 4.33(q, 2H), 4.20(q, 2H), 3.87(s, 3H), 1.37(t, 3H), 1.02(t, 3H) |
| 2-84 | δ 8.28(d 1H), 8.20(s, 1H), 8.12(d, 1H), 8.08(d, 1H), 7.63(dd, 1H), 7.47(d, 1H), 4.32(q, 2H), 4.10(t, 2H), 3.88(s, 3H), 1.37(td, 2H), 1.36(t, 3H), 0.67(t, 3H) |
| 2-85 | δ 8.28(d 1H), 8.20(s, 1H), 8.11(d, 1H), 8.08(d, 1H), 7.63(dd, 1H), 7.47(d, 1H), 5.07(sep, 1H), 4.33(q, 2H), 3.85(s, 3H), 1.37(t, 3H), 1.01(d, 6H) |
| 2-102 | δ 8.51(bs, 1H), 8.18(d, 1H), 8.15(d, 1H), 8.03(d, 1H), 7.64(dd, 1H), 7.50(d, 1H), 3.98(s, 3H), 3.79(s, 3H), 2.34(s, 3H) |
| 2-103 | δ 8.18(d, 1H), 8.15(d, 1H), 8.13(d, 1H), 7.63(dd, 1H), 7.49(d, 1H), 4.10(s, 3H), 3.97(s, 3H), 3.80(s, 3H), 2.31(s, 3H) |

Table 10-7

[Table 10 (Continued)

| Compound No. | $^1$H-NMR Data ($CDCl_3$/TMS, ppm) |
|---|---|
| 2-106 | δ 8.20(d 1H), 8.17(d, 1H), 8.13(d, 1H), 7.63(dd, 1H), 7.49(d, 1H), 4.21(q, 2H), 4.01(s, 3H), 3.80(s, 3H), 2.32(s, 3H), 1.31(1, 3H) |
| 2-110 | δ 8.16(d, 2H), 8.13(d, 1H), 7.63(dd, 1H), 7.49(d, 1H), 4.54(sep, 1H), 3.98(s, 3H), 3.78(s, 3H), 2.31(s, 3H), 1.36(d, 6H) |
| 2-111 | 6 8.16(d, 2H), 8.13(d, 1H), 7.63(dd, 1H), 7.48(d, 1H), 3.98(s, 3H), 3.78(s, 3H), 2.29(s, 3H), 1.40(s, 9H) |
| 2-113 | δ 8.17(d, 1H), 8.14(d, 1H), 8.13(d, 1H), 7.63(dd, 1H), 7.48(d, 1H), 6.08(ddt, 1H), 5.37(dd, 1H), 5.28(dd, 1H), 4.78(ddd, 2H), 3.97(s, 3H), 3.78(s, 3H), 2.35(s, 3H) |
| 2-114 | δ 8.19(d, 1H), 8.13(d, 1H), 8.11(d, 1H), 7.64(dd, 1H), 7.49(d, 1H), 6.09(tt, 1H), 4.45(dt, 2H), 3.98(s, 3H), 3.80(s, 3H), 2.37(s, 3H) |
| 2-116 | δ 8.16(d, 1H), 8.13(d, 1H), 8.13(d, 1H), 7.63(dd, 1H), 7.48(d, 1H), 7.45-7.30(m, 5H), 5.32(s, 2H), 3.96(s, 3H), 3.78(s, 3H), 2.36(s, 3H) |
| 2-117 | δ 8.17(d, 1H), 8.13(d, 1H), 8.10(d, 1H), 7.63(dd, 1H), 7.48(d, 1H), 7.36(s, 4H), 5.27(s, 2H), 3.96(s, 3H), 3.78(s, 3H), 2.35(s, 3H) |
| 2-119 | δ 8.22(d, 1H), 8.19(d, 1H), 8.12(d, 1H), 7.67(dd, 1H), 7.51(d, 1H), 7.28(dd, 2H), 7.19(dd, 2H), 4.47(t, 2H), 3.95(s, 3H), 3.80(s, 3H), 3.05(t, 2H), 2.28(s, 3H) |
| 2-126 | δ 8.27(d, 1H), 8.21(d, 1H), 8.14(s, 1H), 7.64(dd, 1H), 7.48(d, 1H), 5.47(s, 2H), 4.13(t, 2H), 3.85(s, 1H), 3.77(s, 1H)1.77(quin, 2H), 1.00(t, 3H) |
| 2-127 | δ 8.27(d, 1H), 8.21(d, 1H), 8.14(s, 1H), 7.64(d, 1H), 7.48(dd, 1H), 5.47(s, 2H), 4.18(t, 2H), 3.85(s, 3H), 3.77(s, 3H), 1.74(quin, 2H), 1.46(sext, 2H), 0.97(t, 3H) |
| 2-132 | δ 8.32(d, 1H), 8.20(d, 1H), 8.09(s, 1H), 7.60(d, 1H), 7.46-7.08(m, 6H), 6.95(d, 2H),5.51 (s, 2H),5.14 (s, 3H), 3.63(s, 3H) |
| 2-133 | δ 8.26(d, 1H), 8.20(d, 1H), 8.13(s, 1H), 7.64(d, 1H), 7.49-7.30(m, 6H), 5.52(s, 2H), 5.20 (s, 2H), 3.84(s, 3H), 3.77(s, 3H) |

Table 10-7-continued

| [Table 10 (Continued) | |
|---|---|
| Compound No. | $^1$H-NMR Data ($CDCl_3$/TMS, ppm) |
| 2-134 | δ 8.27(d, 1H), 8.02(s, 1H), 7.99(d, 1H), 7.66(dt, 1H), 7.52-7.47(m, 2H), 3.89(s, 3H), 3.78(s, 3H), 3.10(d, 3H) |
| 2-135 | δ 8.19(d, 1H), 8.12(d, 1H), 8.04(d, 1H), 7.57(dd, 1H), 7.36(d, 1H), 4.26(q, 2H), 3.76(s, 3H), 3.59(s, 3H) |
| 2-136 | δ 8.25(d, 1H), 8.11(d, 1H), 7.62(d, 1H), 7.55(d, 1H), 7.47(d, 1H), 3.96(s, 3H), 3.90(q, 2H), 3.80(s, 3H), 2.74(s, 6H), 1.11(t, 3H) |

TABLE 10-8

| Table 10 (Continued) | |
|---|---|
| Compound No. | $^1$H-NMR Data ($CDCl_3$/TMS, ppm) |
| 2-147 | δ 8.66(m, 1H), 8.31(d, 1H), 8.28(s, 1H), 8.16(s, 1H), 8.05(d, 1H), 7.81(d, 1H), 7.69(d, 1H), 4.32(q, 2H), 3.93(s, 3H), 2.91(d, 3H), 1.37(t, 3H) |
| 2-159 | δ 8.32(s, 1H), 8.29(d, 1H), 8.23(s, 1H), 8.08(d, 1H), 7.83(dd, 1H), 7.68(d, 1H), 4.61(q, 2H), 3.97(s, 3H), 3.81(s, 3H) |
| 2-165 | δ 8.72(br-d 1H), 8.28(s, 1H), 8.24(d, 1H), 8.13(d, 1H), 7.82(d, 1H), 7.70(d, 1H), 4.32(q, 2H), 3.96(s, 3H), 2.93(d, 3H), 2.30(s, 3H), 1.37(t, 3H) |
| 2-181 | δ 8.33(d 1H), 8.25(d, 1H), 8.23(d, 1H), 8.75(dd, 1H), 7.68(d, 1H), 5.48(s, 2H), 4.23(q, 2H), 4.19(q, 2H), 3.86(s, 3H), 1.36(t, 3H), 1.01(t, 3H) |
| 2-216 | δ 8.53(s, 1H), 8.31(s, 1H), 8.31(d, 1H), 8.11(d, 1H), 8.01 (dd, 1H), 7.69(d, 1H), 4.63(q, 2H), 3.98(s, 3H), 3.83(s, 3H) |
| 2-221 | δ 8.51(d 1H), 8.25(d, 1H), 8.20(d, 1H), 8.01(dd, 1H), 7.69(d, 1H), 4.34(q, 2H), 4.23(q, 3H), 3.98(s, 3H), 2.31(s, 3H), 1.38(t, 3H), 1.08(t, 3H) |
| 2-243 | δ 8.53(d, 1H), 8.35(d, 1H), 8.27(s, 1H), 8.02(dd, 1H), 7.69(d, 1H), 5.46(s, 2H), 4.24(q, 2H), 4.21(q, 2H), 3.87(s, 3H), 1.37(t, 3H), 1.07(t, 3H) |
| 2-260 | δ 8.30(d, 1H), 8.19(s, 1H), 8.10(d, 1H), 7.22(d, 1H), 7.19(dd, 1H), 4.33(q, 2H), 4.09(s, 3H), 3.78(s, 3H), 1.37(t, 3H) |
| 2-262 | δ 8.21(q, 2H), 7.81(d, 1H), 7.45(d, 1H), 7.40-7.29(m, 2H), 5.46(s, 2H), 4.14(sept, 1H), 3.88(s, 3H), 3.74(s, 3H), 1.34(d, 6H) |
| 2-269 | δ 8.32-8.29 (m, 1H), 8.05-8.02 (m, 1H), 7.67 (dd, 2H), 7.38-7.25 (m, 2H), 6.49-6.44 m, 2H), 4.65 (q, 2H), 3.88-3.86 (m, 3H) |
| 2-270 | δ 8.26-8.12 (m, 2H), 7.82-7.79 (m, 1H), 7.45-7.29 (m, 5H), 5.62 (s, 2H), 4.55-4.47 (m, 2H), 3.88-3.74 (m, 6H) |
| 2-275 | 6 8.08-8.05 (m, 1H), 7.93-7.91 (m, 1H), 7.57-7.52 (m, 1H), 7.17 (d, 1H), 5.65-5.58 (s, 2H), 4.52 (ddd, 2H), 4.05 (s, 3H), 2.80 (s, 6H), 2.48 (s, 3H) |
| 2-283 | δ 8.24-8.22 (m, 1H), 8.13-8.10 (m, 1H), 7.58 (s, 1H), 7.34-7.31 (m, 1H), 5.61 (s, 2H), 4.51 (q, 2H), 3.87-3.86 (m, 3H), 3.75-3.74 (m, 3H), 2.51-2.50 (m, 3H) |
| 2-285 | δ 8.07-8.04 (m, 1H), 7.77-7.75 (m, 1H), 7.48 (s, 1H), 7.16 (dd, 1H), 5.66-5.55 (m, 2H), 4.54-4.47 (m, 2H), 3.98 (s, 3H), 3.34-3.27 (m, 3H), 2.49-2.48 (m, 3H), 1.11-1.06 (m, 3H) |

TABLE 10-9

| Table 10 (Continued) | |
|---|---|
| Compound No. | $^1$H-NMR Data ($CDCl_3$/TMS, ppm) |
| 2-286 | δ 9.40-9.36 (m, 1H), 8.47-8.44 (m, 1H), 8.15-8.12 (m, 1H), 7.58 (s, 1H), 7.37-7.34 (m, 1H), 5.60-5.54 (s, 2H), 4.55-4.47 (m, 2H), 3.78-3.77 (m, 3H), 3.37-3.29 (m, 2H), 2.54-2.53 (m, 3H), 1.09 (t, 3H) |
| 2-288 | δ 8.08-8.05 (m, 1H), 7.93-7.91 (m, 1H), 7.57-7.52 (m, 1H), 7.17 (d, 1H), 5.65-5.58 (s, 2H), 4.52 (ddd, 3H), 4.05 (s, 3H), 2.80 (s, 3H), 2.48 (s, 3H) |
| 2-289 | δ 10.54(s, 1H), 8.52(d, 1H), 8.26(d, 1H), 8.17-8.10(m, 2H), 7.66(dd, 1H), 7.55(dd, 1H), 5.37(s, 2H), 4.41(quin, 1H), 3.90(s, 3H), 1.34(d, 6H) |
| 2-294 | δ 8.33(d, 1H), 8.23(d, 1H), 8.12(s, 1H), 7.64(d, 1H), 7.55(d, 1H), 5.49(s, 2H), 5.03(sep, 1H), 3.99(s, 3H), 3.84(s, 3H), 2.25-2.14(m, 2H), 1.83-1.70(m, 2H), 1.62-1.49(m, 2H) |
| 2-302 | δ 10.20 (s, 1H), 8.47-8.44 (m, 1H), 8.26-8.23 (m, 1H), 8.08 (s, 1H), 7,68 (dd, 1H), 7.59-7.56 (m, 1H), 5.45-5.41 (s, 2H), 4.24 (q, 2H), 3.91-3.90 (m, 3H), 1.37 (t, 3H) |
| 2-304 | δ 12.35-12.31 (m, 1H), 8.37-8.32 (m, 1H), 8.22-8.19 (m, 1H), 8.11 (s, 1H), 7.70-7.67 (m, 1H), 7.59-7.56 (m, 1H), 5.44-5.39 (s, 2H), 4.23 (q, 2H), 3.91 (s, 3H); |

TABLE 10-9-continued

| Table 10 (Continued) | |
|---|---|
| Compound No. | $^1$H-NMR Data ($CDCl_3$/TMS, ppm) |
| 2-305 | δ 12.11 (s, 1H), 8.41-8.36 (m, 1H), 8.24-8.21 (m, 1H), 8.08 (s, 1H), 7.70-7.65 (m, 1H), 7.59-7.55 (m, 1H), 5.44-5.40 (s, 2H), 4.27-4.20 (m, 3H), 3.91 (s, 3H), 1.37 (t, 3H); |
| 2-306 | δ 12.25 (s, 1H), 8.38-8.35 (m, 1H), 8.23-8.20 (m, 1H), 8.10 (s, 1H), 7.70-7.67 (m, 1H), 7.59-7.56 (m, 1H), 5.44-5.39 (s, 2H), 4.23 (q, 2H), 3.95-3.90 (m, 6H), 1.72-1.66 (m, 1H), 1.37 (t, 3H), 1.00-0.93 (m, 3H) |
| 2-308 | δ 9.84-9.80 (m, 1H), 8.42-8.39 (m, 1H), 8.25-8.22 (m, 1H), 8.09 (s, 1H), 7.69 (dd, 1H), 7.60-7.57 (m, 1H), 5.43 (s, 2H), 4.26-4.20 (m, 3H), 3.89-3.88 (m, 3H), 3.05-2.93 (m, 2H), 2.58-2.45 (m, 2H), 1.37 (t, 3H) |
| 2-310 | δ 8.16-8.13 (m, 1H), 7.97 (s, 1H), 7.77-7.75 (m, 1H), 7.59 (dd, 1H), 7.52-7.48 (m, 1H), 5.49-5.45 (s, 2H), 4.22 (q, 2H), 4.05-4.04 (m, 3H), 3.57-3.51 (m, 2H), 3.36 (q, 2H), 1.37 (t, 3H), 1.23-1.12 (m, 3H) |

TABLE 10-10

| Table 10 (Continued) | |
|---|---|
| Compound No. | $^1$H-NMR Data ($CDCl_3$/TMS, ppm) |
| 2-311 | δ 8.17 (m, 1H), 7.90-7.88 (m, 1H), 7.59 (m, 1H), 7.52-7.48 (m, 1H), 5.48 (s, 2H), 4.38 (d, 3H), 4.26-4.20 (m, 3H), 3.17 (s, 2H), 3.06 (s, 3H), 1.39-1.35 (m, 9H) |
| 2-312 | δ 9.66-9.61 (m, 1H), 8.42-8.39 (m, 1H), 8.23-8.21 (m, 1H), 8.13 (s, 1H), 7.67 (dd, 1H), 7.58-7.55 (m, 1H), 5.45-5.41 (m, 2H), 4.23 (q, 2H), 3.88 (s, 3H), 2.13 (t, 1H), 1.37 (t, 3H) |
| 2-313 | δ 12.31-12.28 (m, 1H), 8.40-8.36 (m, 1H), 8.24-8.21 (m, 1H), 8.12 (s, 1H), 7.68 (dd, 1H), 7.59-7.56 (m, 1H), 6.01-5.91 (m, 1H), 5.41 (s, 2H), 5.27-5.14 (m, 2H), 4.49-4.44 (m, 2H), 4.23 (q, 2H), 3.92-3.90 (m, 3H) |
| 2-314 | δ 8.15 (m, 1H), 8.00 (d, 1H), 7.77-7.74 (m, 1H), 7.61-7.57 (m, 1H), 7.52-7.48 (m, 1H), 5.49-5.45 (m, 2H), 4.23 (q, 2H), 4.06 (d, 3H), 3.58-3.53 (m, 1H), 2.99-2.98 (m, 3H), 1.39-1.35 (m, 3H), 1.26-1.18 (m, 3H) |
| 2-315 | δ 8.16-8.13 (m, 1H), 7.97 (m, 1H), 7.73 (m, 1H), 7.60-7.48 (m, 2H), 5.49-5.47 (s, 2H), 4.93-4.85 (m, 1H), 4.26-4.19 (m, 2H), 4.11 (s, 3H), 4.06 (d, 3H), 1.37 (t, 3H), 1.37 (t, 6H) |
| 2-316 | δ 8.16-8.13 (m, 1H), 7.96 (m, 1H), 7.80-7.71 (m, 1H), 7.60-7.57 (m, 1H), 7.52-7.48 (m, 1H), 5.50-5.44 (s, 2H), 4.26-4.19 (m, 2H), 4.05-4.03 (m, 3H), 1.41-1.07 (m, 12H) |
| 2-317 | δ 8.17-8.15 (m, 1H), 8.07 (m, 1H), 7.96-7.90 (m, 1H), 7.61-7.49 (m, 2H), 5.47 (s, 2H), 4.23 (q, 2H), 3.49-3.44 (m, 3H), 3.30-3.29 (m, 3H), 1.37 (t, 3H) |
| 2-319 | δ 8.17-8.14 (m, 1H), 8.00 (m, 1H), 7.81-7.79 (m, 1H), 7.61-7.48 (m, 2H), 5.48-5.45 (s, 2H), 4.13 (m, 2H), 3.60 (t, 2H), 3.43 (t, 2H), 1.58-1.57 (m, 12H), 1.37 (t, 3H), 0.88 (t, 1H) |
| 2-321 | δ 8.17-8.14 (m, 1H), 8.04-8.01 (m, 1H), 7.76-7.74 (m, 1H), 7.61 (m, 1H), 7.53-7.50 (m, 1H), 5.48-5.43 (s, 2H), 4.24-4.10 (m, 6H), 3.93 - 3.83 (m, 4H), 3.50-3.40 (m, 2H), 2.96-2.95 (m, 1H), 2.89-2.88 (m, 1H), 1.39-1.35 (m, 3H) |

TABLE 10-11

| Table 10 (Continued) | |
|---|---|
| Compound No. | $^1$H-NMR Data ($CDCl_3$/TMS, ppm) |
| 2-322 | δ 8.20-8.18 (m, 1H), 7.95 (s, 1H), 7.80-7.77 (m, 1H), 7.61 (m, 1H), 7.54-7.51 (m, 1H), 5.47-5.42 (s, 2H), 4.25-4.17 (m, 9H), 1.37 (t, 3H); |
| 2-323 | δ 8.18-8.16 (m, 1H), 8.03-7.99 (m, 1H), 7.82 (m, 1H), 7.60 (m, 1H), 7.53-7.49 (m, 1H), 5.48-5.44 (s, 2H), 4.26-4.20 (m, 2H), 4.12 (d, 3H), 3.19-3.14 (m, 2H), 1.37 (t, 3H) |
| 2-324 | δ 14.30-14.22 (m, 1H), 8.61-8.58 (m, 1H), 8.34-8.26 (m, 2H), 7.68 (dd, 1H), 7.59-7.50 (m, 2H), 6.99-6.98 (m, 1H), 5.46-5.41 (s, 2H), 4.25 (q, 2H), 3.98-3.97 (m, 3H), 1.38 (t, 3H) |
| 2-325 | δ 9.72-9.67 (m, 1H), 8.41-8.38 (m, 1H), 8.24-8.22 (m, 1H), 8.10 (s, 1H), 7.67 (dd, 1H), 7.58-7.55 (m, 1H), 5.45-5.41 (s, 2H), 4.24 (q, 2H), 3.91-3.90 (m, 3H), 3.81-3.70 (m, 2H), 1.37 (t, 3H) |

TABLE 10-11-continued

| Table 10 (Continued) | |
|---|---|
| Compound No. | $^1$H-NMR Data ($CDCl_3$/TMS, ppm) |
| 2-326 | δ 9.28 (s, 1H), 8.32-8.29 (m, 1H), 8.23-8.20 (m, 1H), 8.07 (s, 1H), 7.67 (dd, 1H), 7.59-7.51 (m, 1H), 5.48-5.42 (s, 2H), 4.26-4.20 (m, 2H), 3.88-3.87 (m, 6H), 1.37 (t, 3H) |
| 2-327 | δ 10.14-10.09 (m, 1H), 8.47-8.44 (m, 1H), 8.15-8.12 (m, 1H), 7.60 (s, 1H), 7.37-7.34 (m, 1H), 5.58-5.54 (s, 2H), 4.56-4.48 (m, 2H), 3.83-3.82 (m, 3H), 3.65 (ddd, 2H) |
| 2-328 | δ 10.49 (t, 1H), 8.48-8.46 (m, 1H), 8.15-8.13 (m, 1H), 7.60 (s, 1H), 7.38-7.35 (m, 1H), 6.00-5.69 (m, 1H), 5.61-5.57 (s, 1H), 4.55-4.48 (m, 2H), 3.85-3.84 (m, 3H), 3.79-3.68 (m, 2H), 2.54-2.53 (m, 3H) |
| 2-329 | δ 9.71-9.69 (m, 1H), 8.50-8.47 (m, 1H), 8.15-8.12 (m, 1H), 7.58 (s, 1H), 7.37-7.34 (m, 1H), 5.61-5.50 (s, 2H), 4.51 (q, 2H), 3.78-3.77 (m, 3H), 2.90-2.84 (m, 1H), 2.55-2.54 (m, 3H), 0.77-0.71 (m, 3H), 0.48-0.43 (m, 2H) |
| 2-330 | δ 8.97-8.93 (m, 1H), 8.43-8.41 (m, 1H), 8.16-8.13 (m, 1H), 7.57-7.57 (m, 1H), 7.36-7.33 (m, 1H), 5.58-5.52 (s, 2H), 4.51 (q, 2H), 3.75-3.74 (m, 3H), 3.43-3.37 (m, 1H), 2.53-2.52 (m, 3H), 1.09-1.06 (m, 3H), 0.72-0.64 (m, 1H), 0.41-0.35 (m, 1H), 0.17-0.11 (m, 3H) |

TABLE 10-12

| Table 10 (Continued) | |
|---|---|
| Compound No. | $^1$H-NMR Data ($CDCl_3$/TMS, ppm) |
| 2-331 | δ 9.68 (t, 3H), 8.48-8.45 (m, 1H), 8.15-8.12 (m, 1H), 7.56 (s, 1H), 7.37-7.34 (m, 1H), 7.25 (d, 1H), 5.82-5.72 (m, 1H), 5.57-5.54 (s, 2H), 5.19-5.06 (m, 2H), 4.51 (q, 2H), 3.97-3.92 (m, 2H), 3.79 (s, 3H), 2.53 (s, 3H) |
| 2-332 | δ 9.33-9.28 (m, 1H), 8.44-8.41 (m, 1H), 8.14-8.11 (m, 1H), 7.61-7.60 (m, 1H), 7.36-7.33 (m, 1H), 7.23 (d, 1H), 5.62-5.52 (s, 2H), 4.55-4.47 (m, 2H), 3.78 (s, 3H), 3.53-3.48 (m, 2H), 3.38 (t, 2H), 3.17 (s, 3H), 2.54-2.52 (m, 3H) |
| 2-333 | δ 10.83 (d, 1H), 8.52-8.48 (m, 1H), 8.15-8.12 (m, 1H), 7.62-7.61 (m, 1H), 7.38-7.34 (m, 1H), 7.25 (d, 1H), 5.57-5.52 (m, 2H), 4.70-4.62 (m, 1H), 4.56-4.46 (m, 3H), 4.32-4.24 (m, 1H), 3.87-3.86 (m, 3H), 2.80-2.72 (m, 1H), 2.54-2.52 (m, 3H), 2.30-2.17 (m, 1H) |
| 2-334 | δ 8.99 (d, 1H), 8.42-8.40 (m, 1H), 8.15-8.12 (m, 1H), 7.59-7.58 (m, 1H), 7.36-7.33 (m, 1H), 7.23 (d, 1H), 5.62-5.55 (s, 2H), 4.51 (q, 2H), 4.20-4.09 (m, 1H), 3.77-3.76 (m, 3H), 3.24-3.20 (m, 3H), 3.15 (s, 3H), 2.53 (s, 3H), 1.10-1.08 (m, 3H) |
| 2-335 | δ 9.30 (t, 1H), 8.45-8.42 (m, 1H), 8.15-8.12 (m, 1H), 7.61 (s, 1H), 7.36-7.33 (m, 1H), 7.22 (d, 1H), 5.57 (s, 2H), 4.51 (q, 2H), 4.32 (t, 1H), 3.79-3.79 (m, 3H), 3.49-3.45 (m, 2H), 3.23-3.22 (m, 6H), 2.53-2.52 (m, 3H) |
| 2-336 | δ 13.34-13.25 (m, 1H), 8.42-8.38 (m, 1H), 8.13-8.10 (m, 1H), 7.62 (s, 1H), 7.38-7.35 (m, 1H), 7.27 (d, 1H), 5.55 (s, 2H), 4.52 (q, 2H), 2.54-2.53 (m, 3H) |
| 2-337 | δ 13.15-13.15 (m, 1H), 8.45-8.41 (m, 1H), 8.13-8.11 (m, 1H), 7.60 (s, 1H), 7.38-7.35 (m, 1H), 7.26 (d, 1H), 5.60-5.55 (s, 2H), 4.52 (q, 2H), 4.09-4.01 (m, 2H), 3.85 (s, 3H), 2.53 (s, 3H), 1.33-1.28 (m, 3H) |
| 2-338 | δ 13.18-13.06 (m, 1H), 8.47-8.42 (m, 1H), 8.15-8.12 (m, 1H), 7.60 (s, 1H), 7.38-7.35 (m, 1H), 7.26 (d, 1H), 6.02-5.91 (m, 1H), 5.60-5.51 (s, 2H), 5.23-5.13 (m, 2H), 4.55-4.44 (m, 4H), 3.84 (s, 3H), 2.54 (s, 3H) |

TABLE 10-13

| Table 10 (Continued) | |
|---|---|
| Compound No. | $^1$H-NMR Data ($CDCl_3$/TMS, ppm) |
| 2-339 | δ 8.07-8.04 (m, 1H), 7.78-7.74 (m, 1H), 7.52-7.49 (m, 1H), 7.29 (dd, 1H), 7.18-7.15 (m, 1H), 5.66-5.61 (s, 2H), 4.51 (q, 2H), 4.00 (d, 3H), 2.49-2.48 (m, 3H), 1.24-1.19 (m, 3H) |
| 2-340 | δ 8.06-8.03 (m, 1H), 7.76-7.71 (m, 1H), 7.49 (d, 1H), 7.29 (dd, 1H), 7.16 (dd, 1H), 5.66-5.55 (s, 2H), 4.51 (ddd, 2H), 4.01-3.98 (m, 3H), 2.49-2.47 (m, 3H), 1.27-1.20 (m, 6H) |

TABLE 10-13-continued

| Table 10 (Continued) | |
|---|---|
| Compound No. | $^1$H-NMR Data ($CDCl_3$/TMS, ppm) |
| 2-341 | δ 8.07-8.04 (m, 1H), 7.80-7.72 (m, 1H), 7.48 (d, 1H), 7.18-7.14 (m, 1H), 5.61-5.55 (s, 2H), 4.61-4.47 (m, 3H), 3.98 (d, 3H), 3.89-3.79 (m, 1H), 2.49-2.47 (m, 3H), 1.30-1.25 (m, 3H) |
| 2-342 | δ 8.10-8.07 (m, 1H), 7.79-7.76 (m, 1H), 7.46 (s, 1H), 7.33-7.29 (m, 1H), 7.19 (dd, 2H), 5.59 (s, 2H), 4.52 (q, 2H), 4.15-4.11 (m, 7H), 2.49 (s, 3H) |
| 2-343 | δ 8.07 (dd, 1H), 7.89-7.78 (m, 1H), 7.51 (m, 1H), 7.17 (dd, 1H), 5.65-5.54 (s, 2H), 4.51 (q, 2H), 4.04-4.03 (m, 3H), 2.49-2.47 (m, 3H), 2.23-2.18 (m, 1H) |
| 2-344 | δ 8.15-8.05 (m, 1H), 7.96-7.86 (m, 1H), 7.53-7.51 (m, 1H), 7.40-7.35 (m, 1H), 7.28-7.23 (m, 1H), 5.59-5.53 (s, 2H), 4.55-4.47 (m, 2H), 4.00 (d, 3H), 2.53-2.51 (m, 3H) |
| 2-345 | δ 8.17-8.14 (m, 1H), 8.08-8.05 (m, 1H), 7.96-7.93 (m, 1H), 7.60-7.57 (m, 1H), 7.53-7.49 (m, 1H), 5.50-5.46 (s, 2H), 4.00-3.99 (m, 3H), 3.49-3.45 (m, 3H), 3.30-3.29 (m, 3H), 3.22 (s, 2H), 2.81-2.80 (m, 3H) |
| 2-346 | δ 8.12-8.09 (m, 1H), 7.91 (d, 1H), 7.57-7.49 (m, 1H), 7.34-7.28 (m, 1H), 7.19-7.15 (m, 1H), 5.44 (s, 2H), 4.23 (q, 2H), 3.97 (d, 3H), 3.24-3.23 (m, 3H), 2.47-2.46 (m, 3H), 1.37 (t, 3H) |
| 3-15 | δ 7.95 (d, 1H), 7.76 (d, 1H), 7.64 (d, 1H), 7.29 (d, 2H), 7.26 (d, 1H), 7.22 (dd, 2H), 7.18 (dd, 1H), 5.44 (s, 2H), 4.10 (s, 2H), 3.95 (s, 3H), 3.77 (s, 3H), 2.50 (s, 3H), 1.28 (s, 9H) |
| 3-19 | δ 8.25(d, 1H), 8.15(d, 1H), 7.66(s, 1H), 7.33(d, 1H), 7.22(d, 1H), 5.47(s, 2H), 4.23(q, 2H), 3.71(s, 3H), 2.52(s, 1H), 1.36(t, 3H) |
| 3-21 | δ 8.07(d, 1H), 7.95(d, 1H), 7.61(s, 1H), 7.36(d, 1H), 7.22(d, 1H), 5.47(s, 2H), 4.91(q, 1H), 4.21(q, 2H), 4.01(s, 3H), 2.52(s, 3H), 1.55(d, 3H), 1.36(t, 3H) |

TABLE 10-14

| Table 10 (Continued) | |
|---|---|
| 3-22 | δ 8.09(d, 1H), 8.03(d, 1H), 7.61(s, 1H), 7.37(d, 1H), 7.24(d, 1H), 6.31(s, 1H), 5.46(s, 2H), 4.95(t, 1H), 4.22(q, 2H), 4.04(dd, 1H), 4.02(s, 3H), 3.83(dd, 1H), 3.67(s, 1H), 2.52(s, 3H), 1.36(t, 3H), |
| 3-23 | δ 8.07(s, 2H), 7.65(s, 1H), 7.33(d, 1H), 7.20(dd, 1H), 7.17(dd, 1H), 5.87(d, 1H), 5.48(s, 2H), 5.43(d, 1H), 4.21 (q, 2H), 3.82(s, 3H), 2.52(s, 3H), 1.36(t, 3H), |
| 3-24 | δ 8.06(d, 1H), 7.77(d, 1H), 7.63(s, 1H), 7.30(d, 1H), 7.18(d, 1H), 5.50(s, 2H), 5.08(d, 2H), 4.20(q, 2H), 3.72(s, 3H), 2.51(s, 3H), 1.35(t, 3H) |
| 3-33 | δ 8.54(d, 1H), 8.27(d, 1H), 7.58(d, 1H), 7.34(d, 1H), 7.22(d, 1H), 5.47(s, 2H), 4.24(q, 2H), 3.71(s, 3H), 3.59(d, 3H), 2.75(s, 1H), 2.51(s, 3H), 1.36(t, 3H) |
| 3-34 | δ 8.17(d, 1H), 8.11(d, 1H), 7.62(s, 1H), 7.34(d, 1H), 7.21(d, 1H), 5.55(t, 1H), 5.47(s, 2H), 4.70(dd, 1H), 4.22(q, 2H), 3.92(s, 3H), 3.80(dd, 1H), 2.53(s, 3H), 1.59(s, 3H), 1.42(s, 3H), 1.36(t, 3H), |
| 3-35 | δ 8.21(d, 1H), 8.11(d, 1H), 7.64(s, 1H), 7.33(d, 1H), 7.20(d, 1H), 6.23(s, 1H), 5.48(s, 2H), 4.21(q, 2H), 4.11(dd, 2H), 3.87(dd, 2H), 3.81(s, 3H), 2.53(s, 3H), 2.15(m, 2H), 1.35(t, 3H) |
| 3-36 | δ 8.14(d, 1H), 8.11(d, 1H), 7.65(s, 1H), 7.32(d, 1H), 7.20(d, 1H), 6.40(s, 1H), 5.49(s, 2H), 4.21(q, 2H), 4.08(m, 2H), 3.95(m, 2H), 3.82(s, 3H), 2.52(s, 3H), 1.36(t, 3H) |
| 3-37 | δ 8.14(d, 1H), 8.11(d, 1H), 8.65(s, 1H), 7.32(d, 1H), 7.20(d, 1H), 6.40(s, 1H), 5.49(s, 2H), 4.21(q, 2H), 4.08(m, 2H), 3.95(m, 2H), 3.82(s, 3H), 2.52(s, 3H), 1.36(t, 3H) |
| 3-44 | δ 8.02(s 1H), 7.59(d, 1H), 7.54(d, 1H), 7.33(dd, 1H), 7.21(d, 1H), 5.43(s, 2H), 4.23(q, 2H), 3.74(s, 3H), 2.85(d, 3H), 2.84(s, 3H), 2.50(s, 3H), 1.36(t, 3H) |
| 3-45 | δ 7.95 (d, 1H), 7.77 (d, 1H), 7.67 (d, 1H), 7.32 (d, 1H), 7.28 (dd, 2H),7.23 (dd, 2H), 7.21 (dd, 1H), 5.43 (s, 2H), 4.11 (s, 2H), 3.95 (s, 3H), 3.77 (s, 3H), 2.80 (q, 2H), 1.30 (t, 3H), 1.28 (s, 9H) |
| 3-47 | δ 8.02(s 1H), 7.63(d, 1H), 7.56(d, 1H), 7.36(dd, 1H), 7.21(d, 1H), 5.42(s, 2H), 4.23(q, 2H), 3.75(s, 3H), 2.86(d, 3H), 2.85(s, 3H), 2.80(q, 2H), 1.36(t, 3H), 1.31(t, 3H) |
| 3-51 | δ 8.52(d, 1H), 8.25(d, 1H), 7.94(s, 1H), 7.54(s, 2H), 6.81(t, 1H), 4.36(q, 2H), 3.80(s, 3H), 3.63(s, 3H), 2.30(s, 3H), 2.04(s, 3H), 1.31(t, 3H) |

TABLE 10-15

| Table 10 (Continued) | |
|---|---|
| Compound No. | $^1$H-NMR Data ($CDCl_3$/TMS, ppm) |
| 3-54 | δ 8.03(d, 1H), 8.02(s, 1H), 7.75(d, 1H), 7.56(d, 1H), 7.52(d, 1H), 6.81(t, 1H), 5.44(s, 2H), 4.20(q, 2H), 3.89(s, 3H), 2.90(t, 2H), 1.68(sext, 2H), 1.35(t, 3H), 1.01(t, 3H) |
| 3-56 | δ 8.05(d, 1H), 8.03(s, 1H), 7.82(d, 1H), 7.56(d, 1H), 7.51(d, 1H), 6.81(t, 1H), 5.44(s, 2H), 4.20(q, 2H), 3.85(s, 3H), 3.50(sep, 1H), 1.35(t, 3H), 1.30(d, 6H) |
| 3-58 | δ 8.16 (s, 1H), 8.00 (d, 1H), 7.80 (d, 1H), 7.61 (dd, 1H), 7.50 (d, 1H), 7.28 (dd, 2H), 7.22 (dd, 2H), 5.42 (s, 2H), 4.13 (s, 2H), 3.96 (s, 3H), 3.82 (s, 3H), 1.28 (s, 9H) |
| 3-59 | δ 8.16(s 1H), 8.01(d, 1H), 7.79(dd, 1H), 7.61(dd, 1H), 7.50(d, 1H), 7.29(d, 2H), 7.22(d, 2H), 5.41(s, 2H), 4.19(q, 2H), 4.13(s, 2H), 3.82(s, 3H), 1.34(t, 3H), 1.28(s, 9H) |
| 3-61 | δ 8.16(s 1H), 8.05(d, 1H), 7.64(dd, 1H), 7.54(d, 1H), 5.44(s, 2H), 4.21(q, 2H), 3.80(s, 3H), 2.91 (q, 2H), 1.36(t, 3H), 1.35(t, 3H) |
| 3-62 | δ 8.13(s 1H), 8.03(d, 1H), 7.62(dd, 1H), 7.52(d, 1H), 5.45(s, 2H), 4.21(q, 2H), 3.70(s, 3H), 3.04(q, 2H), 2.18(s, 3H), 1.36(t, 3H), 1.35(t, 3H) |
| 3-68 | δ 8.13(s 1H), 8.02(d, 1H), 7.62(dd, 1H), 7.52(d, 1H), 5.45(s, 2H), 4.20(q, 2H), 3.72(s, 3H), 2.66(s, 3H), 2.18(s, 3H), 1.36(t, 3H) |
| 3-69 | δ 8.10(s 1H), 8.02(d, 1H), 7.64(dd, 1H), 7.55(d, 1H), 5.46(s, 2H), 4.24(q, 2H), 3.97(s, 3H), 2.37(s, 3H), 2.89(s, 3H), 1.37(t, 3H) |
| 3-72 | δ 8.05(s 1H), 7.63(d, 1H), 7.54(d, 1H), 7.39(s, 1H), 7.18(d, 1H), 5.40(s, 2H), 4.18(q, 2H), 3.79(s, 3H), 2.86(d, 3H), 2.85(s, 3H), 1.34(t, 3H) |
| 3-74 | δ 8.16(s 1H), 8.02(d, 1H), 7.79(dd, 1H), 7.61(dd, 1H), 7.50(d, 1H), 7.29(d, 2H), 7.22(d, 2H), 5.38(s, 2H), 4.38(sep, 1H), 4.12(s, 2H), 3.82(s, 3H), 1.32(d, 6H), 1.28(s, 9H) |
| 3-75 | δ 8.16(s, 1H), 7.80(m, 2H), 7.60(dd, 1H), 7.50(d, 1H), 7.13-7.21(m, 4H), 5.42(s, 2H), 4.13-4.10(m, 2H), 3.85(s, 3H), 3.00(d, 3H), 2.04(s, 2H), 1.32(t, 3H), 1.28(s, 9H) |
| 3-76 | δ 8.16(s, 1H), 7.81(s, 2H), 7.61(dd, 1H), 7.50(d, 1H), 7.30-7.22(m, 4H), 5.46(s, 2H), 4.16-4.09(m, 2H), 3.84(s, 3H), 3.00(s, 2H), 2.81(s, 3H), 2.80(s, 3H), 2.04(s, 9H), 1.37-1.30(m, 3H) |
| 3-84 | δ 8.32(s 1H), 8.18(d, 1H), 7.93(d, 1H), 7.91(d, 1H), 7.69(dd, 1H), 7.54(d, 1H), 6.81(t, 1H), 4.66(d, 2H), 4.61 (q, 2H), 4.17(s, 3H), 2.17(s, 3H) |
| 3-90 | δ 8.14(s 1H), 8.10(d, 1H), 7.88(d, 1H), 7.62(dd, 1H), 7.46(d, 1H), 4.32(q, 2H), 3.93(q, 2H), 3.91(s, 3H), 2.31(s, 3H), 1.99(s, 3H), 1.37(t, 3H), 1.00(t, 3H) |

TABLE 10-16

| Table 10 (Continued) | |
|---|---|
| Compound No. | $^1$H-NMR Data ($CDCl_3$/TMS, ppm) |
| 3-93 | δ 8.11(d, 1H), 8.10(d, 1H), 7.86(d, 1H), 7.60(dd, 1H), 7.44(d, 1H), 4.52(sep, 1H), 4.02(sep, 1H), 3.89(s, 3H), 2.30(s, 3H), 2.03(s, 3H), 1.35(d, 6H), 0.94(d, 6H) |
| 3-94 | δ 8.12(d, 1H), 8.10(d, 1H), 7.85(d, 1H), 7.59(dd, 1H), 7.42(d, 1H), 3.86(s, 3H), 2.28(s, 3H), 2.08(s, 3H), 1.41(s, 9H), 0.91(s, 9H) |
| 3-95 | δ 8.13(d, 1H), 8.06(d, 1H), 7.84(d, 1H), 7.62(dd, 1H), 7.46-7.10(m, 11H), 5.30(s, 2H), 4.94(s, 2H), 3.81(s, 3H), 2.34(s, 3H), 2.07(s, 3H) |
| 3-96 | δ 8.14(s 1H), 8.07(d, 1H), 7.90(d, 1H), 7.64(dd, 1H), 7.49(d, 1H), 4.63(q, 2H), 4.33(q, 2H), 4.00(s, 3H), 2.39(s, 3H), 2.04(s, 3H) |
| 3-97 | δ 8.14(d, 1H), 8.06(d, 1H), 7.88(d, 1H), 7.65(dd, 1H), 7.49(d, 1H), 6.09(tt, 1H), 5.66(tt, 1H), 4.44(dt, 2H), 4.13(dt, 2H), 3.99(s, 3H), 2.37(s, 3H), 2.04(s, 3H) |
| 3-98 | δ 8.13(d, 1H), 8.08(d, 1H), 7.87(d, 1H), 7.62(dd, 1H), 7.46(d, 1H), 6.08(ddt, 1H), 5.63(ddt, 1H), 5.37(dd, 1H), 5.27(dd, 1H), 5.03(dd, 1H), 4.89(dd, 1H), 4.77 (dt, 2H), 4.39(dt, 2H), 3.91(s, 3H), 2.34(s, 3H), 2.06(s, 3H) |
| 3-113 | δ 8.50(s, 1H), 8.24(d, 1H), 7.98(d, 1H), 7.67(d, 1H), 7.66(d, 1H), 4.35(q, 2H), 4.11(s, 3H), 2.37(s, 3H), 2.34(s, 6H), 1.39(t, 3H) |
| 3-114 | δ 8.31(s, 1H), 8.12(d, 1H), 7.99(s, 1H), 7.93(d, 1H), 7.72-7.16(m, 12H), 4.31 (q, 2H), 3.36(s, 3H), 1.38 (t, 3H) |
| 3-117 | δ 7.96 (d, 1H), 7.89 (d, 1H), 7.77 (d, 1H), 7.42 (dd, 1H), 7.36 (ddd, 1H), 7.31 (ddd, 1H), 7.22-7.29 (m, 4H), 5.44 (s, 2H), 4.11 (s, 2H), 3.95 (s, 3H), 3.79 (s, 3H), 1.28 (s, 9H) |
| 3-120 | δ 8.60 (s, 1H), 8.26 (s, 1H), 8.03-7.96 (m, 1H), 7.65-7.59 (m, 2H), 7.43 (t, 1H), 7.19-7.16 (m, 2H), 4.16 (s, 3H), 3.64-3.63 (m, 3H), 3.34-3.29 (m, 2H), 1.97-1.88 (m, 1H), 1.01-0.98 (m, 3H) |

TABLE 10-16-continued

| Table 10 (Continued) | |
|---|---|
| Compound No. | $^1$H-NMR Data ($CDCl_3$/TMS, ppm) |
| 3-121 | δ 8.35-8.21 (m, 2H), 8.11-8.09 (m, 1H), 7.65-7.39 (m, 3H), 5.47 (s, 2H), 4.25-4.21 (m, 2H), 3.78-3.71 (m, 9H), 1.38-1.34 (m, 3H) |
| 3-122 | δ 11.04-10.99 (m, 1H), 8.13-8.11 (m, 1H), 8.02-7.93 (m, 2H), 5.38-5.33 (s, 2H), 4.33-4.32 (m, 3H), 4.29-4.09 (m, 4H), 1.39-133 (m, 6H) |
| 3-123 | δ 12.7(s, 1H), 9.10(d, 1H), 8.04(s, 1H), 7.61(d, 1H), 7.36(dd, 1H), 7.24(d, 1H), 5.39(s, 2H), 4.24(s, 3H), 4.21(q, 2H), 2.54(s, 3H), 2.32(s, 3H), 1.37(t, 3H) |
| 3-126 | δ 8.17(d, 1H), 8.01(s, 1H), 7.72(d, 1H), 7.58(d, 1H), 7.53(d, 1H), 5.45(s, 2H), 4.21(q, 2H), 4.01(m, 2H), 3.95(s, 3H), 2.21(m, 4H), 1.36(t, 3H) |

TABLE 10-17

| Table 10 (Continued) | |
|---|---|
| Compound No. | $^1$H-NMR Data ($CDCl_3$/TMS, ppm) |
| 3-128 | δ 8.12(d, 1H), 7.72(d, 1H), 7.52(s, 1H), 7.30(d, 1H), 7.15(dd, 1H), 5.46(s, 2H), 4.20(q, 2H), 3.93(t, 2H), 3.87(s, 3H), 2.50(s, 3H), 2.24(m, 2H), 2.16(m, 2H), 1.35(t, 3H) |
| 3-129 | δ 8.15(d, 1H), 7.75(dd, 1H), 7.73(d, 1H), 7.44(dd, 1H), 7.31(m, 2H), 5.47(s, 2H), 4.20(q, 2H), 3.94(t, 2H), 2.24(m, 2H), 2.17(m, 2H), 1.35(t, 2H) |
| 3-130 | δ 8.19(d, 1H), 8.04(s, 1H), 7.79(d, 1H), 7.60(dd, 1H), 7.53(d, 1H), 5.45(s, 2H), 4.52(t, 2H), 4.24(t, 2H), 4.22(q, 2H), 3.96(s, 3H), 1.36(t, 3H) |
| 3-138 | δ 8.09(d, 1H), 8.01(s, 1H), 7.94(d, 1H), 7.55(dd, 1H), 7.40(d, 1H), 5.46(s, 2H), 4.19(q, 2H), 3.75(s, 3H), 3.24(t, 2H), 3.00(t, 2H), 1.34(t, 3H) |
| 4-16 | δ 8.17(d, 1H), 7.87(dd, 1H), 7.84(d, 1H), 7.54(s, 1H), 7.30(s, 1H), 7.19(d, 1H), 6.82(q, 1H), 4.83(s, 2H), 4.17(q, 2H), 3.68(s, 3H), 2.71(t, 3H), 2.51(s, 3H), 1.33(t, 3H) |
| 4-46 | δ 8.19(d, 1H), 8.06(s, 1H), 7.92(dd, 1H), 7.88(d, 1H), 7.63(dd, 1H), 7.52(d, 1H), 6.41(q, 1H), 4.84(s, 2H), 4.18(q, 2H), 3.74(s, 3H), 2.72(d, 3H), 1.33(t, 3H) |
| 4-50 | δ 8.08(d, 1H), 8.04(s, 1H), 8.02(dd, 1H), 7.82(d, 1H), 7.60(dd, 1H), 7.49(d, 1H), 4.80(s, 2H), 4.34(m, 1H), 3.63(s, 3H), 2.62(s, 6H), 1.28(d, 6H) |
| 4-60 | δ 8.45(m, 3H), 7.58(d, 1H), 7.35(m, 3H), 4.56(q, 2H), 4.23(q, 2H), 3.55(s, 3H), 2.31(s, 3H), 1.85(s, 3H) |
| 4-62 | δ 8.15(d, 1H), 7.80(dd, 1H), 7.67(dd, 1H), 7.58(d, 1H), 7.41(dd, 1H), 7.32(m, 2H), 4.40(q, 2H), 3.70(s, 3H), 3.61(s, 3H), 2.24(s, 3H) |
| 4-67 | δ 7.78(dd, 1H), 7.72(d, 1H), 7.62(d, 1H), 7.33(d, 1H), 7.28(d, 1H), 7.15(dd, 1H), 4.22(q, 2H), 3.63(s, 3H), 2.51(s, 3H), 2.37(s, 3H), 2.21(s, 3H), 1.32(t, 3H) |
| 4-68 | δ 8.20(d, 1H), 7.99(dd, 1H), 7.86(d, 1H), 7.58(d, 1H), 7.35(d, 1H), 7.18(d, 1H), 4.26(q, 2H), 3.59(s, 3H), 3.23(s, 3H), 2.52(s, 3H), 2.25(s, 3H), 1.32(t, 3H) |
| 4-100 | δ 8.15(d, 1H), 7.75(dd, 1H), 7.70(d, 1H), 7.62(dd, 1H), 7.44(d, 1H), 7.36(d, 1H), 4.42(q, 2H), 3.65(s, 3H), 2.27(s, 3H), 2.23(s, 3H), 1.32(t, 3H) |
| 4-101 | δ 8.16(d, 1H), 7.63(m, 3H), 7.45(d, 1H), 7.40(d, 1H), 4.11(q, 2H), 3.68(s, 3H), 2.31(s, 3H), 2.21(s, 3H), 1.25(t, 3H) |
| 4-104 | δ 8.14(d, 1H), 7.83(dd, 1H), 7.78(d, 1H), 7.61(dd, 1H), 7.44(d, 1H), 7.32(d, 1H), 5.18(s, 2H), 4.11(q, 2H), 3.73(s, 3H), 3.39(s, 3H), 2.22(s, 3H), 1.26(t, 3H) |
| 4-109 | δ 8.11(dd, 1H), 7.61 (dd, 1H), 7.53(d, 1H), 7.48(d, 1H), 7.43(d, 1H), 4.11(q, 2H), 3.75(s, 3H), 3.62(s, 3H), 2.51(s, 3H), 2.22(s, 3H), 1.24(t, 3H) |

TABLE 10-18

| Table 10 (Continued) | |
|---|---|
| Compound No. | $^1$H-NMR Data ($CDCl_3$/TMS, ppm) |
| 4-111 | δ 8.13(m, 2H), 7.91(dd, 1H), 7.84(d, 1H), 7.58(dd, 1H), 7.16(d, 1H), 4.25(q, 2H), 3.70(s, 3H), 3.52(s, 3H), 2.24(s, 3H), 1.32(t, 3H) |
| 4-113 | δ 8.17(d, 1H), 7.95(dd, 1H), 7.89(m, 2H), 7.71(dd, 1H), 7.51(d, 1H), 4.25(q, 2H), 3.75(s, 3H), 3.62(s, 3H), 2.73(s, 6H), 2.25(s, 3H), 1.33(t, 3H) |
| 7-48 | δ 8.81 (s, 1H), 8.09 (s, 1H), 7.60 (dd, 1H), 7.51 (d, 1H), 5.27 (s, 2H), 4.18 (q, 2H), 3.95 (s, 3H), 2.91 (s, 6H), 1.34 (t, 3H) |
| 9-5 | δ 7.79(dd, 1H), 7.36(m, 4H), 7.27(m, 4H), 4.84(s, 2H), 4.64(d, 1H), 4.52(d, 1H), 4.16(m, 1H), 3.53(s, 3H), 1.18(d, 3H), 1.03(d, 3H) |

TABLE 10-18-continued

| Table 10 (Continued) | |
|---|---|
| Compound No. | $^1$H-NMR Data ($CDCl_3$/TMS, ppm) |
| 9-8 | δ 7.83(dd, 1H), 7.40(m, 4H), 5.01(s, 2H), 4.17(m, 1H), 3.63(s, 3H), 1.18(d, 1H), 1.04(d, 1H) |
| 9-11 | δ 7.79(dd, 1H), 7.40(m, 4H), 5.78(q, 1H), 4.62(s, 2H), 4.25(m, 1H), 3.59(s, 3H), 2.90(d, 3H), 1.18(d, 3H), 1.10(d, 3H) |

Examples of useful plants for which the nitrogen-containing condensed heterocyclic compound of the present invention or a salt thereof can be used include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchard grass, *sorghum*, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., *chrysanthemum*, rose, carnation, orchid, tulip, lily, etc.), garden trees (e.g., ginkgo trees, cherry trees, Japanese aucuba, etc.) and forest trees (e.g., *Abies sachalinensis, Picea jezoensis*, pine, yellow cedar, Japanese cedar, hinoki cypress, *eucalyptus*, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr. Such a rice variety is sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The nitrogen-containing condensed heterocyclic compound of the present invention or a salt thereof can be used for these plants as well. The compound of the present invention does not do damage to these useful plants.

Examples of the weed that can be controlled by the nitrogen-containing condensed heterocyclic compound of the present invention or a salt thereof include dicotyledonous genera such as *Ipomoea, Lindernia, Sesbania, Abutilon, Matricaria, Rorippa, Urtica, Lamium, Xanthium, Sinapis, Rotala, Veronica, Papaver, Chenopodium, Trifolium, Portulaca, Viola, Pharbitis, Galeopsis, Datura, Solanum, Capsella, Cirsium, Sonchus, Galinsoga, Stellaria, Senecio, Amaranthus, Ambrosia, Kochia, Lamium, Leipidium, Polygonum, Galium, Centaurea*, and *Artemisia*.

Examples of the weed that can be controlled by the nitrogen-containing condensed heterocyclic compound of the present invention or a salt thereof include monocotyledonous genera such as *Poa, Bolboschoenus, Festuca, Setaria, Eleusine, Sagittaria, Agropyron, Ischaemum, Cyperus, Avena, Bromus, Panicum, Cynodon, Monochoria, Alopecurus, Paspalum, Commelina, Fimbristylis, Lolium, Brachiaria, Agrostis, Eleocharis, Echinochloa esculenta, Scirpus, Schoenoplectus, Digitaria*, and *Sorghum*.

Other examples of the weed that can be controlled by the nitrogen-containing condensed heterocyclic compound of the present invention or a salt thereof include Spirogyra sp., *Amaranthus retroflexus, Amaranthus viridis, Setaria faberi, Leersia japonica, Leptochloa chinensis, Lindernia angustifolia, Lindernia procumbens, Dopatrium junceum, Ipomoea hederacea, Lindernia dubia, Sida spinosa, Polygonum pensylvanicum, Sesbania exaltata, Geranium carolinense, Chenopodium ambrosioides, Conyza bonariensis, Setaria italica, Amaranthus powellii, Polygonum cuspidatum, Abutilon theophrasti, Matricaria perforata, Polygonum longisetum, Veronica polita, Echinochloa crus*-galli, *Amaranthus lividus, Solanum nigrum, Schoenoplectus juncoides* (Roxb.) *Palla, Bromus catharticus, Murdannia keisak, Bolboschoenus fluviatilis, Scirpus maritimus, Bromus tectorum, Sagittaria pygmaea* Miq, *Rumex obtusifolius, Leersia oryzoides* (L.) Sw., *Setaria viridis, Cassia obtusifolia, Conyza sumatrensis, Veronica persica, Spirodela polyrhiza, Xanthium canadens, Coreopsis lanceolata, Panicum dichotomiflorum, Asclepias syriaca, Euphorbia maculata, Plantago*

*asiatica, Rudbeckia laciniata, Amaranthus palmeri, Avena sativa, Xanthium strumarium, Avena sterilis, Eleusine indica, Sagittaria trifolia, Erodium cicutarium, Cerastium glomeratum, Matricaria matricarioides, Matricaria chamomilla, Vicia angustifolia, Bromus secalinus, Avena fatua, Rotala indica* Koehne, *Rumex japonicus, Paspalum distichum, Bromus remotiflorus, Cyperus esculentus, Galium kinuta, Setaria glauca, Pueraria lobata, Eleocharis kuroguwai* Ohwi, *Sagittaria trifolia Caerulea, Ambrosia trifida, Hydrilla verticillata, Bolboschoenus maritimus* (L.) *Palla, Chrysanthemum segetum, Cyperus iria, Monochoria vaginalis, Echinochloa colona, Alisma plantago*-aquatica, *Oryza sativa, Polygonum lapathifolium, Eleusine coracana, Schoenoplectus nipponicus, Cyperus malaccensis, Agropyron repens, Sorghum vulgare, Apera spica*-venti, *Chenopodium album, Trifolium repens, Datura stramonium, Equisetum arvense, Poa annua, Bromus japonicus, Alopecurus aequalis, Portulaca oleracea, Solidago altissima, Sorghum halepense, Brassica juncea, Taraxacum officinale, Convolvulus arvensis, Oenanthe javanica, Polygonum convolvulus, Echinochloa oryzicola* Vasing, *Ischaemum rugosum, Veronica arvensis, Cyperus difformis* L., *Amaranthus rudis, Phleum pratense, Ludwigia prostrata* Roxburgh, *Commelina communis, Panicum texanum, Euphorbia helioscopia, Festuca parvigluma, Rumex crispus, Capsella bursa*-pastoris, *Euphorbia pseudochamaesyce, Brachiaria plantaginea, Lolium multiflorum, Cirsium japonicum, Alopecurus myosuroides, Sinapis arvensis, Senecio vulgaris, Galinsoga ciliata, Amaranthus tricolor, Stellaria media, Cyperus papyrus, Cyperus rotundus, Amaranthus spinosus, Polygonum persicaria, Senecio cannabifolius, Papaver rhoeas, Helianthus annuus, Lamium purpureum, Kyllinga gracillima, Ammannia multiflora, Erigeron canadensis, Potamogeton distinctus* A. Benn, *Amaranthus tuberculatus, Viola arvensis, Cirsium purpuratum, Ambrosia artemisiifolia, Schoenoplectus tabernaemontani, Veronica hederaefolia, Alopecurus myosuroides, Desmodium tortuosum, Plantago lanceolata, Alisma canaliculatum* A. Br. et Bouche, *Kochia scoparia, Lolium rigidum, Ammannia coccinea, Lolium perenne, Scirpus juncoides* Roxburgh, *Lamium amplexicaule, Najas graminea, Amaranthus hybridus, Eleocharis acicularis* L., *Portulaca grandiflora, Ipomoea lacunosa, Ipomoea purpurea, Ipomoea hederacea* var. integriuscula, *Commelina benghalensis, Monochoria korsakowii, Cyperus serotinus* Rottboel, *Elatine triandra* Schk, *Digitaria ciliaris, Digitaria sanguinalis, Sorghum bicolor, Galium aparine, Artemisia princeps, Viola tricolor, Raphanus raphanistrum, Myosotis arvensis, Alisma canaliculatum*, and *Cyperus flaccidus*. The nitrogen-containing condensed heterocyclic compound of the present invention or a salt thereof inhibits growth of these weeds.

When the nitrogen-containing condensed heterocyclic compound of the present invention or a salt thereof is used, it is commonly formulated into a convenient form for application, which is prepared by the usual method for preparing agrochemical formulations.

That is, the compound represented by the general formula (1) of the present invention or a salt thereof and an appropriate inactive carrier, and if needed an adjuvant, are blended at an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural or horticultural herbicide) of the present invention can optionally contain an additive usually used for agrochemical formulations or agricultural or horticultural herbicides in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, and also two or more of them may be used in combination.

Examples of the solid carrier include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these may be used alone, and also two or more of them may be used in combination.

Examples of the liquid carrier include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as gamma-butyrolactone; amides, such as N,N-dimethylformamide, N,N-diethylformamide, N,N-dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these may be used alone, and also two or more of them may be used in combination.

Exemplary surfactants used as a dispersant, a wetting agent, a spreader, a sticking/spreading agent, etc. include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, and also two or more of them may be used in combination.

Examples of the binder or the tackifier include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickener include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorant include inorganic pigments, such as iron oxide, titanium oxide and Prussian blue; and organic dyes, such as alizarin dyes, azo dyes and metal phthalocyanine dyes.

Examples of the antifreezing agent include polyhydric alcohols, such as ethylene glycol, diethylene glycol, propylene glycol and glycerin.

Examples of the adjuvant serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agent include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservative include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the agricultural or horticultural herbicide of the present invention can be adjusted as needed, and basically, the amount of the active ingredient compound is appropriately selected from the range of 0.01 to 90 parts by weight in 100 parts by weight of the agricultural or horticultural herbicide. For example, in the case where the agricultural or horticultural herbicide is a dust, a granule, an emulsifiable concentrate or a wettable powder, it is suitable that the amount of the active ingredient compound is 0.01 to 50 parts by weight (0.01 to 50% by weight relative to the total weight of the agricultural or horticultural herbicide).

The application rate of the nitrogen-containing condensed heterocyclic compound of the present invention or a salt thereof may vary with various factors, for example, the purpose, the target weed, the growing conditions of crops, the tendency of weed infestation, the weather, the environmental conditions, the formulation, the application method, the application site, the application timing, etc., but basically, the application rate of the active ingredient compound is appropriately selected from the range of 0.001 g to 10 kg, and preferably 0.01 g to 1 kg per 10 acres depending on the purpose.

In order to control weeds, the agricultural or horticultural herbicide comprising the nitrogen-containing condensed heterocyclic compound of the present invention or a salt thereof as an active ingredient, with or without appropriate dilution or suspension in water etc., is applied directly to the foliage of weeds in an amount effective for the control of the weeds. In addition to foliar application, seed treatment for useful plants, such as dipping, dust coating and calcium peroxide coating, can be performed. Further, treatment of soil or growing media may also be performed, and examples of such treatment include whole soil incorporation, planting row treatment, bed soil incorporation, plug seedling treatment, planting hole treatment, plant foot treatment, top-dressing, treatment of nursery boxes for paddy rice, and submerged application.

Exemplary methods of seed treatment for useful plants include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of a solid or liquid formulation and an adhesive carrier such as resins and polymers; and application of a solid or liquid formulation to the vicinity of seeds at the same time as seeding. The term "seed" in the seed treatment refers to a plant body which is in the early stages of cultivation and used for useful plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "growing medium" in the method of the present invention for using an agricultural or horticultural herbicide refers to a support medium for crop cultivation, in particular a support medium which allows crop plants to spread their roots therein, and the materials are not particularly limited as long as they allow useful plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

In the case of the application to nursery boxes for paddy rice, the type of the formulation may vary depending on whether the application is performed at the time of seeding, in the greening period, at the time of transplanting, or the like. For example, a dust, a water-dispersible granule, a granule, or the like may be used. Such a formulation can be applied by incorporation into nursery soil. For example, a dust, a water-dispersible granule, a granule, or the like may be incorporated into bed soil, covering soil, or the whole nursery soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner. In the case of using spraying equipment, it can be any equipment that is usually used, and examples include tractor mounted boom sprayers, manned helicopters, radio-controlled helicopters, radio-controlled boats, drones, one-shot sprayers, power (manual or automatic) sprayers, carry power sprayers, backpack power sprayers, and hand operated sprayers.

For the expansion of the range of target weeds and the appropriate time for weed control, or for dose reduction, the nitrogen-containing condensed heterocyclic compound of the present invention or a salt thereof can be used after mixed with other herbicides, plant growth regulators, phytotoxicity reducers (also called safeners), soil conditioners, fertilizers, and/or the like. Further, the compound of the present invention or a salt thereof can be used after mixed with agricultural or horticultural insecticides, acaricides, nematicides, microbicides, biopesticides and/or the like depending on the situation. Non-limiting examples of typical compounds are described below.

Exemplary herbicides used for the same purposes as above include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, iofensulfuron, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epyrifenacil, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, clacyfos, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dioxopyritrione, dicamba, cycluron, cycloate, cycloxydim, diclosulam, cyclosulfamuron, cyclopyranil, cyclopyrimorate, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, cypyrafluone, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimesulfazet, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, tiafenacil, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetflupyrolimet, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, triafamone, tri-allate, trietazine, tricamba, triclopyr, tridiphane, tritac, tritosulfuron, tripyrasulfone, trifludimoxazin, triflusulfuron, triflusulfuron-methyl, trifluralin, trifloxysulfuron, tripropindan, tribenuron-methyl, tribenuron, trifop, trifopsime, trimeturon, tolpyralate, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, halauxifen, haloxyfop, haloxyfop-P, haloxyfop-methyl, halosafen, halosulfuron, halosulfuron-methyl, bixlozone, picloram, picolinafen, bicyclopyrone, bispyribac, bispyribac-sodium, pydanon, pinoxaden, bipyrazone, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenquinotrione, fenthiaprop, fenteracol, fentrazamide, fenpyrazone, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, florpyrauxifen, hexachloroacetone, hexazinone, pethoxamid, benazolin, penoxsulam, pebulate, beflubutamid, beflubutamid-M, vernolate, perfluidone, bencarbazone, benquitrione, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, lancotrione, linuron, rimisoxafen, rimsulfuron, lenacil, rhodethanil, calcium peroxide and methyl bromide. Biopesticides available as herbicides, such as *Xanthomonas campestris*, can also be used after mixed with the compound of the present invention or a salt thereof.

Examples of the phytotoxicity reducer (also called a safener) include 1,8-naphthalic anhydride, isoxadifen-ethyl, furilazole, cyprosulfamide, cyometrinil, dichlormid, dimepiperate, thiencarbazone-methyl, fenchlorazone-ethyl, fenclorim, fluxofenim, flurazole, benoxacor, metcamifen, and mefenpyr-diethyl.

Other examples of the biopesticide include natural predators such as *Encarsia formosa, Aphidius colemani, Aphidoletes aphidimyza, Diglyphus isaea, Dacnusa sibirica, Phytoseiulus persimilis, Amblyseius cucumeris*, and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one, and 14-methyl-1-octadecene.

EXAMPLES

Hereinafter, representative Examples in relation to the present invention are shown, but the present invention is not limited thereto.

Production Example 1

Production of (E)-(5-methylthio)-6-(1-methyl-5-(trifluoromethylthio)benzimidazol-2-yl)-2-pyridinecarboxaldehyde O-ethyl oxime (Compound No. 3-82), (E)-(5-methylsulfinyl)-6-[1-methyl-5-(trifluoromethylthio)benzimidazol-2-yl]-2-pyridinecarboxaldehyde O-ethyl oxime (Compound No. 3-83), and (E)-(5-methylsulfonyl)-6-[1-methyl-5-(trifluoromethylthio)benzimidazol-2-yl]-2-pyridinecarboxaldehyde O-ethyl oxime (Compound No. 1-256)

Production Example 1-1

Production of 2-[6-(1,3-dioxan-2-yl)-3-ethylsulfonylpyridin-2-yl]-1-methy 1-5-(trifluoromethylthio) benzimidazole

[Chem. 36]

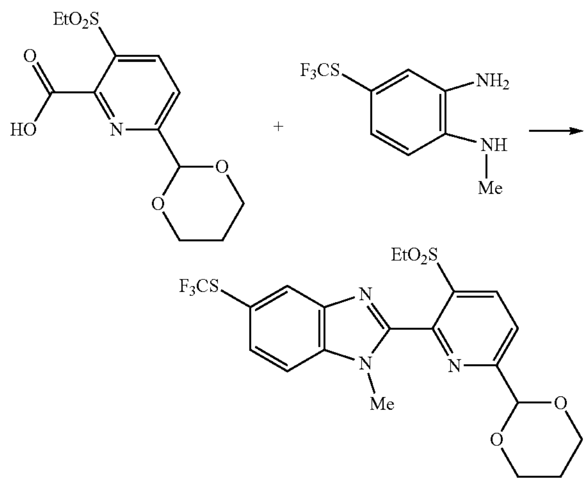

To a pyridine solution (5.0 mL) of 6-(1,3-dioxan-2-yl)-3-ethylsulfonylpyridine-2-carboxylic acid (0.50 g, 1.7 mmol), $N^1$-methyl-4-(trifluoromethylthio)benzene-1,2-diamine (0.37 g, 1.7 mmol), 1-hydroxybenzotriazole monohydrate (0.23 g, 1.7 mmol), and 1-(3-dimethylaminopropyl)-3-ethylcarbodiimide hydrochloride (0.35 g, 1.8 mmol) were added at room temperature, and the mixture was stirred overnight. After the completion of the reaction, the reaction mixture was concentrated in vacuo. Ethyl acetate and 0.5 M hydrochloric acid were added to the residue, and extraction was performed. The organic layer was dried over anhydrous magnesium sulfate and then concentrated in vacuo. Acetic acid (5.0 mL) was added to the residue, and the mixture was stirred at 120° C. for 1 hour. After the completion of the reaction, the reaction mixture was concentrated in vacuo. Ethyl acetate and a saturated aqueous sodium hydrogen carbonate solution were added to the residue, and extraction was performed. The organic layer was dried over anhydrous magnesium sulfate and then dried in vacuo. The residue was purified by silica gel column chromatography to give 2-[6-(1,3-dioxan-2-yl)-3-ethylsulfonylpyridin-2-yl]-1-methy 1-5-(trifluoromethylthio)benzimidazole (0.71 g, 1.5 mmol).

Yield: 88%

Physical property: Melting point: 185 to 186° C.

Production Example 1-2

Production of 2-[6-(1,3-dioxan-2-yl)-3-methylthio-pyridin-2-yl]-1-methyl-5-(trifluoromethylthio)benz-imidazole

[Chem. 37]

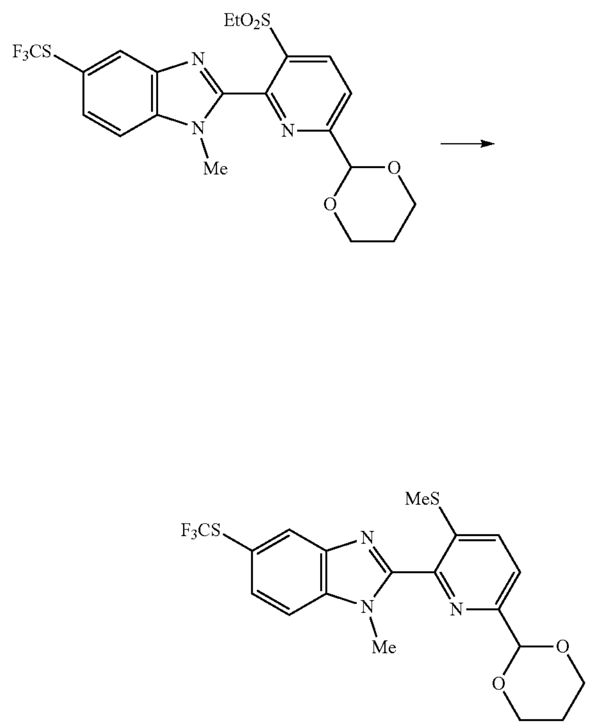

To an N,N-dimethylformamide solution (4 mL) of 2-[6-(1,3-dioxan-2-yl)-3-ethylsulfonylpyridin-2-yl]-1-methy 1-5-(trifluoromethylthio)benzimidazole (0.20 g, 0.41 mmol), a sodium salt of methanethiol (58 mg, 0.82 mmol) was added at room temperature, and the mixture was stirred for 1 hour. After the completion of the reaction, a saturated aqueous ammonium chloride solution was added, and ethyl acetate extraction was performed. The organic layer was dried over anhydrous magnesium sulfate and then dried in vacuo. The residue was purified by silica gel column chromatography to give 2-[6-(1,3-dioxan-2-yl)-3-methylthio-pyridin-2-yl]-1-methyl-5-(trifluoromethylthio)benzimidazole (0.18 g, 0.41 mmol).

Yield: 100%

Physical property: Melting point: 42 to 43° C.

Production Example 1-3

Production of 5-methylthio-6-(1-methyl-5-((trifluo-romethyl)thio)-benzimidazol-2-yl)-2-pyridinecar-boxaldehyde

[Chem. 38]

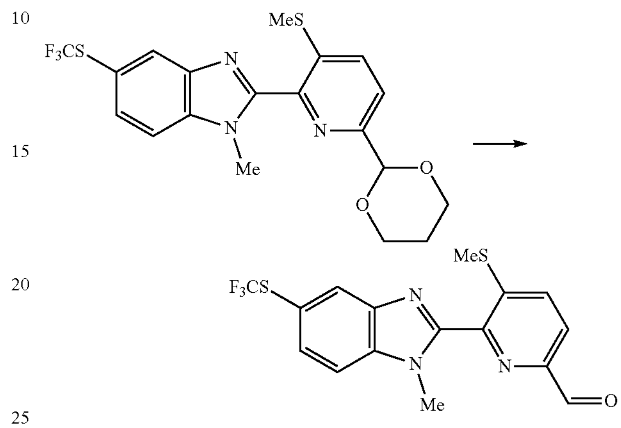

To a trifluoroacetic acid:water (2:1) solution (5 mL) of 2-[6-(1,3-dioxan-2-yl)-3-methylthiopyridin-2-yl]-1-methyl-5-(trifluoromethylthio)benzimidazole (0.18 g, 0.41 mmol), p-toluenesulfonic acid monohydrate (78 mg, 0.41 mmol) was added at room temperature, and the mixture was heated under reflux for 3 hours. After the completion of the reaction, the reaction mixture was dried in vacuo. A saturated aqueous sodium hydrogen carbonate solution was added, and ethyl acetate extraction was performed. The organic layer was dried over anhydrous magnesium sulfate and then dried in vacuo to give 5-methylthio-6-(1-methyl-5-((trifluo-romethyl)thio)-benzimidazol-2-yl)-2-pyridinecarboxalde-hyde (0.16 g, 0.41 mmol).

Yield: 100%

Production Example 1-4

Production of (E)-(5-methylthio)-6-(1-methyl-5-(trifluoromethylthio)benzimidazol-2-yl)-2-pyridin-ecarboxaldehyde O-ethyl oxime (Compound No. 3-82)

[Chem. 39]

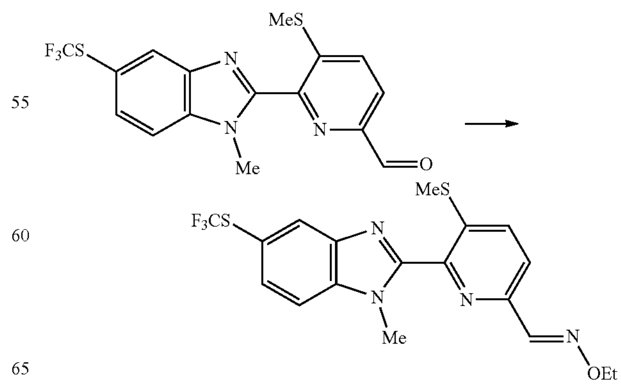

To a chloroform solution (2 mL) of 5-methylthio-6-(1-methyl-5-((trifluoromethyl)thio)-benzimidazol-2-yl)-2-pyridinecarboxaldehyde (160 mg, 0.41 mmol), O-ethylhydroxylamine hydrochloride (60 mg, 0.62 mmol) and pyridine (49 μL, 0.62 mmol) were successively added at room temperature, and the mixture was stirred overnight. After the completion of the reaction, 1 M hydrochloric acid was added, and chloroform extraction was performed. The organic layer was dried over anhydrous magnesium sulfate and then dried in vacuo. The residue was purified by silica gel column chromatography to give (E)-(5-methylthio)-6-(1-methyl-5-(trifluoromethylthio)benzimidazol-2-yl)-2-pyridinecarboxaldehyde O-ethyl oxime (202 mg, 0.41 mmol)

Yield: 100%
Physical property: Melting point: 116 to 117° C.

Production Example 1-5

Production of (E)-(5-methylsulfinyl)-6-[1-methyl-5-(trifluoromethylthio)benzimidazol-2-yl]-2-pyridinecarboxaldehyde O-ethyl Oxime (Compound No. 3-83) and (E)-(5-methylsulfonyl)-6-[1-methyl-5-(trifluoromethylthio)benzimidazol-2-yl]-2-pyridinecarboxaldehyde O-ethyl Oxime (Compound No. 1-256)

[Chem. 40]

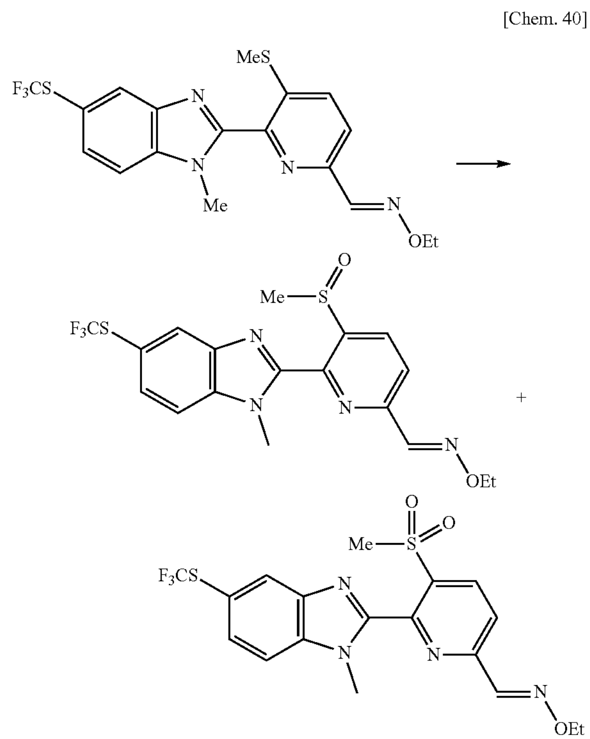

To an ethyl acetate solution (4.0 mL) of (E)-(5-methylthio)-6-(1-methyl-5-(trifluoromethylthio)benzimidazol-2-yl)-2-pyridinecarboxaldehyde O-ethyl oxime (0.16 g, 0.38 mmol), m-chloroperoxybenzoic acid (0.10 g, 0.38 mmol) was added at room temperature, and the mixture was stirred for 2 hours. After the completion of the reaction, a saturated aqueous sodium hydrogen carbonate solution and a saturated aqueous sodium thiosulfate solution were added, and ethyl acetate extraction was performed. The organic layer was washed with a saturated aqueous sodium chloride solution, dried over anhydrous magnesium sulfate, and then concentrated in vacuo. The residue was purified by silica gel column chromatography to give (E)-(5-methylsulfinyl)-6-[1-methyl-5-(trifluoromethylthio)benzimidazol-2-yl]-2-pyridinecarboxaldehyde O-ethyl oxime (0.12 g, 0.26 mmol) and (E)-(5-methylsulfonyl)-6-[1-methyl-5-(trifluoromethylthio)benzimidazol-2-yl]-2-pyridinecarboxaldehyde O-ethyl Oxime (0.014 g, 0.031 mmol)

Compound No. 3-83
Yield: 70%
Physical property: Melting point: 202 to 203° C.
Compound No. 1-256
Yield: 8%
Physical property: Melting point: 73 to 74° C.

Production Example 2

Production of 1-[6-(5-bromo-1-methylbenzimidazol-2-yl)-5-[methylsulfinylpyridin-2-yl]-(E)-N-ethoxyethanimine (Compound No. 1-87)

[Chem. 41]

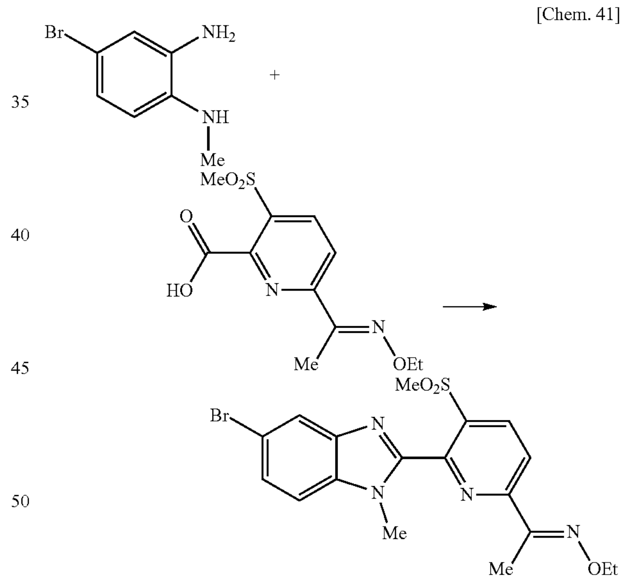

To a pyridine solution (12 mL) of 6-[(E)-N-ethoxy-C-methylcarbonimidoyl]-3-methylsulfonylpyridine-2-carboxylic acid (0.93 g, 4.6 mmol), 4-bromo-$N^1$-methylbenzene-1,2-diamine (1.4 g, 4.9 mmol), 1-hydroxybenzotriazole monohydrate (0.75 g, 4.9 mmol), and 1-(3-dimethylaminopropyl)-3-ethylcarbodiimide hydrochloride (1.2 g, 6.3 mmol) were added, and the mixture was stirred at room temperature overnight. After the completion of the reaction, the reaction mixture was concentrated in vacuo. Water was added to the residue, and the resulting solid was collected by filtration and washed with water. The filtrate was extracted with ethyl acetate. The organic layer was dried over anhydrous magnesium sulfate and then concentrated in vacuo.

Acetic acid (12 mL) was added to the collected solid and the residue, and the mixture was heated under reflux at 120° C. for 7 hours. After the completion of the reaction, the reaction mixture was concentrated in vacuo. Methyl tert-butyl ether and hexane were added to the residue, and the precipitate was collected by filtration to give 1-[6-(5-bromo-1-methylbenzimidazol-2-yl)-5-[methylsulfonylpyridin-2-yl]-(E)-N-ethoxyethanimine (1.3 g, 2.9 mmol).

Yield: 63%

Physical property: Melting point: 171 to 172° C.

Production Example 3

Production of N'-ethoxy-5-methylsulfonyl-6-[1-methyl-5-(trifluoromethyl)benzimidazol-2-yl]pyridine-2-carboxamidine (Compound No. 1-205), N'-ethoxy-N-methyl-5-methylsulfonyl-6-[1-methyl-5-(trifluoromethyl)benzimidazol-2-yl]pyridine-2-carboxamidine (Compound No. 1-216), and N'-ethoxy-N,N-dimethyl-5-methylsulfonyl-6-[1-methyl-5-(trifluoromethyl)benzimidazol-2-yl]pyridine-2-carboxamidine (Compound No. 1-220)

Production Example 3-1

Production of N'-ethoxy-5-methylsulfonyl-6-[1-methyl-5-(trifluoromethyl)benzimidazol-2-yl]pyridine-2-carboxamidine (Compound No. 1-205)

[Chem. 42]

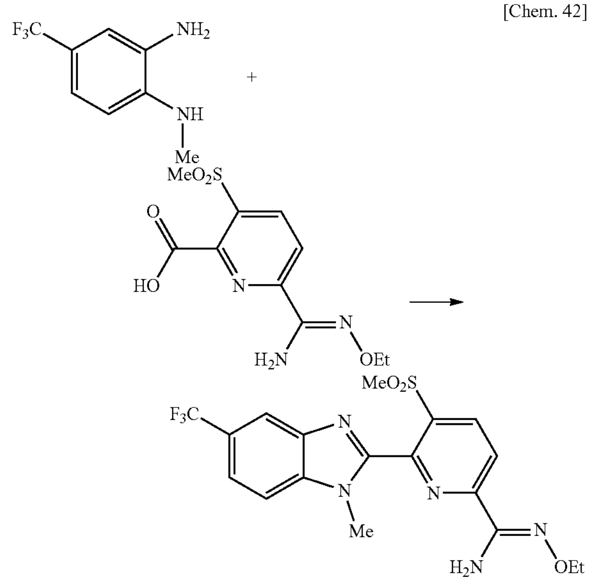

To a pyridine solution (2.0 mL) of 6-[(Z)—N-ethoxy-C-aminocarbonimidoyl]-3-methylsulfonyl-pyri dine-2-carboxylic acid (0.40 g, 1.3 mmol), $N^1$-methylbenzene-4-trifluoromethyl-1,2-diamine (0.25 g, 1.3 mmol), N,N-dimethyl-4-aminopyridine (0.16 g, 1.3 mmol), and 1-(3-dimethylaminopropyl)-3-ethylcarbodiimide hydrochloride (0.38 g, 2.0 mmol) were added at room temperature, and the mixture was stirred overnight. After the completion of the reaction, the reaction mixture was concentrated in vacuo. Ethyl acetate and 0.5 M hydrochloric acid were added to the residue, and extraction was performed. The organic layer was dried over anhydrous magnesium sulfate and then concentrated in vacuo. Acetic acid (10 mL) was added to the residue, and the mixture was stirred at 120° C. for 1 hour. After the completion of the reaction, the reaction mixture was concentrated in vacuo. Ethyl acetate and a saturated aqueous sodium hydrogen carbonate solution were added to the residue, and extraction was performed. The organic layer was dried over anhydrous magnesium sulfate and then dried in vacuo. The residue was purified by silica gel column chromatography to give N'-ethoxy-5-methylsulfonyl-6-[1-methyl-5-(trifluoromethyl)benzimidazol-2-yl]pyridine-2-carboxamidine (0.26 g, 0.58 mmol).

Yield: 43%

Physical property: Melting point: 149 to 150° C.

Production Example 3-2

Production of N'-ethoxy-N-methyl-5-methylsulfonyl-6-[1-methyl-5-(trifluoromethyl)benzimidazol-2-yl]pyridine-2-carboxamidine (Compound No. 1-216) and N'-ethoxy-N,N-dimethyl-5-methylsulfonyl-6-[1-methyl-5-(trifluoromethyl)benzimidazol-2-yl]pyridine-2-carboxamidine (Compound No. 1-220)

[Chem. 43]

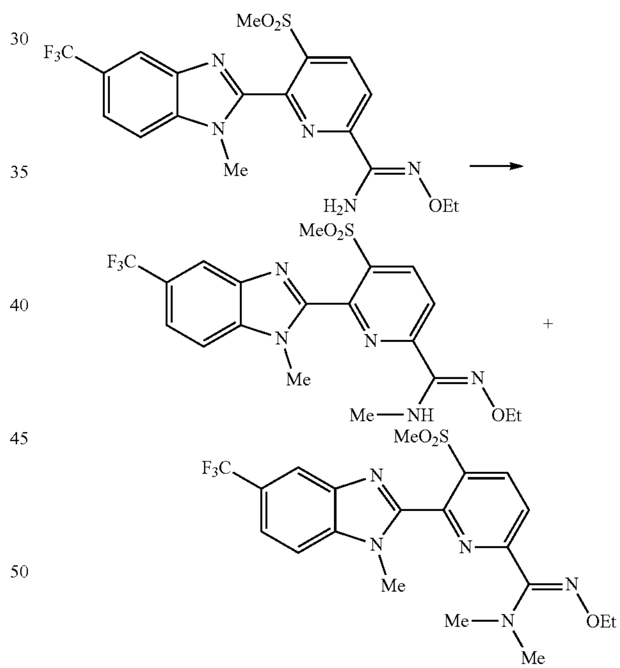

To an N,N-dimethylformamide solution (9 mL) of N'-ethoxy-5-methylsulfonyl-6-[1-methyl-5-(trifluoromethyl)benzimidazol-2-yl]pyridine-2-carboxamidine (0.8 g, 1.8 mmol), 60% sodium hydride (0.22 g, 5.4 mmol) was added under an ice bath, and the mixture was stirred for 5 minutes. Methyl iodide (0.26 g, 1.8 mmol) was added, and the mixture was stirred at room temperature for 4 hours. After the completion of the reaction, a saturated aqueous ammonium chloride solution was added, and extraction was performed. The organic layer was dried over anhydrous magnesium sulfate and then dried in vacuo. The residue was purified by silica gel column chromatography to give N'-ethoxy-N-methyl-5-methylsulfonyl-6-[1-methyl-5-(trifluoromethyl)benzimidazol-2-yl]pyridine-2-carboxamidine (0.079 g, 0.018 mmol) and N'-ethoxy-N,N-dimethyl-5-methylsulfonyl-6-[1-methyl-5-(trifluoromethyl)benzimidazol-2-yl]pyridine-2-carboxamidine (0.065 g, 0.013 mmol).

Compound No. 1-216

Yield: 10%

Physical property: Melting point: 154 to 155° C.

Compound No. 1-220

Yield: 7%

Physical property: Melting point: 150 to 151° C.

Production Example 4

Production of 5-[(4-tert-butylphenyl)methylthio]-N'-ethoxy-6-[1-methyl-5-(trifluoromethyl)benzimidazol-2-yl]pyridine-2-carboxamidine (Compound No. 3-59) and N'-ethoxy-5-methylsulfamoyl-6-[1-methyl-5-(trifluoromethyl) benzimidazol-2-yl]pyridine-2-carboxamidine (Compound No. 1-210)

Production Example 4-1

Production of 5-[(4-tert-butylphenyl)methylthio]-N'-ethoxy-6-[1-methyl-5-(trifluoromethyl)benzimidazol-2-yl]pyridine-2-carboxamidine (Compound No. 3-59)

[Chem. 44]

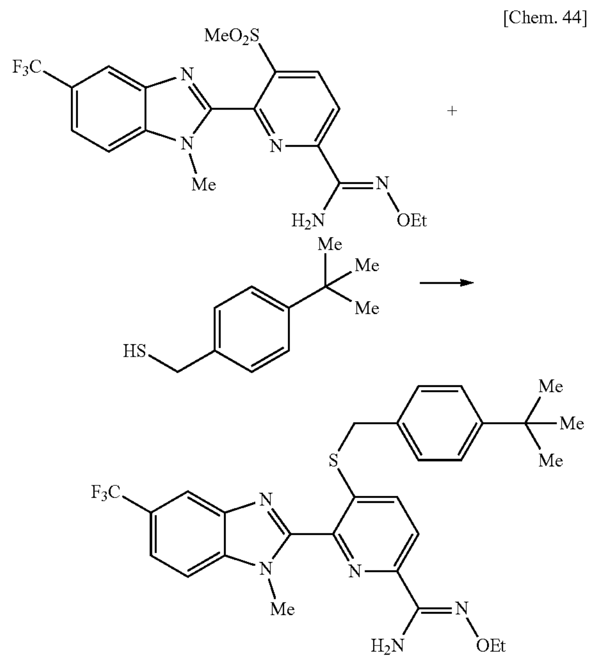

To an N,N-dimethyformamide solution (5.0 mL) of N'-ethoxy-5-methylsulfonyl-6-[1-methyl-5-(trifluoromethyl)benzimidazol-2-yl]pyridine-2-carboxamidine (0.26 g, 0.58 mmol), 4-(tert-butyl)benzylthiol (0.16 mL, 0.86 mmol) and cesium carbonate (0.38 g, 1.2 mmol) were added at room temperature, and the mixture was stirred at 80° C. for 3 hours. After the completion of the reaction, a saturated aqueous ammonium chloride solution was added, and extraction was performed. The organic layer was dried over anhydrous magnesium sulfate and then dried in vacuo. The residue was purified by silica gel column chromatography to give 5-[(4-tert-butylphenyl)methylthio]-N'-ethoxy-6-[1-methyl-5-(trifluoromethyl) benzimidazol-2-yl]pyridine-2-carboxamidine (0.22 g, 0.40 mmol).

Yield: 69%

Physical property: $^{1}$H-NMR ($CDCl_3$): 8.16 (s, 1H), 8.01 (d, 1H), 7.79 (dd, 1H), 7.61 (dd, 1H), 7.50 (d, 1H), 7.29 (d, 2H), 7.22 (d, 2H), 5.41 (s, 2H), 4.19 (q, 2H), 4.13 (s, 2H), 3.82 (s, 3H), 1.34 (t, 3H), 1.28 (s, 9H)

Production Example 4-2

Production of N'-ethoxy-5-methylsulfamoyl-6-[1-methyl-5-(trifluoromethyl) benzimidazol-2-yl]pyridine-2-carboxamidine (Compound No. 1-210)

[Chem. 45]

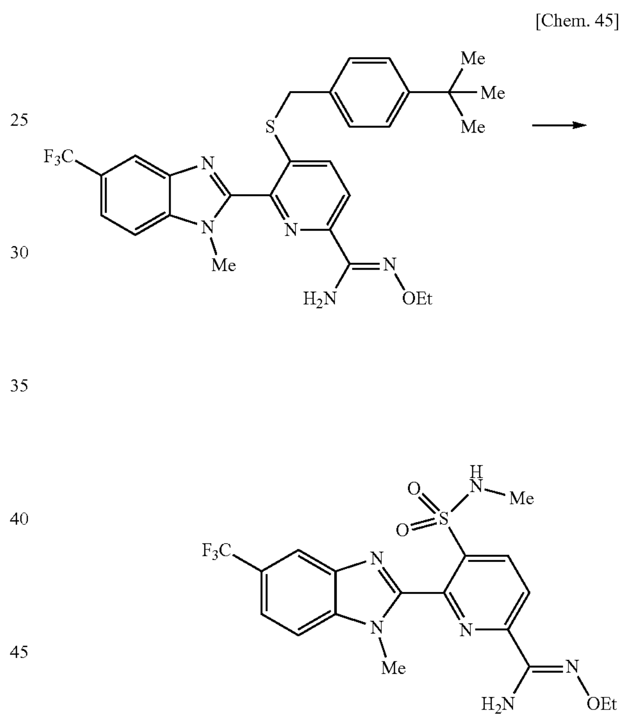

To a chloroform solution (2.0 mL) of 5-[(4-tert-butylphenyl)methylthio]-N'-ethoxy-6-[1-methyl-5-(trifluoromethyl) benzimidazol-2-yl]pyridine-2-carboxamidine (0.13 g, 0.24 mmol), acetic acid (0.041 mL, 0.72 mmol), water (0.026 mL, 1.4 mmol), and 1,3-dichloro-5,5-dimethylhydantoin (0.14 g, 0.72 mmol) were added at 0° C., and the mixture was stirred for 5 minutes. Methylamine (2.0 mL, 40% methanol solution) was added, and the mixture was stirred for 10 minutes. After the completion of the reaction, water was added, and extraction was performed. The organic layer was dried over anhydrous magnesium sulfate and then dried in vacuo. The residue was purified by silica gel column chromatography to give N'-ethoxy-5-methylsulfamoyl-6-[1-methyl-5-(trifluoromethyl) benzimidazol-2-yl]pyridine-2-carboxamidine (0.11 g, 0.24 mmol).

Yield: 100%

Physical property: Melting point: 173 to 174° C.

Production Example 5

Production of 6-[(E)-ethoxyiminomethyl]-2-[1-methyl-5-(trifluoromethylthio)benzimidazol-2-yl] pyridine-3-carboxylic acid methyl ester (Compound No. 2-82), 6-[(E)-ethoxyiminomethyl]-2-[1-methyl-5-(trifluoromethylthio)benzimidazol-2-yl]pyridine-3-carboxylic acid (Compound No. 2-81), 6-[(E)-ethoxyiminomethyl]-2-[1-methyl-5-(trifluoromethylthio)benzimidazol-2-yl]pyridine-3-carboxylic acid ethyl ester (Compound No. 2-83), and 6-[(E)-ethoxyiminomethyl]-N,N-dimethyl-2-[1-methyl-5-(trifluoromethylthio) benzimidazol-2-yl] pyridine-3-carboxamide (Compound No. 2-95)

Production Example 5-1

Production of 6-[1-methyl-5-(trifluoromethylthio) benzimidazol-2-yl]pyridine-2,5-dicarboxylic Acid Methyl Ester

[Chem. 46]

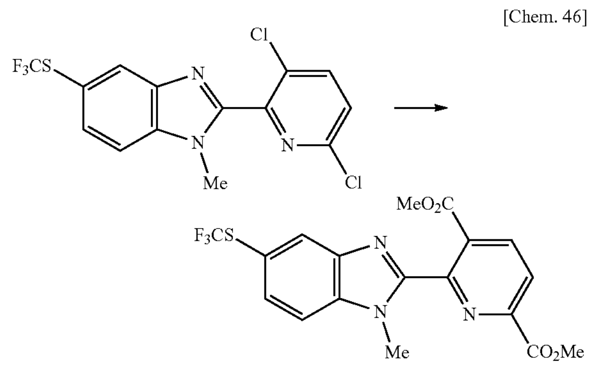

To a methanol solution (40 mL) of 2-(3,6-dichloropyridin-2-yl)-1-methyl-5-(trifluoromethylthio)benzimidazole (3.0 g, 7.95 mmol), 1,4-bis(diphenylphosphino) butane (136 mg, 0.32 mmol), dichlorobis(triphenylphosphine)palladium (II) (112 mg, 0.16 mmol), and triethylamine (2.8 mL, 19.9 mmol) were added, and the mixture was stirred under a carbon monoxide atmosphere of 4 MPa at 130° C. for 3 hours. After the completion of the reaction, filtration and vacuum drying were performed. The residue was purified by silica gel column chromatography to give 6-[1-methyl-5-(trifluoromethylthio)benzimidazol-2-yl]pyridine-2,5-dicarboxylic acid methyl ester (3.1 g, 7.26 mmol).

Yield: 91%

Physical property: Melting point: 142 to 143° C.

Production Example 5-2

Production of 6-(hydroxymethyl)-2-[1-methyl-5-(trifluoromethylthio)benzimidazol-2-yl]pyridine-3-carboxylic acid methyl ester

[Chem. 47]

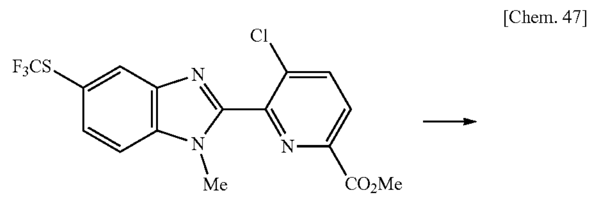

-continued

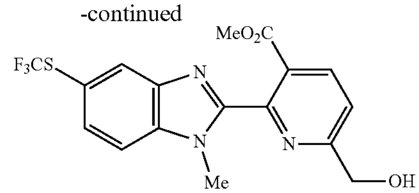

To a toluene solution (23 mL) of 6-[1-methyl-5-(trifluoromethylthio)benzimidazol-2-yl]pyridine-2,5-dicarboxylic acid methyl ester (1.0 g, 2.35 mmol), Red-A1 (registered trademark) (1.7 mL, 5.88 mmol, 3.5 M toluene solution) was added at 0° C., and the mixture was stirred for 15 minutes. After the completion of the reaction, a saturated aqueous potassium sodium tartrate solution was added, and the mixture was stirred for 30 minutes. Ethyl acetate extraction was performed, and the organic layer was dried over anhydrous magnesium sulfate and then concentrated in vacuo. The residue was purified by silica gel column chromatography to give 6-(hydroxymethyl)-2-[1-methyl-5-(trifluoromethylthio)benzimidazol-2-yl]pyridine-3-carboxylic acid methyl ester (290 mg, 0.73 mmol).

Yield: 31%

Production Example 5-3

6-formyl-2-[1-methyl-5-(trifluoromethylthio)benzimidazol-2-yl]pyridine-3-carboxylic Acid Methyl Ester

[Chem. 48]

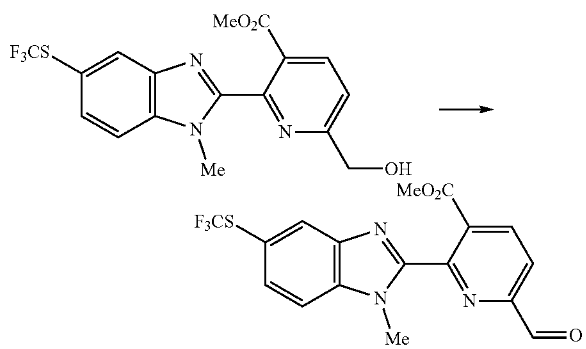

To a chloroform solution (5 mL) of 6-(hydroxymethyl)-2-[1-methyl-5-(trifluoromethylthio)benzimidazol-2-yl]pyridine-3-carboxylic acid methyl ester (204 mg, 0.51 mmol), manganese(IV) dioxide (2.0 g, 23 mmol) was added, and the mixture was heated under reflux for 3 hours. After the completion of the reaction, Celite filtration and vacuum concentration were performed. The residue was purified by silica gel column chromatography to give 6-formyl-2-[1-methyl-5-(trifluoromethylthio)benzimidazol-2-yl]pyridine-3-carboxylic acid methyl ester (193 mg, 0.48 mmol).

Yield: 94%

Physical property: $^1$H-NMR ($CDCl_3$): 10.16 (s, 1H), 8.36 (d, 1H), 8.14 (s, 1H), 8.13 (d, 1H), 7.66 (dd, 1H), 7.52 (d, 1H), 4.08 (s, 3H), 3.85 (s, 3H)

Production Example 5-4

Production of 6-1[(E)-ethoxyiminomethyl]-2-[1-methyl-5-(trifluoromethylthio)benzimidazol-2-yl]pyridine-3-carboxylic Acid Methyl Ester (Compound No. 2-82)

[Chem. 49]

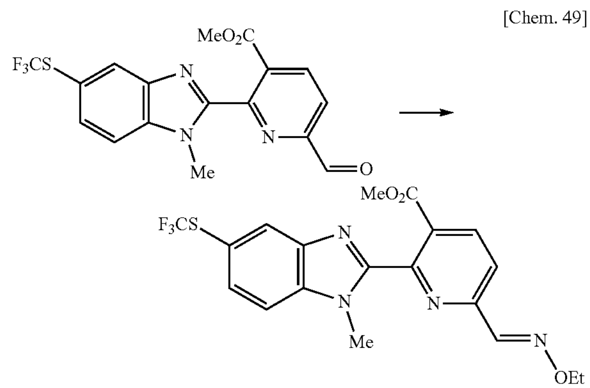

To a chloroform solution (1.0 mL) of 6-formyl-2-[1-methyl-5-(trifluoromethylthio)benzimidazol-2-yl]pyridine-3-carboxylic acid methyl ester (0.10 g, 0.25 mmol), O-ethylhydroxylamine hydrochloride (0.032 g, 0.33 mmol) and pyridine (0.026 mL, 0.33 mmol) were added, and the mixture was stirred overnight. After the completion of the reaction, water was added, and chloroform extraction was performed. The organic layer was dried over anhydrous magnesium sulfate and then concentrated in vacuo. The residue was purified by silica gel column chromatography to give 6-[(E)-ethoxyiminomethyl]-2-[1-methyl-5-(trifluoromethylthio)benzimidazol-2-yl]pyridine-3-carboxylic acid methyl ester (0.10 g, 0.23 mmol).

Yield: 91%

Physical property: $^1$H-NMR ($CDCl_3$): 8.24 (d, 1H), 8.20 (s, 1H), 8.12 (d, 1H), 8.07 (d, 1H), 7.63 (dd, 1H), 7.47 (d, 1H), 4.32 (q, 2H), 3.91 (s, 3H), 3.79 (s, 3H), 1.37 (t, 3H)

Production Example 5-5

Production of 6-[(E)-ethoxyiminomethyl]-2-[1-methyl-5-(trifluoromethylthio)benzimidazol-2-yl]pyridine-3-carboxylic Acid (Compound No. 2-81)

[Chem. 50]

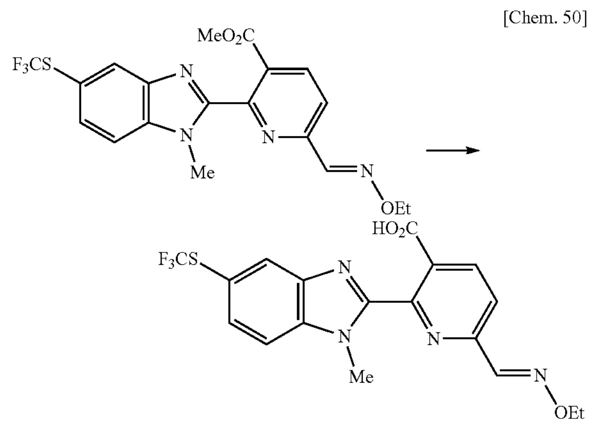

To an ethanol solution (1 mL) of 6-[(E)-ethoxyiminomethyl]-2-[1-methyl-5-(trifluoromethylthio)benzimidazol-2-yl]pyridine-3-carboxylic acid methyl ester (40.9 mg, 0.093 mmol), a 4 M aqueous lithium hydroxide solution (35 μL, 0.14 mmol) was added, and the mixture was stirred for 2 hours. After the completion of the reaction, 2 M hydrochloric acid was added, and the mixture was dried in vacuo. Water was added to the residue, and the resulting solid was collected by filtration to give 6-[(E)-ethoxyiminomethyl]-2-[1-methyl-5-(trifluoromethylthio)benzimidazol-2-yl]pyridine-3-carboxylic acid (18.4 mg, 0.043 mmol).

Yield: 46%

Physical property: Melting point: 195 to 196° C.

Production Example 5-6

Production of 6-[(E)-ethoxyiminomethyl]-2-[1-methyl-5-(trifluoromethylthio)benzimidazol-2-yl]pyridine-3-carboxylic Acid Ethyl Ester (Compound No. 2-83)

[Chem. 51]

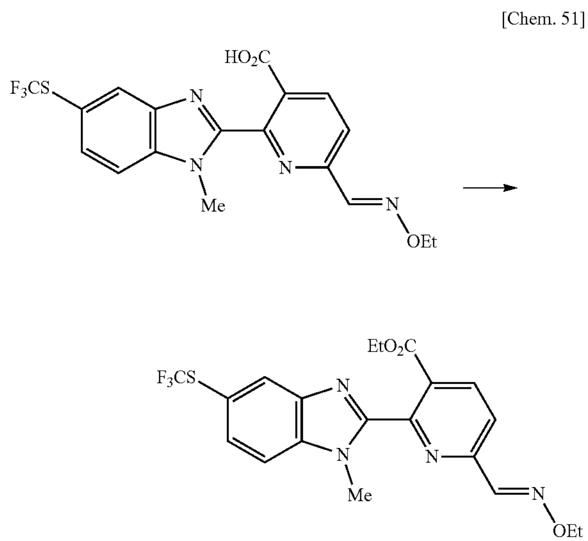

To a tetrahydrofuran solution (1 mL) of 6-[(E)-ethoxyiminomethyl]-2-[1-methyl-5-(trifluoromethylthio)benzimidazol-2-yl]pyridine-3-carboxylic acid (30 mg, 0.07 mmol), N,N-dimethylformamide (1 μL, 0.007 mmol) and oxalyl chloride (9 μL, 0.10 mmol) were added at room temperature, and the mixture was stirred for 1 hour. Ethanol (1 mL) and triethylamine (1 mL) were added, and the mixture was stirred for 30 minutes. The reaction mixture was concentrated in vacuo, and the residue was purified by silica gel column chromatography to give 6-[(E)-ethoxyiminomethyl]-2-[1-methyl-5-(trifluoromethylthio)benzimidazol-2-yl]pyridine-3-carboxylic acid ethyl ester (15.8 mg, 0.035 mmol).

Yield: 49%

Physical property: $^1$H-NMR ($CDCl_3$): 8.28 (d, 1H), 8.21 (s, 1H), 8.12 (d, 1H), 8.08 (d, 1H), 7.63 (dd, 1H), 7.47 (d, 1H), 4.33 (q, 2H), 4.20 (q, 2H), 3.87 (s, 3H), 1.37 (t, 3H), 1.02 (t, 3H)

Production Example 5-7

Production of 6-[(E)-ethoxyiminomethyl]-N,N-dimethyl-2-[1-methyl-5-(trifluoromethylthio) benzimidazol-2-yl]pyridine-3-carboxamide (Compound No. 2-95)

[Chem. 52]

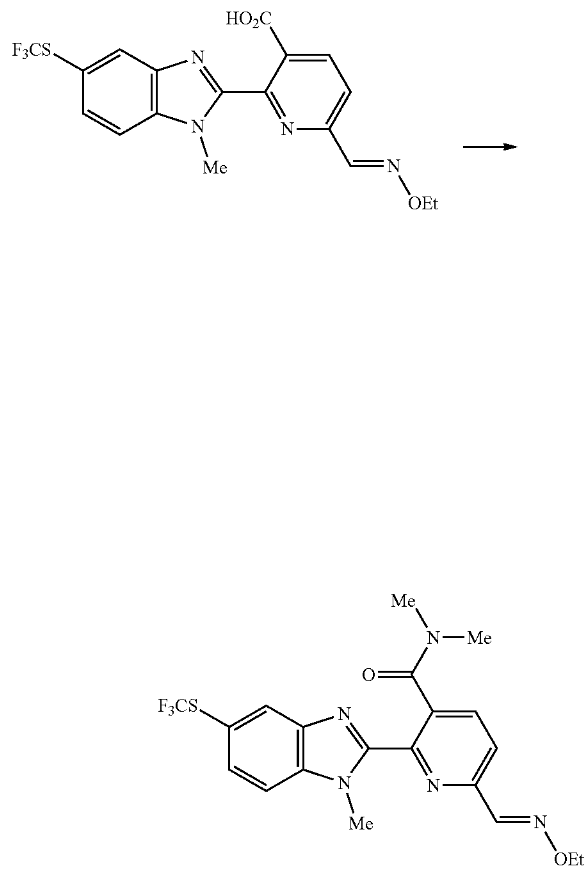

To a tetrahydrofuran solution (1 mL) of 6-[(E)-ethoxyiminomethyl]-2-[1-methyl-5-(trifluoromethylthio)benzimidazol-2-yl]pyridine-3-carboxylic acid (50 mg, 0.12 mmol), N,N-dimethylformamide (5 μL, 0.012 mmol) and oxalyl chloride (15 μL, 0.18 mmol) were added at room temperature, and the mixture was stirred for 1 hour. A 50% aqueous methylamine solution (1 mL) was added, and the mixture was stirred for 30 minutes. The reaction mixture was concentrated in vacuo, and the residue was purified by silica gel column chromatography to give 6-[(E)-ethoxyiminomethyl]-N,N-dimethyl-2-[1-methyl-5-(trifluoromethylthio) benzimidazol-2-yl]pyridine-3-carboxamide (38.6 mg, 0.085 mmol).

Yield: 73%

Physical property: Melting point: 118 to 119° C.

Production Example 6

Production of 6-[(E)-N-ethoxy-C-methyl-carbonimidoyl]-2-[1-methyl-5-(trifluoromethylthio)benzimidazol-2-yl]pyridine-3-carboxylic Acid Methyl Ester (Compound No. 2-105)

Production Example 6-1

Production of 6-(3-tert-butoxy-3-oxo-propanyl)-2-[1-methyl-5-(trifluoromethylthio)benzimidazol-2-yl] pyridine-3-carboxylic Acid Methyl Ester

[Chem. 53]

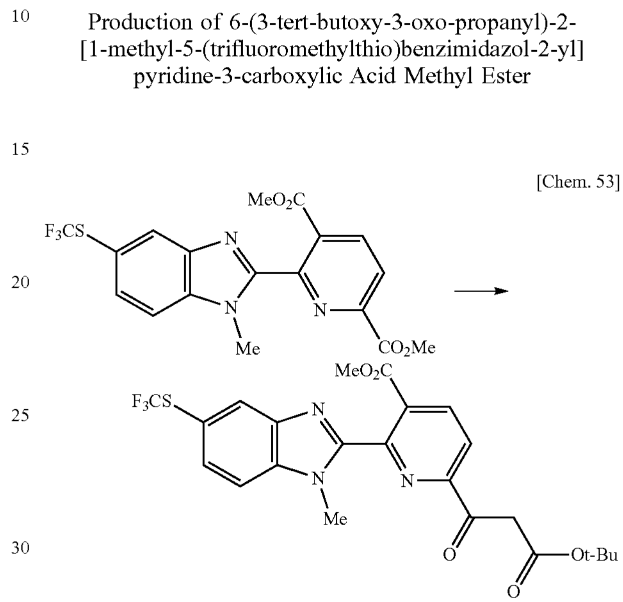

To a tetrahydrofuran solution (80 mL) of 6-[1-methyl-5-(trifluoromethylthio)benzimidazol-2-yl]pyridine-2,5-dicarboxylic acid methyl ester (6.0 g, 21.6 mmol), tert-butyl acetate (1.9 mL, 14.1 mmol) and lithium diisopropylamide (12.8 mL, 14.1 mmol, 1.1 M tetrahydrofuran solution) were added at −78° C., and the mixture was stirred for 1 hour. After the completion of the reaction, 2 M hydrochloric acid was added, and ethyl acetate extraction was performed. The organic layer was dried over anhydrous magnesium sulfate and then dried in vacuo to give 6-(3-tert-butoxy-3-oxo-propanyl)-2-[1-methyl-5-(trifluoromethylthio)benzimidazol-2-yl]pyridine-3-carboxylic acid methyl ester as a crude product.

Physical property: Melting point: 91 to 92° C.

Production Example 6-2

Production of 6-acetyl-2-[1-methyl-5-(trifluoromethylthio)benzimidazol-2-yl]pyridine-3-carboxylic Acid Methyl Ester

[Chem. 54]

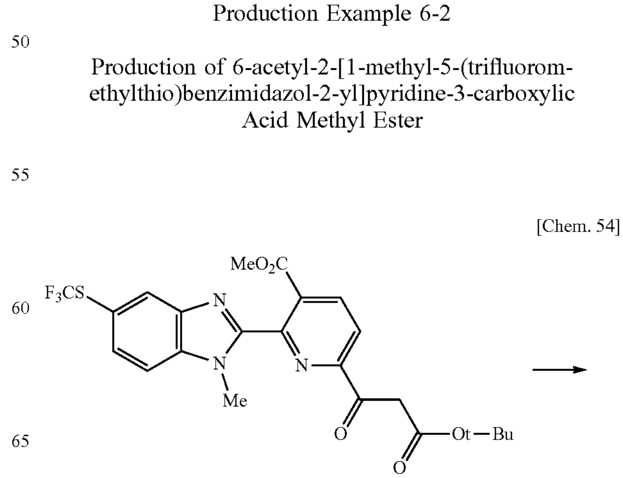

-continued

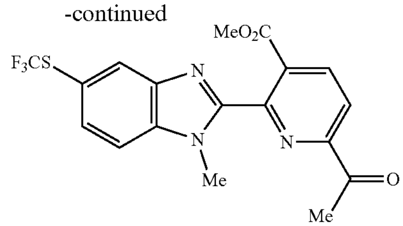

A trifluoroacetic acid solution (14 mL) of the 6-(3-tert-butoxy-3-oxo-propanyl)-2-[1-methyl-5-(trifluoromethylthio)benzimidazol-2-yl]pyridine-3-carboxylic acid methyl ester obtained in Production Example 6-1 was heated under reflux for 3 hours. After the completion of the reaction, the reaction mixture was concentrated in vacuo. A saturated aqueous sodium hydrogen carbonate solution was added, and ethyl acetate extraction was performed. The organic layer was dried over anhydrous magnesium sulfate and then concentrated in vacuo. The residue was purified by silica gel column chromatography to give 6-acetyl-2-[1-methyl-5-(trifluoromethylthio)benzimidazol-2-yl]pyridine-3-carboxylic acid methyl ester (1.47 g, 3.59 mmol).

Yield: 51% (2 steps)

Production Example 6-3

Production of 6-[(E)-N-ethoxy-C-methyl-carbonimidoyl]-2-[1-methyl-5-(trifluoromethylthio)benzimidazol-2-yl]pyridine-3-carboxylic Acid Methyl Ester (Compound No. 2-105)

[Chem. 55]

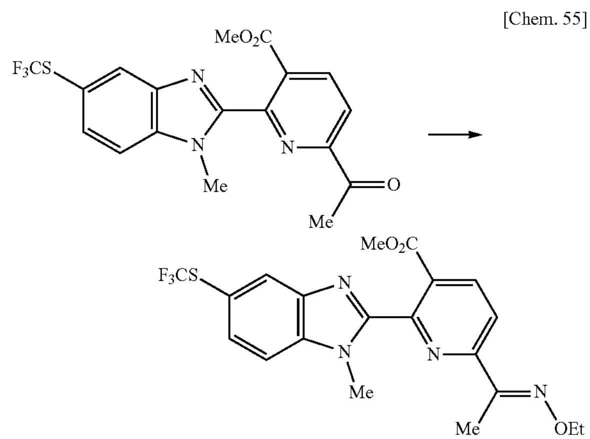

To a chloroform solution (2.0 mL) of 6-acetyl-2-[1-methyl-5-(trifluoromethylthio)benzimidazol-2-yl]pyridine-3-carboxylic acid methyl ester (0.064 g, 0.16 mmol), O-ethylhydroxylamine hydrochloride (0.023 g, 0.23 mmol) and pyridine (0.019 mL, 0.23 mmol) were added, and the mixture was stirred overnight. After the completion of the reaction, water was added, and chloroform extraction was performed. The organic layer was dried over anhydrous magnesium sulfate and then concentrated in vacuo. The residue was purified by silica gel column chromatography to give 6-[(E)-N-ethoxy-C-methyl-carbonimidoyl]-2-[1-methyl-5-(trifluoromethylthio)benzimidazol-2-yl]pyridine-3-carboxylic acid methyl ester (0.047 g, 0.10 mmol).

Yield: 66%

Physical property: Melting point: 121 to 122° C.

Production Example 7

Production of N'-hydroxy-5-methoxycarbonyl-6-[1-methyl-5-(trifluoromethyl)benzimidazol-2-yl]pyridine-2-carboxamidine (Compound No. 2-121) and N'-ethoxy-5-methoxycarbonyl-6-[1-methyl-5-(trifluoromethyl) benzimidazol-2-yl]pyridine-2-carboxamidine (Compound No. 2-123)

Production Example 7-1

Production of 6-carbamoyl-2-[1-methyl-5-(trifluoromethylthio)benzimidazol-2-yl]pyridine-3-carboxylic Acid Methyl Ester

[Chem. 56]

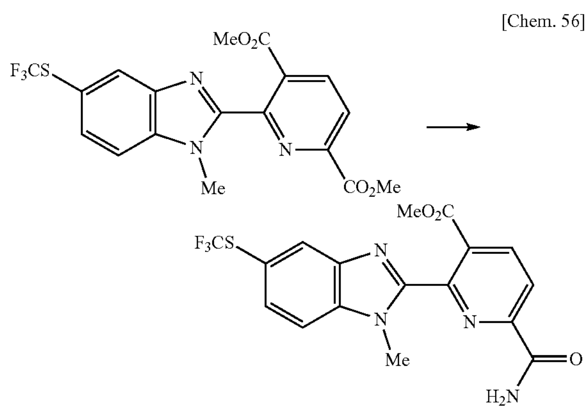

To 6-[1-methyl-5-(trifluoromethylthio)benzimidazol-2-yl]pyridine-2,5-dicarboxylic acid methyl ester (0.79 g, 1.9 mmol), 4% ammonia (9.0 mL, 4% methanol solution) was added, and the mixture was stirred at room temperature overnight. After the completion of the reaction, water was added, and the resulting solid was collected by filtration to give 6-carbamoyl-2-[1-methyl-5-(trifluoromethylthio)benzimidazol-2-yl]pyridine-3-carboxylic acid methyl ester (0.58 g, 1.4 mmol).

Yield: 76%

Physical property: Melting point: 252 to 253° C.

Production Example 7-2

Production of 6-cyano-2-[1-methyl-5-(trifluoromethylthio)benzimidazol-2-yl]pyridine-3-carboxylic Acid Methyl Ester

[Chem. 57]

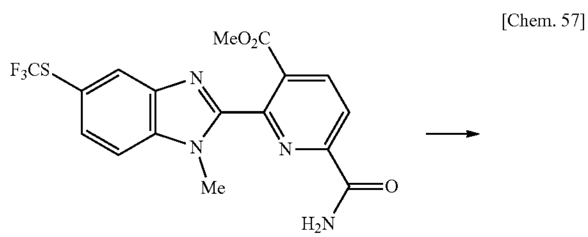

-continued

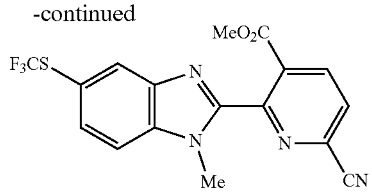

To an N,N-dimethylformamide solution (13 mL) of 6-carbamoyl-2-[1-methyl-5-(trifluoromethylthio)benzimidazol-2-yl]pyridine-3-carboxylic acid methyl ester (0.56 g, 1.4 mmol), phosphorus oxychloride (0.51 mL, 5.8 mmol) was added, and the mixture was stirred at room temperature for 30 minutes. After the completion of the reaction, a saturated aqueous sodium hydrogen carbonate solution was added, and ethyl acetate extraction was performed. The organic layer was dried over anhydrous magnesium sulfate and then dried in vacuo. The residue was purified by silica gel column chromatography to give 6-cyano-2-[1-methyl-5-(trifluoromethylthio)benzimidazol-2-yl]pyridine-3-carboxylic acid methyl ester (0.54 g, 1.4 mmol).

Yield: 100%

Physical property: Melting point: 193 to 194° C.

Production Example 7-3

Production of N'-hydroxy-5-methoxycarbonyl-6-[1-methyl-5-(trifluoromethyl)benzimidazol-2-yl]pyridine-2-carboxamidine (Compound No. 2-121)

[Chem. 58]

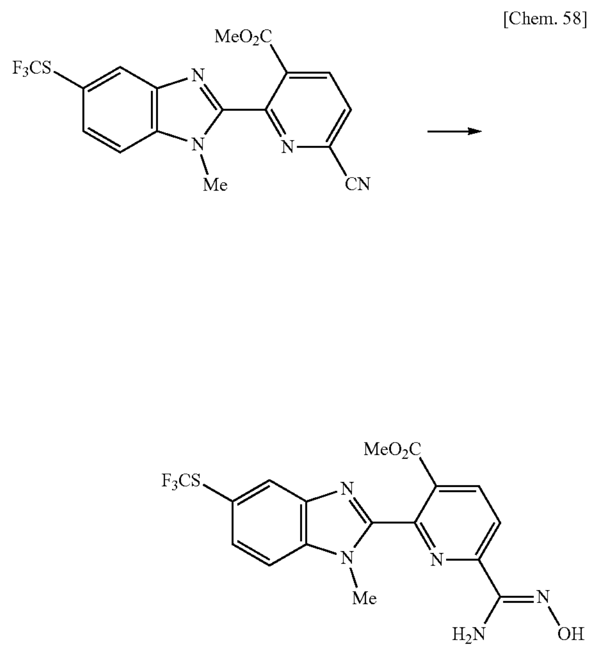

To an ethanol solution (14 mL) of 6-cyano-2-[1-methyl-5-(trifluoromethylthio)benzimidazol-2-yl]pyridine-3-carboxylic acid methyl ester (530 mg, 1.35 mmol), hydroxylamine hydrochloride (141 mg, 2.03 mmol) and sodium acetate (166 mg, 2.03 mmol) were successively added, and the mixture was heated under reflux for 2 hours. After the completion of the reaction, the reaction mixture was dried in vacuo. A saturated aqueous sodium hydrogen carbonate solution was added, and ethyl acetate extraction was performed. The organic layer was dried over anhydrous magnesium sulfate and then concentrated in vacuo. The residue was purified by silica gel column chromatography to give N'-hydroxy-5-methoxycarbonyl-6-[1-methyl-5-(trifluoromethyl)benzimidazol-2-yl]pyridine-2-carboxamidine (529 mg, 1.24 mmol).

Yield: 92%

Physical property: Melting point: 199 to 200° C.

Production Example 7-4

Production of N'-ethoxy-5-methoxycarbonyl-6-[1-methyl-5-(trifluoromethyl) benzimidazol-2-yl]pyridine-2-carboxamidine (Compound No. 2-123)

[Chem. 59]

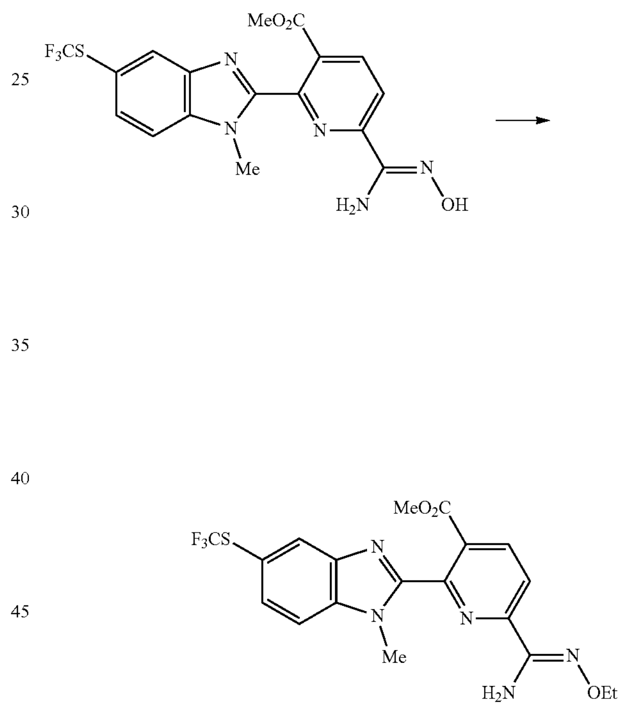

To an N,N-dimethylformamide solution (1 mL) of N'-hydroxy-5-methoxycarbonyl-6-[1-methyl-5-(trifluoromethyl) benzimidazol-2-yl]pyridine-2-carboxamidine (40 mg, 0.094 mmol), cesium carbonate (61 mg, 0.19 mmol) and ethyl iodide (15 μL, 0.19 mmol) were successively added at room temperature, and the mixture was stirred at 50% C for 2 hours. After the completion of the reaction, a saturated aqueous ammonium chloride solution was added, and ethyl acetate extraction was performed. The organic layer was dried over anhydrous magnesium sulfate and then concentrated in vacuo. The residue was purified by silica gel column chromatography to give N'-ethoxy-5-methoxycarbonyl-6-[1-methyl-5-(trifluoromethyl) benzimidazol-2-yl] pyridine-2-carboxamidine (38.9 mg, 0.086 mmol).

Yield: 91%

Physical property: Melting point: 46 to 47° C.

Production Example 8

Production of 5-chloro-N'-ethoxy-4-methyl-6-[1-methyl-5-(trifluoromethyl) benzimidazol-2-yl]pyridine-2-carboxamidine (Compound No. 3-65), N'-ethoxy-4-methyl-5-methylthio-6-[1-methyl-5-(trifluoromethyl)benzimidazol-2-yl]pyridine-2-carboxamidine (Compound No. 3-68), and N'-ethoxy-4-methyl-5-methylsulfonyl-6-[1-methyl-5-(trifluoromethyl)benzimidazol-2-yl]pyridine-2-carboxamidine (Compound No. 3-70)

Production Example 8-1 Production of 5-chloro-6-[1-methyl-5-(trifluoromethyl)benzimidazol-2-yl] pyridine-2-carboxylic Acid Ethyl Ester

[Chem. 60]

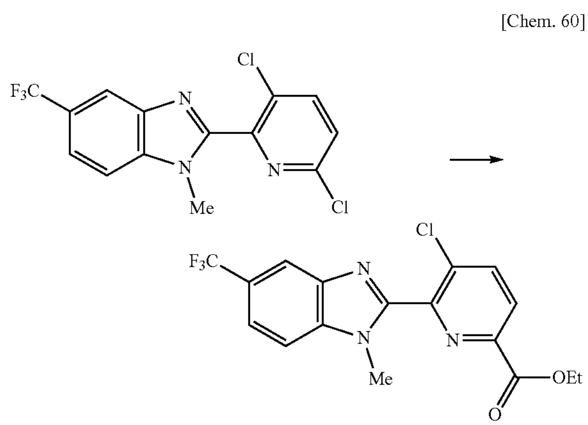

To an ethanol solution (0.15 L) of 2-(3,6-dichloropyridin-2-yl)-1-methyl-5-(trifluoromethyl)benzimidazole (15 g, 44 mmol), palladium(II) acetate (0.098 g, 0.44 mmol), 1,4-bis (diphenylphosphino)butane (0.37 g, 0.87 mmol), and sodium acetate (3.6 g, 44 mmol) were added, and the mixture was stirred under a carbon monoxide atmosphere (4 MPa) at 100° C. for 2 hours. The reaction mixture was concentrated in vacuo. A saturated aqueous sodium hydrogen carbonate solution was added to the residue, and ethyl acetate extraction was performed. The organic layer was washed with a saturated aqueous sodium chloride solution, dried over anhydrous magnesium sulfate, and then concentrated in vacuo to give 5-chloro-6-[1-methyl-5-(trifluoromethyl)benzimidazol-2-yl]pyridine-2-carboxylic acid ethyl ester as a crude product.

Production Example 8-2

Production of 5-chloro-6-[1-methyl-5-(trifluoromethyl)benzimidazol-2-yl]pyridine-2-carboxamide

[Chem. 61]

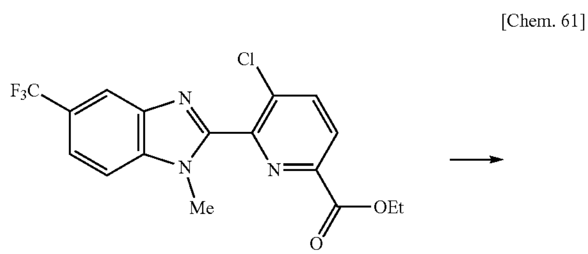

-continued

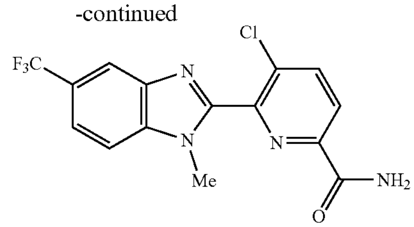

To the 5-chloro-6-[1-methyl-5-(trifluoromethyl)benzimidazol-2-yl]pyridine-2-carboxylic acid ethyl ester obtained in Production Example 8-1, a 4% ammonia solution (0.10 L) in ethanol was added, and the mixture was stirred at room temperature overnight. After the completion of the reaction, the reaction mixture was concentrated in vacuo to give 5-chloro-6-[1-methyl-5-(trifluoromethyl)benzimidazol-2-yl]pyridine-2-carboxamide (9.1 g, 26 mmol).

Yield: 59% (2 steps)

Physical property: Melting point: 246 to 247° C.

Production Example 8-3

Production of 5-amino-6-[1-methyl-5-(trifluoromethyl)benzimidazol-2-yl]pyridine-2-carboxamide

[Chem. 62]

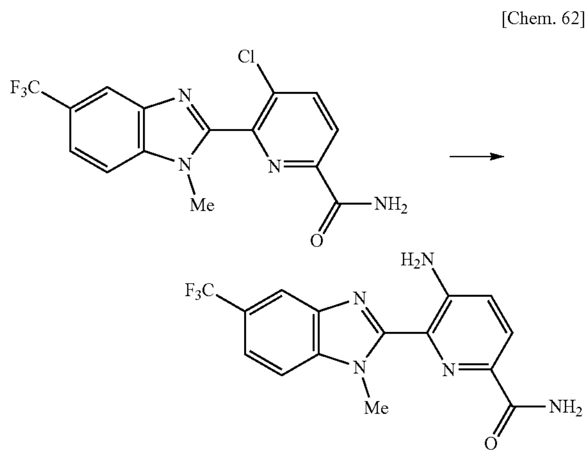

To a dimethyl sulfoxide solution (0.12 L) of 5-chloro-6-[1-methyl-5-(trifluoromethyl)benzimidazol-2-yl]pyridine-2-carboxamide (8.7 g, 24 mmol), sodium azide (2.4 g, 36 mmol) and triphenylphosphine (9.6 g, 36 mmol) were added, and the mixture was stirred at 130° C. for 2 hours. After the completion of the reaction, the reaction mixture was cooled to room temperature, water and methyl tert-butyl ether were added, and the resulting solid was collected by filtration. To a tetrahydrofuran solution (0.12 mL) of the resulting solid, 2 M hydrochloric acid (24 mL) was added, and the mixture was stirred at 40° C. for 1 hour. After the completion of the reaction, the reaction mixture was concentrated in vacuo. Water and methyl tert-butyl ether were added, and the resulting solid was collected by filtration to give 5-amino-6-[1-methyl-5-(trifluoromethyl)benzimidazol-2-yl]pyridine-2-carboxamide (5.1 g, 15 mmol).

Yield: 62%

Physical property: $^1$H-NMR ($CDCl_3$): 8.09 (s, 1H), 8.08 (d, 1H), 7.63 (dd, 1H), 7.54 (d, 1H), 7.30 (br-s, 1H), 7.24 (d, 1H), 6.70 (br-s, 2H), 5.46 (br-s, 1H), 4.29 (s, 3H)

Production Example 8-4

Production of 5-amino-4-bromo-6-[1-methyl-5-(trifluoromethyl)benzimidazol-2-yl]pyridine-2-carboxamide

[Chem. 63]

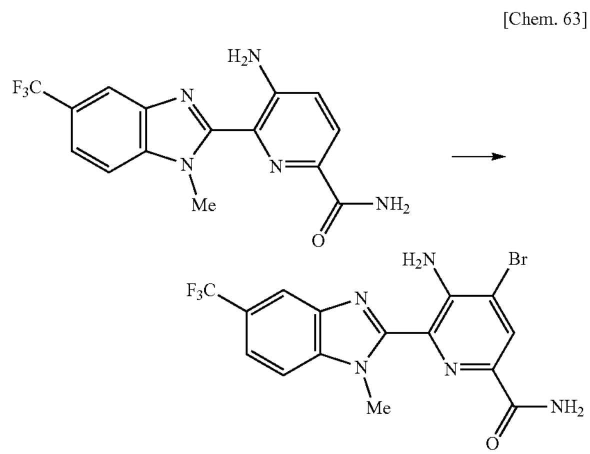

To an N,N-dimethylformamide solution (7.0 mL) of 5-amino-6-[1-methyl-5-(trifluoromethyl)benzimidazol-2-yl]pyridine-2-carboxamide (0.76 g, 2.3 mmol), N-bromosuccinimide (0.52 g, 2.9 mmol) was added at room temperature, and the mixture was stirred at 60° C. for 1 hour. After the completion of the reaction, the reaction mixture was cooled to room temperature. Water was added, and the resulting solid was collected by filtration to give 5-amino-4-bromo-6-[1-methyl-5-(trifluoromethyl)benzimidazol-2-yl]pyridine-2-carboxamide as a crude product. Physical property: $^1$H-NMR ($CDCl_3$): 8.40 (s, 1H), 8.11 (d, 1H), 7.65 (dd, 1H), 7.55 (d, 1H), 7.32 (br-s, 1H), 5.49 (br-s, 1H), 4.28 (s, 3H)

Production Example 8-5

5-amino-4-methyl-6-[1-methyl-5-(trifluoromethyl) benzimidazo 1-2-yl]pyridine-2-carboxamide

[Chem. 64]

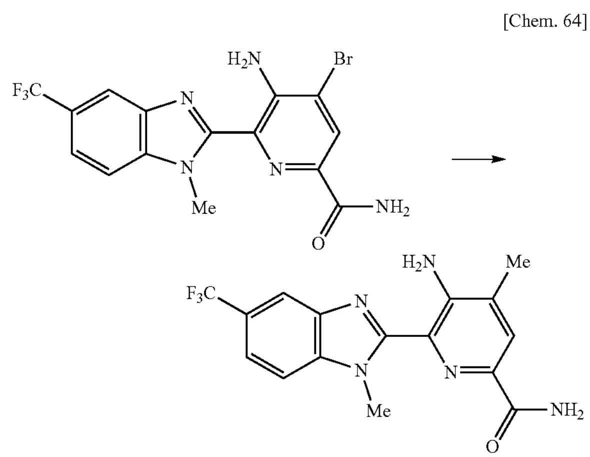

To a 1,2-dimethoxyethane:water (2:1) solution (24 mL) of the 5-amino-4-bromo-6-[1-methyl-5-(trifluoromethyl)benzimidazol-2-yl]pyridine-2-carboxamide obtained in Production Example 8-4, trimethylboroxine (1.5 g, 12 mmol), dichloro[1,1'-bis(diphenylphosphino) ferrocene]palladium (II) acetone adduct (0.18 g, 0.24 mmol), and sodium carbonate (2.4 g, 23 mmol) were added, and the mixture was heated under reflux for 2 hours. After the completion of the reaction, water was added, and ethyl acetate extraction was performed. The organic layer was washed with a saturated aqueous sodium chloride solution, dried over anhydrous magnesium sulfate, and then concentrated in vacuo. The residue was purified by silica gel column chromatography to give 5-amino-4-methyl-6-[1-methyl-5-(trifluoromethyl) benzimidazo 1-2-yl]pyridine-2-carboxamide (0.78 g, 2.2 mmol).

Yield: 99% (2 steps)

Physical property: $^1$H-NMR ($CDCl_3$): 8.09 (d, 1H), 8.02 (s, 1H), 7.62 (dd, 1H), 7.53 (d, 1H), 7.35 (br-s, 1H), 6.69 (br-s, 2H), 5.47 (br-s, 1H), 4.27 (s, 3H), 2.33 (s, 3H)

Production Example 8-6

Production of 5-chloro-4-methyl-6-[1-methyl-5-(trifluoromethyl)benzimidazol-2-yl]pyridine-2-carboxamide

[Chem. 65]

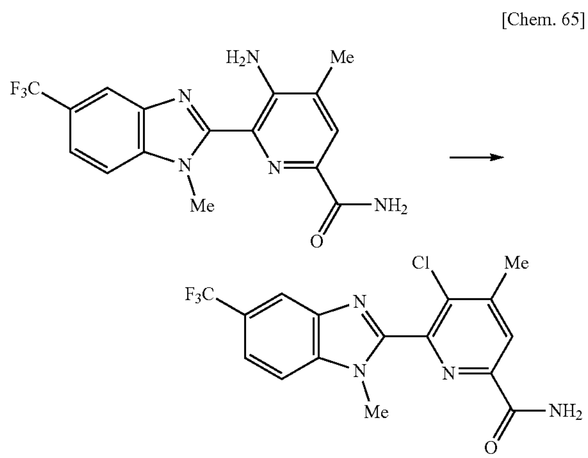

To an acetonitrile solution (11 mL) of 5-amino-4-methyl-6-[1-methyl-5-(trifluoromethyl)benzimidazo 1-2-yl]pyridine-2-carboxamide (0.40 g, 1.1 mmol), copper(II) chloride (0.31 g, 2.3 mmol) and tert-butyl nitrite (0.27 mL, 2.3 mmol) were added at room temperature, and the mixture was stirred at 60° C. for 1 hour. After the completion of the reaction, the reaction mixture was cooled to room temperature. An aqueous ammonia solution was added, and ethyl acetate extraction was performed. The organic layer was washed with a saturated aqueous sodium chloride solution, dried over anhydrous magnesium sulfate, and then concentrated in vacuo to give 5-chloro-4-methyl-6-[1-methyl-5-(trifluoromethyl)benzimidazol-2-yl]pyridine-2-carboxamide as a crude product. Physical property: $^1$H-NMR ($CDCl_3$): 8.28 (s, 1H), 8.17 (d, 1H), 7.66 (dd, 1H), 7.56 (d, 1H), 5.57 (br-s, 2H), 3.81 (s, 3H), 2.17 (s, 3H)

Production Example 8-7

5-chloro-4-methyl-6-[1-methyl-5-(trifluoromethyl) benzimidazol-2-yl]pyridine-2-carbonitrile

[Chem. 66]

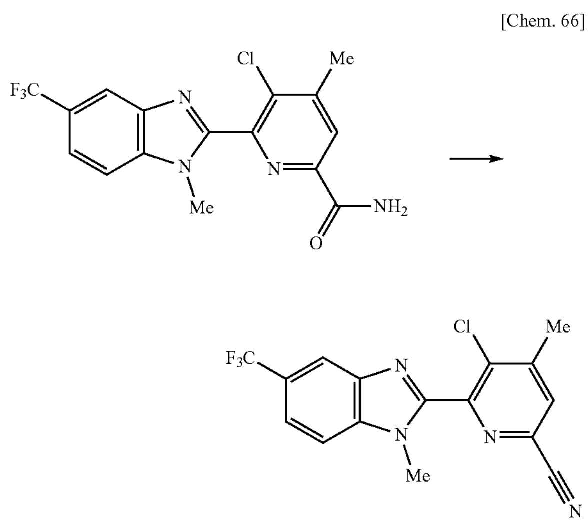

To an N,N-dimethylformamide solution (11 mL) of the 5-chloro-4-methyl-6-[1-methyl-5-(trifluoromethyl)benzimidazol-2-yl]pyridine-2-carboxamide obtained in Production Example 8-6, phosphorus oxychloride (0.56 mL, 4.6 mmol) was added at room temperature, and the mixture was stirred at 60° C. for 30 minutes. After the completion of the reaction, a saturated aqueous sodium hydrogen carbonate solution was added, and ethyl acetate extraction was performed. The organic layer was washed with a saturated aqueous sodium chloride solution, dried over anhydrous magnesium sulfate, and then concentrated in vacuo. The residue was purified by silica gel column chromatography to give 5-chloro-4-methyl-6-[1-methyl-5-(trifluoromethyl) benzimidazol-2-yl]pyridine-2-carbonitrile (0.30 g, 0.84 mmol). Yield: 74% (two steps) Physical property: $^1$H-NMR ($CDCl_3$): 8.16 (s, 1H), 7.73 (d, 1H), 7.65 (dd, 1H), 7.55 (d, 1H), 3.88 (s, 3H), 2.61 (s, 3H)

Production Example 8-8

Production of 5-chloro-N'-ethoxy-4-methyl-6-[1-methyl-5-(trifluoromethyl) benzimidazol-2-yl]pyridine-2-carboxamidine (Compound No. 3-65)

[Chem. 67]

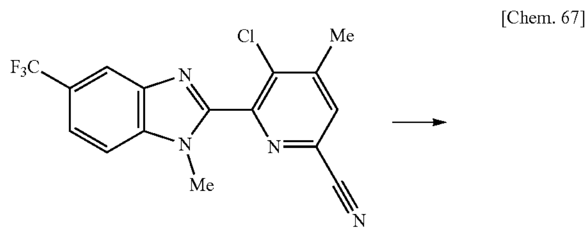

-continued

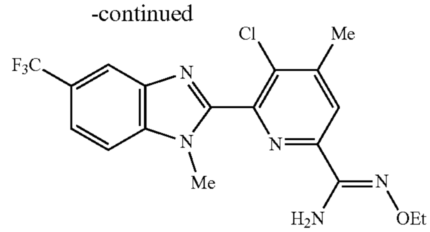

To a methanol solution (8.0 mL) of 5-chloro-4-methyl-6-[1-methyl-5-(trifluoromethyl)benzimidazol-2-yl]pyridine-2-carbonitrile (0.30 g, 0.84 mmol), sodium methoxide (0.17 mL, 0.84 mmol, 5 M methanol solution) was added at room temperature, and the mixture was stirred for 1 hour. After the disappearance of the starting compound was confirmed, O-ethylhydroxylamine hydrochloride (0.12 g, 1.3 mmol) was added, and the mixture was stirred for 1 hour. After the completion of the reaction, the reaction mixture was concentrated in vacuo. A saturated aqueous sodium hydrogen carbonate solution was added to the residue, and ethyl acetate extraction was performed. The organic layer was washed with a saturated aqueous sodium chloride solution, dried over anhydrous magnesium sulfate, and then concentrated in vacuo. The residue was purified by silica gel column chromatography to give 5-chloro-N'-ethoxy-4-methyl-6-[1-methyl-5-(trifluoromethyl) benzimidazol-2-yl] pyridine-2-carboxamidine (0.32 g, 0.77 mmol).

Yield: 92%

Physical property: Melting point: 144 to 145° C.

Production Example 8-9

N'-ethoxy-4-methyl-5-methylthio-6-[1-methyl-5-(trifluoromethyl)benzimidazol-2-yl]pyridine-2-carboxamidine (Compound No. 3-68)

[Chem. 68]

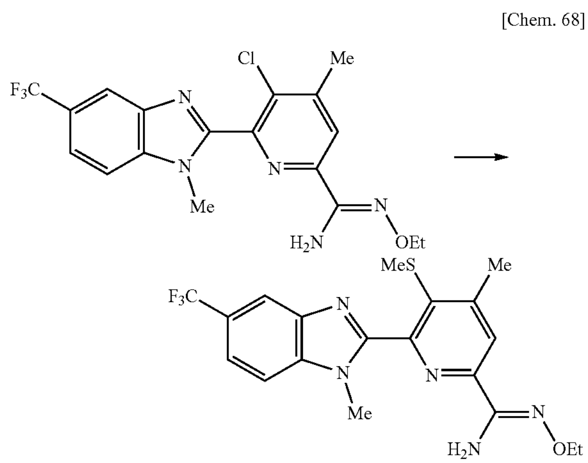

To an N,N-dimethylformamide solution (3.0 mL) of 5-chloro-N'-ethoxy-4-methyl-6-[1-methyl-5-(trifluoromethyl) benzimidazol-2-yl]pyridine-2-carboxamidine (0.15 g, 0.34 mmol), sodium thiomethoxide (0.048 g, 0.68 mmol) was added at room temperature, and the mixture was stirred for 1 hour. After the completion of the reaction, a saturated aqueous ammonium chloride solution was added, and ethyl acetate extraction was performed. The organic layer was washed with a saturated aqueous sodium chloride solution, dried over anhydrous magnesium sulfate, and then concentrated in vacuo. The residue was purified by silica gel column chromatography to give N'-ethoxy-4-methyl-5-methylthio-6-[1-methyl-5-(trifluoromethyl)benzimidazol-2-yl]pyridine-2-carboxamidine (0.13 g, 0.30 mmol, 90%).

Yield: 90%

Physical property: $^1$H-NMR ($CDCl_3$): 8.13 (s, 1H), 8.02 (d, 1H), 7.62 (dd, 1H), 7.52 (d, 1H), 5.45 (s, 2H), 4.20 (q, 2H), 3.72 (s, 3H), 2.66 (s, 3H), 2.18 (s, 3H), 1.36 (t, 3H)

Production Example 8-10

N'-ethoxy-4-methyl-5-methylsulfonyl-6-[1-methyl-5-(trifluoromethyl)benzimidazol-2-yl]pyridine-2-carboxamidine (Compound No. 3-70)

[Chem. 69]

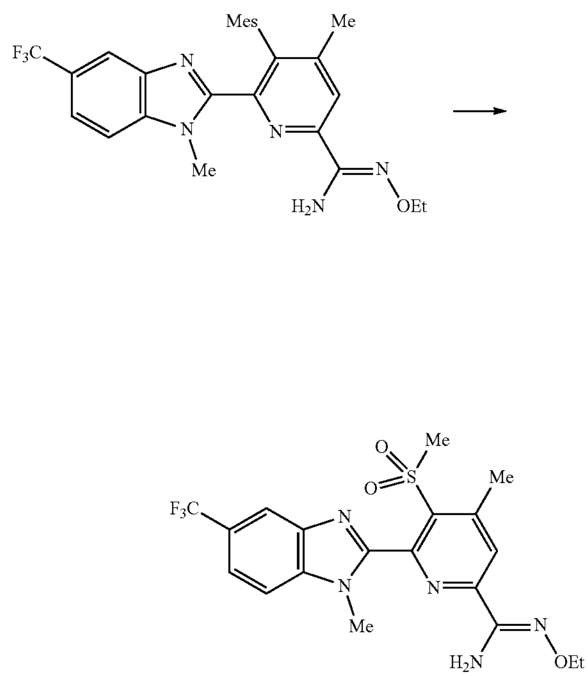

To an ethyl acetate solution (3.0 mL) of N'-ethoxy-4-methyl-5-methylthio-6-[1-methyl-5-(trifluoromethyl)benzimidazol-2-yl]pyridine-2-carboxamidine (0.12 g, 0.27 mmol), m-chloroperoxybenzoic acid (0.18 g, 0.68 mmol) was added at room temperature, and the mixture was stirred for 2 hours. After the completion of the reaction, a saturated aqueous sodium hydrogen carbonate solution and a saturated aqueous sodium thiosulfate solution were added, and ethyl acetate extraction was performed. The organic layer was washed with a saturated aqueous sodium chloride solution, dried over anhydrous magnesium sulfate, and then concentrated in vacuo. The residue was purified by silica gel column chromatography to give N'-ethoxy-4-methyl-5-methylsulfonyl-6-[1-methyl-5-(trifluoromethyl)benzimidazol-2-yl]pyridine-2-carboxamidine (0.090 g, 0.19 mmol).

Yield: 72%

Physical property: Melting point: 246 to 247° C.

Production Example 9

6-[(E)-N-ethoxy-C-methyl-carbonimidoyl]-5-methyl-2-[1-methy 1-5-(trifluoromethylthio)benzimidazol-2-yl]pyridine-3-carboxylic acid ethyl ester (Compound No. 3-91)

Production Example 9-1

Production of 6-[1-methyl-5-(trifluoromethylthio) benzimidazol-2-yl]pyridine-2,5-dicarboxylic Acid Ethyl Ester

[Chem. 70]

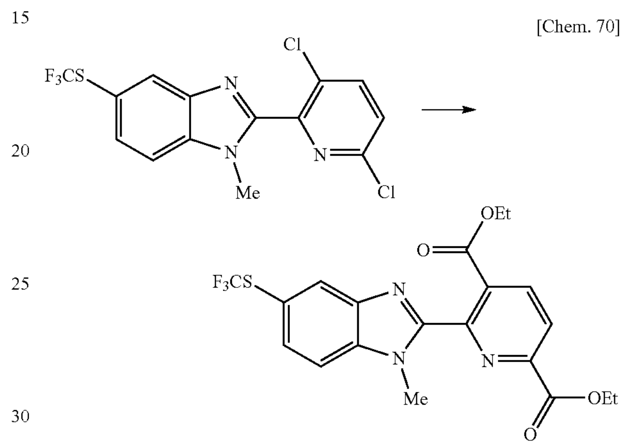

As described in Production Example 5-1 except for using ethanol instead of methanol, 6-[1-methyl-5-(trifluoromethylthio) benzimidazol-2-yl]pyridine-2,5-dicarboxylic acid ethyl ester was obtained.

Physical property: Melting point: 127 to 128° C.

Production Example 9-2

Production of 5-ethoxycarbonyl-6-[1-methyl-5-(trifluoromethylthio)benzimidazol-2-yl]pyridine-2-carboxylic Acid

[Chem. 71]

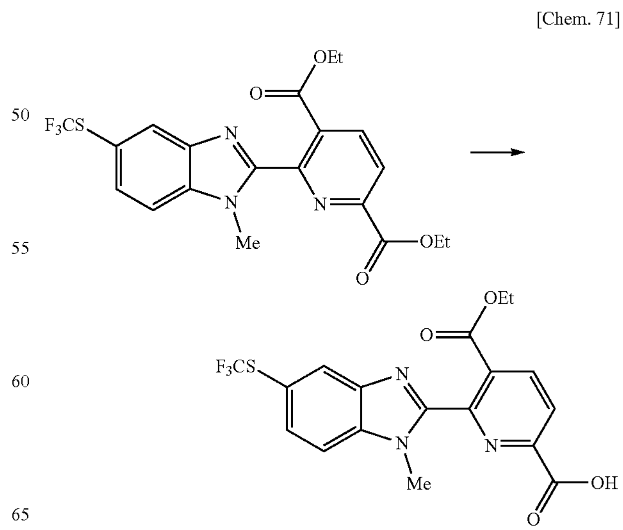

6-[1-Methyl-5-(trifluoromethylthio)benzimidazol-2-yl] pyridine-2,5-dicarboxylic acid ethyl ester (9.2 g, 20 mmol) was dissolved in tetrahydrofuran (40 mL) and ethanol (20 mL). Lithium hydroxide monohydrate (0.85 g, 20 mmol) was added, and the mixture was stirred for 3 hours. After the completion of the reaction, water was added, and methyl tert-butyl ether extraction was performed. To the aqueous layer, 2 M hydrochloric acid was added to adjust the pH to 1, and ethyl acetate extraction was performed. The organic layer was washed with water, dried over anhydrous sodium sulfate, and filtered through a cotton plug. The solvent was evaporated off in vacuo to give 5-ethoxycarbonyl-6-[1-methyl-5-(trifluoromethylthio)benzimidazol-2-yl]pyridine-2-carboxylic acid as a crude product.

Physical property: $^1$H-NMR ($CDCl_3$): 8.42 (d, 1H), 8.29 (d, 1H), 8.16 (d, 1H), 7.66 (dd, 1H), 7.19 (d, 1H), 4.24 (q, 2H), 3.49 (s, 3H), 1.11 (t, 3H)

Production Example 9-3

Production of 6-amino-2-[1-methyl-5-(trifluoromethylthio) benzimidazol-2-yl]pyridine-3-carboxylic acid ethyl ester

[Chem. 72]

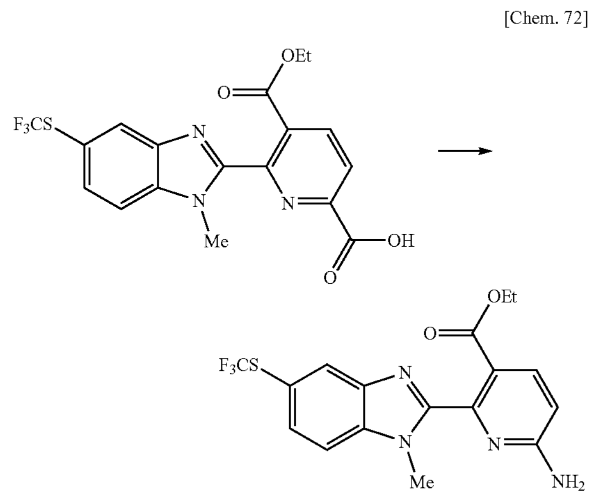

The 5-ethoxycarbonyl-6-[1-methyl-5-(trifluoromethylthio)benzimidazol-2-yl]pyridine-2-carboxylic acid obtained in Production Example 9-2 was dissolved in tert-butanol (40 mL). Triethylamine (3.9 mL, 28 mmol) and diphenylphosphoric acid amide (4.8 mL, 22 mmol) were added, and the mixture was heated under reflux for 2 hours. After the completion of the reaction, the reaction mixture was cooled to room temperature, and the solvent was evaporated off in vacuo. A saturated aqueous sodium hydrogen carbonate solution was added, and ethyl acetate extraction was performed. The organic layer was washed with water, dried over anhydrous sodium sulfate, and filtered through a cotton plug. The solvent was evaporated off in vacuo. The residue was dissolved in chloroform (20 mL) and trifluoroacetic acid (10 mL), and the mixture was stirred at room temperature for 6 hours. After the completion of the reaction, the solvent was evaporated off in vacuo. Water was added, and ethyl acetate extraction was performed. The organic layer was washed with a saturated aqueous sodium hydrogen carbonate solution, dried over anhydrous sodium sulfate, and filtered through a cotton plug. The solvent was evaporated off in vacuo to give 6-amino-2-[1-methyl-5-(trifluoromethylthio) benzimidazol-2-yl]pyridine-3-carboxylic acid ethyl ester as a crude product.

Production Example 9-4

Production of 6-amino-5-iodo-2-[1-methyl-5-(trifluoromethylthio)benzimidazol-2-yl]pyridine-3-carboxylic Acid Ethyl Ester

[Chem. 73]

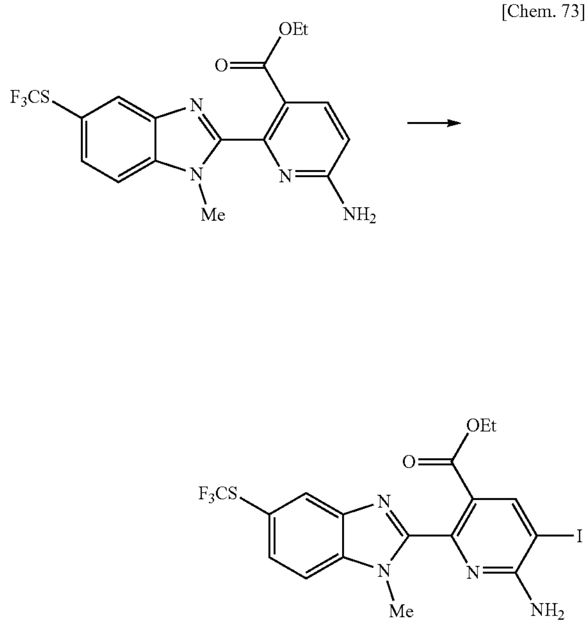

The 6-amino-2-[1-methyl-5-(trifluoromethylthio)benzimidazol-2-yl]pyridine-3-carboxylic acid ethyl ester obtained in Production Example 9-3 was dissolved in acetic acid (60 mL). 1,3-Diiodo-5,5-dimethylhydantoin (3.8 g, 10 mmol) was added, and the mixture was stirred at 90° C. for 2 hours. After the completion of the reaction, the reaction mixture was cooled to room temperature, and the solvent was evaporated off in vacuo. Water was added, and ethyl acetate extraction was performed. The organic layer was washed with a saturated aqueous sodium hydrogen carbonate solution, dried over anhydrous sodium sulfate, and filtered through a cotton plug. The solvent was evaporated off in vacuo. The residue was dissolved in ethyl acetate (50 mL) and tetrahydrofuran (10 mL). A saturated aqueous sodium thiosulfate solution (30 mL) and a saturated aqueous sodium hydrogen carbonate solution (30 mL) were added, and the mixture was stirred for several hours. Ethyl acetate extraction was performed, and the organic layer was washed with water, dried over anhydrous sodium sulfate, and filtered through a cotton plug. The solvent was evaporated off in vacuo, and the residue was purified by silica gel column chromatography to give 6-amino-5-iodo-2-[1-methyl-5-(trifluoromethylthio)benzimidazol-2-yl]pyridine-3-carboxylic acid ethyl ester (2.5 g, 4.9 mmol).

Yield: 24% (4 steps)

Physical property: Melting point: 168 to 171° C.

Production Example 9-5

Production of 6-amino-5-methyl-2-[1-methyl-5-(trifluoromethylthio)benzimidazol-2-yl]pyridine-3-carboxylic Acid Ethyl Ester

[Chem. 74]

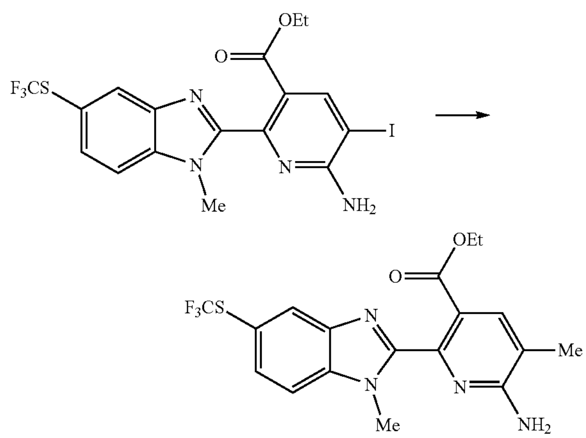

To a 1,2-dimethoxyethane:water (4:1) solution (5.0 mL) of 6-amino-5-iodo-2-[1-methyl-5-(trifluoromethylthio)benzimidazol-2-yl]pyridine-3-carboxylic acid ethyl ester (300 mg, 0.58 mmol), trimethylboroxine (241 mg, 1.7 mmol), dichloro[1,1'-bis(diphenylphosphino) ferrocene]palladium (II) acetone adduct (44 mg, 0.058 mmol), and cesium carbonate (749 mg, 2.3 mmol) were added, and the mixture was heated under reflux for 2 hours. After the completion of the reaction, Celite filtration and vacuum concentration were performed. The residue was purified by silica gel column chromatography to give 6-amino-5-methyl-2-[1-methyl-5-(trifluoromethylthio)benzimidazol-2-yl]pyridine-3-carboxylic acid ethyl ester (235 mg, 0.57 mmol).

Yield: 99%

Physical property: Melting point: 154 to 156° C.

Production Example 9-6

6-bromo-5-methyl-2-[1-methyl-5-(trifluoromethylthio)benzimidazol-2-yl]pyridine-3-carboxylic Acid Ethyl Ester

[Chem. 75]

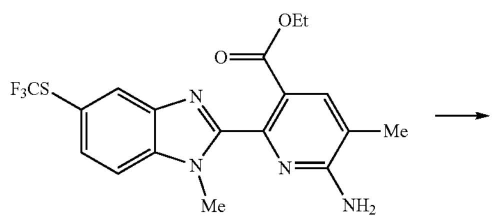

-continued

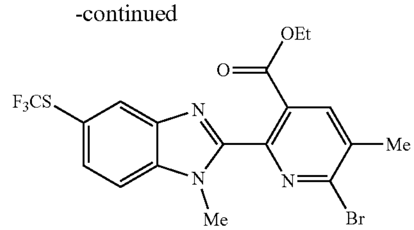

6-Amino-5-methyl-2-[1-methyl-5-(trifluoromethylthio) benzimidazol-2-yl]pyridine-3-carboxylic acid ethyl ester (235 mg, 0.57 mmol) was dissolved in tetrahydrofuran (3.0 mL). Copper (II) bromide (192 mg, 0.86 mmol) and tert-butyl nitrite (136 mL, 1.2 mmol) were added, and the mixture was stirred at 60° C. for 1 hour. After the completion of the reaction, the reaction mixture was filtered through Celite. Water was added, and ethyl acetate extraction was performed. The organic layer was washed with water, dried over anhydrous sodium sulfate, and filtered through a cotton plug. The solvent was evaporated off in vacuo. The residue was purified by silica gel column chromatography to give 6-bromo-5-methyl-2-[1-methyl-5-(trifluoromethylthio)benzimidazol-2-yl]pyridine-3-carboxylic acid ethyl ester (148 mg, 0.31 mmol).

Yield: 55%

Physical property: Melting point: 154 to 157° C.

Production Example 9-7

Production of 6-acetyl-5-methyl-2-[1-methyl-5-(trifluoromethylthio)benzimidazol-2-yl]pyridine-3-carboxylic Acid Ethyl Ester

[Chem. 76]

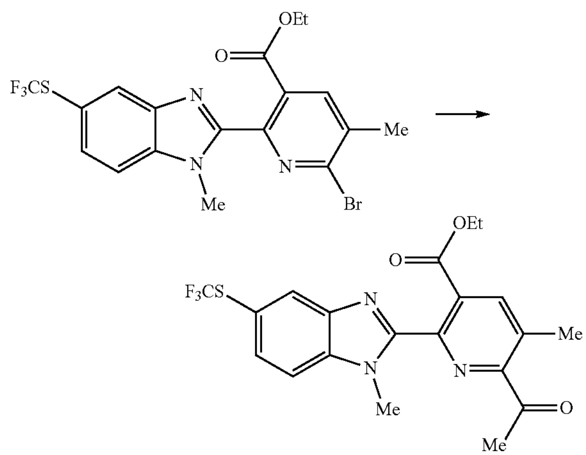

6-Bromo-5-methyl-2-[1-methyl-5-(trifluoromethylthio) benzimidazol-2-yl]pyridine-3-carboxylic acid ethyl ester (118 mg, 0.25 mmol) was dissolved in 1,2-dimethoxyethane (1.5 mL). Tributyl(1-ethoxyvinyl)stannane (0.17 mL, 0.50 mmol) and tetrakis(triphenylphosphine)palladium(0) (29 mg, 0.025 mmol) were added, and the mixture was heated under reflux for 3 hours. After cooling to room temperature, 2 M hydrochloric acid (2 mL) was added, and the mixture was stirred for 2 hours. After the completion of the reaction, ethyl acetate extraction was performed. The organic layer was washed with water, dried over anhydrous sodium sulfate, and filtered through a cotton plug. The solvent was evaporated off in vacuo. The residue was purified by silica gel column chromatography to give 6-acetyl-5-methyl-2-[1-methyl-5-(trifluoromethylthio)benzimidazol-2-yl]pyridine-3-carboxylic acid ethyl ester (35 mg, 0.08 mmol).

Yield: 32%

Physical property: Melting point: 85 to 88° C.

Production Example 9-8

Production of 6-[(E)-N-ethoxy-C-methyl-carbonimidoyl]-5-methyl-2-[1-methy 1-5-(trifluoromethylthio) benzimidazol-2-yl]pyridine-3-carboxylic Acid Ethyl Ester (Compound No. 3-91)

[Chem. 77]

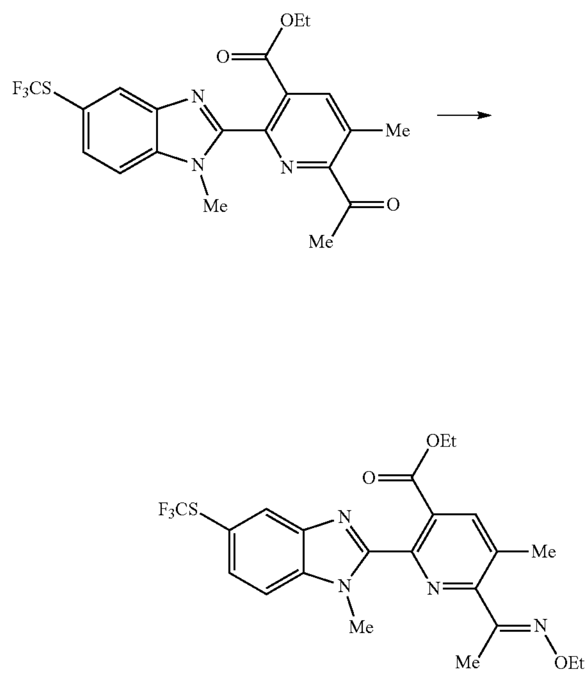

6-Acetyl-5-methyl-2-[1-methyl-5-(trifluoromethylthio) benzimidazol-2-yl]pyridine-3-carboxylic acid ethyl ester (25 mg, 0.057 mmol) was dissolved in pyridine (1.0 mL). O-ethylhydroxylamine hydrochloride (28 mg, 0.29 mmol) was added, and the mixture was stirred at room temperature for 2 hours. After the completion of the reaction, the solvent was evaporated off in vacuo. A saturated aqueous sodium hydrogen carbonate solution was added, and ethyl acetate extraction was performed. The organic layer was washed with water, dried over anhydrous sodium sulfate, and filtered through a cotton plug. The solvent was evaporated off in vacuo. The residue was purified by silica gel column chromatography to give 6-[(E)-N-ethoxy-C-methyl-carbonimidoyl]-5-methyl-2-[1-methy 1-5-(trifluoromethylthio)benzimidazol-2-yl]pyridine-3-carboxylic acid ethyl ester (7.4 mg, 0.015 mmol).

Yield: 27%

Physical property: Refractive index: 1.3386 (22.2° C.)

Production Example 10

1-{6-[5-(difluoromethyl)-1-methylbenzimidazol-2-yl]-5-(meth ylsulfonimidoyl)pyridin-2-yl}-N-ethoxy-ethanimine (Compound No. 3-50)

[Chem. 78]

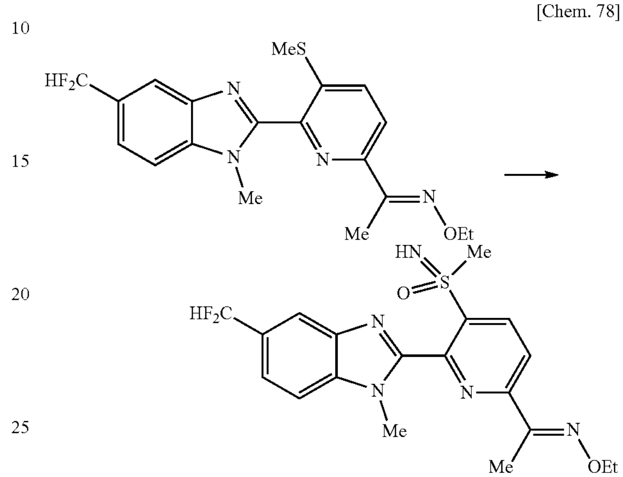

To a methanol solution (5.1 mL) of 1-{6-[5-(difluoromethyl)-1-methylbenzimidazol-2-yl]-5-methylthiopyridin-2-yl}-N-ethoxy-ethanimine (0.20 g, 0.51 mmol), ammonium carbonate (0.11 g, 1.10 mmol) and bisacetoxyiodobenzene (0.38 g, 1.70 mmol) were added at room temperature, and the mixture was stirred at room temperature for 1 hour. After the completion of the reaction, the reaction mixture was concentrated in vacuo, and the residue was purified by silica gel column chromatography to give 1-{6-[5-(difluoromethyl)-1-methylbenzimidazol-2-yl]-5-(meth ylsulfonimidoyl)pyridin-2-yl}-N-ethoxy-ethanimine (0.25 g, 0.60 mmol).

Yield: 100%

Physical property: Melting point: 100 to 101° C.

Production Example 11

Production of (Z)—N'-ethoxy-3-(1-methyl-5-(trifluoromethyl)-1H-benzo[d]imidazol-2-yl)-4-(N-methylsulfamoyl)benzimidamide (Compound No. 4-46)

Production Example 11-1

Production of 2-(2-fluoro-5-iodophenyl)-1-methyl-5-(trifluoromethyl)-1H-benzo[d]imidazole

[Chem. 79]

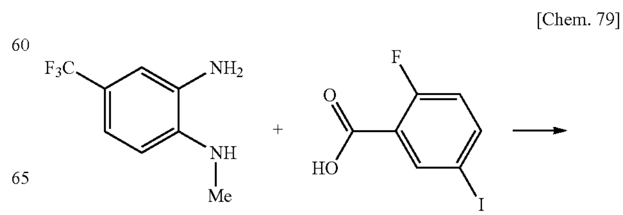

-continued

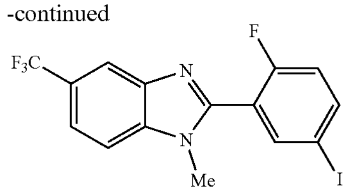

To a pyridine solution (45 mL) of 2-fluoro-5-iodobenzoic acid (5.0 g, 19 mmol), 2-amino-1-methylamino-4-trifluorobenzene (3.6 g, 19 mmol), 1-(3-dimethylaminopropyl)-3-ethylcarbodiimide (4.0 g, 21 mmol), and N,N-dimethyl-4-aminopyridine (2.3 g, 19 mmol) were added at room temperature, and the mixture was stirred at room temperature overnight. After the completion of the reaction, the reaction mixture was concentrated in vacuo. 0.5N hydrochloric acid was added to the residue, and ethyl acetate extraction was performed. The organic layer was dried over anhydrous magnesium sulfate and then concentrated in vacuo. Acetic acid (40 mL) was added to the residue, and the mixture was stirred at 120° C. for 2 hours. After the completion of the reaction, the reaction mixture was concentrated in vacuo. A saturated aqueous sodium hydrogen carbonate solution was added to the residue, and ethyl acetate extraction was performed. The organic layer was dried over anhydrous magnesium sulfate and then concentrated in vacuo. The residue was purified by silica gel column chromatography to give 2-(2-fluoro-5-iodophenyl)-1-methyl-5-(trifluoromethyl)-1H-benzo[d]imidazole (4.1 g, 7.1 mmol).

Yield: 37%

Physical property: $^1$H-NMR ($CDCl_3$): 8.05 (dd, 1H), 7.81 (m, 1H), 7.61 (d, 1H), 7.30 (d, 1H), 7.18 (dd, 1H), 7.00 (dd, 1H), 2.51 (s, 3H)

Production Example 11-2

Production of 2-(2-((4-(tert-butyl)benzyl)thio)-5-iodophenyl)-1-methyl-5-(trifluoromethyl)-1H-benzo[d]imidazole

[Chem. 80]

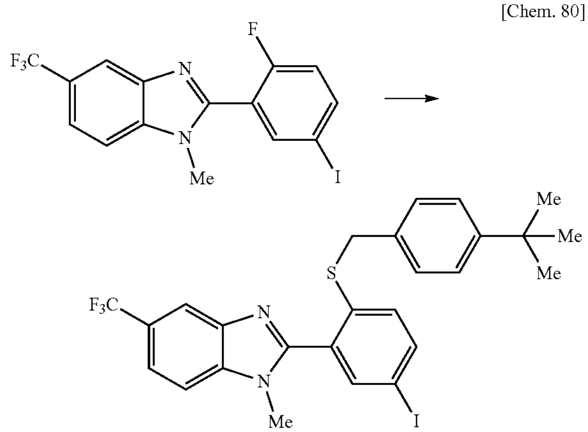

To an N,N-dimethylacetamide solution (10 mL) of 2-(2-fluoro-5-iodophenyl)-1-methyl-5-(trifluoromethyl)-1H-benzo[d]imidazole (1.2 g, 2.9 mmol), 4-(tert-butyl)benzylthiol (0.63 mL, 3.4 mmol) and cesium carbonate (1.3 g, 4.0 mmol) were added at room temperature, and the mixture was stirred at 80° C. for 3 hours. After the completion of the reaction, a saturated aqueous ammonium chloride solution was added, and ethyl acetate extraction was performed. The organic layer was dried over anhydrous magnesium sulfate and then concentrated in vacuo. The residue was purified by silica gel column chromatography to give 2-(2-((4-(tert-butyl)benzyl)thio)-5-iodophenyl)-1-methyl-5-(trifluoromethyl)-1H-benzo[d]imidazole (1.1 g, 1.8 mmol).

Yield: 64%

Physical property: $^1$H-NMR ($CDCl_3$): 8.10 (d, 1H), 7.79 (d, 1H), 7.74 (dd, 1H), 7.60 (dd, 1H), 7.46 (dd, 1H), 7.24 (d, 2H), 7.17 (dd, 1H), 7.10 (d, 2H), 3.98 (s, 2H), 3.61 (s, 3H), 1.27 (s, 9H)

Production Example 11-3

Production of 2-((4-(tert-butyl)benzyl)thio)-3-(1-methyl-5-(trifluoromethyl)-1H-benzo[d]imidazol-2-yl)benzonitrile

[Chem. 81]

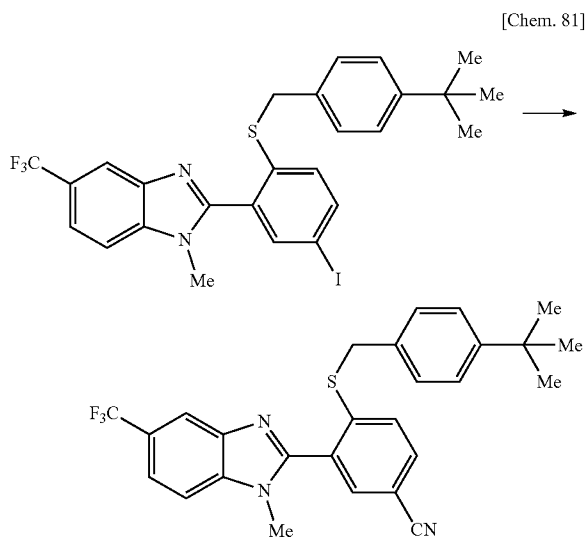

To an N,N-dimethylacetamide solution (6.3 mL) of 2-(2-((4-(tert-butyl)benzyl)thio)-5-iodophenyl)-1-methyl-5-(trifluoromethyl)-1H-benzo[d]imidazole (1.1 g, 1.9 mmol), zinc cyanide (0.45 g, 3.8 mmol), tetrakis(triphenylphosphine)palladium(0) (0.66 g, 0.57 mmol), and triethylamine (0.53 mL, 3.8 mmol) were added at room temperature, and the mixture was stirred and heated under reflux for 3 hours. After the completion of the reaction, water was added, and ethyl acetate extraction was performed. The organic layer was dried over anhydrous magnesium sulfate and then concentrated in vacuo. The residue was purified by silica gel column chromatography to give 2-((4-(tert-butyl)benzyl)thio)-3-(1-methyl-5-(trifluoromethyl)-1H-benzo[d]imidazol-2-yl)benzonitrile (0.44 g, 0.91 mmol).

Yield: 48%

Physical property: $^1$H-NMR ($CDCl_3$): 8.11 (d, 1H), 7.70 (m, 2H), 7.61 (dd, 1H), 7.51 (dd, 1H), 7.30 (d, 2H), 7.21 (d, 2H), 7.13 (d, 1H), 4.14 (s, 2H), 3.66 (s, 3H), 1.28 (s, 9H)

Production Example 11-4

Production of (Z)-4-((4-(tert-butyl)benzyl)thio)-N'-hydroxy-3-(1-methyl-5-(trifluoromethyl)-1H-benzo[d]imidazol-2-yl)benzimidamide

[Chem. 82]

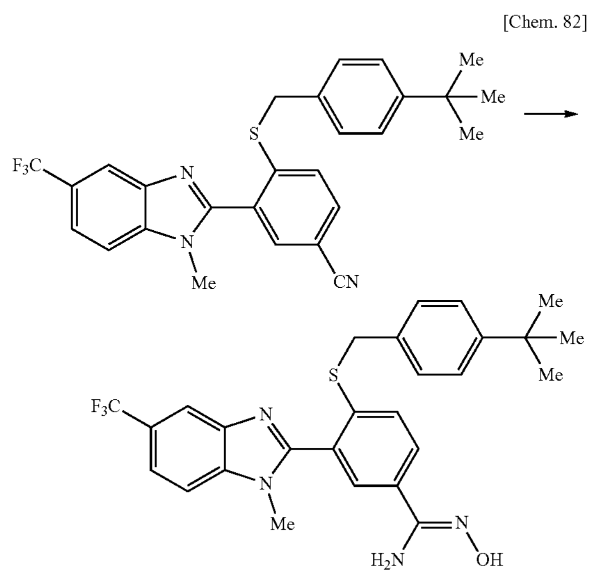

To an ethanol solution (1.0 mL) of 2-((4-(tert-butyl)benzyl)thio)-3-(1-methyl-5-(trifluoromethyl)-1H-benzo[d]imidazol-2-yl)benzonitrile (0.10 g, 0.21 mmol), hydroxylamine hydrochloride (22 mg, 0.31 mmol) and sodium acetate (26 mg, 0.31 mmol) were added at room temperature, and the mixture was stirred and heated under reflux for 2 hours. After the completion of the reaction, water was added, and ethyl acetate extraction was performed. The organic layer was dried over anhydrous magnesium sulfate and then concentrated in vacuo to give (Z)-4-((4-(tert-butyl)benzyl)thio)-N'-hydroxy-3-(1-methyl-5(trifluoromethyl)-1H-benzo[d]imidazol-2-yl)benzimidamide (0.11 g, 0.21 mmol).

Yield: 100%

Production Example 11-5

Production of (Z)-4-((4-(tert-butyl)benzyl)thio)-N'-ethoxy-3-(1-methyl-5-(trifluoromethyl)-1H-benzo[d]imidazol-2-yl)benzimidamide

[Chem. 83]

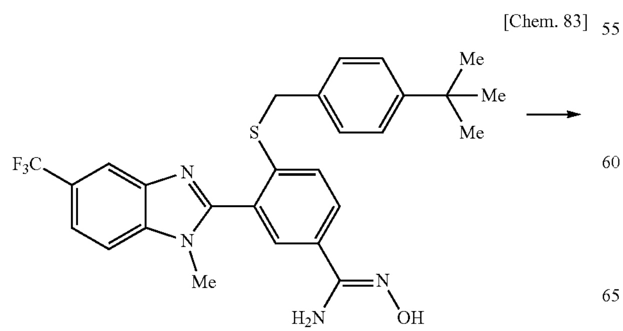

-continued

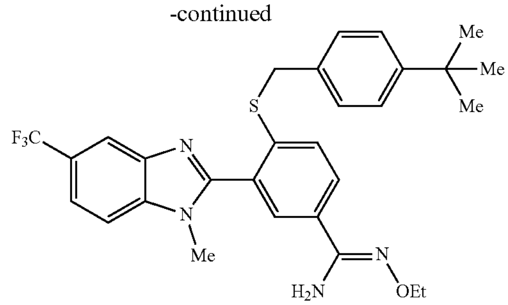

To an N,N-dimethylformamide solution (1.0 mL) of (Z)-4-((4-(tert-butyl)benzyl)thio)-N'-hydroxy-3-(1-methyl-5-(trifluoromethyl)-1H-benzo[d]imidazol-2-yl)benzimidamide (0.11 g, 0.21 mmol), ethyl iodide (20 μL, 0.26 mmol) and cesium carbonate (0.11 g, 0.32 mmol) were added at room temperature, and the mixture was stirred at room temperature for 2 hours. After the completion of the reaction, a saturated aqueous ammonium chloride solution was added, and ethyl acetate extraction was performed. The organic layer was dried over anhydrous magnesium sulfate and then concentrated in vacuo. The residue was purified by silica gel column chromatography to give (Z)-4-((4-(tert-butyl)benzyl)thio)-N'-ethoxy-3-(l-methyl-5-(trifluoromethyl)-1H-benzo[d]imidazol-2-yl) benzimidamide (70 mg, 0.13 mmol).

Yield: 60%

Production Example 11-6

(Z)—N'-ethoxy-3-(1-methyl-5-(trifluoromethyl)-1H-benzo[d]imidazol-2-yl)-4-(N-methylsulfamoyl)benzimidamide (Compound No. 4-46)

[Chem. 84]

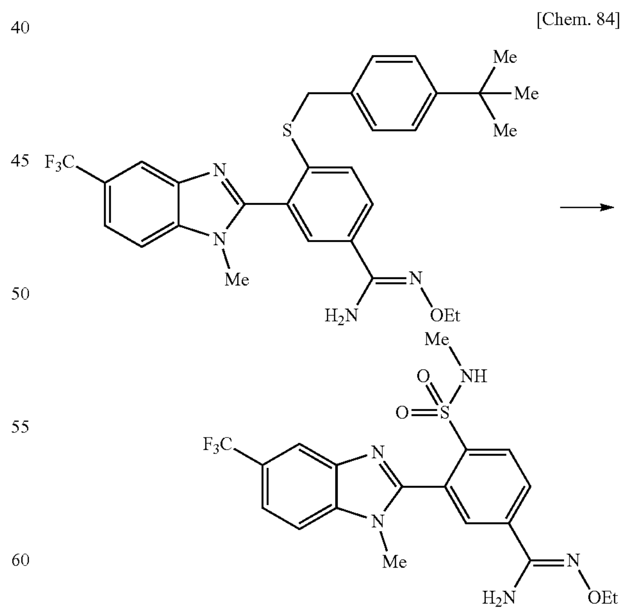

To a chloroform solution (1.0 mL) of (Z)-4-((4-(tert-butyl)benzyl)thio)-N'-ethoxy-3-(1-methyl-5-(trifluoromethyl)-1H-benzo[d]imidazol-2-yl)benzimidamide (70 mg, 0.13 mmol), 1,3-dichloro-5,5-dimethylhydantoin (80 mg, 0.39 mmol), acetic acid (25 μL, 0.39 mmol), and water (15 μL, 0.78 mmol) were added at 0° C., and the mixture was stirred at 0° C. for 15 minutes. Then, methylamine (40% methanol solution) (0.13 mL, 1.3 mmol) was added, and the mixture was stirred for 10 minutes. After the completion of the reaction, water was added to the reaction mixture, and chloroform extraction was performed. The organic layer was dried over anhydrous magnesium sulfate and then concentrated in vacuo. The residue was purified by silica gel column chromatography to give (Z)—N'-ethoxy-3-(1-methyl-5-(trifluoromethyl)-1H-benzo[d]imidazol-2-yl)-4-(N-methylsulfamoyl)benzimidamide (37 mg, 0.081 mmol).

Yield: 62%

Physical property: $^1$H-NMR ($CDCl_3$): 8.19 (d, 1H), 8.06 (d, 1H), 7.92 (dd, 1H), 7.88 (d, 1H), 7.63 (dd, 1H), 7.52 (d, 1H), 6.41 (q, 1H), 4.84 (s, 2H), 4.18 (q, 2H), 3.74 (s, 3H), 2.72 (d, 3H)), 1.33 (t, 3H)

Production Example 12

Production of (Z)—N'-ethoxy-6-(1-methyl-5-(trifluoromethyl)-1H-benzo[d]imidazol-2-yl)-5-(2-oxo-oxazolidin-3-yl)picolinimidamide (Compound No. 3-130)

[Chem. 85]

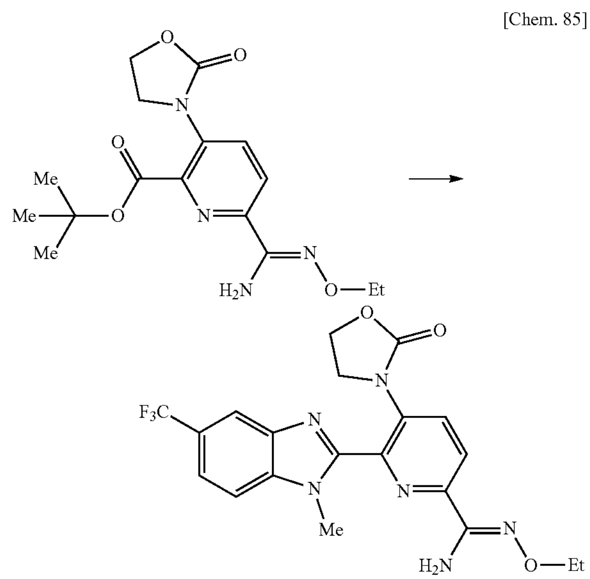

To 6-(N'-ethoxycarbamimidoyl)-3-(2-oxo-oxazolidin-3-yl)picolinic acid (Z)-tert-butyl ester (48 mg, 0.13 mmol), trifluoroacetic acid (1.0 mL) was added at room temperature, and the mixture was stirred at 60° C. for 3 hours. After the completion of the reaction, the reaction mixture was concentrated in vacuo. Pyridine (1.0 mL), 1-(3-dimethylaminopropyl)-3-ethylcarbodiimide (30 mg, 0.16 mmol), and N,N-dimethyl-4-aminopyridine (20 mg, 0.13 mmol) were added to the residue at room temperature, and the mixture was stirred at room temperature overnight. After the completion of the reaction, 0.5N hydrochloric acid was added to the reaction mixture, and ethyl acetate extraction was performed. The organic layer was dried over anhydrous magnesium sulfate and then concentrated in vacuo. Acetic acid (1.0 mL) was added to the residue, and the mixture was stirred at 120° C. for 3 hours. After the completion of the reaction, a saturated aqueous sodium hydrogen carbonate solution was added to the reaction mixture, and ethyl acetate extraction was performed. The organic layer was dried over anhydrous magnesium sulfate and then concentrated in vacuo. The residue was purified by silica gel column chromatography to give (Z)—N'-ethoxy-6-(1-methyl-5-(trifluoromethyl)-1H-benzo[d]imidazol-2-yl)-5-(2-oxo-oxazolidin-3-yl)picolinimidamide (36 mg, 0.080 mmol).

Yield: 58%

Physical property: $^1$H-NMR ($CDCl_3$): 8.19 (d, 1H), 8.04 (s, 1H), 7.79 (d, 1H), 7.60 (dd, 1H), 7.53 (d, 1H), 5.45 (s, 2H), 4.52 (t, 2H), 4.24 (t, 2H), 4.22 (q, 2H), 3.96 (s, 3H), 1.36 (t, 3H)

Production Example 13

Production of (Z)—N'-ethoxy-6-(1-methyl-5-(trifluoromethyl)-1H-benzo[d]imidazol-2-yl)-5-(N-methylsulfamoyl)pyrazine-2-carboximidamide (Compound No. 7-46)

Production Example 13-1

Production of (Z)-5-((4-(tert-butyl)benzyl)thio)-N'-ethoxy-6-(1-methyl-5-(trifluoromethyl)-1H-benzo[d]imidazol-2-yl)pyrazine-2-carboximidamide

[Chem. 86]

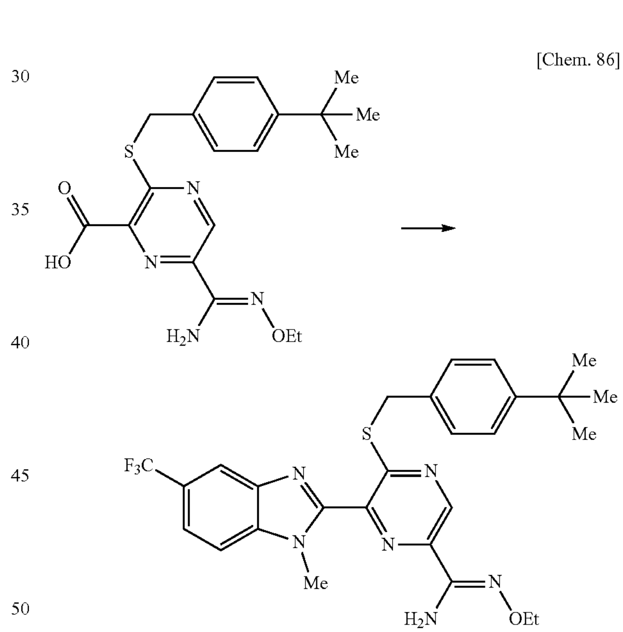

To a pyridine solution (3.0 mL) of (Z)-3-((4-(tert-butyl)benzyl)thio)-6-(N'-ethoxycarbamimidoyl)pyrazine-2-carboxylic acid (0.19 g, 0.50 mmol), N-methyl-4-trifluoromethylbenzene-1,2-diamine (0.10 g, 0.50 mmol), N,N-dimethyl-4-aminopyridine (0.061 g, 0.50 mmol), and 1-(3-dimethylaminopropyl)-3-ethylcarbodiimide hydrochloride (0.14 g, 0.75 mmol) were added, and the mixture was stirred at room temperature for 16 hours. The reaction mixture was concentrated in vacuo, water and ethyl acetate were added to the residue, and extraction was performed. The organic layer was dried over anhydrous sodium sulfate and then concentrated in vacuo. Acetic acid (3.0 mL) was added to the residue, and the mixture was stirred at 120% C for 2 hours. After the completion of the reaction, the reaction mixture was concentrated in vacuo. A saturated aqueous sodium hydrogen carbonate solution was added to the residue, and ethyl acetate extraction was performed. The organic layer was dried over anhydrous magnesium sulfate and then concentrated in vacuo. The residue was purified by silica gel column chromatography to give (Z)-5-((4-(tert-butyl)benzyl)thio)-N'-ethoxy-6-(1-methyl-5-(trifluoromethyl)-1H-benzo[d]imidazol-2-yl)pyrazine-2-carboximidamide (0.20 g, 0.37 mmol).

Yield: 74%

Physical property: Melting point: 180 to 181° C.

Production Example 13-2

Production of (Z)—N'-ethoxy-6-(1-methyl-5-(trifluoromethyl)-1H-benzo[d]imidazol-2-yl)-5-(N-methylsulfamoyl) pyrazine-2-carboximidamide (Compound No. 7-46)

[Chem. 87]

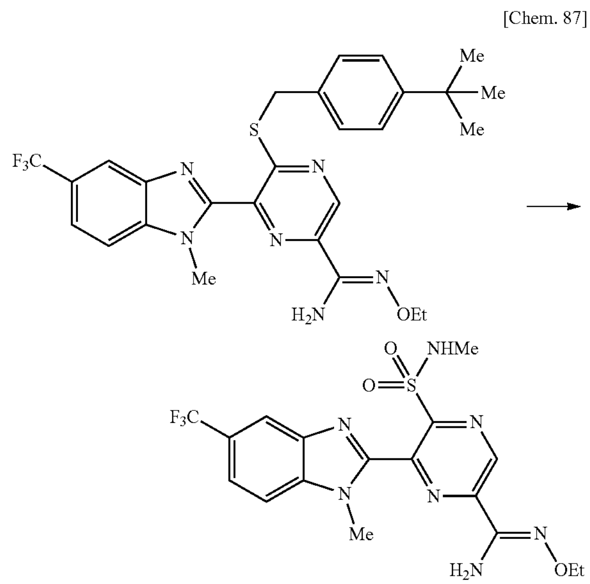

To a chloroform solution (2.0 mL) of (Z)-5-((4-(tert-butyl)benzyl)thio)-N'-ethoxy-6-(1-methyl-5-(trifluoromethyl)-1H-benzo[d]imidazol-2-yl)pyrazine-2-carboximidamide (0.095 g, 0.18 mmol), 1,3-dichloro-5,5-dimethylhydantoin (0.10 g, 0.53 mmol), acetic acid (0.030 mL, 0.53 mmol), and water (0.019 mL, 1.1 mmol) were added at 0° C., and the mixture was stirred at 0° C. for 5 minutes. Then, methylamine (40% methanol solution) (2.0 mL, 20 mmol) was added, and the mixture was stirred for 5 minutes. After the completion of the reaction, water was added to the reaction mixture, and chloroform extraction was performed. The organic layer was dried over anhydrous magnesium sulfate and then concentrated in vacuo. The residue was purified by silica gel column chromatography to give (Z)—N'-ethoxy-6-(1-methyl-5-(trifluoromethyl)-1H-benzo[d]imidazol-2-yl)-5-(N-methylsulfamoyl) pyrazine-2-carboximidamide (0.017 g, 0.038 mmol).

Yield: 21%

Physical property: Melting point: 244 to 246° C.

Production Example 14

Production of (Z)—N'-ethoxy-4-(1-methyl-1H-benzo[d]imidazol-2-yl)-5-(N-methylsulfamoyl)pyrimidine-2-carboximidamide (Compound No. 8-6)

Production Example 14-1

Production of 2-(5-((4-(tert-butyl)benzyl)thio)-2-chloropyrimidin-4-yl)-1H-benzo[d]imidazole

[Chem. 88]

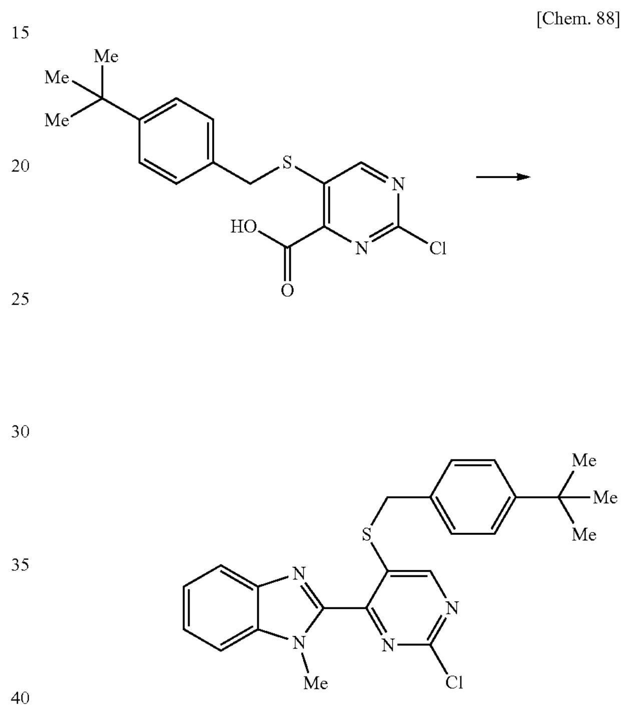

To a pyridine solution (10 mL) of 5-((4-(tert-butyl)benzyl)thio)-2-chloropyrimidine-4-carboxylic acid (1.5 g, 4.5 mmol), N-methyl-1,2-phenylenediamine dihydrochloride (0.87 g, 4.5 mmol), 1-hydroxybenzotriazole (34 mg, 0.89 mmol), and 1-(3-dimethylaminopropyl)-3-ethylcarbodiimide hydrochloride (1.0 g, 5.34 mmol) were added, and the mixture was stirred at room temperature for 16 hours. The reaction mixture was concentrated in vacuo, water and ethyl acetate were added to the residue, and extraction was performed. The organic layer was dried over anhydrous sodium sulfate and then concentrated in vacuo. Acetic acid (10 mL) was added to the residue, and the mixture was stirred at 120° C. for 2 hours. After the completion of the reaction, the reaction mixture was concentrated in vacuo. A saturated aqueous sodium hydrogen carbonate solution was added to the residue, and ethyl acetate extraction was performed. The organic layer was dried over anhydrous magnesium sulfate and then concentrated in vacuo. The residue was purified by silica gel column chromatography to give 2-(5-((4-(tert-butyl)benzyl)thio)-2-chloropyrimidin-4-yl)-1H-benzo[d]imidazole (1.1 g, 2.7 mmol).

Yield: 61%

Physical property: $^1$H-NMR ($CDCl_3$): 8.63 (s, 1H), 7.89 (d, 1H), 7.45-7.41 (m, 2H), 7.36-7.31 (m, 5H), 4.21 (s, 2H), 4.10 (s, 3H), 1.29 (s, 9H)

Production Example 14-2

Production of (Z)-5-((4-(tert-butyl)benzyl)thio)-N'-hydroxy-4-(1-methyl-1H-benzo[d]imidazol-2-yl)pyrimidine-2-carboximidamide

[Chem. 89]

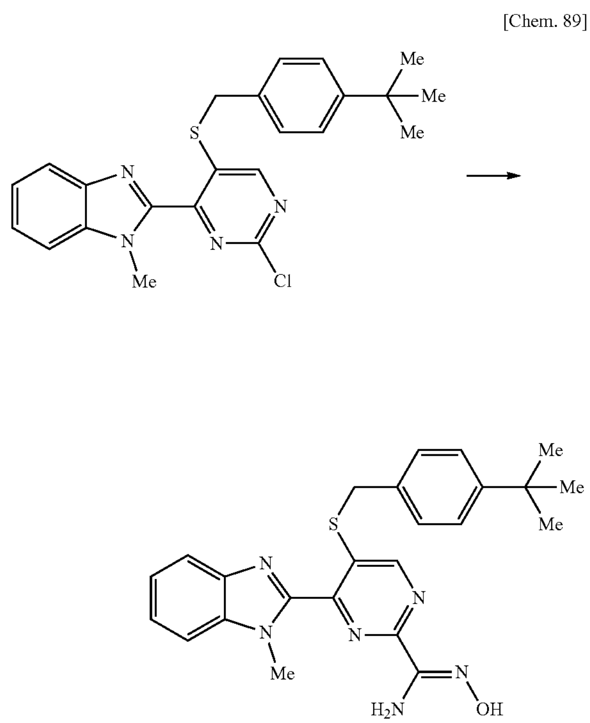

To a dimethyl sulfoxide solution (10 mL) of 2-(5-((4-(tert-butyl)benzyl)thio)-2-chloropyrimidin-4-yl)-1H-benzo[d]imidazole (0.48 g, 1.1 mmol), 1,4-diazabicyclo[2.2.2]octane (25 mg, 0.23 mmol) was added at room temperature, and the mixture was stirred at room temperature for 5 minutes. Then, an aqueous solution (1.0 mL) of sodium cyanide (66 mg, 1.4 mmol) was added dropwise at room temperature, and the mixture was stirred at the same temperature for 2 hours. After the completion of the reaction, a saturated aqueous sodium chloride solution was added to the reaction mixture, and ethyl acetate extraction was performed. The organic layer was dried over anhydrous sodium sulfate and then concentrated in vacuo. To an ethanol solution (10 mL) of the resulting crude product, hydroxylamine hydrochloride (48 mg, 0.69 mmol) and sodium acetate (56 mg, 0.69 mmol) were added at room temperature, and the mixture was stirred and heated under reflux for 1 hour. After the completion of the reaction, the reaction mixture was concentrated in vacuo. A saturated aqueous sodium hydrogen carbonate solution was added to the residue, and ethyl acetate extraction was performed. The organic layer was dried over anhydrous sodium sulfate and then concentrated in vacuo to give (Z)-5-((4-(tert-butyl)benzyl)thio)-N'-hydroxy-4-(1-methyl-1H-benzo[d]imidazol-2-yl)pyrimidine-2-carboximidamide (0.24 g, 0.54 mmol).

Yield: 48%

Physical property: $^1$H-NMR ($CDCl_3$): 8.82 (s, 1H), 7.89 (d, 1H), 7.45-7.31 (m, 7H), 5.52 (br-s, 2H), 4.24 (s, 2H), 4.05 (s, 3H), 1.29 (s, 9H)

Production Example 14-3 (Z)-5-((4-(tert-butyl)benzyl)thio)-N'-ethoxy-4-(1-methyl-1H-benzo[d]imidazol-2-yl)pyrimidine-2-carboximidamide

[Chem. 90]

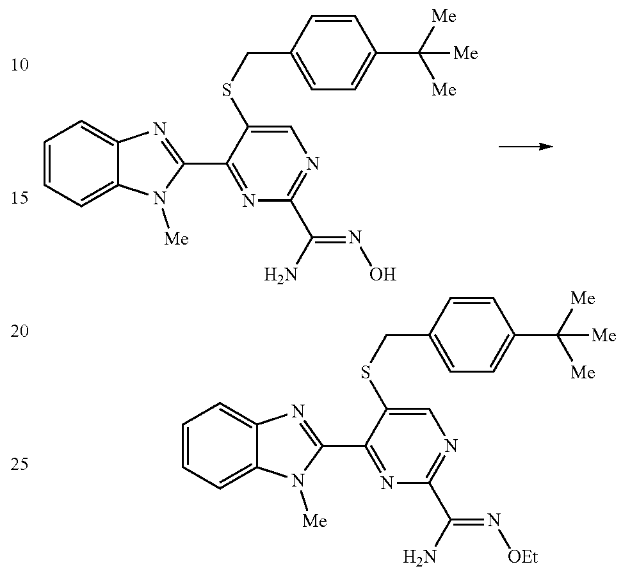

To an N,N-dimethylacetamide solution (1.0 mL) of (Z)-5-((4-(tert-butyl)benzyl)thio)-N'-hydroxy-4-(1-methyl-1H-benzo[d]imidazol-2-yl)pyrimidine-2-carboximidamide (0.10 g, 0.22 mmol), ethyl iodide (0.054 mL, 0.67 mmol) and cesium carbonate (0.22 g, 0.67 mmol) were added at room temperature, and the mixture was stirred at the same temperature for 2 hours. After the completion of the reaction, a saturated aqueous ammonium chloride solution was added to the reaction mixture, and ethyl acetate extraction was performed. The organic layer was dried over anhydrous sodium sulfate and then concentrated in vacuo to give (Z)-5-((4-(tert-butyl)benzyl)thio)-N'-ethoxy-4-(1-methyl-1H-benzo[d]imidazol-2-yl)pyrimidine-2-carboximidamide (55 mg, 0.12 mmol).

Yield: 51%

Production Example 14-4

Production of (Z)—N'-ethoxy-4-(1-methyl-1H-benzo[d]imidazol-2-yl)-5-(N-methylsulfamoyl)pyrimidine-2-carboximidamide (Compound No. 8-6)

[Chem. 91]

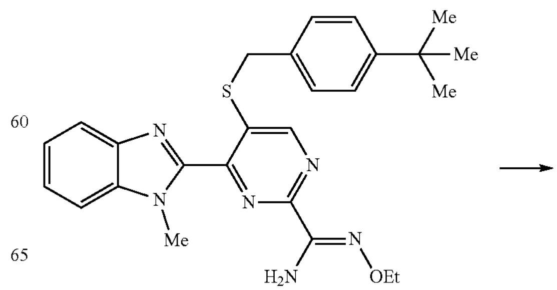

-continued

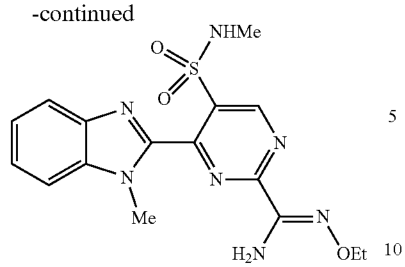

To a chloroform solution (1.0 mL) of (Z)-5-((4-(tert-butyl)benzyl)thio)-N'-ethoxy-4-(1-methyl-1H-benzo[d]imidazol-2-yl)pyrimidine-2-carboximidamide (0.055 g, 0.12 mmol), 1,3-dichloro-5,5-dimethylhydantoin (0.068 g, 0.35 mmol), acetic acid (0.020 mL, 0.35 mmol), and water (0.012 ml, 0.69 mmol) were added at 0° C., and the mixture was stirred at 0° C. for 10 minutes. Then, methylamine (40% methanol solution) (0.10 mL, 0.98 mmol) was added, and the mixture was stirred for 10 minutes. After the completion of the reaction, water was added to the reaction mixture, and chloroform extraction was performed. The organic layer was dried over anhydrous magnesium sulfate and then concentrated in vacuo. The residue was purified by silica gel column chromatography to give (Z)—N'-ethoxy-4-(1-methyl-1H-benzo[d]imidazol-2-yl)-5-(N-methylsulfamoyl) pyrimidine-2-carboximidamide (0.026 g, 0.067 mmol).

Yield: 59%

Physical property: Melting point: 222 to 223° C.

Reference Example 1

Production of 6-(1,3-dioxan-2-yl)-3-ethylsulfonylpyridine-2-carboxylic Acid (Starting Compound of Production Example 1-1)

Reference Production Example 1-1

Production of 6-chloro-3-ethylsulfonylpyridine-2-carboxylic Acid Ethyl Ester

[Chem. 92]

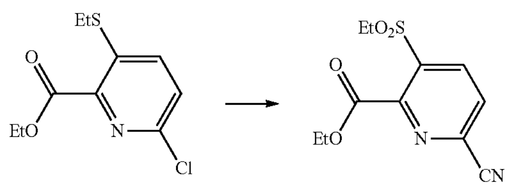

To an ethyl acetate solution (60 mL) of 6-chloro-3-ethylthiopyridine-2-carboxylic acid ethyl ester (4.0 g, 16 mmol), m-chloroperoxybenzoic acid (11 g, 41 mmol) was added, and the mixture was stirred at room temperature for 2 hours. After the completion of the reaction, a saturated aqueous sodium hydrogen carbonate solution and a saturated aqueous sodium thiosulfate solution were added. The resulting layers were separated. The organic layer was washed with a saturated aqueous sodium chloride solution, dried over anhydrous magnesium sulfate, and then concentrated in vacuo to give 6-chloro-3-ethylsulfonylpyridine-2-carboxylic acid ethyl ester (4.2 g, 15 mmol).

Yield: 92%

Reference Production Example 1-2

Production of 3-ethylsulfonyl-6-vinylpyridine-2-carboxylic Acid Ethyl Ester

[Chem. 93]

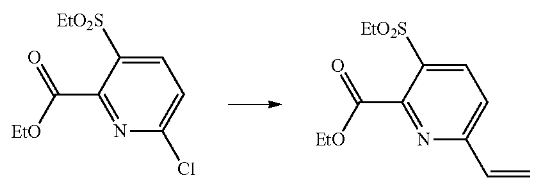

To a 1,2-dimethoxyethane solution (0.11 L) of 6-chloro-3-ethylsulfonylpyridine-2-carboxylic acid ethyl ester (4.2 g, 15 mmol), a 2 M aqueous sodium carbonate solution (36 mL, 73 mmol), potassium vinyltrifluoroborate (3.3 g, 24 mmol), and dichloro[1,1'-bis(diphenylphosphino)ferrocene] palladium(II) acetone adduct (0.38 g, 0.49 mmol) were added, and the mixture was heated under reflux for 2 hours. After the completion of the reaction, water was added. The resulting layers were separated. The organic layer was washed with a saturated aqueous sodium chloride solution, dried over anhydrous magnesium sulfate, and then concentrated in vacuo. The residue was purified by silica gel column chromatography to give 3-ethylsulfonyl-6-vinylpyridine-2-carboxylic acid ethyl ester (3.0 g, 11 mmol).

Yield: 75%

Reference Production Example 1-3

Production of 3-ethylsulfonyl-6-formylpyridine-2-carboxylic Acid Ethyl Ester

[Chem. 94]

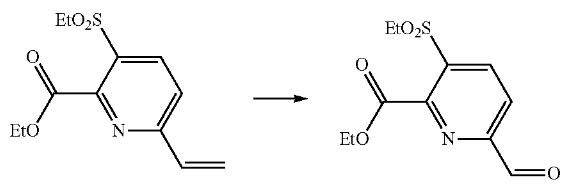

To a tetrahydrofuran solution (0.10 L) of 3-ethylsulfonyl-6-vinylpyridine-2-carboxylic acid ethyl ester (3.0 g, 11 mmol), a pH 7 buffer (50 mL), N-methylmorpholine N-oxide (11 g, 48 mmol, 50% aqueous solution), and osmium (VIII) oxide (1.6 mL, 0.16 mmol, 0.1 M tert-butanol solution) were added, and the mixture was stirred at room temperature overnight. After the completion of the reaction, sodium periodate (5.2 g, 24 mmol) was added, and the mixture was further stirred at room temperature for 1 hour. After the completion of the reaction, a saturated aqueous sodium bicarbonate solution and a saturated aqueous sodium thiosulfate solution were added, and ethyl acetate extraction was performed. The organic layer was dried over anhydrous magnesium sulfate and then concentrated in vacuo. The residue was purified by silica gel column chromatography to give 3-ethylsulfonyl-6-formylpyridine-2-carboxylic acid ethyl ester (2.1 g, 7.6 mmol).

Yield: 71%

Physical property: $^1$H-NMR ($CDCl_3$): 10.15 (s, 1H), 8.53 (d, 1H), 8.19 (d, 1H), 4.56 (q, 2H), 3.54 (q, 2H), 1.48 (t, 3H), 1.36 (t, 3H)

Reference Production Example 1-4

Production of 6-(1,3-dioxan-2-yl)-3-ethylsulfonylpyridine-2-carboxylic Acid Ethyl Ester

[Chem. 95]

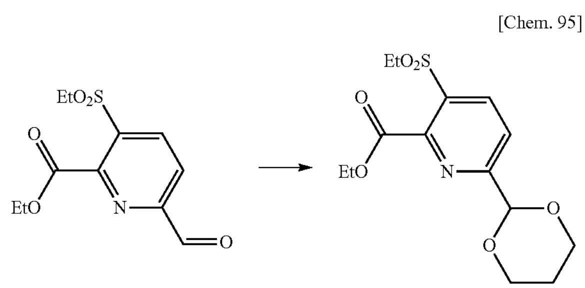

To a toluene solution (85 mL) of 3-ethylsulfonyl-6-formylpyridine-2-carboxylic acid ethyl ester (4.7 g, 17 mmol), 1,3-propanediol (2.0 g, 26 mmol) and p-toluenesulfonic acid monohydrate (3.3 g, 17 mmol) were added, and the mixture was heated under reflux for 1 hour. After the completion of the reaction, a saturated aqueous sodium bicarbonate solution was added, and ethyl acetate extraction was performed. The organic layer was dried over anhydrous magnesium sulfate and then concentrated in vacuo. The residue was purified by silica gel column chromatography to give 6-(1,3-dioxan-2-yl)-3-ethylsulfonylpyridine-2-carboxylic acid ethyl ester (5.0 g, 15 mmol).

Yield: 87%

Physical property: Melting point: 85 to 86° C.

Reference Production Example 1-5

Production of 6-(1,3-dioxan-2-yl)-3-ethylsulfonylpyridine-2-carboxylic Acid

[Chem. 96]

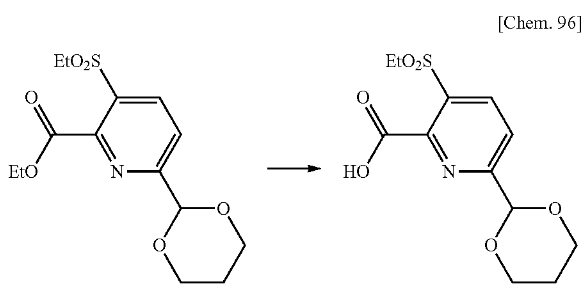

To an ethanol solution (50 mL) of 6-(1,3-dioxan-2-yl)-3-ethylsulfonylpyridine-2-carboxylic acid ethyl ester (5.0 g, 15 mmol), lithium hydroxide (8.6 mL, 34 mmol, 4 M aqueous solution) was added, and the mixture was stirred for 3 hours. After the completion of the reaction, 2 M hydrochloric acid was added to adjust the pH to 2, and ethyl acetate extraction was performed. The organic layer was dried over anhydrous magnesium sulfate and then concentrated in vacuo to give 6-(1,3-dioxan-2-yl)-3-ethylsulfonylpyridine-2-carboxylic acid (4.1 g, 13 mmol).

Yield: 90%

Physical property: Melting point: 145 to 146° C.

Reference Example 2

Production of 6-[(E)-N-ethoxy-C-methyl-carbonimidoyl]-3-ethylsulfonylpyridine-2-carboxylic Acid (Starting Compound of Production Example 2)

Reference Production Example 2-1

Production of 6-acetyl-3-ethylsulfonylpyridine-2-carboxylic Acid Methyl Ester

[Chem. 97]

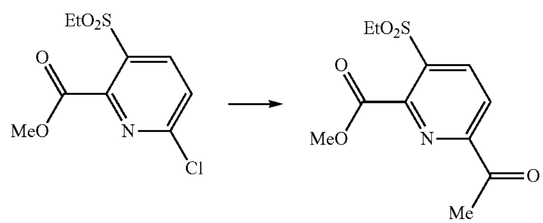

To a 1,2-dimethoxyethane solution (200 mL) of 6-chloro-3-ethylsulfonylpyridine-2-carboxylic acid methyl ester (11 g, 41 mmol), tributyl(1-ethoxyvinyl)tin (17 mL, 49 mmol) and tetrakis(triphenylphosphine)palladium(0) (2.5 g, 2.2 mmol) were added under an argon atmosphere at room temperature, and the mixture was stirred at 110° C. for 3 hours. After cooling to room temperature, tetrahydrofuran (100 mL) and 2 N hydrochloric acid (100 mL) were added, and the mixture was stirred at 50° C. for 3 hours. After the completion of the reaction, ethyl acetate and water were added to the reaction mixture, and extraction was performed. The organic layer was dried over anhydrous magnesium sulfate and then concentrated in vacuo. The residue was purified by silica gel column chromatography to give 6-acetyl-3-ethylsulfonylpyridine-2-carboxylic acid methyl ester as a crude product.

Physical property: $^1$H-NMR ($CDCl_3$): 8.54 (d, 1H), 8.28 (d, 1H), 4.08 (s, 3H), 3.35 (s, 3H), 2.77 (s, 3H)

Reference Production Example 2-2

Production of 6-[(E)-N-ethoxy-C-methyl-carbonimidoyl]-3-ethylsulfonylpyridine-2-carboxylic Acid Methyl Ester

[Chem. 98]

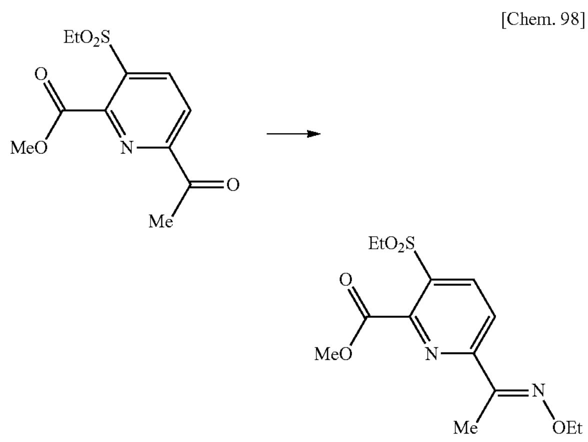

To a chloroform solution (200 mL) of the 6-acetyl-3-ethylsulfonylpyridine-2-carboxylic acid methyl ester obtained in Reference Production Example 2-1, pyridine (60.0 mL) and O-ethylhydroxylamine hydrochloride (5.94 g, 60.9 mmol) were added at room temperature, and the mixture was stirred overnight. After the completion of the reaction, 1 N hydrochloric acid and chloroform were added to the reaction mixture, and extraction was performed. The organic layer was dried over anhydrous magnesium sulfate and then concentrated in vacuo to give 6-[(E)-N-ethoxy-C-methyl-carbonimidoyl]-3-ethylsulfonylpyridine-2-carboxylic acid methyl ester as a crude product.

Physical property: Melting point: 111 to 112° C.

Reference Production Example 2-3

Production of 6-[(E)-N-ethoxy-C-methyl-carbonimidoyl]-3-ethylsulfonylpyridine-2-carboxylic Acid

[Chem. 99]

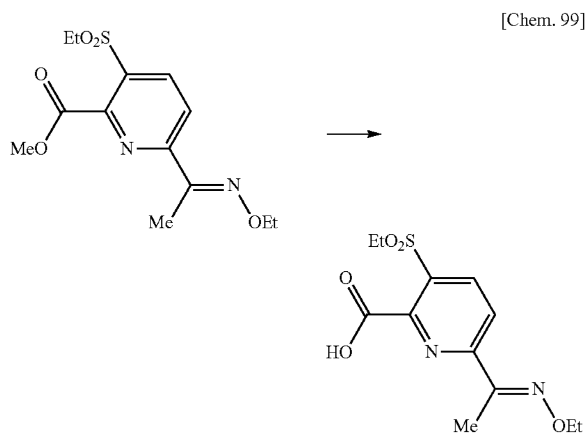

To a methanol solution (150 mL) of the 6-[(E)-N-ethoxy-C-methyl-carbonimidoyl]-3-ethylsulfonylpyridine-2-carboxylic acid methyl ester obtained in Reference Production Example 2-2, a 4 M aqueous lithium hydroxide solution (16 mL) was added at room temperature, and the mixture was stirred for 1 hour. After the completion of the reaction, 2 N hydrochloric acid and chloroform were added to the reaction mixture, and extraction was performed. A 2 N aqueous sodium hydroxide solution was additionally added, and the aqueous layer was subjected to extraction. 2 N hydrochloric acid was further added to the extract until it became acidic again, and ethyl acetate extraction was performed. The organic layer was dried over anhydrous magnesium sulfate and then concentrated in vacuo. Methyl tert-butyl ether and n-hexane were added to the residue. The precipitated solid was filtered to give 6-[(E)-N-ethoxy-C-methyl-carbonimidoyl]-3-ethylsulfonylpyridine-2-carboxylic acid (8.4 g, 32 mmol).

Yield: 80% (3 steps)

Physical property: Melting point: 137 to 138° C.

Reference Example 3

Production of 6-[(Z)—N'-ethoxy-C-methylcarbonimidoyl-3-methylsulfonylpyridine-2-carboxylic Acid (Starting Compound of Production Example 3-1)

Reference Production Example 3-1

Production of 6-cyano-3-methylsulfonylpyridine-2-carboxylic Acid Methyl Ester

[Chem. 100]

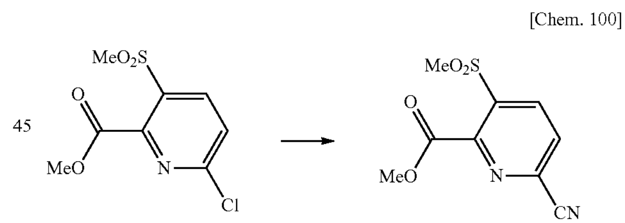

To a dimethyl sulfoxide solution (0.16 L) of 6-chloro-3-methylsulfonylpyridine-2-carboxylic acid methyl ester (10 g, 40 mmol), sodium cyanide (2.4 g, 48 mmol) dissolved in water (16 mL) was added at room temperature, and the mixture was stirred at room temperature for 1 hour. After the completion of the reaction, water was added, and ethyl acetate extraction was performed. The organic layer was dried over anhydrous magnesium sulfate and then concentrated in vacuo. Methyl tert-butyl ether was added to the residue, and the precipitated solid was collected by filtration and dried in vacuo to give 6-cyano-3-methylsulfonylpyridine-2-carboxylic acid methyl ester (7.2 g, 30 mmol).

Yield: 75%

Physical property: Melting point: 159 to 160° C.

Reference Production Example 3-2

Production of 6-[(Z)—N'-ethoxy-C-methylcarbonimidoyl-3-methylsulfonylpyridine-2-carboxylic Acid Methyl Ester

[Chem. 101]

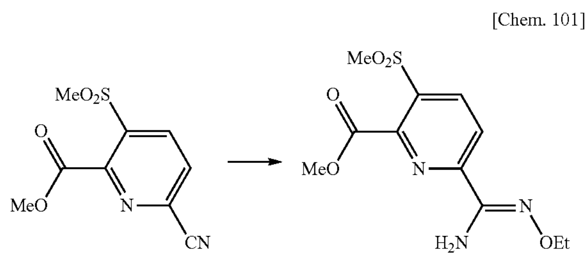 [SMILES: COC(=O)c1nc(C#N)ccc1S(C)(=O)=O ; CCO/N=C(\N)c1ccc(S(C)(=O)=O)c(C(=O)OC)n1]

To a methanol solution (60 L) of 6-cyano-3-methylsulfonylpyridine-2-carboxylic acid methyl ester (3.0 g, 12 mmol), sodium methoxide (2.5 mL, 12 mmol, 5 M aqueous solution) was added, and the mixture was stirred at room temperature for 30 minutes. O-Ethylhydroxylamine hydrochloride (1.6 g, 16 mmol) was added, and the mixture was stirred for 1 hour. After the completion of the reaction, water was added, and ethyl acetate extraction was performed. The organic layer was dried over anhydrous magnesium sulfate and then concentrated in vacuo. MTBE and hexane were added to the residue, and the precipitated solid was collected by filtration and dried in vacuo to give 6-[(Z)—N'-ethoxy-C-methylcarbonimidoyl-3-methylsulfonylpyridine-2-carboxylic acid methyl ester (3.1 g, 10 mol).

Yield: 83%

Physical property: Melting point: 104 to 105° C.

Reference Production Example 3-3

Production of 6-[(Z)—N'-ethoxy-C-methylcarbonimidoyl-3-methylsulfonylpyridine-2-carboxylic Acid

[Chem. 102]

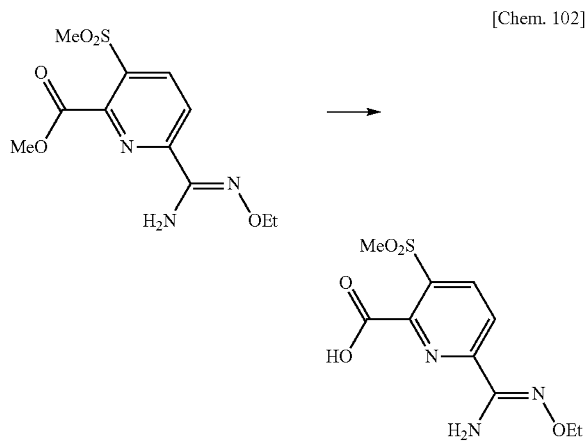

To a methanol:water (2:1) solution (60 mL) of 6-[(Z)—N'-ethoxy-C-methylcarbonimidoyl-3-methylsulfonylpyridine-2-carboxylic acid methyl ester (3.1 g, 10 mmol), lithium hydroxide monohydrate (0.79 g, 19 mmol) was added, and the mixture was stirred at room temperature overnight. After the completion of the reaction, 2.0 M hydrochloric acid was added to adjust the pH to 2, and ethyl acetate extraction was performed. The organic layer was dried over anhydrous magnesium sulfate and then concentrated in vacuo to give 6-[(Z)—N'-ethoxy-C-methylcarbonimidoyl-3-methylsulfonylpyridine-2-carboxylic acid (2.5 g, 8.7 mmol).

Yield: 84%

Physical property: Melting point: 154 to 155° C.

Reference Example 4

Production of 6-(N'-ethoxycarbamimidoyl)-3-(2-oxo-oxazolidin-3-yl)picolinic Acid (Z)-tert-butyl Ester (Starting Compound of Production Example 12)

Reference Production Example 4-1

Production of 3-chloropyridine-2,6-dicarboxylic acid-6-ethyl-2-tert-butyl Ester

[Chem. 103]

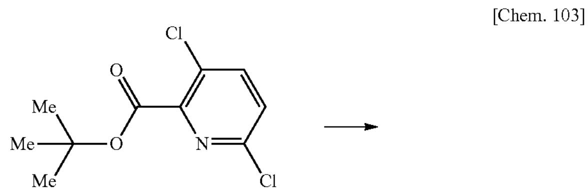

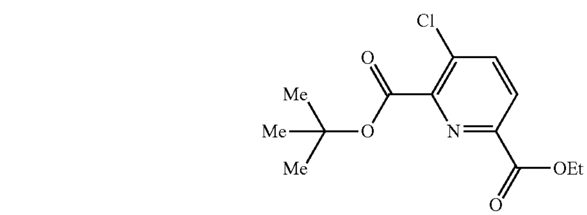

To an ethanol solution (0.11 L) of 3,6-dichloropicolinic acid tert-butyl ester (28 g, 0.11 mol), sodium acetate (9.3 g, 0.11 mol), palladium(II) acetate (0.51 g, 2.3 mmol) and 1,4-bis(diphenylphosphino) butane (1.9 g, 4.5 mmol) were added at room temperature, and the mixture was stirred under a carbon monoxide atmosphere (4 MPa) at 110° C. for 2 hours. After the completion of the reaction, a saturated aqueous sodium hydrogen carbonate solution was added to the reaction mixture, and ethyl acetate extraction was performed. The organic layer was dried over anhydrous magnesium sulfate and then concentrated in vacuo to give 3-chloropyridine-2,6-dicarboxylic acid-6-ethyl-2-tert-butyl ester (24 g, 84 mmol).

Yield: 74%

Physical property: $^1$H-NMR ($CDCl_3$): 8.09 (d, 1H), 7.88 (d, 1H), 4.46 (q, 2H), 1.64 (s, 9H), 1.43 (t, 3H)

Reference Production Example 4-2

Production of 6-carbamoyl-3-chloropicolic Acid Tert-Butyl Ester

[Chem. 104]

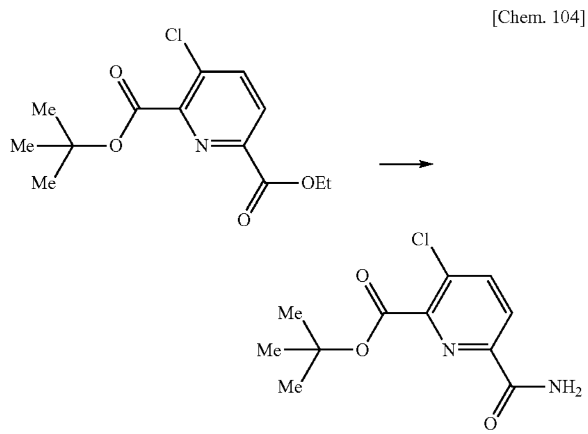

To an ethanol solution (30 mL) of 3-chloropyridine-2,6-dicarboxylic acid-6-ethyl-2-tert-butyl ester (24 g, 84 mmol), ammonia (4% ethanol solution) (50 mL, 0.56 mol) was added at room temperature, and the mixture was stirred at room temperature overnight. After the completion of the reaction, the reaction mixture was concentrated in vacuo to give 6-carbamoyl-3-chloropicolic acid tert-butyl ester (20 g, 78 mmol).

Yield: 93%

Physical property: $^1$H-NMR ($CDCl_3$): 8.20 (d, 1H), 7.92 (d, 1H), 7.73 (s, 1H), 5.83 (s, 1H), 1.64 (s, 9H)

Reference Production Example 4-3

Production of 3-chloro-6-cyanopicolic Acid Tert-Butyl Ester

[Chem. 105]

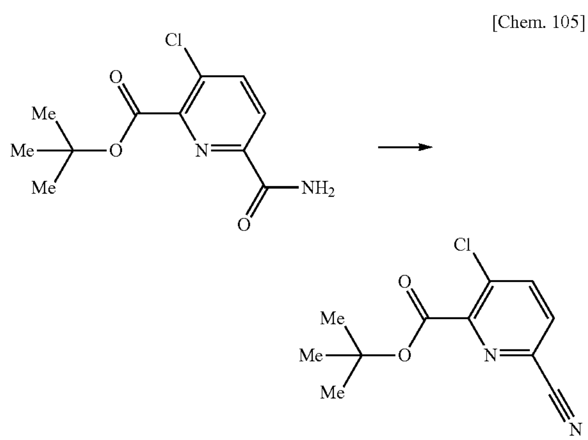

To an N,N-dimethylformamide solution (0.18 L) of 6-carbamoyl-3-chloropicolic acid tert-butyl ester (20 g, 78 mmol), phosphoryl chloride (22 mL, 0.23 mol) was added at 0° C., and the mixture was stirred at room temperature for 1 hour. After the completion of the reaction, a saturated aqueous sodium hydrogen carbonate solution was added to the reaction mixture, and ethyl acetate extraction was performed. The organic layer was dried over anhydrous magnesium sulfate and then concentrated in vacuo to give 3-chloro-6-cyanopicolic acid tert-butyl ester (16 g, 66 mmol).

Yield: 85%

Physical property: $^1$H-NMR ($CDCl_3$): 7.91 (d, 1H), 7.69 (d, 1H), 1.64 (s, 9H)

Reference Production Example 4-4

Production of 3-chloro-6-(N'-ethoxycarbamimidoyl) picolinic Acid (Z)-tert-butyl Ester

[Chem. 106]

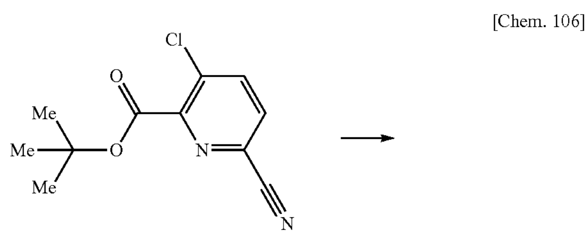

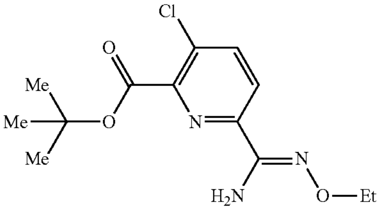

To a methanol solution (14 mL) of 3-chloro-6-cyanopicolic acid tert-butyl ester (1.0 g, 4.2 mmol), sodium methoxide (28% methanol solution) (0.43 mL, 4.2 mmol) was added at 0° C., and the mixture was stirred at 0° C. for 1 hour. Then, o-ethylhydroxylamine hydrochloride (0.41 g, 4.2 mmol) was added, and the mixture was stirred for 1 hour. After the completion of the reaction, water was added to the reaction mixture, and ethyl acetate extraction was performed. The organic layer was dried over anhydrous magnesium sulfate and then concentrated in vacuo. The residue was purified by silica gel column chromatography to give 3-chloro-6-(N'-ethoxycarbamimidoyl)picolinic acid (Z)-tert-butyl ester (1.21 g, 4.0 mmol).

Yield: 96%

Physical property: $^1$H-NMR ($CDCl_3$): 7.98 (d, 1H), 7.70 (d, 1H), 5.49 (s, 2H), 4.17 (q, 2H), 1.64 (s, 9H), 1.33 (t, 3H)

Reference Production Example 4-5

Production of 6-(N'-ethoxycarbamimidoyl)-3-(2-oxo-oxazolidin-3-yl)picolinic Acid (Z)-tert-butyl Ester

[Chem. 107]

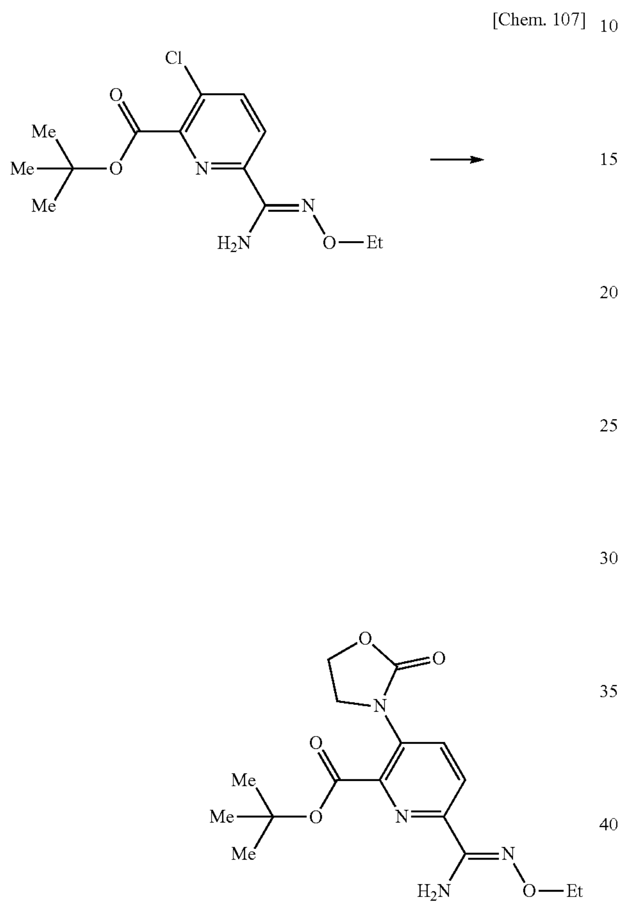

To a toluene solution (8.0 mL) of 3-chloro-6-(N'-ethoxycarbamimidoyl) picolinic acid (Z)-tert-butyl ester (0.50 g, 1.7 mmol), 2-oxazolidone (0.30 g, 3.3 mmol), cesium carbonate (2.2 g, 6.6 mmol), 4,5-bis(diphenylphosphino)-9,9-dimethylxanthene (0.39 g, 0.67 mmol), and tris(dibenzylideneacetone)dipalladium(0) (0.31 g, 0.30 mmol) were added at room temperature, and the mixture was stirred at 110° C. for 4 hours. After the completion of the reaction, a saturated aqueous ammonium chloride solution was added to the reaction mixture, and ethyl acetate extraction was performed. The organic layer was dried over anhydrous magnesium sulfate and then concentrated in vacuo. The residue was purified by silica gel column chromatography to give 6-(N'-ethoxycarbamimidoyl)-3-(2-oxo-oxazolidin-3-yl)picolinic acid (Z)-tert-butyl ester (48 mg, 0.14 mmol).

Yield: 8%

Physical property: $^1$H-NMR ($CDCl_3$): 8.10 (d, 2H), 5.47 (s, 2H), 4.17 (q, 2H), 3.10 (m, 4H), 1.63 (s, 9H), 1.33 (t, 3H)

Reference Example 5

Production of (Z)-3-((4-(tert-butyl)benzyl)thio)-6-(N'-ethoxycarbamimidoyl)pyrazine-2-carboxylic Acid (Starting Compound of Production Example 13-1)

Reference Production Example 5-1

Production of 3-((4-(tert-butyl)benzyl)thio)-6-iodopyrazine-2-carboxylic Acid Methyl Ester

[Chem. 108]

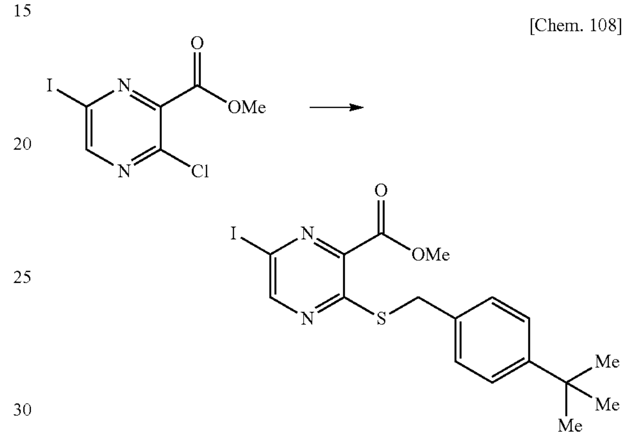

To an N,N-dimethylacetamide solution (25 mL) of 3-chloro-6-iodopyrazine-2-carboxylic acid methyl ester (2.0 g, 7.0 mmol), cesium carbonate (4.5 g, 14 mmol) and 4-(tert-butyl)benzylthiol (1.5 mL, 8.4 mmol) were added at room temperature, and the mixture was stirred at room temperature for 1 hour. After the completion of the reaction, a saturated aqueous ammonium chloride solution was added to the reaction mixture, and ethyl acetate extraction was performed. The organic layer was dried over anhydrous magnesium sulfate and then concentrated in vacuo. The residue was purified by silica gel column chromatography to give 3-((4-(tert-butyl)benzyl)thio)-6-iodopyrazine-2-carboxylic acid methyl ester (0.82 g, 1.9 mmol).

Yield: 26%

Physical property: $^1$H-NMR ($CDCl_3$): 8.77 (s, 1H), 7.32 (s, 4H), 4.32 (s, 2H), 1.30 (s, 9H)

Reference Production Example 5-2

Production of 3-((4-(tert-butyl)benzyl)thio)-6-cyanopyrazine-2-carboxylic Acid Methyl Ester

[Chem. 109]

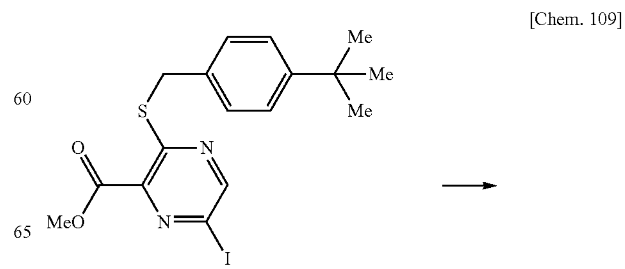

-continued

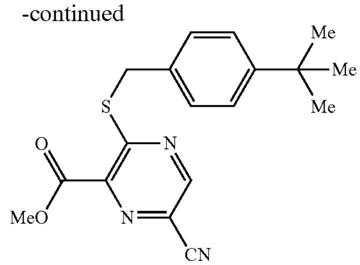

To an N-methyl-2-pyrrolidone solution (15 mL) of 3-((4-(tert-butyl) benzyl)thio)-6-iodopyrazine-2-carboxylic acid methyl ester (0.81 g, 1.8 mmol), copper cyanide (I) (0.20 g, 2.2 mmol) was added at room temperature, and the mixture was stirred at 120° C. for 2 hours. After the completion of the reaction, water was added to the reaction mixture, and ethyl acetate extraction was performed. The organic layer was dried over anhydrous magnesium sulfate and then concentrated in vacuo. The residue was purified by silica gel column chromatography to give 3-((4-(tert-butyl)benzyl) thio)-6-cyanopyrazine-2-carboxylic acid methyl ester (0.50 g, 1.5 mmol).

Yield: 80%

Physical property: $^1$H-NMR ($CDCl_3$): 8.80 (s, 1H), 7.33 (s, 4H), 4.40 (s, 2H), 1.30 (s, 9H)

Reference Production Example 5-3

Production of (Z)-3-((4-(tert-butyl)benzyl)thio)-6-(N'-ethoxycarbamimidoyl)pyrazine-2-carboxylic Acid Methyl Ester

[Chem. 110]

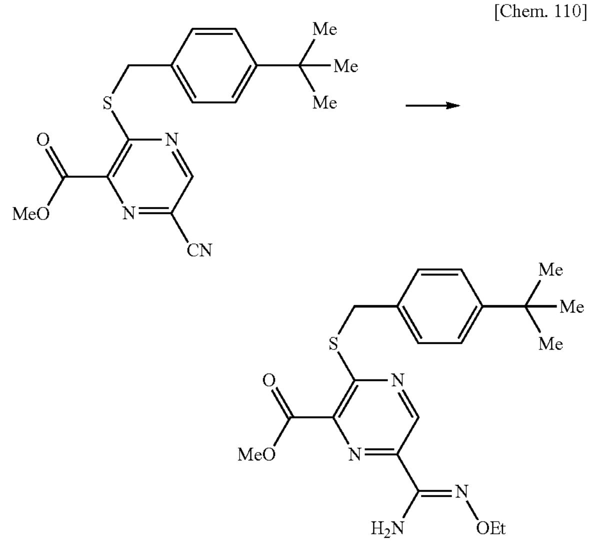

To a methanol solution (10 mL) of 3-((4-(tert-butyl) benzyl)thio)-6-cyanopyrazine-2-carboxylic acid methyl ester (0.48 g, 1.4 mmol), sodium methoxide (0.28 mL, 1.4 mmol, 5.0 M methanol solution) was added, and the mixture was stirred at room temperature for 1 hour. Then, o-ethyl-hydroxylamine hydrochloride (0.18 g, 1.8 mmol) was added, and the mixture was stirred at room temperature for 1 hour. After the completion of the reaction, the reaction mixture was concentrated in vacuo. A saturated aqueous sodium hydrogen carbonate solution and ethyl acetate were added to the residue, and extraction was performed. The organic layer was dried over anhydrous sodium sulfate and then concentrated in vacuo to give (Z)-3-((4-(tert-butyl) benzyl)thio)-6-(N'-ethoxycarbamimidoyl)pyrazine-2-carboxylic acid methyl ester (0.58 g, 1.4 mmol).

Yield: 100%

Physical property: $^1$H-NMR ($CDCl_3$): 9.17 (s, 1H), 7.35-7.30 (m, 4H), 5.42 (s, 2H), 4.40 (s, 2H), 4.20 (q, 2H), 3.97 (s, 3H), 1.35 (t, 3H), 1.30 (s, 9H)

Reference Production Example 5-4

Production of (Z)-3-((4-(tert-butyl)benzyl)thio)-6-(N'-ethoxycarbamimidoyl)pyrazine-2-carboxylic Acid

[Chem. 111]

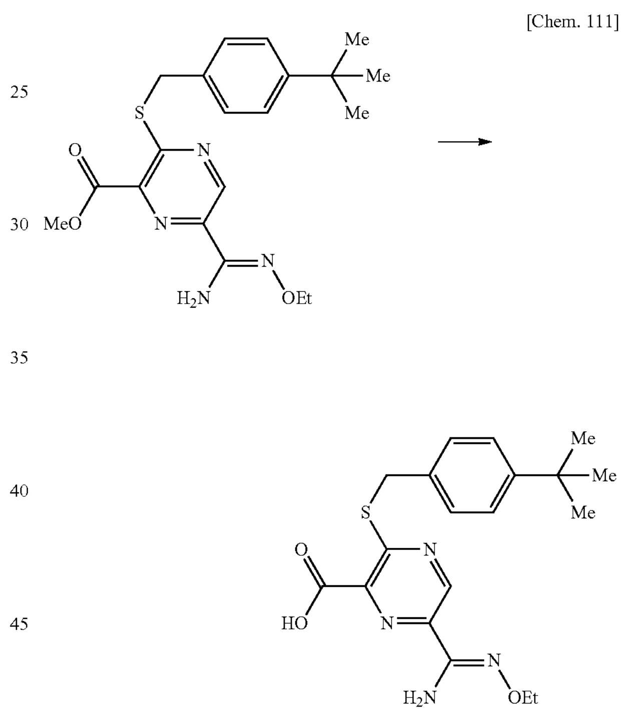

To a solution of (Z)-3-((4-(tert-butyl)benzyl)thio)-6-(N'-ethoxycarbamimidoyl)pyrazine-2-carboxylic acid methyl ester (0.58 g, 1.4 mmol) in a mixed solvent of tetrahydrofuran (4.0 mL) and water (2.0 mL), lithium hydroxide monohydrate (0.091 g, 2.2 mmol) was added, and the mixture was stirred at room temperature for 1 hour. 1 N hydrochloric acid and ethyl acetate were added to the reaction mixture, and extraction was performed. The organic layer was dried over anhydrous sodium sulfate and then concentrated in vacuo to give (Z)-3-((4-(tert-butyl)benzyl) thio)-6-(N'-ethoxycarbamimidoyl)pyrazine-2-carboxylic acid (0.58 g, 1.5 mmol).

Yield: 100%

Physical property: $^1$H-NMR ($CDCl_3$): 9.29 (s, 1H), 7.36-7.30 (m, 4H), 5.33 (br-s, 2H), 4.42 (s, 2H), 4.22 (q, 2H), 1.36 (t, 3H), 1.29 (s, 9H)

Reference Example 6

Production of 5-((4-(tert-butyl)benzyl)thio)-2-chloropyrimidine-4-carboxylic Acid (Starting Compound of Production Example 14-1)

Reference Production Example 6-1 Production of 5-((4-(tert-butyl)benzyl)thio)-2-chloropyrimidine-4-carboxylic Acid Ethyl Ester

[Chem. 112]

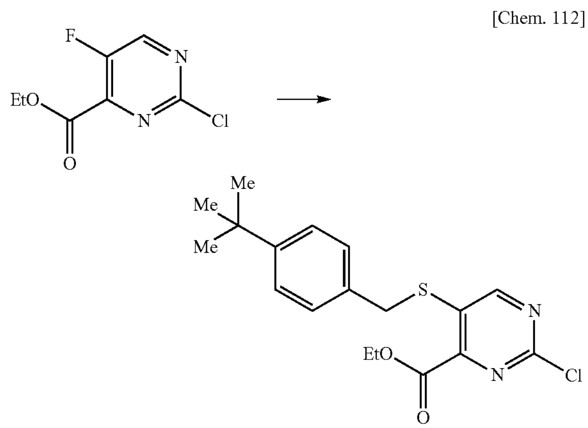

To a tetrahydrofuran solution (100 mL) of 2-chloro-5-fluoropyrimidine-4-carboxylic acid ethyl ester (4.8 g, 23 mmol), 4-(tert-butyl)benzylthiol (4.3 mL, 23 mmol) and sodium hydride (0.93 g, 23 mmol) were added under an argon atmosphere at 0° C., and the mixture was stirred at the same temperature for 1 hour. After the completion of the reaction, a saturated aqueous ammonium chloride solution was added to the reaction mixture, and ethyl acetate extraction was performed. The organic layer was dried over anhydrous sodium sulfate and then concentrated in vacuo. The residue was purified by silica gel column chromatography to give 5-((4-(tert-butyl)benzyl)thio)-2-chloropyrimidine-4-carboxylic acid ethyl ester (5.4 g, 15 mmol).

Yield: 64%

Physical property: $^{1}$H-NMR ($CDCl_3$): 8.55 (s, 1H), 7.34 (d, 2H), 7.27 (d, 2H), 4.49 (q, 2H), 4.17 (s, 2H), 1.43 (t, 3H), 1.30 (s, 9H)

Reference Production Example 6-2

Production of 5-((4-(tert-butyl)benzyl)thio)-2-chloropyrimidine-4-carboxylic Acid

[Chem. 113]

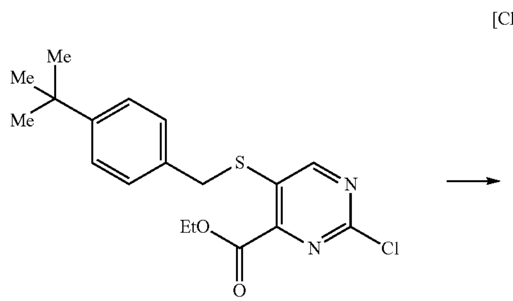

-continued

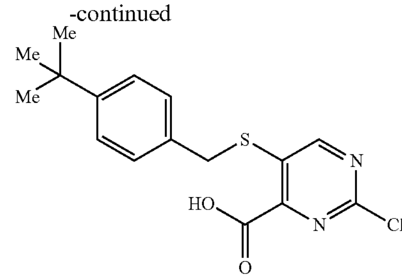

To a tetrahydrofuran:water (2:1) solution (90 mL) of 5-((4-(tert-butyl)benzyl)thio)-2-chloropyrimidine-4-carboxylic acid ethyl ester (3.3 g, 16 mmol), lithium hydroxide monohydrate (0.68 g, 16 mmol) was added, and the mixture was stirred at room temperature for 1 hour. After the completion of the reaction, a 2 N aqueous hydrochloric acid solution was added to adjust the pH to 2, and the mixture was extracted with ethyl acetate. The organic layer was washed with a saturated aqueous sodium chloride solution, dried over anhydrous magnesium sulfate, and then concentrated in vacuo to give 5-((4-(tert-butyl)benzyl)thio)-2-chloropyrimidine-4-carboxylic acid (2.2 g, 12 mmol).

Yield: 76%

Hereinafter, formulation examples are shown, but the present invention is not limited thereto. In the formulation examples, "part" means part by weight.

Formulation Example 1

Compound of the present invention 10 parts
Xylene 70 parts
N-methylpyrrolidone 10 parts
Mixture of polyoxyethylene nonylphenyl ether 10 parts and calcium alkylbenzene sulfonate The above ingredients are uniformly mixed for dissolution to give an emulsifiable concentrate formulation.

Formulation Example 2

Compound of the present invention 3 parts
Clay powder 82 parts
Diatomite powder 15 parts The above ingredients are uniformly mixed and then pulverized to give a dust formulation.

Formulation Example 3

Compound of the present invention 5 parts
Mixture of bentonite powder and clay powder 90 parts
Calcium lignosulfonate 5 parts The above ingredients are uniformly mixed. After addition of an appropriate volume of water, the mixture is kneaded, granulated and dried to give a granular formulation.

Formulation Example 4

Compound of the present invention 20 parts
Kaolin and synthetic high-dispersion silicic 75 parts acid
Mixture of polyoxyethylene nonylphenyl ether 5 parts and calcium alkylbenzene sulfonate The above ingredients are uniformly mixed and then pulverized to give a wettable powder formulation.

Test Example 1

Test for Post-Emergence Herbicidal Effect Against Paddy Weeds

Barnyard grass (*Echinochloa crus*-galli) was seeded and grown in test tubes containing hydroponic medium in an artificial climate chamber or a phytotron. Agrochemical formulations containing the compounds of the present invention as active ingredients prepared according to Formulation Example 1 were separately diluted with water so that the concentration of the active ingredient would be a predetermined concentration and used for drop treatment of the barnyard grass. The barnyard grass was grown in the artificial climate chamber at 30° C. under full light conditions. Six days after agrochemical treatment, the herbicidal effect was evaluated as compared to the non-treatment group according to the following criteria.

Criteria for Herbicidal Effect (Degree of Growth Inhibition) and Phytotoxicity

Score 4 90% to 100% herbicidal effect

Score 3 70% to 89% herbicidal effect

Score 2 40% to 69% herbicidal effect

Score 1 1% to 39% herbicidal effect

Score 0 0% herbicidal effect

As a result of Test Example 1, among the compounds represented by the general formula (1) of the present invention, compounds numbered 1-6, 1-7, 1-11, 1-12, 1-13, 1-15, 1-16, 1-17, 1-18, 1-19, 1-22, 1-39, 1-41, 1-51, 1-54, 1-57, 1-58, 1-61, 1-63, 1-64, 1-65, 1-66, 1-67, 1-69, 1-70, 1-71, 1-74, 1-75, 1-76, 1-77, 1-80, 1-84, 1-86, 1-87, 1-90, 1-102, 1-103, 1-104, 1-107, 1-108, 1-109, 1-110, 1-111, 1-114, 1-115, 1-116, 1-117, 1-118, 1-121, 1-124, 1-125, 1-126, 1-128, 1-131, 1-132, 1-134, 1-135, 1-136, 1-139, 1-140, 1-141, 1-143, 1-148, 1-151, 1-154, 1-155, 1-156, 1-157, 1-158, 1-160, 1-161, 1-163, 1-164, 1-165, 1-167, 1-174, 1-175, 1-177, 1-179, 1-180, 1-181, 1-183, 1-184, 1-185, 1-186, 1-188, 1-189, 1-190, 1-191, 1-192, 1-193, 1-194, 1-195, 1-196, 1-198, 1-200, 1-204, 1-205, 1-206, 1-208, 1-209, 1-210, 1-211, 1-214, 1-216, 1-217, 1-220, 1-221, 1-225, 1-226, 1-227, 1-228, 1-229, 1-233, 1-234, 1-237, 1-238, 1-239, 1-240, 1-241, 1-242, 1-243, 1-245, 1-246, 1-249, 1-252, 1-255, 1-256, 1-257, 1-262, 1-263, 1-264, 1-265, 1-269, 1-270, 1-271, 1-272, 1-273, 1-274, 1-275, 1-279, 1-280, 1-283, 1-286, 1-288, 1-289, 1-290, 1-291, 1-301, 1-304, 1-305, 1-306, 1-309, 1-313, 1-314, 1-322, 1-323, 1-324, 1-325, 1-327, 1-336, 1-337, 1-338, 1-339, 1-340, 1-341, 1-342, 1-343, 1-350, 1-355, 1-356, 1-360, 1-361, 1-362, 1-363, 1-364, 1-368, 1-369, 1-370, 1-373, 1-379, 1-380, 1-382, 1-390, 1-391, 1-392, 1-393, 1-394, 1-395, 1-396, 1-397, 1-398, 1-399, 1-400, 1-401, 1-402, 1-403, 2-1, 2-3, 2-5, 2-7, 2-10, 2-11, 2-16, 2-18, 2-21, 2-23, 2-25, 2-28, 2-31, 2-32, 2-33, 2-35, 2-36, 2-37, 2-42, 2-44, 2-45, 2-46, 2-48, 2-49, 2-50, 2-51, 2-52, 2-54, 2-55, 2-56, 2-57, 2-58, 2-59, 2-61, 2-62, 2-63, 2-65, 2-66, 2-67, 2-68, 2-69, 2-70, 2-71, 2-72, 2-73, 2-77, 2-80, 2-82, 2-83, 2-85, 2-89, 2-90, 2-91, 2-92, 2-95, 2-97, 2-101, 2-103, 2-105, 2-106, 2-107, 2-108, 2-109, 2-122, 2-123, 2-126, 2-135, 2-136, 2-138, 2-147, 2-159, 2-163, 2-165, 2-181, 2-204, 2-216, 2-220, 2-221, 2-223, 2-224, 2-225, 2-226, 2-227, 2-243, 2-249, 2-250, 2-259, 2-262, 2-266, 2-270, 2-275, 2-276, 2-277, 2-281, 2-283, 2-285, 2-286, 2-288, 2-302, 2-310, 2-314, 2-315, 2-317, 2-319, 2-321, 2-325, 2-327, 2-328, 2-329, 2-330, 2-331, 2-334, 2-336, 2-337, 2-338, 2-339, 2-340, 2-341, 2-343, 2-344, 2-345, 2-346, 3-10, 3-11, 3-12, 3-13, 3-17, 3-19, 3-21, 3-23, 3-24, 3-27, 3-29, 3-31, 3-33, 3-36, 3-37, 3-39, 3-41, 3-43, 3-44, 3-47, 3-48, 3-50, 3-51, 3-52, 3-54, 3-56, 3-60, 3-62, 3-63, 3-64, 3-65, 3-66, 3-67, 3-68, 3-69, 3-70, 3-71, 3-72, 3-73, 3-84, 3-90, 3-91, 3-101, 3-115, 3-120, 3-121, 3-130, 3-134, 4-14, 4-15, 4-16, 4-22, 4-46, 4-49, 4-50, 4-54, 4-61, 4-67, 4-68, 4-108, 4-109, 4-111, 4-117, 4-118, 4-119, 4-120, 4-121, 5-97, 5-100, 6-89, 7-6, 7-17, 7-46, 7-48, 8-6, 8-9, 8-42, and 8-44 showed herbicidal effect against barnyard grass in score 3 or higher according to the above criteria when applied at an active ingredient concentration of 10 ppm.

INDUSTRIAL APPLICABILITY

The nitrogen-containing condensed heterocyclic compound of the present invention or a salt thereof is a highly effective agricultural or horticultural herbicide.

The invention claimed is:

1. A compound of formula (1):

(1)

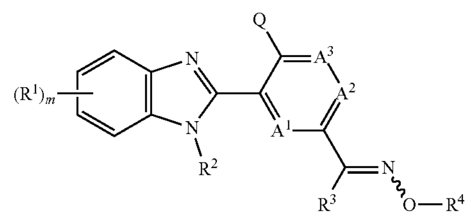

wherein $R^1$ is (a1) a halogen atom;

(a2) a cyano group;

(a3) a nitro group;

(a4) a formyl group;

(a5) a carboxyl group;

(a6) a $(C_1-C_6)$ alkyl group;

(a7) a $(C_2-C_6)$ alkenyl group;

(a8) a $(C_2-C_6)$ alkynyl group;

(a9) a $(C_3-C_6)$ cycloalkyl group;

(a10) a halo$(C_1-C_6)$ alkyl group;

(a11) a halo$(C_2-C_6)$ alkenyl group;

(a12) a halo$(C_2-C_6)$ alkynyl group;

(a13) a halo$(C_3-C_6)$ cycloalkyl group;

(a14) a hydroxy $(C_1-C_6)$ alkyl group;

(a15) a hydroxy halo$(C_1-C_6)$ alkyl group;

(a16) a $(C_1-C_6)$ alkoxy $(C_1-C_6)$ alkyl group;

(a17) a di-$(C_1-C_6)$ alkoxy $(C_1-C_6)$ alkyl group;

(a18) a halo$(C_1-C_6)$ alkoxy $(C_1-C_6)$ alkyl group;

(a19) a $(C_1-C_6)$ alkoxy halo$(C_1-C_6)$ alkyl group;

(a20) a halo$(C_1-C_6)$ alkoxy halo$(C_1-C_6)$ alkyl group;

(a21) a $(C_3-C_6)$ cycloalkyl $(C_1-C_6)$ alkyl group;

(a22) a $(C_1-C_6)$ alkoxy group;

(a23) a halo$(C_1-C_6)$ alkoxy group;

(a24) a $(C_1-C_6)$ alkylthio group;

(a25) a $(C_1-C_6)$ alkylsulfinyl group;

(a26) a $(C_1-C_6)$ alkylsulfonyl group;

(a27) a halo$(C_1-C_6)$ alkylthio group;

(a28) a halo$(C_1-C_6)$ alkylsulfinyl group;

(a29) a halo$(C_1-C_6)$ alkylsulfonyl group;

(a30) an $R^8(R^9)N$ group;

(a31) an $R^{10}(R^{11})N(C_1-C_6)$ alkyl group;

(a32) a $(C_1-C_6)$ alkylthio $(C_1-C_6)$ alkyl group;

(a33) a $(C_1-C_6)$ alalkylsulfinyl $(C_1-C_6)$ alkyl group;

(a34) a $(C_1-C_6)$ alkylsulfonyl $(C_1-C_6)$ alkyl group;

(a35) a halo$(C_1-C_6)$ alkylthio $(C_1-C_6)$ alkyl group;

(a36) a halo$(C_1-C_6)$ alkylsulfinyl $(C_1-C_6)$ alkyl group;

(a37) a halo$(C_1-C_6)$ alkylsulfonyl $(C_1-C_6)$ alkyl group;

(a38) a $(C_1-C_6)$ alkylthio halo$(C_1-C_6)$ alkyl group;
(a39) a $(C_1-C_6)$ alkylsulfinyl halo$(C_1-C_6)$ alkyl group;
(a40) a $(C_1-C_6)$ alkylsulfonyl halo$(C_1-C_6)$ alkyl group;
(a41) a halo$(C_1-C_6)$ alkylthio halo$(C_1-C_6)$ alkyl group;
(a42) a halo$(C_1-C_6)$ alkylsulfinyl halo$(C_1-C_6)$ alkyl group;
(a43) a halo$(C_1-C_6)$ alkylsulfonyl halo$(C_1-C_6)$ alkyl group;
(a44) a $(C_1-C_6)$ alkylthiol group;
(a45) a $(C_1-C_6)$ alkoxycarbonyl group;
(a46) a halo$(C_1-C_6)$ alkylcarbonyl group;
(a47) a halo$(C_1-C_6)$ alkoxycarbonyl group;
(a48) a $(C_1-C_6)$ alkylcarbonyloxy group;
(a49) a halo$(C_1-C_6)$ alkylcarbonyloxy group;
(a50) an $R^{10}(R^{11})N$ carbonyl group;
(a51) an $R^{10}(R^{11})N$ carbonyloxy group;
(a52) an $R^{10}(R^{11})N$ sulfonyl group;
(a53) a $(C_1-C_6)$ alkylsulfonyloxy group;
(a54) a halo$(C_1-C_6)$ alkylsulfonyloxy group;
(a55) a $(C_1-C_6)$ alkoxyimino $(C_1-C_3)$ alkyl group;
(a56) a halo$(C_1-C_6)$ alkoxyimino $(C_1-C_3)$ alkyl group;
(a57) a phenyl group;
(a58) a phenyl group having, on the ring, 1 to 5 substituting groups which may be the same or different and are selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ $(C_1-C_6)$ alkyl group, an $R^{10}(R^{11})N$ group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;
(a59) a pyridyl group;
(a60) a pyridyl group having, on the ring, 1 to 4 substituting groups which may be the same or different and are selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ $(C_1-C_6)$ alkyl group, an $R^{10}(R^{11})N$ group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;
(a61) a pyrazolyl group;
(a62) a pyrazolyl group having, on the ring, 1 to 3 substituting groups which may be the same or different and are selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ $(C_1-C_6)$ alkyl group, an $R^{10}(R^{11})N$ group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;
(a63) a phenoxy group;
(a64) a phenoxy group having, on the ring, 1 to 5 substituting groups which may be the same or different and are selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ $(C_1-C_6)$ alkyl group, an $R^{10}(R^{11})N$ group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;
(a65) a dioxolanyl group;
(a66) a dioxolanyl group having, on the ring, 1 to 4 substituting groups which may be the same or different and are selected from the group consisting of a halogen atom, a cyano group, a nitro group, a formyl group, a carbonyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N(C_1-C_6)$ alkyl group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;
(a67) a dioxanyl group;
(a68) a dioxanyl group having, on the ring, 1 to 6 substituting groups which may be the same or different and are selected from the group consisting of a halogen atom, a cyano group, a nitro group, a formyl group, a carbonyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N(C_1-C_6)$ alkyl group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;
(a69) a $(C_1-C_6)$ alkylene group formed together with one adjacent substituting group, wherein the $(C_1-C_6)$ alkylene group may be substituted with 1 to 4 substituting groups which may be the same or different and are selected from the group consisting of a halogen atom, a phenyl group, and a $(C_1-C_6)$ alkyl group; or
(a70) a methylenedioxy group formed together with one adjacent substituting group, wherein the methylenedioxy group may be substituted by 1 or 2 substituting groups which may be the same or different and are selected from the group consisting of a halogen atom, a phenyl group, and a $(C_1-C_6)$ alkyl group, wherein, when m is an integer of 2 or more, $R^1$s may be the same or different,
m is 1, 2, 3, or 4,
$R^2$ is
(b1) a hydrogen atom;
(b2) a $(C_1-C_6)$ alkyl group;
(b3) a $(C_3-C_6)$ cycloalkyl group;
(b4) a $(C_2-C_6)$ alkenyl group;
(b5) a $(C_2-C_6)$ alkynyl group;
(b6) a halo$(C_1-C_6)$ alkyl group;
(b7) a halo$(C_2-C_6)$ alkenyl group;
(b8) a halo$(C_2-C_6)$ alkynyl group;
(b9) a $(C_1-C_6)$ alkoxy $(C_1-C_6)$ alkyl group;
(b10) a $(C_1-C_6)$ alkylthio $(C_1-C_6)$ alkyl group;
(b11) a $(C_1-C_6)$ alkylsulfinyl $(C_1-C_6)$ alkyl group;
(b12) a $(C_1-C_6)$ alkylsulfonyl $(C_1-C_6)$ alkyl group;
(b13) a $(C_3-C_6)$ cycloalkyl $(C_1-C_6)$ alkyl group;
(b14) a $(C_1-C_6)$ alkoxy group;
(b15) a $(C_1-C_6)$ alkylcarbonyl group;
(b16) a $(C_1-C_6)$ alkoxycarbonyl group;
(b17) a halo$(C_1-C_6)$ alkoxy group;
(b18) a halo$(C_1-C_6)$ alkylcarbonyl group;
(b19) a halo$(C_1-C_6)$ alkoxycarbonyl group;

(b20) an $R^{10}(R^{11})N$ carbonyl group; or
(b21) an $R^{10}(R^{11})N$ sulfonyl group,
$R^3$ is:
(c1) a hydrogen atom;
(c2) a halogen group;
(c3) a cyano group;
(c4) a carboxyl group;
(c5) a carboxamide group;
(c6) a $(C_1-C_6)$ alkyl group;
(c7) a $(C_2-C_6)$ alkenyl group;
(c8) a $(C_2-C_6)$ alkynyl group;
(c9) a halo$(C_1-C_6)$ alkyl group;
(c10) a halo$(C_2-C_6)$ alkenyl group;
(c11) a halo$(C_2-C_6)$ alkynyl group;
(c12) an $R^8(R^9)N$ group;
(c13) a $(C_1-C_6)$ alkoxy group;
(c14) a halo$(C_1-C_6)$ alkoxy group;
(c15) a $(C_1-C_6)$ alkoxy $(C_1-C_6)$ alkyl group; or
(c16) a $(C_1-C_6)$ alkoxycarbonyl $(C_1-C_6)$ alkyl group,
$R^4$ is:
(d1) a hydrogen atom;
(d2) a $(C_1-C_6)$ alkyl group;
(d3) a $(C_2-C_6)$ alkenyl group;
(d4) a $(C_2-C_6)$ alkynyl group;
(d5) a $(C_3-C_6)$ cycloalkyl group;
(d6) a halo$(C_1-C_6)$ alkyl group;
(d7) a halo$(C_2-C_6)$ alkenyl group;
(d8) a halo$(C_2-C_6)$ alkynyl group;
(d9) a $(C_1-C_6)$ alkoxy $(C_1-C_6)$ alkyl group;
(d10) a halo$(C_1-C_6)$ alkoxy $(C_1-C_6)$ alkyl group;
(d11) a $(C_1-C_6)$ alkoxy halo$(C_1-C_6)$ alkyl group;
(d12) a halo$(C_1-C_6)$ alkoxy halo$(C_1-C_6)$ alkyl group;
(d13) a $(C_3-C_6)$ cycloalkyl $(C_1-C_6)$ alkyl group;
(d14) a cyano $(C_1-C_6)$ alkyl group;
(d15) a $(C_1-C_6)$ alkylthio $(C_1-C_6)$ alkyl group;
(d16) a $(C_1-C_6)$ alkylsulfinyl $(C_1-C_6)$ alkyl group;
(d17) a $(C_1-C_6)$ alkylsulfonyl $(C_1-C_6)$ alkyl group;
(d18) a carboxyl $(C_1-C_6)$ alkyl group;
(d19) a phenyl$(C_1-C_6)$ alkyl group;
(d20) a phenyl$(C_1-C_6)$ alkyl group having, on the ring, 1 to 5 substituting groups which may be the same or different and are selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo $(C_1-C_6)$ alkylsulfonyl group;
(d21) an $R^{10}(R^{11})N$ alkyl group;
(d22) a $(C_1-C_6)$ alkylcarbonyl group;
(d23) a $(C_1-C_6)$ alkoxycarbonyl group;
(d24) a $(C_1-C_6)$ alkylsulfonyl group;
(d25) a halo$(C_1-C_6)$ alkylcarbonyl group;
(d26) a halo$(C_1-C_6)$ alkoxycarbonyl group;
(d27) a halo$(C_1-C_6)$ alkylsulfonyl group;
(d28) an $R^{10}(R^{11})N$ carbonyl group;
(d29) an $R^{10}(R^{11})N$ sulfonyl group;
(d30) a phenyl group;
(d31) a phenyl group having, on the ring, 1 to 5 substituting groups which may be the same or different and are selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ group wherein $R^{10}$ and $R^{11}$ are the same as above, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo $(C_1-C_6)$ alkylsulfonyl group; or
(d32) a $(C_1-C_6)$ alkoxycarbonyl $(C_1-C_6)$ alkyl group,
$A^1$, $A^2$, and $A^3$ may be the same or different and each is $CR^5$ (wherein $R^5$ is hydrogen atom, a halogen atom, a cyano group, a $(C_1-C_6)$ alkyl group, a halo$(C_1-C_6)$ alkyl group, a $(C_1-C_6)$ alkoxy group, a halo$(C_1-C_6)$ alkoxy group, an $R^{10}(R^{11})N$ group, a $(C_1-C_6)$ alkylthio group, a $(C_1-C_6)$ alkylsulfinyl group, or a $(C_1-C_6)$ alkylsulfonyl group) or a nitrogen atom,
Q is
(e1) a halogen atom;
(e2) a cyano group;
(e3) a nitro group;
(e4) a formyl group;
(e5) a $(C_1-C_6)$ alkyl group;
(e6) a $(C_2-C_6)$ alkenyl group;
(e7) a $(C_2-C_6)$ alkynyl group;
(e8) a halo$(C_1-C_6)$ alkyl group;
(e9) a halo$(C_2-C_6)$ alkenyl group;
(e10) a halo$(C_2-C_6)$ alkynyl group;
(e11) a $(C_1-C_6)$ alkoxy group;
(e12) a halo$(C_1-C_6)$ alkoxy group;
(e13) a hydroxy $(C_1-C_6)$ alkyl group;
(e14) a dihydroxy $(C_1-C_6)$ alkyl group;
(e15) a $(C_1-C_6)$ alkoxy $(C_1-C_6)$ alkyl group;
(e16) a $(C_1-C_6)$ alkoxy $(C_2-C_6)$ alkenyl group;
(e17) an $R^8(R^9)N$ group;
(e18) a dioxolanyl group;
(e19) a dioxolanyl group having, on the ring, 1 or 2 substituting groups which may be the same or different and are selected from the group consisting of a halogen atom, a cyano group, a nitro group, a formyl group, a carbonyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N(C_1-C_6)$ alkyl group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;
(e20) a dioxanyl group;
(e21) a dioxanyl group having, on the ring, 1 to 3 substituting groups which may be the same or different and are selected from the group consisting of a halogen atom, a cyano group, a nitro group, a formyl group, a carbonyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N(C_1-C_6)$ alkyl group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;
(e22) a phenyl group;
(e23) a phenyl group having, on the ring, 1 to 5 substituting groups which may be the same or different and are selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(e24) an imidazolyl group;

(e25) an imidazolyl group having, on the ring, 1 to 3 substituting groups which may be the same or different and are selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(e26) an oxadiazolyl group;

(e27) an oxadiazolyl group having, on the ring, a substituting group selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(e28) an $S(O)_pR^6$ group;

(e29) a $C(O)R^7$ group;

(e30) a thiocarboxamide group;

(e31) an N—$(C_1-C_6)$ alkylaminothiocarbonyl group;

(e32) an N,N-di-$(C_1-C_6)$ alkylaminothiocarbonyl group;

(e33)

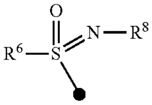

(e34) a hydroxyimino $(C_1-C_3)$ alkyl group;

(e35) a $(C_1-C_6)$ alkoxyimino $(C_1-C_3)$ alkyl group;

(e36) a halo$(C_1-C_6)$ alkoxyimino $(C_1-C_3)$ alkyl group;

(e37) a hydrazono $(C_1-C_3)$ alkyl group;

(e38) a $(C_1-C_6)$ alkylhydrazono $(C_1-C_3)$ alkyl group;

(e39) a di-$(C_1-C_6)$ alkylhydrazono $(C_1-C_3)$ alkyl group;

(e40) a phenyl$(C_1-C_6)$ alkoxyimino $(C_1-C_3)$ alkyl group;

(e41) a $(C_2-C_6)$ alkenyloxyimino $(C_1-C_3)$ alkyl group;

(e42) a di-$(C_1-C_6)$ alkoxyphosphoryl group;

(e43) a di-$(C_1-C_6)$ alkoxyphosphorylamino group;

(e44) a hydroxyl group;

(e45) a $(C_1-C_6)$ alkoxy $(C_1-C_6)$ alkoxy group;

(e46) a $(C_1-C_6)$ alkoxyiminoamino $(C_1-C_3)$ alkyl group;

(e47) a cyano $(C_1-C_6)$ alkyl group;

(e48) a cyano $(C_2-C_6)$ alkenyl group;

(e49) a dicyano $(C_1-C_6)$ alkyl group; or (e50) a dicyano $(C_2-C_6)$ alkenyl group, $R^6$ is a hydrogen atom, a $(C_1-C_6)$ alkyl group, a $(C_2-C_6)$ alkenyl group, a $(C_2-C_6)$ alkynyl group, a halo$(C_1-C_6)$ alkyl group, a halo$(C_2-C_6)$ alkenyl group, a halo$(C_2-C_6)$ alkynyl group, a $(C_1-C_6)$ alkoxy group, a $(C_3-C_6)$ cycloalkyl group, a halo$(C_3-C_6)$ cycloalkyl group, a phenyl $(C_1-C_6)$ alkyl group, a $(C_1-C_6)$ alkoxyphenyl $(C_1-C_6)$ alkyl group, a $(C_1-C_6)$ alkylphenyl $(C_1-C_6)$ alkyl group, a tri-$(C_1-C_6)$ alkylsilylphenyl $(C_1-C_6)$ alkyl group, or an $N(R^8)R^9$ group, p is 0.1, or 2, $R^7$ is a hydroxyl group, a $(C_1-C_6)$ alkyl group, a $(C_2-C_6)$ alkenyl group, a $(C_2-C_6)$ alkynyl group, a halo$(C_1-C_6)$ alkyl group, a halo$(C_2-C_6)$ alkenyl group, a halo$(C_2-C_6)$ alkynyl group, a $(C_1-C_6)$ alkoxycarbonyl $(C_1-C_6)$ alkyl group, a phenyl $(C_1-C_6)$ alkyl group, a phenyl $(C_1-C_6)$ alkoxy group, a $(C_1-C_6)$ alkoxy group, a $(C_2-C_6)$ alkenyloxy group, a $(C_2-C_6)$ alkynyloxy group, a $(C_3-C_6)$ cycloalkoxy group, a halo$(C_1-C_6)$ alkoxy group, a halo$(C_2-C_6)$ alkynyloxy group, a phenyloxy group, a $(C_1-C_6)$ alkoxycarbonyl $(C_1-C_6)$ alkoxy group, a $(C_1-C_6)$ alkylthio group, a phenyl group, a thiazolidinyl group, or an $N(R^8)R^9$ group, $R^8$ and $R^9$ may be the same or different and each is a hydrogen atom, a hydroxyl group, an amino group, a di-$(C_1-C_6)$ alkylamino group, a $(C_1-C_6)$ alkyl group, a $(C_3-C_6)$ cycloalkyl group, a $(C_2-C_6)$ alkenyl group, a $(C_2-C_6)$ alkynyl group, a $(C_1-C_6)$ alkoxy group, a $(C_2-C_6)$ alkenyloxy group, a halo$(C_1-C_6)$ alkyl group, a halo$(C_2-C_6)$ alkenyl group, a halo$(C_2-C_6)$ alkynyl group, a halo$(C_1-C_6)$ alkoxy group, a halo$(C_3-C_6)$ cycloalkyl group, a $(C_3-C_6)$ cycloalkyl $(C_1-C_6)$ alkyl group, a cyano $(C_1-C_6)$ alkyl group, a $(C_1-C_6)$ alkylcarbonyl group, a halo$(C_1-C_6)$ alkylcarbonyl group, a $(C_1-C_6)$ alkoxycarbonyl group, a halo$(C_1-C_6)$ alkoxycarbonyl group, a $(C_1-C_6)$ alkylsulfanylcarbonyl group, a $(C_1-C_6)$ alkylsulfonyl group, a halo$(C_1-C_6)$ alkylsulfonyl group, an N—$(C_1-C_6)$ alkylcarboxamide group, an N,N-di-$(C_1-C_6)$ alkylcarboxamide group, an N—$(C_1-C_6)$ alkylsulfamoyl group, an N,N-di-$(C_1-C_6)$ alkylsulfamoyl group, an N-halo$(C_1-C_6)$ alkylcarboxamide group, a $(C_1-C_6)$ alkoxycarbonyl $(C_1-C_6)$ alkyl group, a $(C_1-C_6)$ alkoxy $(C_1-C_6)$ alkyl group, a di-$(C_1-C_6)$ alkoxy $(C_1-C_6)$ alkyl group, a $(C_1-C_6)$ alkoxy $(C_1-C_6)$ alkylcarbonyl group, a thietanyl group, a 1,1-dioxothietanyl group, a tetrahydrofuranyl group, a thiazolyl group, a 2-oxotetrahydrofuranyl group, a phenyl group, a phenyl group having, on the ring, 1 to 5 substituting groups which may be the same or different and are selected from the group consisting of a halogen atom, a cyano group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group, or a phenyl $(C_1-C_6)$ alkyl group, or $R^8$ and $R^9$ may join together to form a 4- to 6-membered ring, and $R^{10}$ and $R^{11}$ may be the same or different and each is a hydrogen atom, a $(C_1-C_6)$ alkyl group, a halo$(C_1-C_6)$ alkyl group, a $(C_3-C_6)$ cycloalkyl group, a $(C_3-C_6)$ cycloalkyl $(C_1-C_6)$ alkyl group, a $(C_1-C_6)$ alkylcarbonyl group, a halo$(C_1-C_6)$ alkylcarbonyl group, a $(C_1-C_6)$ alkoxycarbonyl group, a halo$(C_1-C_6)$ alkoxycarbonyl group, a $(C_1-C_6)$ alkylsulfonyl group, or a halo$(C_1-C_6)$ alkylsulfonyl group, or $R^{10}$ and $R^{11}$ may join together to form a 4- to 6-membered ring, or a salt thereof.

2. The compound or the salt thereof according to claim 1, wherein $R^1$ is (a1) a halogen atom;

(a2) a cyano group;

(a3) a nitro group;

(a4) a formyl group;

(a5) a carboxyl group;

(a6) a $(C_1-C_6)$ alkyl group;

(a7) a $(C_2-C_6)$ alkenyl group;

(a8) a $(C_2-C_6)$ alkynyl group;

(a9) a $(C_3-C_6)$ cycloalkyl group;

(a10) a halo$(C_1-C_6)$ alkyl group;

(a11) a halo$(C_2-C_6)$ alkenyl group;

(a12) a halo$(C_2-C_6)$ alkynyl group;

(a14) a hydroxy $(C_1-C_6)$ alkyl group;

(a15) a hydroxy halo$(C_1-C_6)$ alkyl group;

(a16) a $(C_1-C_6)$ alkoxy $(C_1-C_6)$ alkyl group;

(a17) a di-$(C_1-C_6)$ alkoxy $(C_1-C_6)$ alkyl group;

(a18) a halo$(C_1-C_6)$ alkoxy $(C_1-C_6)$ alkyl group;

(a19) a $(C_1-C_6)$ alkoxy halo$(C_1-C_6)$ alkyl group;

(a20) a halo$(C_1-C_6)$ alkoxy halo$(C_1-C_6)$ alkyl group;

(a21) a $(C_3-C_6)$ cycloalkyl $(C_1-C_6)$ alkyl group;

(a22) a $(C_1-C_6)$ alkoxy group;

(a23) a halo$(C_1-C_6)$ alkoxy group;

(a24) a $(C_1-C_6)$ alkylthio group;

(a25) a $(C_1-C_6)$ alkylsulfinyl group;

(a26) a $(C_1-C_6)$ alkylsulfonyl group;

(a27) a halo$(C_1-C_6)$ alkylthio group;

(a28) a halo$(C_1-C_6)$ alkylsulfinyl group;

(a29) a halo$(C_1-C_6)$ alkylsulfonyl group;

(a30) an $R^8(R^9)N$ group;

(a31) an $R^{10}(R^{11})N(C_1-C_6)$ alkyl group;

(a32) a $(C_1-C_6)$ alkylthio $C_1-C_6)$ alkyl group;

(a33) a $(C_1-C_6)$ alkylsulfinyl $(C_1-C_6)$ alkyl group;

(a34) a $(C_1-C_6)$ alkylsulfonyl $(C_1-C_6)$ alkyl group;

(a35) a halo$(C_1-C_6)$ alkylthio $(C_1-C_6)$ alkyl group;

(a36) a halo$(C_1-C_6)$ alkylsulfinyl $(C_1-C_6)$ alkyl group;

(a37) a halo$(C_1-C_6)$ alkylsulfonyl $(C_1-C_6)$ alkyl group;

(a44) a $(C_1-C_6)$ alkylcarbonyl group;

(a45) a $(C_1-C_6)$ alkoxycarbonyl group;

(a46) a halo$(C_1-C_6)$ alkylcarbonyl group;

(a47) a halo$(C_1-C_6)$ alkoxycarbonyl group;

(a50) an $R^{10}(R^{11})N$ carbonyl group;

(a52) an $R^{10}(R^{11})N$ sulfonyl group;

(a55) a $(C_1-C_6)$ alkoxyimino $(C_1-C_3)$ alkyl group;

(a56) a halo$(C_1-C_6)$ alkoxyimino $(C_1-C_3)$ alkyl group;

(a57) a phenyl group;

(a58) a phenyl group having, on the ring, 1 to 5 substituting groups which may be the same or different and are selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ $(C_1-C_6)$ alkyl group, an $R^{10}(R^{11})N$ group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(a59) a pyridyl group;

(a60) a pyridyl group having, on the ring, 1 to 4 substituting groups which may be the same or different and are selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ $(C_1-C_6)$ alkyl group, an $R^{10}(R^{11})N$ group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(a61) a pyrazolyl group;

(a62) a pyrazolyl group having, on the ring, 1 to 3 substituting groups which may be the same or different and are selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ $(C_1-C_6)$ alkyl group, an $R^{10}(R^{11})N$ group, are the same as above, a $(C_1-C_6)$ alkylthio group, a halo$(C_1-C_6)$ alkylthio group, a $(C_1-C_6)$ alkylsulfinyl group, a halo $(C_1-C_6)$ alkylsulfinyl group, a $(C_1-C_6)$ alkylsulfonyl group, and a halo$(C_1-C_6)$ alkylsulfonyl group;

(a63) a phenoxy group;

(a64) a phenoxy group having, on the ring, 1 to 5 substituting groups which may be the same or different and are selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ $(C_1-C_6)$ alkyl group, an $R^{10}(R^{11})N$ group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(a65) a dioxolanyl group;

(a66) a dioxolanyl group having, on the ring, 1 to 4 substituting groups which may be the same or different and are selected from the group consisting of a halogen atom, a cyano group, a nitro group, a formyl group, a carbonyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N(C_1-C_6)$ alkyl group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(a67) a dioxanyl group;

(a68) a dioxanyl group having, on the ring, 1 to 6 substituting groups which may be the same or different and are selected from the group consisting of a halogen atom, a cyano group, a nitro group, a formyl group, a carbonyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N(C_1-C_6)$ alkyl group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(a69) a $(C_1-C_6)$ alkylene group formed together with one adjacent substituting group, wherein the $(C_1-C_6)$ alkylene group may be substituted with 1 or 2 substituting groups which may be the same or different and are selected from the group consisting of a halogen atom, a phenyl group, and a $(C_1-C_6)$ alkyl group; or (a70) a methylenedioxy group formed together with one adjacent substituting group, wherein the methylenedioxy group may be substituted by 1 or 2 substituting groups which may be the same or different and are selected from the group consisting of a halogen atom, a phenyl group, and a ($C_1$-$C_6$) alkyl group, wherein, when m is an integer of 2 or more, $R^1$s may be the same or different, m is 0, 1, 2, 3, or 4, $R^2$ is (b1) a hydrogen atom;

(b2) a ($C_1$-$C_6$) alkyl group;

(b3) a ($C_3$-$C_6$) cycloalkyl group;

(b4) a ($C_2$-$C_6$) alkenyl group;

(b5) a ($C_2$-$C_6$) alkynyl group;

(b6) a halo($C_1$-$C_6$) alkyl group;

(b7) a halo($C_2$-$C_6$) alkenyl group;

(b8) a halo($C_2$-$C_6$) alkynyl group;

(b9) a ($C_1$-$C_6$) alkoxy ($C_1$-$C_6$) alkyl group;

(b10) a ($C_1$-$C_6$) alkylthio ($C_1$-$C_6$) alkyl group;

(b11) a ($C_1$-$C_6$) alkylsulfinyl ($C_1$-$C_6$) alkyl group;

(b12) a ($C_1$-$C_6$) alkylsulfonyl ($C_1$-$C_6$) alkyl group;

(b13) a ($C_3$-$C_6$) cycloalkyl ($C_1$-$C_6$) alkyl group;

(b15) a ($C_1$-$C_6$) alkylcarbonyl group;

(b16) a ($C_1$-$C_6$) alkoxycarbonyl group;

(b18) a halo($C_1$-$C_6$) alkylcarbonyl group; or (b21) an $R^{10}$($R^{11}$)N sulfonyl group, $R^3$ is (c1) a hydrogen atom;

(c2) a halogen group;

(c3) a cyano group;

(c4) a carboxyl group;

(c5) a carboxamide group;

(c6) a ($C_1$-$C_6$) alkyl group;

(c9) a halo($C_1$-$C_6$) alkyl group;

(c12) an $R^8$($R^9$)N group;

(c13) a ($C_1$-$C_6$) alkoxy group;

(c14) a halo($C_1$-$C_6$) alkoxy group;

(c15) a ($C_1$-$C_6$) alkoxy ($C_1$-$C_6$) alkyl group; or (c16) a ($C_1$-$C_6$) alkoxycarbonyl ($C_1$-$C_6$) alkyl group, $R^4$ is (d1) a hydrogen atom;

(d2) a ($C_1$-$C_6$) alkyl group;

(d3) a ($C_2$-$C_6$) alkenyl group;

(d4) a ($C_2$-$C_6$) alkynyl group;

(d5) a ($C_3$-$C_6$) cycloalkyl group;

(d6) a halo($C_1$-$C_6$) alkyl group;

(d7) a halo($C_2$-$C_6$) alkenyl group;

(d8) a halo($C_2$-$C_6$) alkynyl group;

(d9) a ($C_1$-$C_6$) alkoxy ($C_1$-$C_6$) alkyl group;

(d10) a halo($C_1$-$C_6$) alkoxy ($C_1$-$C_6$) alkyl group;

(d13) a ($C_3$-$C_6$) cycloalkyl ($C_1$-$C_6$) alkyl group;

(d14) a cyano ($C_1$-$C_6$) alkyl group;

(d15) a ($C_1$-$C_6$) alkylthio ($C_1$-$C_6$) alkyl group;

(d16) a ($C_1$-$C_6$) alkylsulfinyl ($C_1$-$C_6$) alkyl group;

(d17) a ($C_1$-$C_6$) alkylsulfonyl ($C_1$-$C_6$) alkyl group;

(d18) a carboxyl ($C_1$-$C_6$) alkyl group;

(d19) a phenyl($C_1$-$C_6$) alkyl group;

(d20) a phenyl($C_1$-$C_6$) alkyl group having, on the ring, 1 to 5 substituting groups which may be the same or different and are selected from the group consisting of a halogen atom, a cyano group, a nitro group, a formyl group, a ($C_1$-$C_6$) alkyl group, a halo($C_1$-$C_6$) alkyl group, a ($C_1$-$C_6$) alkoxy group, a halo($C_1$-$C_6$) alkoxy group, a ($C_3$-$C_6$) cycloalkyl ($C_1$-$C_6$) alkyl group, a ($C_1$-$C_6$) alkylthio group, a halo($C_1$-$C_6$) alkylthio group, a ($C_1$-$C_6$) alkylsulfinyl group, a halo($C_1$-$C_6$) alkylsulfinyl group, a ($C_1$-$C_6$) alkylsulfonyl group, and a halo ($C_1$-$C_6$) alkylsulfonyl group;

(d22) a ($C_1$-$C_6$) alkylcarbonyl group;

(d23) a ($C_1$-$C_6$) alkoxycarbonyl group;

(d24) a ($C_1$-$C_6$) alkylsulfonyl group;

(d25) a halo($C_1$-$C_6$) alkylcarbonyl group;

(d26) a halo($C_1$-$C_6$) alkoxycarbonyl group;

(d27) a halo($C_1$-$C_6$) alkylsulfonyl group;

(d30) a phenyl group;

(d31) a phenyl group having, on the ring, 1 to 5 substituting groups which may be the same or different and are selected from the group consisting of a halogen atom, a cyano group, a nitro group, a formyl group, a ($C_1$-$C_6$) alkyl group, a halo($C_1$-$C_6$) alkyl group, a ($C_1$-$C_6$) alkoxy group, a halo($C_1$-$C_6$) alkoxy group, a ($C_3$-$C_6$) cycloalkyl ($C_1$-$C_6$) alkyl group, an $R^{10}$($R^{11}$)N group, a ($C_1$-$C_6$) alkylthio group, a halo($C_1$-$C_6$) alkylthio group, a ($C_1$-$C_6$) alkylsulfinyl group, a halo($C_1$-$C_6$) alkylsulfinyl group, a ($C_1$-$C_6$) alkylsulfonyl group, and a halo($C_1$-$C_6$) alkylsulfonyl group; or (d32) a ($C_1$-$C_6$) alkoxycarbonyl ($C_1$-$C_6$) alkyl group, and Q is (e1) a halogen atom;

(e2) a cyano group;

(e4) a formyl group;

(e5) a ($C_1$-$C_6$) alkyl group;

(e6) a ($C_2$-$C_6$) alkenyl group;

(e7) a ($C_2$-$C_6$) alkynyl group;

(e8) a halo($C_1$-$C_6$) alkyl group;

(e11) a ($C_1$-$C_6$) alkoxy group;

(e12) a halo($C_1$-$C_6$) alkoxy group;

(e13) a hydroxy ($C_1$-$C_6$) alkyl group;

(e14) a dihydroxy ($C_1$-$C_6$) alkyl group;

(e15) a ($C_1$-$C_6$) alkoxy ($C_1$-$C_6$) alkyl group;

(e16) a ($C_1$-$C_6$) alkoxy ($C_2$-$C_6$) alkenyl group;

(e17) an $R^8$($R^9$)N group;

(e18) a dioxolanyl group;

(e19) a dioxolanyl group having, on the ring, 1 or 2 substituting groups which may be the same or different and are selected from the group consisting of a carbonyl group and a ($C_1$-$C_6$) alkyl group;

(e20) a dioxanyl group;

(e21) a dioxanyl group having, on the ring, 1 to 3 substituting groups which may be the same or different and are selected from the group consisting of a halogen atom, a cyano group, a nitro group, a formyl group, a carbonyl group, a ($C_1$-$C_6$) alkyl group, a halo($C_1$-$C_6$) alkyl group, a ($C_1$-$C_6$) alkoxy group, a halo($C_1$-$C_6$) alkoxy group, a ($C_3$-$C_6$) cycloalkyl ($C_1$-$C_6$) alkyl group, an $R^{10}$($R^{11}$)N($C_1$-$C_6$) alkyl group, a ($C_1$-$C_6$) alkylthio group, a halo($C_1$-$C_6$) alkylthio group, a ($C_1$-$C_6$) alkylsulfinyl group, a halo($C_1$-$C_6$) alkylsulfinyl group, a ($C_1$-$C_6$) alkylsulfonyl group, and a halo($C_1$-$C_6$) alkylsulfonyl group;

(e22) a phenyl group;

(e23) a phenyl group having, on the ring, 1 to 5 substituting groups which may be the same or different and are selected from the group consisting of a halogen atom, a cyano group, a nitro group, a formyl group, a ($C_1$-$C_6$) alkyl group, a halo($C_1$-$C_6$) alkyl group, a ($C_1$-$C_6$) alkoxy group, a halo($C_1$-$C_6$) alkoxy group, a ($C_3$-$C_6$) cycloalkyl ($C_1$-$C_6$) alkyl group, an $R^{10}$($R^{11}$)N group, a ($C_1$-$C_6$) alkylthio group, a halo($C_1$-$C_6$) alkylthio group, a ($C_1$-$C_6$) alkylsulfinyl group, a halo($C_1$-$C_6$) alkylsulfinyl group, a ($C_1$-$C_6$) alkylsulfonyl group, and a halo($C_1$-$C_6$) alkylsulfonyl group;

(e24) an imidazolyl group;

(e25) an imidazolyl group having, on the ring, 1 to 3 substituting groups which may be the same or different and are selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(e26) an oxadiazolyl group;

(e27) an oxadiazolyl group having, on the ring, a substituting group selected from the group consisting of a halogen atom, a cyano group, a nitro group, a formyl group, a $(C_1-C_6)$ alkyl group, a halo$(C_1-C_6)$ alkyl group, a $(C_1-C_6)$ alkoxy group, a halo$(C_1-C_6)$ alkoxy group, a $(C_3-C_6)$ cycloalkyl $(C_1-C_6)$ alkyl group, an $R^{10}(R^{11})N$ group, a $(C_1-C_6)$ alkylthio group, a halo$(C_1-C_6)$ alkylthio group, a $(C_1-C_6)$ alkylsulfinyl group, a halo$(C_1-C_6)$ alkylsulfinyl group, a $(C_1-C_6)$ alkylsulfonyl group, and a halo$(C_1-C_6)$ alkylsulfonyl group;

(e28) an $S(O)_pR^6$ group;

(e29) a $C(O)R^7$ group;

(e30) a thiocarboxamide group;

(e31) an N—$(C_1-C_6)$ alkylaminothiocarbonyl group;

(e32) an N,N-di-$(C_1-C_6)$ alkylaminothiocarbonyl group;

(e33)

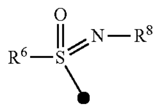

(e34) a hydroxyimino $(C_1-C_3)$ alkyl group;

(e35) a $(C_1-C_6)$ alkoxyimino $(C_1-C_3)$ alkyl group;

(e36) a halo$(C_1-C_6)$ alkoxyimino $(C_1-C_3)$ alkyl group;

(e37) a hydrazono $(C_1-C_3)$ alkyl group;

(e38) a $(C_1-C_6)$ alkylhydrazono $(C_1-C_3)$ alkyl group;

(e39) a di-$(C_1-C_6)$ alkylhydrazono $(C_1-C_3)$ alkyl group;

(e40) a phenyl$(C_1-C_6)$ alkoxyimino $(C_1-C_3)$ alkyl group;

(e41) a $(C_2-C_6)$ alkenyloxyimino $(C_1-C_3)$ alkyl group;

(e42) a di-$(C_1-C_6)$ alkoxyphosphoryl group;

(e43) a di-$(C_1-C_6)$ alkoxyphosphorylamino group;

(e44) a hydroxyl group;

(e45) a $(C_1-C_6)$ alkoxy $(C_1-C_6)$ alkoxy group; or (e46) a $(C_1-C_6)$ alkoxyiminoamino $(C_1-C_3)$ alkyl group;

$R^6$ is a hydrogen atom, a $(C_1-C_6)$ alkyl group, a $(C_2-C_6)$ alkenyl group, a $(C_2-C_6)$ alkynyl group, a halo$(C_1-C_6)$ alkyl group, a halo$(C_2-C_6)$ alkenyl group, a halo$(C_2-C_6)$ alkynyl group, a $(C_1-C_6)$ alkoxy group, a $(C_3-C_6)$ cycloalkyl group, a halo$(C_3-C_6)$ cycloalkyl group, a phenyl $(C_1-C_6)$ alkyl group, a $(C_1-C_6)$ alkoxyphenyl $(C_1-C_6)$ alkyl group, a $(C_1-C_6)$ alkylphenyl $(C_1-C_6)$ alkyl group, a tri-$(C_1-C_6)$ alkylsilylphenyl $(C_1-C_6)$ alkyl group, or an $N(R^8)R^9$ group, p is 0.1, or 2, $R^7$ is a hydroxyl group, a $(C_1-C_6)$ alkyl group, a $(C_2-C_6)$ alkenyl group, a $(C_2-C_6)$ alkynyl group, a halo$(C_1-C_6)$ alkyl group, a halo$(C_2-C_6)$ alkenyl group, a halo$(C_2-C_6)$ alkynyl group, a $(C_1-C_6)$ alkoxycarbonyl $(C_1-C_6)$ alkyl group, a phenyl $(C_1-C_6)$ alkyl group, a phenyl $(C_1-C_6)$ alkoxy group, a $(C_1-C_6)$ alkoxy group, a $(C_2-C_6)$ alkenyloxy group, a $(C_2-C_6)$ alkynyloxy group, a $(C_3-C_6)$ cycloalkoxy group, a halo$(C_1-C_6)$ alkoxy group, a halo$(C_2-C_6)$ alkynyloxy group, a phenyloxy group, a $(C_1-C_6)$ alkoxycarbonyl $(C_1-C_6)$ alkoxy group, a $(C_1-C_6)$ alkylthio group, a phenyl group, a thiazolidinyl group, or an $N(R^8)R^9$ group, $R^8$ and $R^9$ may be the same or different and each is a hydrogen atom, a hydroxyl group, an amino group, a di-$(C_1-C_6)$ alkylamino group, a $(C_1-C_6)$ alkyl group, a $(C_3-C_6)$ cycloalkyl group, a $(C_2-C_6)$ alkenyl group, a $(C_2-C_6)$ alkynyl group, a $(C_1-C_6)$ alkoxy group, a $(C_2-C_6)$ alkenyloxy group, a halo$(C_1-C_6)$ alkyl group, a halo$(C_2-C_6)$ alkenyl group, a halo$(C_2-C_6)$ alkynyl group, a halo$(C_3-C_6)$ cycloalkyl group, a $(C_3-C_6)$ cycloalkyl $(C_1-C_6)$ alkyl group, a cyano $(C_1-C_6)$ alkyl group, a $(C_1-C_6)$ alkylcarbonyl group, a halo$(C_1-C_6)$ alkylcarbonyl group, a $(C_1-C_6)$ alkoxycarbonyl group, a halo$(C_1-C_6)$ alkoxycarbonyl group, a $(C_1-C_6)$ alkylsulfanylcarbonyl group, a $(C_1-C_6)$ alkylsulfonyl group, a halo$(C_1-C_6)$ alkylsulfonyl group, an N—$(C_1-C_6)$ alkylcarboxamide group, an N,N-di-$(C_1-C_6)$ alkylcarboxamide group, an N—$(C_1-C_6)$ alkylsulfamoyl group, an N,N-di-$(C_1-C_6)$ alkylsulfamoyl group, an N-halo$(C_1-C_6)$ alkylcarboxamide group, a $(C_1-C_6)$ alkoxycarbonyl $(C_1-C_6)$ alkyl group, a $(C_1-C_6)$ alkoxy $(C_1-C_6)$ alkyl group, a di-$(C_1-C_6)$ alkoxy $(C_1-C_6)$ alkyl group, a $(C_1-C_6)$ alkoxy $(C_1-C_6)$ alkylcarbonyl group, a thietanyl group, a 1,1-dioxothietanyl group, a tetrahydrofuranyl group, a thiazolyl group, a 2-oxotetrahydrofuranyl group, a phenyl group, a phenyl group having, on the ring, 1 to 5 substituting groups which may be the same or different and are selected from the group consisting of a halogen atom, a cyano group, a $(C_1-C_6)$ alkyl group, a halo$(C_1-C_6)$ alkyl group, a $(C_1-C_6)$ alkoxy group, and a halo$(C_1-C_6)$ alkoxy group, or a phenyl $(C_1-C_6)$ alkyl group, or $R^8$ and $R^9$ may join together to form a 4- to 6-membered ring, and $R^{10}$ and $R^{11}$ may be the same or different and each is a hydrogen atom, a $(C_1-C_6)$ alkyl group, a halo$(C_1-C_6)$ alkyl group, a $(C_3-C_6)$ cycloalkyl group, a $(C_3-C_6)$ cycloalkyl $(C_1-C_6)$ alkyl group, a $(C_1-C_6)$ alkylcarbonyl group, a halo$(C_1-C_6)$ alkylcarbonyl group, a $(C_1-C_6)$ alkoxycarbonyl group, a halo$(C_1-C_6)$ alkoxycarbonyl group, a $(C_1-C_6)$ alkylsulfonyl group, or a halo$(C_1-C_6)$ alkylsulfonyl group, or $R^{10}$ and $R^{11}$ may join together to form a 4- to 6-membered ring.

3. The compound or the salt thereof according to claim 1, wherein $R^1$ is (a1) a halogen atom;

(a2) a cyano group;

(a3) a nitro group;

(a4) a formyl group;

(a5) a carboxyl group;

(a6) a $(C_1-C_6)$ alkyl group;

(a7) a $(C_2-C_6)$ alkenyl group;

(a9) a $(C_3-C_6)$ cycloalkyl group;

(a10) a halo$(C_1-C_6)$ alkyl group;

(a14) a hydroxy $(C_1-C_6)$ alkyl group;

(a16) a $(C_1-C_6)$ alkoxy $(C_1-C_6)$ alkyl group;

(a17) a di-$(C_1-C_6)$ alkoxy $(C_1-C_6)$ alkyl group;

(a22) a $(C_1-C_6)$ alkoxy group;

(a23) a halo$(C_1-C_6)$ alkoxy group;

(a24) a $(C_1-C_6)$ alkylthio group;

(a26) a $(C_1-C_6)$ alkylsulfonyl group;

(a27) a halo$(C_1-C_6)$ alkylthio group;

(a28) a halo$(C_1-C_6)$ alkylsulfinyl group;

(a29) a halo$(C_1-C_6)$ alkylsulfonyl group;

(a30) an $R^8(R^9)N$ group;

(a31) an $R^{10}(R^{11})N(C_1-C_6)$ alkyl group;

(a32) a $(C_1-C_6)$ alkylthio $(C_1-C_6)$ alkyl group;

(a33) a $(C_1-C_6)$ alkylsulfinyl $(C_1-C_6)$ alkyl group;
(a34) a $(C_1-C_6)$ alkylsulfonyl $(C_1-C_6)$ alkyl group;
(a45) a $(C_1-C_6)$ alkoxycarbonyl group;
(a52) an $R^{10}(R^{11})N$ sulfonyl group;
(a55) a $(C_1-C_6)$ alkoxyimino $(C_1-C_3)$ alkyl group;
(a57) a phenyl group;
(a58) a phenyl group having, on the ring, 1 to 5 substituting groups which may be the same or different and are selected from the group consisting of a halogen atom and a $(C_1-C_6)$ alkoxy group;
(a59) a pyridyl group;
(a62) a pyrazolyl group having, on the ring, 1 to 3 $(C_1-C_6)$ alkyl groups which may be the same or different;
(a65) a dioxolanyl group;
(a67) a dioxanyl group;
(a69) a $(C_1-C_6)$ alkylene group formed together with one adjacent substituting group; or
(a70) a methylenedioxy group formed together with one adjacent substituting group, wherein the methylenedioxy group may be substituted with 1 or 2 halogen atoms, wherein, when m is an integer of 2 or more, $R^1$s may be the same or different,
m is 0, 1, 2, 3, or 4,
$R^2$ is
(b1) a hydrogen atom;
(b2) a $(C_1-C_6)$ alkyl group;
(b3) a $(C_3-C_6)$ cycloalkyl group;
(b5) a $(C_2-C_6)$ alkynyl group;
(b6) a halo$(C_1-C_6)$ alkyl group; or
(b9) a $(C_1-C_6)$ alkoxy $(C_1-C_6)$ alkyl group,
$R^3$ is
(c1) a hydrogen atom;
(c3) a cyano group;
(c5) a carboxamide group;
(c6) a $(C_1-C_6)$ alkyl group;
(c12) an $R^8(R^9)N$ group;
(c13) a $(C_1-C_6)$ alkoxy group; or
(c16) a $(C_1-C_6)$ alkoxycarbonyl $(C_1-C_6)$ alkyl group,
$R^4$ is
(d1) a hydrogen atom;
(d2) a $(C_1-C_6)$ alkyl group;
(d3) a $(C_2-C_6)$ alkenyl group;
(d4) a $(C_2-C_6)$ alkynyl group;
(d6) a halo$(C_1-C_6)$ alkyl group;
(d9) a $(C_1-C_6)$ alkoxy $(C_1-C_6)$ alkyl group;
(d13) a $(C_3-C_6)$ cycloalkyl $(C_1-C_6)$ alkyl group;
(d14) a cyano $(C_1-C_6)$ alkyl group;
(d15) a $(C_1-C_6)$ alkylthio $(C_1-C_6)$ alkyl group;
(d16) a $(C_1-C_6)$ alkylsulfinyl $(C_1-C_6)$ alkyl group;
(d17) a $(C_1-C_6)$ alkylsulfonyl $(C_1-C_6)$ alkyl group;
(d18) a carboxyl $(C_1-C_6)$ alkyl group;
(d19) a phenyl$(C_1-C_6)$ alkyl group;
(d20) a phenyl$(C_1-C_6)$ alkyl group having, on the ring, 1 to 5 halogen atoms which may be the same or different;
(d22) a $(C_1-C_6)$ alkylcarbonyl group;
(d23) a $(C_1-C_6)$ alkoxycarbonyl group;
(d24) a $(C_1-C_6)$ alkylsulfonyl group;
(d30) a phenyl group; or
(d32) a $(C_1-C_6)$ alkoxycarbonyl $(C_1-C_6)$ alkyl group,
$A^1$, $A^2$, and $A^3$ may be the same or different and each is $CR^5$ (wherein $R^5$ is a hydrogen atom, a halogen atom, a $(C_1-C_6)$ alkyl group, or an $R^{10}(R^{11})N$ group) or a nitrogen atom, and
Q is
(e1) a halogen atom;
(e2) a cyano group;
(e4) a formyl group;

(e5) a $(C_1-C_6)$ alkyl group;
(e6) a $(C_2-C_6)$ alkenyl group;
(e8) a halo$(C_1-C_6)$ alkyl group;
(e11) a $(C_1-C_6)$ alkoxy group;
(e13) a hydroxy $(C_1-C_6)$ alkyl group;
(e14) a dihydroxy $(C_1-C_6)$ alkyl group;
(e16) a $(C_1-C_6)$ alkoxy $(C_2-C_6)$ alkenyl group;
(e17) an $R^8(R^9)N$ group;
(e18) a dioxolanyl group;
(e19) a dioxolanyl group having, on the ring, 1 or 2 substituting groups which may be the same or different and are selected from the group consisting of a carbonyl group and a $(C_1-C_6)$ alkyl group;
(e20) a dioxanyl group;
(e22) a phenyl group;
(e24) an imidazolyl group;
(e27) an oxadiazolyl group having, on the ring, a $(C_1-C_6)$ alkyl group;
(e28) an $S(O)_pR^6$ group;
(e31) an N—$(C_1-C_6)$ alkylaminothiocarbonyl group;
(e33)

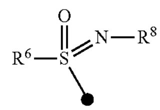

(e35) a $(C_1-C_6)$ alkoxyimino $(C_1-C_3)$ alkyl group;
(e36) a halo$(C_1-C_6)$ alkoxyimino $(C_1-C_3)$ alkyl group;
(e37) a hydrazono $(C_1-C_3)$ alkyl group;
(e40) a phenyl$(C_1-C_6)$ alkoxyimino $(C_1-C_3)$ alkyl group;
(e41) a $(C_2-C_6)$ alkenyloxyimino $(C_1-C_3)$ alkyl group;
(e42) a di-$(C_1-C_6)$ alkoxyphosphoryl group;
(e43) a di-$(C_1-C_6)$ alkoxyphosphorylamino group;
(e44) a hydroxyl group; or
(e45) a $(C_1-C_6)$ alkoxy $(C_1-C_6)$ alkoxy group,
$R^6$ is a hydrogen atom, a $(C_1-C_6)$ alkyl group, a halo$(C_1-C_6)$ alkyl group, a phenyl $(C_1-C_6)$ alkyl group, a $(C_1-C_6)$ alkoxyphenyl $(C_1-C_6)$ alkyl group, a $(C_1-C_6)$ alkylphenyl $(C_1-C_6)$ alkyl group, a tri-$(C_1-C_6)$ alkylsilylphenyl$(C_1-C_6)$ alkyl group, or an $N(R^8)R^9$ group,
p is 0, 1, or 2,
$R^7$ is a hydroxyl group, a $(C_1-C_6)$ alkyl group, a $(C_1-C_6)$ alkoxycarbonyl $(C_1-C_6)$ alkyl group, a phenyl $(C_1-C_6)$ alkoxy group, a $(C_1-C_6)$ alkoxy group, a $(C_2-C_6)$ alkynyloxy group, a $(C_3-C_6)$ cycloalkoxy group, a phenyloxy group, a $(C_1-C_6)$ alkoxycarbonyl $(C_1-C_6)$ alkoxy group, a $(C_1-C_6)$ alkylthio group, a thiazolidinyl group, or an $N(R^8)R^9$ group,
$R^8$ and $R^9$ may be the same or different and each is a hydrogen atom, a hydroxyl group, an amino group, a di-$(C_1-C_6)$ alkylamino group, a $(C_1-C_6)$ alkyl group, a $(C_3-C_6)$ cycloalkyl group, a $(C_2-C_6)$ alkenyl group, a $(C_2-C_6)$ alkynyl group, a $(C_1-C_6)$ alkoxy group, a $(C_2-C_6)$ alkenyloxy group, a halo$(C_1-C_6)$ alkyl group, a halo$(C_3-C_6)$ cycloalkyl group, a $(C_3-C_6)$ cycloalkyl $(C_1-C_6)$ alkyl group, a $(C_1-C_6)$ alkylcarbonyl group, a halo$(C_1-C_6)$ alkylcarbonyl group, a $(C_1-C_6)$ alkoxycarbonyl group, a $(C_1-C_6)$ alkylsulfonyl group, an N,N-di-$(C_1-C_6)$ alkylsulfamoyl group, a $(C_1-C_6)$ alkoxy $(C_1-C_6)$ alkyl group, a di-$(C_1-C_6)$ alkoxy $(C_1-C_6)$ alkyl group, a thietanyl group, a thiazolyl group, or a 2-oxotetrahydrofuranyl group, or R and $R^9$ may join together to form a 4- to 6-membered ring, and $R^{10}$ and $R^{11}$ may be the same or different and each is a hydrogen atom or a ($C_1$-$C_6$) alkyl group, or $R^{10}$ and $R^{11}$ may join together to form a 4- to 6-membered ring.

4. The compound or the salt thereof according to claim 1, wherein $A^1$ is a nitrogen atom, and $A^2$ and $A^3$ may be the same or different and are $CR^5$s.

5. The compound or the salt thereof according to claim 2, wherein $A^1$ is a nitrogen atom, and $A^2$ and $A^3$ may be the same or different and $CR^5$s.

6. The compound or the salt thereof according to claim 3, wherein $A^1$ is a nitrogen atom, and $A^2$ and $A^3$ may be the same or different and are $CR^5$s.

7. The compound or the salt thereof according to claim 2, wherein $A^1$, $A^2$, and $A^3$ may be the same or different and are $CR^5$s.

8. The compound or the salt thereof according to claim 3, wherein $A^1$, $A^2$, and $A^3$ may be the same or different and are $CR^5$s.

9. The compound or the salt thereof according to claim 3, wherein $A^1$ and $A^3$ may be the same or different and are $CR^5$s, and $A^2$ is a nitrogen atom.

10. The compound or the salt thereof according to claim 3, wherein $A^1$ and $A^2$ may be the same or different and are $CR^5$s, and $A^3$ is a nitrogen atom.

11. The compound or the salt thereof according to claim 3, wherein $A^1$ and $A^3$ are nitrogen atoms, and $A^2$ is $CR^5$.

12. The compound or the salt thereof according to claim 2, wherein $A^1$ and $A^2$ are nitrogen atoms, and $A^3$ is $CR^5$.

13. The compound or the salt thereof according to claim 3, wherein $A^1$ and $A^2$ are nitrogen atoms, and $A^3$ is $CR^5$.

14. The compound or the salt thereof according to claim 3, wherein $A^1$ is $CR^5$, and $A^2$ and $A^3$ are nitrogen atoms.

15. An agricultural or horticultural herbicide comprising the compound or the salt thereof according to claim 1 as an active ingredient.

16. A method for using an agricultural or horticultural herbicide, comprising treating weeds, soil, paddy field, or growing media with an effective amount of the agricultural or horticultural herbicide according to claim 15.

17. A method for controlling weeds, comprising treating weeds, soil, paddy field, or growing media with an effective amount of the agricultural or horticultural herbicide according to claim 15.

* * * * *